(12) United States Patent
Enoki et al.

(10) Patent No.: US 12,428,686 B2
(45) Date of Patent: Sep. 30, 2025

(54) SET OF RANDOM PRIMERS AND METHOD FOR PREPARING DNA LIBRARY USING THE SAME

(71) Applicant: TOYOTA JIDOSHA KABUSHIKI KAISHA, Toyota (JP)

(72) Inventors: Hiroyuki Enoki, Hamamatsu (JP); Yoshie Takeuchi, Hamamatsu (JP); Minoru Inamori, Kariya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/613,532

(22) PCT Filed: May 18, 2018

(86) PCT No.: PCT/JP2018/019258
§ 371 (c)(1),
(2) Date: Nov. 14, 2019

(87) PCT Pub. No.: WO2018/212318
PCT Pub. Date: Nov. 22, 2018

(65) Prior Publication Data
US 2020/0071776 A1    Mar. 5, 2020

(30) Foreign Application Priority Data
May 19, 2017 (JP) ................. 2017-099408

(51) Int. Cl.
*C12Q 1/6895* (2018.01)
*C12N 15/10* (2006.01)
*C12Q 1/6806* (2018.01)

(52) U.S. Cl.
CPC ....... *C12Q 1/6895* (2013.01); *C12N 15/1093* (2013.01); *C12Q 1/6806* (2013.01)

(58) Field of Classification Search
CPC ................. C12Q 1/68; C12N 15/10
See application file for complete search history.

(56) References Cited

U.S. PATENT DOCUMENTS

| | | | |
|---|---|---|---|
| 5,487,985 A | 1/1996 | McClelland et al. | |
| 7,718,403 B2 | 5/2010 | Kamberov et al. | |
| 9,247,720 B2 * | 2/2016 | Chemin | A01K 67/027 |
| 10,023,907 B2 | 7/2018 | Van Eijk et al. | |
| 10,093,976 B2 | 10/2018 | Lo et al. | |
| 10,095,832 B2 | 10/2018 | Van Eijk et al. | |
| 10,214,769 B2 | 2/2019 | Enoki et al. | |
| 2003/0113715 A1 | 6/2003 | Santi | |
| 2003/0157515 A1 | 8/2003 | Ohtsubo et al. | |
| 2004/0259100 A1 | 12/2004 | Gunderson et al. | |
| 2005/0233305 A1 | 10/2005 | Yamamoto et al. | |
| 2007/0020667 A1 * | 1/2007 | Ruff | C12Q 1/6846 |
| | | | 435/6.1 |
| 2008/0057499 A1 | 3/2008 | Fu | |
| 2009/0131275 A1 | 5/2009 | Shimamoto et al. | |
| 2010/0055703 A1 | 3/2010 | Thines et al. | |
| 2011/0195457 A1 * | 8/2011 | Nelson | C12P 19/34 |
| | | | 435/194 |
| 2012/0190582 A1 | 7/2012 | Enoki et al. | |
| 2013/0085083 A1 * | 4/2013 | Kamberov | C12Q 1/6806 |
| | | | 506/16 |
| 2014/0011694 A1 | 1/2014 | Couronne | |
| 2015/0360193 A1 * | 12/2015 | Fan | C12Q 1/6844 |
| | | | 506/26 |
| 2016/0326572 A1 | 11/2016 | Schupp et al. | |
| 2017/0121765 A1 | 5/2017 | Lee et al. | |
| 2017/0166951 A1 | 6/2017 | Enoki et al. | |
| 2017/0335371 A1 | 11/2017 | Osborne et al. | |
| 2018/0010120 A1 | 1/2018 | Mellor et al. | |
| 2018/0016632 A1 * | 1/2018 | Penkler | C12Q 1/6806 |
| 2018/0016632 A1 * | 1/2018 | Penkler | C12Q 1/6806 |
| 2019/0233889 A1 | 8/2019 | Enoki et al. | |
| 2019/0233889 A1 * | 8/2019 | Enoki | C12N 15/1093 |
| 2020/0120340 A1 | 4/2020 | Park et al. | |

FOREIGN PATENT DOCUMENTS

| | | |
|---|---|---|
| CN | 107513576 A | 12/2017 |
| EP | 1 721 970 A1 | 11/2006 |
| EP | 1 910 562 A1 | 4/2008 |
| EP | 2 514 820 A1 | 10/2012 |
| JP | 20039079375 A | 3/2003 |
| JP | 2005-245297 A | 9/2005 |
| JP | 2006-519621 A | 8/2006 |
| JP | 2007-525963 A | 9/2007 |
| JP | 3972106 B2 | 9/2007 |
| JP | 2008-546404 A | 12/2008 |
| JP | 5389638 B2 | 1/2014 |
| JP | 2014-193165 A | 10/2014 |
| JP | 2014-204730 A | 10/2014 |
| JP | 5799484 B2 | 10/2015 |
| JP | 2017-79735 A | 5/2017 |
| JP | 2018-042548 A | 3/2018 |
| WO | 2005/003304 A2 | 1/2005 |
| WO | 2007/114693 A2 | 10/2007 |
| WO | 2008/101701 A2 | 8/2008 |

(Continued)

OTHER PUBLICATIONS

Saavedra et al., Mapping Transposon Insertions in Bacterial Genomes by Arbitrarily Primed PCR, Supplement 228, Current Protocols in Molecular Biology, 2017, 1-18. (Year: 2017).*

(Continued)

*Primary Examiner* — Amy M Bunker
(74) *Attorney, Agent, or Firm* — Sughrue Mion, PLLC

(57) ABSTRACT

When preparing a DNA library via a nucleic acid amplification reaction using a random primer in a convenient and highly reproducible manner, amplification of DNA fragments derived from the chloroplast genome is reduced to a significant extent. A random primer comprises oligonucleotides selected from oligonucleotides group represented by TAAGAGACAGNN excluding those in which 2 bases at the 3' terminus are TG and oligonucleotides group represented by TAAGAGACAGNNN excluding those in which 3 bases at the 3' terminus are TGC.

5 Claims, 123 Drawing Sheets
Specification includes a Sequence Listing.

(56) References Cited

FOREIGN PATENT DOCUMENTS

| WO | 2018/039991 A2 | 4/2010 | |
| WO | WO-2010039991 A2 * | 4/2010 | ........... C12Q 1/6811 |
| WO | 2014/140309 A1 | 9/2014 | |
| WO | 2015/058097 A1 | 4/2015 | |
| WO | 2016/083933 A1 | 6/2016 | |
| WO | 2016/115550 A1 | 7/2016 | |
| WO | 2017/123758 A1 | 7/2017 | |
| WO | 2017/222164 A1 | 12/2017 | |
| WO | 2019/197712 A1 | 10/2019 | |

OTHER PUBLICATIONS

Pickard et a., A Genomewide Mutagenesis Screen Identifies Multiple Genes Contributing to Vi Capsular Expression in Salmonella enterica Serovar Typhi, Journal of Bacteriology, 2013, 195(6), 1320-1326. (Year: 2013).*

Shchelkunov et al., Plant-Based Vaccines Against Human Hepatitis B Virus, Expert Reviews, 2010, 9(8), 947-955. (Year: 2010).*

Welch et al., Data Characterizing the Chloroplast Genomes of Extinct and Endangered Hawaiian Endemic Mints (Lamiaceae) and Their Close Relatives, Data in Brief, 2016, 7, 900-922. (Year: 2016).*

Welch and Collins et al., The Quest to Resolve Recent Radiations: Plastid Phylogenomics of Extinct and Endangered Hawaiian Endemic Mints (Lamiaceae), Molecular Phylogenetics and Evolution, 2016, 99, 16-33. (Year: 2016).*

Scitable, Primer, Nature Education, 2014, 1-2. Obtained from: https://www.nature.com/scitable/definition/primer-305/# :~: text=A%20primer%20is%20a%20short,before%20DNA%20replication%20can%20occur on May 9, 2023. (Year: 2014).*

McMaster University, Amplicon Libraries for Illumina Sequencing, 2017, 1-6. Obtained from: https://genomics.healthsci.mcmaster.ca /wp-content/uploads/2022/06/amplicon_libraries_171031.pdf on May 10, 2023. (Year: 2017).*

Welch et al., Data Characterizing the Chloroplast Genomes of Extinct and Endangered Hawaiian Endemic Mints (Lamiaceae) and Their Close Relatives, Data in Brief 7, 2016, 900-922. (Year: 2016).*

Welch et al., Data Characterizing the Chloroplast Genomes of Extinct and Endangered Hawaiian Endemic Mints (Lamiaceae) and Their Close Relatives, Supplementary Information, Data in Brief 7, 2016, 1-3. (Year: 2016).*

Welch et al., Data Characterizing the Chloroplast Genomes of Extinct and Endangered Hawaiian Endemic Mints (Lamiaceae) and Their Close Relatives, Data in Brief, 2016, 7, 900-922. (Year: 2016).*

Welch et al., Data Characterizing the Chloroplast Genomes of Extinct and Endangered Hawaiian Endemic Mints (Lamiaceae) and Their Close Relatives, Supplementary Information, Data in Brief, 2016, 7, 1-3. (Year: 2016).*

Gemma C. Langridge, et al., "Simultaneous assay of every Salmonella Typhi gene using one million transposon mutants", Genome Research, 2009, pp. 2308-2316, vol. 19, No. 12.

Erbsay Yigit, et al., "Genome And Metagenome Sequencing: Using The Human Methyl-Binding Domain To Partition Genomic DNA Derived From Plant Tissues", Applications in Plant Sciences, 2014, pp. 1-6, vol. 2, No. 11.

U.S. Appl. No. 15/445,262, filed Feb. 28, 2017 (Enoki et al.).

Craig et al., "Identification of Genetic Variants Using Barcoded Multiplexed Sequencing", Nat Methods, Oct. 2008, vol. 5, No. 10, pp. 887-893 (16 pages total).

Illumina, New uses of NGS, Library Preparation Using Tailed PCR Method, [online], Jun. 13, 2014, Internet: URL: https://jp.illumina.com/contant/dam/illumina-marketing/apac/japan/documents/pdf/2014_techsupport_session5.pdf, 56 total pages (with unedited computer-generated English translation).

Lamble et al., "Improved workflows for high throughput library preparation using the transposome-based nextera system", BMC Biotechnology, 2013, vol. 13, No. 104, pp. 1-10 (12 pages total).

SeQanswers, [online], Jul. 4, 2012, 01:46AM, Internet URL: https://seqanswers.com/forums/showthread.php?p=72834, 6 total pages.

Zhang et al., "Whole genome amplification from a single cell: Implications for genetic analysis", Proc. Natl. Acad. Sci. USA, vol. 89, pp. 5847-5851, Jul. 1992 (5 pages total).

Julio Cesar Masaru Iehisa et al., "A High-Density Genetic Map with Array-Based Markers Facilitates Structural and Quantitative Trait Locus Analyses of the Common Wheat Genome", DNA Research, 2014, pp. 555-567, vol. 21.

Shiori Yabe et al., "Rapid genotyping with DNA micro-arrays for high-density linkage mapping and QTL mapping in common buckwheat (*Fagopyrum esculentum* Moench)", Breeding Science, 2014, pp. 291-299, vol. 64.

Restriction/Election Requirement dated Jul. 14, 2020, issued by the U.S. Patent and Trademark Office in U.S. Appl. No. 16/313,706.

Non-Final Office Action dated Sep. 17, 2020, issued by the U.S. Patent and Trademark Office in U.S. Appl. No. 16/313,706.

Restriction/Election Requirement dated Sep. 24, 2020, issued by the U.S. Patent and Trademark Office in U.S. Appl. No. 16/314,274.

Illumina Adapter Sequences, Illumina®, Oct. 2015, pp. 1-34.

International Search Report dated Jan. 25, 2022 in International Application No. PCT/US21/55036.

Written Opinion of the International Searching Authority dated Jan. 25, 2022 in International Application No. PCT/US21/55036.

Final Office Action, dated Nov. 19, 2021, issued by the United States Patent and Trademark Office in U.S. Appl. No. 16/314,274.

Final Office Action, dated Aug. 19, 2021, issued by the U.S. Patent and Trademark Office in U.S. Appl. No. 16/313,706.

Non-Final Office Action, dated Aug. 1, 2022, issued by the United States Patent and Trademark Office in U.S. Appl. No. 16/313,706.

Wolfgang Dietmaier et al., "Multiple Mutation Analyses in Single Tumor Cells with Improved Whole Genome Amplification", American Journal of Pathology, 1999, vol. 154, No. 1, pp. 83-95 (13 pages total).

Advisory Action, dated Jan. 28, 2022, issued by the United States Patent and Trademark Office in U.S. Appl. No. 16/313,706.

Non-Final Office Action, dated Aug. 8, 2022, issued by the U.S. Patent and Trademark Office in U.S. Appl. No. 16/314,274.

Yoon et at., "PrimerDesign-M: a multiple-alignment based multiple-primer design tool for walking across variable genomes", Bioinformatics, 2015, vol. 31, No. 9, pp. 1472-1474 (3 pages).

Mallona et al., "pcrEfficiency: a Web tool for PCR amplification efficiency prediction", BMC Bioinformatics, 2011, vol. 12, No. 404, pp. 1-7 (7 pages).

Kämpke et al., "Efficient primer design algorithms", Bioinformatics, 2001, vol. 17, No. 3, pp. 214-225 (12 pages).

Kozarewa et al., "96-Plex Molecular Barcoding for the Illumina Genome Analyzer", Young Min Kwon and Steven C. Ricke (eds.), High-Throughput Next Generation Sequencing: Methods and Applications, Methods in Molecular Biology, Chapter 20, 2011, vol. 733, pp. 279-298 (20 pages).

Best et al., "Computational analysis of stochastic heterogeneity in PCR amplification efficiency revealed by single molecule barcoding", Scientific Reports, 2015, vol. 5, No. 14629, pp. 1-13 (13 pages).

O'Donnell et al., "Indexed PCR Primers Induce Template-Specific Bias in Large-Scale DNA Sequencing Studies", PLOS ONE, 2016, vol. 11, No. 3, e0148698, pp. 1-11 (11 pages).

Frank, "Barcrawl and Bartab: software tools for the design and implementation of barcoded primers for highly multiplexed DNA sequencing", BMC Bioinformatics, 2009, vol. 10, No. 362, pp. 1-13 (13 pages).

Communication dated Dec. 12, 2022, issued in U.S. Appl. No. 16/769,859.

Advisory Action issued Nov. 21, 2023 by the United States Patent and Trademark Office in U.S. Appl. No. 16/313,706.

Office Action issued Jul. 27, 2023 in U.S. Appl. No. 16/313,706.

Office Action issued Jul. 27, 2023 in U.S. Appl. No. 16/314,274.

(56) References Cited

OTHER PUBLICATIONS

Sumio Kanno et al., "Cell Engineering Supplement", Next generation sequencer, Purpose-specific advanced methods, 2012, pp. 212-219 (10 pages total).

Notice of Allowance issued Jun. 26, 2023 in U.S. Appl. No. 16/769,859.

Hadrys et al., "Applications of random amplified polymorphic DNA (RAPD) in molecular ecology", Molecular Ecology, 1992, vol. 1, pp. 55-63 (9 pages total).

Final Office Action from the United States Patent and Trademark Office in U.S. Appl. No. 16/314,274 dated May 22, 2024.

Yunzhou Wang et al., Molecular analysis of single oocyst of Eimeria by whole genome amplification(WGA) based nested PCR, Experimental Parasitology, 2014, 144, pp. 96-99 (4 pages total).

Rene Hubert et al., "A New Source of Plymorphic DNA Markers for Sperm Typing: Analysis of Microsatellite Repeats in Single Cells", Am. J. Hum. Genet., 1992, 51, pp. 985-991 (7 pages total).

Advisory Action from the United States Patent and Trademark Office in U.S. Appl. No. 16/314,274 dated Aug. 2, 2024.

Final Office Action from the United States Patent and Trademark Office in U.S. Appl. No. 16/641,274 dated May 22, 2024.

Yunzhou Wang et al., Molecular analysis of single oocyst of Eimeria by whole genome amplification(WGA) based nested PCR, Experimental Parasitology, 2014, 144, pp. 96-99 (4 pages total).

Renee Hubert et al., "A New source of Polymorphic DNA Markers for Sperm Typing: Analysis of Microsatellite Repeats in Single Cells", Am. J. Hum. Genet., 1992, 51, pp. 985-991 (7 pages total).

Advisory Action from the United States Patent and Trademark Office in U.S. Appl. No. 16/314,274 dated Aug. 2, 2024.

Hadrys et al., "Applications of random amplified polymorphics DNA (RAPD) in molecular ecology", Molecular Ecology, 1992, vol. 1, pp. 55-63 (9 pages total).

Robert Pinard, et al., "Assessment of whole genome amplication-induced bias through high-throughput, massively parallel whole genome sequencing", BMC Genomics, 2006, vol. 7, No. 216 (21 pages total).

Advisory Action issued Jul. 29, 2024 in U.S. Appl. No. 16/313,706.

Advisory Action issued Nov. 21, 2023 by the United States Patent and Trademark Office in U.S. Appl. No. 16/313,706.

Final Office Action from the United States Patent and Trademark Office in U.S. Appl. No. 16/314,274 dated May 22, 2024.

Yunzhou Wang et al., Molecular analysis of single oocyst of Eimeria by whole genome amplification(WGA) based nested PCR, Experimental Parasitology, 2014, 144, pp. 96-99 (4 pages total).

Renee Hubert et al., "A New source of Polymorphic DNA Markers for Sperm Typing: Analysis of Microsatellite Repeats in Single Cells", Am. J. Hum. Genet., 1992, 51, pp. 985-991 (7 pages total).

Advisory Action from the United States Patent and Trademark Office in U.S. Appl. No. 16/314,274 dated Aug. 2, 2024.

Hadrys et al., "Applications of random amplified polymorphics DNA (RAPD) in molecular ecology", Molecular Ecology, 1992, vol. 1, pp. 55-63 (9 pages total).

Advisory Action issued Nov. 21, 2023 by the United States Patent and Trademark Office in U.S. Appl. No. 16/313,706.

U.S. Office Action dated Dec. 9, 2024 issued in U.S. Appl. No. 16/314,274.

\* cited by examiner

Fig. 120-1

```
Region_1_1_Corn     100794:GTGGGTAGGTAGAGAATACCTAGGGGCGGAGACAACTCTCTAAGGAACTCGGCAAAA 100853
Region_1_1_Oryza     96947:GTGGGTAGGTAGAGAATACCTAGGGGCGGAGACAACTCTCTAAGGAACTCGGCAAAA  97006
Region_1_1_Potato   107147:GTGGGTAGGTAGAGAATACCTAGGGGCGGAGACAACTCTCTAAGGAACTCGGCAAAA 107206
Region_1_1_Soybean  105184:GTGGGTAGGTAGAGAATACCTAGGGGCGGAGACAACTCTCTAAGGAACTCGGCAAAA 105243
Region_2_1_Corn     121943:GTGGGTAGGTAGAGAATACCTAGGGGCGGAGACAACTCTCTAAGGAACTCGGCAAAA 121884
Region_2_1_Oryza    118171:GTGGGTAGGTAGAGAATACCTAGGGGCGGAGACAACTCTCTAAGGAACTCGGCAAAA 118112
Region_2_1_Potato   133887:GTGGGTAGGTAGAGAATACCTAGGGGCGGAGACAACTCTCTAAGGAACTCGGCAAAA 133828
Region_2_1_Soybean  130210:GTGGGTAGGTAGAGAGTACCTAGAGGCGCGAGACAACTCTCTAAGGAACTCGGCAAAA 130151
                           ****** ******** ****** ** ** ************************

Region_1_1_Corn     100854:TAGCCCCGTAACTTCGGGAGAAGGGGTGCCCCTCGCAAAAGGGGGGTCCAGTGACCAGG 100913
Region_1_1_Oryza     97007:TAGCCCCGTAACTTCGGGAGAAGGGGTGCCCCTTCACAAAGGGGGTGCAGTGACCAGG  97066
Region_1_1_Potato   107207:TAGCCCCGTAACTTCGGGAGAAGGGGTGCCCCTCCTCACAAA-GGGGGTGCAGTGACCAGG 107265
Region_1_1_Soybean  105244:TAGCCCCGTAACTTCGGAGAGAAGGGGTGCCCCTTCACAA-GGGGGTGCAGTGACCAGG 105302
Region_2_1_Corn     121883:TAGCCCCGTAACTTCGGGAGAAGGGGTGCCCTCGCAAAGGGGGTGCAGTGACCAGG 121824
Region_2_1_Oryza    118061:TAGCCCCGTAACTTCGGGAGAAGGGGTGCCTCCTCGGCAAAGGGGGTCCAGTGACCAGG 118002
Region_2_1_Potato   133827:TAGCCCCGTAACTTCGGGAGAAGGGGTGCCTCCTCACAA-TGGGGTCCAGTGACCAGG 133769
Region_2_1_Soybean  130150:TAGCCCCGTAACTTCGGAGAGAAGGGGTGCCTCCTCACAA-GGGGGTCCAGTGACCAGG 130092
                           ***************  ********** ****    ****   ***************

Region_1_1_Corn     100914:CCGGGCGACTGTATACCAAAACACAGGTCTCCGCAAGTCGTAAGACCATGTATGGG 100973
Region_1_1_Oryza     97067:CCGGGCGACTGTTTACCAAAACACAGGTCTCCGCAAGTCGTAAGACCATGTATGGG  97126
Region_1_1_Potato   107266:CCGGGCGACTGTTTACCAAAACACAGGTCTCCGCAAGTCGTAAGACCATGTATGGG 107325
Region_1_1_Soybean  105303:CCGGGCGACTGTTTACCAAAACACAGGTCTCCGCAAGTCGTAAGACCATGTATGGG 105362
Region_2_1_Corn     121823:CCGGGCGACTGTATACCAAAACACAGGTCTCCGCAAGTCGTAAGACCATGTATGGG 121764
Region_2_1_Oryza    118051:CCGGGCGACTGTTTACCAAAACACAGGTCTCCGCAAGTGTAAGACCATGTATGGG 117992
Region_2_1_Potato   133768:CCGGGCGACTGTTTACCAAAACACAGGTCTCCGCAAGTCGTAAGACCATGTATGGG 133709
Region_2_1_Soybean  130091:CCGGGCGACTGTTTACCAAAACACAGGTCTCCGCAAGTCGTAAGACCATGTATGGG 130032
                           ************ ****************************** ***************
```

Fig. 120-2

```
Region_1_1_Corn    100974:GCTGACGCCTGCCAGTGCCGCCGAAGGTCAAGGAGAAGTTGGTGAACTGATGACAGGGAAGCC 101033
Region_1_1_Oryza    97127:GCTGACGCCTGCCAGTGCCGCCGAAG-TCAAGGAGAGTTGGTGAACTGATGACAGGGAAGCC  97185
Region_1_1_Potato  107326:GCTGACGCCTGCCAGTGCCGCCGAAGGTCAAGGAAGTTGGTGACTGATGACAGGGAAGCC   107385
Region_1_1_Soybean 105363:GCTGACGCCTGCCAGTGCCGCCGAAGGTCAAGGAAGTTGGTGACTGATGACAGGGGAAGCC  105422
Region_2_1_Corn    121763:GCTGACGCGCCTGCCCAGTGCCGGCGGAAGGTCAAGGAAGTTGTGACTGATGACAGGGAAGCC 121704
Region_2_1_Oryza   117991:GCTGACGCCTGCCCAGTGCCGCCGAAG-TCAAGGAAGTTGGTGAACTGATGACAGGAAGCC   117933
Region_2_1_Potato  133708:GCTGACGCCTGCCAGTGCCGCCGAAGGTCAAGGAAGTTGGTGACTGATGACAGGGGAGCC   133649
Region_2_1_Soybean 130031:GCTGACGCCTGCCAGTGCCGCCGAAGGTCAAGGAAGTTGGTGACTGATGACAGGGAGCC    129972
                          ****************** ******* ********   *******  *  *  *****

Region_*_2

Region_1_1_Corn    101034:GGGGACCGAAGCCCCGGTGAACGGGGCCGTAACTATAACGGTCCTAAGGTAGCGAAATT 101093
Region_1_1_Oryza    97186:GGTGACCGAAGCCCCGGTGAACGGCGGCCGTAACTATAACGGTCCTAAGGTAGCGAAATT  97245
Region_1_1_Potato  107386:GGTGACCGAAGCCCCGGTGAACGGCGGCCGTAACTATAACGGTCCTAAGGTAGCGAAATT 107445
Region_1_1_Soybean 105423:GACGACCGAAGCCCGGTGAACGGCGGCCGTAACTATAACGGTCCTAAGGTAGCGAAATT   105482
Region_2_1_Corn    121703:GGGGACCGAAGCCCGGTGAACGGCGGCCGTAACTATAACGGTCCTAAGGTAGCGAAATT   121644
Region_2_1_Oryza   117932:GGGGACCGAAGCCCCGGTGAACGGCGGCCGTAACTATAACGGTCCTAAGGTAGCGAAATT 117873
Region_2_1_Potato  133648:GGGGACCGAAGCCCCGGTGAACGGCGGCCGTAACTATAACGGTCCTAAGGTAGCGAAATT 133589
Region_2_1_Soybean 129971:GACGACCGAAGCCCGGTGAACGGCGGCCGTAACTATAACGGTCCTAAGGTAGCGAAATT   129912
                         *  ****************************************************

Common region

Region_1_1_Corn    101094:CCTTGTCGGGTAAGTTCCGACCTCGCACGAAAAGGCGTAACGATCTGGGCA 101142
Region_1_1_Oryza    97246:CCTTGTCGGGTAAGTTCCGACCCGCACGAAAAGGCGTAACGATCTGGGCA   97294
Region_1_1_Potato  107446:CCTTGTCGGGTAAGTTCCGACCCGCACGAAAAGGCGTAACGATCTGGGCA  107494
Region_1_1_Soybean 105483:CCTTGTCGGGTAAGTTCCGACCCGCACGAAAAGGCGTAACGATCTGGGCA  105531
Region_2_1_Corn    121643:CCTTGTCGGGTAAGTTCCGACCCGCACGAAAAGGCGTAACGATCTGGGCA  121595
Region_2_1_Oryza   117872:CCTTGTCGGGTAAGTTCCGACCCGCACGAAAAGGCGTAACGATCTGGGCA  117824
Region_2_1_Potato  133588:CCTTGTCGGGTAAGTTCCGACCCGCACGAAAAGGCGTAACGATCTGGGCA  133540
Region_2_1_Soybean 129911:CCTTGTCGGGTAAGTTCCGACCCGCACGAAAAGGCGTAACGATCTGGGCA  129863
                         *********************  ***************************
```

Region_*_2
Common region

Fig. 121

```
Region_3_1_Oryza 32151:GTATTGCGAGACAGCCAGAAGCAGAAGGTAAAATACGCGGTACTTTATTGCTTAGTCTAG 32210
Region_3_2_Oryza 32165:-------------CCAGAAGCAGAAGGTAAAATACGCGGTACTTTATTGCTTAGTCTAG 32210
                                    ************************************************

Region_3_1_Oryza 32211:CTTTTATGGAAGCTTAACAATTTATGGACTAGTTGTGGCACTGGCGCTTTAT         32264
Region_3_2_Oryza 32211:CTTTTATGGAAGCTTAACAATTTATGGACTAGTAGTGGCA------------         32251
                       ********************************* *******
```

SET OF RANDOM PRIMERS AND METHOD FOR PREPARING DNA LIBRARY USING THE SAME

CROSS REFERENCE TO RELATED APPLICATIONS

This application is a National Stage of International Application No. PCT/JP2018/019258 filed May 18, 2018, claiming priority based on Japanese Patent Application No. 2017-099408 filed May 19, 2017.

TECHNICAL FIELD

The present invention relates to a set of random primers used in a method for preparing a DNA library that can be used for DNA marker analysis and so on, and a method for preparing a DNA library using such set of random primers.

BACKGROUND ART

In general, genomic analysis is performed to conduct comprehensive analysis of genetic information contained in the genome, such as nucleotide sequence information. However, an analysis aimed at determination of the nucleotide sequence for the whole genome is disadvantageous in terms of the number of processes and the cost. In cases of organisms with large genomic sizes, in addition, genomic analysis based on nucleotide sequence analysis has limitations because of genome complexity.

Patent Literature 1 discloses an amplified fragment length polymorphism (AFLP) marker technique wherein a sample-specific marker is incorporated into a restriction-enzyme-treated fragment that had been ligated to an adaptor and only a part of the sequence of the restriction-enzyme-treated fragment is to be determined. According to the technique disclosed in Patent Literature 1, the complexity of genomic DNA is reduced by treating genomic DNA with a restriction enzyme, the nucleotide sequence of a target part of the restriction-enzyme-treated fragment is determined, and the target restriction-enzyme-treated fragment is thus identified sufficiently. The technique disclosed in Patent Literature 1, however, requires processes such as treatment of genomic DNA with a restriction enzyme and ligation reaction with the use of an adaptor. Thus, it is difficult to achieve a cost reduction.

Meanwhile, Patent Literature 2 discloses as follows. That is, a DNA marker for identification that is highly correlated with the results of taste evaluation was found from among DNA bands obtained by amplifying DNAs extracted from a rice sample via PCR in the presence of adequate primers by the so-called RAPD (randomly amplified polymorphic DNA) technique. The method disclosed in Patent Literature 2 involves the use of a plurality of sequence-tagged sites (STSs, which are primers) identified by particular sequences. According to the method disclosed in Patent Literature 2, a DNA marker for identification amplified using an STS primer is detected via electrophoresis. However, the RAPD technique disclosed in Patent Literature 2 yields significantly poor reproducibility of PCR amplification, and, accordingly, such technique cannot be generally adopted as a DNA marker technique.

Patent Literature 3 discloses a method for preparing a genomic library wherein PCR is carried out with the use of a single type of primer designed on the basis of a sequence that appears relatively frequently in the target genome, the entire genomic region is substantially uniformly amplified, and a genomic library can be thus prepared. While Patent Literature 3 describes that a genomic library can be prepared by conducting PCR with the use of a random primer containing a random sequence, it does not describe any actual procedures or results of experimentation. Accordingly, the method described in Patent Literature 3 is deduced to require nucleotide sequence information of the genome so as to identify the genome appearing frequency, which would increase the number of procedures and the cost. According to the method described in Patent Literature 3, in addition, the entire genome is to be amplified, and complexity of genomic DNA cannot be reduced, disadvantageously.

CITATION LIST

Patent Literature

PTL 1: JP Patent No. 5389638
PTL 2: JP 2003-79375 A
PTL 3: JP Patent No. 3972106

SUMMARY OF INVENTION

Technical Problem

For a technique of genome information analysis, such as genetic linkage analysis conducted with the use of DNA markers, it is desired to prepare a DNA library in a more convenient and highly reproducible manner. As described above, a wide variety of techniques of preparing a DNA library are known. To date, however, there have been no techniques known to be sufficient in terms of convenience and/or reproducibility. Under the above circumstances, the present inventors have developed a system for preparing a highly reproducible DNA library in a very convenient method of PCR involving the use of random primers in which the concentration of the random primers in a reaction solution is regulated within a predetermined range.

When random primers comprising particular sequences are used in such system, however, large quantities of DNA fragments derived from the chloroplast genome were found to be amplified. Under the above circumstances, the present invention provides a set of random primers that is used when preparing a highly reproducible DNA library in a convenient manner via a nucleic acid amplification reaction involving the use of random primers and capable of significantly reducing amplification of DNA fragments derived from the chloroplast genome. The present invention also provides a method for preparing a DNA library involving the use of such set of random primers.

Solution to Problem

The present inventors discovered that amplification of DNA fragments derived from the chloroplast genome could be reduced to a significant extent with the use of a set of random primers, excluding the random primers comprising particular sequences. This has led to the completion of the present invention.

The present invention includes the following.
(1) A set of random primers comprising, as random primers, one or more oligonucleotides selected from among 15 types of oligonucleotides represented by TAAGAGACAGNN (SEQ ID NO: 2060, wherein N represents any of A, G, C, or T) excluding those in which 2 bases at the 3' terminus are TG and 63 types of oligonucleotides represented by TAAGAGACAGNNN (SEQ ID NO: 2061, wherein N represents any of A, G, C, or T) excluding those in which 3 bases at the 3' terminus are TGC.

(2) The set of random primers according to (1), which does not comprise at least one oligonucleotide comprising the nucleotide sequence as shown in SEQ ID NO: 2060 in which 2 bases at the 3' terminus are GG, GT, AT, or CC among the 15 types of oligonucleotides.

(3) The set of random primers according to (1), which does not comprise at least one oligonucleotide comprising the nucleotide sequence as shown in SEQ ID NO: 2061 in which 3 bases at the 3' terminus are GGA, GGG, GTG, GTA, ATA, or CCA among the 63 types of oligonucleotides.

(4) A method for preparing a DNA library comprising conducting a nucleic acid amplification reaction in a reaction solution containing genomic DNA and a random primer selected from the set of random primers according to any one of (1) to (3) at high concentration using genomic DNA as a template to obtain a DNA fragment.

(5) The method for preparing a DNA library according to (4), wherein the reaction solution contains the random primers at a concentration of 4 to 200 microM.

(6) The method for preparing a DNA library according to (4), wherein the reaction solution contains the random primers at a concentration of 4 to 100 microM.

(7) A method for preparing a DNA library comprising: a step of conducting a nucleic acid amplification reaction in a first reaction solution containing genomic DNA and a random primer selected from the set of random primers according to any one of (1) to (3) at high concentration using genomic DNA as a template to obtain a first DNA fragment; and a step of conducting a nucleic acid amplification reaction in a second reaction solution containing the first DNA fragment and, as a primer, a nucleotide comprising at the 3' terminus a nucleotide sequence exhibiting at least 70% identity to the nucleotide sequence at the 5' terminus of the random primer to obtain a second DNA fragment comprising the first DNA fragment and the nucleotide ligated thereto.

(8) The method for preparing a DNA library according to (7), wherein the first reaction solution contains the random primers at a concentration of 4 to 200 microM.

(9) The method for preparing a DNA library according to (7), wherein the first reaction solution contains the random primers at a concentration of 4 to 100 microM.

(10) The method for preparing a DNA library according to (7), wherein the primer that amplifies the second DNA fragment includes a region used for nucleotide sequencing or the primer that is used for a nucleic acid amplification reaction involving the use of the second DNA fragment as a template or repeated nucleic acid amplification reactions includes a region used for nucleotide sequencing.

(11) A DNA library prepared by the method for preparing a DNA library according to any one of (4) to (10).

Advantageous Effects of Invention

When the set of random primers of the present invention is used for a nucleic acid amplification reaction within a particular concentration range, a highly reproducible DNA library can be prepared in a very convenient manner. Since the set of random primers of the present invention does not contain a random primer comprising the particular nucleotide sequence, in such a case, amplification of DNA fragments derived from the chloroplast genome can be suppressed to a greater extent, compared with the case where the set of random primers comprises a random primer comprising a particular nucleotide sequence.

In addition, the method for preparing a DNA library of the present invention involves the use of a set of random primers that does not comprise a random primer comprising a particular nucleotide sequence. Thus, a highly reproducible DNA library capable of suppressing amplification of DNA fragments derived from the chloroplast genome to a significant extent can be prepared in a very convenient manner.

Figure 1:
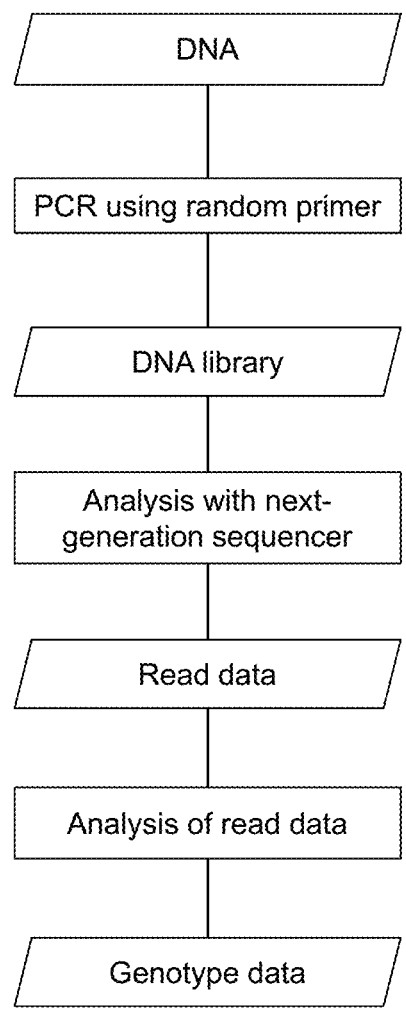
FIG. 1 shows a flow chart demonstrating the method for preparing a DNA library and the method for genomic DNA analysis with the use of the DNA library of the present invention.

FIG. 120-1 shows a characteristic diagram demonstrating the results of comparison of particular regions of corn, rice, potato, and soybean to which large quantities of read data are mapped (Region_1_1_Corn: SEQ ID NO: 2153, Region_1_1_Oryza: SEQ ID NO: 2154, Region_1_1_Potato: SEQ ID NO: 2155, Region_1_1_Soybean: SEQ ID NO: 2156, Region_2_1_Corn: SEQ ID NO: 2157, Region_2_1_Oryza: SEQ ID NO: 2158, Region_2_1_Potato: SEQ ID NO: 2159, and Region_2_1_Soybean: SEQ ID NO: 2160).

Figure 2:
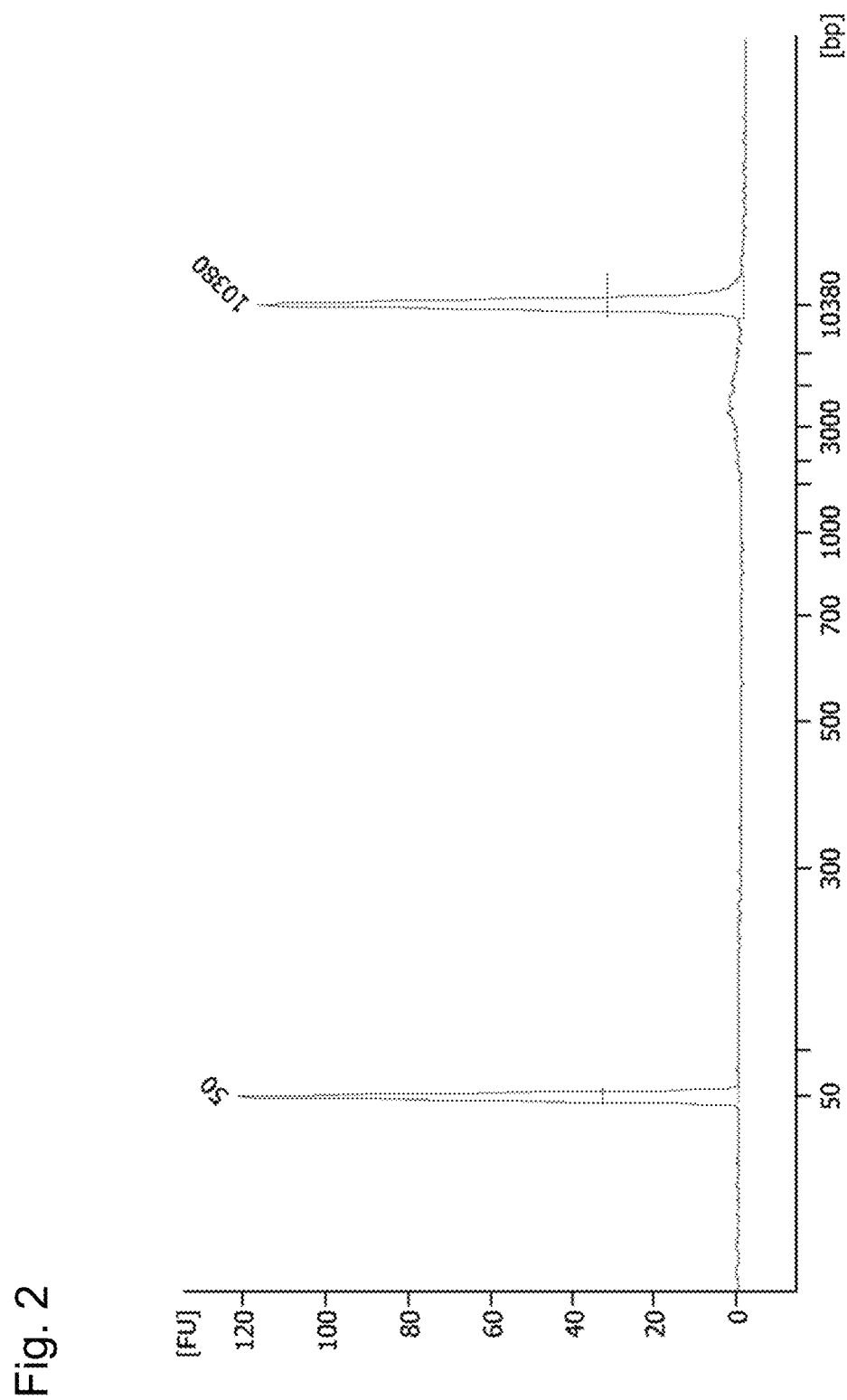
FIG. 2 shows a characteristic diagram demonstrating a correlation between an amplified fragment length and a fluorescence unit (FU) in which the amplified fragment length is determined based on an electrophoretic pattern of the DNA library amplified via PCR using DNA of the sugarcane variety NiF8 as a template under general conditions.

FIG. 120-2 shows a characteristic diagram demonstrating the results of comparison of particular regions of corn, rice, potato, and soybean to which large quantities of read data are mapped (Region_1_1_Corn: SEQ ID NO: 2153, Region_1_1_Oryza: SEQ ID NO: 2154, Region_1_1_Potato: SEQ ID NO: 2155, Region_1_1_Soybean: SEQ ID NO: 2156, Region_2_1_Corn: SEQ ID NO: 2157, Region_2_1_Oryza: SEQ ID NO: 2158, Region_2_1_Potato: SEQ ID NO: 2159, and Region_2_1_Soybean: SEQ ID NO: 2160).

FIG. 121 shows a characteristic diagram demonstrating the results of comparison of particular regions of rice to which large quantities of read data are mapped (Region_3_1_Oryza: SEQ ID NO: 2161 and Region_3_2_Oryza: SEQ ID NO: 2162).

Figure 122:
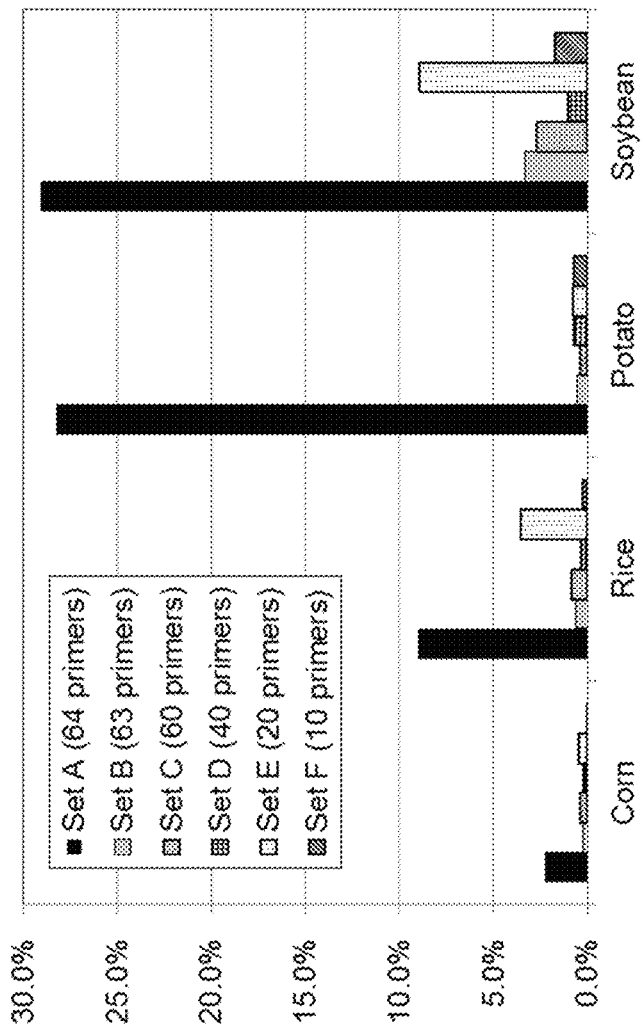

FIG. 122 shows a characteristic diagram demonstrating a comparison of the proportion of the read data derived from the chloroplast genome observed when the sets of random primers A to F are used.

DESCRIPTION OF EMBODIMENTS

Hereafter, the present invention is described in detail.

According to the method for preparing a DNA library of the present invention, a nucleic acid amplification reaction is carried out in a reaction solution, which is prepared to contain a random primer contained in the primers described below (hereafter, referred to as "sets of random primers") at high concentration, and a DNA library of the resulting amplified nucleic acid fragments is prepared. When a reaction solution contains a random primer at high concentration, such concentration is higher than the concentration of a primer used in a general nucleic acid amplification reaction. According to the method for preparing a DNA library of the present invention, specifically, a random primer is used at concentration higher than that of a primer used in a general nucleic acid amplification reaction. As a template contained in a reaction solution, genomic DNA prepared from a target organism for which a DNA library is to be prepared can be used.

In the method for preparing a DNA library of the present invention, a target organism species is not particularly limited. Specific examples of targets include organisms comprising the chloroplast genome, such as plants and algae. According to the method for preparing a DNA library of the present invention, specifically, a DNA library can be prepared from the organisms comprising the chloroplast genome as mentioned above, such as plants and algae.

In particular, the method for preparing a DNA library of the present invention involves the use of a set of random primers described in detail below. Thus, amplification of nucleic acid fragments derived from the chloroplast genome can be suppressed to a significant extent. With the use of the set of random primers described in detail below, specifically, large quantities of nucleic acid fragments derived from the nuclear genome can be amplified, and a DNA library primarily concerning the nuclear genome can be constructed.

According to the method for preparing a DNA library, the concentration of a random primer may be prescribed as described below. Thus, nucleic acid fragments (or a group of nucleic acid fragments) can be amplified with high reproducibility. The term "reproducibility" used herein refers to an extent of concordance among nucleic acid fragments amplified by a plurality of nucleic acid amplification reactions carried out with the use of the same template and the same set of random primers. That is, the term "high reproducibility (or the expression "reproducibility is high")" refers to a high extent of concordance among nucleic acid fragments amplified by a plurality of nucleic acid amplification reactions carried out with the use of the same template and the same set of random primers.

The extent of reproducibility can be evaluated by, for example, conducting a plurality of nucleic acid amplification reactions with the use of the same template and the same set of random primers, subjecting the obtained amplified fragments to electrophoresis, calculating the Spearman's rank correlation coefficient for the obtained fluorescence unit (FU), and evaluating the extent of reproducibility on the basis of such coefficient. The Spearman's rank correlation coefficient is generally represented by the symbol ρ (rho). When ρ (rho) is greater than 0.9, for example, the reproducibility of the amplification reaction of interest can be evaluated to be sufficient.

Random Primer

In order to obtain a particular amplicon via a nucleic acid amplification reaction, in general, a nucleotide sequence of a primer is designed in accordance with the amplicon of interest. For example, a pair of primers is designed so as to sandwich a position corresponding to an amplicon in template DNA, such as genomic DNA. In such a case, a primer is designed to hybridize to a particular region in the template. Thus, such primer can be referred to as a "specific primer."

Unlike a primer that is designed to obtain a particular amplicon, in contrast, a random primer is not designed to hybridize to a particular region in template DNA, but it is designed to obtain a random amplicon.

The set of random primers of the present invention comprises, as random primers, one or more oligonucleotides selected from among 15 types of oligonucleotides selected from among oligonucleotides represented by TAAGAGACAGNN (SEQ ID NO: 2060, wherein N represents any of A, G, C, or T) excluding those in which 2 bases at the 3' terminus are TG and 63 types of oligonucleotides represented by TAAGAGACAGNNN (SEQ ID NO: 2061, wherein N represents any of A, G, C, or T) excluding those in which 3 bases at the 3' terminus are TGC.

In other words, the set of random primers of the present invention comprises, as random primers, one or more oligonucleotides selected from among a group of oligonucleotides each comprising TAAGAGACAG (SEQ ID NO: 2062) at the 5' terminus and 2 or 3 arbitrary bases at the 3' terminus from this nucleotide sequence, excluding TAAGAGACAGTG (SEQ ID NO: 2063) and TAAGAGACAGTGC (SEQ ID NO: 2064).

As shown in Table 1 below, 15 types of oligonucleotides selected from among oligonucleotides represented by TAAGAGACAGNN (SEQ ID NO: 2060, wherein N represents any of A, G, C, or T) excluding those in which 2 bases at the 3' terminus are TG, include 15 types of oligonucleotides comprising the nucleotide sequences as shown in SEQ ID NOs: 2065 to 2079.

TABLE 1

| Sequence | |
|---|---|
| TAAGAGACAGAA | SEQ ID NO: 2065 |
| TAAGAGACAGAT | SEQ ID NO: 2066 |
| TAAGAGACAGAC | SEQ ID NO: 2067 |
| TAAGAGACAGAG | SEQ ID NO: 2068 |
| TAAGAGACAGTA | SEQ ID NO: 2069 |
| TAAGAGACAGTT | SEQ ID NO: 2070 |
| TAAGAGACAGTC | SEQ ID NO: 2071 |
| TAAGAGACAGCA | SEQ ID NO: 2072 |
| TAAGAGACAGCT | SEQ ID NO: 2073 |
| TAAGAGACAGCC | SEQ ID NO: 2074 |
| TAAGAGACAGCG | SEQ ID NO: 2075 |
| TAAGAGACAGGA | SEQ ID NO: 2076 |
| TAAGAGACAGGT | SEQ ID NO: 2077 |
| TAAGAGACAGGC | SEQ ID NO: 2078 |
| TAAGAGACAGGG | SEQ ID NO: 2079 |

The 63 types of oligonucleotides selected from among the oligonucleotides represented by TAAGAGACAGNNN (SEQ ID NO: 2061, wherein N represents any of A, G, C, or T) excluding oligonucleotides in which 3 bases at the 3' terminus are TGC, include 63 types of oligonucleotides comprising the nucleotide sequences as shown in SEQ ID NOs: 2080 to 2142, as shown in Table 2 below.

TABLE 2

| Sequence | |
|---|---|
| TAAGAGACAGAAA | SEQ ID NO: 2080 |
| TAAGAGACAGAAC | SEQ ID NO: 2081 |
| TAAGAGACAGAAG | SEQ ID NO: 2082 |
| TAAGAGACAGAAT | SEQ ID NO: 2083 |
| TAAGAGACAGACA | SEQ ID NO: 2084 |
| TAAGAGACAGACC | SEQ ID NO: 2085 |
| TAAGAGACAGACG | SEQ ID NO: 2086 |
| TAAGAGACAGACT | SEQ ID NO: 2087 |
| TAAGAGACAGAGA | SEQ ID NO: 2088 |
| TAAGAGACAGAGC | SEQ ID NO: 2089 |
| TAAGAGACAGAGG | SEQ ID NO: 2090 |
| TAAGAGACAGAGT | SEQ ID NO: 2091 |
| TAAGAGACAGATA | SEQ ID NO: 2092 |
| TAAGAGACAGATC | SEQ ID NO: 2093 |
| TAAGAGACAGATG | SEQ ID NO: 2094 |
| TAAGAGACAGATT | SEQ ID NO: 2095 |
| TAAGAGACAGCAA | SEQ ID NO: 2096 |
| TAAGAGACAGCAC | SEQ ID NO: 2097 |
| TAAGAGACAGCAG | SEQ ID NO: 2098 |
| TAAGAGACAGCAT | SEQ ID NO: 2099 |
| TAAGAGACAGCCA | SEQ ID NO: 2100 |
| TAAGAGACAGCCC | SEQ ID NO: 2101 |
| TAAGAGACAGCCG | SEQ ID NO: 2102 |
| TAAGAGACAGCCT | SEQ ID NO: 2103 |
| TAAGAGACAGCGA | SEQ ID NO: 2104 |
| TAAGAGACAGCGC | SEQ ID NO: 2105 |
| TAAGAGACAGCGG | SEQ ID NO: 2106 |
| TAAGAGACAGCGT | SEQ ID NO: 2107 |
| TAAGAGACAGCTA | SEQ ID NO: 2108 |
| TAAGAGACAGCTC | SEQ ID NO: 2109 |
| TAAGAGACAGCTG | SEQ ID NO: 2110 |
| TAAGAGACAGCTT | SEQ ID NO: 2111 |
| TAAGAGACAGGAA | SEQ ID NO: 2112 |
| TAAGAGACAGGAC | SEQ ID NO: 2113 |
| TAAGAGACAGGAG | SEQ ID NO: 2114 |
| TAAGAGACAGGAT | SEQ ID NO: 2115 |
| TAAGAGACAGGCA | SEQ ID NO: 2116 |
| TAAGAGACAGGCC | SEQ ID NO: 2117 |
| TAAGAGACAGGCG | SEQ ID NO: 2118 |

TABLE 2-continued

| Sequence | |
|---|---|
| TAAGAGACAGGCT | SEQ ID NO: 2119 |
| TAAGAGACAGGGA | SEQ ID NO: 2120 |
| TAAGAGACAGGGC | SEQ ID NO: 2121 |
| TAAGAGACAGGGG | SEQ ID NO: 2122 |
| TAAGAGACAGGGT | SEQ ID NO: 2123 |
| TAAGAGACAGGTA | SEQ ID NO: 2124 |
| TAAGAGACAGGTC | SEQ ID NO: 2125 |
| TAAGAGACAGGTG | SEQ ID NO: 2126 |
| TAAGAGACAGGTT | SEQ ID NO: 2127 |
| TAAGAGACAGTAA | SEQ ID NO: 2128 |
| TAAGAGACAGTAC | SEQ ID NO: 2129 |
| TAAGAGACAGTAG | SEQ ID NO: 2130 |
| TAAGAGACAGTAT | SEQ ID NO: 2131 |
| TAAGAGACAGTCA | SEQ ID NO: 2132 |
| TAAGAGACAGTCC | SEQ ID NO: 2133 |
| TAAGAGACAGTCG | SEQ ID NO: 2134 |
| TAAGAGACAGTCT | SEQ ID NO: 2135 |
| TAAGAGACAGTGA | SEQ ID NO: 2136 |
| TAAGAGACAGTGG | SEQ ID NO: 2137 |
| TAAGAGACAGTGT | SEQ ID NO: 2138 |
| TAAGAGACAGTTA | SEQ ID NO: 2139 |
| TAAGAGACAGTTC | SEQ ID NO: 2140 |
| TAAGAGACAGTTG | SEQ ID NO: 2141 |
| TAAGAGACAGTTT | SEQ ID NO: 2142 |

As described above, random primers can be arbitrarily selected from among a total of 78 types of oligonucleotides; that is, the 15 types of oligonucleotides shown in Table 1 and the 63 types of oligonucleotides shown in Table 2. Random primers included in the set of random primers of the present invention may be all of the 78 types of oligonucleotides or a single type of oligonucleotide, 5 types of oligonucleotides, 10 types of oligonucleotides, 20 types of oligonucleotides, 40 types of oligonucleotides, or 60 types of oligonucleotides selected from among the 78 types of oligonucleotides. Any oligonucleotide can be selected from among such 78 types of oligonucleotides without particular limitation.

Alternatively, the set of random primers of the present invention may comprise the 15 types of oligonucleotides shown in Table 1 as random primers, or it may comprise 1 to 14 types of oligonucleotides selected from among the 15 types of oligonucleotides shown in Table 1, such as 5 types of oligonucleotides or 10 types of oligonucleotides, as random primers.

When random primers are selected from among the 15 types of oligonucleotides shown in Table 1, in particular, it is preferable that selection be made to exclude at least one oligonucleotide from among TAAGAGACAGGG (SEQ ID NO: 2079), TAAGAGACAGGT (SEQ ID NO: 2077), TAAGAGACAGAT (SEQ ID NO: 2066), and TAAGAGACAGCC (SEQ ID NO: 2074). When random primers are selected from among the 15 types of oligonucleotides shown in Table 1, in other words, it is preferable that selection be made to exclude all, 3 types, 2 types, or a single type of oligonucleotide(s) from among the 4 types of oligonucleotides; i.e., TAAGAGACAGGG (SEQ ID NO: 2079), TAAGAGACAGGT (SEQ ID NO: 2077), TAAGAGACAGAT (SEQ ID NO: 2066), and TAAGAGACAGCC (SEQ ID NO: 2074).

The set of random primers of the present invention may comprise the 63 types of oligonucleotides shown in Table 2 as random primers, or it may comprise 1 to 62 types of oligonucleotides selected from among the 63 types of oligonucleotides shown in Table 2, such as 10 types of oligonucleotides, 20 types of oligonucleotides, 40 types of oligonucleotides, or 60 types of oligonucleotides, as random primers.

When random primers are selected from among the 63 types of oligonucleotides shown in Table 2, in particular, it is preferable that selection be made to exclude at least one oligonucleotide from among TAAGAGACAGGGA (SEQ ID NO: 2120), TAAGAGACAGGGG (SEQ ID NO: 2122), TAAGAGACAGGTG (SEQ ID NO: 2126), TAAGAGACAGGTA (SEQ ID NO: 2124), TAAGAGACAGATA (SEQ ID NO: 2092), and TAAGAGACAGCCA (SEQ ID NO: 2100). When random primers are selected from among the 63 types of oligonucleotides shown in Table 2, in other words, it is preferable that selection be made to exclude all, 5 types, 4 types, 3 types, 2 types, or a single type of oligonucleotide(s) from among the six types of oligonucleotides; i.e., TAAGAGACAGGGA (SEQ ID NO: 2120), TAAGAGACAGGGG (SEQ ID NO: 2122), TAAGAGACAGGTG (SEQ ID NO: 2126), TAAGAGACAGGTA (SEQ ID NO: 2124), TAAGAGACAGATA (SEQ ID NO: 2092), and TAAGAGACAGCCA (SEQ ID NO: 2100).

TAAGAGACAG (SEQ ID NO: 2062) at the 5' terminus that is common among a total of the 78 types of oligonucleotides described above is used as an adaptor sequence applied to the next-generation sequencer.

Nucleic Acid Amplification Reaction

According to the method for preparing a DNA library of the present invention, many amplified fragments are obtained via the nucleic acid amplification reaction carried out with the use of the random primers described above and genomic DNA as a template. At the time of the nucleic acid amplification reaction, in particular, the concentration of random primes in a reaction solution is prescribed higher than the concentration of primers in a conventional nucleic acid amplification reaction. Thus, many amplified fragments can be obtained with the use of genomic DNA as a template while achieving high reproducibility. Thus, many amplified fragments can be used as a DNA library applicable to genotyping or other purposes.

The method for preparing a DNA library of the present invention involves the use of the set of random primers described above. Thus, amplification of genomic DNA (in particular, nucleic acid fragments derived from the chloroplast genome) can be suppressed to a significant extent. According to the method for preparing a DNA library of the present invention, accordingly, large quantities of nucleic acid fragments derived from the nuclear genome can be amplified, and a DNA library primarily concerning the nuclear genome can be constructed.

A nucleic acid amplification reaction is aimed at synthesis of amplified fragments in a reaction solution containing genomic DNA as a template, the random primers, DNA polymerase, deoxynucleotide triphosphate as a substrate (i.e., dNTP, which is a mixture of dATP, dCTP, dTTP, and dGTP), and a buffer under the given thermal cycling conditions. It is necessary that a nucleic acid amplification reaction be carried out in a reaction solution containing $Mg^{2+}$ at a given concentration. In the reaction solution of the composition described above, the buffer contains $MgCl_2$. When the buffer does not contain $MgCl_2$, the reaction solution of the composition described above further contains $MgCl_2$.

In a nucleic acid amplification reaction, in particular, it is preferable that the concentration of random primers be adequately determined in accordance with the base lengths of the random primers. When a plurality of types of nucleotide sequences having different numbers of bases are used as random primers, the number of bases constituting the random primers may be the average of such plurality of nucleotide sequences (the average may be a simple average or the weight average taking the amount of bases into account).

Specifically, a nucleic acid amplification reaction is carried out with the use of a random primer at a concentration of 4 to 200 microM, and preferably at 4 to 100 microM. Under such conditions, many amplified fragments, and, in particular, many amplified fragments comprising 100 to 500 bases, can be obtained via a nucleic acid amplification reaction while achieving high reproducibility.

When a random primer comprises 10 to 14 bases, more specifically, it is preferable that the concentration of such random primer satisfy the conditions defined by an inequation: $y>3E+08x^{-6.974}$ and be 100 microM or less, provided that the base length of the random primer is represented by "y" and the concentration of the random primer is represented by "x."

As described in the examples below, the inequation: $y>3E+08x^{-6.974}$ is developed to be able to represent the concentration of a random primer at which many DNA fragments comprising 100 to 500 bases can be amplified with high reproducibility as a result of thorough inspection of the correlation between random primer length and random primer concentration.

While the amount of genomic DNA serving as a template in a nucleic acid amplification reaction is not particularly limited, it is preferably 0.1 to 1000 ng, more preferably 1 to 500 ng, further preferably 5 to 200 ng, and most preferably 10 to 100 ng, when the amount of the reaction solution is 50 microliters. By designating the amount of genomic DNA as a template within such range, many amplified fragments can be obtained without inhibiting the amplification reaction from a random primer, while achieving high reproducibility.

Genomic DNA can be prepared in accordance with a conventional technique without particular limitation. With the use of a commercialized kit, also, genomic DNA can be easily prepared from a target organism species. Genomic DNA extracted from an organism in accordance with a conventional technique or with the use of a commercialized kit may be used without further processing, genomic DNA extracted from an organism and then purified may be used, or genomic DNA subjected to restriction enzyme treatment or ultrasonic treatment may be used. In the method for preparing a DNA library of the present invention, in particular, a step of removing the chloroplast genome from the extracted genomic DNA is not necessary, and genomic DNA including the chloroplast genome and the nuclear genome can be used as a template for the nucleic acid amplification reaction. This is because the use of the set of random primers described above enables suppression of amplification of DNA fragments derived from the chloroplast genome to a significant extent.

DNA polymerase used in a nucleic acid amplification reaction is not particularly limited, and an enzyme having DNA polymerase activity under thermal cycling conditions for a nucleic acid amplification reaction can be used. Specifically, heat-stable DNA polymerase used for a general nucleic acid amplification reaction can be used. Examples of DNA polymerases include thermophilic bacteria-derived DNA polymerase, such as Taq DNA polymerase, and hyperthermophilic archaea-derived DNA polymerase, such as KOD DNA polymerase and Pfu DNA polymerase. In a nucleic acid amplification reaction, it is particularly preferable that Pfu DNA polymerase be used as DNA polymerase in combination with the random primer described above. With the use of such DNA polymerase, many amplified fragments can be obtained with more certainty while achieving high reproducibility.

In a nucleic acid amplification reaction, the concentration of deoxynucleotide triphosphate as a substrate (i.e., dNTP, which is a mixture of dATP, dCTP, dTTP, and dGTP) is not particularly limited, and it can be 5 microM to 0.6 mM, preferably 10 microM to 0.4 mM, and more preferably 20 microM to 0.2 mM. By designating the concentration of dNTP serving as a substrate within such range, errors caused by incorrect incorporation by DNA polymerase can be prevented, and many amplified fragments can be obtained while achieving high reproducibility.

A buffer used in a nucleic acid amplification reaction is not particularly limited. For example, a solution comprising $MgCl_2$ as described above, Tris-HCl (pH 8.3), and KCl can be used. The concentration of $Mg^{2+}$ is not particularly limited. For example, it can be 0.1 to 4.0 mM, preferably 0.2 to 3.0 mM, more preferably 0.3 to 2.0 mM, and further preferably 0.5 to 1.5 mM. By designating the concentration of $Mg^{2+}$ in the reaction solution within such range, many amplified fragments can be obtained while achieving high reproducibility.

Thermal cycling conditions of a nucleic acid amplification reaction are not particularly limited, and a general thermal cycle can be adopted. A specific example of a thermal cycle comprises a first step of thermal denaturation in which genomic DNA as a template is dissociated into single strands, a cycle comprising thermal denaturation, annealing, and extension repeated a plurality of times (e.g., 20 to 40 times), a step of extension for a given period of time according to need, and the final step of storage.

Thermal denaturation can be performed at, for example, 93 degrees C. to 99 degrees C., preferably 95 degrees C. to 98 degrees C., and more preferably 97 degrees C. to 98 degrees C. Annealing can be performed at, for example, 30 degrees C. to 70 degrees C., preferably 35 degrees C. to 68 degrees C., and more preferably 37 degrees C. to 65 degrees C., although it varies depending on a Tm value of the random primer. Extension can be performed at, for example, 70 degrees C. to 76 degrees C., preferably 71 degrees C. to 75 degrees C., and more preferably 72 degrees C. to 74 degrees C. Storage can be performed at, for example, 4 degrees C.

The first step of thermal denaturation can be performed within the temperature range described above for a period of, for example, 5 seconds to 10 minutes, preferably 10 seconds to 5 minutes, and more preferably 30 seconds to 2 minutes. In the cycle comprising "thermal denaturation, annealing, and extension," thermal denaturation can be performed within the temperature range described above for a period of, for example, 2 seconds to 5 minutes, preferably 5 seconds to 2 minutes, and more preferably 10 seconds to 1 minute. In the cycle comprising "thermal denaturation, annealing, and extension," annealing can be performed within the temperature range described above for a period of, for example, 1 second to 3 minutes, preferably 3 seconds to 2 minutes, and more preferably 5 seconds to 1 minute. In the cycle comprising "thermal denaturation, annealing, and extension," extension can be performed within the temperature range described above for a period of, for example, 1 second to 3 minutes, preferably 3 seconds to 2 minutes, and more preferably 5 seconds to 1 minute.

In the method for preparing a DNA library, amplified fragments may be obtained by a nucleic acid amplification reaction that employs a hot start method. The hot start method is intended to prevent mis-priming or non-specific amplification caused by primer-dimer formation prior to the cycle comprising "thermal denaturation, annealing, and extension." The hot start method involves the use of an enzyme in which DNA polymerase activity has been suppressed by binding an anti-DNA polymerase antibody thereto or chemical modification thereof. Thus, DNA polymerase activity can be suppressed and a non-specific reaction prior to the thermal cycle can be prevented. According to the hot start method, a temperature is set high in the first thermal cycle, DNA polymerase activity is thus recovered, and the subsequent nucleic acid amplification reaction is then allowed to proceed.

As described above, many amplified fragments (primarily derived from the nuclear genome) can be obtained by conducting a nucleic acid amplification reaction with the use of the set of random primers while prescribing the concentration thereof to 4 to 200 microM in a reaction solution and genomic DNA as a template. With the use of the set of random primers by prescribing the concentration thereof to 4 to 200 microM in a reaction solution, a nucleic acid amplification reaction can be performed with very high reproducibility. According to the nucleic acid amplification reaction, specifically, many amplified fragments (primarily derived from the nuclear genome) can be obtained while achieving very high reproducibility. Accordingly, such many amplified fragments can be used for a DNA library in genetic analysis targeting genomic DNA (primarily the nuclear genome).

By performing a nucleic acid amplification reaction with the use of the set of random primers and prescribing the concentration thereof in a reaction solution to 4 to 200 microM, in particular, many amplified fragments comprising about 100 to 500 bases can be obtained with the use of genomic DNA (primarily the nuclear genome) as a template. Such many amplified fragments comprising about 100 to 500 bases are suitable for mass analysis of nucleotide sequences with the use of, for example, a next-generation sequencer, and highly accurate sequence information can thus be obtained. Specifically, a DNA library, including DNA fragments comprising about 100 to 500 bases primarily derived from the nuclear genome, can be prepared.

By performing a nucleic acid amplification reaction with the use of the set of random primers and prescribing the concentration thereof to 4 to 200 microM in a reaction solution, in particular, the entire genomic DNA (primarily the nuclear genome) can be uniformly amplified. In other words, amplified DNA fragments are not obtained from a particular region of genomic DNA by the nucleic acid amplification reaction with the use of such random primers, but amplified fragments are obtained from the entire nuclear genome. Specifically, a DNA library can be prepared uniformly across the entire nuclear genome.

After the nucleic acid amplification reaction is performed with the use of the set of random primers described above, the amplified fragments may be subjected to restriction enzyme treatment, size selection, sequence capturing, or other processing. Thus, a particular amplified fragment (i.e., a fragment having a particular restriction enzyme site, an amplified fragment of a particular size, or an amplified fragment comprising a particular sequence) can be obtained from among the resulting amplified fragments. Particular amplified fragments obtained as a result of such various types of processing can be used as a DNA library.

Method of Genomic DNA Analysis

With the use of the DNA library prepared in the manner described above, analysis of genomic DNA, such as genotyping, can be performed. As described above, the DNA library has very high reproducibility, the size of which is suitable for a next-generation sequencer, and it is uniform across the entire genome. Accordingly, the DNA library can be used as a DNA marker (it is also referred to as a genetic marker or a gene marker). The term "DNA marker" used herein refers to a characteristic nucleotide sequence existing in the genomic DNA in a broad sense. A DNA marker can be a nucleotide sequence in the genome serving as a marker associated with genetic traits. A DNA marker can be used for, for example, breeding comprising a step of selection with the use of genotype identification, linkage maps, gene mapping, or a marker, back crossing with the use of a marker, quantitative trait locus mapping, bulked segregant analysis, variety identification, or discontinuous imbalance mapping.

For example, a next-generation sequencer or the like may be used to determine the nucleotide sequence of the DNA library prepared in the manner described above, and the presence or absence of a DNA marker can be determined on the basis of the determined nucleotide sequence.

For example, the presence or absence of a DNA marker can be determined on the basis of the number of reads of the nucleotide sequence. While a next-generation sequencer is not particularly limited, such sequencer is also referred to as a second-generation sequencer, and such sequencer is an apparatus for nucleotide sequencing that is capable of simultaneous determination of nucleotide sequences of several tens of millions of DNA fragments. A sequencing principle of the next-generation sequencer is not particularly limited. For example, sequencing can be carried out in accordance with the method in which target DNA is amplified on flow cells and sequencing is carried out while conducting synthesis via bridge PCR and sequencing-by-synthesis or in accordance with emulsion PCR and pyrosequencing in which sequencing is carried out by assaying the amount of pyrophosphoric acids released at the time of DNA synthesis. More specific examples of next-generation sequencers include MiniSeq, MiSeq, NextSeq, HiSeq, and HiSeq X Series (Illumina) and Roche 454 GS FLX sequencers (Roche).

Alternatively, the presence or absence of a DNA marker can be examined by comparing the nucleotide sequences of the DNA library prepared in the manner described above with a reference nucleotide sequence. The term "reference nucleotide sequence" used herein refers to a known sequence serving as a standard. For example, it can be a known sequence stored in a database. Specifically, a DNA library is prepared in the manner described above concerning a particular organism, the nucleotide sequences thereof are determined, and the nucleotide sequences of the DNA library is compared with the reference nucleotide sequence. Nucleotide sequences that differ from the reference nucleotide sequence can be designated as the DNA markers concerning the particular organism (i.e., characteristic nucleotide sequences existing in genomic DNA). The identified DNA markers can further be analyzed in accordance with a conventional technique, so that relevancy in genetic traits (phenotypes) can be determined. From among the DNA markers identified in the manner described above, specifically, DNA marker associated with phenotypes (occasionally referred to as "selection markers") can be identified.

Alternatively, the presence or absence of a DNA marker can be examined by comparing the nucleotide sequences of the DNA library prepared in the manner described above with a nucleotide sequence of the DNA library prepared with the use of genomic DNA derived from another organism or genomic DNA derived from another tissue. Specifically, DNA libraries of two or more organisms or two different tissues are prepared in the manner described above, the nucleotide sequences are determined, and the nucleotide sequences of a DNA library are compared with the nucleotide sequences of another DNA library. Nucleotide sequences that differ between DNA libraries can be designated as DNA markers associated with the organisms or tissues examined (i.e., characteristic nucleotide sequences existing in the genomic DNA). The identified DNA markers can further be analyzed in accordance with conventional techniques, so that relevancy in genetic traits (phenotypes) can be determined. From among the DNA markers identified in the manner described above, specifically, DNA markers associated with phenotypes (occasionally referred to as "selection markers") can be identified.

A pair of primers that specifically amplify the DNA marker of interest may be designed on the basis of the determined nucleotide sequence. With the use of the designed pair of primers, nucleic acid amplification reactions may be carried out using genomic DNA extracted from the target organism as a template. Thus, the presence or absence of a DNA marker in the extracted genomic DNA can be determined.

Alternatively, the DNA library prepared in the manner described above can be used for metagenomic analysis aimed at investigation of diversity of microorganisms, analysis of somatic genome mutation of tumor tissues, genotype analysis using microarrays, evaluation of ploidy, calculation of the number of chromosomes, analysis of an increase or a decrease in chromosomes, analysis of partial insertion, deletion, replication, and translocation of chromosomes, analysis of inclusion of a foreign genome, parental diagnosis, or purity analysis of crossed seeds.

Application to Next-Generation Sequencing Technique

A nucleic acid amplification reaction is carried out with the use of the set of random primers while adjusting the concentration of the random primers at high level in the reaction solution, as described above. Thus, many amplified fragments can be obtained with the use of genomic DNA as a template with high reproducibility. Since the amplified fragments have nucleotide sequences same as those of the random primers at the both ends, next-generation sequencing can be easily carried out with the use of such nucleotide sequences.

Specifically, a nucleic acid amplification reaction is first carried out in a reaction solution containing genomic DNA and random primers at high concentration (the first reaction solution), and many amplified fragments (the first DNA fragments) are obtained by the nucleic acid amplification reaction using genomic DNA as a template. Subsequently, a nucleic acid amplification reaction is carried out in a reaction solution containing the many amplified fragments (the first DNA fragments) and primers designed based on the nucleotide sequences of the random primers (referred to as "primers for the next-generation sequencer") (the second reaction solution). The primers for the next-generation sequencer are bases containing regions used for nucleotide sequence determination. More specifically, the nucleotide sequence at the 3' terminus of the primer for the next-generation sequencer can be, for example, a nucleotide sequence exhibiting 70% or higher, preferably 80% or higher, more preferably 90% or higher, further preferably 95% or higher, still further preferably 97% or higher, and most preferably 100% identity to the nucleotide sequence at the 5' terminus of the first DNA fragment, which comprises a region necessary for nucleotide sequence determination (sequencing) using a next-generation sequencer.

A "region used for nucleotide sequence determination" included in the primer for the next-generation sequencer is not particularly limited since it differs depending on a type of next-generation sequencer. When a next-generation sequencer executes nucleotide sequence determination using a primer for sequencing, for example, a nucleotide sequence complementary to the nucleotide sequence of the primer for sequencing can be used. When a next-generation sequencer executes nucleotide sequence determination using capture beads to which a particular DNA has bound, a "region used for nucleotide sequence determination" can be a nucleotide sequence complementary to the nucleotide sequence of DNA that has bound to the capture beads. When a next-generation sequencer reads a sequence based on a current change when a DNA strand comprising a hairpin loop at its terminus passes through a protein comprising nano-sized pores, the "region used for nucleotide sequence determination" can be a nucleotide sequence complementary to a nucleotide sequence forming the hairpin loop.

By designing the nucleotide sequence at the 3' terminus of the primer for the next-generation sequencer as described above, the primer for the next-generation sequencer can hybridize to the 3' terminus of the first DNA fragment under stringent conditions, and the second DNA fragment can be amplified using the first DNA fragment as a template. Under stringent conditions, a so-called specific hybrid is formed, but a non-specific hybrid is not formed. Stringent conditions can be adequately determined with reference to, for example, Molecular Cloning: A Laboratory Manual (Third Edition). Specifically, a degree of stringency can be determined in terms of temperature and salt concentration of a reaction solution at the time of Southern hybridization. More specifically, it can be determined in terms of temperature and salt concentration of a reaction solution in the step of washing in Southern hybridization. Under stringent conditions, further specifically, sodium concentration is 25 to 500 mM, and preferably 25 to 300 mM, and temperature is 42 degrees C. to 68 degrees C., and preferably 42 degrees C. to 65 degrees C. Still further specifically, hybridization is carried out in the presence of 5× SSC (83 mM NaCl, 83 mM sodium citrate) at 42 degrees C.

When the first DNA fragment is obtained using the set of random primers described above, in particular, primers for the next-generation sequencer corresponding to all of the random primers may be prepared, or primers for the next-generation sequencer corresponding to some of the random primers may be prepared.

When the set of random primers of the present invention includes a plurality of types of random primers, in particular, such primers comprise nucleotide sequences that are common thereamong, except for several (e.g., 1 to 3) bases at the 3' terminus. Thus, all the 5' termini of many first DNA fragments are of the same sequences. The nucleotide sequence at the 3' terminus of the primer for the next-generation sequencer is designed to exhibit 70% or higher, preferably 80% or higher, more preferably 90% or higher, and most preferably 100% identity to the nucleotide sequence that is common at the 5' terminus of the first DNA fragment. By designing the primers for the next-generation sequencer in such a manner, the resulting primers for the next-generation sequencer are corresponding to all the random primers. With the use of the resulting primers for the next-generation sequencer, the second DNA fragment can be amplified using all the first DNA fragments as templates.

Also, the set of random primers of the present invention comprises common nucleotide sequences other than 2 or 3 bases at the 3' terminus of a plurality of random primers. The second DNA fragment can be obtained using some of many first DNA fragments as templates. Specifically, the nucleotide sequence at the 3' terminus of the primer for the next-generation sequencer is designed to exhibit 70% or higher, preferably 80% or higher, more preferably 90% or higher, and most preferably 100% identity to the common nucleotide sequence at the 5' terminus of the first DNA fragment and a sequence of 1 to 3 bases adjacent thereto, so that the second DNA fragment can be amplified using some first DNA fragments as templates.

As described above, the second DNA fragment amplified using the primers for the next-generation sequencer has a region necessary for nucleotide sequence determination (sequencing) using a next-generation sequencer included in the primers for the next-generation sequencer. A region necessary for sequencing is not particularly limited because it varies depending on a next-generation sequencer. When a next-generation sequencer based on the principle such that target DNA is amplified on a flow cell via bridge PCR and sequencing-by-synthesis and sequencing is carried out by synthesis is used, for example, the primers for the next-generation sequencer would comprise a region necessary for bridge PCR and a region necessary for sequencing-by-synthesis. A region necessary for bridge PCR hybridizes to an oligonucleotide immobilized on a flow cell, which comprises 9 bases including the 5' terminus of the primer for the next-generation sequencer. A primer used for sequencing hybridizes to a region necessary for sequencing-by-synthesis, which is located in the middle of the primer for the next-generation sequencer.

An example of a next-generation sequencer is the Ion Torrent sequencer. When the Ion Torrent sequencer is used, the primer for the next-generation sequencer comprises a so-called ion adaptor at the 5' terminus, and it binds to a particle that executes emulsion PCR. With the use of the Ion Torrent sequencer, sequencing is performed by mounting particles coated with a template amplified via emulsion PCR on the ion chip.

A nucleic acid amplification reaction using the second reaction solution containing the primers for the next-generation sequencer and the first DNA can be carried out under general conditions without particular limitation. Specifically, the conditions described in the section [Nucleic acid amplification reaction] above can be adopted. For example, the second reaction solution contains the first DNA fragment as a template, the primers for the next-generation sequencer described above, DNA polymerase, deoxynucleotide triphosphates as a substrate (i.e., dNTP, which is a mixture of dATP, dCTP, dTTP, and dGTP), and a buffer.

The concentration of the primer for the next-generation sequencer can be 0.01 to 5.0 microM, preferably 0.1 to 2.5 microM, and most preferably 0.3 to 0.7 microM.

The amount of the first DNA fragment used in the nucleic acid amplification reaction as a template is not particularly limited. When the amount of the reaction solution is 50 microliters, such amount is preferably 0.1 to 1000 ng, more preferably 1 to 500 ng, further preferably 5 to 200 ng, and most preferably 10 to 100 ng.

A method for preparing the first DNA fragment as a template is not particularly limited. The reaction solution after the completion of the nucleic acid amplification reaction using the set of random primers described above may be used in that state, or the reaction solution from which the first DNA fragment has been purified may be used.

A type of DNA polymerase used in a nucleic acid amplification reaction, concentration of deoxynucleotide triphosphate as a substrate (i.e., dNTP, which is a mixture of dATP, dCTP, dTTP, and dGTP), a buffer composition, and thermal cycling conditions as described in the section [Nucleic acid amplification reaction] can be adopted. Also, a nucleic acid amplification reaction involving the use of the primers for the next-generation sequencer may be performed by the hot start method, or an amplified fragment may be obtained by the nucleic acid amplification reaction.

With the use of the first DNA fragment obtained using a set of random primers as a template and the second DNA fragment amplified using the primers for the next-generation sequencer, as described above, a DNA library applicable to a next-generation sequencer can be prepared in a convenient manner.

In the examples described above, the DNA library was prepared using the first DNA fragment obtained with the use of a set of random primers as a template and the second DNA fragment amplified using the primers for the next-generation sequencer. It should be noted that the technical scope of the present invention is not limited to such examples. For example, the first DNA fragment obtained with the use of a set of random primers is used as a template to amplify the second DNA fragment, the third DNA fragment is obtained using the second DNA fragment as a template and the primers for the next-generation sequencer, the third DNA fragment is obtained using the primers for the next-generation sequencer, and the resulting third DNA fragment may be designated as the DNA library applicable to the next-generation sequencer.

A DNA library applicable to the next-generation sequencer can be prepared by performing a nucleic acid amplification reaction using the second DNA fragment as a template, repeating a nucleic acid amplification reaction using the resulting DNA fragment as a template, and performing the final nucleic acid amplification reaction with the use of the primers for the next-generation sequencer. In such a case, the number of repetition of the nucleic acid amplification reactions is not particularly limited, and the nucleic acid amplification reactions is repeated 2 to 10 times, preferably 2 to 5 times, and more preferably 2 or 3 times.

As described above, amplification of DNA fragments derived from the chloroplast genome can be suppressed to a significant extent in the nucleic acid amplification reaction performed with the use of the set of random primers of the present invention at high concentration and genomic DNA as a template. Accordingly, the second DNA fragment obtained as described above is primarily derived from the nuclear genome. In general, the copy number of the chloroplast genome is as large as several tens to several hundreds per cell, and it is highly likely that large quantities of a particular region are amplified as a result of nucleic acid amplification reaction. According to the analysis involving the use of a next-generation sequencer as described above, the presence of particular amplicons in large quantities would affect the preparation of a calculation formula for nucleotide sequence identification (i.e., the matrix), and the accuracy for nucleotide sequence identification would deteriorate. Also, the recommended redundancy of the read data is approximately several tens, and large quantities of overlapping data would result in data loss. When the analyzed nucleotide sequence data is subjected to the genomic analysis described above, also, the read data of the chloroplast genome are unnecessary.

With the use of the set of random primers of the present invention, as described above, the amount of amplicons derived from the chloroplast genome can be reduced in the analysis involving the use of the next-generation sequencer. Thus, the nuclear genome can be analyzed with excellent accuracy.

EXAMPLES

Hereafter, the present invention is described in greater detail with reference to the following examples, although the technical scope of the present invention is not limited to these examples.

Example 1

1. Flow Chart

In this example, a DNA library was prepared via PCR using genomic DNAs extracted from various types of organism species as templates and various sets of random primers in accordance with the flow chart shown in FIG. 1. With the use of the prepared DNA library, also, sequence analysis was performed with the use of a so-called next-generation sequencer, and the genotype was analyzed based on the read data.

2. Materials

In this example, genomic DNAs were extracted from the sugarcane varieties NiF8 and Ni9, 22 hybrid progeny lines thereof, and the rice variety Nipponbare using the DNeasy Plant Mini kit (QIAGEN), and the extracted genomic DNAs were purified. The purified genomic DNAs were used as NiF8-derived genomic DNA, Ni9-derived genomic DNA, 22 hybrid sugarcane progeny-derived genomic DNAs, and Nipponbare-derived genomic DNA, respectively. In this example, human genomic DNA was purchased from Takara-Bio and used as human-derived genomic DNA.

3. Method 3.1 Correlation Between PCR Condition and DNA Fragment Size 3.1.1 Random Primer Designing In order to design random primers, GC content was set between 20% and 70%, and the number of continuous bases was adjusted to 5 or fewer. Sequence length was set at 16 levels (i.e., sequences of 8, 9, 10, 11, 12, 14, 16, 18, 20, 22, 24, 26, 28, 29, 30, and 35 bases). For each sequence length, 96 types of nucleotide sequences were designed, and 96 sets of random primers were prepared. Concerning 10-base primers, 6 sets of random primers each comprising 96 types of random primers were designed (these 6 sets are referred to as "10-base primer A" to "10-base primer F," respectively). In this example, specifically, 21 different sets of random primers were prepared.

Tables 3 to 23 show nucleotide sequences of random primers contained in such 21 different sets of random primers.

TABLE 3

List of random primers (10-base primers A)

| No | Primer sequence | SEQ ID NO: |
|---|---|---|
| 1 | AGACGTCGTT | 1 |
| 2 | GAGGCGATAT | 2 |
| 3 | GTGCGAACGT | 3 |
| 4 | TTATACTGCC | 4 |
| 5 | CAAGTTCGCA | 5 |
| 6 | ACAAGGTAGT | 6 |
| 7 | ACACAGCGAC | 7 |
| 8 | TTACCGATGT | 8 |
| 9 | CACAGAGTCG | 9 |
| 10 | TTCAGCGCGT | 10 |
| 11 | AGGACCGTGA | 11 |
| 12 | GTCTGTTCGC | 12 |
| 13 | ACCTGTCCAC | 13 |
| 14 | CCGCAATGAC | 14 |
| 15 | CTGCCGATCA | 15 |
| 16 | TACACGGAGC | 16 |
| 17 | CCGCATTCAT | 17 |
| 18 | GACTCTAGAC | 18 |
| 19 | GGAGAACTTA | 19 |
| 20 | TCCGGTATGC | 20 |
| 21 | GGTCAGGAGT | 21 |
| 22 | ACATTGGCAG | 22 |
| 23 | CGTAGACTGC | 23 |
| 24 | AGACTGTACT | 24 |
| 25 | TAGACGCAGT | 25 |
| 26 | CCGATAATCT | 26 |
| 27 | GAGAGCTAGT | 27 |
| 28 | GTACCGCGTT | 28 |
| 29 | GACTTGCGCA | 29 |
| 30 | CGTGATTGCG | 30 |
| 31 | ATCGTCTCTG | 31 |
| 32 | CGTAGCTACG | 32 |
| 33 | GCCGAATAGT | 33 |
| 34 | GTACCTAGGC | 34 |
| 35 | GCTTACATGA | 35 |
| 36 | TCCACGTAGT | 36 |

TABLE 3-continued

List of random primers (10-base primers A)

| No | Primer sequence | SEQ ID NO: |
|---|---|---|
| 37 | AGAGGCCATC | 37 |
| 38 | CGGTGATGCT | 38 |
| 39 | CACTGTGCTT | 39 |
| 40 | CATGATGGCT | 40 |
| 41 | GCCACACATG | 41 |
| 42 | CACACACTGT | 42 |
| 43 | CAGAATCATA | 43 |
| 44 | ATCGTCTACG | 44 |
| 45 | CGAGCAATAC | 45 |
| 46 | ACAAGCGCAC | 46 |
| 47 | GCTTAGATGT | 47 |
| 48 | TGCATTCTGG | 48 |
| 49 | TGTCGGACCA | 49 |
| 50 | AGGCACTCGT | 50 |
| 51 | CTGCATGTGA | 51 |
| 52 | ACCACGCCTA | 52 |
| 53 | GAGGTCGTAC | 53 |
| 54 | AATACTCTGT | 54 |
| 55 | TGCCAACTGA | 55 |
| 56 | CCTGTTCGGT | 56 |
| 57 | GTAGAGAGTT | 57 |
| 58 | TACAGCGTAA | 58 |
| 59 | TGACGTGATG | 59 |
| 60 | AGACGTCGGT | 60 |
| 61 | CGCTAGGTTC | 61 |
| 62 | GCCTTATAGC | 62 |
| 63 | CCTTCGATCT | 63 |
| 64 | AGGCAACGTG | 64 |
| 65 | TGAGCGGTGT | 65 |
| 66 | GTGTCGAACG | 66 |
| 67 | CGATGTTGCG | 67 |
| 68 | AACAAGACAC | 68 |
| 69 | GATGCTGGTT | 69 |
| 70 | ACCGGTAGTC | 70 |
| 71 | GTGACTAGCA | 71 |
| 72 | AGCCTATATT | 72 |
| 73 | TCGTGAGCTT | 73 |
| 74 | ACACTATGGC | 74 |

TABLE 3-continued

List of random primers (10-base primers A)

| No | Primer sequence | SEQ ID NO: |
|---|---|---|
| 75 | GACTCTGTCG | 75 |
| 76 | TCGATGATGC | 76 |
| 77 | CTTGGACACT | 77 |
| 78 | GGCTGATCGT | 78 |
| 79 | ACTCACAGGC | 79 |
| 80 | ATGTGCGTAC | 80 |
| 81 | CACCATCGAT | 81 |
| 82 | AGCCATTAAC | 82 |
| 83 | AATCGACTGT | 83 |
| 84 | AATACTAGCG | 84 |
| 85 | TCGTCACTGA | 85 |
| 86 | CAGGCTCTTA | 86 |
| 87 | GGTCGGTGAT | 87 |
| 88 | CATTAGGCGT | 88 |
| 89 | ACTCGCGAGT | 89 |
| 90 | TTCCGAATAA | 90 |
| 91 | TGAGCATCGT | 91 |
| 92 | GCCACGTAAC | 92 |
| 93 | GAACTACATG | 93 |
| 94 | TCGTGAGGAC | 94 |
| 95 | GCGGCCTTAA | 95 |
| 96 | GCTAAGGACC | 96 |

TABLE 4

List of random primers (10-base primers B)

| No | Primer sequence | SEQ ID NO: |
|---|---|---|
| 1 | ATAGCCATTA | 97 |
| 2 | CAGTAATCAT | 98 |
| 3 | ACTCCTTAAT | 99 |
| 4 | TCGAACATTA | 100 |
| 5 | ATTATGAGGT | 101 |
| 6 | AATCTTAGAG | 102 |
| 7 | TTAGATGATG | 103 |
| 8 | TACATATCTG | 104 |
| 9 | TCCTTAATCA | 105 |
| 10 | GTTGAGATTA | 106 |
| 11 | TGTTAACGTA | 107 |

TABLE 4-continued

List of random primers (10-base primers B)

| No | Primer sequence | SEQ ID NO: |
|---|---|---|
| 12 | CATACAGTAA | 108 |
| 13 | CTTATACGAA | 109 |
| 14 | AGATCTATGT | 110 |
| 15 | AAGACTTAGT | 111 |
| 16 | TGCGCAATAA | 112 |
| 17 | TTGGCCATAT | 113 |
| 18 | TATTACGAGG | 114 |
| 19 | TTATGATCGC | 115 |
| 20 | AACTTAGGAG | 116 |
| 21 | TCACAATCGT | 117 |
| 22 | GAGTATATGG | 118 |
| 23 | ATCAGGACAA | 119 |
| 24 | GTACTGATAG | 120 |
| 25 | CTTATACTCG | 121 |
| 26 | TAACGGACTA | 122 |
| 27 | GCGTTGTATA | 123 |
| 28 | CTTAAGTGCT | 124 |
| 29 | ATACGACTGT | 125 |
| 30 | ACTGTTATCG | 126 |
| 31 | AATCTTGACG | 127 |
| 32 | ACATCACCTT | 128 |
| 33 | GGTATAGTAC | 129 |
| 34 | CTAATCCACA | 130 |
| 35 | GCACCTTATT | 131 |
| 36 | ATTGACGGTA | 132 |
| 37 | GACATATGGT | 133 |
| 38 | GATAGTCGTA | 134 |
| 39 | CAATTATCGC | 135 |
| 40 | CTTAGGTGAT | 136 |
| 41 | CATACTACTG | 137 |
| 42 | TAACGCGAAT | 138 |
| 43 | CAAGTTACGA | 139 |
| 44 | AATCTCAAGG | 140 |
| 45 | GCAATCATCA | 141 |
| 46 | TGTAACGTTC | 142 |
| 47 | TATCGTTGGT | 143 |
| 48 | CGCTTAAGAT | 144 |
| 49 | TTAGAACTGG | 145 |
| 50 | GTCATAACGT | 146 |
| 51 | AGAGCAGTAT | 147 |
| 52 | CAACATCACT | 148 |
| 53 | CAGAAGCTTA | 149 |
| 54 | AACTAACGTG | 150 |
| 55 | TTATACCGCT | 151 |
| 56 | GAATTCGAGA | 152 |
| 57 | TTACGTAACC | 153 |
| 58 | GCATGGTTAA | 154 |
| 59 | GCACCTAATT | 155 |
| 60 | TGTAGGTTGT | 156 |
| 61 | CCATCTGGAA | 157 |
| 62 | TTCGCGTTGA | 158 |
| 63 | AACCGAGGTT | 159 |
| 64 | GTACGCTGTT | 160 |
| 65 | AGTATCCTGG | 161 |
| 66 | GGTTGTACAG | 162 |
| 67 | ACGTACACCA | 163 |
| 68 | TGTCGAGCAA | 164 |
| 69 | GTCGTGTTAC | 165 |
| 70 | GTGCAATAGG | 166 |
| 71 | ACTCGATGCT | 167 |
| 72 | GAATCGCGTA | 168 |
| 73 | CGGTCATTGT | 169 |
| 74 | ATCAGGCGAT | 170 |
| 75 | GTAAGATGCG | 171 |
| 76 | GGTCTCTTGA | 172 |
| 77 | TCCTCGCTAA | 173 |
| 78 | CTGCGTGATA | 174 |
| 79 | CATACTCGTC | 175 |
| 80 | ATCTGAGCTC | 176 |
| 81 | ACGGATAGTG | 177 |
| 82 | ACTGCAATGC | 178 |
| 83 | TAACGACGTG | 179 |
| 84 | TAGACTGTCG | 180 |
| 85 | CAGCACTTCA | 181 |
| 86 | AACATTCGCC | 182 |
| 87 | ACTAGTGCGT | 183 |

TABLE 4-continued

List of random primers (10-base primers B)

| No | Primer sequence | SEQ ID NO: |
|---|---|---|
| 88 | ACGCTGTTCT | 184 |
| 89 | CGTCGAATGC | 185 |
| 90 | CTCTGACGGT | 186 |
| 91 | GTCGCCATGT | 187 |
| 92 | GGTCCACGTT | 188 |
| 93 | CGAGCGACTT | 189 |
| 94 | TTGACGCGTG | 190 |
| 95 | CTGAGAGCCT | 191 |
| 96 | CGCGCTAACT | 192 |

TABLE 5

List of random primers (10-base primers C)

| No | Primer sequence | SEQ ID NO: |
|---|---|---|
| 1 | GGTCGTCAAG | 193 |
| 2 | AGGTTGACCA | 194 |
| 3 | TAACGGCAAC | 195 |
| 4 | GAGGCTGGAT | 196 |
| 5 | GTGCACACCT | 197 |
| 6 | TGAGGACCAG | 198 |
| 7 | TACTTGCGAG | 199 |
| 8 | AACTGTGAGA | 200 |
| 9 | CTCCATCAAC | 201 |
| 10 | CGGACTGTTA | 202 |
| 11 | TAGGACAGTC | 203 |
| 12 | AGAGGACACA | 204 |
| 13 | ACATTCGCGG | 205 |
| 14 | GCTTACTGCA | 206 |
| 15 | CAATACGTAA | 207 |
| 16 | AGACTTGCGC | 208 |
| 17 | GAGCGGTGTT | 209 |
| 18 | CGTGAGAGGT | 210 |
| 19 | AATCCGTCAG | 211 |
| 20 | ATACGTACCG | 212 |
| 21 | AACTGATTCC | 213 |
| 22 | CTGAGCGTAC | 214 |
| 23 | GTCGGATTCG | 215 |
| 24 | GCCGACCATA | 216 |
| 25 | GCAGAACTAA | 217 |
| 26 | CTAACGACCG | 218 |
| 27 | GCTGGACCAT | 219 |
| 28 | GACGCGGTTA | 220 |
| 29 | AGTGGTGAGC | 221 |
| 30 | CAGGCAGTCA | 222 |
| 31 | TCTGACGTCA | 223 |
| 32 | TACATGACGT | 224 |
| 33 | TGAGGCAACC | 225 |
| 34 | CAACTGCAGT | 226 |
| 35 | CGGAGATACG | 227 |
| 36 | CTTCGCAAGT | 228 |
| 37 | CTGGCATACG | 229 |
| 38 | TAACGTTCGC | 230 |
| 39 | CCGGCGTTAA | 231 |
| 40 | ACAAGACGCC | 232 |
| 41 | CCATTAGACT | 233 |
| 42 | GTCTGTGACA | 234 |
| 43 | GGCATTGGAC | 235 |
| 44 | TCTTCGCACG | 236 |
| 45 | TAGCCTGTGC | 237 |
| 46 | CACTGACCTA | 238 |
| 47 | CCGCACGATT | 239 |
| 48 | ATAGCACACG | 240 |
| 49 | GCACGTCATA | 241 |
| 50 | AAGCCGTTGG | 242 |
| 51 | CGGACCGTTA | 243 |
| 52 | TACACAGCGT | 244 |
| 53 | CGGACTTCAG | 245 |
| 54 | TAGAACGTCA | 246 |
| 55 | GGCATTGGAG | 247 |
| 56 | GGCACTCGTT | 248 |
| 57 | GTACCGTTAA | 249 |
| 58 | AATACGTGTC | 250 |
| 59 | CCATTGACGT | 251 |
| 60 | CGTGAATCGC | 252 |
| 61 | ATCAACGCGG | 253 |
| 62 | CGCCAAGGTA | 254 |
| 63 | AGAAGACGCC | 255 |

TABLE 5-continued

List of random primers (10-base primers C)

| No | Primer sequence | SEQ ID NO: |
|---|---|---|
| 64 | CCGCATAGTC | 256 |
| 65 | CTTATATGTG | 257 |
| 66 | GGTCTCATCG | 258 |
| 67 | CCACCATGTC | 259 |
| 68 | ACGAATGTGT | 260 |
| 69 | GGTAGTAACA | 261 |
| 70 | GCCACTTAAT | 262 |
| 71 | ATATTGCGCC | 263 |
| 72 | GACCAATAGT | 264 |
| 73 | AACAACACGG | 265 |
| 74 | ATAGCCGATG | 266 |
| 75 | CGAGAGCATA | 267 |
| 76 | CGAGACATGA | 268 |
| 77 | CGCCAAGTTA | 269 |
| 78 | TTATAATCGC | 270 |
| 79 | TAGAAGTGCA | 271 |
| 80 | GGAGGCATGT | 272 |
| 81 | GCCACTTCGA | 273 |
| 82 | TCCACGGTAC | 274 |
| 83 | CAACTATGCA | 275 |
| 84 | CAAGGAGGAC | 276 |
| 85 | GAGGTACCTA | 277 |
| 86 | GAGCGCATAA | 278 |
| 87 | TCGTCACGTG | 279 |
| 88 | AACTGTGACA | 280 |
| 89 | TCCACGTGAG | 281 |
| 90 | ACACTGCTCT | 282 |
| 91 | TACGGTGAGC | 283 |
| 92 | CGGACTAAGT | 284 |
| 93 | AAGCCACGTT | 285 |
| 94 | CAATTACTCG | 286 |
| 95 | TCTGGCCATA | 287 |
| 96 | TCAGGCTAGT | 288 |

TABLE 6

List of random primers (10-base primers D)

| No | Primer sequence | SEQ ID NO: |
|---|---|---|
| 1 | TTGACCCGGA | 289 |
| 2 | TTTTTATGGT | 290 |
| 3 | ATGTGGTGCG | 291 |
| 4 | AAGGCGCTAG | 292 |
| 5 | TCCAACTTTG | 293 |
| 6 | CCATCCCATC | 294 |
| 7 | CAATACGAGG | 295 |
| 8 | GAGTGTTACC | 296 |
| 9 | GCCTCCTGTA | 297 |
| 10 | CGAAGGTTGC | 298 |
| 11 | GAGGTGCTAT | 299 |
| 12 | TAGGATAATT | 300 |
| 13 | CGTTGTCCTC | 301 |
| 14 | TGAGACCAGC | 302 |
| 15 | TGCCCAAGCT | 303 |
| 16 | TACTGAATCG | 304 |
| 17 | TTACATAGTC | 305 |
| 18 | ACAAAGGAAA | 306 |
| 19 | CTCGCTTGGG | 307 |
| 20 | CCTTGCGTCA | 308 |
| 21 | TAATTCCGAA | 309 |
| 22 | GTGAGCTTGA | 310 |
| 23 | ATGCCGATTC | 311 |
| 24 | GCTTGGGCTT | 312 |
| 25 | ACAAAGCGCC | 313 |
| 26 | GAAAGCTCTA | 314 |
| 27 | TACCGACCGT | 315 |
| 28 | TCGAAGAGAC | 316 |
| 29 | GTCGCTTACG | 317 |
| 30 | GGGCTCTCCA | 318 |
| 31 | GCGCCCTTGT | 319 |
| 32 | GGCAATAGGC | 320 |
| 33 | CAAGTCAGGA | 321 |
| 34 | GGGTCGCAAT | 322 |
| 35 | CAGCAACCTA | 323 |
| 36 | TTCCCGCCAC | 324 |
| 37 | TGTGCATTTT | 325 |
| 38 | ATCAACGACG | 326 |

TABLE 6-continued

List of random primers (10-base primers D)

| No | Primer sequence | SEQ ID NO: |
|---|---|---|
| 39 | GTGACGTCCA | 327 |
| 40 | CGATCTAGTC | 328 |
| 41 | TTACATCCTG | 329 |
| 42 | AGCCTTCAAT | 330 |
| 43 | TCCATCCGAT | 331 |
| 44 | GACTGGGTCT | 332 |
| 45 | TTCGGTGGAG | 333 |
| 46 | GACCAGCACA | 334 |
| 47 | CATTAACGGA | 335 |
| 48 | TTTTTCTTGA | 336 |
| 49 | CATTGCACTG | 337 |
| 50 | TGCGGCGATC | 338 |
| 51 | ATATTGCGGT | 339 |
| 52 | GACGTCGCTC | 340 |
| 53 | TCGCTTATCG | 341 |
| 54 | GCGCAGACAC | 342 |
| 55 | CATGTATTGT | 343 |
| 56 | TCTATAACCT | 344 |
| 57 | GTGGAGACAA | 345 |
| 58 | CGAAGATTAT | 346 |
| 59 | TAGCAACTGC | 347 |
| 60 | ATAATCGGTA | 348 |
| 61 | CAGGATGGGT | 349 |
| 62 | GACGATTCCC | 350 |
| 63 | CACGCCTTAC | 351 |
| 64 | AGTTGGTTCC | 352 |
| 65 | TCTTATCAGG | 353 |
| 66 | CGAGAAGTTC | 354 |
| 67 | GTGGTAGAAT | 355 |
| 68 | TAGGCTTGTG | 356 |
| 69 | ATGCGTTACG | 357 |
| 70 | ACTACCGAGG | 358 |
| 71 | CGAGTTGGTG | 359 |
| 72 | GGACGATCAA | 360 |
| 73 | AACAGTATGC | 361 |
| 74 | TTGGCTGATC | 362 |
| 75 | AGGATTGGAA | 363 |
| 76 | CATATGGAGA | 364 |

TABLE 6-continued

List of random primers (10-base primers D)

| No | Primer sequence | SEQ ID NO: |
|---|---|---|
| 77 | CTGCAGGTTT | 365 |
| 78 | CTCTCTTTTT | 366 |
| 79 | AGTAGGGGTC | 367 |
| 80 | ACACCGCAAG | 368 |
| 81 | GAAGCGGGAG | 369 |
| 82 | GATACGGACT | 370 |
| 83 | TACGACGTGT | 371 |
| 84 | GTGCCTCCTT | 372 |
| 85 | GGTGACTGAT | 373 |
| 86 | ATATCTTACG | 374 |
| 87 | AATCATACGG | 375 |
| 88 | CTCTTGGGAC | 376 |
| 89 | GACGACAAAT | 377 |
| 90 | GTTGCGAGGT | 378 |
| 91 | AAACCGCACC | 379 |
| 92 | GCTAACACGT | 380 |
| 93 | ATCATGAGGG | 381 |
| 94 | GATTCACGTA | 382 |
| 95 | TCTCGAAAAG | 383 |
| 96 | CTCGTAACCA | 384 |

TABLE 7

List of random primers (10-base primers E)

| No | Primer sequence | SEQ ID NO: |
|---|---|---|
| 1 | GTTACACACG | 385 |
| 2 | CGTGAAGGGT | 386 |
| 3 | ACGAGCATCT | 387 |
| 4 | ACGAGGGATT | 388 |
| 5 | GCAACGTCGG | 389 |
| 6 | CACGGCTAGG | 390 |
| 7 | CGTGACTCTC | 391 |
| 8 | TCTAGACGCA | 392 |
| 9 | CTGCGCACAT | 393 |
| 10 | ATGCTTGACA | 394 |
| 11 | TTTGTCGACA | 395 |
| 12 | ACGTGTCAGC | 396 |
| 13 | GAAAACATTA | 397 |
| 14 | ACATTAACGG | 398 |

TABLE 7-continued

List of random primers (10-base primers E)

| No | Primer sequence | SEQ ID NO: |
|---|---|---|
| 15 | GTACAGGTCC | 399 |
| 16 | CTATGTGTAC | 400 |
| 17 | GCGTACATTA | 401 |
| 18 | GATTTGTGGC | 402 |
| 19 | TCGCGCGCTA | 403 |
| 20 | ACAAGGGCGA | 404 |
| 21 | AACGCGCGAT | 405 |
| 22 | CGTAAATGCG | 406 |
| 23 | TAGGCACTAC | 407 |
| 24 | GCGAGGATCG | 408 |
| 25 | CACGTTTACT | 409 |
| 26 | TACCACCACG | 410 |
| 27 | TTAACAGGAC | 411 |
| 28 | GCTGTATAAC | 412 |
| 29 | GTTGCTGGCA | 413 |
| 30 | AGTGTGGCCA | 414 |
| 31 | CTGCGGTTGT | 415 |
| 32 | TAGATCAGCG | 416 |
| 33 | TTCCGGTTAT | 417 |
| 34 | GATAAACTGT | 418 |
| 35 | TACAGTTGCC | 419 |
| 36 | CGATGGCGAA | 420 |
| 37 | CCGACGTCAG | 421 |
| 38 | TATGGTGCAA | 422 |
| 39 | GACGACAGTC | 423 |
| 40 | GTCACCGTCC | 424 |
| 41 | GGTTTTAACA | 425 |
| 42 | GAGGACAGTA | 426 |
| 43 | GTTACCTAAG | 427 |
| 44 | ATCACGTGTT | 428 |
| 45 | TAAGGCCTGG | 429 |
| 46 | TGTTCGTAGC | 430 |
| 47 | TGAGGACGTG | 431 |
| 48 | GTGCTGTGTA | 432 |
| 49 | GAGGGTACGC | 433 |
| 50 | CCGTGATTGT | 434 |
| 51 | AAAATCGCCT | 435 |
| 52 | CGATCGCAGT | 436 |
| 53 | ACGCAATAAG | 437 |
| 54 | AAGGTGCATC | 438 |
| 55 | CGCGTAGATA | 439 |
| 56 | CGAGCAGTGC | 440 |
| 57 | ATACGTGACG | 441 |
| 58 | AGATTGCGCG | 442 |
| 59 | ACGTGATGCC | 443 |
| 60 | GTACGCATCG | 444 |
| 61 | TCCCGACTTA | 445 |
| 62 | GTTTTTACAC | 446 |
| 63 | CCTGAGCGTG | 447 |
| 64 | CGGCATTGTA | 448 |
| 65 | TAGAGTGCGT | 449 |
| 66 | ATGGCCAGAC | 450 |
| 67 | CTTAGCATGC | 451 |
| 68 | ACAACACCTG | 452 |
| 69 | AGTGACTATC | 453 |
| 70 | CATGCTACAC | 454 |
| 71 | AAAGCGGGCG | 455 |
| 72 | AGATCGCCGT | 456 |
| 73 | CGTAGATATT | 457 |
| 74 | AATGGCAGAC | 458 |
| 75 | GTATAACGTG | 459 |
| 76 | ATGTGCGTCA | 460 |
| 77 | CCTGCCAACT | 461 |
| 78 | TTTATAACTC | 462 |
| 79 | ACGGTTACGC | 463 |
| 80 | TAGCCTCTTG | 464 |
| 81 | TCGCGAAGTT | 465 |
| 82 | GTCTACAACC | 466 |
| 83 | GTCTACTGCG | 467 |
| 84 | GTTGCGTCTC | 468 |
| 85 | GGGCCGCTAA | 469 |
| 86 | GTACGTCGGA | 470 |
| 87 | AGCGAGAGAC | 471 |
| 88 | TGGCTACGGT | 472 |
| 89 | AGGCATCACG | 473 |
| 90 | TAGCTCCTCG | 474 |

TABLE 7-continued

List of random primers (10-base primers E)

| No | Primer sequence | SEQ ID NO: |
|---|---|---|
| 91 | GGCTAGTCAG | 475 |
| 92 | CTCACTTTAT | 476 |
| 93 | ACGGCCACGT | 477 |
| 94 | AGCGTATATC | 478 |
| 95 | GACACGTCTA | 479 |
| 96 | GCCAGCGTAC | 480 |

TABLE 8

List of random primers (10-base primers F)

| No | Primer sequence | SEQ ID NO: |
|---|---|---|
| 1 | AACATTAGCG | 481 |
| 2 | AGTGTGCTAT | 482 |
| 3 | CACGAGCGTT | 483 |
| 4 | GTAACGCCTA | 484 |
| 5 | CACATAGTAC | 485 |
| 6 | CGCGATATCG | 486 |
| 7 | CGTTCTGTGC | 487 |
| 8 | CTGATCGCAT | 488 |
| 9 | TGGCGTGAGA | 489 |
| 10 | TTGCCAGGCT | 490 |
| 11 | GTTATACACA | 491 |
| 12 | AGTGCCAACT | 492 |
| 13 | TCACGTAGCA | 493 |
| 14 | TAATTCAGCG | 494 |
| 15 | AAGTATCGTC | 495 |
| 16 | CACAGTTACT | 496 |
| 17 | CCTTACCGTG | 497 |
| 18 | ACGGTGTCGT | 498 |
| 19 | CGCGTAAGAC | 499 |
| 20 | TTCGCACCAG | 500 |
| 21 | CACGAACAGA | 501 |
| 22 | GTTGGACATT | 502 |
| 23 | GGTGCTTAAG | 503 |
| 24 | TCGGTCTCGT | 504 |
| 25 | TCTAGTACGC | 505 |
| 26 | TTAGGCCGAG | 506 |
| 27 | CGTCAAGAGC | 507 |

TABLE 8-continued

List of random primers (10-base primers F)

| No | Primer sequence | SEQ ID NO: |
|---|---|---|
| 28 | ACATGTCTAC | 508 |
| 29 | ATCGTTACGT | 509 |
| 30 | ACGGATCGTT | 510 |
| 31 | AATCTTGGCG | 511 |
| 32 | AGTATCTGGT | 512 |
| 33 | CAACCGACGT | 513 |
| 34 | TGGTAACGCG | 514 |
| 35 | GTGCAGACAT | 515 |
| 36 | GTCTAGTTGC | 516 |
| 37 | CAATTCGACG | 517 |
| 38 | CTTAGCACCT | 518 |
| 39 | TAATGTCGCA | 519 |
| 40 | CAATCGGTAC | 520 |
| 41 | AGCACGCATT | 521 |
| 42 | AGGTCCTCGT | 522 |
| 43 | TTGTGCCTGC | 523 |
| 44 | ACCGCCTGTA | 524 |
| 45 | GTACGTCAGG | 525 |
| 46 | GCACACAACT | 526 |
| 47 | TGAGCACTTA | 527 |
| 48 | GTGCCGCATA | 528 |
| 49 | ATGTTTTCGC | 529 |
| 50 | ACACTTAGGT | 530 |
| 51 | CGTGCCGTGA | 531 |
| 52 | TTACTAATCA | 532 |
| 53 | GTGGCAGGTA | 533 |
| 54 | GCGCGATATG | 534 |
| 55 | GAACGACGTT | 535 |
| 56 | ATCAGGAGTG | 536 |
| 57 | GCCAGTAAGT | 537 |
| 58 | GCAAGAAGCA | 538 |
| 59 | AACTCCGCCA | 539 |
| 60 | ACTTGAGCCT | 540 |
| 61 | CGTGATCGTG | 541 |
| 62 | AATTAGCGAA | 542 |
| 63 | ACTTCCTTAG | 543 |
| 64 | TGTGCTGATA | 544 |
| 65 | AGGCGGCTGA | 545 |

TABLE 8-continued

List of random primers (10-base primers F)

| No | Primer sequence | SEQ ID NO: |
|---|---|---|
| 66 | CGTTTAGAGC | 546 |
| 67 | ACGCGTCTAA | 547 |
| 68 | GCGAATGTAC | 548 |
| 69 | CGTGATCCAA | 549 |
| 70 | CAACCAGATG | 550 |
| 71 | ACCATTAACC | 551 |
| 72 | CGATTCACGT | 552 |
| 73 | CTAGAACCTG | 553 |
| 74 | CCTAACGACA | 554 |
| 75 | GACGTGCATG | 555 |
| 76 | ATGTAACCTT | 556 |
| 77 | GATACAGTCG | 557 |
| 78 | CGTATGTCTC | 558 |
| 79 | AGATTATCGA | 559 |
| 80 | ATACTGGTAA | 560 |
| 81 | GTTGAGTAGC | 561 |
| 82 | ACCATTATCA | 562 |
| 83 | CACACTTCAG | 563 |
| 84 | GACTAGCGGT | 564 |
| 85 | AATTGTCGAG | 565 |
| 86 | CTAAGGACGT | 566 |
| 87 | ATTACGATGA | 567 |
| 88 | ATTGAAGACT | 568 |
| 89 | GCTTGTACGT | 569 |
| 90 | CCTACGTCAC | 570 |
| 91 | CACAACTTAG | 571 |
| 92 | GCGGTTCATC | 572 |
| 93 | GTACTCATCT | 573 |
| 94 | GTGCATCAGT | 574 |
| 95 | TCACATCCTA | 575 |
| 96 | CACGCGCTAT | 576 |

TABLE 9

List of random primers (8-base primers)

| No | Primer sequence | SEQ ID NO: |
|---|---|---|
| 1 | CTATCTTG | 577 |
| 2 | AAGTGCGT | 578 |
| 3 | ACATGCGA | 579 |

TABLE 9-continued

List of random primers (8-base primers)

| No | Primer sequence | SEQ ID NO: |
|---|---|---|
| 4 | ACCAATGG | 580 |
| 5 | TGCGTTGA | 581 |
| 6 | GACATGTC | 582 |
| 7 | TTGTGCGT | 583 |
| 8 | ACATCGCA | 584 |
| 9 | GAAGACGA | 585 |
| 10 | TCGATAGA | 586 |
| 11 | TCTTGCAA | 587 |
| 12 | AGCAAGTT | 588 |
| 13 | TTCATGGA | 589 |
| 14 | TCAATTCG | 590 |
| 15 | CGGTATGT | 591 |
| 16 | ACCACTAC | 592 |
| 17 | TCGCTTAT | 593 |
| 18 | TCTCGACT | 594 |
| 19 | GAATCGGT | 595 |
| 20 | GTTACAAG | 596 |
| 21 | CTGTGTAG | 597 |
| 22 | TGGTAGAA | 598 |
| 23 | ATACTGCG | 599 |
| 24 | AACTCGTC | 600 |
| 25 | ATATGTGC | 601 |
| 26 | AAGTTGCG | 602 |
| 27 | GATCATGT | 603 |
| 28 | TTGTTGCT | 604 |
| 29 | CCTCTTAG | 605 |
| 30 | TCACAGCT | 606 |
| 31 | AGATTGAC | 607 |
| 32 | AGCCTGAT | 608 |
| 33 | CGTCAAGT | 609 |
| 34 | AAGTAGAC | 610 |
| 35 | TCAGACAA | 611 |
| 36 | TCCTTGAC | 612 |
| 37 | GTAGCTGT | 613 |
| 38 | CGTCGTAA | 614 |
| 39 | CCAATGGA | 615 |
| 40 | TTGAGAGA | 616 |
| 41 | ACAACACC | 617 |

TABLE 9-continued

List of random primers (8-base primers)

| No | Primer sequence | SEQ ID NO: |
|---|---|---|
| 42 | TCTAGTAC | 618 |
| 43 | GAGGAAGT | 619 |
| 44 | GCGTATTG | 620 |
| 45 | AAGTAGCT | 621 |
| 46 | TGAACCTT | 622 |
| 47 | TGTGTTAC | 623 |
| 48 | TAACCTGA | 624 |
| 49 | GCTATTCC | 625 |
| 50 | GTTAGATG | 626 |
| 51 | CAGGATAA | 627 |
| 52 | ACCGTAGT | 628 |
| 53 | CCGTGTAT | 629 |
| 54 | TCCACTCT | 630 |
| 55 | TAGCTCAT | 631 |
| 56 | CGCTAATA | 632 |
| 57 | TACCTCTG | 633 |
| 58 | TGCACTAC | 634 |
| 59 | CTTGGAAG | 635 |
| 60 | AATGCACG | 636 |
| 61 | CACTGTTA | 637 |
| 62 | TCGACTAG | 638 |
| 63 | CTAGGTTA | 639 |
| 64 | GCAGATGT | 640 |
| 65 | AGTTCAGA | 641 |
| 66 | CTCCATCA | 642 |
| 67 | TGGTTACG | 643 |
| 68 | ACGTAGCA | 644 |
| 69 | CTCTTCCA | 645 |
| 70 | CGTCAGAT | 646 |
| 71 | TGGATCAT | 647 |
| 72 | ATATCGAC | 648 |
| 73 | TTGTGGAG | 649 |
| 74 | TTAGAGCA | 650 |
| 75 | TAACTACC | 651 |
| 76 | CTATGAGG | 652 |
| 77 | CTTCTCAC | 653 |
| 78 | CGTTCTCT | 654 |
| 79 | GTCACTAT | 655 |
| 80 | TCGTTAGC | 656 |
| 81 | ATCGTGTA | 657 |
| 82 | GAGAGCAA | 658 |
| 83 | AGACGCAA | 659 |
| 84 | TCCAGTTA | 660 |
| 85 | AATGCCAC | 661 |
| 86 | ATCACGTG | 662 |
| 87 | ACTGTGCA | 663 |
| 88 | TCACTGCA | 664 |
| 89 | GCATCCAA | 665 |
| 90 | AGCACTAT | 666 |
| 91 | CGAAGGAT | 667 |
| 92 | CCTTGTGT | 668 |
| 93 | TGCGGATA | 669 |
| 94 | AGGAATGG | 670 |
| 95 | ATCGTAAC | 671 |
| 96 | GAATGTCT | 672 |

TABLE 10

List of random primers (9-base primers)

| No | Primer sequence | SEQ ID NO: |
|---|---|---|
| 1 | TTGCTACAT | 673 |
| 2 | TAACGTATG | 674 |
| 3 | CAGTATGTA | 675 |
| 4 | TCAATAACG | 676 |
| 5 | CACACTTAT | 677 |
| 6 | GACTGTAAT | 678 |
| 7 | TATACACTG | 679 |
| 8 | ACTGCATTA | 680 |
| 9 | ACATTAAGC | 681 |
| 10 | CATATTACG | 682 |
| 11 | ATATCTACG | 683 |
| 12 | AGTAACTGT | 684 |
| 13 | ATGACGTTA | 685 |
| 14 | ATTATGCGA | 686 |
| 15 | AGTATACAC | 687 |
| 16 | TTAGCGTTA | 688 |

TABLE 10-continued

List of random primers (9-base primers)

| No | Primer sequence | SEQ ID NO: |
|---|---|---|
| 17 | TATGACACT | 689 |
| 18 | ATTAACGCT | 690 |
| 19 | TAGGACAAT | 691 |
| 20 | AAGACGTTA | 692 |
| 21 | TATAAGCGT | 693 |
| 22 | ATACCTGGC | 694 |
| 23 | CTCGAGATC | 695 |
| 24 | ATGGTGAGG | 696 |
| 25 | ATGTCGACG | 697 |
| 26 | GACGTCTGA | 698 |
| 27 | TACACTGCG | 699 |
| 28 | ATCGTCAGG | 700 |
| 29 | TGCACGTAC | 701 |
| 30 | GTCGTGCAT | 702 |
| 31 | GAGTGTTAC | 703 |
| 32 | AGACTGTAC | 704 |
| 33 | TGCGACTTA | 705 |
| 34 | TGTCCGTAA | 706 |
| 35 | GTAATCGAG | 707 |
| 36 | GTACCTTAG | 708 |
| 37 | ATCACGTGT | 709 |
| 38 | ACTTAGCGT | 710 |
| 39 | GTAATCGTG | 711 |
| 40 | ATGCCGTTA | 712 |
| 41 | ATAACGTGC | 713 |
| 42 | CTACGTTGT | 714 |
| 43 | TATGACGCA | 715 |
| 44 | CCGATAACA | 716 |
| 45 | ATGCGCATA | 717 |
| 46 | GATAAGCGT | 718 |
| 47 | ATATCTGCG | 719 |
| 48 | ACTTAGACG | 720 |
| 49 | ATCACCGTA | 721 |
| 50 | TAAGACACG | 722 |
| 51 | AATGCCGTA | 723 |
| 52 | AATCACGTG | 724 |
| 53 | TCGTTAGTC | 725 |
| 54 | CATCATGTC | 726 |
| 55 | TAAGACGGT | 727 |
| 56 | TGCATAGTG | 728 |
| 57 | GAGCGTTAT | 729 |
| 58 | TGCCTTACA | 730 |
| 59 | TTCGCGTTA | 731 |
| 60 | GTGTTAACG | 732 |
| 61 | GACACTGAA | 733 |
| 62 | CTGTTATCG | 734 |
| 63 | GGTCGTTAT | 735 |
| 64 | CGAGAGTAT | 736 |
| 65 | ATACAGTCC | 737 |
| 66 | AATTCACGC | 738 |
| 67 | TATGTGCAC | 739 |
| 68 | GATGACGTA | 740 |
| 69 | GATGCGATA | 741 |
| 70 | GAGCGATTA | 742 |
| 71 | TGTCACAGA | 743 |
| 72 | TACTAACCG | 744 |
| 73 | CATAACGAG | 745 |
| 74 | CGTATACCT | 746 |
| 75 | TATCACGTG | 747 |
| 76 | GAACGTTAC | 748 |
| 77 | GTCGTATAC | 749 |
| 78 | ATGTCGACA | 750 |
| 79 | ATACAGCAC | 751 |
| 80 | TACTTACGC | 752 |
| 81 | AACTACGGT | 753 |
| 82 | TAGAACGGT | 754 |
| 83 | GAATGTCAC | 755 |
| 84 | TGTACGTCT | 756 |
| 85 | AACATTGCG | 757 |
| 86 | TTGAACGCT | 758 |
| 87 | AATCAGGAC | 759 |
| 88 | ATTCGCACA | 760 |
| 89 | CCATGTACT | 761 |
| 90 | TGTCCTGTT | 762 |
| 91 | TAATTGCGC | 763 |
| 92 | GATAGTGTG | 764 |

TABLE 10-continued

List of random primers (9-base primers)

| No | Primer sequence | SEQ ID NO: |
|---|---|---|
| 93 | ATAGACGCA | 765 |
| 94 | TGTACCGTT | 766 |
| 95 | ATTGTCGCA | 767 |
| 96 | GTCACGTAA | 768 |

TABLE 11

List of random primers (11-base primers)

| No | Primer sequence | SEQ ID NO: |
|---|---|---|
| 1 | TTACACTATGC | 769 |
| 2 | GCGATAGTCGT | 770 |
| 3 | CTATTCACAGT | 771 |
| 4 | AGAGTCACTGT | 772 |
| 5 | AGAGTCGAAGC | 773 |
| 6 | CTGAATATGTG | 774 |
| 7 | ACTCCACAGGA | 775 |
| 8 | ATCCTCGTAAG | 776 |
| 9 | TACCATCGCCT | 777 |
| 10 | AACGCCTATAA | 778 |
| 11 | CTGTCGAACTT | 779 |
| 12 | TCAGATGTCCG | 780 |
| 13 | CTGCTTATCGT | 781 |
| 14 | ACATTCGCACA | 782 |
| 15 | CCTTAATGCAT | 783 |
| 16 | GGCTAGCTACT | 784 |
| 17 | TTCCAGTTGGC | 785 |
| 18 | GAGTCACAAGG | 786 |
| 19 | CAGAAGGTTCA | 787 |
| 20 | TCAACGTGCAG | 788 |
| 21 | CAAGCTTACTA | 789 |
| 22 | AGAACTCGTTG | 790 |
| 23 | CCGATACAGAG | 791 |
| 24 | GTACGCTGATC | 792 |
| 25 | TCCTCAGTGAA | 793 |
| 26 | GAGCCAACATT | 794 |
| 27 | GAGATCGATGG | 795 |
| 28 | ATCGTCAGCTG | 796 |
| 29 | GAAGCACACGT | 797 |
| 30 | ATCACGCAACC | 798 |

TABLE 11-continued

List of random primers (11-base primers)

| No | Primer sequence | SEQ ID NO: |
|---|---|---|
| 31 | TCGAATAGTCG | 799 |
| 32 | TATTACCGTCT | 800 |
| 33 | CAGTCACGACA | 801 |
| 34 | TTACTCGACGT | 802 |
| 35 | GCAATGTTGAA | 803 |
| 36 | GACACGAGCAA | 804 |
| 37 | CGAGATTACAA | 805 |
| 38 | TACCGACTACA | 806 |
| 39 | ACCGTTGCCAT | 807 |
| 40 | ATGTAATCGCC | 808 |
| 41 | AAGCCTGATGT | 809 |
| 42 | AAGTAACGTGG | 810 |
| 43 | GTAGAGGTTGG | 811 |
| 44 | CTCTTGCCTCA | 812 |
| 45 | ATCGTGAAGTG | 813 |
| 46 | ACCAGCACTAT | 814 |
| 47 | CACCAGAATGT | 815 |
| 48 | GAGTGAACAAC | 816 |
| 49 | TAACGTTACGC | 817 |
| 50 | CTTGGATCTTG | 818 |
| 51 | GTTCCAACGTT | 819 |
| 52 | CAAGGACCGTA | 820 |
| 53 | GACTTCACGCA | 821 |
| 54 | CACACTACTGG | 822 |
| 55 | TCAGATGAATC | 823 |
| 56 | TATGGATCTGG | 824 |
| 57 | TCTTAGGTGTG | 825 |
| 58 | TGTCAGCGTCA | 826 |
| 59 | GTCTAGGACAG | 827 |
| 60 | GCCTCTTCATA | 828 |
| 61 | AGAAGTGTTAC | 829 |
| 62 | CATGAGGCTTG | 830 |
| 63 | TGGATTGCTCA | 831 |
| 64 | ATCTACCTAAG | 832 |
| 65 | ATGAGCAGTGA | 833 |
| 66 | CCAGGAGATAC | 834 |
| 67 | CCGTTATACTT | 835 |
| 68 | CTCAGTACAAG | 836 |

TABLE 11-continued

List of random primers (11-base primers)

| No | Primer sequence | SEQ ID NO: |
|---|---|---|
| 69 | GGTGATCGTAG | 837 |
| 70 | CGAACGAGACA | 838 |
| 71 | ACTACGAGCTT | 839 |
| 72 | TTGCCACAGCA | 840 |
| 73 | GTCAACTCTAC | 841 |
| 74 | TGGACTGTGTC | 842 |
| 75 | GGAATGGACTT | 843 |
| 76 | CGAGAACATAA | 844 |
| 77 | ACCTGGTCAGT | 845 |
| 78 | CGAACGACACA | 846 |
| 79 | AGTCTAGCCAT | 847 |
| 80 | AGGCCTAGATG | 848 |
| 81 | GGTGCGTTAGT | 849 |
| 82 | ATTGTGTCCGA | 850 |
| 83 | GCAGACATTAA | 851 |
| 84 | ATTGGCTCATG | 852 |
| 85 | GAGGTTACATG | 853 |
| 86 | CCTATAGGACC | 854 |
| 87 | TTAGACGGTCT | 855 |
| 88 | GATTGACGCAC | 856 |
| 89 | AAGACACCTCG | 857 |
| 90 | TCGAATAATCG | 858 |
| 91 | TCTATGTCGGA | 859 |
| 92 | TCGCATGAACC | 860 |
| 93 | TGTTATGTCTC | 861 |
| 94 | TGGATCCTACA | 862 |
| 95 | ATCGTTCAGCC | 863 |
| 96 | TACCGCAAGCA | 864 |

TABLE 12

List of random primers (12-base primers)

| No | Primer sequence | SEQ ID NO: |
|---|---|---|
| 1 | GCTGTTGAACCG | 865 |
| 2 | ATACTCCGAGAT | 866 |
| 3 | CTTAAGGAGCGC | 867 |
| 4 | TATACTACAAGC | 868 |
| 5 | TAGTGGTCGTCA | 869 |
| 6 | GTGCTTCAGGAG | 870 |
| 7 | GACGCATACCTC | 871 |
| 8 | CCTACCTGTGGA | 872 |
| 9 | GCGGTCACATAT | 873 |
| 10 | CTGCATTCACGA | 874 |
| 11 | TGGATCCTTCAT | 875 |
| 12 | TTGTGCTGGACT | 876 |
| 13 | ATTGAGAGCTAT | 877 |
| 14 | TCGCTAATGTAG | 878 |
| 15 | CTACTGGCACAA | 879 |
| 16 | AGAGCCAGTCGT | 880 |
| 17 | AATACTGGCTAA | 881 |
| 18 | CTGCATGCATAA | 882 |
| 19 | TTGTCACAACTC | 883 |
| 20 | TGCTAACTCTCC | 884 |
| 21 | TCTCTAGTTCGG | 885 |
| 22 | TTACGTCCGCAA | 886 |
| 23 | GTGTTGCTACCA | 887 |
| 24 | CGCATGTATGCC | 888 |
| 25 | CCTGTTCTGATT | 889 |
| 26 | TAAGATGCTTGA | 890 |
| 27 | ATATATCTCAGC | 891 |
| 28 | TTCCTCGTGGTT | 892 |
| 29 | ATGTCGATCTAG | 893 |
| 30 | CATCCACTAATC | 894 |
| 31 | GCCTCTGGTAAC | 895 |
| 32 | AGTCAAGAGATT | 896 |
| 33 | ACTGAGGCGTTC | 897 |
| 34 | TAAGGCTGACAT | 898 |
| 35 | AGTTCGCATACA | 899 |
| 36 | GCAGAATTGCGA | 900 |
| 37 | GGTTATGAAGAA | 901 |
| 38 | AGAAGTCGCCTC | 902 |
| 39 | TTCGCGTTATTG | 903 |
| 40 | TACCTGGTCGGT | 904 |
| 41 | GGTTACCGAGGA | 905 |
| 42 | ACACACTTCTAG | 906 |
| 43 | GGAAGTGATTAA | 907 |

TABLE 12-continued

List of random primers (12-base primers)

| No | Primer sequence | SEQ ID NO: |
|----|----------------|------------|
| 44 | TCCATCAGATAA | 908 |
| 45 | TGTCTGTATCAT | 909 |
| 46 | AATTGGCTATAG | 910 |
| 47 | ACGTCGGAAGGT | 911 |
| 48 | AGGCATCCGTTG | 912 |
| 49 | ACCGTCGCTTGA | 913 |
| 50 | TACCGTCAAGTG | 914 |
| 51 | CTCGATATAGTT | 915 |
| 52 | CGTCAACGTGGT | 916 |
| 53 | TAGTCAACGTAG | 917 |
| 54 | TGAGTAGGTCAG | 918 |
| 55 | CTTGGCATGTAC | 919 |
| 56 | TGCCGAGACTTC | 920 |
| 57 | CTAAGACTTAAG | 921 |
| 58 | TTCTCGTGTGCG | 922 |
| 59 | CACCTGCACGAT | 923 |
| 60 | ATTAAGCCTAAG | 924 |
| 61 | GGTGGAACCATG | 925 |
| 62 | ACTAACGCGACT | 926 |
| 63 | CAGTTGTGCTAT | 927 |
| 64 | ACGCTGTTAGCA | 928 |
| 65 | GTCAACGCTAAG | 929 |
| 66 | AGCTTAGGTATG | 930 |
| 67 | CGCAGGACGATT | 931 |
| 68 | AACCGGCTGTCT | 932 |
| 69 | GTTGCTCACGTG | 933 |
| 70 | GAATCTTCCGCG | 934 |
| 71 | AGAGCGTACACG | 935 |
| 72 | AAGGCTAATGTC | 936 |
| 73 | TCTATGTAGACG | 937 |
| 74 | AGACGGTCTAGT | 938 |
| 75 | TTGGTCACACGC | 939 |
| 76 | GTCGATATATGG | 940 |
| 77 | AACATGGATACG | 941 |
| 78 | TTCGCAGTTCCT | 942 |
| 79 | CGCATGTTGTGC | 943 |
| 80 | TGTTAAGTTGGA | 944 |
| 81 | CAAGTGTGATGA | 945 |
| 82 | CTGGTACCACGT | 946 |
| 83 | CGCTAGGATCAC | 947 |
| 84 | TGCTCATTACGG | 948 |
| 85 | TGCTCAGTAACA | 949 |
| 86 | ACGATCATAGCC | 950 |
| 87 | ACGATACGTGGA | 951 |
| 88 | GTTCGATGATGG | 952 |
| 89 | AAGAGCTGTGCC | 953 |
| 90 | GGTTGGATCAAC | 954 |
| 91 | GCGCGCTTATGA | 955 |
| 92 | CGTCGATCATCA | 956 |
| 93 | GAGACTGCACTC | 957 |
| 94 | GATAGATCGCAT | 958 |
| 95 | GGCCATCATCAG | 959 |
| 96 | GGTGTTCCACTG | 960 |

TABLE 13

List of random primers (14-base primers)

| No | Primer sequence | SEQ ID NO: |
|----|----------------|------------|
| 1 | AGCTATACAGAGGT | 961 |
| 2 | AGGCCGTTCTGTCT | 962 |
| 3 | CATTGGTCTGCTAT | 963 |
| 4 | CTACATACGCGCCA | 964 |
| 5 | GCTTAACGGCGCTT | 965 |
| 6 | TACGATACTCCACC | 966 |
| 7 | ACCGGCATAAGAAG | 967 |
| 8 | GGATGCTTCGATAA | 968 |
| 9 | GTGTACCTGAATGT | 969 |
| 10 | CGCGGATACACAGA | 970 |
| 11 | TTCCACGGCACTGT | 971 |
| 12 | TAGCCAGGCAACAA | 972 |
| 13 | AGCGTCAACACGTA | 973 |
| 14 | TAACGCTACTCGCG | 974 |
| 15 | TAGATAGACGATCT | 975 |
| 16 | ACTCTTGCAATGCT | 976 |
| 17 | ACTCGGTTAGGTCG | 977 |
| 18 | CATTATCTACGCAT | 978 |
| 19 | CACACCGGCGATTA | 979 |

TABLE 13-continued

List of random primers (14-base primers)

| No | Primer sequence | SEQ ID NO: |
|---|---|---|
| 20 | TACGCAGTACTGTG | 980 |
| 21 | CAAGCGCGTGAATG | 981 |
| 22 | GAATGGACTGACGA | 982 |
| 23 | CTAGCGCTGAAGTT | 983 |
| 24 | TGCGGCAGACCAAT | 984 |
| 25 | AAGGCATAGAGATT | 985 |
| 26 | TTCTCCTCGCCATG | 986 |
| 27 | TCATTGGTCGTGAA | 987 |
| 28 | ATTACGCTATACGA | 988 |
| 29 | ATGATCCTCCACGG | 989 |
| 30 | CGTCGTTAGTAATC | 990 |
| 31 | TGCACATAGTCTCA | 991 |
| 32 | GTCAAGGAGTCACG | 992 |
| 33 | GGTTGGAATCTTGC | 993 |
| 34 | CATCGGTGCACTCA | 994 |
| 35 | AATGCACTAGACGT | 995 |
| 36 | TACAGTCAGGCTCG | 996 |
| 37 | AGAGAAGCTTAGCC | 997 |
| 38 | CCATAGGATCGTAT | 998 |
| 39 | TTGTGCTACACCTG | 999 |
| 40 | CTCCAGTAATACTA | 1000 |
| 41 | TGATGCCGATGTGG | 1001 |
| 42 | GTCATACCGCTTAA | 1002 |
| 43 | ACGTTCTCTTGAGA | 1003 |
| 44 | CAGCCATATCGTGT | 1004 |
| 45 | TTGAACGTAGCAAT | 1005 |
| 46 | ACAATCGCGGTAAT | 1006 |
| 47 | GTTCCTGTAGATCC | 1007 |
| 48 | AGAGCCTTACGGCA | 1008 |
| 49 | AATATGGCGCCACC | 1009 |
| 50 | ACCATATAGGTTCG | 1010 |
| 51 | ATGCACCACAGCTG | 1011 |
| 52 | CTACTATTGAACAG | 1012 |
| 53 | TGCCATCACTCTAG | 1013 |
| 54 | GCGAACGAGAATCG | 1014 |
| 55 | GAATCAAGGAGACC | 1015 |
| 56 | CAACATCTATGCAG | 1016 |
| 57 | CAATCCGTCATGGA | 1017 |
| 58 | AGCTCTTAGCCATA | 1018 |
| 59 | AACAAGGCAACTGG | 1019 |
| 60 | GTCGTCGCTCCTAT | 1020 |
| 61 | GTCATCATTAGATG | 1021 |
| 62 | GCACTAAGTAGCAG | 1022 |
| 63 | ACCTTACCGGACCT | 1023 |
| 64 | GCTCAGGTATGTCA | 1024 |
| 65 | TGTCACGAGTTAGT | 1025 |
| 66 | CAGATGACTTACGT | 1026 |
| 67 | GAAGTAGCGATTGA | 1027 |
| 68 | GCAGGCAATCTGTA | 1028 |
| 69 | CCTTATACAACAAG | 1029 |
| 70 | CCTTAGATTGATTG | 1030 |
| 71 | AGCCACGAGTGATA | 1031 |
| 72 | GGATGACTCGTGAC | 1032 |
| 73 | CTTCGTTCGCCATT | 1033 |
| 74 | TCTTGCGTATTGAT | 1034 |
| 75 | CTTAACGTGGTGGC | 1035 |
| 76 | TGCTGTTACGGAAG | 1036 |
| 77 | CTGAATTAGTTCTC | 1037 |
| 78 | CCTCCAAGTACAGA | 1038 |
| 79 | CTGGTAATTCGCGG | 1039 |
| 80 | CGACTGCAATCTGG | 1040 |
| 81 | TGGATCGCGATTGG | 1041 |
| 82 | CGACTATTCCTGCG | 1042 |
| 83 | CAAGTAGGTCCGTC | 1043 |
| 84 | AGTAATCAGTGTTC | 1044 |
| 85 | TTATTCTCACTACG | 1045 |
| 86 | CATGTCTTCTTCGT | 1046 |
| 87 | AGGCACATACCATC | 1047 |
| 88 | AGGTTAGAGGATGT | 1048 |
| 89 | CAACTGGCAAGTGC | 1049 |
| 90 | CGCTCACATAGAGG | 1050 |
| 91 | GCAATGTCGAGATC | 1051 |
| 92 | GTTCTGTGGTGCTC | 1052 |
| 93 | AAGTGATCAGACTA | 1053 |
| 94 | ATTGAAGGATTCCA | 1054 |

TABLE 13-continued

List of random primers (14-base primers)

| No | Primer sequence | SEQ ID NO: |
|---|---|---|
| 95 | ACGCCATGCTACTA | 1055 |
| 96 | CTGAAGATGTCTGC | 1056 |

TABLE 14

List of random primers (16-base primers)

| No | Primer sequence | SEQ ID NO: |
|---|---|---|
| 1 | GACAATCTCTGCCGAT | 1057 |
| 2 | GGTCCGCCTAATGTAA | 1058 |
| 3 | AGCCACAGGCAATTCC | 1059 |
| 4 | ATCTCAAGTTCTCAAC | 1060 |
| 5 | TGTAACGCATACGACG | 1061 |
| 6 | TATCTCGAATACCAGC | 1062 |
| 7 | ACCGCAACACAGGCAA | 1063 |
| 8 | GGCCAGTAACATGACT | 1064 |
| 9 | GTGAACAGTTAAGGTG | 1065 |
| 10 | CCAGGATCCGTATTGC | 1066 |
| 11 | GACCTAGCACTAGACC | 1067 |
| 12 | CGCCATCCTATTCACG | 1068 |
| 13 | AAGTGCAGTAATGGAA | 1069 |
| 14 | TCAACGCGTTCGTCTA | 1070 |
| 15 | AGCGGCCACTATCTAA | 1071 |
| 16 | CTCGGCGCCATATAGA | 1072 |
| 17 | CGATAACTTAGAAGAA | 1073 |
| 18 | CATAGGATGTGACGCC | 1074 |
| 19 | GGCTTGTCGTCGTATC | 1075 |
| 20 | CTTGTCTGAATATTAG | 1076 |
| 21 | ACAGTTCGAGTGTCGG | 1077 |
| 22 | CTCTAACCTGTGACGT | 1078 |
| 23 | CGCGCTAATTCAACAA | 1079 |
| 24 | ACTCACGAATGCGGCA | 1080 |
| 25 | AATCTTCGGCATTCAT | 1081 |
| 26 | AAGTATCAGGATCGCG | 1082 |
| 27 | AGTAACTCTGCAGACA | 1083 |
| 28 | GGATTGAACATTGTGC | 1084 |
| 29 | GTGATGCTCACGCATC | 1085 |
| 30 | CGTAGCGTAACGGATA | 1086 |
| 31 | TGCGATGCACCGTTAG | 1087 |
| 32 | CCAGTATGCTCTCAGG | 1088 |

TABLE 14-continued

List of random primers (16-base primers)

| No | Primer sequence | SEQ ID NO: |
|---|---|---|
| 33 | AATGACGTTGAAGCCT | 1089 |
| 34 | TCGATTCTATAGGAGT | 1090 |
| 35 | CGATAGGTTCAGCTAT | 1091 |
| 36 | CCATGTTGATAGAATA | 1092 |
| 37 | GAGCCACTTCTACAGG | 1093 |
| 38 | GCGAACTCTCGGTAAT | 1094 |
| 39 | GACCTGAGTAGCTGGT | 1095 |
| 40 | CGAGTCTATTAGCCTG | 1096 |
| 41 | GTAGTGCCATACACCT | 1097 |
| 42 | CCAGTGGTCTATAGCA | 1098 |
| 43 | GTCAGTGCGTTATTGC | 1099 |
| 44 | AGTGTCGGAGTGACGA | 1100 |
| 45 | AATCTCCGCTATAGTT | 1101 |
| 46 | CGAGTAGGTCTGACTT | 1102 |
| 47 | CTGTCGCTCTAATAAC | 1103 |
| 48 | GCTGTCAATATAACTG | 1104 |
| 49 | AGCTCAAGTTGAATCC | 1105 |
| 50 | AATTCATGCTCCTAAC | 1106 |
| 51 | CCAAGGTCTGGTGATA | 1107 |
| 52 | CTCCACGTATCTTGAA | 1108 |
| 53 | TAGCCGAACAACACTT | 1109 |
| 54 | AGTACACGACATATGC | 1110 |
| 55 | ACGTTCTAGACTCCTG | 1111 |
| 56 | CGACTCAAGCACTGCT | 1112 |
| 57 | TGAAGCTCACGATTAA | 1113 |
| 58 | TATCTAACGTATGGTA | 1114 |
| 59 | TATACCATGTTCCTTG | 1115 |
| 60 | TTCCTACGATGACTTC | 1116 |
| 61 | CTCTCCAATATGTGCC | 1117 |
| 62 | GAGTAGAGTCTTGCCA | 1118 |
| 63 | GCGAGATGTGGTCCTA | 1119 |
| 64 | AAGCTACACGGACCAC | 1120 |
| 65 | ATACAACTGGCAACCG | 1121 |
| 66 | CGGTAGATGCTATGCT | 1122 |
| 67 | TCTTGACCGGTCATCA | 1123 |
| 68 | AGATCGTGCATGCGAT | 1124 |
| 69 | TCCTCGAGACAGCCTT | 1125 |
| 70 | TAGCCGGTACCACTTA | 1126 |

TABLE 14-continued

List of random primers (16-base primers)

| No | Primer sequence | SEQ ID NO: |
|---|---|---|
| 71 | GTAAGGCAGCGTGCAA | 1127 |
| 72 | TAGTCTGCTCCTGGTC | 1128 |
| 73 | TGGATTATAGCAGCAG | 1129 |
| 74 | AAGAATGATCAGACAT | 1130 |
| 75 | CAGCGCTATATACCTC | 1131 |
| 76 | GAGTAGTACCTCCACC | 1132 |
| 77 | GACGTGATCCTCTAGA | 1133 |
| 78 | GTTCCGTTCACTACGA | 1134 |
| 79 | TGCAAGCACCAGGATG | 1135 |
| 80 | TTAGTTGGCGGCTGAG | 1136 |
| 81 | CAGATGCAGACATACG | 1137 |
| 82 | GACGCTTGATGATTAT | 1138 |
| 83 | TGGATCACGACTAGGA | 1139 |
| 84 | CTCGTCGGTATAACGC | 1140 |
| 85 | AAGCACGGATGCGATT | 1141 |
| 86 | AGATCTTCCGGTGAAC | 1142 |
| 87 | GGACAATAGCAACCTG | 1143 |
| 88 | GATAATCGGTTCCAAT | 1144 |
| 89 | CTCAAGCTACAGTTGT | 1145 |
| 90 | GTTGGCATGATGTAGA | 1146 |
| 91 | CAGCATGAGGTAAGTG | 1147 |
| 92 | GCCTCATCACACGTCA | 1148 |
| 93 | TCGATACTACACATCG | 1149 |
| 94 | TACACGAGGCTTGATC | 1150 |
| 95 | TTCTCGTGTCCGCATT | 1151 |
| 96 | GGTGAAGCAACAGCAT | 1152 |

TABLE 15

List of random primers (18-base primers)

| No | Primer sequence | SEQ ID NO: |
|---|---|---|
| 1 | CGAACCGACTGTACAGTT | 1153 |
| 2 | CCGACTGCGGATAAGTTA | 1154 |
| 3 | CGACAGGTAGGTAAGCAG | 1155 |
| 4 | TGATACGTTGGTATACAG | 1156 |
| 5 | CTACTATAGAATACGTAG | 1157 |
| 6 | AGACTGTGGCAATGGCAT | 1158 |
| 7 | GGAAGACTGATACAACGA | 1159 |
| 8 | TATGCACATATAGCGCTT | 1160 |
| 9 | CATGGTAATCGACCGAGG | 1161 |
| 10 | GTCATTGCCGTCATTGCC | 1162 |
| 11 | CCTAAGAACTCCGAAGCT | 1163 |
| 12 | TCGCTCACCGTACTAGGA | 1164 |
| 13 | TATTACTGTCACAGCAGG | 1165 |
| 14 | TGAGACAGGCTACGAGTC | 1166 |
| 15 | AAGCTATGCGAACACGTT | 1167 |
| 16 | AACGGAGGAGTGAGCCAA | 1168 |
| 17 | CCACTATGGACATCATGG | 1169 |
| 18 | ATGGTGGTGGATAGCTCG | 1170 |
| 19 | TCACCGGTTACACATCGC | 1171 |
| 20 | AAGATACTGAGATATGGA | 1172 |
| 21 | GACCTGTTCTTGAACTAG | 1173 |
| 22 | AAGTAGAGCTCTCGGTTA | 1174 |
| 23 | CTATGTTCTTACTCTCTT | 1175 |
| 24 | CAAGGCTATAAGCGGTTA | 1176 |
| 25 | GAAGCTAATTAACCGATA | 1177 |
| 26 | TTCACGTCTGCCAAGCAC | 1178 |
| 27 | ATCGTATAGATCGAGACA | 1179 |
| 28 | GTCACAGATTCACATCAT | 1180 |
| 29 | GTGCCTGTGAACTATCAG | 1181 |
| 30 | CAGCGTACAAGATAGTCG | 1182 |
| 31 | GCATGGCATGGTAGACCT | 1183 |
| 32 | GGTATGCTACTCTTCGCA | 1184 |
| 33 | ATGTTCAGTCACAAGCGA | 1185 |
| 34 | TAGGAAGTGTGTAATAGC | 1186 |
| 35 | AATCCATGTAGCTGTACG | 1187 |
| 36 | CCAGATTCACTGGCATAG | 1188 |
| 37 | TTGTCTCTACGTAATATC | 1189 |
| 38 | GTGGTGCTTGTGACAATT | 1190 |
| 39 | CAGCCTACTTGGCTGAGA | 1191 |
| 40 | TACTCAATGCATCTGTGT | 1192 |
| 41 | TGTAGAGAGACGAATATA | 1193 |
| 42 | GCCTACAACCATCCTACT | 1194 |
| 43 | GCGTGGCATTGAGATTCA | 1195 |
| 44 | GCATGCCAGCTAACTGAG | 1196 |
| 45 | GCGAGTAATCCGGTTGGA | 1197 |

TABLE 15-continued

List of random primers (18-base primers)

| No | Primer sequence | SEQ ID NO: |
|---|---|---|
| 46 | GCCTCTACCAGAACGTCA | 1198 |
| 47 | GTCAGCAGAAGACTGACC | 1199 |
| 48 | GATAACAGACGTAGCAGG | 1200 |
| 49 | CAGGAGATCGCATGTCGT | 1201 |
| 50 | CTGGAAGGAATGGAGCCA | 1202 |
| 51 | ATTGGTTCTCTACCACAA | 1203 |
| 52 | CTCATTGTTGACGGCTCA | 1204 |
| 53 | TTCAGGACTGTAGTTCAT | 1205 |
| 54 | AGACCGCACTAACTCAAG | 1206 |
| 55 | GGAATATTGTGCAGACCG | 1207 |
| 56 | CCTATTACTAATAGCTCA | 1208 |
| 57 | ATGGCATGAGTACTTCGG | 1209 |
| 58 | GACACGTATGCGTCTAGC | 1210 |
| 59 | GAAGGTACGGAATCTGTT | 1211 |
| 60 | TATAACGTCCGACACTGT | 1212 |
| 61 | GCTAATACATTACCGCCG | 1213 |
| 62 | GAAGCCAACACTCCTGAC | 1214 |
| 63 | CGAATAACGAGCTGTGAT | 1215 |
| 64 | GCCTACCGATCGCACTTA | 1216 |
| 65 | CTGAGGAGAATAGCCTGC | 1217 |
| 66 | CAGCATGGACAGTACTTC | 1218 |
| 67 | GGTATAGAGCCTTCCTTA | 1219 |
| 68 | CGCTCTGCATATATAGCA | 1220 |
| 69 | CGGCTCTACTATGCTCGT | 1221 |
| 70 | CCTAATGCGAAGCTCACC | 1222 |
| 71 | ACAACCGGTGAGGCAGTA | 1223 |
| 72 | TTGGTTCGAACCAACCGC | 1224 |
| 73 | ATACTAGGTTGAACTAAG | 1225 |
| 74 | GCGTTGAGAGTAACATAT | 1226 |
| 75 | AGTTGTATAATAAGCGTC | 1227 |
| 76 | GTATGATGCCGTCCAATT | 1228 |
| 77 | GGACTCTCTGAAGAGTCT | 1229 |
| 78 | GGACTCTCTTGACTTGAA | 1230 |
| 79 | GATAACAGTGCTTCGTCC | 1231 |
| 80 | GGCCATTATAGATGAACT | 1232 |
| 81 | ATAGAGAGCACAGAGCAG | 1233 |
| 82 | GTGTGAGTGTATCATAAC | 1234 |
| 83 | ATAACCTTAGTGCGCGTC | 1235 |

TABLE 15-continued

List of random primers (18-base primers)

| No | Primer sequence | SEQ ID NO: |
|---|---|---|
| 84 | CCGACTGATATGCATGGA | 1236 |
| 85 | GGATATCTGATCGCATCA | 1237 |
| 86 | CAGCATTAACGAGGCGAA | 1238 |
| 87 | GCGAGGCCTACATATTCG | 1239 |
| 88 | CGATAAGTGGTAAGGTCT | 1240 |
| 89 | AGATCCTGAGTCGAGCAA | 1241 |
| 90 | AAGATATAACGAGACCGA | 1242 |
| 91 | CCGACTGATTGAGAACGT | 1243 |
| 92 | TCGGCTTATATGACACGT | 1244 |
| 93 | AATAACGTACGCCGGAGG | 1245 |
| 94 | AACACAGCATTGCGCACG | 1246 |
| 95 | GTAGTCTGACAGCAACAA | 1247 |
| 96 | AGAATGACTTGAGCTGCT | 1248 |

TABLE 16

List of random primers (20-base primers)

| No | Primer sequence | SEQ ID NO: |
|---|---|---|
| 1 | ACTGGTAGTAACGTCCACCT | 1249 |
| 2 | AGACTGGTTGTTATTCGCCT | 1250 |
| 3 | TATCATTGACAGCGAGCTCA | 1251 |
| 4 | TGGAGTCTGAAGAAGGACTC | 1252 |
| 5 | CATCTGGACTACGGCAACGA | 1253 |
| 6 | AACTGTCATAAGACAGACAA | 1254 |
| 7 | CCTCAACATGACATACACCG | 1255 |
| 8 | CAATACCGTTCGCGATTCTA | 1256 |
| 9 | GCGTCTACGTTGATTCGGCC | 1257 |
| 10 | TGAACAGAGGCACTTGCAGG | 1258 |
| 11 | CGACTAGAACCTACTACTGC | 1259 |
| 12 | GCACCGCACGTGGAGAGATA | 1260 |
| 13 | CTGAGAGACCGACTGATGCG | 1261 |
| 14 | TCGTCCTTCTACTTAATGAT | 1262 |
| 15 | CAAGCTATACCATCCGAATT | 1263 |
| 16 | CAATACGTATAGTCTTAGAT | 1264 |
| 17 | CCATCCACAGTGACCTATGT | 1265 |
| 18 | TATCCGTTGGAGAAGGTTCA | 1266 |
| 19 | CGCCTAGGTACCTGAGTACG | 1267 |
| 20 | CAGAGTGCTCGTGTTCGCGA | 1268 |
| 21 | CGCTTGGACATCCTTAAGAA | 1269 |

TABLE 16-continued

List of random primers (20-base primers)

| No | Primer sequence | SEQ ID NO: |
|---|---|---|
| 22 | GACCGCATGATTAGTCTTAC | 1270 |
| 23 | CTTGGCCGTAGTCACTCAGT | 1271 |
| 24 | GATAGCGATATTCAGTTCGC | 1272 |
| 25 | ATCCAACACTAAGACAACCA | 1273 |
| 26 | CCATTCTGTTGCGTGTCCTC | 1274 |
| 27 | ACATTCTGTACGCTTGCAGC | 1275 |
| 28 | TGCTGAACGCCAATCGCTTA | 1276 |
| 29 | TCCTCTACAAGAATATTGCG | 1277 |
| 30 | CGACCAACGCAGCCTGATTC | 1278 |
| 31 | ATTGCGAGCTTGAGTAGCGC | 1279 |
| 32 | AAGGTGCGAGCATAGGAATC | 1280 |
| 33 | CACTTAAGTGTGATATAGAT | 1281 |
| 34 | ATCGGTATGCTGACCTAGAC | 1282 |
| 35 | TACAATCTCGAATGCAGGAT | 1283 |
| 36 | CCATATGAAGCGCAGCCGTC | 1284 |
| 37 | CGTCTCGTGGACATTCGAGG | 1285 |
| 38 | CCGAGTACAGAAGCGTGGAA | 1286 |
| 39 | TTACGTGGTCGACAGGCAGT | 1287 |
| 40 | AGCTGCAATCTGCATGATTA | 1288 |
| 41 | ACCTGCCGAAGCAGCCTACA | 1289 |
| 42 | AACATGATAACCACATGGTT | 1290 |
| 43 | ATCCGACTGATTGAATTACC | 1291 |
| 44 | TCACGCTGACTCTTATCAGG | 1292 |
| 45 | GCGCGCTCGAAGTACAACAT | 1293 |
| 46 | ACAGCCAGATGCGTTGTTCC | 1294 |
| 47 | GGAGCTCTGACCTGCAAGAA | 1295 |
| 48 | AACATTAGCCTCAAGTAAGA | 1296 |
| 49 | TGTGATTATGCCGAATGAGG | 1297 |
| 50 | GAGTAATAATCCAATCAGTA | 1298 |
| 51 | CTCCTTGGCGACAGCTGAAC | 1299 |
| 52 | TTACGCACACATACACAGAC | 1300 |
| 53 | ACGCCGTATGGCGACTTAGG | 1301 |
| 54 | AGAACGACAATTACGATGGC | 1302 |
| 55 | TGCTAACGTACCACTGCCAC | 1303 |
| 56 | CATCCAGAATGTCTATCATA | 1304 |
| 57 | GGAGAACGCCTATAGCACTC | 1305 |
| 58 | ACCTCTTGTGACGGCCAGTC | 1306 |
| 59 | TGCCATAACTTGGCATAAGA | 1307 |
| 60 | ACAATTGTCTGACCACGCTC | 1308 |
| 61 | TCGTCACCTTCACAGAACGA | 1309 |
| 62 | AGCAGCAGATGATGATCCAA | 1310 |
| 63 | TCGTGCCTTGGATTCCAGGA | 1311 |
| 64 | TGTTATAGCCACGATACTAT | 1312 |
| 65 | AATCTCACCTGTACCTTCCG | 1313 |
| 66 | GAGTAGCGGAAGCGTTAGCG | 1314 |
| 67 | AATACTCCGGCGAGGTATAC | 1315 |
| 68 | TTCGCATCCTTGCACGAACA | 1316 |
| 69 | AACCGGCTAATACTACTGGC | 1317 |
| 70 | CTAGCATCTTAGACACCAGA | 1318 |
| 71 | TAGTTGCGTGATACAAGATA | 1319 |
| 72 | TCGTCTCGACACAGTTGGTC | 1320 |
| 73 | TCCGTTCGCGTGCGAACTGA | 1321 |
| 74 | TCTGACTCTGGTGTACAGTC | 1322 |
| 75 | ACAGCGCAATTATATCCTGT | 1323 |
| 76 | AGATCCGTACGTGAGACTAG | 1324 |
| 77 | TACATTGAAGCATCCGAACA | 1325 |
| 78 | CTCCTGAGAGATCAACGCCA | 1326 |
| 79 | TCACCTCGAATGAGTTCGTT | 1327 |
| 80 | TAGCGACTTAAGGTCCAAGC | 1328 |
| 81 | AGTACGTATTGCCGTGCAAG | 1329 |
| 82 | AGCCACGAACCGACGTCATA | 1330 |
| 83 | TGATGTGTACGCTACTACTA | 1331 |
| 84 | CCACTGTGTGCAGCAGACGA | 1332 |
| 85 | CTATTGTACAGCGAACGCTG | 1333 |
| 86 | CTCCGATATCGCACGGATCG | 1334 |
| 87 | AACTTATCGTCGGACGCATG | 1335 |
| 88 | TATCCTAATTCGTGCCGGTC | 1336 |
| 89 | ACAGCCTTCCTGTGTGGACT | 1337 |
| 90 | CCTCCGTGAGGATCGTACCA | 1338 |
| 91 | GCTCTAAGTAACAGAACTAA | 1339 |
| 92 | GACTTACCGCGCGTTCTGGT | 1340 |
| 93 | TCTGAGGATACACATGTGGA | 1341 |
| 94 | TGTAATCACACTGGTGTCGG | 1342 |
| 95 | CACTAGGCGGCAGACATACA | 1343 |
| 96 | CTAGAGCACAGTACCACGTT | 1344 |

TABLE 17

List of random primers (22-base primers)

| No | Primer sequence | SEQ ID NO: |
|---|---|---|
| 1 | TTCAGAGGTCTACGCTTCCGGT | 1345 |
| 2 | AACACAGACTGCGTTATGCCAA | 1346 |
| 3 | TGCTGAGTTCTATACAGCAGTG | 1347 |
| 4 | ACCTATTATATGATAGCGTCAT | 1348 |
| 5 | ATCGTGAGCTACAGTGAATGCA | 1349 |
| 6 | CGTGATGTATCCGGCCTTGCAG | 1350 |
| 7 | TCTTCTGGTCCTAGAGTTGTGC | 1351 |
| 8 | TGATGTCGGCGGCGGATCAGAT | 1352 |
| 9 | TCGGCCTTAGCGTTCAGCATCC | 1353 |
| 10 | TTAAGTAGGTCAGCCACTGCAC | 1354 |
| 11 | CCAGGTGAGTTGATCTGACACC | 1355 |
| 12 | TATACTATTACTGTGTTCGATC | 1356 |
| 13 | CCGCAGTATGTCTAGTGTTGTC | 1357 |
| 14 | GTCTACCGCGTACGAAGCTCTC | 1358 |
| 15 | ATGCGAGTCCGTGGTCGATCCT | 1359 |
| 16 | TGGTAGATTGGTGTGAGAACTA | 1360 |
| 17 | AGGTTCGTCGATCAACTGCTAA | 1361 |
| 18 | ACGACAAGCATCCTGCGATATC | 1362 |
| 19 | TTGAATCACAGAGAGCGTGATT | 1363 |
| 20 | GTACTTAGTGCTTACGTCAGCT | 1364 |
| 21 | GATTATTAAGGCCAAGCTCATA | 1365 |
| 22 | GCATGCAGAGACGTACTCATCG | 1366 |
| 23 | TAGCGGATGGTGTCCTGGCACT | 1367 |
| 24 | TACGGCTGCCAACTTAATAACT | 1368 |
| 25 | CTCATATGACAACTTCTATAGT | 1369 |
| 26 | CAAGCAATAGTTGTCGGCCACC | 1370 |
| 27 | TTCAGCAATCCGTACTGCTAGA | 1371 |
| 28 | TGAGACGTTGCTGACATTCTCC | 1372 |
| 29 | GTTCCGATGAGTTAGATGTATA | 1373 |
| 30 | TTGACGCTTGGAGGAGTACAAG | 1374 |
| 31 | TTCATGTTACCTCCACATTGTG | 1375 |
| 32 | GAGCACGTGCCAGATTGCAACC | 1376 |
| 33 | GGTCGACAAGCACAAGCCTTCT | 1377 |
| 34 | TAGGCAGGTAAGATGACCGACT | 1378 |
| 35 | CGAGGCATGCCAAGTCGCCAAT | 1379 |
| 36 | AGTGTTGATAGGCGGATGAGAG | 1380 |
| 37 | TTCGGTCTAGACCTCTCACAAT | 1381 |
| 38 | GTGACGCTCATATCTTGCCACC | 1382 |
| 39 | GATGTAATTCTACGCGCGGACT | 1383 |
| 40 | GATGGCGATGTTGCATTACATG | 1384 |
| 41 | TATGCTCTGAATTAACGTAGAA | 1385 |
| 42 | AGGCAATATGGTGATCCGTAGC | 1386 |
| 43 | TGACAGCGATGCATACAGTAGT | 1387 |
| 44 | TTCTGCTAACGGTATCCAATAC | 1388 |
| 45 | GAGTCGTCCATACGATCTAGGA | 1389 |
| 46 | AGACGGACTCAACGCCAATTCC | 1390 |
| 47 | GTAGTGTTGAGCGGACCGAGCT | 1391 |
| 48 | AATATAACTAGATCATAGCCAG | 1392 |
| 49 | TCAATCGGAGAATACAGAACGT | 1393 |
| 50 | ATCTCCGTCGTCCGAACCAACA | 1394 |
| 51 | TAGGCGTTCAGCGGTATGCTTA | 1395 |
| 52 | TGCGTGCTATACAACCTATACG | 1396 |
| 53 | ATGGCCGGCATACATCTGTATG | 1397 |
| 54 | TGATGCTGACATAACACTGAAT | 1398 |
| 55 | ATCCAAGGTACCTGAACATCCT | 1399 |
| 56 | TAGTGACGACCAGGTGAGCCTC | 1400 |
| 57 | AGGAGGATCCGTCAAGTCGACC | 1401 |
| 58 | AGAGTATGCCAGATCGTGAGGC | 1402 |
| 59 | CCACTCACTAGGATGGCTGCGT | 1403 |
| 60 | TATCCAACCTGTTATAGCGATT | 1404 |
| 61 | TCTTGCAGTGAGTTGAGTCTGC | 1405 |
| 62 | CCACTGTTGTACATACACCTGG | 1406 |
| 63 | ATGCGCGTAGGCCACTAAGTCC | 1407 |
| 64 | ACAGCGGTCTACAACCGACTGC | 1408 |
| 65 | TCGCGCTCCAGACAATTGCAGC | 1409 |
| 66 | CCGGTAGACCAGGAGTGGTCAT | 1410 |
| 67 | ATCTCCTAACCTAGAGCCATCT | 1411 |
| 68 | CCACATCGAATCTAACAACTAC | 1412 |
| 69 | TAGTCTTATTGAATACGTCCTA | 1413 |
| 70 | TCCTTAAGCCTTGGAACTGGCG | 1414 |
| 71 | CCGTGATGGATTGACGTAGAGG | 1415 |
| 72 | GCCTGGATAACAGATGTCTTAG | 1416 |
| 73 | CTCGACCTATAATCTTCTGCCA | 1417 |
| 74 | AGCTACTTCTCCTTCCTAATCA | 1418 |
| 75 | ACACGTATTGCCTTCCAGTTA | 1419 |
| 76 | AAGCCTGTGCATGCAATGAGAA | 1420 |

TABLE 17-continued

List of random primers (22-base primers)

| No | Primer sequence | SEQ ID NO: |
|---|---|---|
| 77 | TCGTTGGTTATAGCACAACTTC | 1421 |
| 78 | GCGATGCCTTCCAACATACCAA | 1422 |
| 79 | CCACCGTTAGCACGTGCTACGT | 1423 |
| 80 | GTTACCACAATGCCGCCATCAA | 1424 |
| 81 | GGTGCATTAAGAACGAACTACC | 1425 |
| 82 | TCCTTCCGGATAATGCCGATTC | 1426 |
| 83 | AACCGCAACTTCTAGCGGAAGA | 1427 |
| 84 | TCCTTAAGCAGTTGAACCTAGG | 1428 |
| 85 | TACTAAGTCAGATAAGATCAGA | 1429 |
| 86 | TTCGCCATAACTAGATGAATGC | 1430 |
| 87 | AAGAAGTTAGACGCGGTGGCTG | 1431 |
| 88 | GTATCTGATCGAAGAGCGGTGG | 1432 |
| 89 | TCAAGAGCTACGAAGTAAGTCC | 1433 |
| 90 | CGAGTACACAGCAGCATACCTA | 1434 |
| 91 | CTCGATAAGTTACTCTGCTAGA | 1435 |
| 92 | ATGGTGCTGGTTCTCCGTCTGT | 1436 |
| 93 | TCAAGCGGTCCAAGGCTGAGAC | 1437 |
| 94 | TGTCCTGCTCTGTTGCTACCGT | 1438 |
| 95 | AGTCATATCGCGTCACACGTTG | 1439 |
| 96 | GGTGAATAAGGACATGAGAAGC | 1440 |

TABLE 18

List of random primers (24-base primers)

| No | Primer sequence | SEQ ID NO: |
|---|---|---|
| 1 | CCTGATCTTATCTAGTAGAGACTC | 1441 |
| 2 | TTCTGTGTAGGTGTGCCAATCACC | 1442 |
| 3 | GACTTCCAGATGCTTAAGACGACA | 1443 |
| 4 | GTCCTTCGACGGAGAACATCCGAG | 1444 |
| 5 | CTTGGTTAGTGTACCGTCAACGTC | 1445 |
| 6 | AAGCGGCATGTGCCTAATCGACGT | 1446 |
| 7 | CGACCGTCGTTACACGGAATCCGA | 1447 |
| 8 | TCGCAAGTGTGCCGTTCTGTTCAT | 1448 |
| 9 | CGTACTGAAGTTCGGAGTCGCCGT | 1449 |
| 10 | CCACTACAGAATGGTAGCAGATCA | 1450 |
| 11 | AGTAGGAGAGAGGCCTACACAACA | 1451 |
| 12 | AGCCAAGATACTCGTTCGGTATGG | 1452 |
| 13 | GTTCCGAGTACATTGAATCCTGGC | 1453 |
| 14 | AGGCGTACGAGTTATTGCCAGAGG | 1454 |
| 15 | GTGGCATCACACATATCTCAGCAT | 1455 |
| 16 | GAGACCGATATGTTGATGCCAGAA | 1456 |
| 17 | CAACTGTAGCCAGTCGATTGCTAT | 1457 |
| 18 | TATCAATGCAATGAGAGGATGCAG | 1458 |
| 19 | GTATGCTCGGCTCCAAGTACTGTT | 1459 |
| 20 | AGAGACTCTTATAGGCTTGACGGA | 1460 |
| 21 | ACTTAACAGATATGGATCATCGCC | 1461 |
| 22 | AATCAGAGCGAGTCTCGCTTCAGG | 1462 |
| 23 | ACCACCGAGGAACAGGTGCGACAA | 1463 |
| 24 | TGGTACATGTCAACCGTAAGCCTG | 1464 |
| 25 | CGTGCCGCGGTGTTCTTGTATATG | 1465 |
| 26 | GACAAGCGCGCGTGAGACATATCA | 1466 |
| 27 | AGTGCACTCCGAACAAGAGTTAGT | 1467 |
| 28 | CCTCATTACCGCGTTAGGAGTCCG | 1468 |
| 29 | TGCTTATTGCTTAGTTGCTATCTC | 1469 |
| 30 | GCGTGATCCTGTTCTATTCGTTAG | 1470 |
| 31 | GGCCAGAACTATGACGAGTATAAG | 1471 |
| 32 | GATGGCGACTATCTAATTGCAATG | 1472 |
| 33 | TAGTAACCATAGCTCTGTACAACT | 1473 |
| 34 | CGTGATCGCCAATACACATGTCGC | 1474 |
| 35 | TAATAACGGATCGATATGCACGCG | 1475 |
| 36 | ATCATCGCGCTAATACTATCTGAA | 1476 |
| 37 | CACGTGCGTGCAGGTCACTAGTAT | 1477 |
| 38 | AGGTCCAATGCCGAGCGATCAGAA | 1478 |
| 39 | CAGCATAACAACGAGCCAGGTCAG | 1479 |
| 40 | ATGGCGTCCAATACTCCGACCTAT | 1480 |
| 41 | AGGAACATCGTGAATAATGAAGAC | 1481 |
| 42 | TCTCGACGTTCATGTAATTAAGGA | 1482 |
| 43 | TCGCGGTTAACCTTACTTAGACGA | 1483 |
| 44 | ATCATATCTACGGCTCTGGCGCCG | 1484 |
| 45 | GCAGATGGAGACCAGAGGTACAGG | 1485 |
| 46 | AGACAGAAGATTACCACGTGCTAT | 1486 |
| 47 | CCACGGACAACATGCCGCTTAACT | 1487 |
| 48 | CTTGAAGTCTCAAGCTATGAGAGA | 1488 |
| 49 | ACAGCAGTCGTGCTTAGGTCACTG | 1489 |
| 50 | AGGTGTTAATGAACGTAGGTGAGA | 1490 |
| 51 | AGCCACTATGTTCAAGGCTGAGCC | 1491 |
| 52 | GCAGGCGGTGTCGTGTGACAATGA | 1492 |

TABLE 18-continued

List of random primers (24-base primers)

| No | Primer sequence | SEQ ID NO: |
|---|---|---|
| 53 | AGCCATTGCTACAGAGGTTACTTA | 1493 |
| 54 | ACAATCGAACCTACACTGAGTCCG | 1494 |
| 55 | CCGATCTCAATAGGTACCACGAAC | 1495 |
| 56 | GATACGTGGCGCTATGCTAATTAA | 1496 |
| 57 | AGAGAGATGGCACACATTGACGTC | 1497 |
| 58 | CTCAACTCATCCTTGTAGCCGATG | 1498 |
| 59 | GTGGAATAACGCGATACGACTCTT | 1499 |
| 60 | ATCTACCATGCGAATGCTCTCTAG | 1500 |
| 61 | ATACGCACGCCTGACACAAGGACC | 1501 |
| 62 | GTCCACTCTCAGTGTGTAGAGTCC | 1502 |
| 63 | AATATATCCAGATTCTCTGTGCAG | 1503 |
| 64 | CCTTCCGCCACATGTTCGACAAGG | 1504 |
| 65 | ACTGTGCCATCATCCGAGGAGCCA | 1505 |
| 66 | TCTATGCCGCTATGGCGTCGTGTA | 1506 |
| 67 | CGTAACCTAAGGTAATATGTCTGC | 1507 |
| 68 | TACTGACCGTATCAAGATTACTAA | 1508 |
| 69 | TCATCGGAGCGCCATACGGTACGT | 1509 |
| 70 | GCAAGAGGAATGAACGAAGTGATT | 1510 |
| 71 | GGCTGATTGACATCCTGACTTAGT | 1511 |
| 72 | AAGGCGCTAGATTGGATTAACGTA | 1512 |
| 73 | GCTAGCTAGAAGAATAGGATTCGT | 1513 |
| 74 | CAGGTGACGGCCTCTATAACTCAT | 1514 |
| 75 | CAGGTTACACATACCACTATCTTC | 1515 |
| 76 | TTGCTACGTACCGTCTTAATCCGT | 1516 |
| 77 | CTCAACATGTCTTGCAAGCTTCGA | 1517 |
| 78 | GGTGCGGTACGTAGAACCAGATCA | 1518 |
| 79 | AATGCTCTCCAAGATCCTGACCTA | 1519 |
| 80 | GCTTCGCAGGTCTGGATGATGGAG | 1520 |
| 81 | ACATTGACCAGACAGCACCTTGCG | 1521 |
| 82 | AGGTATCAATGTGCTTAATAGGCG | 1522 |
| 83 | TCCGGACACACGATTAGTAACGGA | 1523 |
| 84 | TACGAAGTACTACAGATCGGTCAG | 1524 |
| 85 | AATTGTCAGACGAATACTGCTGGA | 1525 |
| 86 | TGAATCATGAGCCAGAGGTTATGC | 1526 |
| 87 | CACAAGACACGTCATTAACATCAA | 1527 |
| 88 | GAATGACTACATTACTCCGCCAGG | 1528 |
| 89 | AGCCAGAGATACTGGAACTTGACT | 1529 |
| 90 | TATCAGACACATCACAATGGATAC | 1530 |

TABLE 18-continued

List of random primers (24-base primers)

| No | Primer sequence | SEQ ID NO: |
|---|---|---|
| 91 | CTAGGACACCGCTAGTCGGTTGAA | 1531 |
| 92 | GTATAACTGCGTGTCCTGGTGTAT | 1532 |
| 93 | ATGCAATACTAAGGTGGACCTCCG | 1533 |
| 94 | ATGCAGACGCTTGCGATAAGTCAT | 1534 |
| 95 | TTGCTCGATACACGTAGACCAGTG | 1535 |
| 96 | TACTGGAGGACGATTGTCTATCAT | 1536 |

TABLE 19

List of random primers (26-base primers)

| No | Primer sequence | SEQ ID NO: |
|---|---|---|
| 1 | ACTAAGGCACGCTGATTCGAGCATTA | 1537 |
| 2 | CGGATTCTGGCACGTACAAGTAGCAG | 1538 |
| 3 | TTATGGCTCCAGATCTAGTCACCAGC | 1539 |
| 4 | CATACACTCCAGGCATGTATGATAGG | 1540 |
| 5 | AGTTGTAAGCCAACGAGTGTAGCGTA | 1541 |
| 6 | GTATCAGCTCCTTCCTCTGATTCCGG | 1542 |
| 7 | AACATACAGAATGTCTATGGTCAGCT | 1543 |
| 8 | GACTCATATTCATGTTCAGTATAGAG | 1544 |
| 9 | AGAGTGAACGAACGTGACCGACGCTC | 1545 |
| 10 | AATTGGCGTCCTTGCCACAACATCTT | 1546 |
| 11 | TCGTAGACGCCTCGTACATCCGAGAT | 1547 |
| 12 | CCGGCTCGTGAGGCGATAATCATATA | 1548 |
| 13 | AGTCCTGATCACGACCACGACTCACG | 1549 |
| 14 | GGCACTCAATCCTCCATGGAGAAGCT | 1550 |
| 15 | TCATCATTCCTCACGTTCACCGGTGA | 1551 |
| 16 | TCAACTCTGTGCTAACCGGTCGTACA | 1552 |
| 17 | TGTTCTTATGCATTAATGCCAGGCTT | 1553 |
| 18 | GATTCACGACCTCAACAGCATCACTC | 1554 |
| 19 | GGCGAGTTCGACCAGAATGCTGGACA | 1555 |
| 20 | TTCCGTATACAATGCGATTAAGATCT | 1556 |
| 21 | GAGTAATCCGTAACCGGCCAACGTTG | 1557 |
| 22 | CGCTTCCATCATGGTACGGTACGTAT | 1558 |
| 23 | CCGTCGTGGTGTGTTGACTGGTCAAC | 1559 |
| 24 | TATTCGCATCTCCGTATTAGTTGTAG | 1560 |
| 25 | TATTATTGTATTCTAGGCGGTGCAAC | 1561 |
| 26 | AGGCTGCCTACTTCCTCGTCATCTCG | 1562 |
| 27 | GTAACATACGGCTCATCGAATGCATC | 1563 |

TABLE 19-continued

List of random primers (26-base primers)

| No | Primer sequence | SEQ ID NO: |
|---|---|---|
| 28 | TTATGGCACGGATATTACCGTACGCC | 1564 |
| 29 | ATAGCACTTCCTCTAATGCTCTGCTG | 1565 |
| 30 | TCACAGGCAATAGCCTAATATTATAT | 1566 |
| 31 | GGCGGATGTTCGTTAATATTATAAGG | 1567 |
| 32 | TGCAATAGCCGTTGTCTCTGCCAGCG | 1568 |
| 33 | TACAGCGCGTTGGCGAGTACTGATAG | 1569 |
| 34 | TGCAGTTAGTACCTTCTCACGCCAAC | 1570 |
| 35 | CCATTGGCTACCTAGCAGACTCTACC | 1571 |
| 36 | AACAGTAGCTCGCGTCTTGCTCTCGT | 1572 |
| 37 | GCAGTCCATCAGCTCTCGCTTATAGA | 1573 |
| 38 | TATCTCTCTGTCGCCAGCTTGACCAA | 1574 |
| 39 | CAGACTGTTCAAGCTTGCTGTAGGAG | 1575 |
| 40 | TAACCGGAACTCGTTCAGCAACATTC | 1576 |
| 41 | TCAATTATGCATGTCGTCCGATCTCT | 1577 |
| 42 | TTGTCTAAGTCAACCTGTGGATAATC | 1578 |
| 43 | TCTAAGAGTGGTATGACCAGGAGTCC | 1579 |
| 44 | TCGTAGTACTACTGGAACAGGTAATC | 1580 |
| 45 | ATGTCAACATTCTAATCATCTCTCGG | 1581 |
| 46 | AGCGCGCAACTGTTACGGTGATCCGA | 1582 |
| 47 | GCGATAGAATAATGGTGTCACACACG | 1583 |
| 48 | AAGGCTGCGATGAGAGGCGTACATCG | 1584 |
| 49 | GGTTCATGGTCTCAGTCGTGATCGCG | 1585 |
| 50 | TAGTGACTCTATGTCACCTCGGAGCC | 1586 |
| 51 | ATGTGATAGCAATGGCACCTCTAGTC | 1587 |
| 52 | TCGCGAAGTGTAATGCATCATCCGCT | 1588 |
| 53 | ATGTGGCGACGATCCAAGTTCAACGC | 1589 |
| 54 | ACCTTGTATGAGTCGGAGTGTCCGGC | 1590 |
| 55 | ACCTCAAGAGAGTAGACAGTTGAGTT | 1591 |
| 56 | GGTGTAATCCTGTGTGCGAAGCTGGT | 1592 |
| 57 | ATAGCGGAACTGTACGACGCTCCAGT | 1593 |
| 58 | AAGCACGAGTCGACCATTAGCCTGGA | 1594 |
| 59 | ATTCCGGTAACATCAGAAGGTACAAT | 1595 |
| 60 | GTGCAACGGCAGTCCAGTATCCTGGT | 1596 |
| 61 | CCATCTTATACACGGTGACCGAAGAT | 1597 |
| 62 | GCACTTAATCAAGCTTGAGTGATGCT | 1598 |
| 63 | AGTATTACGTGAGTACGAAGATAGCA | 1599 |
| 64 | TTCTTAGGTTAAGTTCCTTCTGGACC | 1600 |
| 65 | GTCCTTGCTAGACACTGACCGTTGCT | 1601 |
| 66 | GCCGCTATGTGTGCTGCATCCTAAGC | 1602 |
| 67 | CCATCAATAACAGACTTATGTTGTGA | 1603 |
| 68 | CGCGTGTGCTTACAAGTGCTAACAAG | 1604 |
| 69 | CGATATGTGTTCGCAATAAGAGAGCC | 1605 |
| 70 | CGCGGATGTGAGCGGCTCAATTAGCA | 1606 |
| 71 | GCTGCATGACTATCGGATGGAGGCAT | 1607 |
| 72 | CTATGCCGTGTATGGTACGAGTGGCG | 1608 |
| 73 | CCGGCTGGAGTTCATTACGTAGGCTG | 1609 |
| 74 | TGTAGGCCTACTGAGCTAGTATTAGA | 1610 |
| 75 | CCGTCAAGTGACTATTCTTCTAATCT | 1611 |
| 76 | GGTCTTACGCCAGAGACTGCGCTTCT | 1612 |
| 77 | CGAAGTGTGATTATTAACTGTAATCT | 1613 |
| 78 | GCACGCGTGGCCGTAAGCATCGATTA | 1614 |
| 79 | ATCCTGCGTCGGAACGTACTATAGCT | 1615 |
| 80 | AGTATCATCATATCCATTCGCAGTAC | 1616 |
| 81 | AGTCCTGACGTTCATATATAGACTCC | 1617 |
| 82 | CTTGCAGTAATCTGAATCTGAAGGTT | 1618 |
| 83 | ATAACTTGGTTCCAGTAACGCATAGT | 1619 |
| 84 | GATAAGGATATGGCTGTAGCGAAGTG | 1620 |
| 85 | GTGGAGCGTTACAGACATGCTGAACA | 1621 |
| 86 | CGCTTCCGGCAGGCGTCATATAAGTC | 1622 |
| 87 | ATAACATTCTAACCTCTATAAGCCGA | 1623 |
| 88 | ACGATCTATGATCCATATGGACTTCC | 1624 |
| 89 | TGAAGCTCAGATATCATGCCTCGAGC | 1625 |
| 90 | AGACTTCACCGCAATAACTCGTAGAT | 1626 |
| 91 | AGACTAAGACATACGCCATCACCGCT | 1627 |
| 92 | TGTAGCGTGATGTATCGTAATTCTGT | 1628 |
| 93 | TGTGCTATTGGCACCTCACGCTGACC | 1629 |
| 94 | TGTAGATAAGTATCCAGCGACTCTCT | 1630 |
| 95 | AATTCGCCAATTGTGTGTAGGCGCAA | 1631 |
| 96 | CGATTATGAGTACTTGTAGACCAGCT | 1632 |

TABLE 20

List of random primers (28-base primers)

| No | Primer sequence | SEQ ID NO: |
|---|---|---|
| 1 | TTGCAAGAACAACGTATCTCATATGAAC | 1633 |
| 2 | CACCGTGCTGTTATTACTTGGTATTCGG | 1634 |
| 3 | CACGTGTATTGTTGCACCAGAACGACAA | 1635 |

TABLE 20-continued

List of random primers (28-base primers)

| No | Primer sequence | SEQ ID NO: |
|---|---|---|
| 4 | ATGCACGTAATTACTTCCGGAGAAGACG | 1636 |
| 5 | TATGTTGTCTGATATGGTTCATGTGGCA | 1637 |
| 6 | AGCGCGACTAGTTGATGCCAACATTGTA | 1638 |
| 7 | ATAGGCAGGTCCAGGCTCGGAACAAGTC | 1639 |
| 8 | GCGGTAGTCGGTCAAGAACTAGAACCGT | 1640 |
| 9 | ACTATACACTCTAGCTATTAGGAAGCAT | 1641 |
| 10 | GATCATCTTGCTTCTCCTGTGGAGATAA | 1642 |
| 11 | CTACTACGAGTCCATAACTGATAGCCTC | 1643 |
| 12 | GCACAGACACCTGTCCTATCTAGCAGGA | 1644 |
| 13 | AAGCGAGGCGCGAAGGAGATGGAAGGAT | 1645 |
| 14 | CTGAAGACGCCAGTCTGGATAGGTGCCT | 1646 |
| 15 | GTAAGCTCTGTCCTTCGAGATTGATAAG | 1647 |
| 16 | GGTTAGAGAGATTATTGTGCGCATCCAT | 1648 |
| 17 | CCAGGAGGACCTATGATCTTGCCGCCAT | 1649 |
| 18 | ACTATTCGAGCTACTGTATGTGTATCCG | 1650 |
| 19 | GACATCGCGATACGTAACTCCGGAGTGT | 1651 |
| 20 | CCGCAATTCGTCTATATATTCTAGCATA | 1652 |
| 21 | CTACACTTGAGGTTGATGCTCAAGATCA | 1653 |
| 22 | CGATCAGTTCTAGTTCACCGCGGACAAT | 1654 |
| 23 | AAGAATGATGATTGGCCGCGAACCAAGC | 1655 |
| 24 | CACGACCGGAACTAGACTCCTACCAATT | 1656 |
| 25 | AGTTGCCTGTGAGTGAGGCTACTATCTC | 1657 |
| 26 | GATTCTTCCGATGATCATGCCACTACAA | 1658 |
| 27 | CGCTGAAGTGAACTATGCAAGCACCGCA | 1659 |
| 28 | ATTATCGTGATGGTGAGACTGAGCTCGT | 1660 |
| 29 | CGAGGCCACTCTGAGCCAGGTAAGTATC | 1661 |
| 30 | TGCCGAGGACAGCCGATCACATCTTCGT | 1662 |
| 31 | GTTGACATGAAGGTTATCGTCGATATTC | 1663 |
| 32 | GTGGTCCAGGTCAAGCTCTGATCGAATG | 1664 |
| 33 | CCAGTCCGGTGTACTCAGACCTAATAAC | 1665 |
| 34 | CGAGACACTGCATGAGCGTAGTCTTATT | 1666 |
| 35 | GACGGCTTGTATACTTCTCTACGGTCTG | 1667 |
| 36 | TTAGCTGGATGGAAGCCATATTCCGTAG | 1668 |
| 37 | CAGCCTACACTTGATTACTCAACAACTC | 1669 |
| 38 | GTACGTAGTGTCACGCGCCTACGTTCGT | 1670 |
| 39 | CTACAACTTCTCAATCATGCCTCTGTTG | 1671 |
| 40 | CGAGGACAGAATTCGACATAAGGAGAGA | 1672 |
| 41 | GCCGAACGACACAGTGAGTTGATAGGTA | 1673 |
| 42 | GAACACTATATGCTGTCGCTGTCTGAGG | 1674 |
| 43 | GTTAAGTTCTTCGGCGGTCATGCTCATT | 1675 |
| 44 | TTGCTTACAGATCGCGTATCCATAGTAT | 1676 |
| 45 | GAGGACCACCTCTGCGAAGTTCACTGTG | 1677 |
| 46 | AATCCTAGCATATCGAGAACGACACTGA | 1678 |
| 47 | TGAATACTATAGCCATAGTCGACTTCCG | 1679 |
| 48 | GACATCCACGAAGCTGGTAATCGGAACC | 1680 |
| 49 | TTAGCCGTCTTAGAAGTGTCTGACCGGC | 1681 |
| 50 | CTATTCTGCCGTAATTGATTCCTTCGTT | 1682 |
| 51 | ACGCCTCTGGTCGAAGGTAGATTAGCTC | 1683 |
| 52 | CAGCCTATTGATCGTAAGTAGATGGTCC | 1684 |
| 53 | TTAAGTGAGGTGGACAACCATCAACTTC | 1685 |
| 54 | AAGGCCTTGCGGCTAAGTAGTATTCATC | 1686 |
| 55 | TTGTGATACTAATTCTTCTCAAGAGTCA | 1687 |
| 56 | GCATTAGGTGACGACCTTAGTCCATCAC | 1688 |
| 57 | GCGGATGGACGTATACAGTGAGTCGTGC | 1689 |
| 58 | GAACATGCCAGCCTCAACTAGGCTAAGA | 1690 |
| 59 | TCCGTCATTAGAGTATGAGTGACTACTA | 1691 |
| 60 | AACACTTAGTAACCAGTTCGGACTGGAC | 1692 |
| 61 | CGCTAACTATTGCGTATATTCGCGGCTT | 1693 |
| 62 | GCCATCTACGATCTTCGGCTTATCCTAG | 1694 |
| 63 | CCTGAGAATGTTGACTAAGATCTTGTGA | 1695 |
| 64 | TCGGTTAGTCTAATCATCACGCAACGGA | 1696 |
| 65 | ATTATCTATTGAAGCAGTGACAGCGATC | 1697 |
| 66 | GAGGAGAATCACGGAACACGGTCACATG | 1698 |
| 67 | GCTGCAAGCATTATGACCATGGCATCTG | 1699 |
| 68 | GAACAACCTATAACGACGTTGTGGACAA | 1700 |
| 69 | TTAATCATCGATAGACGACATGGAATCA | 1701 |
| 70 | TCGAGTGTAAGCACACTACGATCTGGAA | 1702 |
| 71 | GCTACGCACAGTCTCTGCACAGCTACAC | 1703 |
| 72 | CCTGTATGTACGTTCTGGCTAATACCTT | 1704 |
| 73 | TGAAGCACCGGTACATGGTGTATCCGGA | 1705 |
| 74 | TGCTGGAACCTAACTCGGTGATGACGAT | 1706 |
| 75 | CGCTATCTTACTGCCAAGTTCTCATATA | 1707 |
| 76 | AACGCGCGCGTATCGGCAATAATCTCAA | 1708 |
| 77 | CCATTAGGATGACCATCGACTATTAGAG | 1709 |
| 78 | TACTGCTAGACTGCGTGCATTCATGGCG | 1710 |
| 79 | CATTGCGCGCTCCACGAACTCTATTGTC | 1711 |

TABLE 20-continued

List of random primers (28-base primers)

| No | Primer sequence | SEQ ID NO: |
|---|---|---|
| 80 | GACGCGCCTAGAACTGTATAGCTCTACG | 1712 |
| 81 | CATTGCAACTTGTCGGTGATGGCAATCC | 1713 |
| 82 | TTAATGCACATGCAGTACGGCACCACAG | 1714 |
| 83 | AGCGGTACGTGGACGAGTGGTAATTAAT | 1715 |
| 84 | GACGTATTGCTATGCATTGGAAGATGCT | 1716 |
| 85 | AACACTTCGACCATTGCGCCTCAATGGT | 1717 |
| 86 | CGGTACGCTCTAGCGGTCATAAGATGCA | 1718 |
| 87 | CCTGAATAACAGCCGCGCCTAATTAGAT | 1719 |
| 88 | AAGCGTCTAATGTGCCTTAAGTCACATG | 1720 |
| 89 | GCTCTCCAAGAACCAGAAGTAAGCATCG | 1721 |
| 90 | GAGGAGAGTTGTCCGAGTGGTGTGATGT | 1722 |
| 91 | TAACGAGTGGTGCGTCTAAGCAATTGAG | 1723 |
| 92 | CCAACAGTATGCTGACATAACTATGATA | 1724 |
| 93 | GATCCTTGCCACGCCTATGAGATATCGC | 1725 |
| 94 | AACGCGCTACCGTCCTTGTGCATAGAGG | 1726 |
| 95 | CTACATGTGCCTTATAGTACAGAGGAAC | 1727 |
| 96 | CAGCCTCGTAGTTAGCGTGATTCATGCG | 1728 |

TABLE 21

List of random primers (29-base primers)

| No | Primer sequence | SEQ ID NO: |
|---|---|---|
| 1 | CTCCTCGCCGATTGAAGTGCGTAGAACTA | 1729 |
| 2 | CAGCAGGCCTCAATAGGATAAGCCAACTA | 1730 |
| 3 | GACCATCAATCTCGAAGACTACGCTCTGT | 1731 |
| 4 | GGTTGCTCCGTCTGTTCAGCACACTGTTA | 1732 |
| 5 | AATGTCGACTGGCCATTATCGCCAAGTGT | 1733 |
| 6 | GATAGCTTGCCATGCGAATGGATCTCCAG | 1734 |
| 7 | CCAGACCGGAGCCAATTGGCTGCCAATAT | 1735 |
| 8 | AACGTCGCTCCATACGTTACCTAATGCAG | 1736 |
| 9 | GAATATGACGCGAACAGTCTATTCGGATC | 1737 |
| 10 | GACGAGAATGTATTAAGGATAAGCAAGGT | 1738 |
| 11 | AAGTCGTATGAATCGCTATCACATGAGTC | 1739 |
| 12 | GTCGTGGAGACTACAATTCTCCTCACGTT | 1740 |
| 13 | GTTGCCACCGTTACACGACTATCGACAGT | 1741 |
| 14 | AGGATAGGCTACGCCTTACTCTCCTAAGC | 1742 |
| 15 | TAATCATCCTGTTCGCCTCGAGGTTGTTA | 1743 |
| 16 | GACAAGCAGTAATAATTACTGAGTGGACG | 1744 |

TABLE 21-continued

List of random primers (29-base primers)

| No | Primer sequence | SEQ ID NO: |
|---|---|---|
| 17 | TACAGCGTTACGCAGGTATATCAAGGTAG | 1745 |
| 18 | CTAACATCACTTACTATTAGCGGTCTCGT | 1746 |
| 19 | CCGCGCTTCTTGACACGTTCTCCACTAGG | 1747 |
| 20 | CAAGTAACATGAGATGCTATCGGTACATT | 1748 |
| 21 | CGACCACTAGGCTGTGACCACGATACGCT | 1749 |
| 22 | CAGGTCATGTGACGCAGTCGGCAGTCAAC | 1750 |
| 23 | ACTCCATCGTTAGTTCTTCCGCCGTGCTG | 1751 |
| 24 | CTCACCACGTATGCGTCACTCGGTTACGT | 1752 |
| 25 | TGCCTATGCTATGGACCTTGCGCGACTCT | 1753 |
| 26 | AATGAAGGTCAACGCTCTGTAGTTACGCG | 1754 |
| 27 | CACCATTGATTCATGGCTTCCATCACTGC | 1755 |
| 28 | GACACGCAAGGTAATTCGAGATTGCAGCA | 1756 |
| 29 | CACCGAGAGGAAGGTTCGATCGCTTCTCG | 1757 |
| 30 | CAGTTATCGGATTGTGATATTCACTCCTG | 1758 |
| 31 | ATACTGTAACGCCTCAACCTATGCTGACT | 1759 |
| 32 | ATCTGTCTTATTCTGGCACACTCAGACTT | 1760 |
| 33 | TCCAACCGGTGACGTGCTCTTGATCCAAC | 1761 |
| 34 | CACACTCAGTTCGGCTATCTCTGCGATAG | 1762 |
| 35 | AGCTGTAAGTCAGGTCTACGACTCGTACT | 1763 |
| 36 | GTCGGCGGCACGCACAGCTAACATTCGTA | 1764 |
| 37 | ATATGGTAGCCAGCCACGTATACTGAACA | 1765 |
| 38 | TGGACAATCCGACTCTAACACAGAGGTAG | 1766 |
| 39 | TCCGCCGCTGACAGTTCAATCTATCAATT | 1767 |
| 40 | GGTTCCTTAGAATATGCACCTATCAGCGA | 1768 |
| 41 | CGGCTGTACGACATGGATCATAAGAGTGT | 1769 |
| 42 | TGCAGATGTACGCTGTGGCCAGTGGAGAG | 1770 |
| 43 | CCTACTCACTTAACAATAATCGGTTCGGT | 1771 |
| 44 | CGCTTCCTACTGCCTGTGCCGCGACATAA | 1772 |
| 45 | CTAGACCGACCGGTTATGCGCTATTGTTC | 1773 |
| 46 | TTGTGAGCACGTCTGCGGCAAGCCTATGG | 1774 |
| 47 | TCATCGGCCGGCGCTGTTGTTGTTACCAT | 1775 |
| 48 | GCGGTTAGGTGCAGTTAGGAAGACTATCA | 1776 |
| 49 | TATGCGGTCGTGAGGCGTAGCATTCTAGA | 1777 |
| 50 | CCATCTATTCGTCGAACTCTCAGCTCGTA | 1778 |
| 51 | ATCGATCTACTGATCGCGGTAGAGTATC | 1779 |
| 52 | TACACATAGGCGGCGCAGCCTTCTAATTA | 1780 |
| 53 | TTAACCGTAGTTCTTAGCTTACGCCGCTC | 1781 |
| 54 | ACTATAGAGGACATGGCACTCCTCTTCTA | 1782 |

TABLE 21-continued

List of random primers (29-base primers)

| No | Primer sequence | SEQ ID NO: |
|---|---|---|
| 55 | CAGTTCGTATTAAGATTGAATGTAGCGGT | 1783 |
| 56 | AGTTATCGGTATCCGCTTATCCGTACGTA | 1784 |
| 57 | AGCTTATTCATACACTGCACCACAGCAAG | 1785 |
| 58 | CCGTCGGCTAGTCTATCCTCTAATTAGAA | 1786 |
| 59 | GTCCGCTTCCATGCCTGCTGTACGAACAC | 1787 |
| 60 | TCTCTTCCTCCTTCATTGTTCGCTAGCTC | 1788 |
| 61 | TCTCTTGAGCGGTCCTCATACAGGTCTGC | 1789 |
| 62 | GACCAAGTGTAGGTGATATCACCGGTACT | 1790 |
| 63 | AAGATTGTGATAGGTTGGTAGTTACCACA | 1791 |
| 64 | TCGCCTCCGAAGAGTATAGCATCGGCAGA | 1792 |
| 65 | GAGGTAGTTATGAGCATCGAGGTCCTGTT | 1793 |
| 66 | GGACGCAAGATCGCAGGTACTTGTAAGCT | 1794 |
| 67 | ACTCGTACACGTCATCGTGCAGGTCTCAG | 1795 |
| 68 | TAATCCGTCAGGAGTGAGATGGCTCGACA | 1796 |
| 69 | AAGATGGTTCCGCGCATTGACTAGCAAGT | 1797 |
| 70 | TCCGCGATCTGCGGATCTTGAATGCTCAC | 1798 |
| 71 | TTCACGAGAGTCAACTGCTAGTATCCTAG | 1799 |
| 72 | TTCCAACTGGATTCTTCCAACTCCTCGAA | 1800 |
| 73 | CACTACTACTCAAGTTATACGGTGTTGAC | 1801 |
| 74 | CAACTGGATTCTCAGGATGCGTCTCTAGC | 1802 |
| 75 | TGGACTAGAGTGGAGCGATTACGTAATAT | 1803 |
| 76 | GAGGTCATTCAACTGGACTCGCCACGGAC | 1804 |
| 77 | CAGGTGTGTAACGCTGCAATCACATGAAT | 1805 |
| 78 | TATGCTGAGGTATTAGTTCTAACTATGCG | 1806 |
| 79 | CGTCTGAGTCGGATAAGGAAGGTTACCGC | 1807 |
| 80 | GTACTATCGTCGCAGGCACTATCTCTGCC | 1808 |
| 81 | GCTTCCTCCTTGCAACTTCATTGCTTCGA | 1809 |
| 82 | TGTCTACGAAGTAGAAGACACGAATAATG | 1810 |
| 83 | CCGTCATCTAAGGCAGAGTACATCCGCGA | 1811 |
| 84 | CCGGAGGCGTACTAACTGACCACAACACC | 1812 |
| 85 | AACTCGTCGCTGCCTGAATAGGTCAGAGT | 1813 |
| 86 | TTATAAGATTAATGTCGGTCAGTGTCGGA | 1814 |
| 87 | CGTCTCGATGGATCCACACGAACCTGTTG | 1815 |
| 88 | ATGCCATCATGGTCGTCCTATCTTAAGGC | 1816 |
| 89 | GCGCTTCAGCGATTCGTCATGCAAGGCAC | 1817 |
| 90 | CCAAGCGATACCGAGGTACGGTTAACGAG | 1818 |
| 91 | ATATGACAGACAGGTGGACCTAAGCAAGC | 1819 |
| 92 | CACTACATCGTCAGGCCTGGAAGCCTCAG | 1820 |
| 93 | GCCGTGTAGACGAGGACATTATGTCGTAT | 1821 |
| 94 | CAACGTATATATACACCTTGTGAAGAGAA | 1822 |
| 95 | TCCAACGTAATTCCGCCGTCTGTCGAGAC | 1823 |
| 96 | AATTCGTGCTTCGATCACCGTAGACTCAG | 1824 |

TABLE 22

List of random primers (30-base primers)

| No | Primer sequence | SEQ ID NO: |
|---|---|---|
| 1 | ACTATATTGTATTCACGTCCGACGACTCGC | 1825 |
| 2 | GACGAGCTTGTGGTACACTATACCTATGAG | 1826 |
| 3 | TGATTCAAGCACCAGGCATGCTTAAGCTAG | 1827 |
| 4 | CGGTCTCCTATAGGAAGGCTCATTCTGACG | 1828 |
| 5 | AGTCAGTGTCGAATCAATCAAGGCGTCCTT | 1829 |
| 6 | CGAACGTAATGGCCATCACGCGCTGGCCTA | 1830 |
| 7 | CGAACCTGGACCACCTGGCATTACCATTAC | 1831 |
| 8 | ACATTAGGTTCCTGTAATGTCTTATCAACG | 1832 |
| 9 | CGTCTAATGCACCGTATCGTCTTCGCGCAT | 1833 |
| 10 | TCTATGACTTACAACGGAATCTTACTTCGT | 1834 |
| 11 | GTAACCGATCGGTACCGTCTGCTATTGTTC | 1835 |
| 12 | GGTGATTGATAAGCAACACATATTAGGAGG | 1836 |
| 13 | AATTATCGACGCTAATAGGCGAGCTGTTCA | 1837 |
| 14 | GGAGGTACATGACGAGTGGACAGACAGACC | 1838 |
| 15 | CTCTAATCCGTTATGCGGTGATGTAATCCG | 1839 |
| 16 | GCAAGCACGCGGCTTGGCGAACTTCTATGC | 1840 |
| 17 | TAGATGTAGGCCTGGTAGGCAGAGGAGTAA | 1841 |
| 18 | CCGAGTGGCGACCACACAGGTACGCATTAA | 1842 |
| 19 | GTCCTGGCTCAGATTAGTGCACTTAGTTAT | 1843 |
| 20 | GCGGTACCTACATGTTATGACTCAGACGAC | 1844 |
| 21 | TCTCTGCCAATGCTGGTCTCATCGAATCCA | 1845 |
| 22 | TCTCTACACAGCTACATACTATACTGTAAC | 1846 |
| 23 | TACGACGGACGCTGGTGGTGTAAGAGAAGG | 1847 |
| 24 | GCCTCGATATATCTACGTATAGTTCAAGTT | 1848 |
| 25 | GGCTCCTGCATTCATTGAAGGTCGGCCTTG | 1849 |
| 26 | CAGTTCGGTGATTCAAGAGAACAATGGTGG | 1850 |
| 27 | TATAACGAAGCCGGCTGGAACGGTAACTCA | 1851 |
| 28 | CTGTATCAATTCAAGTGACAGTGGCACGTC | 1852 |
| 29 | AGCAATTGCGGTTCATAGGCGTAATTATAT | 1853 |
| 30 | CATATGGACCTGGAGATCACCGTTCAGTCC | 1854 |

TABLE 22-continued

List of random primers (30-base primers)

| No | Primer sequence | SEQ ID NO: |
|---|---|---|
| 31 | GAAGGCCGTTGGTCTATCTCTTACTGGAGC | 1855 |
| 32 | GTGCGTTCATCTAGCCTAAGACGCTGACCT | 1856 |
| 33 | GAGTAACTTATATCCTCTCTACGACATCGA | 1857 |
| 34 | ATTCTACGCTGATGTCTCCGCTGAACAGGA | 1858 |
| 35 | TCATCAACGTTACTCACTAGTACCACGGCT | 1859 |
| 36 | AACCATTCTTGAACGTTGAGAACCTGGTGG | 1860 |
| 37 | ACGACACCTCCGCGGAACATACCTGATTAG | 1861 |
| 38 | GCGCACTTATTGAAGTAATCTCATGGCCAA | 1862 |
| 39 | GCGCCAATTCAGCCAGTTAGCGTCTCCGTG | 1863 |
| 40 | AGCAACAAGTCGCTGTATATCGACTGGCCG | 1864 |
| 41 | CCTTACAATAGACCTCGCGGCGTTCATGCC | 1865 |
| 42 | GGATCCAACTTCAGCGAAGCACCAACGTCG | 1866 |
| 43 | GCGCCAGTTCTCGTACTCTCGAGAAGCGAC | 1867 |
| 44 | GAGTGCGGCCAATCTGGAACTCATGACGTT | 1868 |
| 45 | CCTGAGAGTGATTCGTGTCTGCGAAGATGC | 1869 |
| 46 | GTGACTGGTTAAGGCAATATTGGTCGACCG | 1870 |
| 47 | CTATCAAGCCTTACAAGGTCACGTCCACTA | 1871 |
| 48 | ACTGCGTCCTTGCGTCGGAACTCCTTGTGT | 1872 |
| 49 | TGCAACTCAGTGGCGGCGACACCAAGAGCT | 1873 |
| 50 | TTCGGTTCTACTAGGATCTCTATCTGAGCT | 1874 |
| 51 | AGCTAATCTATTAAGACAGATTAGACAGGA | 1875 |
| 52 | GGACCGCTCTTAGGTTATGCACCTGCGTAT | 1876 |
| 53 | CTCTAATACTAGTCCACAGGTTAGTACGAA | 1877 |
| 54 | ATCCATATATGCTCGTCGTCAGCCAGTGTT | 1878 |
| 55 | GCTATTACTGTGTTGATGTCCACAGGAGAA | 1879 |
| 56 | GCTACGGCGCAGATCTAGACAACTGGAAGT | 1880 |
| 57 | GCCTCTTGTGTTAGCCGAATACCAATGACC | 1881 |
| 58 | TGAGGACGATAACATTACCTCTCGAGTCGC | 1882 |
| 59 | CGATTACCAATCCGACGACTTCGCAGCAGC | 1883 |
| 60 | ATGACACGAGTCCAGTACATATGCGAAGAC | 1884 |
| 61 | GCGCTCGCATGCACTAGTGTAGACTGACGA | 1885 |
| 62 | GCACATCTCAGAATTGATGGTCTATGTCGC | 1886 |
| 63 | TTCTTCGACGCCGCGTACTAATAGGTCAAT | 1887 |
| 64 | GGAAGCGCCTCTAACAACCGATGCTTGTGG | 1888 |
| 65 | CTCTAGACGCGTCGTGACTCCAATCTGTTG | 1889 |
| 66 | GTAGTTCGTCGGAGTGACCTCGTACTCACT | 1890 |
| 67 | ATGCTGTCGAGTGTCCGGCATAGAGCACAC | 1891 |
| 68 | GCGCATCTTGCAGCGTCCTGTAGTTCTGAA | 1892 |
| 69 | GCGATTGTTGAGGAACCACAGCGGCACCTA | 1893 |
| 70 | CACGCGTACTCTGCTTGCTGTGTGGTCGGT | 1894 |
| 71 | CATCCAACGCAGGACCTAGTAGTCATGCTT | 1895 |
| 72 | TTCTAGTTGTGATGAGAATCGCTAGCGTGC | 1896 |
| 73 | CATTCTGAATCTGGTCTCTCTCGATCATCC | 1897 |
| 74 | ATTAATGTAGAGGATAGTTCCGTTCTCTCC | 1898 |
| 75 | GTATCGCGCTTACGAATGAGGTGTGGCTTC | 1899 |
| 76 | GCTGGTGAGAGAGCCAGATTATCGGTGGAG | 1900 |
| 77 | GGCACGAGCAGGTAGAACTAGAACCTAGAT | 1901 |
| 78 | TGTATTATCTCGAAGCGGTGCGTTAGAGTC | 1902 |
| 79 | CACGTGTTCTAGCTACTAATGGCGTCAATT | 1903 |
| 80 | CGCGCTACATTACTTCCTACACCATGCGTA | 1904 |
| 81 | TGAGGCAACTAGTGTTCGCAAGATGACGGA | 1905 |
| 82 | TTATTATTGTCTGTGGAACGCACGCCAGTC | 1906 |
| 83 | GCTATAGTATTATCCATGAATTCCGTCGGC | 1907 |
| 84 | GTATCAATAGCTCAATTCGTCAGAGTTGTG | 1908 |
| 85 | TAGTCCATGCGTGGATATATTGAGAGCTGA | 1909 |
| 86 | GCACAGTACGACTTATAACAGGTCTAGATC | 1910 |
| 87 | ACTCAATGGTGGCACGCTCGGCGCAGCATA | 1911 |
| 88 | GTAGTACCACTCCGCCTTAGGCAGCTTAAG | 1912 |
| 89 | CGCTCAACTGATGCGTGCAACCAATGTTAT | 1913 |
| 90 | GCAGCTTGACTGCCTAGACAGCAGTTACAG | 1914 |
| 91 | GCAACTTCTTAGTACGAATTCATCGTCCAA | 1915 |
| 92 | ATCCGTATGCTGCGGCAGTGGAGGTGGCTT | 1916 |
| 93 | TGCGGATCAATCCAGTTCTGTGTACTGTGA | 1917 |
| 94 | TTATGATTATCACCGGCGTAACATTCCGAA | 1918 |
| 95 | GCTACCTAGATTCTTCAACTCATCGCTACC | 1919 |
| 96 | CAGTGTTAGAATGGCGGTGTGTAGCCGCTA | 1920 |

TABLE 23

List of random primers (35-base primers)

| No | Primer sequence | SEQ ID NO: |
|---|---|---|
| 1 | GCTTATAGACTACAGCTGCGAGGTATAAGGTCACT | 1921 |
| 2 | CGCTCAGCAGGATGCTATCCTAAGTTAATGTGGTG | 1922 |
| 3 | GAACTGAGCGGACATCAGCTAGGCCTACAATACAT | 1923 |
| 4 | TCGTGAACTTCTGCGTTGGTCTCTACCAAGGCGGT | 1924 |
| 5 | TAAGTCAGGTATCTTATCAGTGGTACACGGTACGA | 1925 |

TABLE 23-continued

List of random primers (35-base primers)

| No | Primer sequence | SEQ ID NO: |
|---|---|---|
| 6 | TAATAATGTTGCGCGTGACCGAGGAGGAATCCACT | 1926 |
| 7 | CTAGGAGTTCTCGTAAGCTGGAGTACCGTAACGTG | 1927 |
| 8 | GGACTCTCCTCAGAGGATCCTTCTTGCGCAGGCAT | 1928 |
| 9 | GCTAGAGGCCTGAGTACACCTTCTCGCATCAGGAT | 1929 |
| 10 | ATATCGCGAGCACTAACGTCGTTGTCGTTCTAGGA | 1930 |
| 11 | AGCGGTTACTATACCTGGCGGCTGACGTTGTTAGT | 1931 |
| 12 | GAGCTAGGTAGATCTCCAAGTGTAGCTAAGAAGAG | 1932 |
| 13 | GGAGTCGCTGGTGACGTATGCCGAGGATGAGCTTC | 1933 |
| 14 | CGCCGACCTCCTGTTCACGAAGCCGCCTGATGTAA | 1934 |
| 15 | AGTAGGCACTTAGTTATCGATTACGTTAGTTAGTC | 1935 |
| 16 | GGATGACGTCTCAGTCTACCTCGCAGTGTCGTCTA | 1936 |
| 17 | CTGGTTCGCGTTAGCAATACTAAGGCAGTCAGGAG | 1937 |
| 18 | ATATGGTCATATTGGCCTCTTCGAACACAGACTGT | 1938 |
| 19 | TATCAGAGGATAGCAGGTCTGAGTTGCAAGGCTAA | 1939 |
| 20 | GGTGGTCTGACCATAGCTGTTCTTCTCACAGAGAC | 1940 |
| 21 | GCAATACCAACGAGATGAGTATTCGTTGAAGCTCT | 1941 |
| 22 | CCAAGTCGACGCTGCATGAATGAGCGCTATTCACT | 1942 |
| 23 | CCATTAGATCGCTTCGAGACAATTAGGAGACATGA | 1943 |
| 24 | GATGACTGTACCTCCTATCATTGAGTGTGGACCAA | 1944 |
| 25 | ATATCTGGATGAATAGTGGTTAGGTAAGCAAGTAA | 1945 |
| 26 | ACCGACTATGTTAATTCGTGTCTGGATGGCAGAAT | 1946 |
| 27 | GTGGCAGTCTTGCTAGTATCTTAGACCATCACCAA | 1947 |
| 28 | CGCTATCTTAGTCGAGCACAATGTCTTCGTATAGG | 1948 |
| 29 | ATTAGTACGGCACGAACCGGCCATTCATGGCAGCT | 1949 |
| 30 | AGTACGACTATCAAGACTCCAGCGCTCTCCTTGGA | 1950 |
| 31 | ATGAGCCTCGGAGCGAACGTTATCGATCAGGCTGT | 1951 |
| 32 | TTGCGTGCAGTAGCACCGATACACAGCGCTTGTAT | 1952 |
| 33 | AACGGCTGCATCACCTACACTATACTCAACATCTA | 1953 |
| 34 | GTCGCTATGCGAGAAGTGGCGTGGAATGCTATGGT | 1954 |
| 35 | CATGGATACCTACTGACTTGACTTCTAGAGGACCG | 1955 |
| 36 | GAGTGACGCAGACACCGTAACGTCGAATCTTCTAG | 1956 |
| 37 | AGTACCGTCTGTGTGAATATTGTTCCTACGTTACA | 1957 |
| 38 | GGCTAATCGATAGTGACGAGTTCTGCACGCCTGAA | 1958 |
| 39 | GGCGAGCGCTCGTGGTTCTGAGTCGCTGTTAGATG | 1959 |
| 40 | TATCTCCAGCGTTATAAGCTACTGGAGCCGCTCGG | 1960 |
| 41 | CCTTCTGCGCAAGTCAAGGATTCGCTTAGATGGAC | 1961 |
| 42 | GTTGCTGACAGCCGTTGCGTACTTGCCTTAAGAAC | 1962 |
| 43 | GTGGCCTAATCACTCGCGCTTCATAGGCCGATAGG | 1963 |
| 44 | TGCATCTAGCCTACATCGGACCTTGTTATGGTAAT | 1964 |
| 45 | GGACAGCTACTGGACACCACCGAACTGGTAGTGTC | 1965 |
| 46 | AACTGGCGATGGACGGCCGCTCTTCCGCTACATAG | 1966 |
| 47 | GGAGCAGTTAGCTATGGAGCAGGCCGATAACCTGA | 1967 |
| 48 | ACTCTACGGTGCACCTCAGCCTTCATGCAATAGGC | 1968 |
| 49 | CTTGTAGCACAATACATTACTCTCCACGTGATAGC | 1969 |
| 50 | GGACGCTATCGATACCGTTATTCCTACTCTGTCGG | 1970 |
| 51 | GGATGATCGTCAACGATCAACTGACAGTTAGTCGA | 1971 |
| 52 | TGACAGTAGCAATGTCTCACGTCTGCACAACGGAA | 1972 |
| 53 | GTCGCAGGACCTCACGGATAGTAGTGCGAGGTCTA | 1973 |
| 54 | ATATCGGCGGACGCAATGACAGTTGTTGGCTGATG | 1974 |
| 55 | AAGCACCAAGGAGGTATGTTCCATCGAGGCGCTCG | 1975 |
| 56 | GACCGCACCTTATAGCTATATCCTGGTCTAGTACT | 1976 |
| 57 | TCTCAGAGGAAGGTTGAGCGTCTGACCAGGTTGGC | 1977 |
| 58 | TGGACCTAGAGACCTAGCTCGTCTCTTCGCGATCG | 1978 |
| 59 | CGGAGTGGTTCCACGCGACCTCGCAACTAATCCTT | 1979 |
| 60 | GGAGCCGCGCGCAGACTGACCTTGCTTGATCTACT | 1980 |
| 61 | ACTCTAAGTATATGCGCAGTTAGTATACTGAACCA | 1981 |
| 62 | GAGCATTGCTTCGCTTCGATGTCTATTCTGATCAG | 1982 |
| 63 | GCTTGTATTGCCACTCGAGTAGGTCGTGGCAGTAG | 1983 |
| 64 | ATCTGGACATTGCATTCGGTGTGTATACAGAAGGC | 1984 |
| 65 | GGTTGCGATCAGCTTGATAGCAGGTCATATCCTCA | 1985 |
| 66 | GCAGGTACTAACCTGAGATGCGTAGCTAACACAGG | 1986 |
| 67 | ATCTGCAAGGACGTAACGTCCTCGGAAGGTGAGGT | 1987 |
| 68 | ATAATCTTACGAGCCTCCAGTGAATAATGCAAGCA | 1988 |
| 69 | CAATCTCCGCACAGTCTTGTTCAGGTACAGACTTA | 1989 |
| 70 | ATGTGCGCAATTCAGCGTAAGTGCCTATTCATAAT | 1990 |
| 71 | TCGGACGCACACATCCTGTTGTCGAGAAGAGGAAG | 1991 |
| 72 | TCGGAAGCATCACATGAGCATCAGGAGTTCATTGC | 1992 |
| 73 | ATCTGGTTGTGGACTTCTATACAGTACCAGAGTGG | 1993 |
| 74 | CGTCTGAATATAGTTAGCTAGTAGTGTAATCCAGG | 1994 |
| 75 | TAATATCTGATCCGACCTATTATCTAGGACTACTC | 1995 |
| 76 | TATGCGGCCGTCCGTACCTCGTCTGCTTCAGTTGG | 1996 |
| 77 | TGGCTCAAGTTCCATATTGCCAAGACGACCTGGAG | 1997 |
| 78 | GCAGTTCTGCTAGGCGGTCCGAGGCAATTGAAGAG | 1998 |
| 79 | CATGGCACAGACGAAGTATGCACCACGCTCATTAA | 1999 |
| 80 | GGAGCGTACTACGACCATTCAACCGAATATGTTAC | 2000 |
| 81 | GCGTAGATCTCGCGACAGAGACAAGGTGCGAATGG | 2001 |

TABLE 23-continued

List of random primers (35-base primers)

| No | Primer sequence | SEQ ID NO: |
|---|---|---|
| 82 | TGGACTGAGGTTCTCCGGTCTATACTCCTGTAGGA | 2002 |
| 83 | TGGCTATAGCAACGGCTTCTTGTGATCGCATTGCA | 2003 |
| 84 | GGCGAAGAATCATGCGAGACGGAGTAGACGGACGT | 2004 |
| 85 | GAGCATTGCGAGTTGCACACGTGATATCAGACTGT | 2005 |
| 86 | CTGTTGACCTATGCCAGAATCAATACCTCAGATTA | 2006 |
| 87 | GTTAACAAGTAGATGCCAAGATACAACGAGAGACC | 2007 |
| 88 | GAGCAAGATTATAGTTAGGAAGATAGTTAACTCGC | 2008 |
| 89 | TCCGGAGTCGAGCATATGTGACCAACTCTCAACGC | 2009 |
| 90 | GGAGCTGCGATGCCGTTACCGACGTCATCTTCAAG | 2010 |
| 91 | GCTCTATCTTACACATTGGCGTACTGGACTCGCGA | 2011 |
| 92 | TTCTACATATTCATCGCCTACCGAGTTGCGCGAAG | 2012 |
| 93 | TGGACGTCTGACCTGTGTCTACATCGGTGGTGCTA | 2013 |
| 94 | GGCAGGACAGCTCGGTGTTCTACTCGAACCGCACT | 2014 |
| 95 | TGACAACCTCATGTCTCCGACCGCAGGCATACAAT | 2015 |
| 96 | GCAGGCCTAACAAGTGGTCACGAGGAGTCCTTATT | 2016 |

3.1.2 Standard PCR

To the genomic DNA described in 2. above (30 ng, NiF8-derived genomic DNA), a random primer (final concentration: 0.6 microM, 10-base primer A), a 0.2 mM dNTP mixture, 1.0 mM MgCl2, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. In this example, numerous nucleic acid fragments obtained via PCR using random primers, including the standard PCR described above, are referred to as DNA libraries.

3.1.3 Purification of DNA Library and Electrophoresis

The DNA library obtained in 3.1.2 above was purified with the use of the MinElute PCR Purification Kit (QIAGEN) and subjected to electrophoresis with the use of the Agilent 2100 bioanalyzer (Agilent Technologies) to obtain a fluorescence unit (FU).

3.1.4 Examination of Annealing Temperature

To the genomic DNA described in 2. above (30 ng, NiF8-derived genomic DNA), a random primer (final concentration: 0.6 microM, 10-base primer A), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, various annealing temperatures for 15 seconds, and 72 degrees C. for 20 seconds, followed by storage at 4 degrees C. In this example, annealing temperature of 37 degrees C., 40 degrees C., and 45 degrees C. were examined. The DNA library obtained in this experiment was subjected to purification and electrophoresis in the same manner as in 3.1.3.

3.1.5 Examination of Enzyme Amount

To the genomic DNA described in 2. above (30 ng, NiF8-derived genomic DNA), a random primer (final concentration: 0.6 microM, 10-base primer A), a 0.2 mM dNTP mixture, 1.0 mM MgCl$_2$, and 2.5 units or 12.5 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3.

3.1.6 Examination of MgCl$_2$ Concentration

To the genomic DNA described in 2. above (30 ng, NiF8-derived genomic DNA), a random primer (final concentration: 0.6 microM, 10-base primer A), a 0.2 mM dNTP mixture, MgCl$_2$ at a given concentration, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. In this example, MgCl$_2$ concentrations, which are 2 times (2.0 mM), 3 times (3.0 mM), and 4 times (4.0 mM) greater than a common level, respectively, were examined. The DNA library obtained in this experiment was subjected to purification and electrophoresis in the same manner as in 3.1.3.

3.1.7 Examination of Base Length of Random Primer

To the genomic DNA described in 2. above (30 ng, NiF8-derived genomic DNA), a random primer (final concentration: 0.6 microM), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. In this example, 8-base random primers (Table 9), 9-base random primers (Table 10), 11-base random primers (Table 11), 12-base random primers (Table 12), 14-base random primers (Table 13), 16-base random primers (Table 14), 18-base random primers (Table 15), and 20-base random primers (Table 16) were examined. The DNA library obtained in this experiment was subjected to purification and electrophoresis in the same manner as in 3.1.3.

3.1.8 Examination of Random Primer Concentration

To the genomic DNA described in 2. above (30 ng, NiF8-derived genomic DNA), a random primer at a given concentration (10-base primer A), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. In this example, random primer concentrations of 2, 4, 6, 8, 10, 20, 40, 60, 100, 200, 300, 400, 500, 600, 700, 800, 900, and 1000 microM were examined. The DNA library obtained in this experiment was subjected to purification and electrophoresis in the same manner as in 3.1.3. In this experiment, the reproducibility of the repeated data was evaluated on the basis of the Spearman's rank correlation (rho>0.9).

3.2 Verification of Reproducibility via MiSeq 3.2.1 Preparation of DNA Library

To the genomic DNA described in 2. above (30 ng, NiF8-derived genomic DNA), a random primer (final concentration: 60 microM, 10-base primer A), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3.

3.2.2 Preparation of Sequence Library

From the DNA library obtained in 3.2.1, a sequence library for MiSeq analysis was prepared using the KAPA Library Preparation Kit (Roche).

3.2.3 MiSeq Analysis

With the use of the MiSeq Reagent Kit V2 500 Cycle (Illumina), the sequence library for MiSeq analysis obtained in 3.2.2 was analyzed via 100 base paired-end sequencing.

3.2.4 Read Data Analysis

Random primer sequence information was deleted from the read data obtained in 3.2.3, and the read patterns were identified. The number of reads was counted for each read pattern, the number of reads of the repeated analyses was compared, and the reproducibility was evaluated using the correlational coefficient.

3.3 Analysis of Rice Variety Nipponbare 3.3.1 Preparation of DNA Library

To the genomic DNA described in 2. above (30 ng, Nipponbare-derived genomic DNA), a random primer (final concentration: 60 microM, 10-base primer A), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3.

3.3.2 Preparation of Sequence Library, MiSeq Analysis, and Read Data Analysis

Preparation of a sequence library using the DNA library prepared from Nipponbare-derived genomic DNA, MiSeq analysis, and analysis of the read data were performed in accordance with the methods described in 3.2.2, 3.2.3, and 3.2.4, respectively.

3.3.3 Evaluation of Genomic Homogeneity

The read patterns obtained in 3.3.2 were mapped to the genomic information of Nipponbare (NC_008394 to NC_008405) using bowde2, and the genomic positions of the read patterns were identified.

3.3.4 Non-Specific Amplification

On the basis of the positional information of the read patterns identified in 3.3.3, the sequences of random primers were compared with the genome sequences to which such random primers would anneal, and the number of mismatches was determined.

3.4 Detection of Polymorphism and Identification of Genotype 3.4.1 Preparation of DNA Library To the genomic DNA described in 2. above (30 ng, NiF8-derived genomic DNA, Ni9-derived genomic DNA, hybrid progeny-derived genomic DNA, or Nipponbare-derived genomic DNA), a random primer (final concentration: 60 microM, 10-base primer A), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3.

3.4.2 HiSeq Analysis

Analysis of the DNA libraries prepared in 3.4.1 was consigned to TakaraBio under conditions in which the number of samples was 16 per lane via 100 base paired-end sequencing, and the read data were obtained.

3.4.3 Read Data Analysis

Random primer sequence information was deleted from the read data obtained in 3.4.2, and the read patterns were identified. The number of reads was counted for each read pattern.

3.4.4 Detection of Polymorphism and Identification of Genotype

On the basis of the read patterns and the number of reads obtained as a results of analysis conducted in 3.4.3, polymorphisms peculiar to NiF8 and Ni9 were detected, and the read patterns thereof were designated as markers. On the basis of the number of reads, the genotypes of the 22 hybrid progeny lines were identified. The accuracy for genotype identification was evaluated on the basis of the reproducibility of the repeated data concerning the 22 hybrid progeny lines.

3.5 Experiment for Confirmation with PCR Marker 3.5.1 Primer Designing

Primers were designed for a total of 6 markers (i.e., 3 NiF8 markers and 3 Ni9 markers) among the markers identified in 3.4.4 based on the marker sequence information obtained via paired-end sequencing (Table 24).

TABLE 24

Marker sequence information and PCR marker primer information

| Genotype | Marker name | Marker sequence I* | Marker sequence II* |
|---|---|---|---|
| NiF8 type | N80521152 | CCCATACACACACCATGAAGCTTGAACTAATT AACATTCTCAAACTAATTAACAAGCATGCAAG CATCTTTTTACACAATGACAATATAT (SEQ ID NO: 2017) | ATGGGTGAGGGCGCAGAGGCAAAGACATGGAG GTCCGGAAGGGTAGAAGCTCACATCAAGTCGA GTATGTTGAATGCAATCCCATATATA (SEQ ID NO: 2018) |

TABLE 24-continued

Marker sequence information and PCR marker primer information

| | | | |
|---|---|---|---|
| | N80997192 | AATCACAGAACGAGGTCTGGACGAGAACAGAG CTGGACATCTACACGCACCGCATGGTAGTAGA GCATGTACTGCAAAAGCTTGAAGCGC (SEQ ID NO: 2021) | GATGCTGAGGGCGAAGTTGTCAGCCAAGTCCT CAATGTCATAGGCGAGATCGCAGTAGTTCTGT AACCATTCCCTGCTAAACTGGTCCAT (SEQ ID NO: 2022) |
| | N80533142 | AGACCAACAAGCAGCAAGTAGTCAGAGAAGTA CAAGAGAAGGAGAGCAAGAAGGATAGTAAGTT GCAAGCTTACCGTTACAAAGATGATA (SEQ ID NO: 2025) | GGAGGAGCACAACTAGGCGTTTATCAAGATGG GTCATCGAGCTCTTGGTGTCTTCAACCTTCTT GACATCAACTTCTCCAATCTTCGTCT (SEQ ID NO: 2026) |
| Ni9 type | N91552391 | TGGGGTAGTCCTGAAGCTCTAGGTATGCCTCT TCATCTCCCTGCACCTCTGGTGCTAGCACCTC CTGCTCTTCGGGCACCTCTACCGGGG (SEQ ID NO: 2029) | GGATACTGATGTAGCTTTCACCCGGGAGTATT CCAAGGTATCGATTTTCCACGGGGAACGCGAA GTGCACTAGTTGAGGTTTAGATTGCC (SEQ ID NO: 2030) |
| | N91653962 | TCGGGAAAACGAACGGGCGAACTACAGATGTC AGTACGAAGTAGTCTATGGCAGGAAATACGTA GTCCATACGTGGTGCCAGCCCAAGCC (SEQ ID NO: 2033) | AGCAGGAGGGAGAAAGGAAACGTGGCATTCAT CGGCTGTCTGCCATTGCCATGTGAGACAAGGA AATCTACTTCACCCCCATCTATCGAG (SEQ ID NO: 2034) |
| | N91124801 | AGACATAAGATTAACTATGAACAAATTCACGG GTCCGATTCCTTTGGGATTTGCAGCTTGCAAG AACCTTCAAATACTCATTATATCTTC (SEQ ID NO: 2037) | TTAAGTTGCAGAATTTGATACGAAGAACTTGA AGCATGGTGACGTTGCCGAGCTCATTGGGGAT GGTTCCAGAAAGGCTATTGTAGCTTA (SEQ ID NO: 2038) |

| Genotype | Marker name | Primer I | Primer II |
|---|---|---|---|
| NiF8 type | N80521152 | CCCATACACACACCA TGAAGCTTG (SEQ ID NO: 2019) | GGTAGAAGCTCACAT CAAGTCGAG (SEQ ID NO: 2020) |
| | N80997192 | ACGAGAACAGAGCTG GACATCTAC (SEQ ID NO: 2023) | TCAATGTCATAGGCG AGATCGCAG (SEQ ID NO: 2024) |
| | N80533142 | GGAGAGCAAGAAGGA TAGTAAGTTGC (SEQ ID NO: 2027) | CGAGCTCTTGGTGTC TTCAACCTTC (SEQ ID NO: 2028) |
| Ni9 type | N91552391 | GAAGCTCTAGGTATG CCTCTTCATC (SEQ ID NO: 2031) | GTGCACTAGTTGAGG TTTAGATTGC (SEQ ID NO: 2032) |
| | N91653962 | GGGCGAACTACAGAT GTCAGTACG (SEQ ID NO: 2035) | CTGTCTGCCATTGCC ATGTGAGAC (SEQ ID NO: 2036) |
| | N91124801 | GAACAAATTCACGGG TCCGATTCC (SEQ ID NO: 2039) | CGAAGAACTTGAAGC ATGGTGAGG (SEQ ID NO: 2040) |

*Marker sequences are pair-ended

3.5.2 PCR and Electrophoresis

With the use of the TaKaRa Multiplex PCR Assay Kit Ver.2 (TAKARA) and the genomic DNA described in 2. above (15 ng, NiF8-derived genomic DNA, Ni9-derived genomic DNA, or hybrid progeny-derived genomic DNA) as a template, 1.25 microliters of Multiplex PCR enzyme mix, 12.5 microliters of 2x Multiplex PCR buffer, and the 0.4 microM primer designed in 3.5.1 were added to prepare a reaction solution while adjusting the final reaction level to 25 microliters. The resultant was subjected to PCR under thermal cycling conditions comprising 94 degrees C. for 1 minute, 30 cycles of 94 degrees C. for 30 seconds, 60 degrees C. for 30 seconds, and 72 degrees C. for 30 seconds, and retention at 72 degrees C. for 10 minutes, followed by storage at 4 degrees C. The amplified DNA fragment was subjected to electrophoresis with the use of TapeStation (Agilent Technologies).

3.5.3 Comparison of Genotype Data

On the basis of the results of electrophoresis obtained in 3.5.2, the genotype of the marker was identified on the basis of the presence or absence of a band, and the results were compared with the number of reads of the marker.

3.6 Correlation Between Random Primer Concentration and Length

3.6.1 Influence of Random Primer Length at High Concentration

To the genomic DNA described in 2. above (30 ng, NiF8-derived genomic DNA), a random primer of a given length (final concentration: 10 microM), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. In this experiment, the random primer lengths of 9 bases (Table 10), 10 bases (Table 3, 10-base primer A), 11 bases (Table 11), 12 bases (Table 12), 14 bases (Table 13), 16 bases (Table 14), 18 bases (Table 15), and 20 bases (Table 16) were examined. In the reaction system using a 9-base random primer, PCR was carried out under thermal cycling conditions comprising 98 degrees C. for 2 minutes and 30 cycles of 98 degrees C. for 10 seconds, 37 degrees C. for 15 seconds, and 72 degrees C. for 20 seconds, followed by storage at 4 degrees C. In the reaction system using a 10-base or greater random primer bases, PCR was carried out under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3.

3.6.2 Correlation Between Random Primer Concentration and Length

To the genomic DNA described in 2. above (30 ng, NiF8-derived genomic DNA), a random primer of a given length was added to result in a given concentration therein, a 0.2 mM dNTP mixture, 1.0 mM MgCl$_2$, and 1.25 units of DNA polymerase (PrimeSTAR, TAKARA) were added thereto, and a reaction solution was prepared while adjusting the final reaction level to 50 microliters. In this experiment, 8- to 35-base random primers shown in Tables 3 to 23 were examined, and the random primer concentration from 0.6 to 300 microM was examined.

In the reaction system using 8-base and 9-base random primers, PCR was carried out under thermal cycling conditions comprising 98 degrees C. for 2 minutes and 30 cycles of 98 degrees C. for 10 seconds, 37 degrees C. for 15 seconds, and 72 degrees C. for 20 seconds, followed by storage at 4 degrees C. In the reaction system using a 10-base or greater random primer, PCR was carried out under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3. Also, the reproducibility of the repeated data was evaluated on the basis of the Spearman's rank correlation (rho>0.9).

3.7 Number of Random Primers

To the genomic DNA described in 2. above (30 ng, NiF8-derived genomic DNA), 1, 2, 3, 12, 24, or 48 types of random primers selected from the 96 types of 10-base random primers (10-base primer A) shown in Table 3 were added to result in the final concentration of 60 microM therein, a 0.2 mM dNTP mixture, 1.0 mM MgCl$_2$, and 1.25 units of DNA polymerase (PrimeSTAR, TAKARA) were added thereto, and a reaction solution was prepared while adjusting the final reaction level to 50 microliters. In this experiment, as the 1, 2, 3, 12, 24, or 48 types of random primers, random primers were selected successively from No. 1 shown in Table 1, and the selected primers were then examined. PCR was carried out under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3. Also, the reproducibility of the repeated data was evaluated on the basis of the Spearman's rank correlation (rho>0.9).

3.8 Random Primer Sequence

To the genomic DNA described in 2. above (30 ng, NiF8-derived genomic DNA), a set of primers selected from the 5 sets of random primers shown in Tables 4 to 8 was added to result in the final concentration of 60 microM therein, a 0.2 mM dNTP mixture, 1.0 mM MgCl$_2$, and 1.25 units of DNA polymerase (PrimeSTAR, TAKARA) were added thereto, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3. Also, the reproducibility of the repeated data was evaluated on the basis of the Spearman's rank correlation (rho>0.9).

3.9 DNA Library Using Human-Derived Genomic DNA

To the genomic DNA described in 2. above (30 ng, human-derived genomic DNA), a random primer (final concentration: 60 microM, 10-base primer A), a 0.2 mM dNTP mixture, 1.0 mM MgCl$_2$, and 1.25 units of DNA polymerase (PrimeSTAR, TAKARA) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. The DNA library obtained in this experiment was subjected to purification and electrophoresis in the same manner as in 3.1.3. Also, the reproducibility of the repeated data was evaluated on the basis of the Spearman's rank correlation (rho>0.9).

4. Results and Examination 4.1 Correlation Between PCR Conditions and DNA Library Size When PCR was conducted with the use of random primers in accordance with conventional PCR conditions (3.1.2 described above), the amplified DNA library size was as large as 2 kbp or more, but amplification of the DNA library of a target size (i.e., 100-bp to 500-bp) was not observed (FIG. 2). A DNA library of 100 bp to 500 bp could not be obtained because it was highly unlikely that a random primer would function as a primer in a region of 500 bp or smaller. In order to prepare a DNA library of the target size (i.e., 100 bp to 500 bp), it was considered necessary to induce non-specific amplification with high reproducibility.

The correlation between the conditions that may affect PCR specificity; i.e., the annealing temperature (3.1.4 above), the enzyme amount (3.1.5 above), the MgCl$_2$ concentration (3.1.6 above), the primer length (3.1.7 above), and the primer concentration (3.18 above), and the DNA library size were examined.

Figure 3:
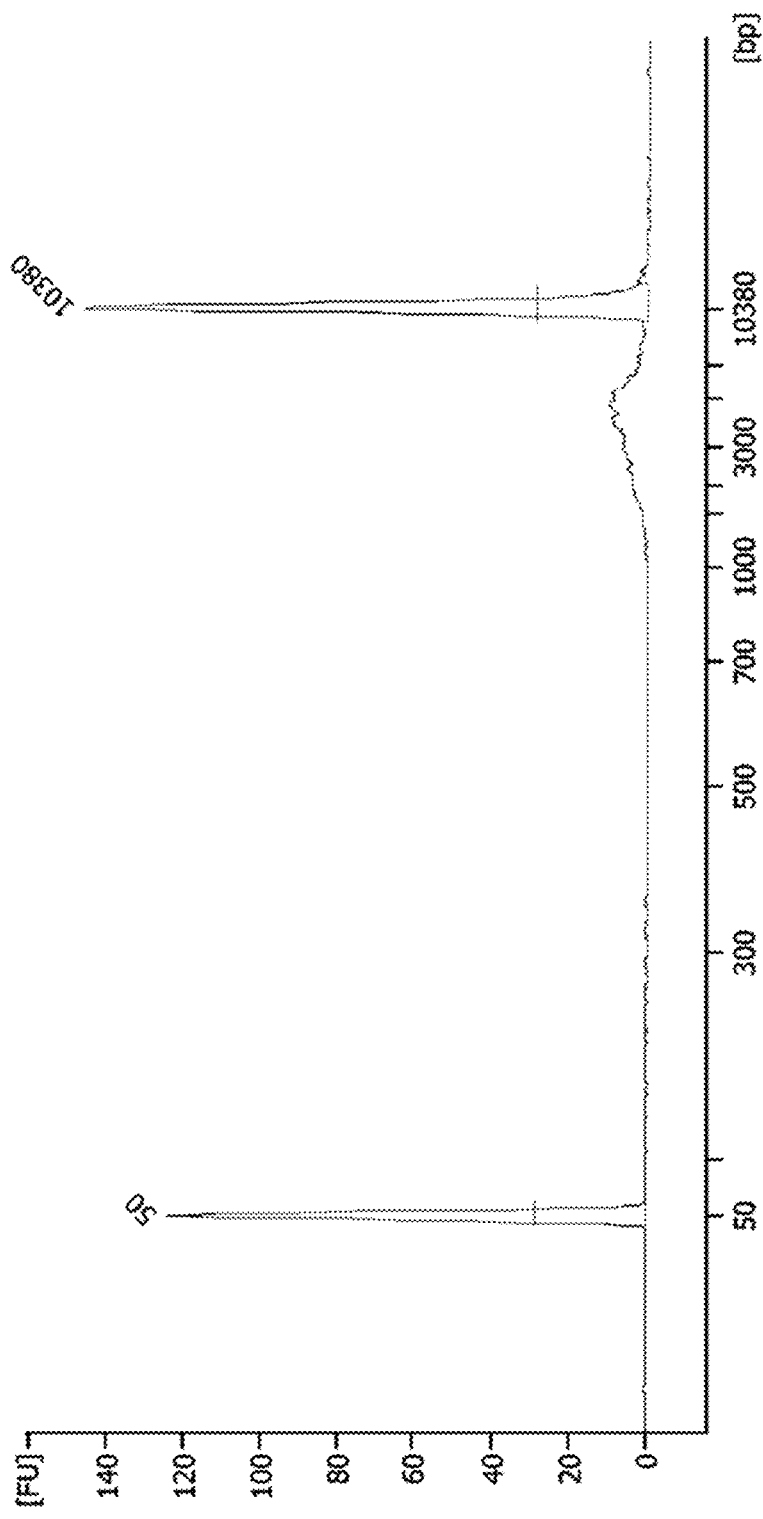
FIG. 3 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template at an annealing temperature of 45 degrees C.
Figure 4:
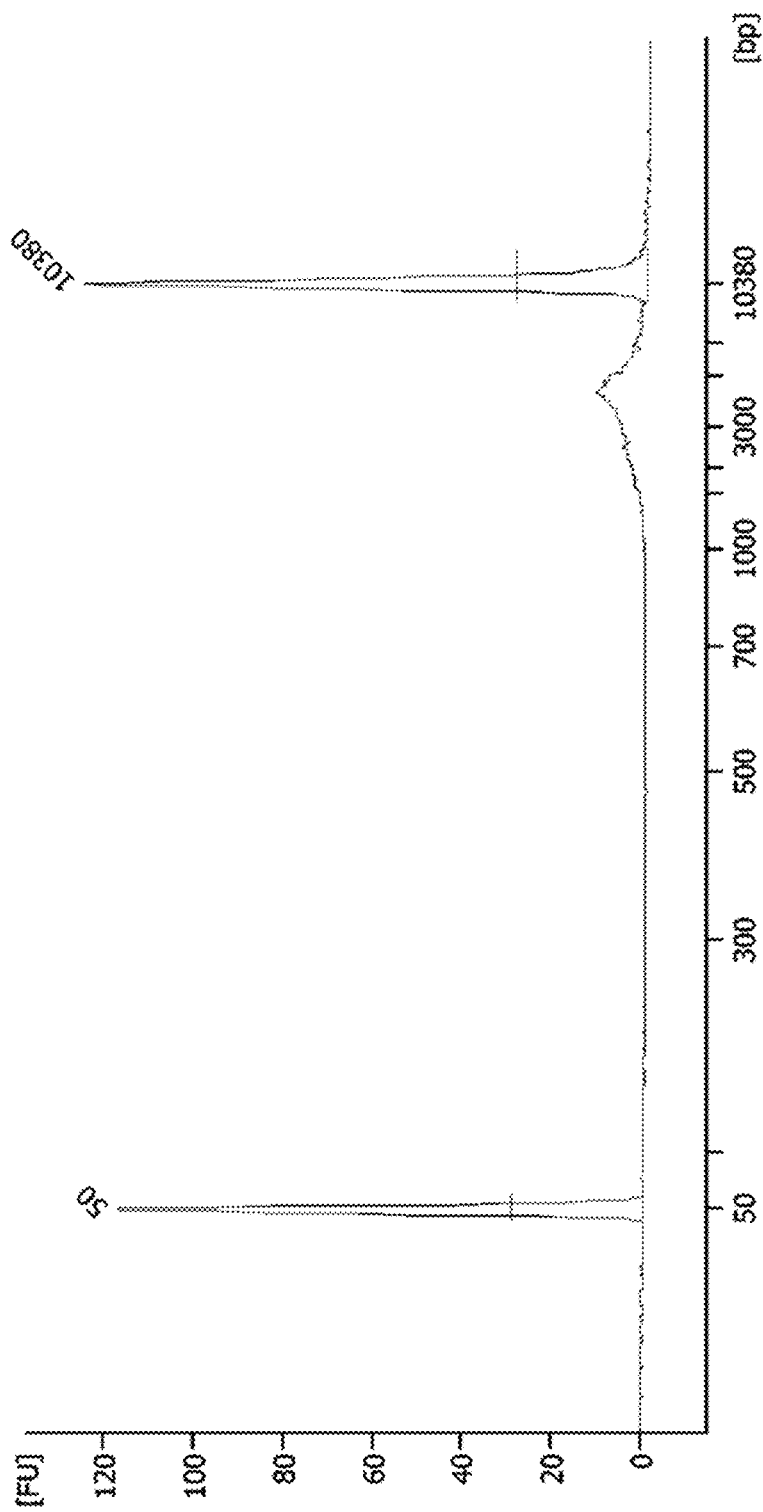
FIG. 4 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template at an annealing temperature of 40 degrees C.
Figure 5:
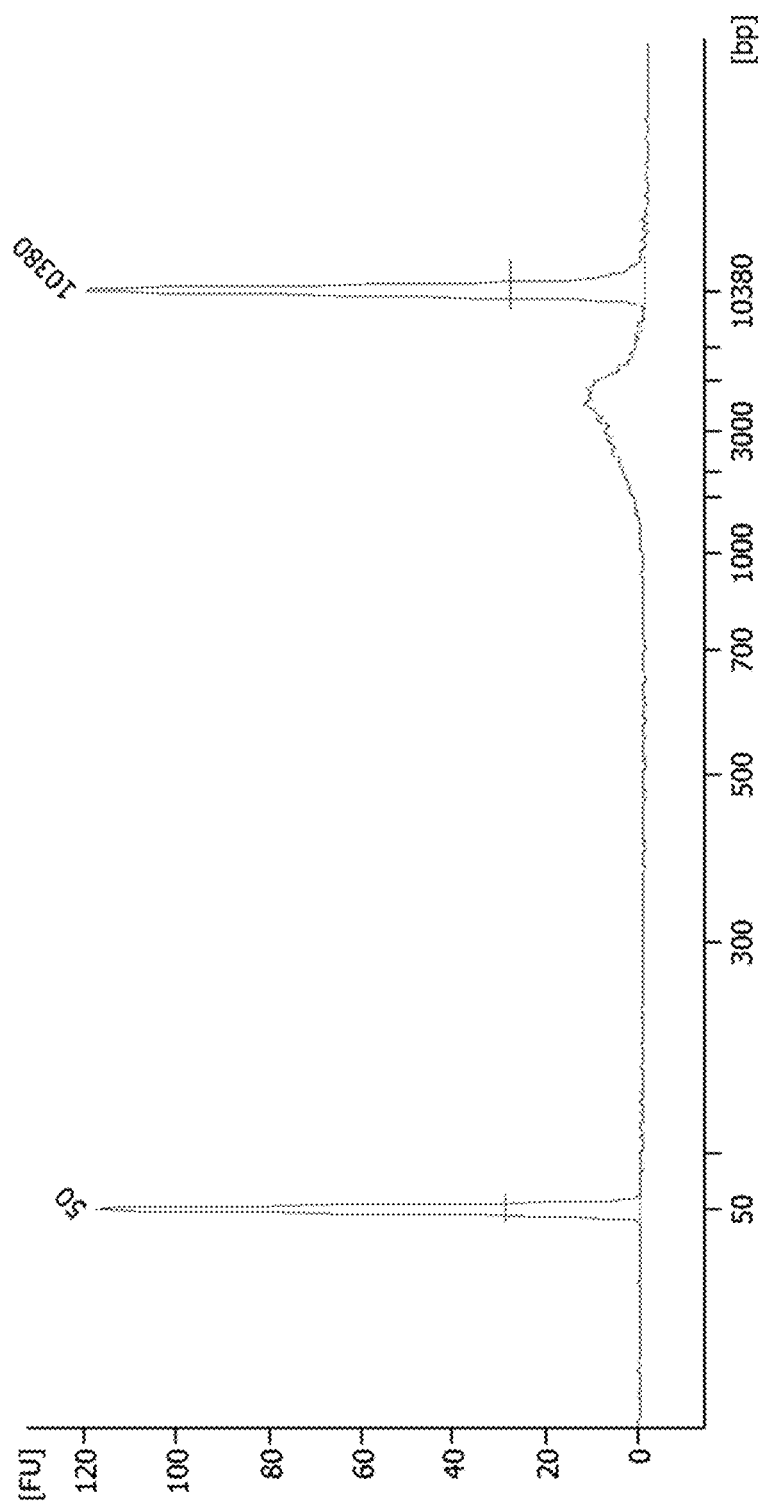
FIG. 5 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template at an annealing temperature of 37 degrees C.

FIG. 3 shows the results of the experiment described in 3.1.4 attained at an annealing temperature of 45 degrees C., FIG. 4 shows the results attained at an annealing temperature of 40 degrees C., and FIG. 5 shows the results attained at an annealing temperature of 37 degrees C. As the annealing temperature was lowered from 45 degrees C., 40 degrees C., to 37 degrees C., as shown in FIGS. 3 to 5, the amounts of high-molecular-weight DNA library amplified increased, although amplification of low-molecular-weight DNA library was not observed.

Figure 6:
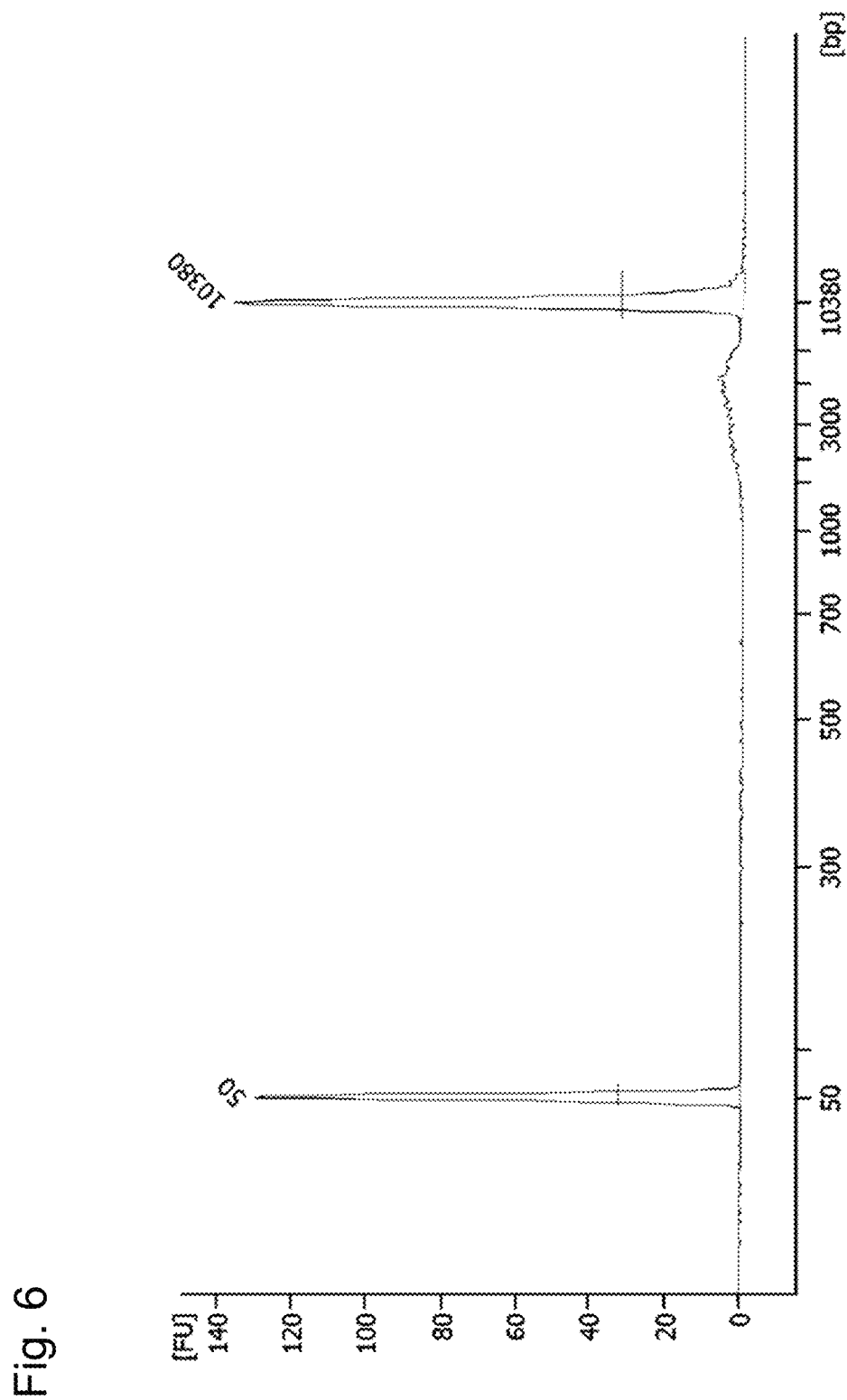
FIG. 6 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and 2.5 units of an enzyme.
Figure 7:
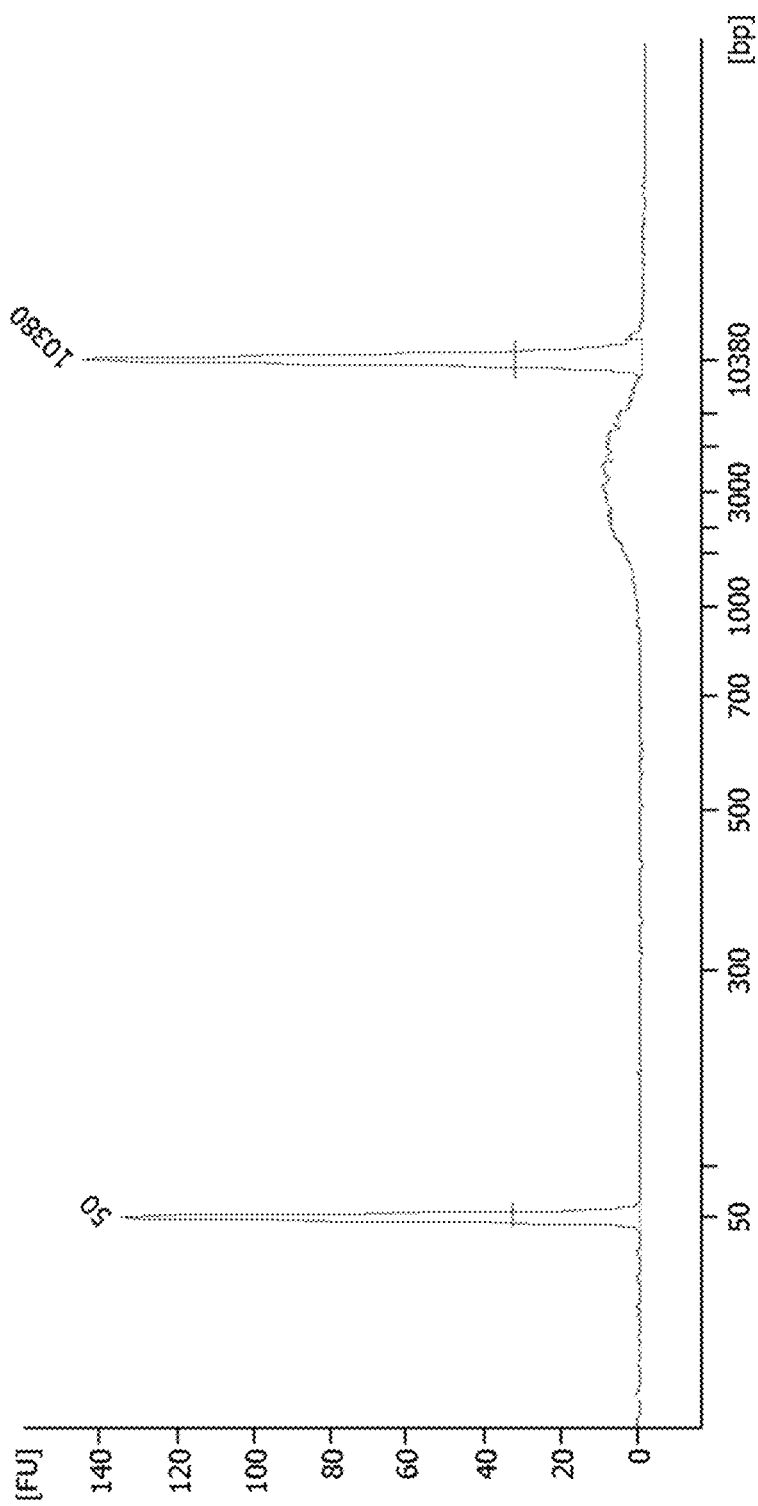
FIG. 7 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and 12.5 units of an enzyme.

FIG. 6 shows the results of the experiment described in 3.1.5 attained when the enzyme amount is increased by 2 times, and FIG. 7 shows the results attained when the enzyme amount is increased by 10 times the general amount. As the enzyme amount was increased by 2 times or 10 times the common amount, as shown in FIGS. 6 and 7, the amounts of high-molecular-weight DNA library amplified increased, although amplification of low-molecular-weight DNA library was not observed.

Figure 8:
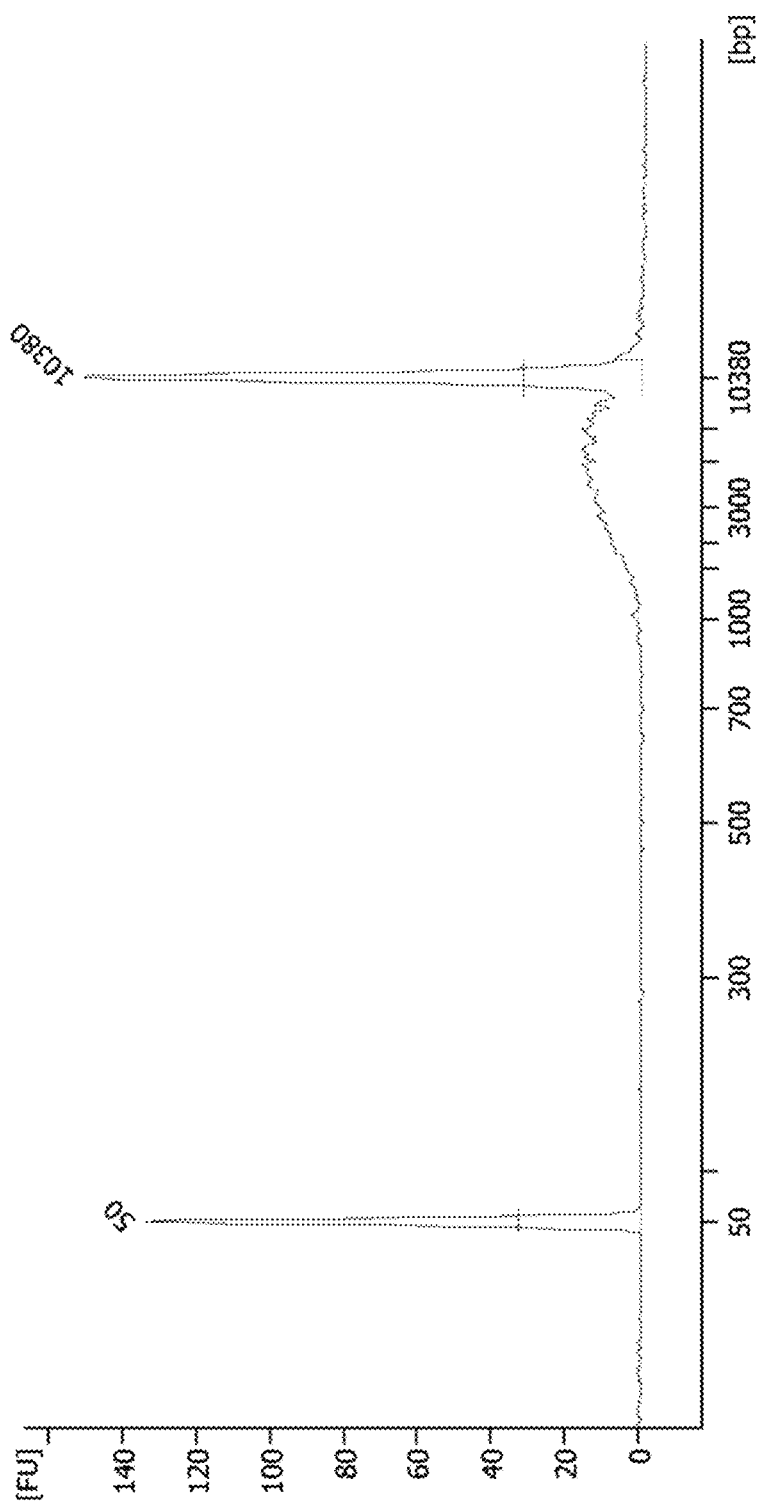
FIG. 8 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and $MgCl_2$ at the concentration doubled from the original level.
Figure 9:
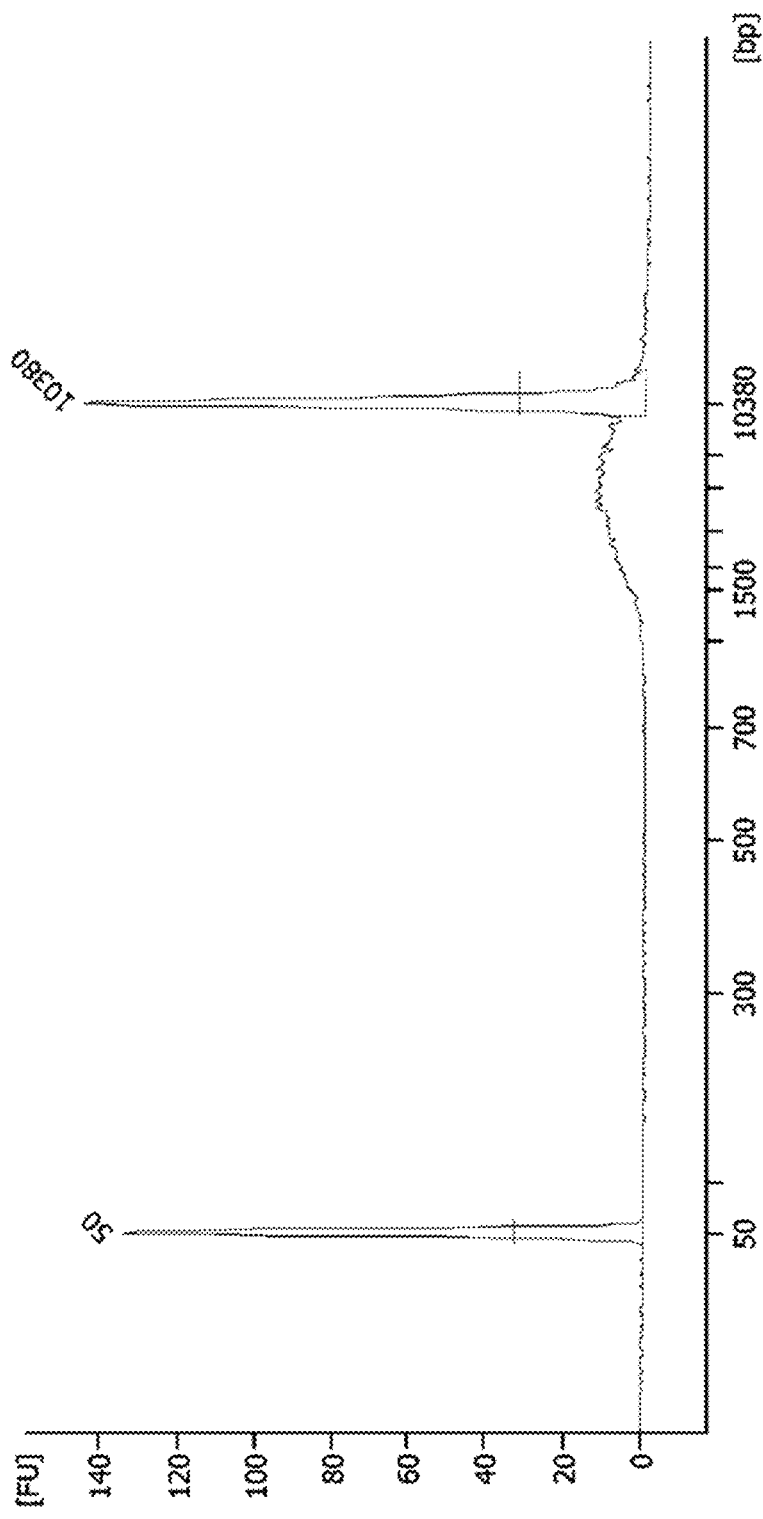
FIG. 9 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and MgCl$_2$ at the concentration tripled from the original level.
Figure 10:
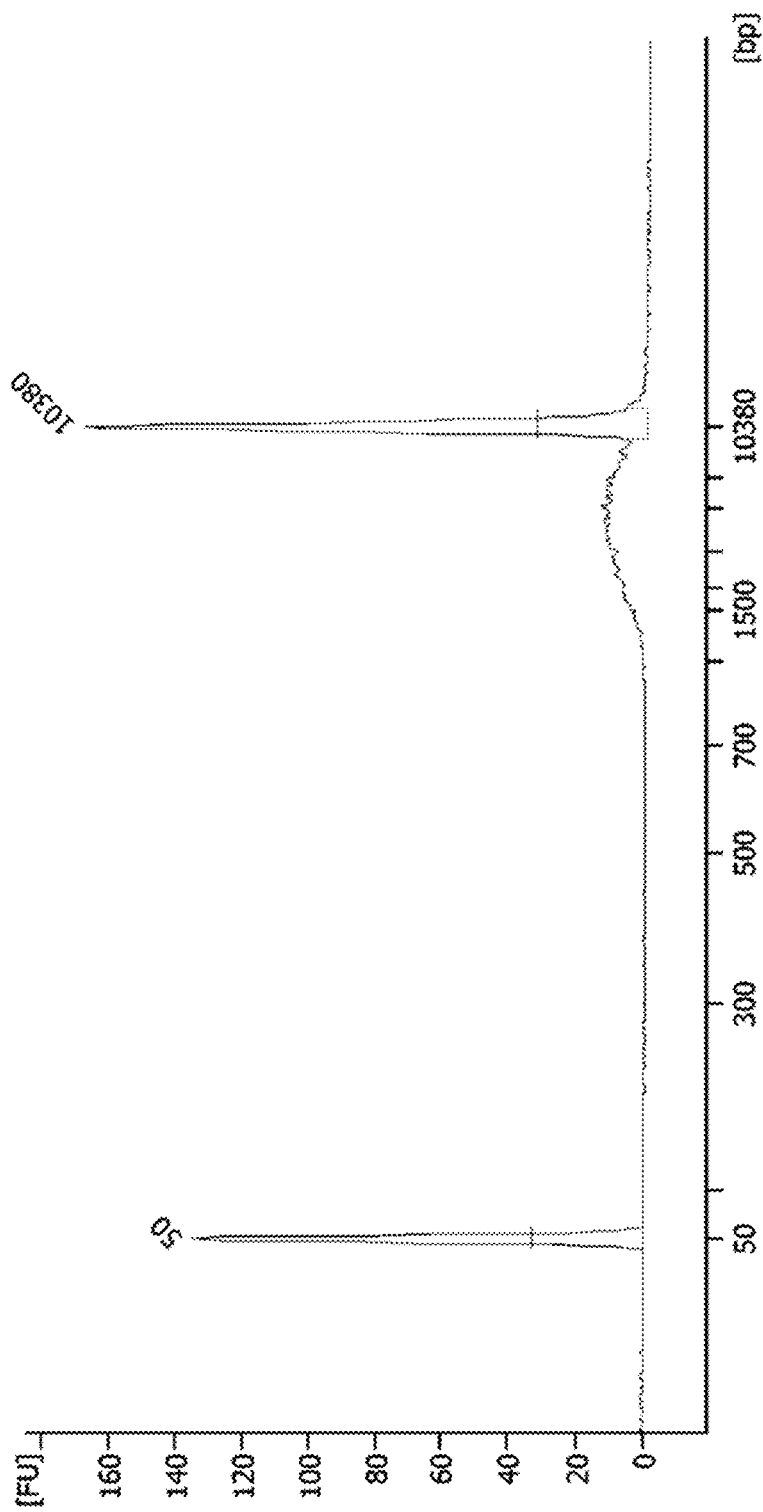
FIG. 10 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and MgCl$_2$ at the concentration quadrupled from the original level.
Figure 11:
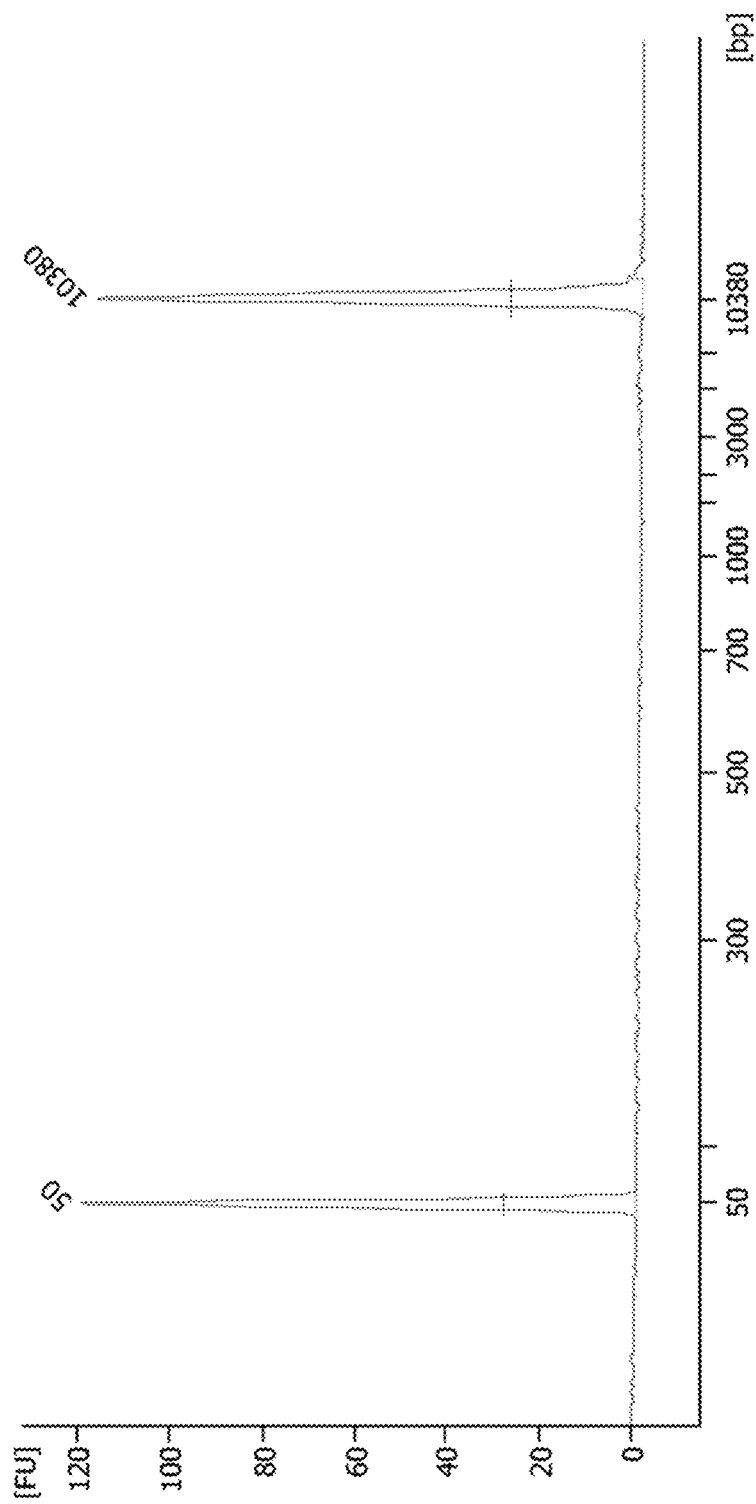
FIG. 11 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and an 8-base random primer.
Figure 12:
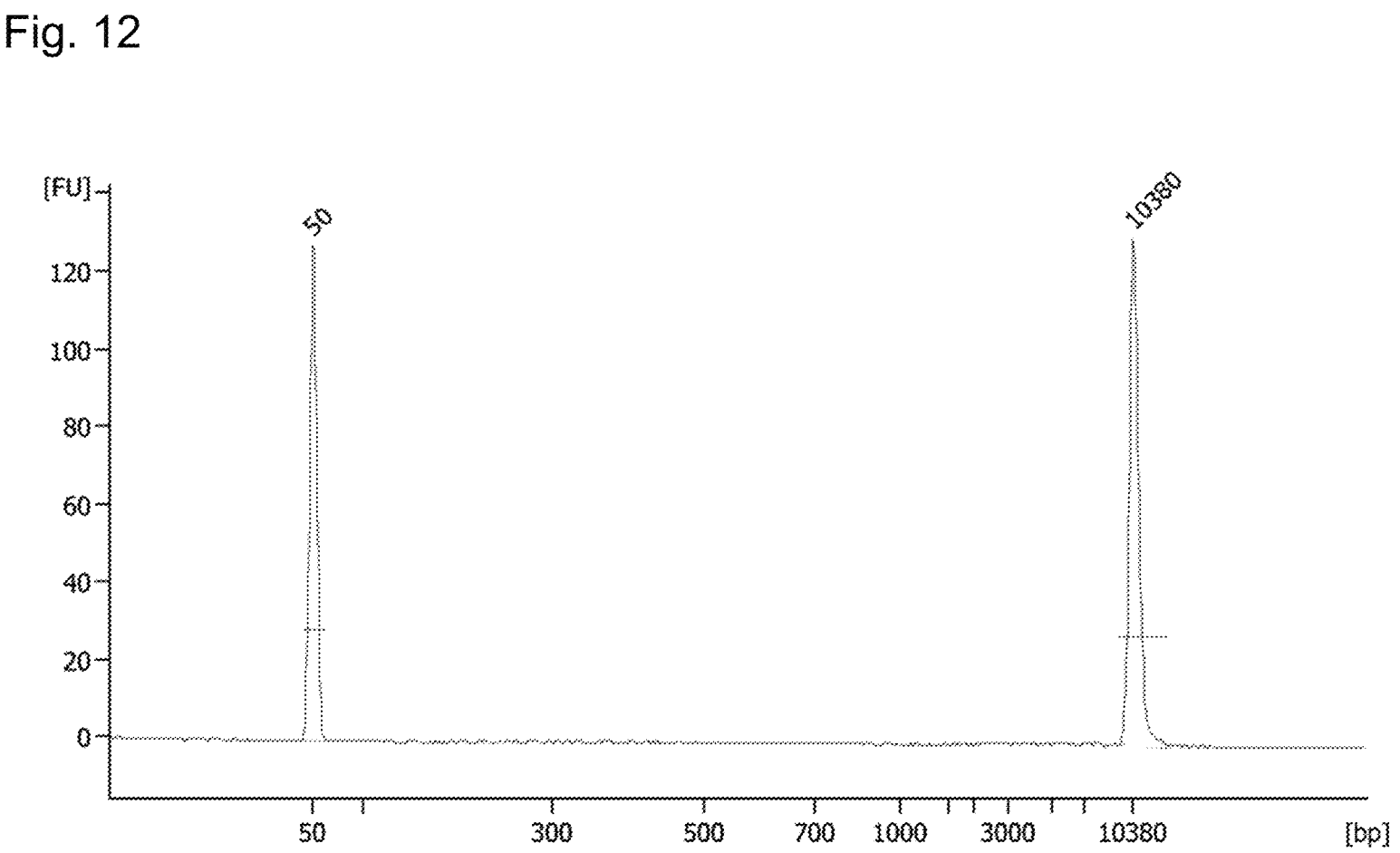
FIG. 12 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a 9-base random primer.
Figure 13:
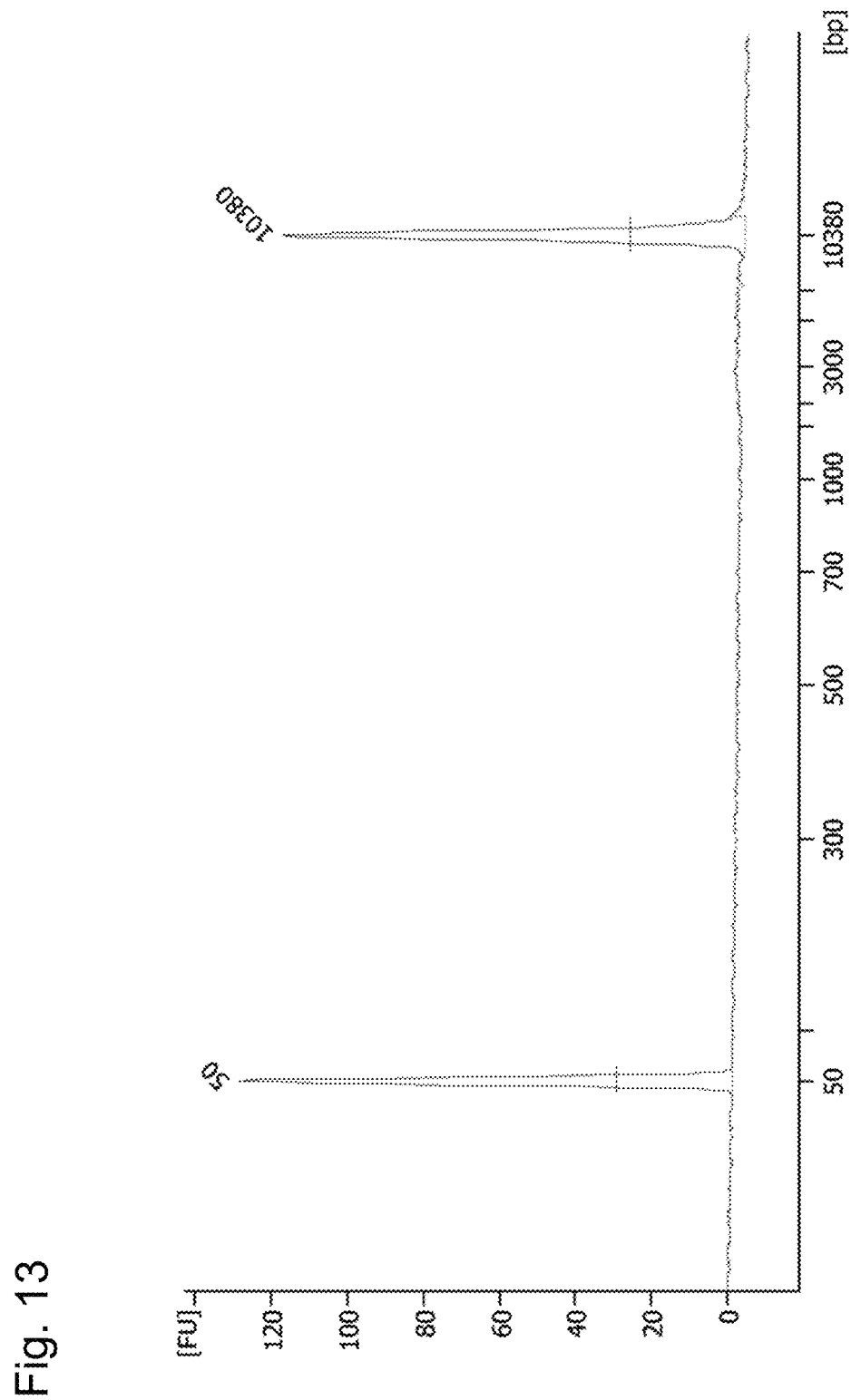
FIG. 13 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and an 11-base random primer.
Figure 14:
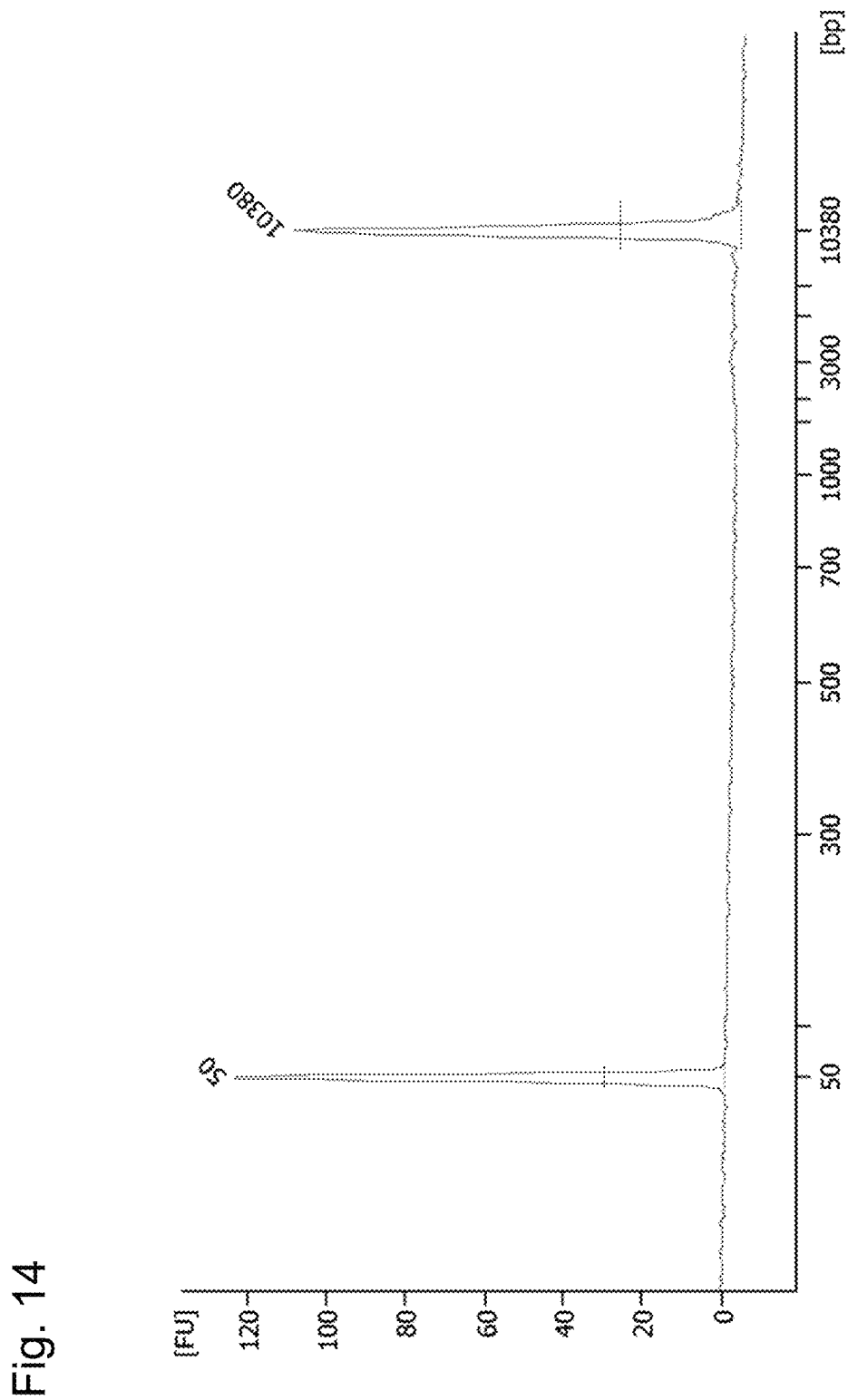
FIG. 14 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a 12-base random primer.
Figure 15:
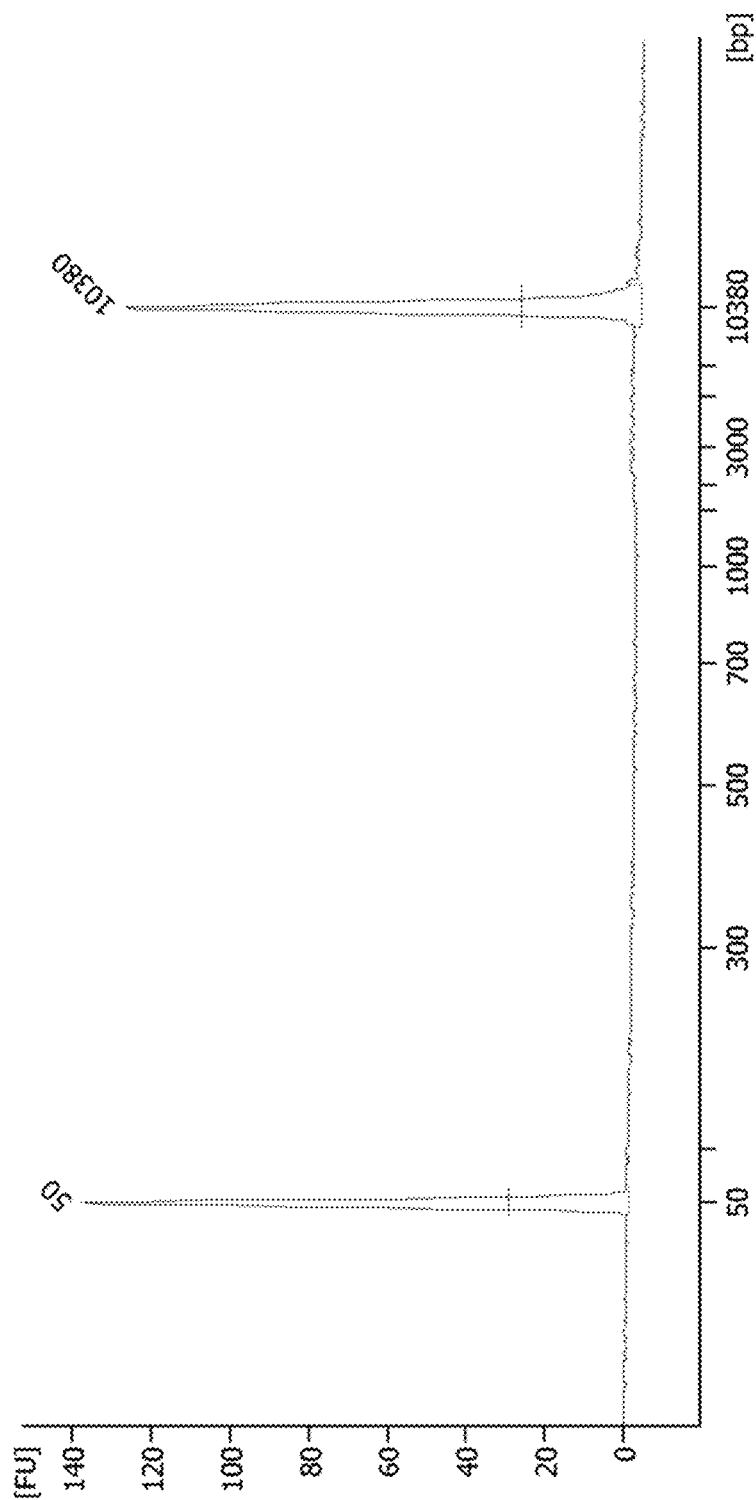
FIG. 15 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a 14-base random primer.
Figure 16:
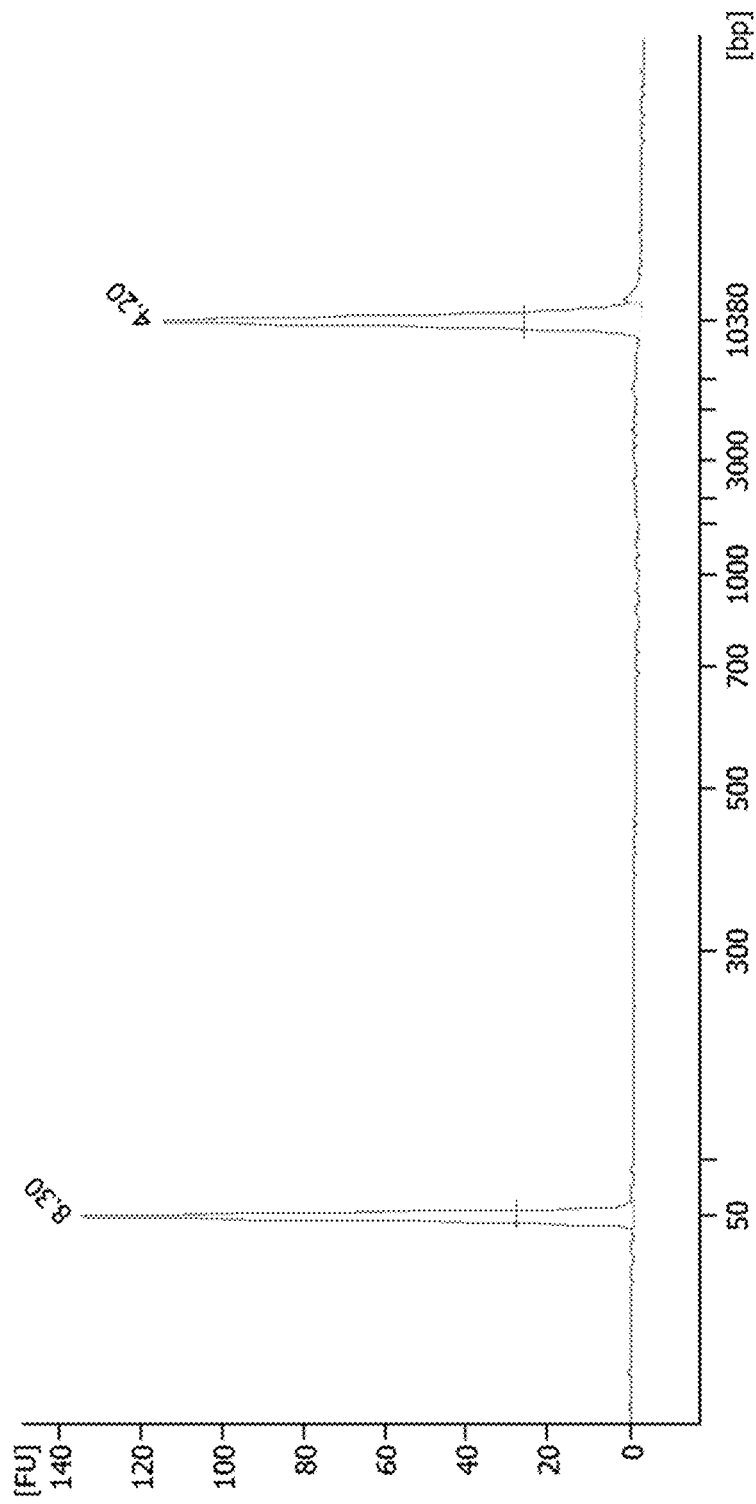
FIG. 16 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a 16-base random primer.
Figure 17:
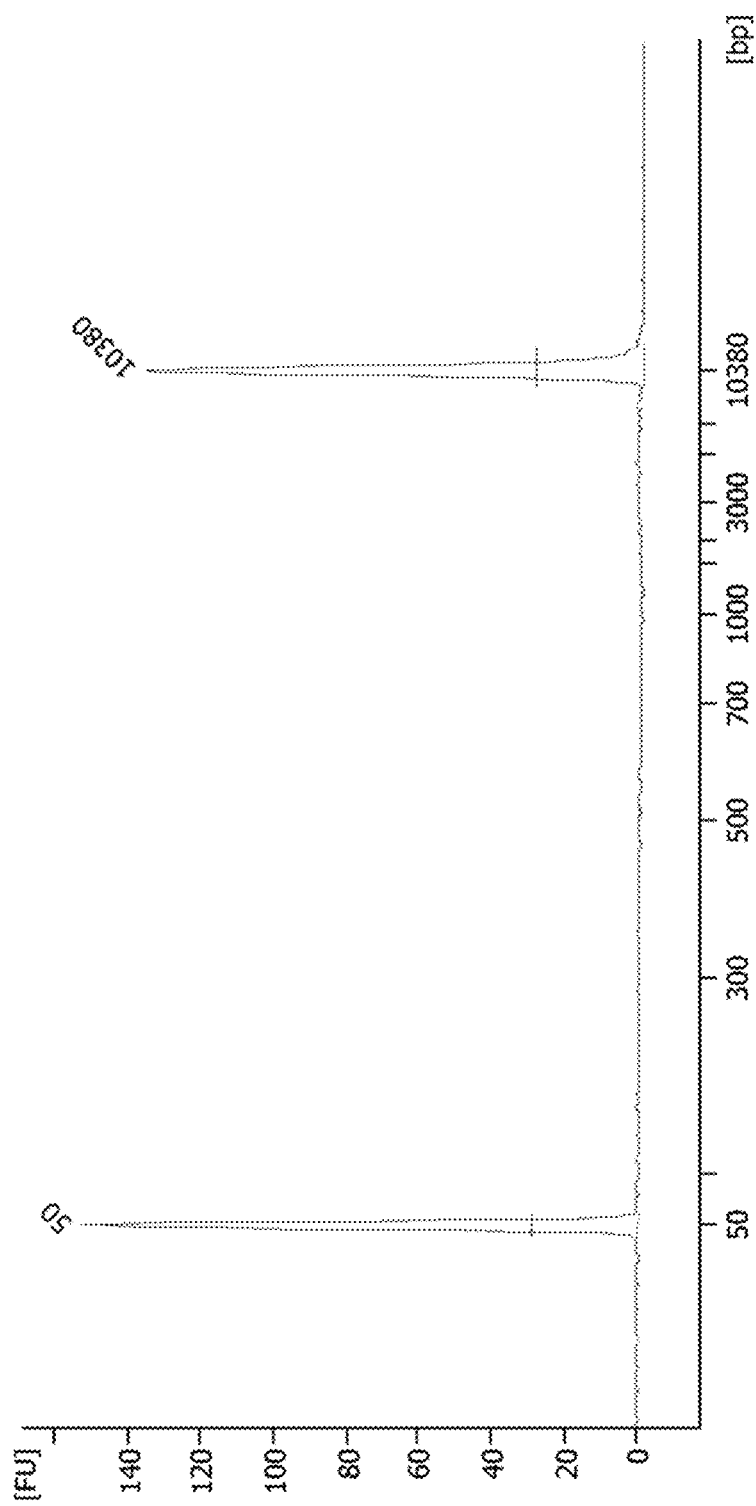
FIG. 17 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and an 18-base random primer.
Figure 18:
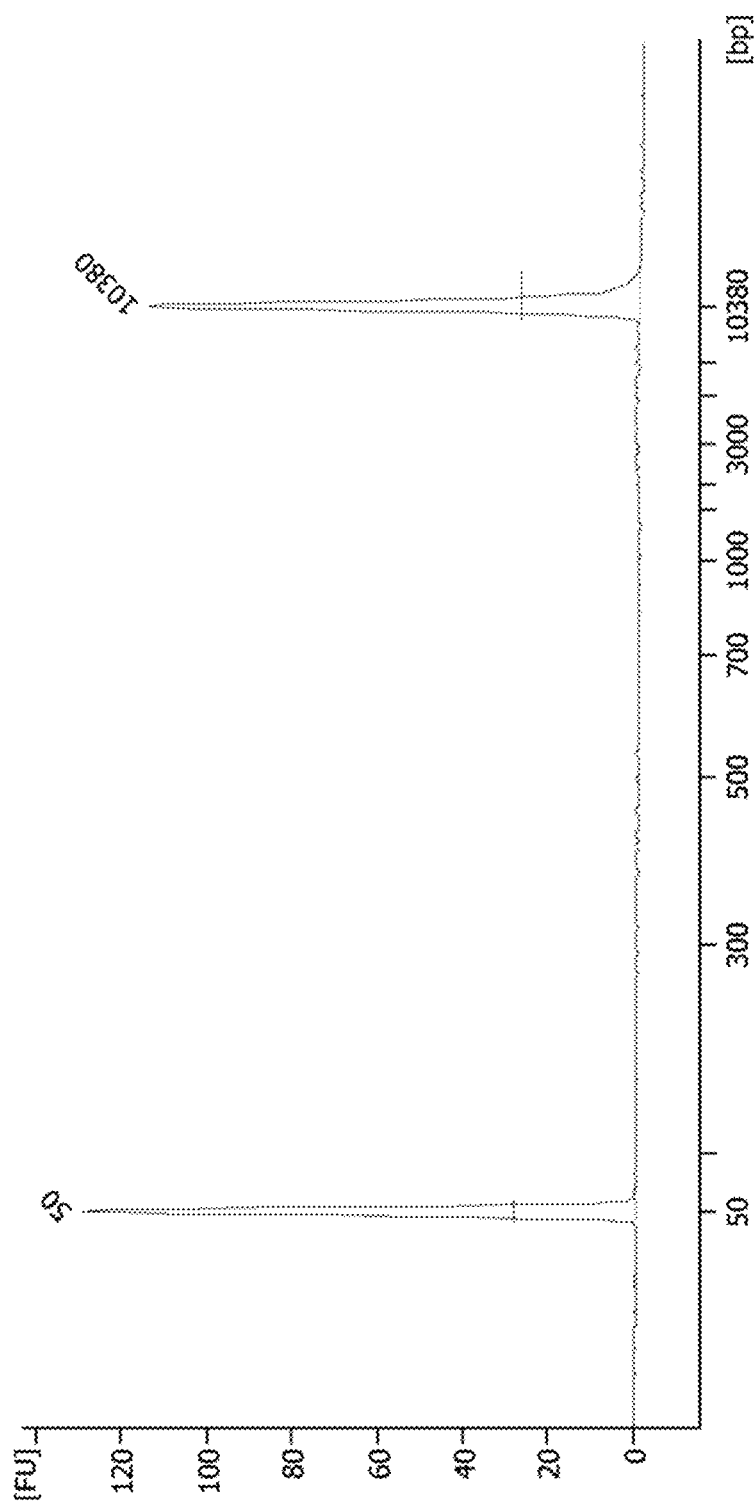
FIG. 18 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a 20-base random primer.

FIG. 8 shows the results of the experiment described in 3.1.6 attained when the MgCl$_2$ concentration is increased by 2 times, FIG. 9 shows the results attained when the MgCl$_2$ concentration is increased by 3 times, and FIG. 10 shows the results attained when the MgCl$_2$ concentration is increased by 4 times the general amount. By increasing the MgCl$_2$ concentration by 2 times, 3 times, and 4 times the common amount, as shown in FIGS. 8 to 10, the amounts of high-molecular-weight DNA library amplified varied, although amplification of a low-molecular-weight DNA library was not observed.

FIGS. 11 to 18 show the results of the experiment described in 3.1.7 attained at the random primer lengths of 8 bases, 9 bases, 11 bases, 12 bases, 14 bases, 16 bases, 18 bases, and 20 bases, respectively. Regardless of the length of a random primer, as shown in FIGS. 11 to 18, no significant change was observed in comparison with the results shown in FIG. 2 (a 10-base random primer).

The results of experiment described in 3.1.8 are summarized in Table 25.

TABLE 25

Figure 19:
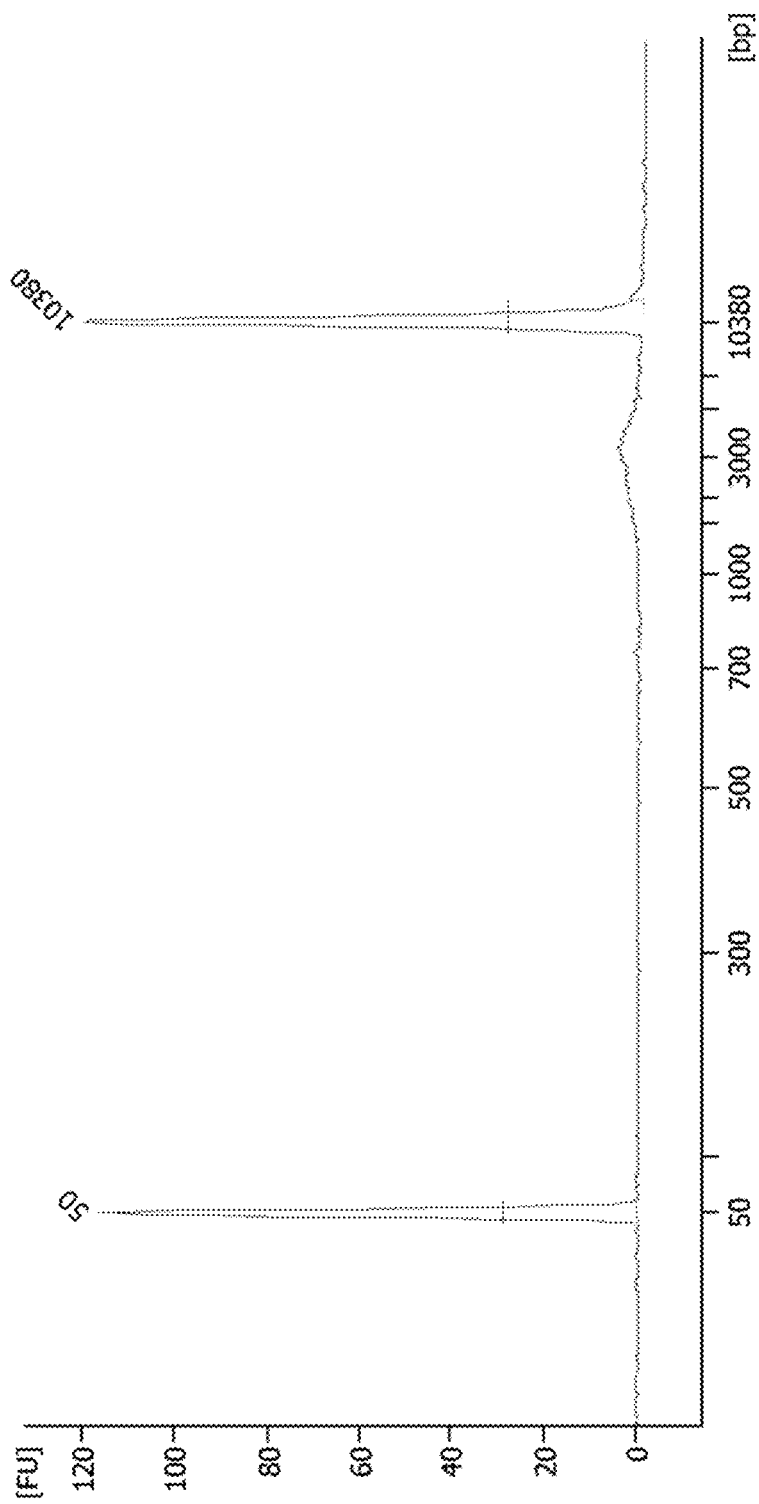
FIG. 19 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 2 microM.
Figure 20:
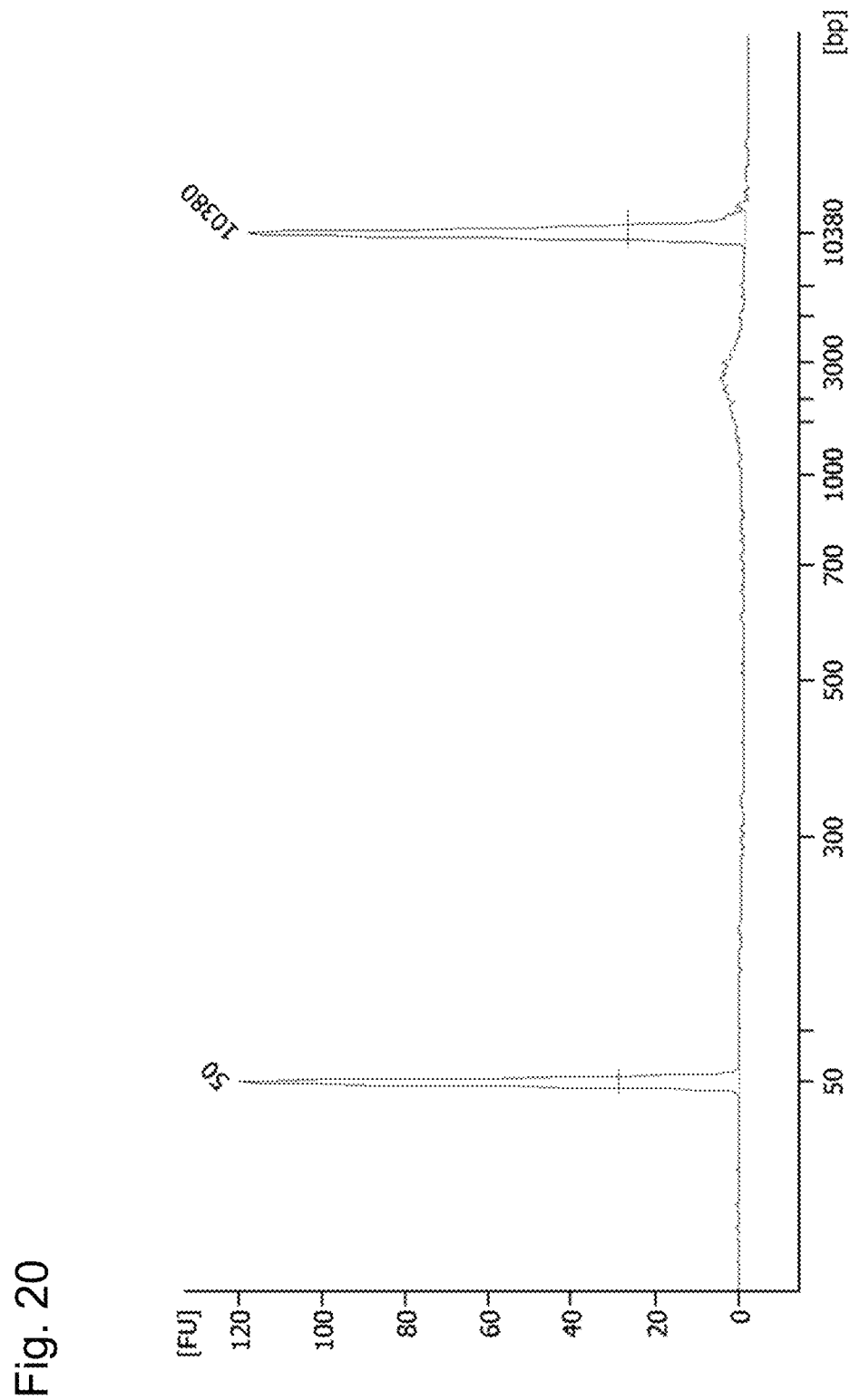
FIG. 20 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 4 microM.
Figure 21:
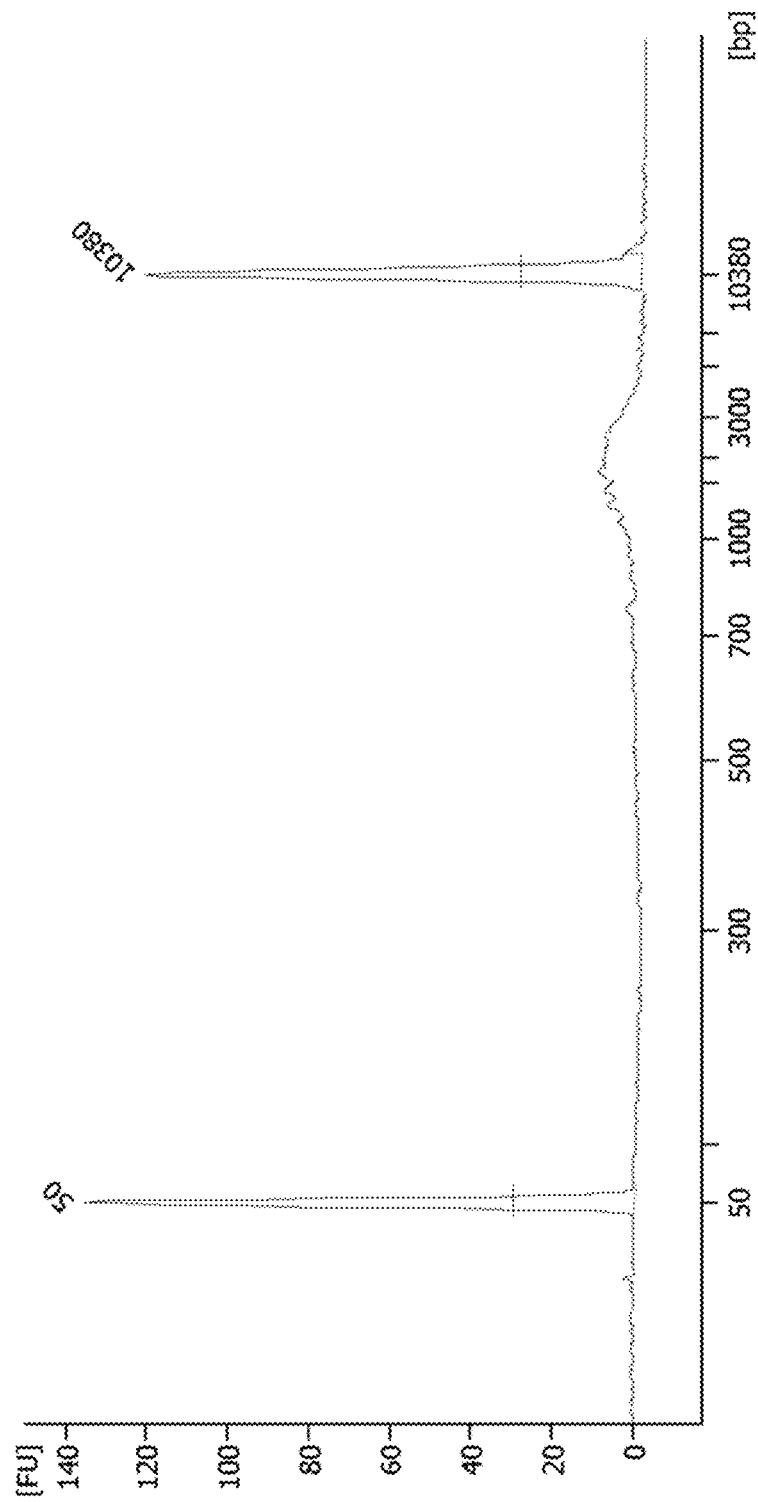
FIG. 21 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 6 microM.
Figure 22:
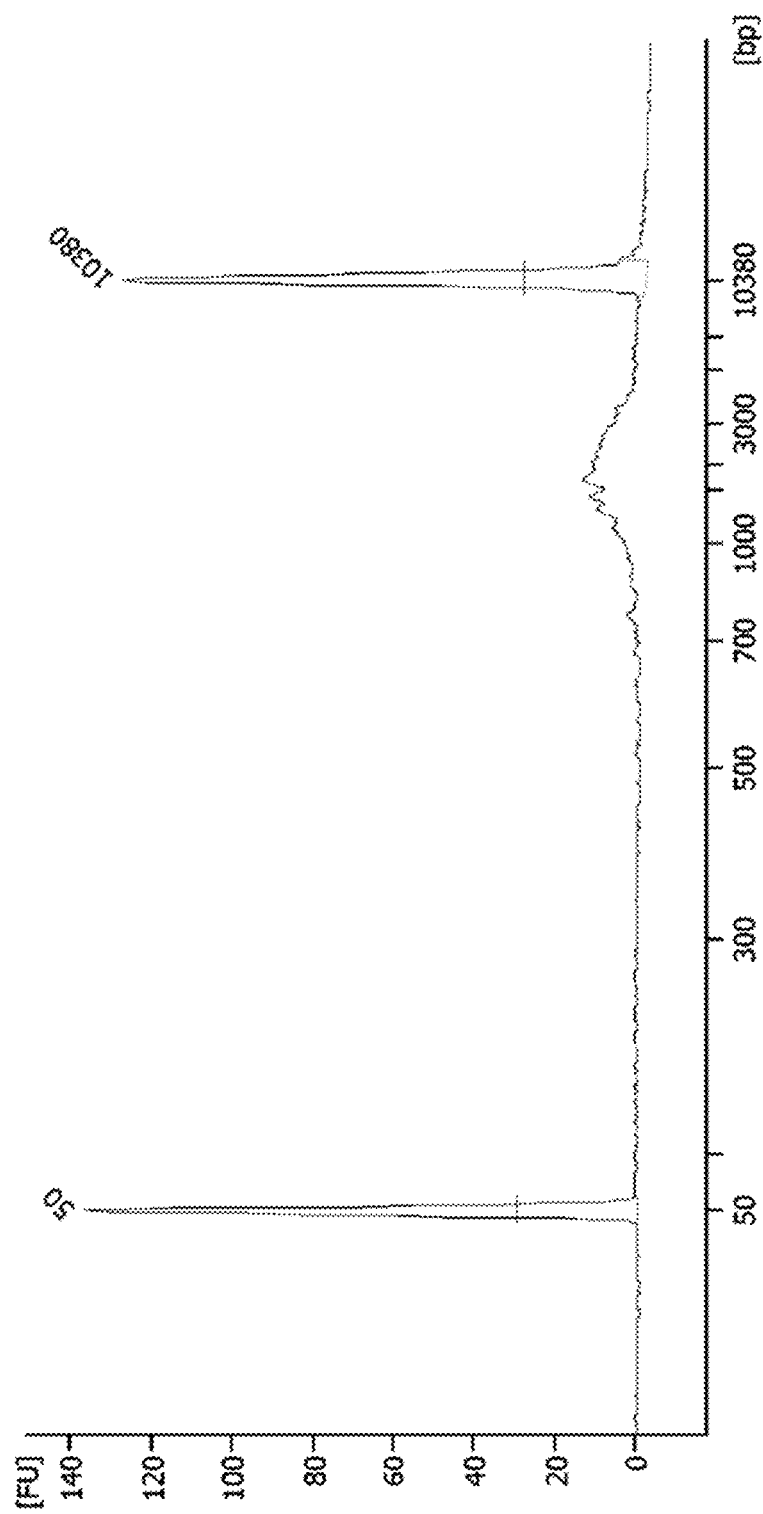
FIG. 22 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 6 microM.
Figure 23:
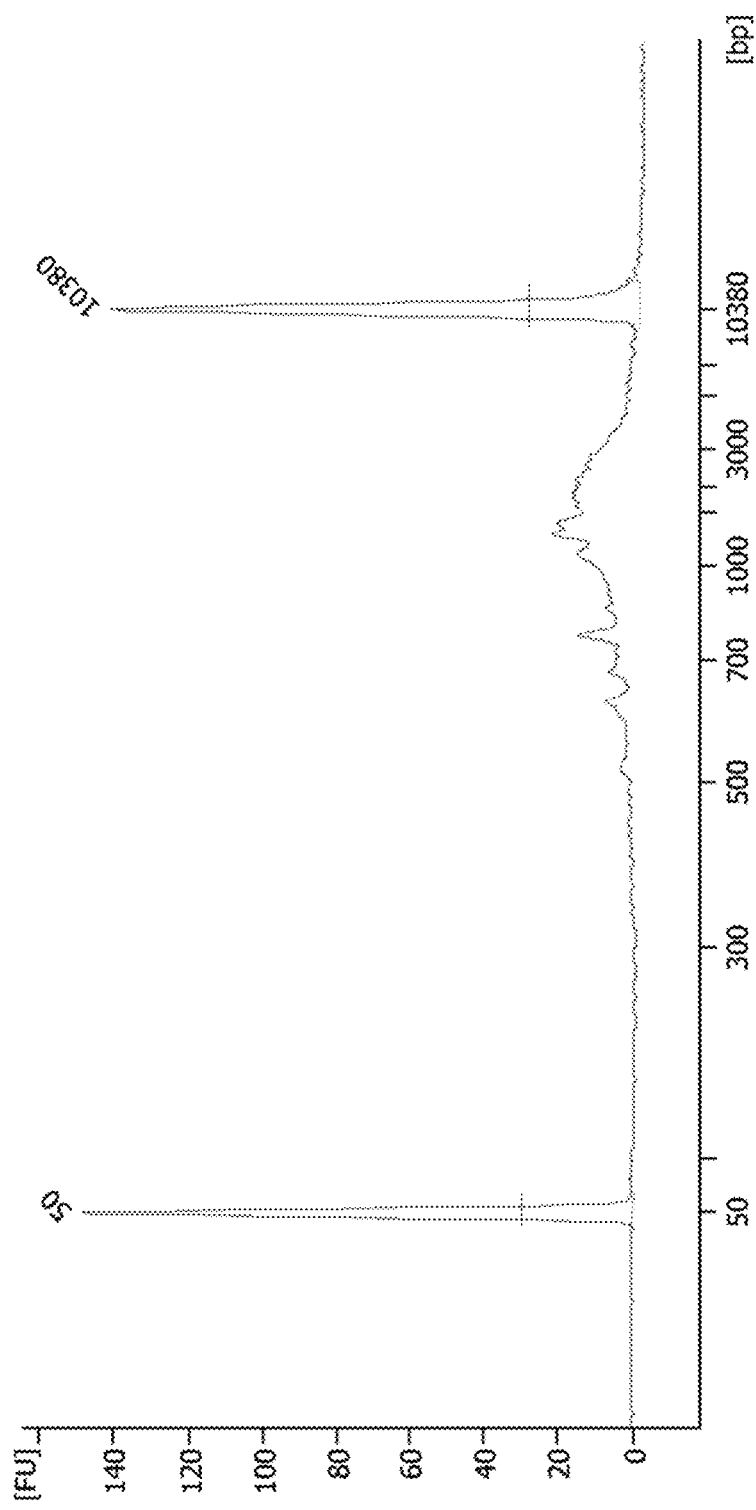
FIG. 23 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 8 microM.
Figure 24:
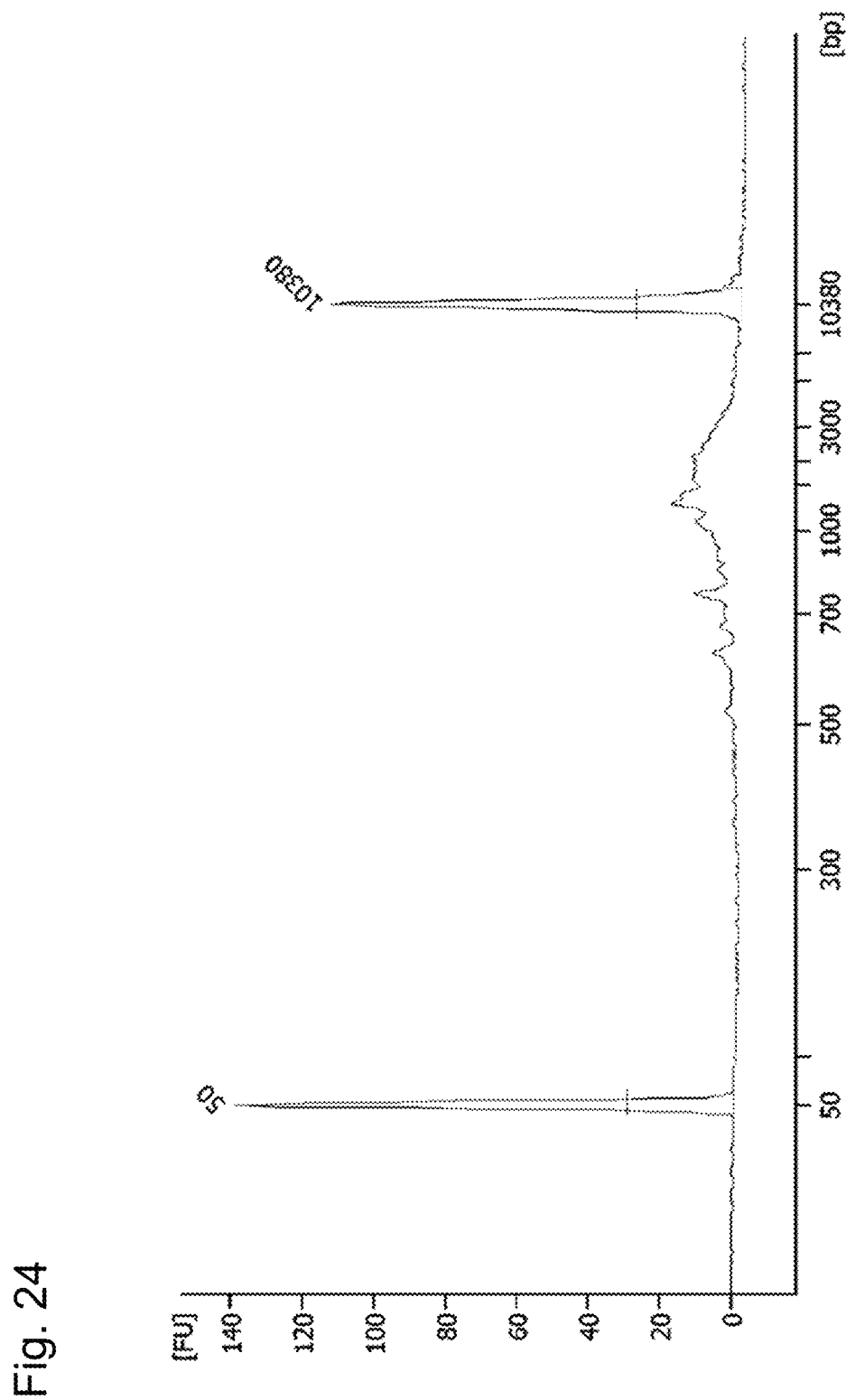
FIG. 24 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 8 microM.
Figure 25:
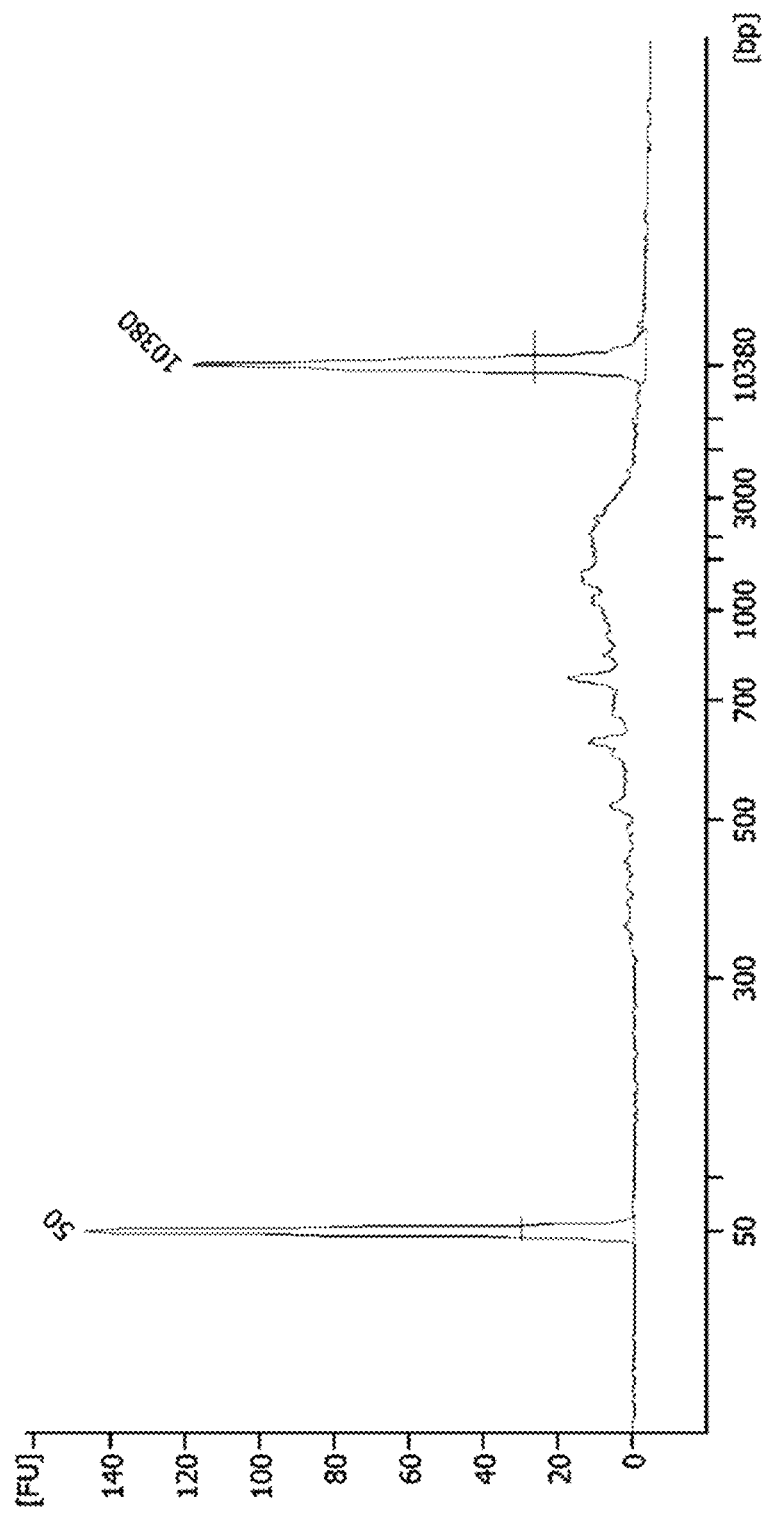
FIG. 25 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 10 microM.
Figure 26:
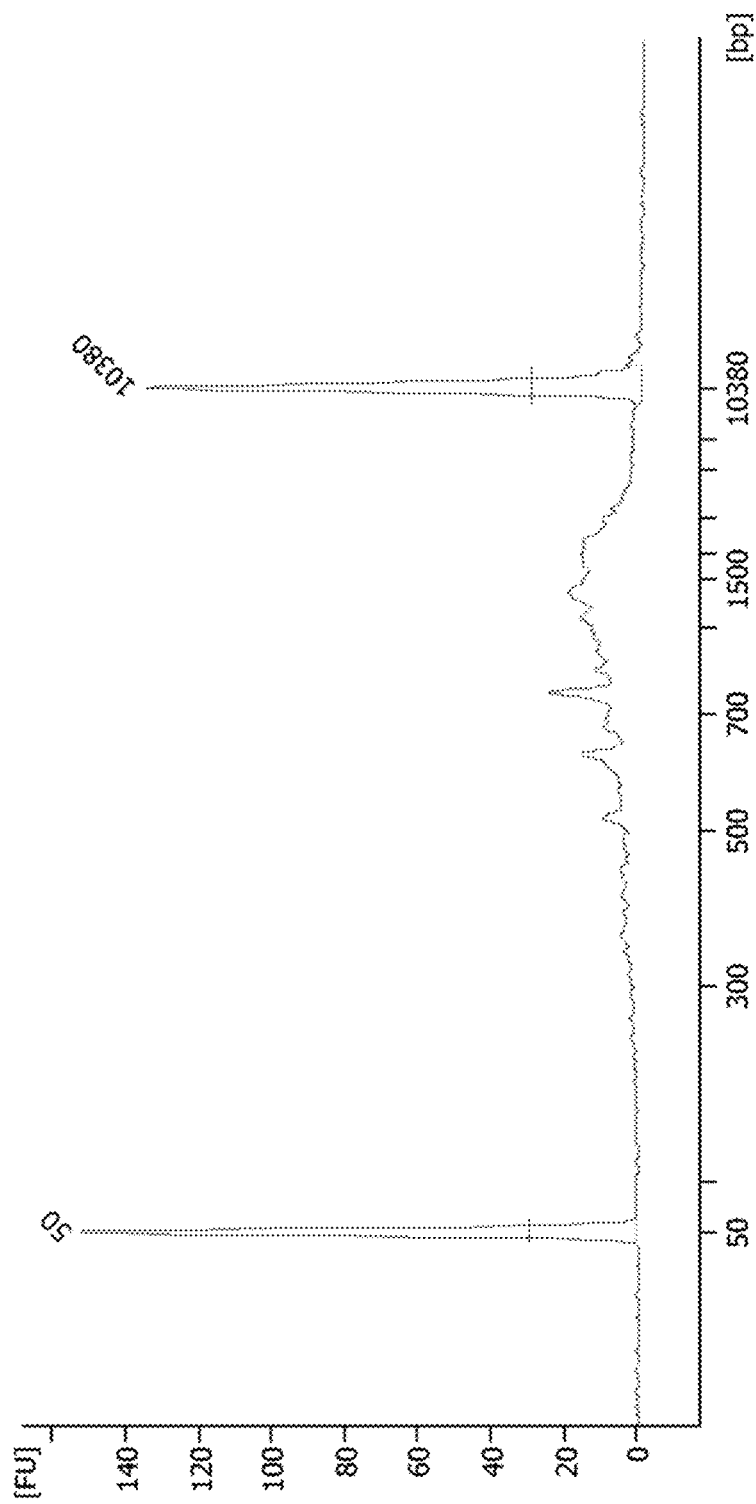
FIG. 26 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 10 microM.
Figure 27:
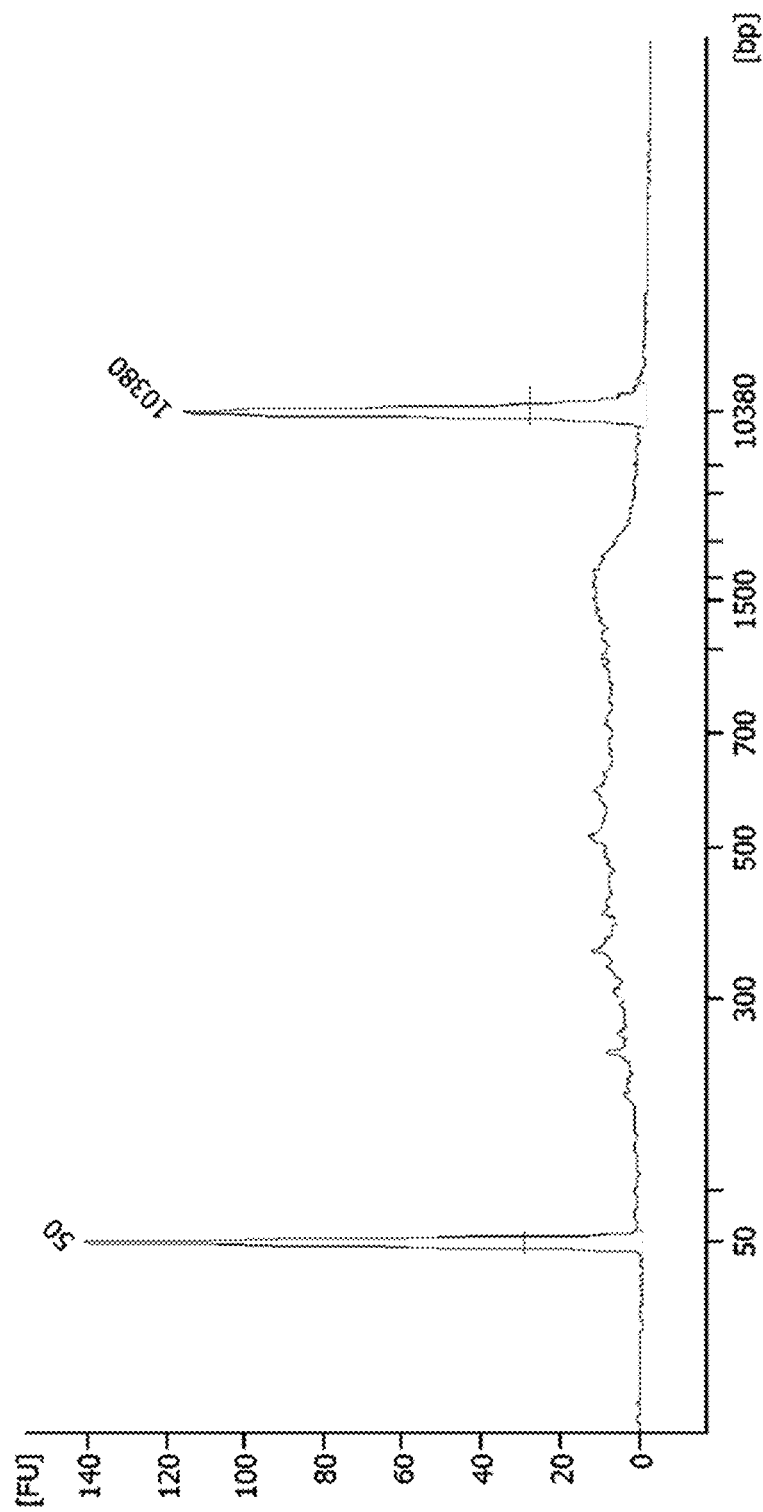
FIG. 27 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 20 microM.
Figure 28:
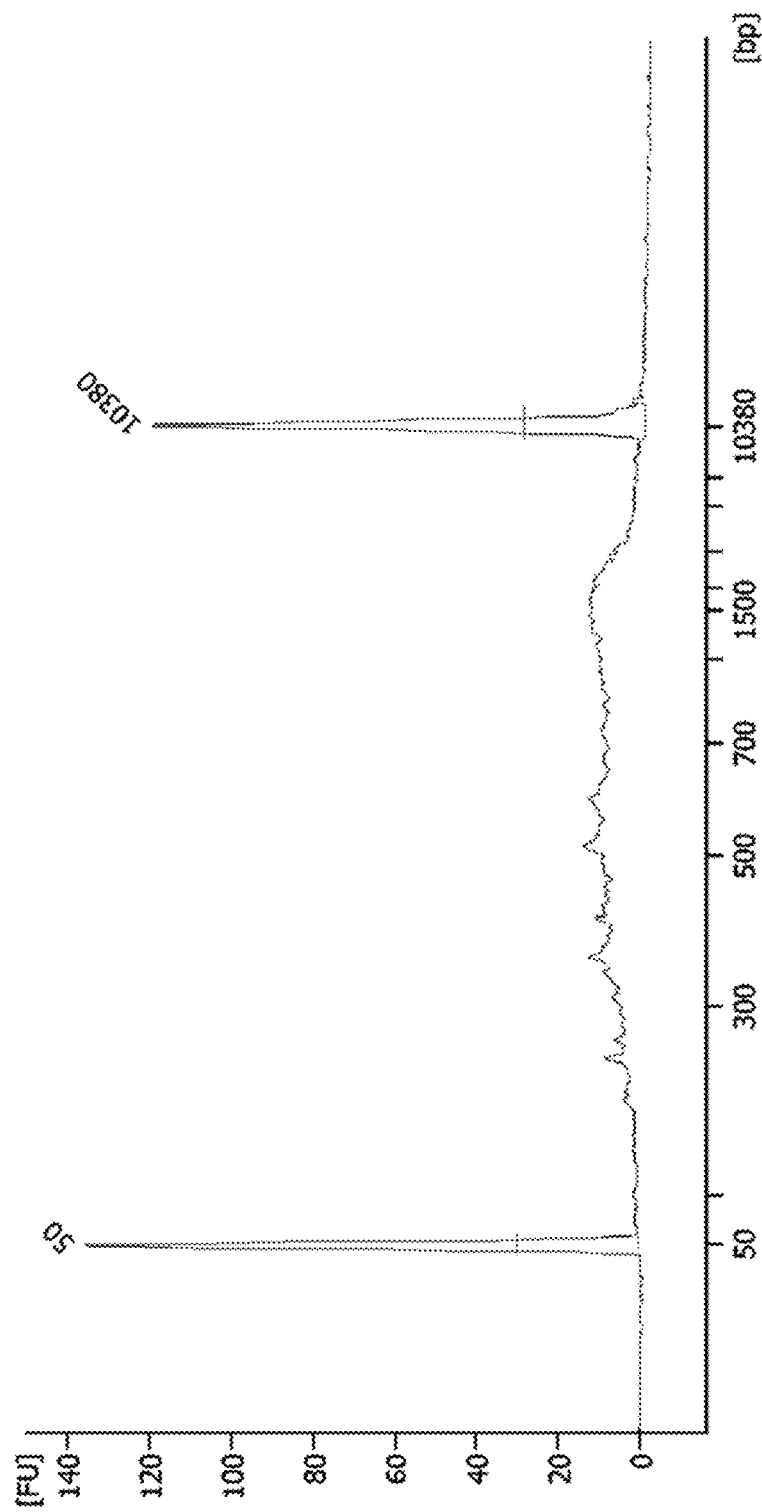
FIG. 28 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 20 microM.
Figure 29:
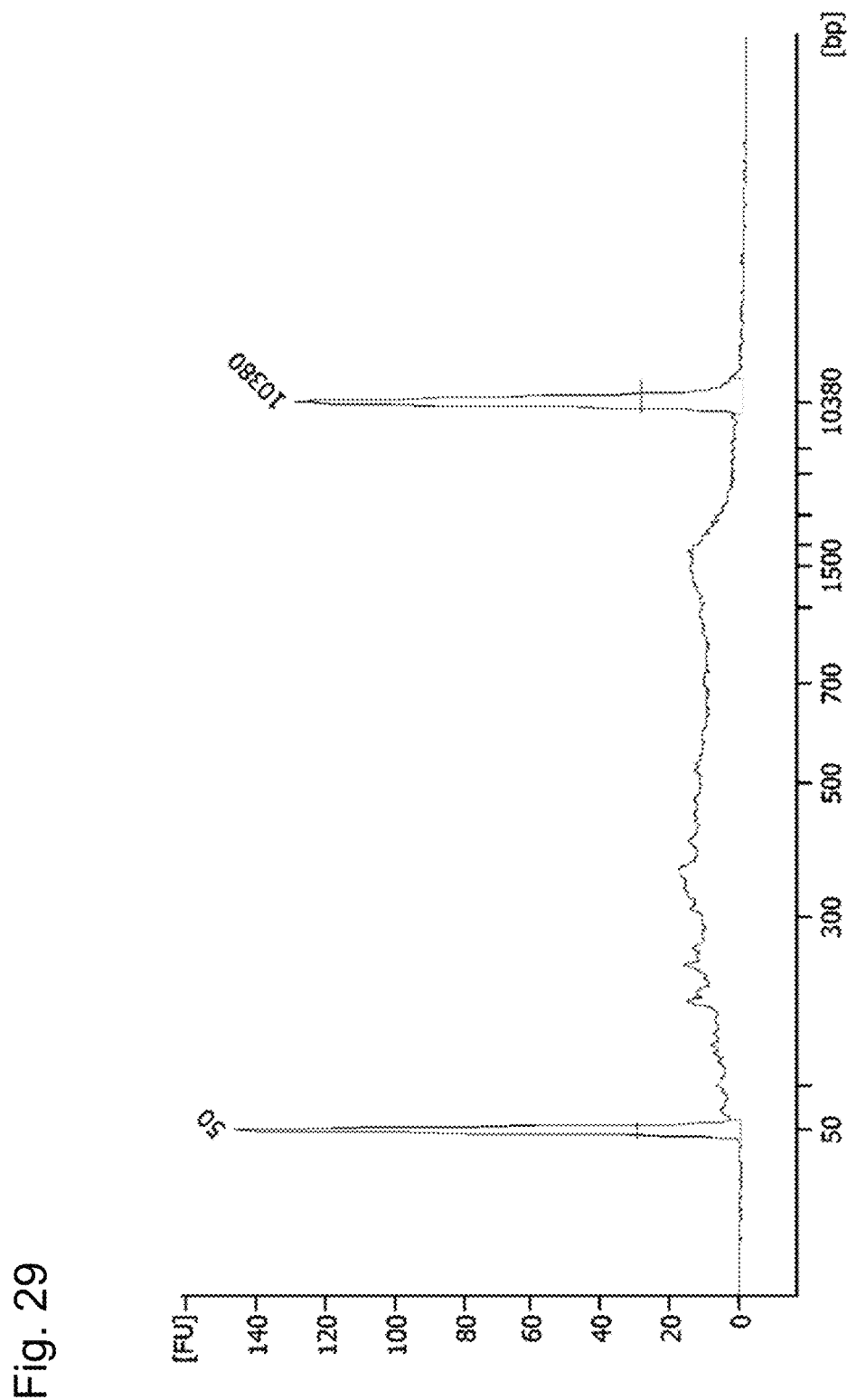
FIG. 29 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 40 microM.
Figure 30:
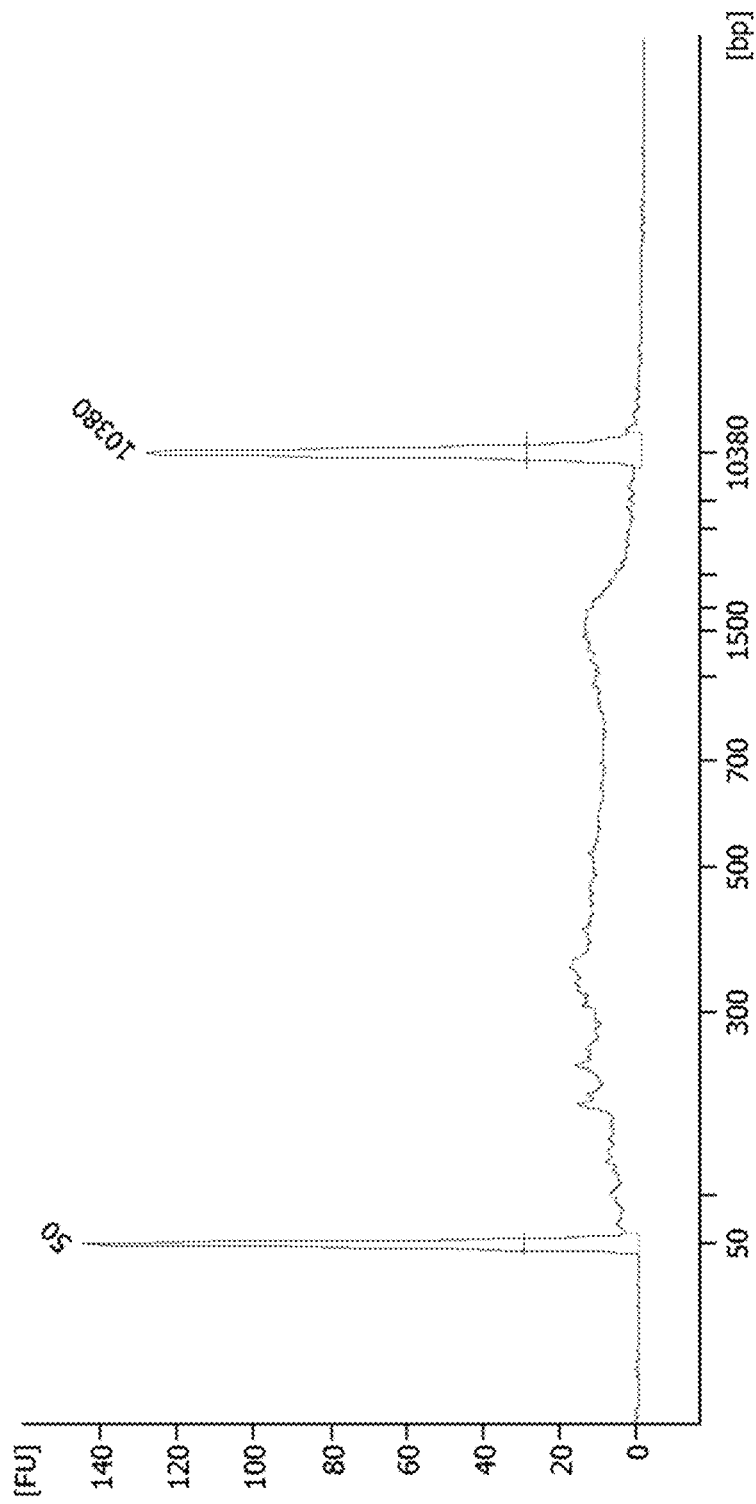
FIG. 30 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 40 microM.
Figure 31:
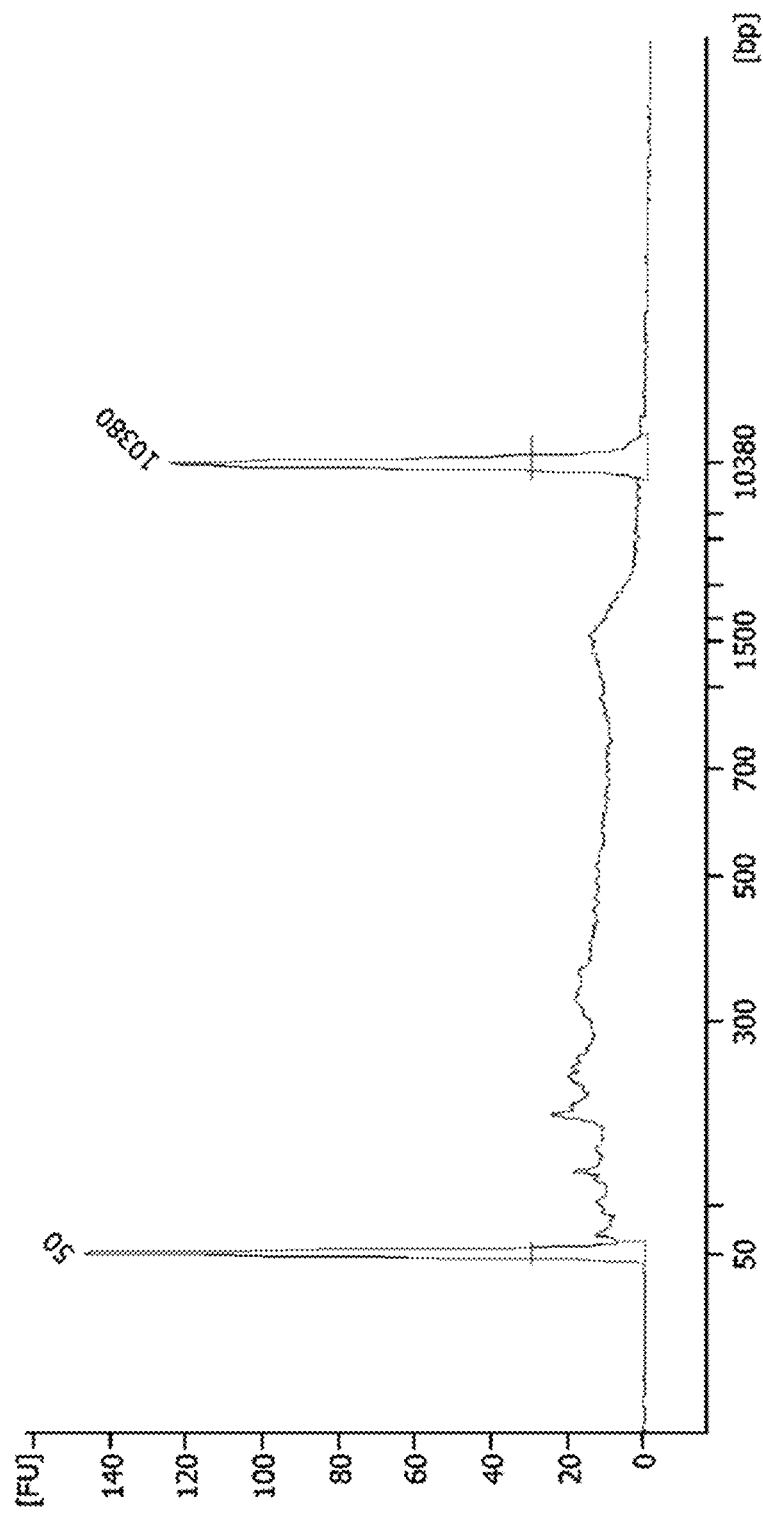
FIG. 31 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 60 microM.
Figure 32:
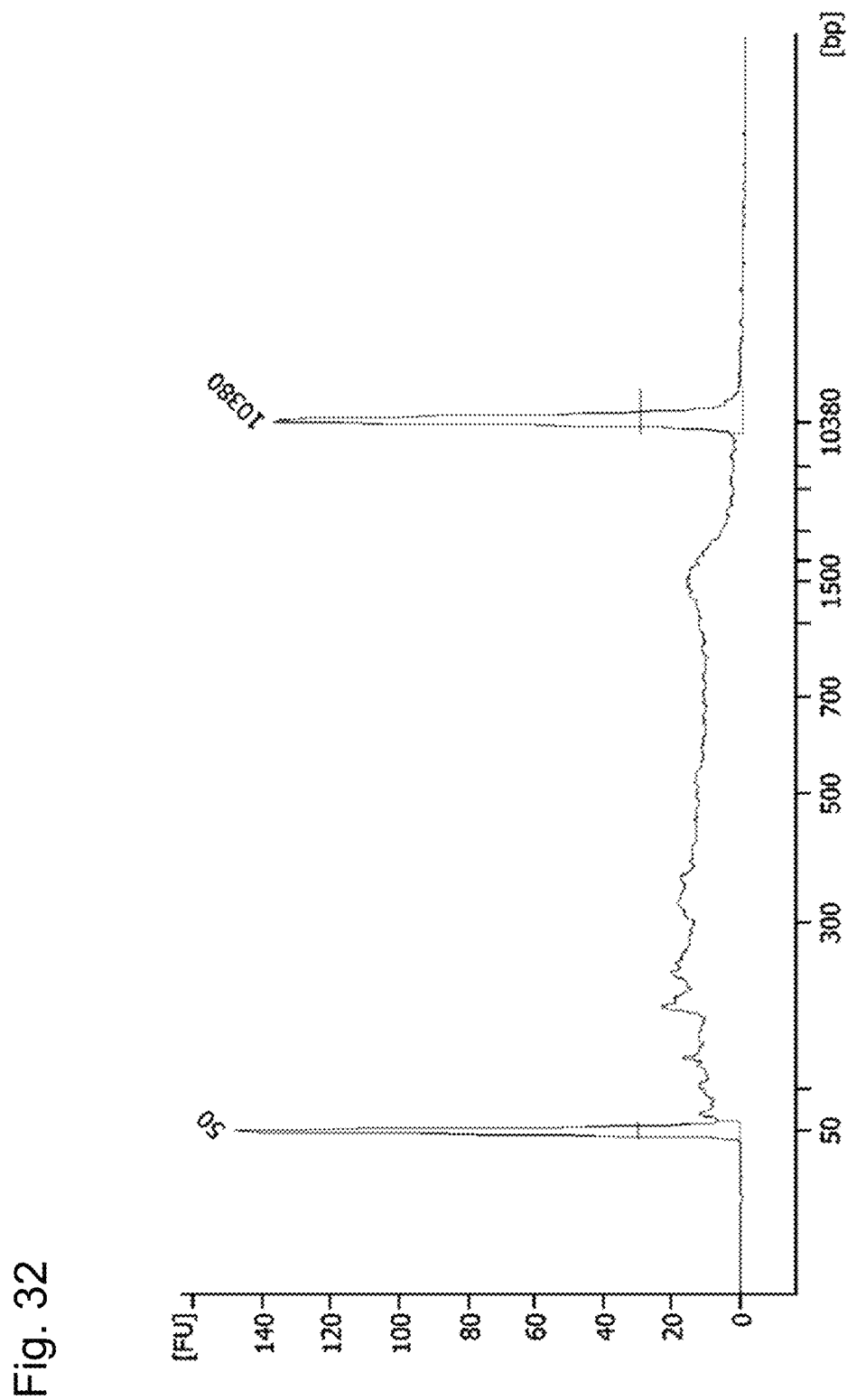
FIG. 32 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 60 microM.
Figure 33:
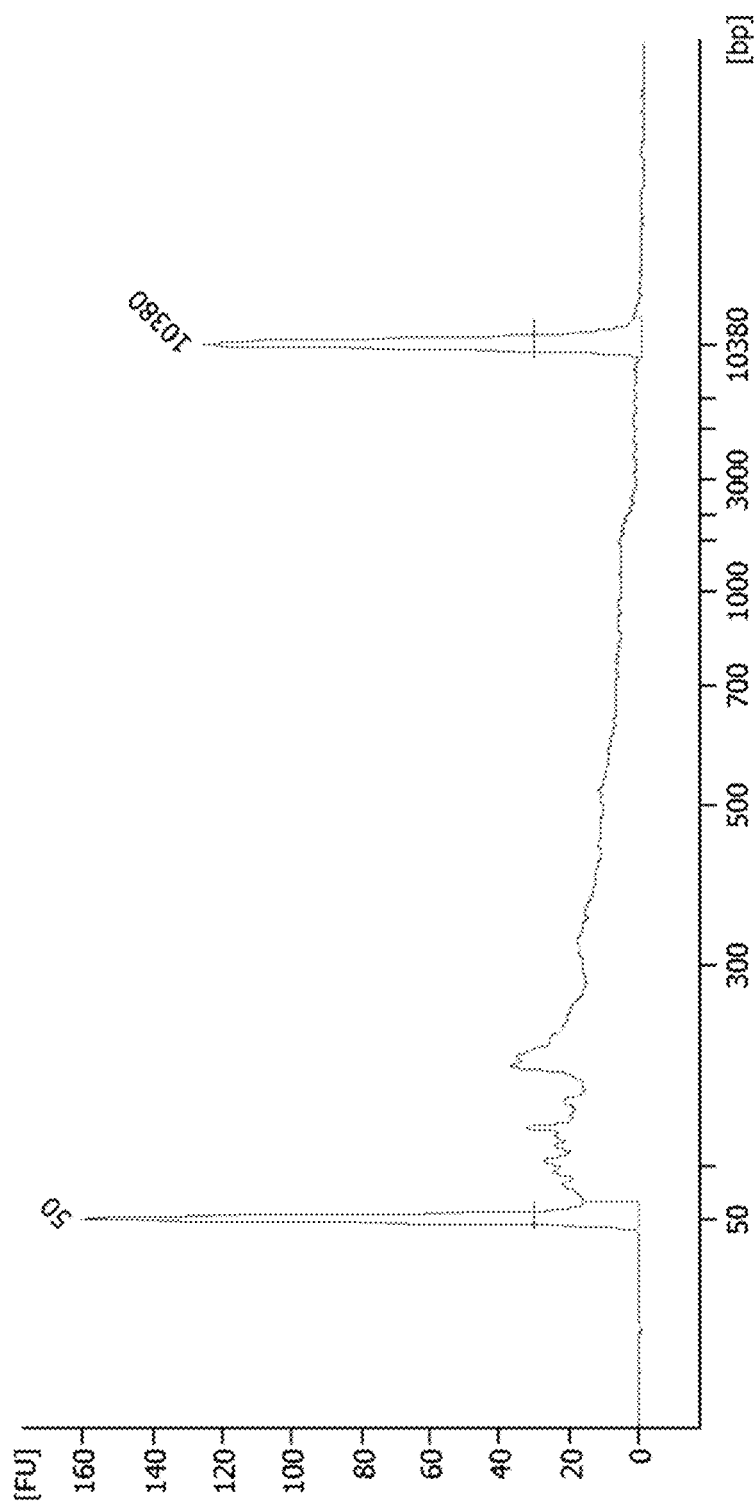
FIG. 33 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 100 microM.
Figure 34:
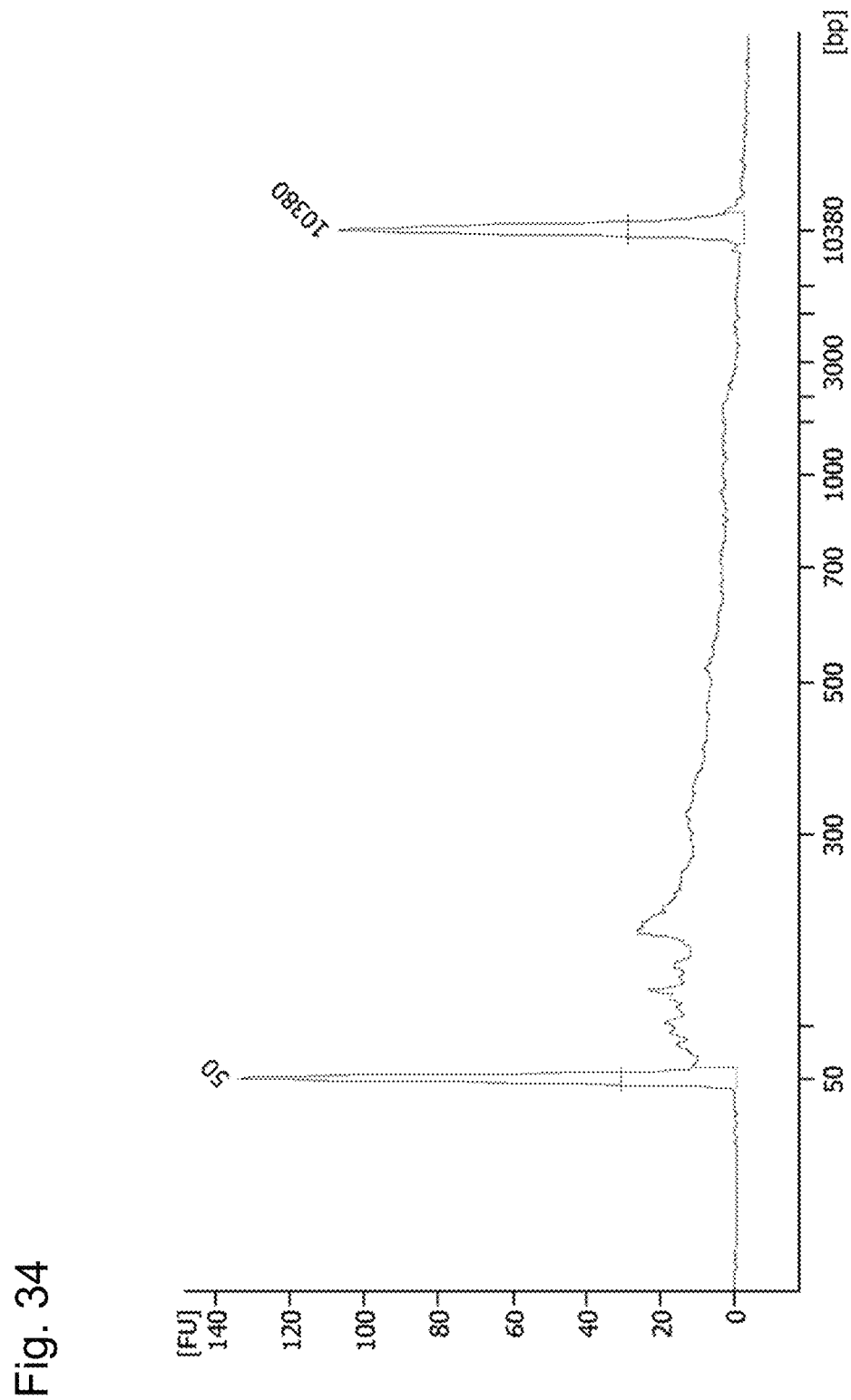
FIG. 34 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 100 microM.
Figure 35:
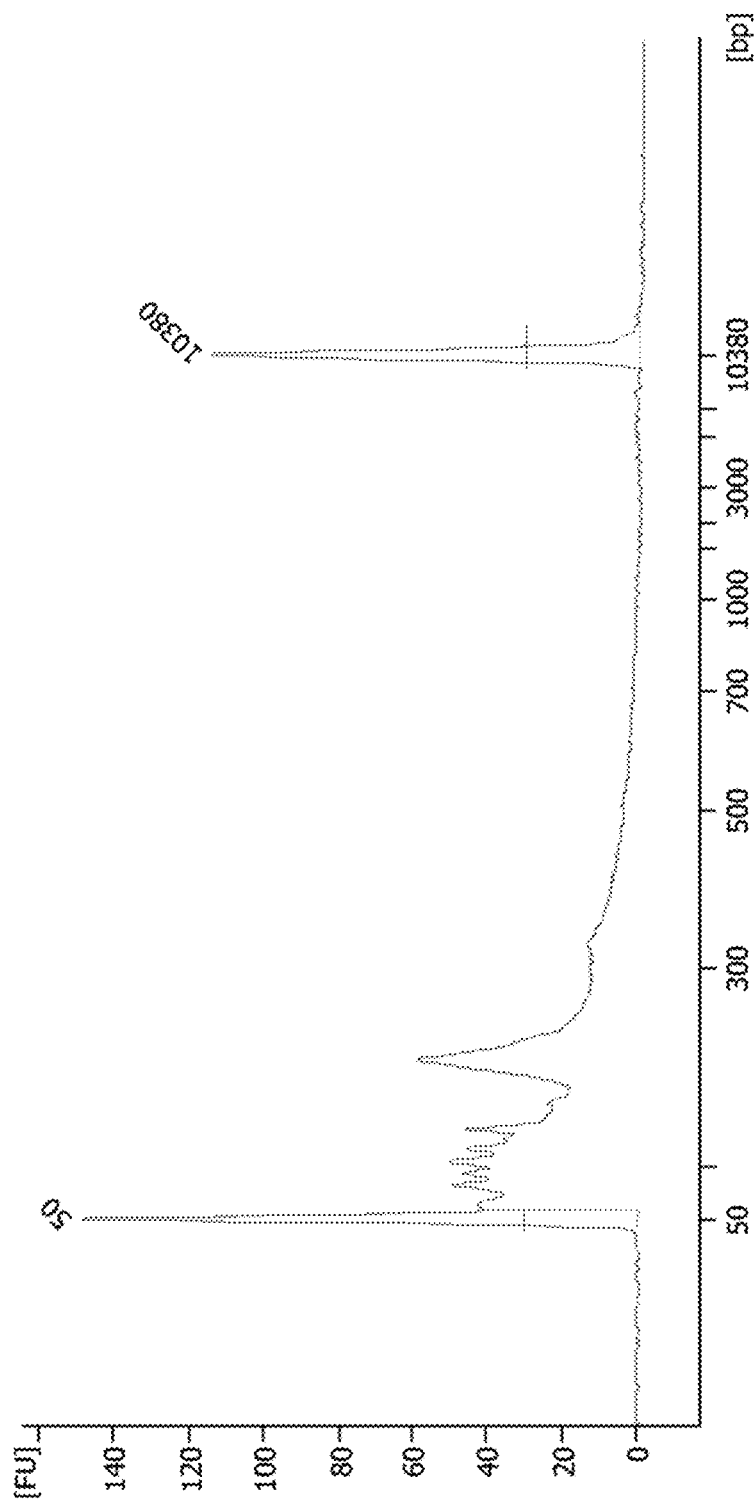
FIG. 35 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 200 microM.
Figure 36:
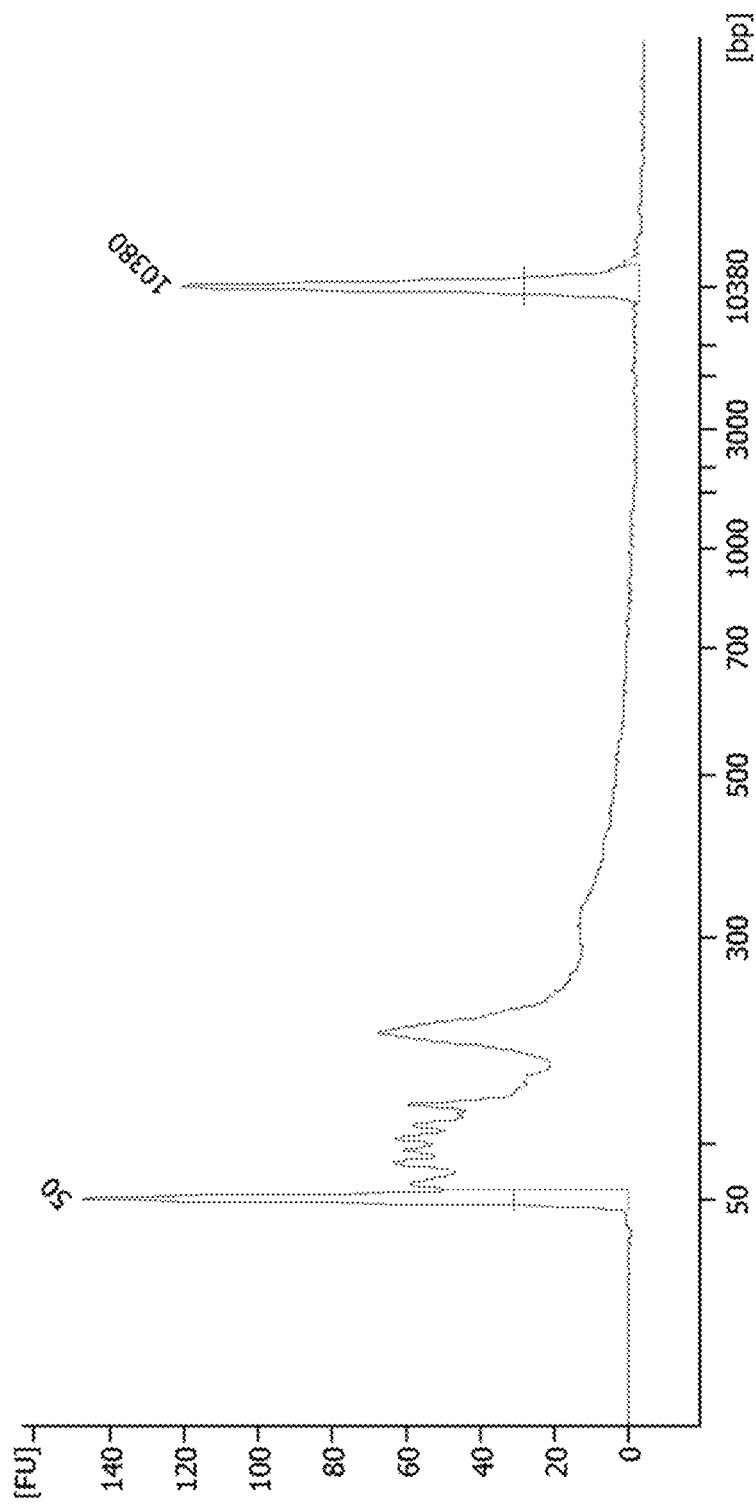
FIG. 36 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 200 microM.
Figure 37:
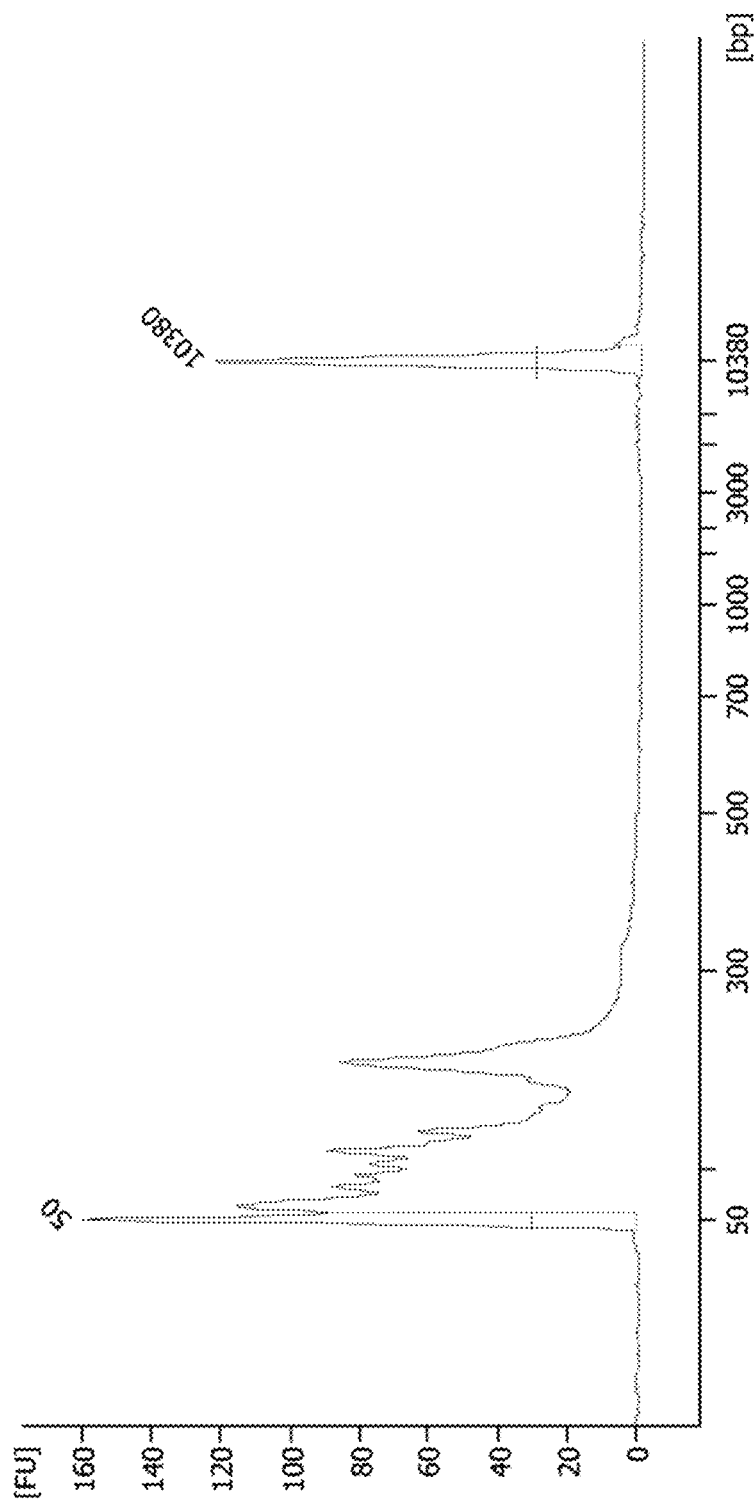
FIG. 37 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 300 microM.
Figure 38:
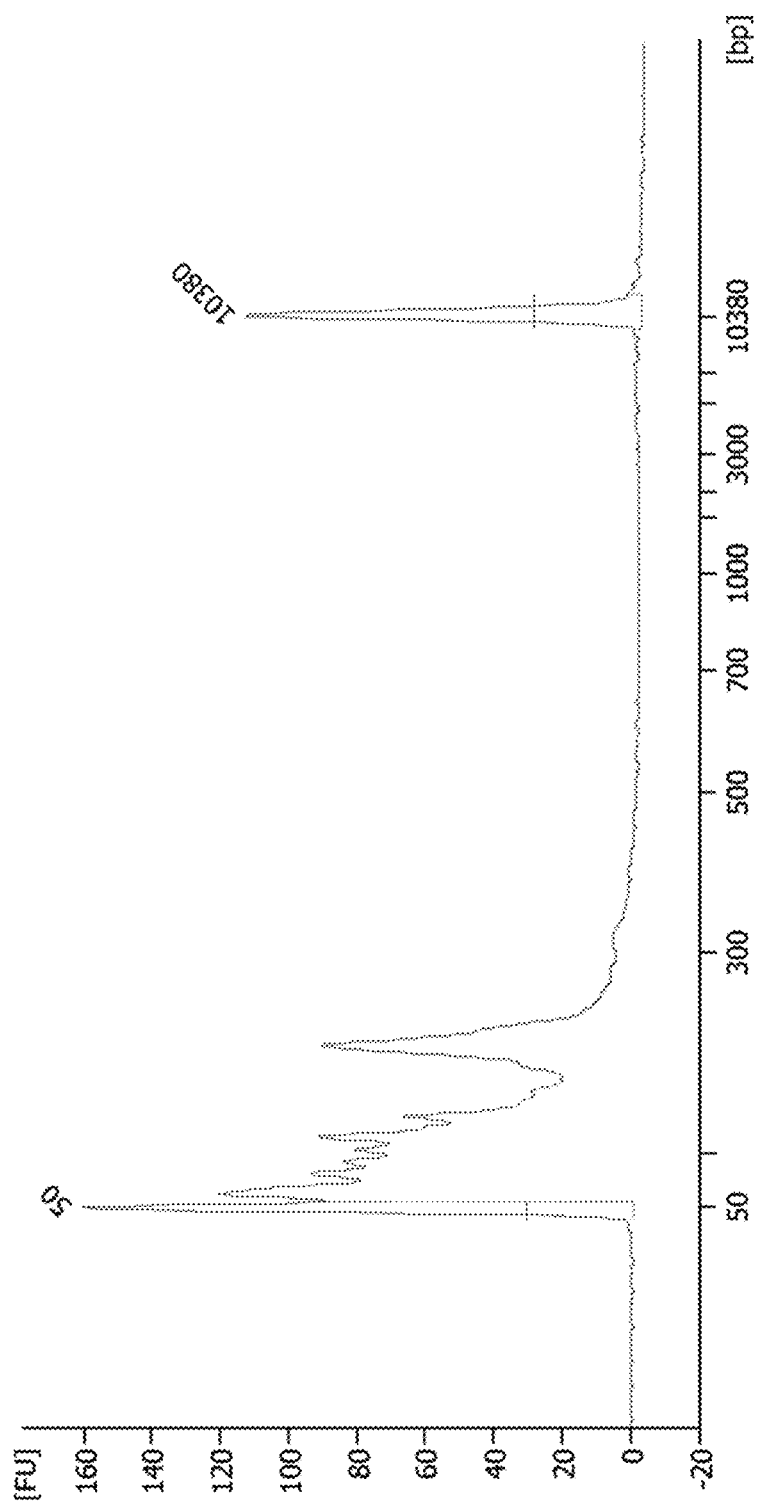
FIG. 38 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 300 microM.
Figure 39:
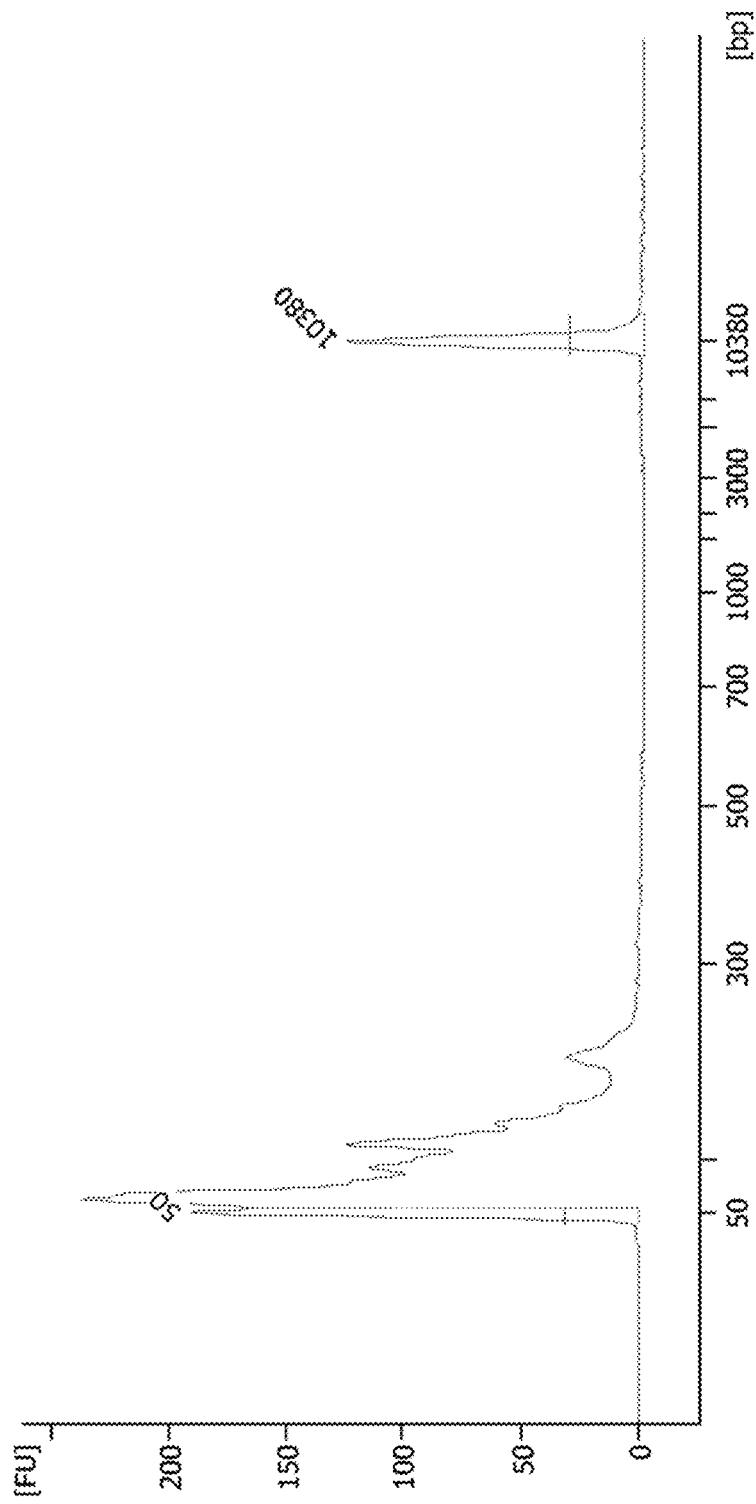
FIG. 39 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 400 microM.
Figure 40:
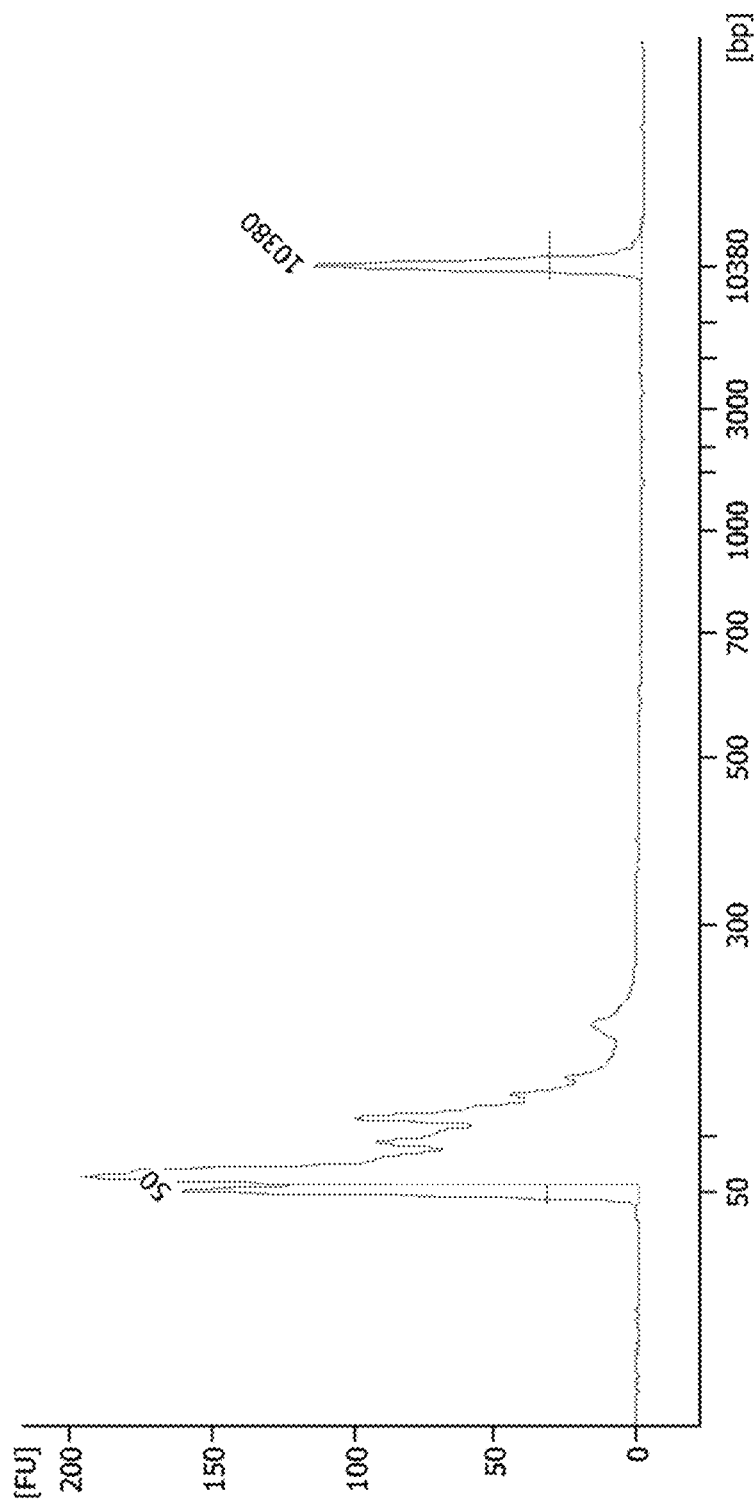
FIG. 40 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 400 microM.
Figure 41:
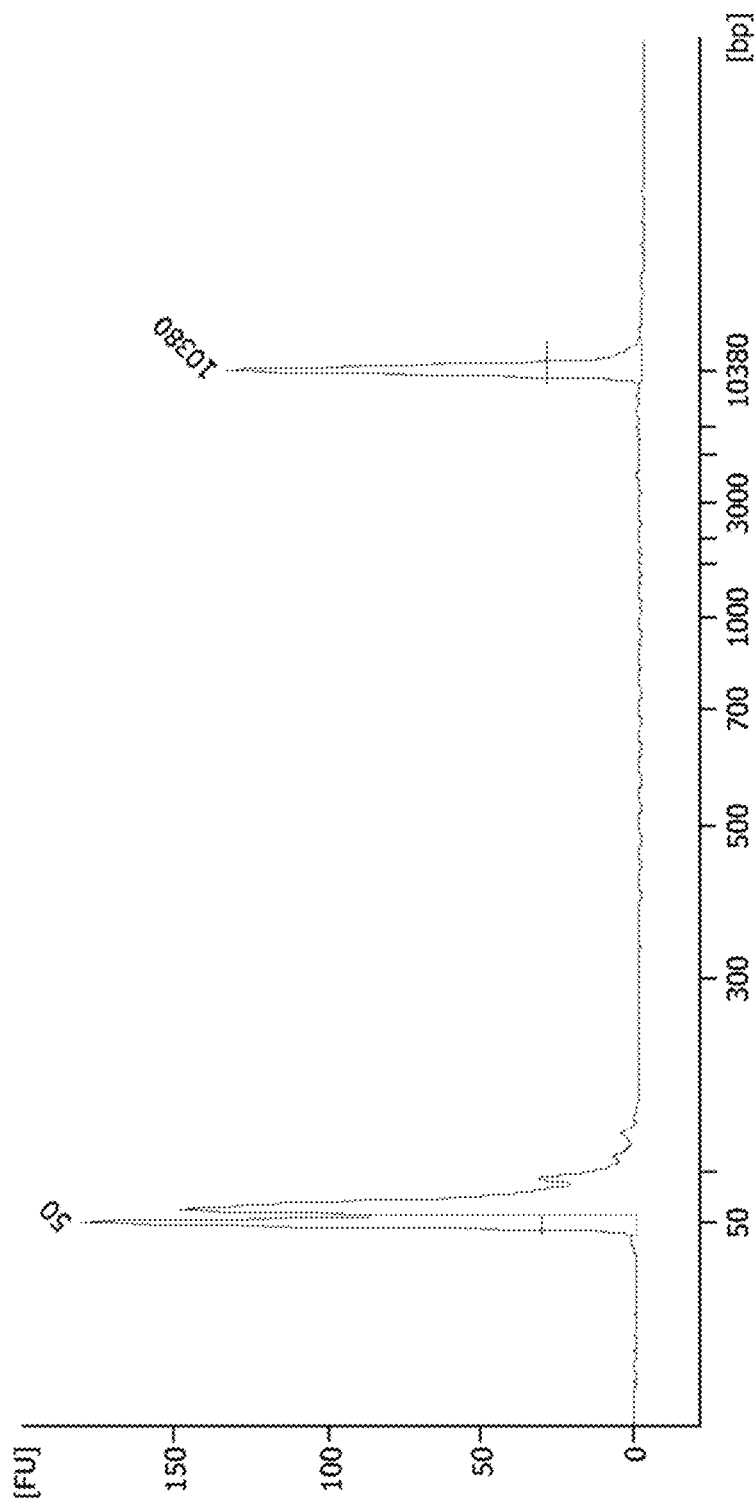
FIG. 41 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a random primer at a concentration of 500 microM.
Figure 42:
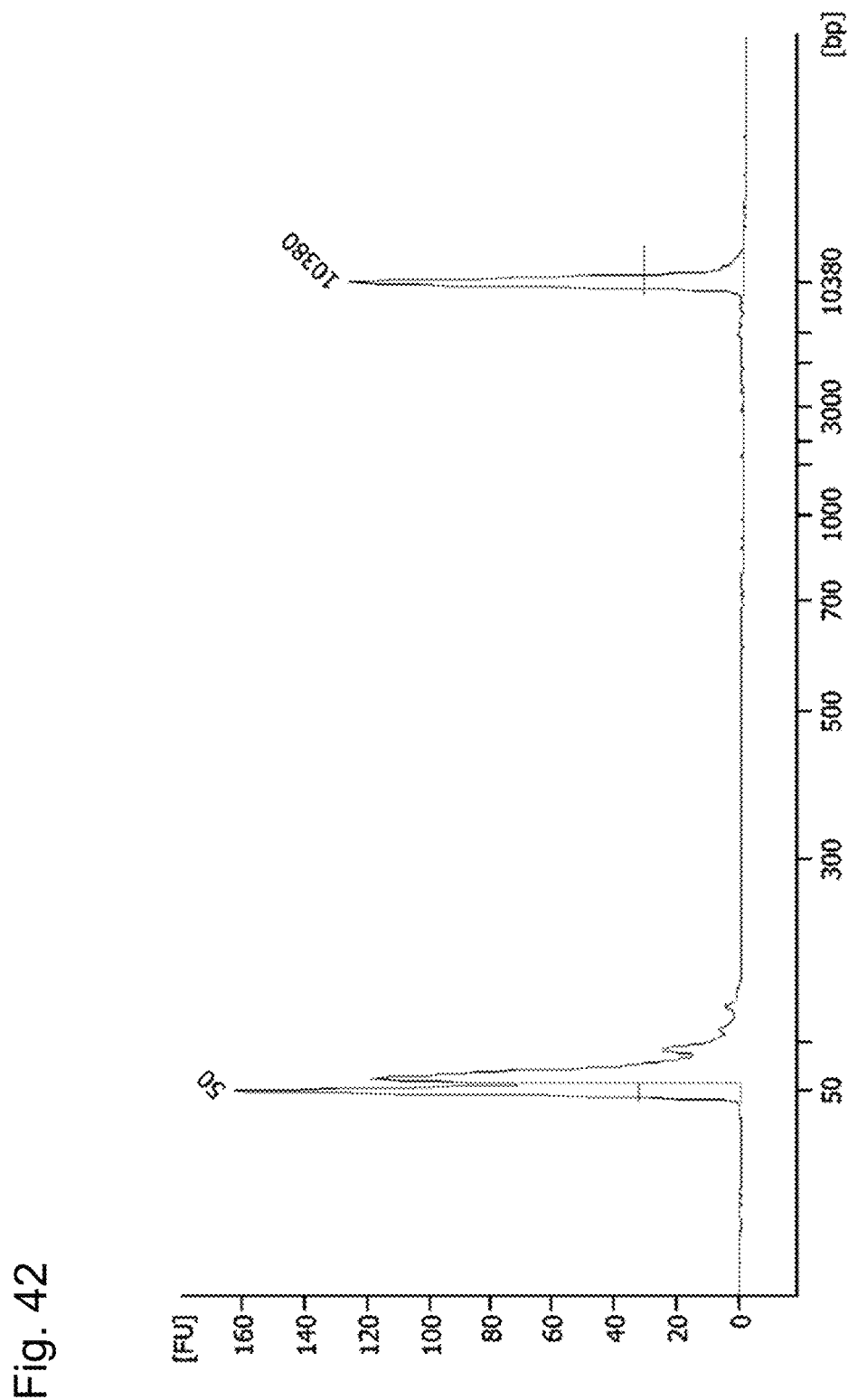
FIG. 42 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a random primer at a concentration of 500 microM.
Figure 43:
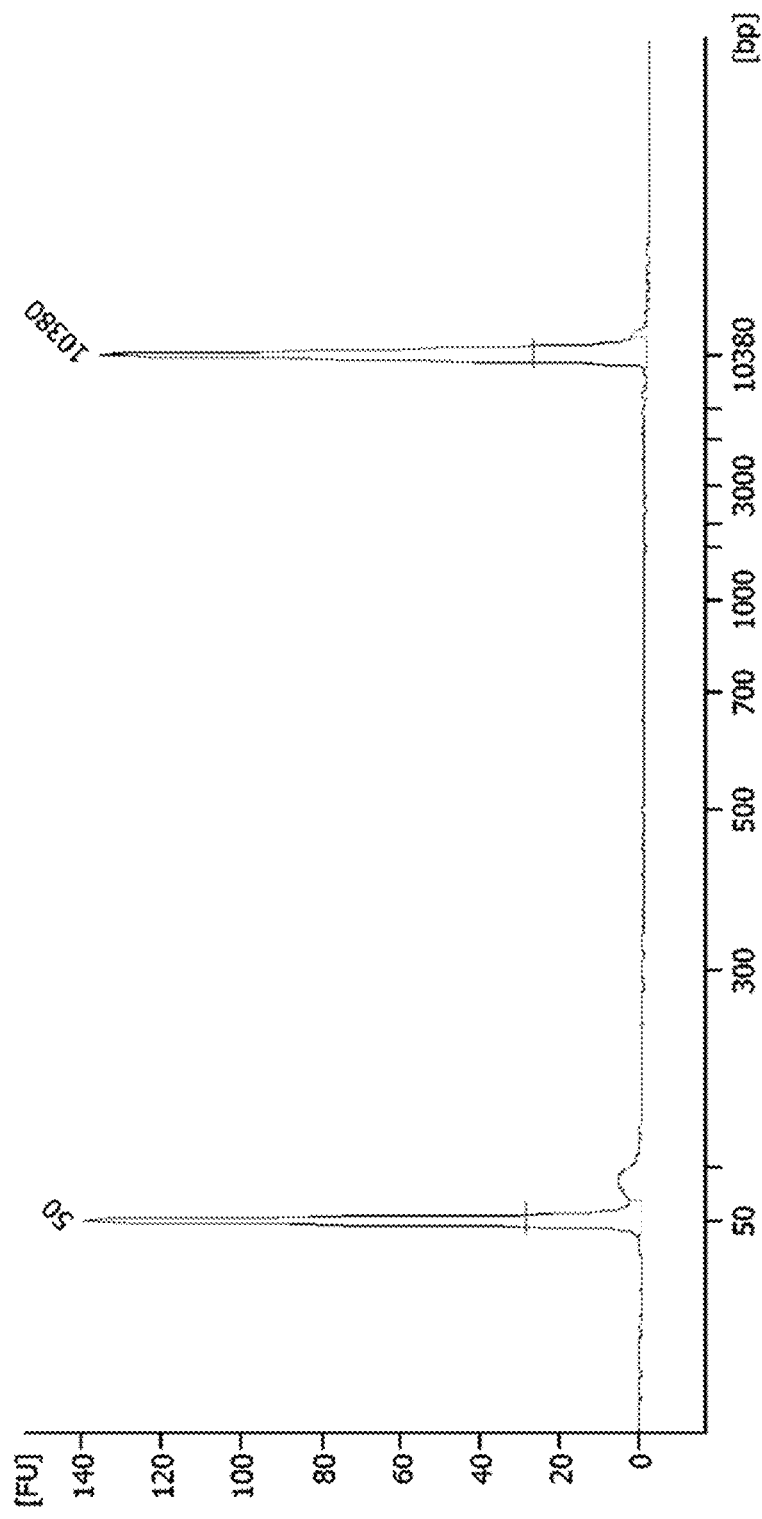
FIG. 43 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 600 microM.
Figure 44:
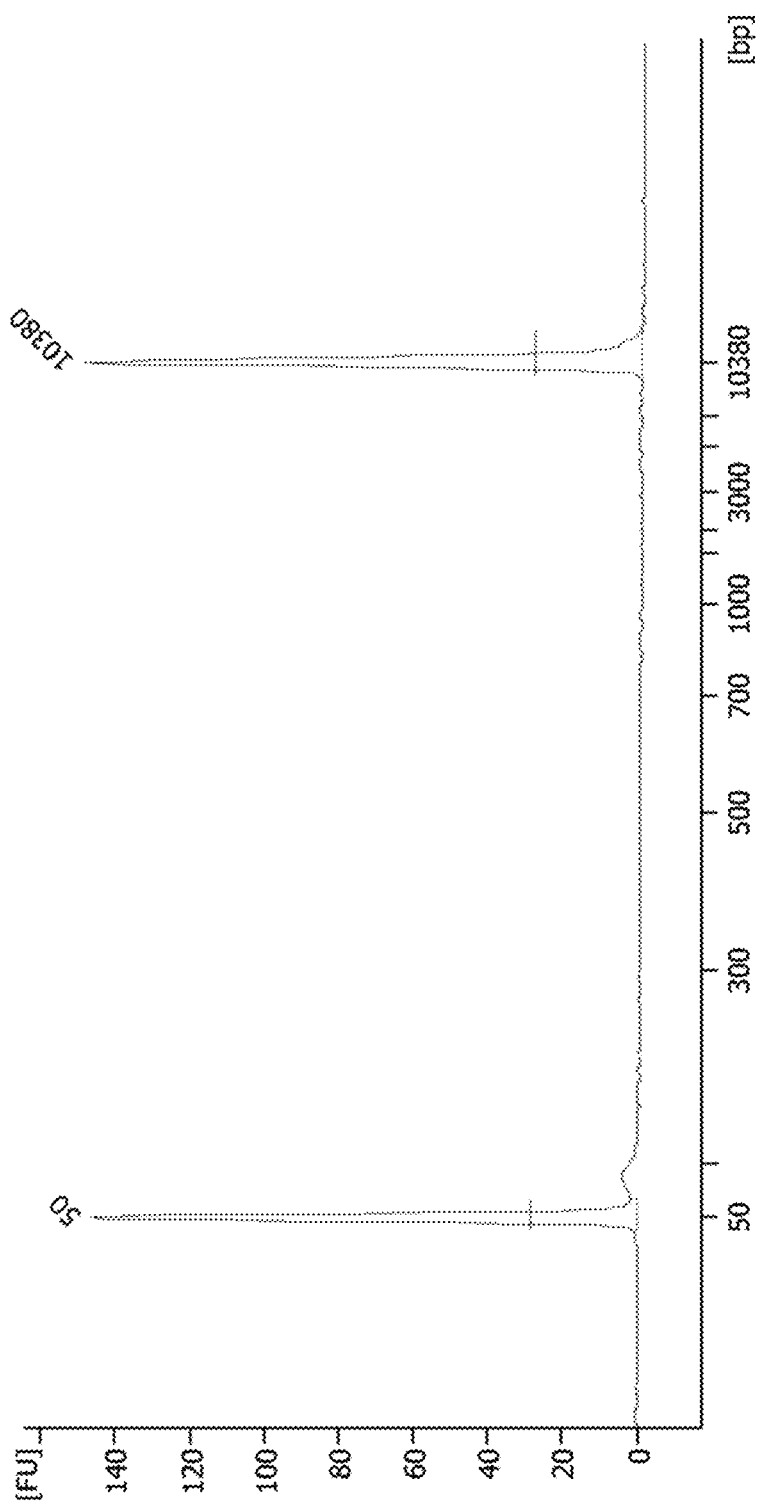
FIG. 44 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 700 microM.
Figure 45:
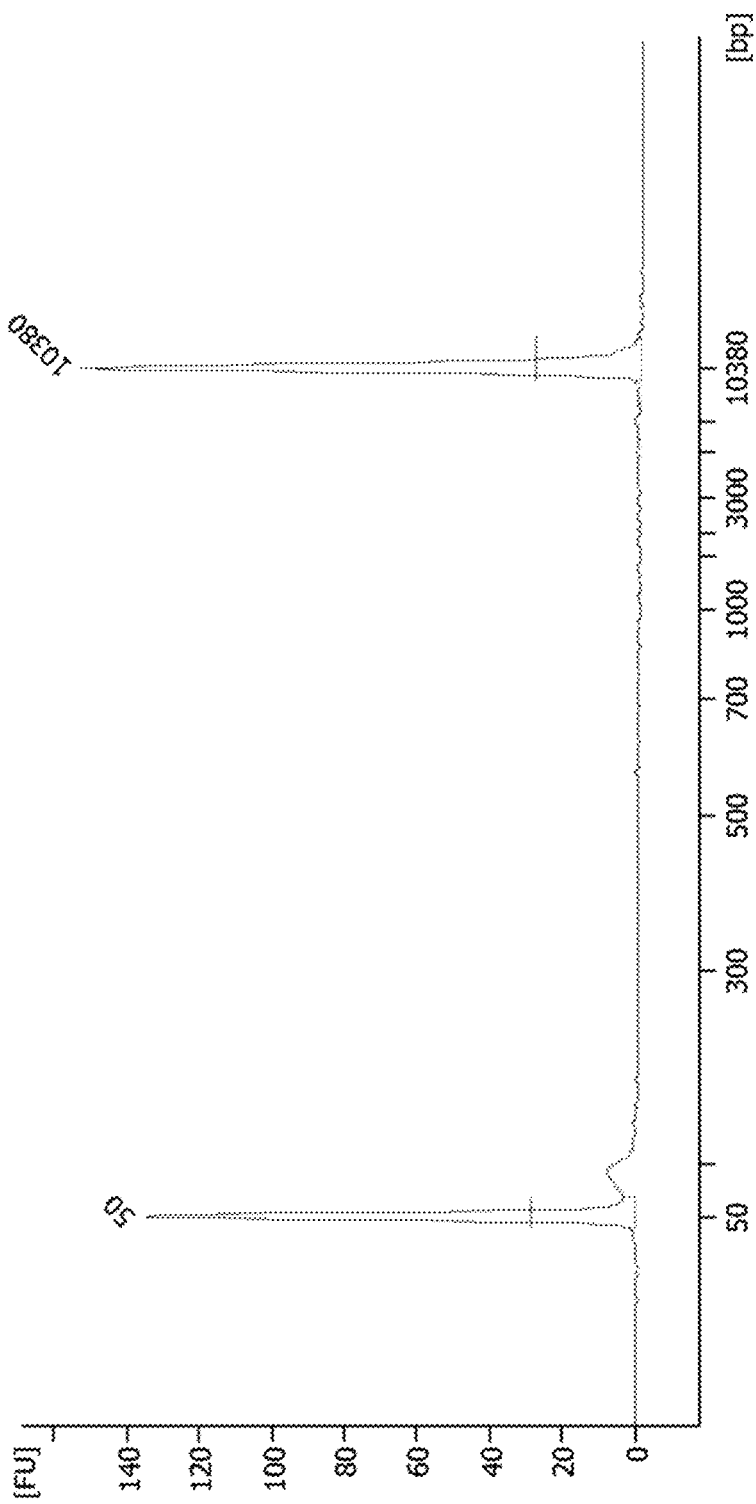
FIG. 45 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 800 microM.
Figure 46:
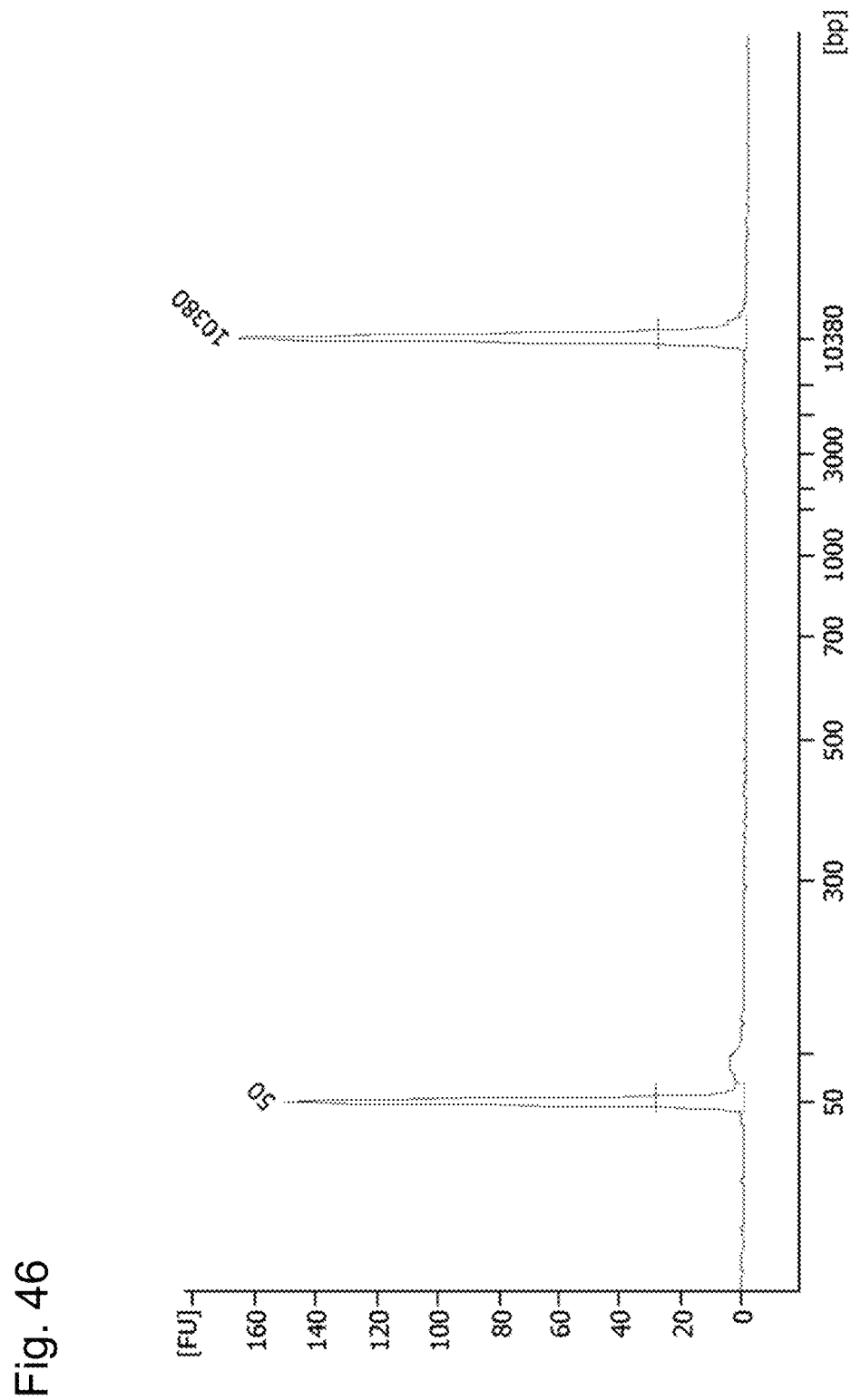
FIG. 46 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 900 microM.
Figure 47:
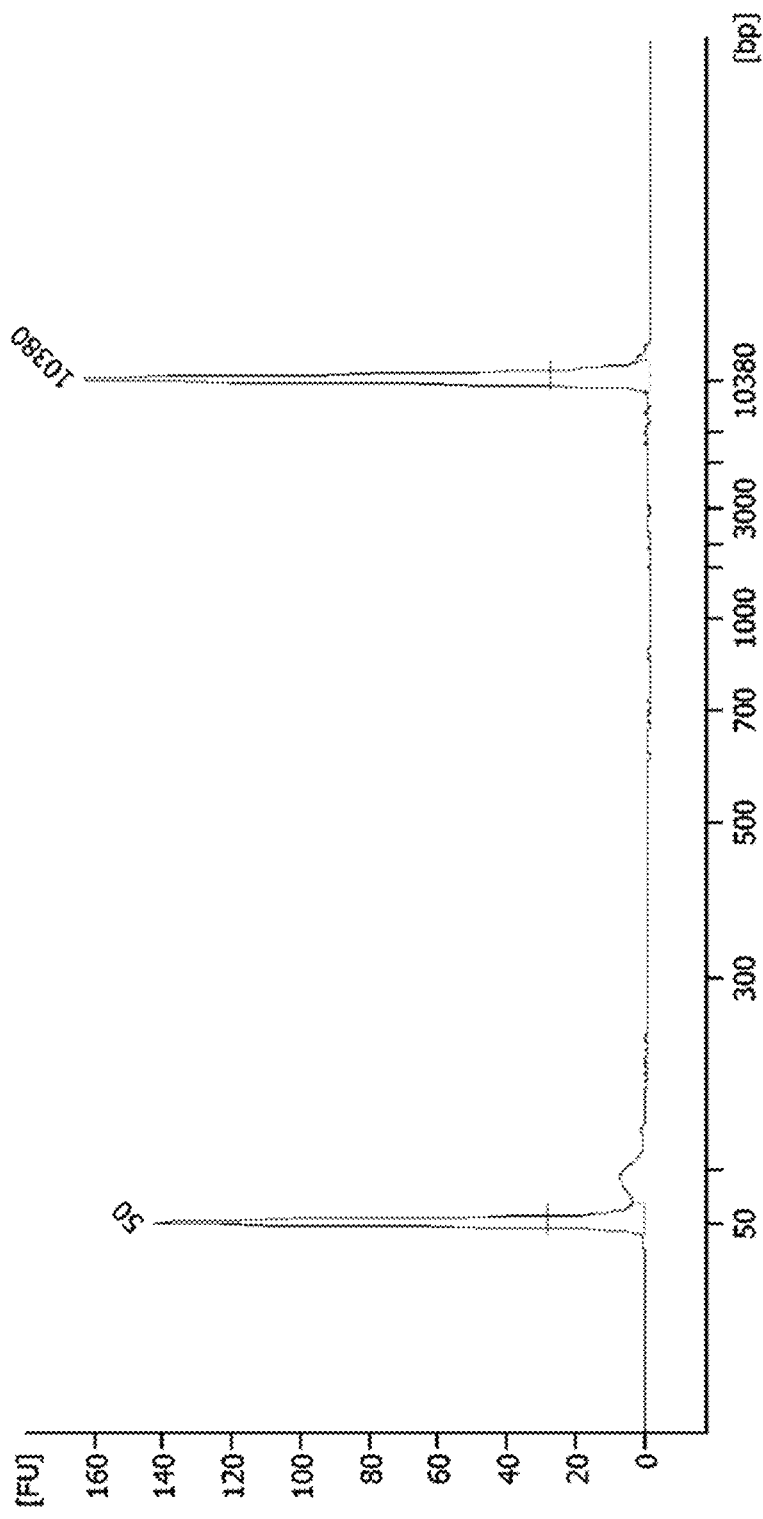
FIG. 47 shows a characteristic diagram demonstrating a correlation between an amplified fragment length and a fluorescence unit (FU) in which the amplified fragment length is determined based on an electrophoretic pattern of the DNA library amplified using DNA of the sugarcane variety NiF8 as a template and a random primer at a concentration of 1000 microM.

| Concentration (μM) | Repeat | FIG. No. | Correlational coefficient (ρ) |
|---|---|---|---|
| 2 | — | FIG. 19 | — |
| 4 | — | FIG. 20 | — |
| 6 | First | FIG. 21 | 0.889 |
|   | Second | FIG. 22 |   |
| 8 | First | FIG. 23 | 0.961 |
|   | Second | FIG. 24 |   |
| 10 | First | FIG. 25 | 0.979 |
|    | Second | FIG. 26 |   |
| 20 | First | FIG. 27 | 0.950 |
|    | Second | FIG. 28 |   |
| 40 | First | FIG. 29 | 0.975 |
|    | Second | FIG. 30 |   |
| 60 | First | FIG. 31 | 0.959 |
|    | Second | FIG. 32 |   |
| 100 | First | FIG. 33 | 0.983 |
|     | Second | FIG. 34 |   |
| 200 | First | FIG. 35 | 0.991 |
|     | Second | FIG. 36 |   |
| 300 | First | FIG. 37 | 0.995 |
|     | Second | FIG. 38 |   |
| 400 | First | FIG. 39 | 0.988 |
|     | Second | FIG. 40 |   |
| 500 | First | FIG. 41 | 0.971 |
|     | Second | FIG. 42 |   |
| 600 | — | FIG. 43 | — |
| 700 | — | FIG. 44 | — |
| 800 | — | FIG. 45 | — |
| 900 | — | FIG. 46 | — |
| 1000 | — | FIG. 47 | — |

With the use of 10-base random primers, as shown in FIGS. 19 to 47, amplification was observed in a 1-kbp DNA fragment at the random primer concentration of 6 microM. As the concentration increased, the molecular weight of a DNA fragment decreased. Reproducibility at the random primer concentration of 6 to 500 microM was examined. As a result, a relatively low rho value of 0.889 was attained at the concentration of 6 microM, which is 10 times higher than the usual level. At the concentration of 8 microM or higher, which is equivalent to 13.3 times higher than the usual level, and at 500 microM, which is 833.3 times higher than the usual level, a high rho value of 0.9 or more was attained. The results demonstrate that a DNA fragment of 1 kbp or smaller can be amplified while achieving high reproducibility by elevating the random primer concentration to a level significantly higher than the concentration employed under general PCR conditions. When the random primer concentration is excessively higher than 500 microM, amplification of a DNA fragment of a desired size cannot be observed. In order to amplify a low-molecular-weight DNA fragment with excellent reproducibility, accordingly, it was found that the random primer concentration should fall within an optimal range, which is higher than the concentration employed in a general PCR procedure and equivalent to or lower than a given level.

4.2 Confirmation of Reproducibility via MiSeq

Figure 48:
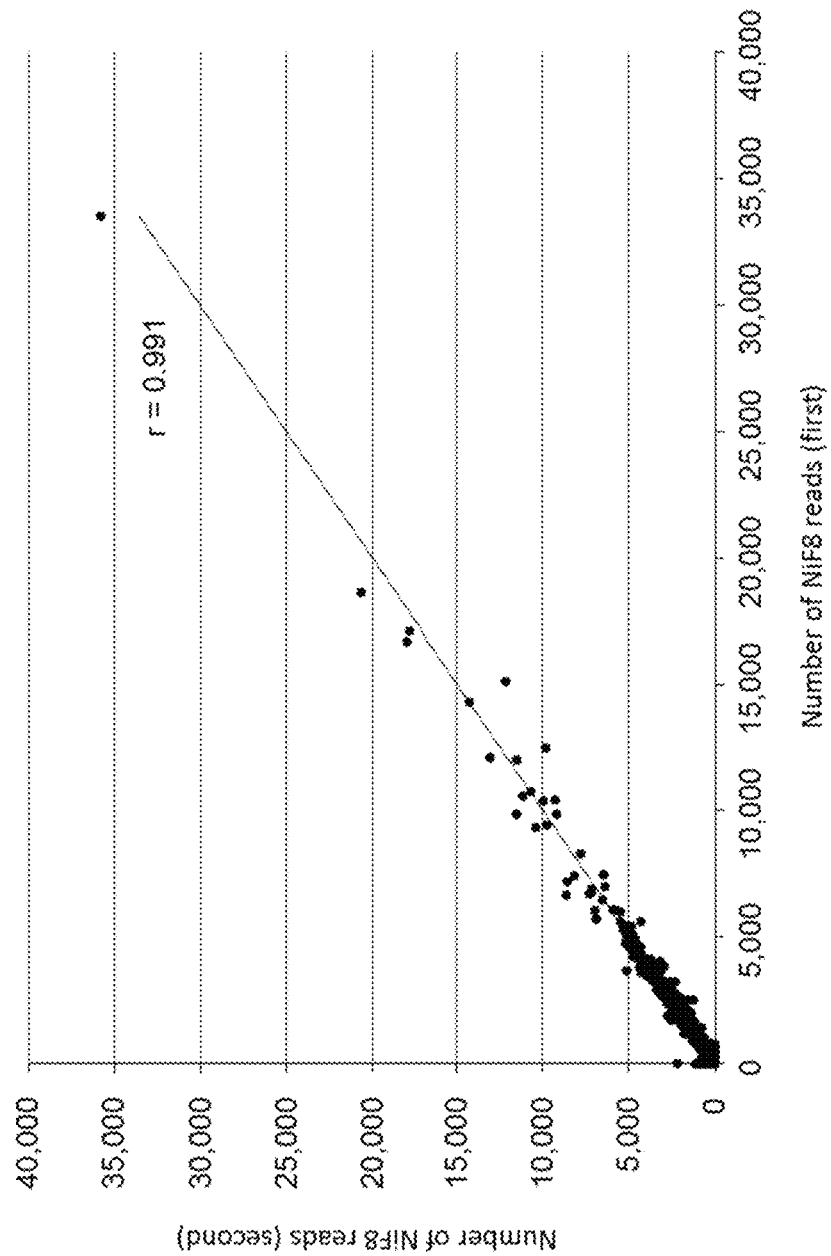
FIG. 48 shows a characteristic diagram demonstrating the results of MiSeq analysis of the DNA library amplified using DNA of the sugarcane variety NiF8 as a template and a random primer.

In order to confirm the reproducibility for DNA library preparation, as described in 3.2 above, the DNA library amplified using the genomic DNA extracted from NiF8 as a template and random primers was analyzed with the use of a next-generation sequencer (MiSeq), and the results are shown in FIG. 48. As a result of 3.2.4 above, 47,484 read patterns were obtained. As a result of comparison of the number of reads obtained through repeated measurements, a high correlation (i.e., a correlational coefficient "r" of 0.991) was obtained, as with the results of electrophoresis. Accordingly, it was considered that a DNA library could be prepared with satisfactory reproducibility with the use of random primers.

4.3 Analysis of Rice Variety Nipponbare

Figure 49:
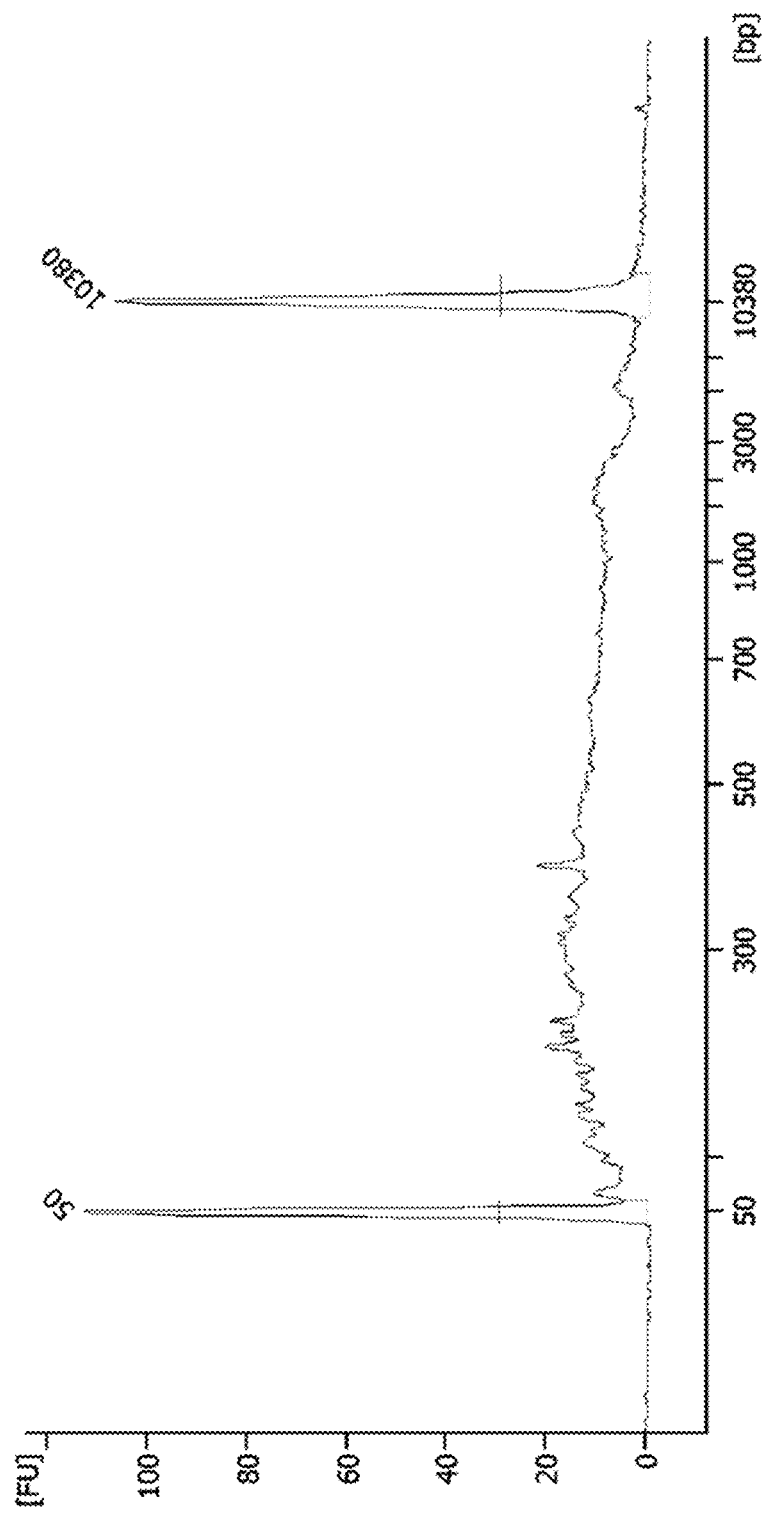
FIG. 49 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the rice variety Nipponbare as a template and a random primer.
Figure 50:
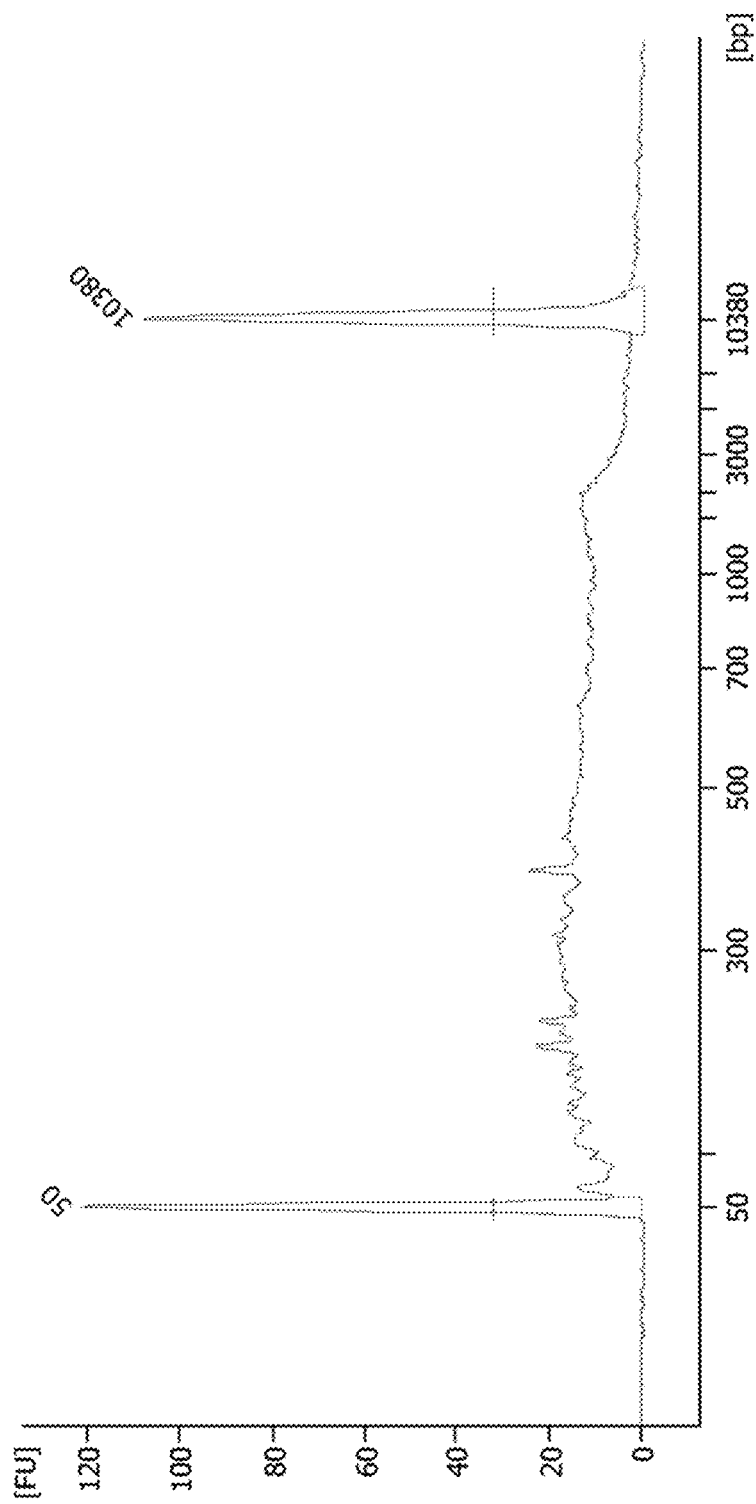
FIG. 50 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the rice variety Nipponbare as a template and a random primer.
Figure 51:
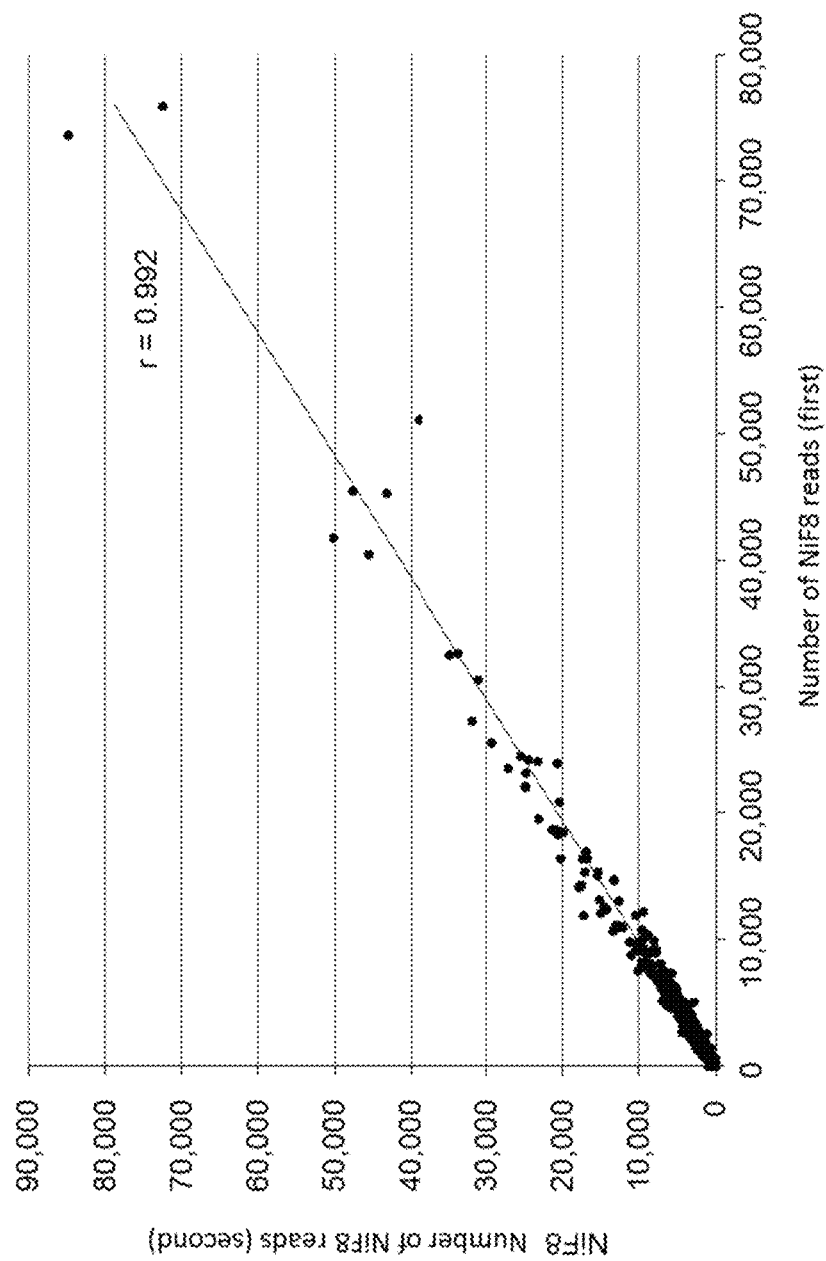
FIG. 51 shows a characteristic diagram demonstrating the results of MiSeq analysis of the DNA library amplified using DNA of the rice variety Nipponbare as a template and a random primer.

As described in 3.3 above, a DNA library was prepared with the use of genomic DNA extracted from the rice variety Nipponbare, the genomic information of which has been disclosed, as a template, and random primers and subjected to electrophoresis, and the results are shown in FIGS. 49 and 50. On the basis of the results shown in FIGS. 49 and 50, the rho value was found to be as high as 0.979. Also, FIG. 51 shows the results of MiSeq analysis of the read data. On the basis of the results shown in FIG. 51, the correlational coefficient "r" was found to be as high as 0.992. These results demonstrate that a DNA library of rice could be prepared with very high reproducibility with the use of random primers.

Figure 52:
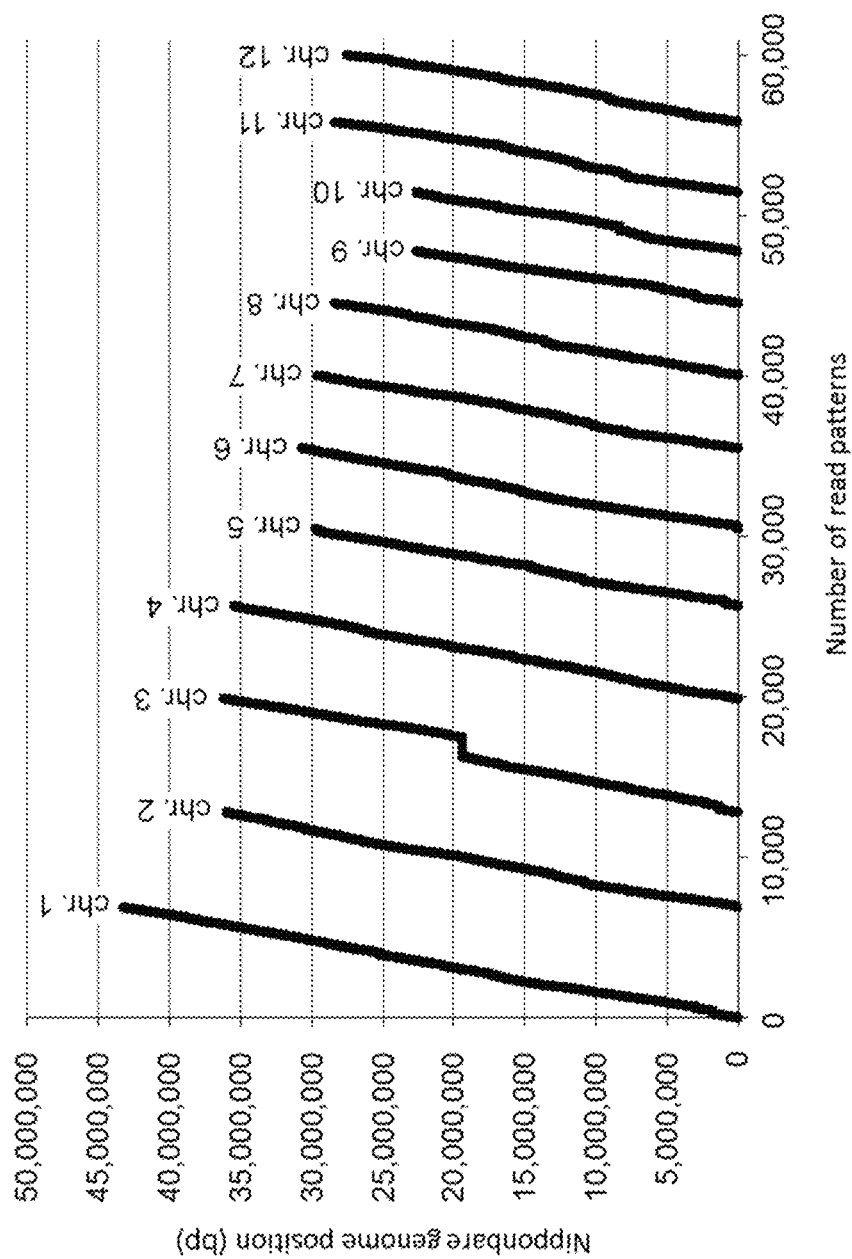
FIG. 52 shows a characteristic diagram demonstrating positions of MiSeq read patterns in the genome information of the rice variety Nipponbare.
Figure 53:
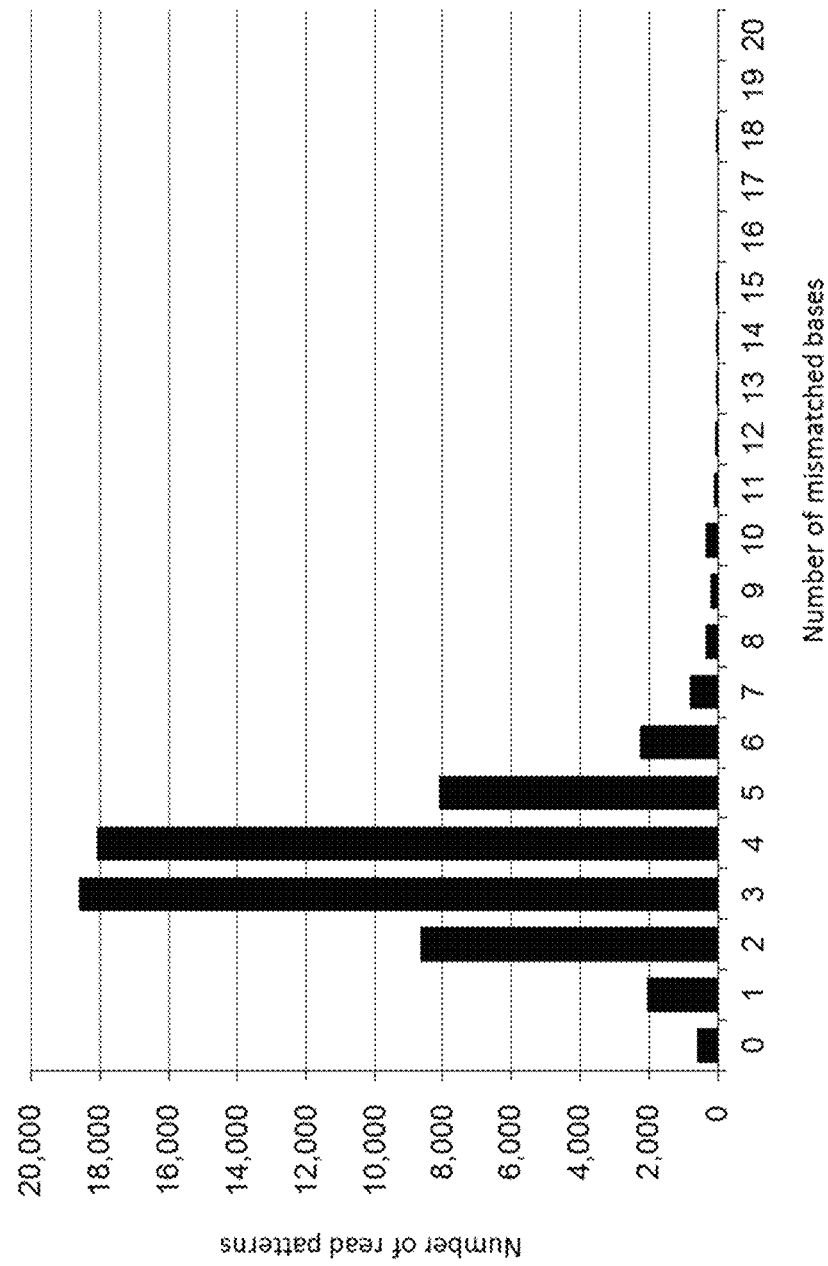
FIG. 53 shows a characteristic diagram demonstrating the frequency distribution of the number of mismatched bases between the random primer and the rice genome.

As described in 3.3.3, the obtained read pattern was mapped to the genomic information of Nipponbare. As a result, DNA fragments were found to be evenly amplified throughout the genome at intervals of 6.2 kbp (FIG. 52). As a result of comparison of the sequence and genome information of random primers, 3.6 mismatches were found on average, and one or more mismatches were observed in 99.0% of primer pairs (FIG. 53). The results demonstrate that a DNA library involving the use of random primers is prepared with satisfactory reproducibility via non-specific amplification evenly throughout the genome.

4.4 Detection of Polymorphism and Genotype Identification of Sugarcane

As described in 3.4, DNA libraries of the sugarcane varieties NiF8 and Ni9 and 22 hybrid progeny lines thereof were prepared with the use of random primers, the resulting DNA libraries were analyzed with the next-generation sequencer (HiSeq), the polymorphisms of the parent varieties were detected, and the genotypes of the hybrid progenies were identified on the basis of the read data. Table 26 shows the results.

TABLE 26

Number of sugarcane NiF8 and Ni9 markers and accuracy for genotype identification

|  | Number of markers | FI_01 Concordance | FI_01 Reproducibility | FI_02 Concordance | FI_02 Reproducibility | Total Concordance | Total Reproducibility |
|---|---|---|---|---|---|---|---|
| NiF8 type | 8,683 | 8,680 | 99.97% | 8,682 | 99.99% | 17,362 | 99.98% |
| Ni9 type | 11,655 | 11,650 | 99.96% | 11,651 | 99.97% | 23,301 | 99.96% |
| Total | 20,338 | 20,330 | 99.96% | 20,333 | 99.98% | 40,663 | 99.97% |

As shown in Table 26, 8,683 NiF8 markers and 11,655 Ni9 markers; that is, a total of 20,338 markers, were prepared. In addition, reproducibility for genotype identification of hybrid progeny lines was as high as 99.97%. This indicates that the accuracy for genotype identification is very high. In particular, sugarcane is polyploid (8x+n), the number of chromosomes is as large as 100 to 130, and the genome size is as large as 10 Gbp, which is at least 3 times greater than that of humans. Accordingly, it is very difficult to identify the genotype throughout the genomic DNA. As described above, numerous markers can be prepared with the use of random primers, and the sugarcane genotype can thus be identified with high accuracy.

4.5 Experiment for Confirmation with PCR Marker

Figure 54:
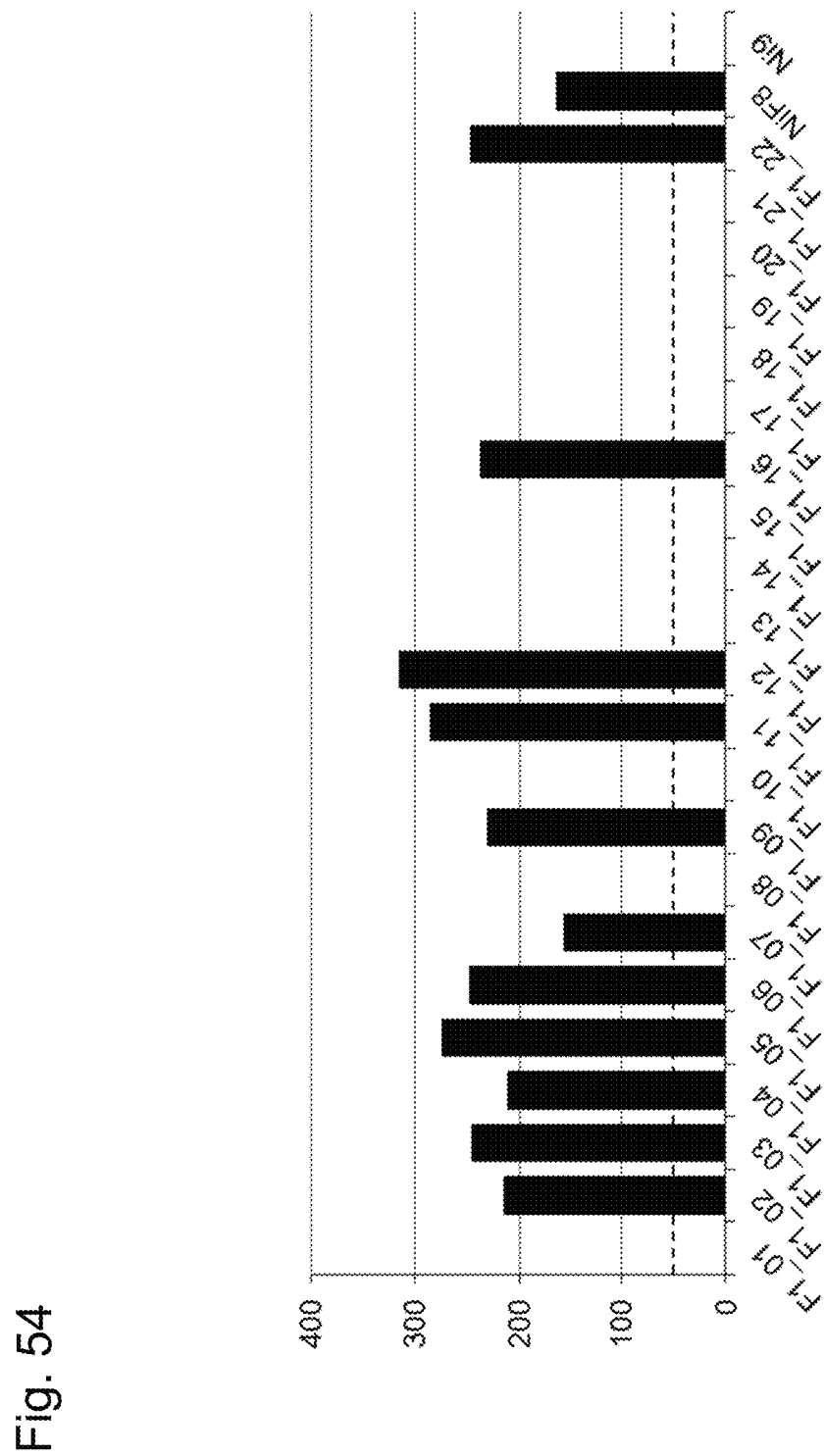
FIG. 54 shows a characteristic diagram demonstrating the number of reads of the sugarcane varieties NiF8 and Ni9 and hybrid progeny lines thereof at the marker N80521152.
Figure 55:
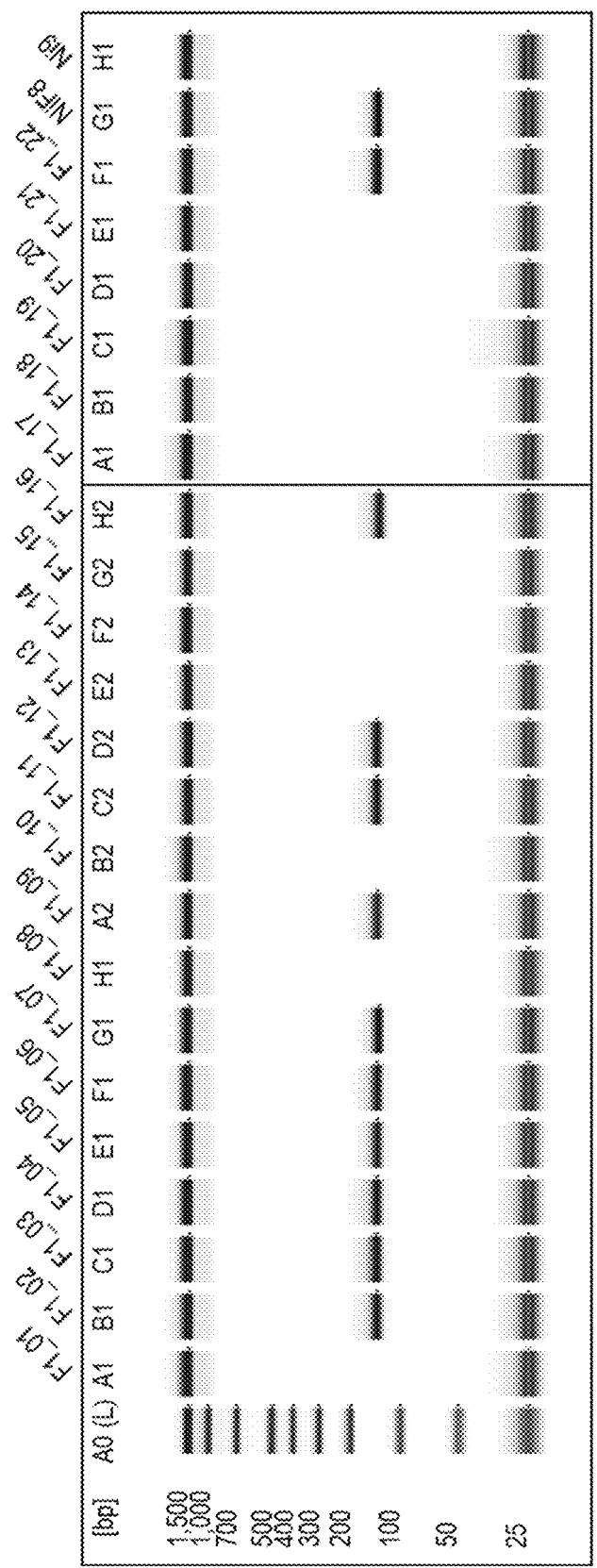
FIG. 55 shows a photograph demonstrating electrophoretic patterns of the sugarcane varieties NiF8 and Ni9 and hybrid progeny lines thereof at the PCR marker N80521152.
Figure 56:
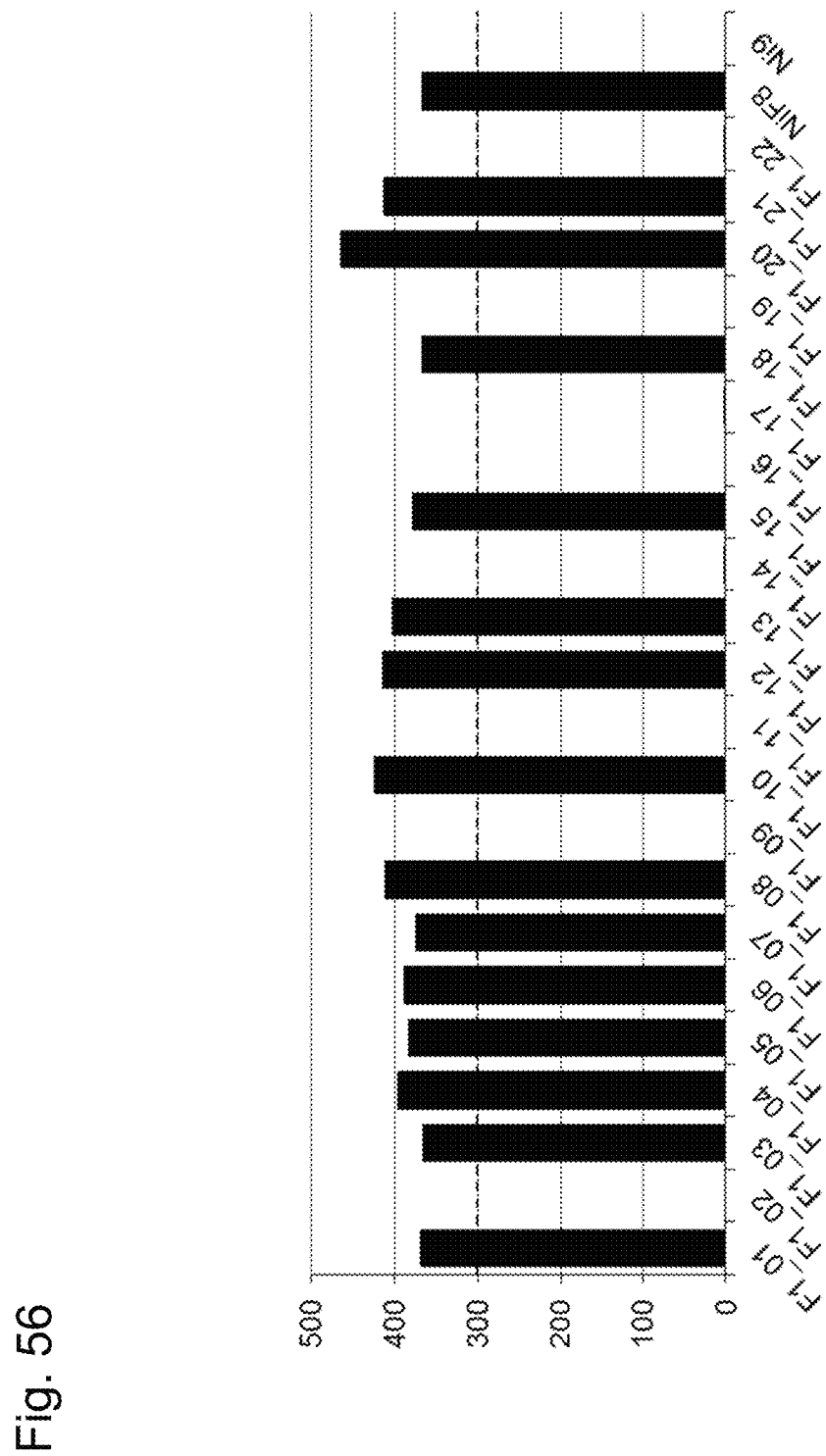
FIG. 56 shows a characteristic diagram demonstrating the number of reads of the sugarcane varieties NiF8 and Ni9 and hybrid progeny lines thereof at the marker N80997192.
Figure 57:
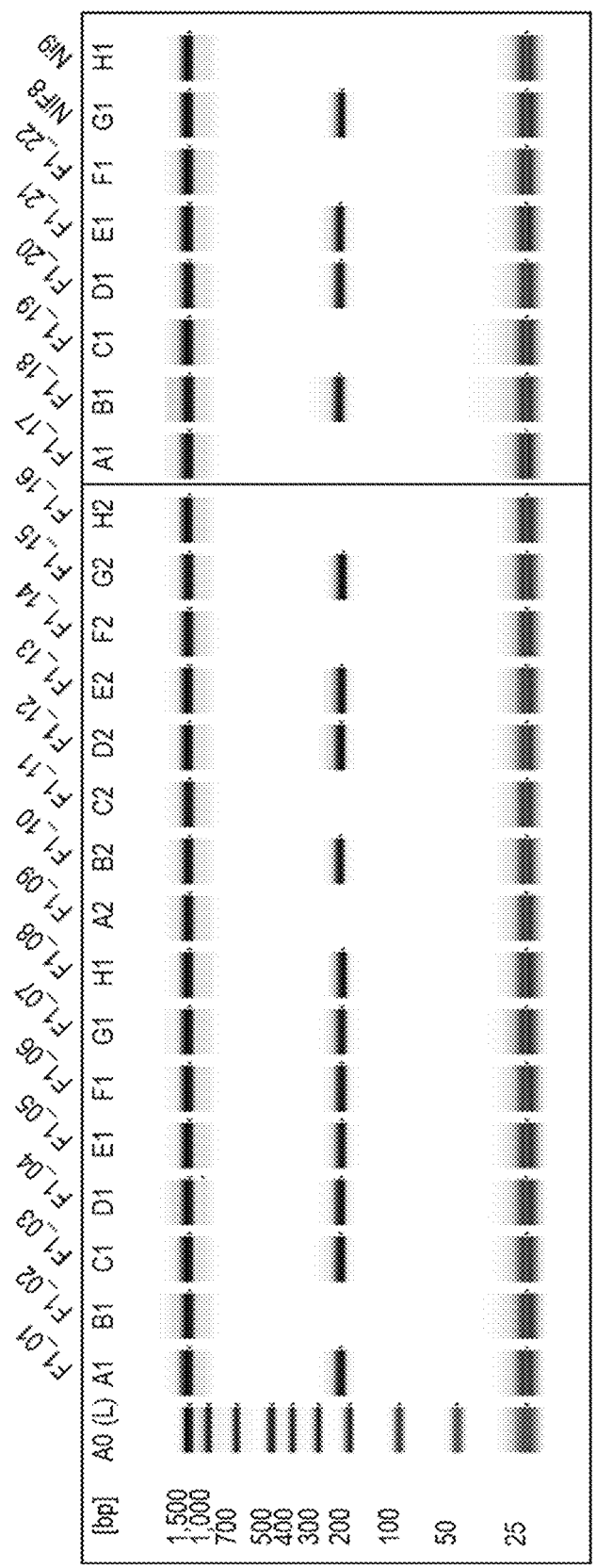
FIG. 57 shows a photograph demonstrating electrophoretic patterns of the sugarcane varieties NiF8 and Ni9 and hybrid progeny lines thereof at the PCR marker N80997192.
Figure 58:
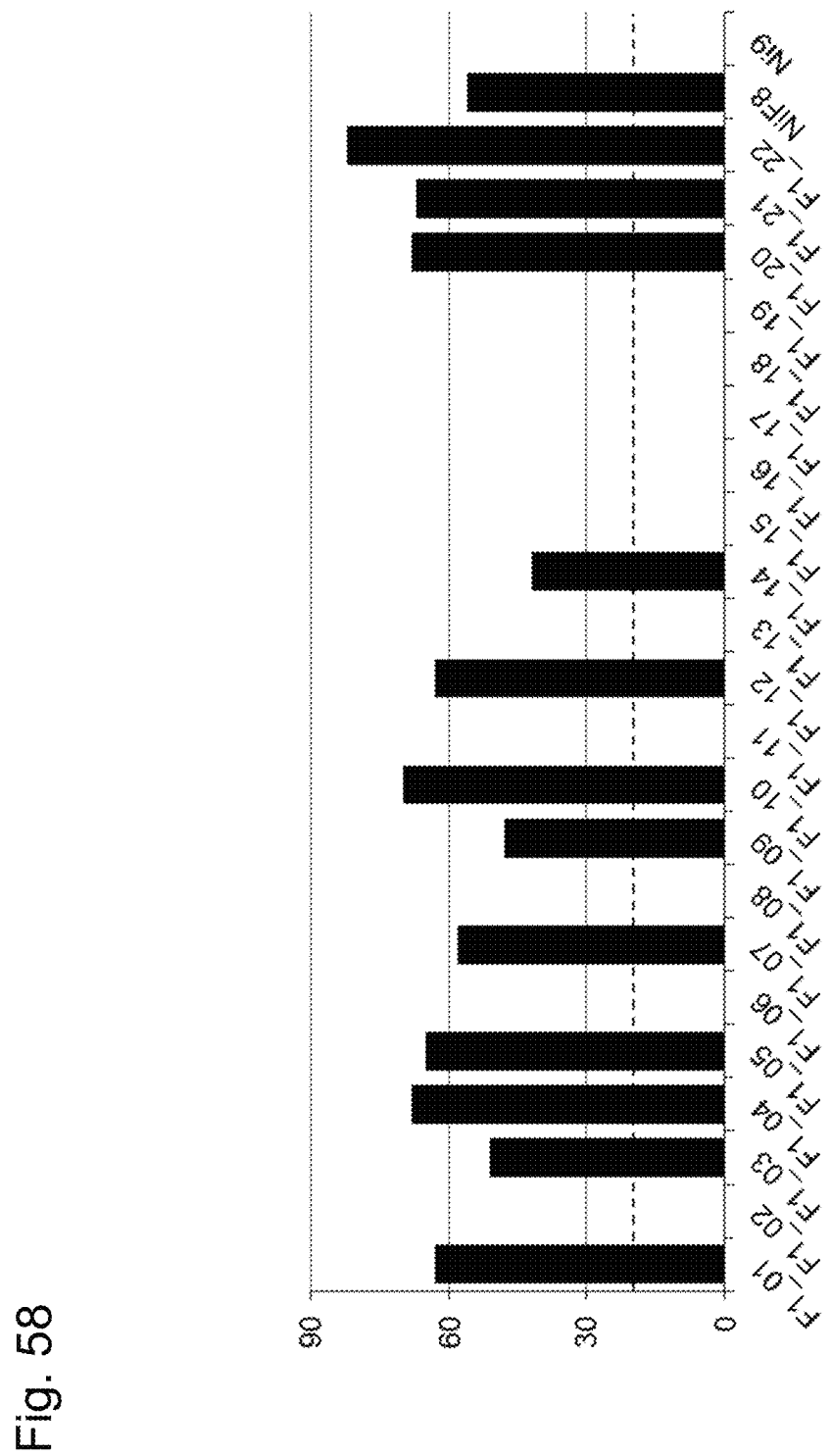
FIG. 58 shows a characteristic diagram demonstrating the number of reads of the sugarcane varieties NiF8 and Ni9 and hybrid progeny lines thereof at the marker N80533142.
Figure 59:
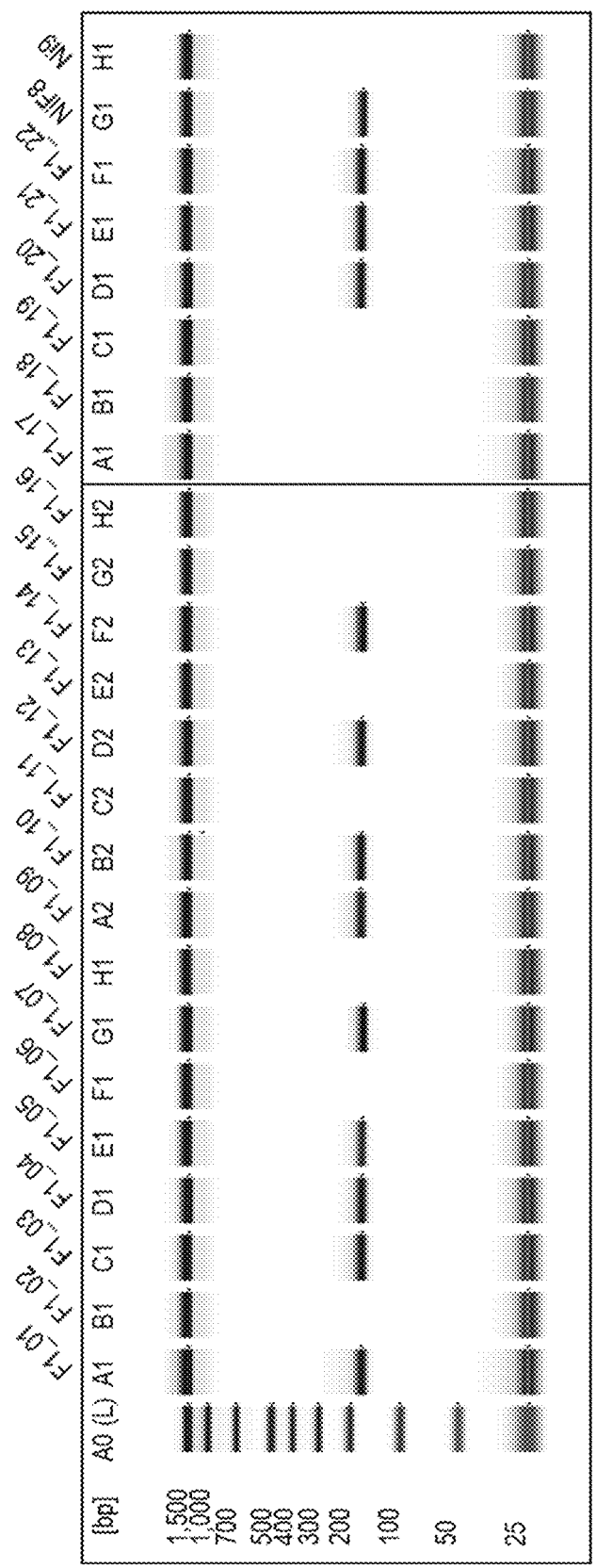
FIG. 59 shows a photograph demonstrating electrophoretic patterns of the sugarcane varieties NiF8 and Ni9 and hybrid progeny lines thereof at the PCR marker N80533142.
Figure 60:
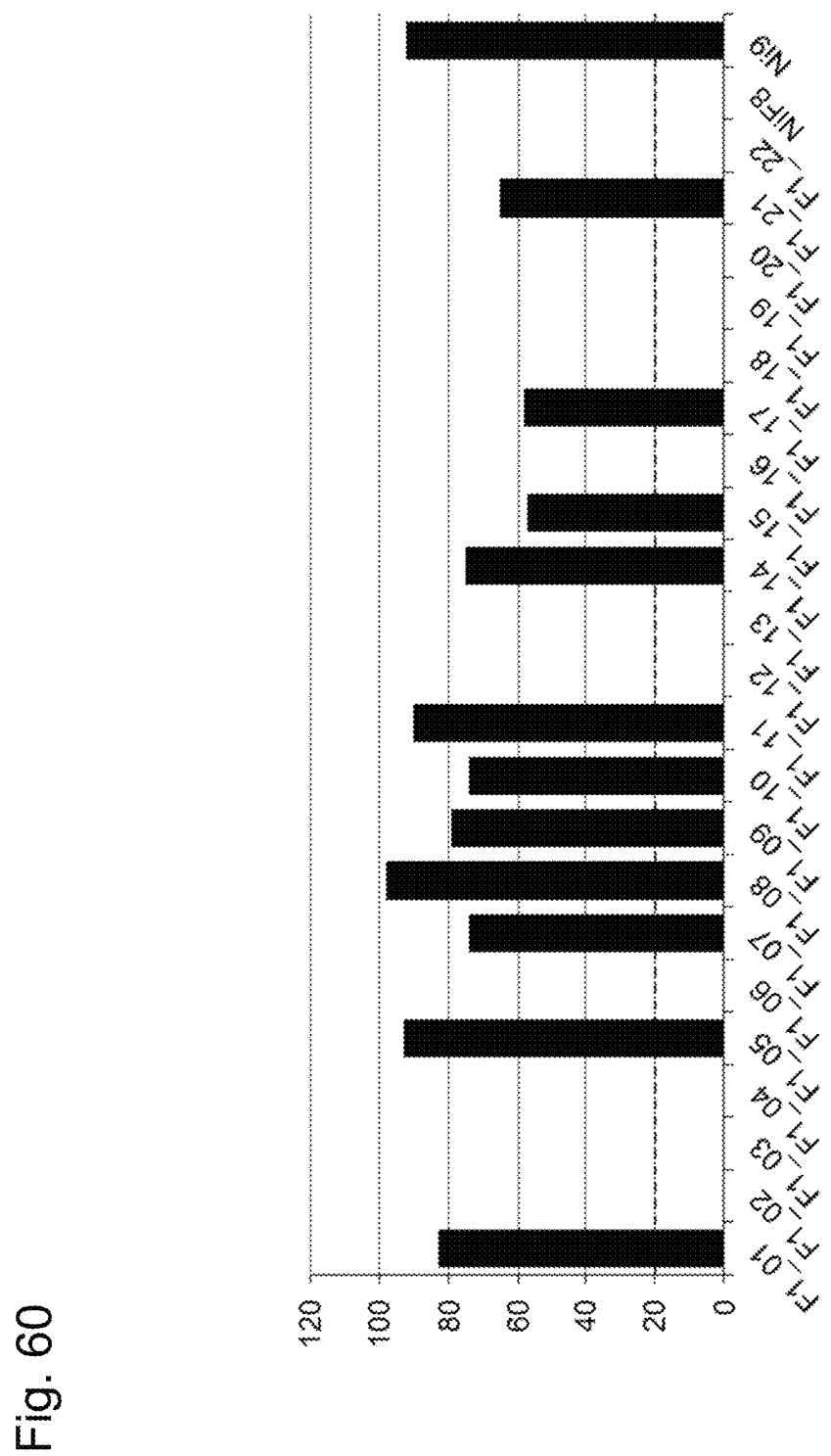
FIG. 60 shows a characteristic diagram demonstrating the number of reads of the sugarcane varieties NiF8 and Ni9 and hybrid progeny lines thereof at the marker N91552391.
Figure 61:
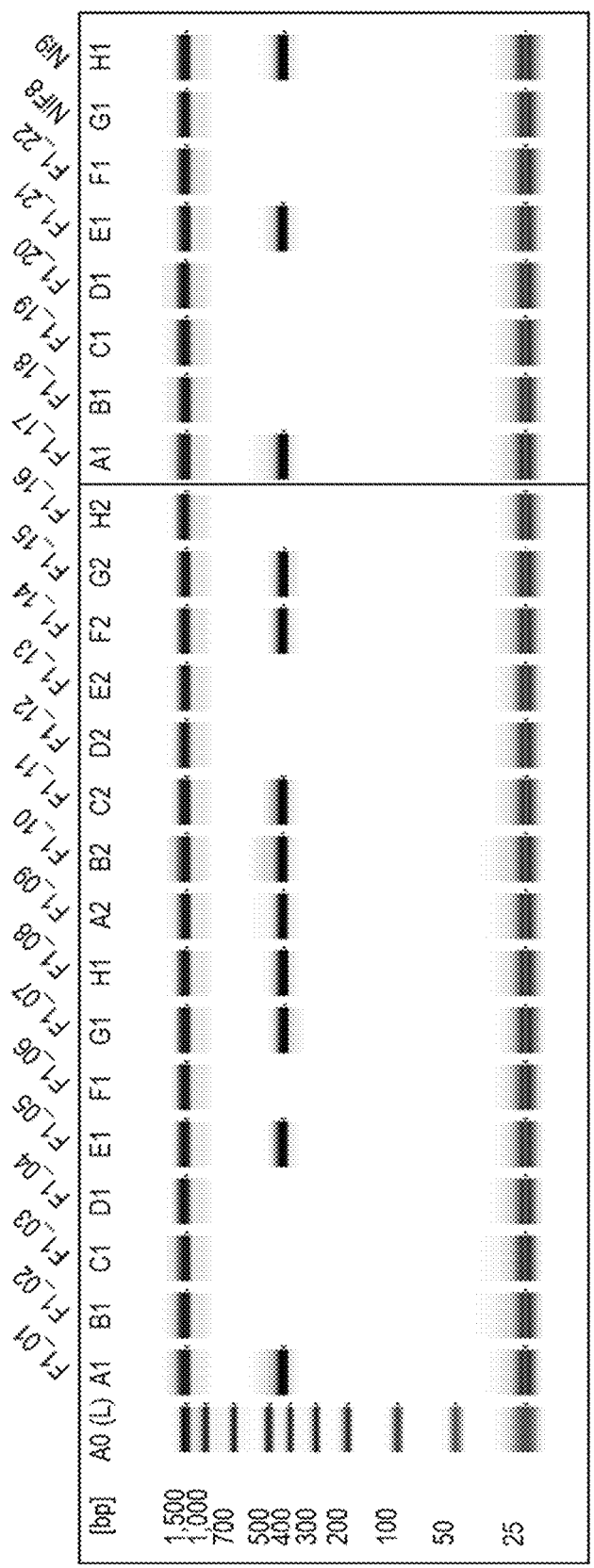
FIG. 61 shows a photograph demonstrating electrophoretic patterns of the sugarcane varieties NiF8 and Ni9 and hybrid progeny lines thereof at the PCR marker N91552391.
Figure 62:
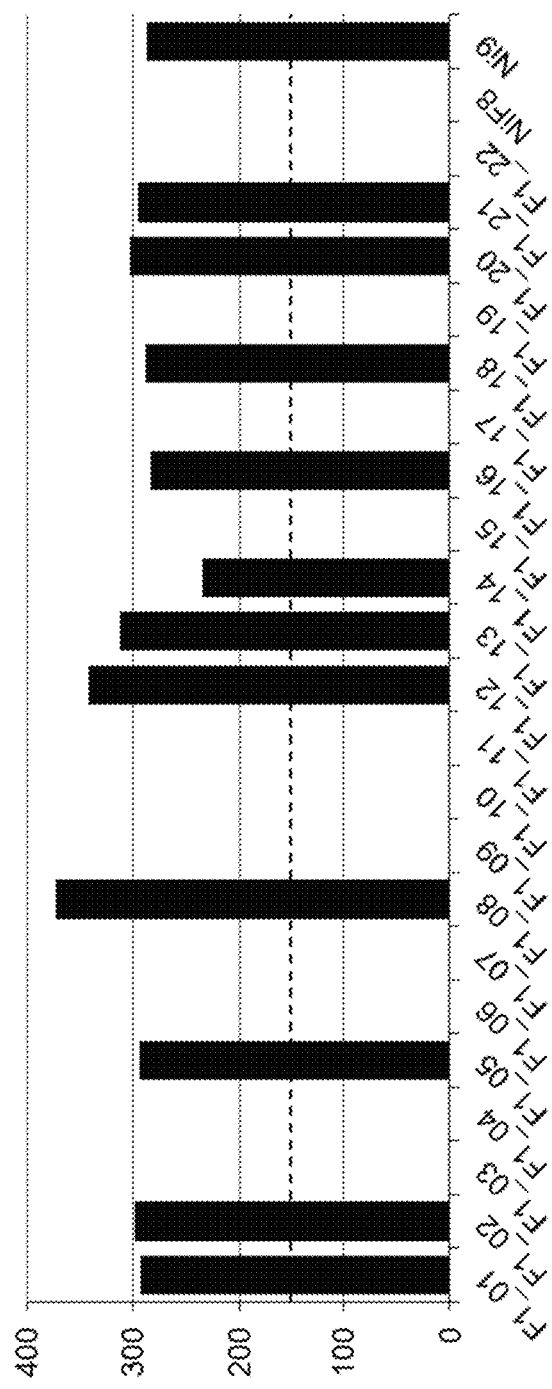
FIG. 62 shows a characteristic diagram demonstrating the number of reads of the sugarcane varieties NiF8 and Ni9 and hybrid progeny lines thereof at the marker N91653962.
Figure 63:
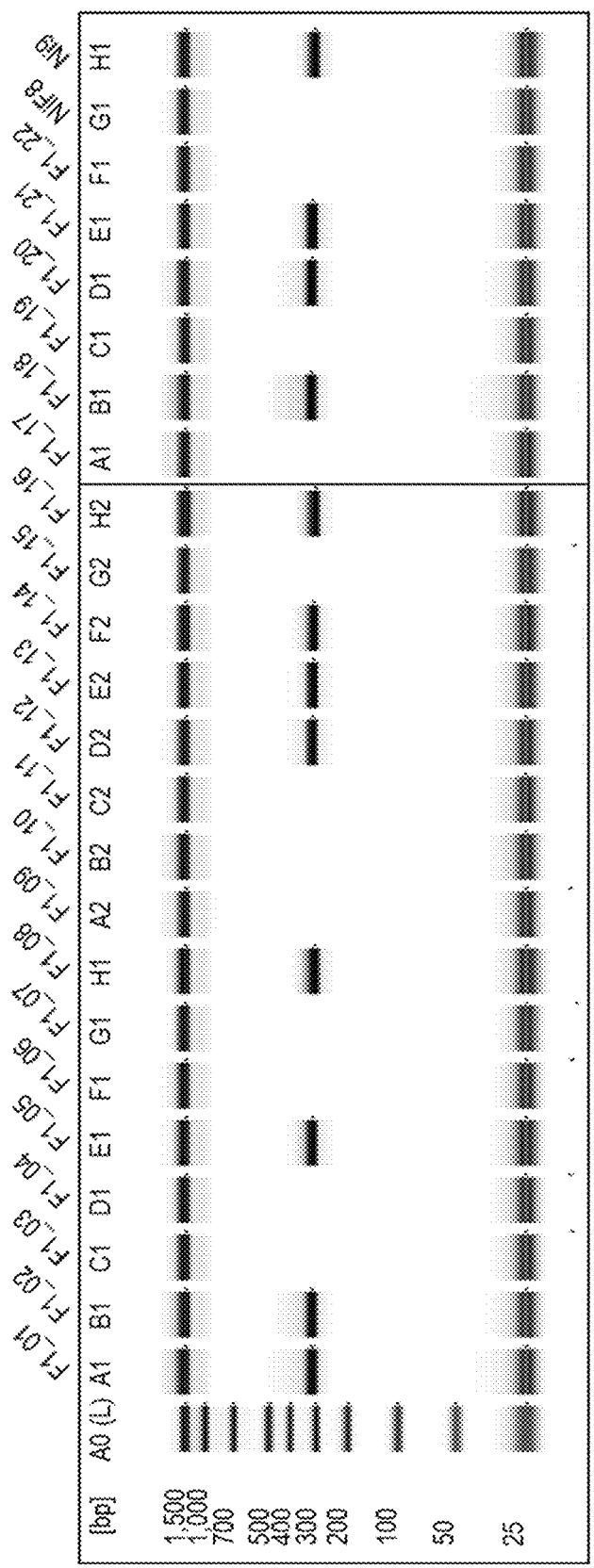
FIG. 63 shows a photograph demonstrating electrophoretic patterns of the sugarcane varieties NiF8 and Ni9 and hybrid progeny lines thereof at the PCR marker N91653962.
Figure 64:
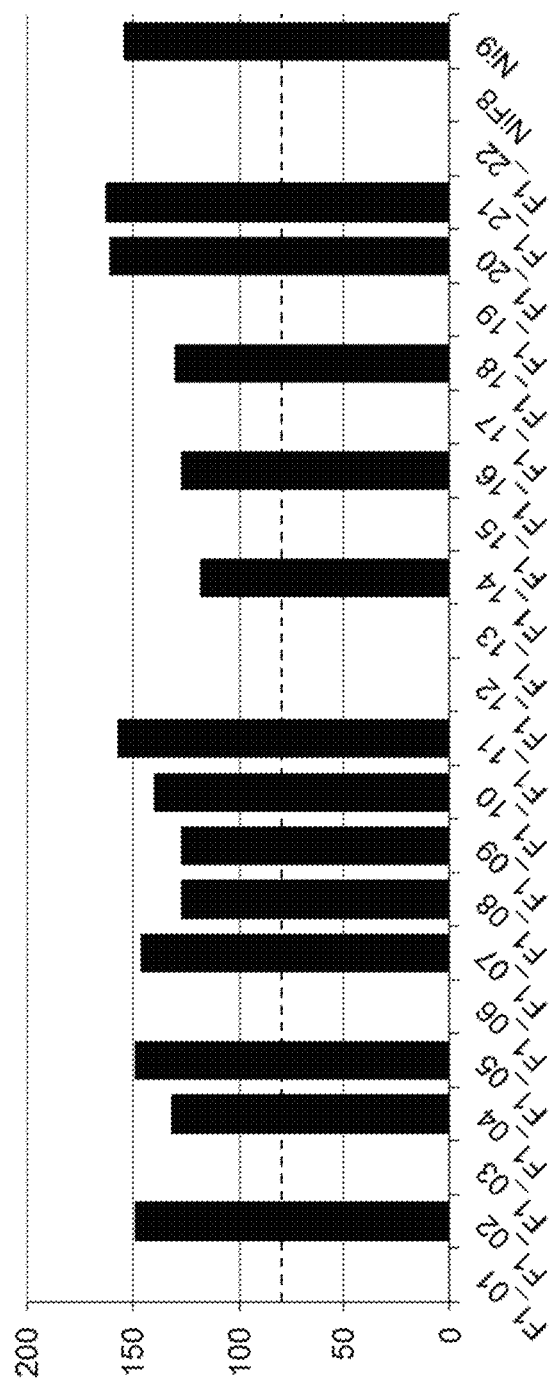
FIG. 64 shows a characteristic diagram demonstrating the number of reads of the sugarcane varieties NiF8 and Ni9 and hybrid progeny lines thereof at the marker N91124801.
Figure 65:
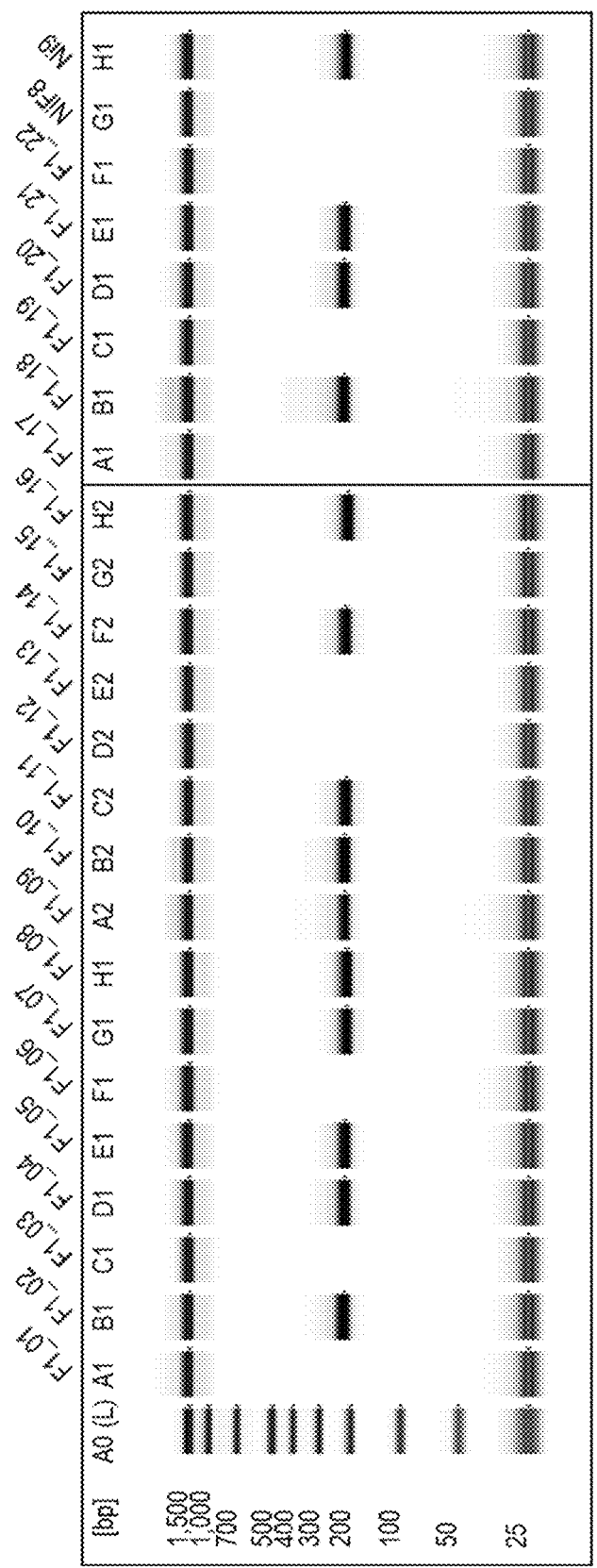
FIG. 65 shows a photograph demonstrating electrophoretic patterns of the sugarcane varieties NiF8 and Ni9 and hybrid progeny lines thereof at the PCR marker N91124801.

As described in 3.5 above, the sugarcane varieties NiF8 and Ni9 and 22 hybrid progeny lines thereof were subjected to PCR with the use of the primers shown in Table 22, genotypes were identified via electrophoresis, and the results were compared with the number of reads. FIGS. 54 and 55 show the number of reads and the electrophoretic pattern of the NiF8 marker N80521152, respectively. FIGS. 56 and 57 show the number of reads and the electrophoretic pattern of the NiF8 marker N80997192, respectively. FIGS. 58 and 59 show the number of reads and the electrophoretic pattern of the NiF8 marker N80533142, respectively. FIGS. 60 and 61 show the number of reads and the electrophoretic pattern of the Ni9 marker N91552391, respectively. FIGS. 62 and 63 show the number of reads and the electrophoretic pattern of the Ni9 marker N91653962, respectively. FIGS. 64 and 65 show the number of reads and the electrophoretic pattern of the Ni9 marker N91124801, respectively.

As shown in FIGS. 54 to 65, the results for all the PCR markers designed in 3.5 above were concordant with the results of analysis with the use of a next-generation sequencer. It was thus considered that genotype identification with the use of a next-generation sequencer would be applicable as a marker technique.

4.6 Correlation Between Random Primer Concentration and Length

As described in 3.6.1, the results of DNA library preparation with the use of 9-base random primers (Table 10), 10-base random primers (Table 3, 10-base primer A), 11-base random primers (Table 11), 12-base random primers (Table 12), 14-base random primers (Table 13), 16-base random primers (Table 14), 18-base random primers (Table 15), and 20-base random primers (Table 16) are shown in FIGS. 66 to 81. The results are summarized in Table 27.

TABLE 27

Figure 66:
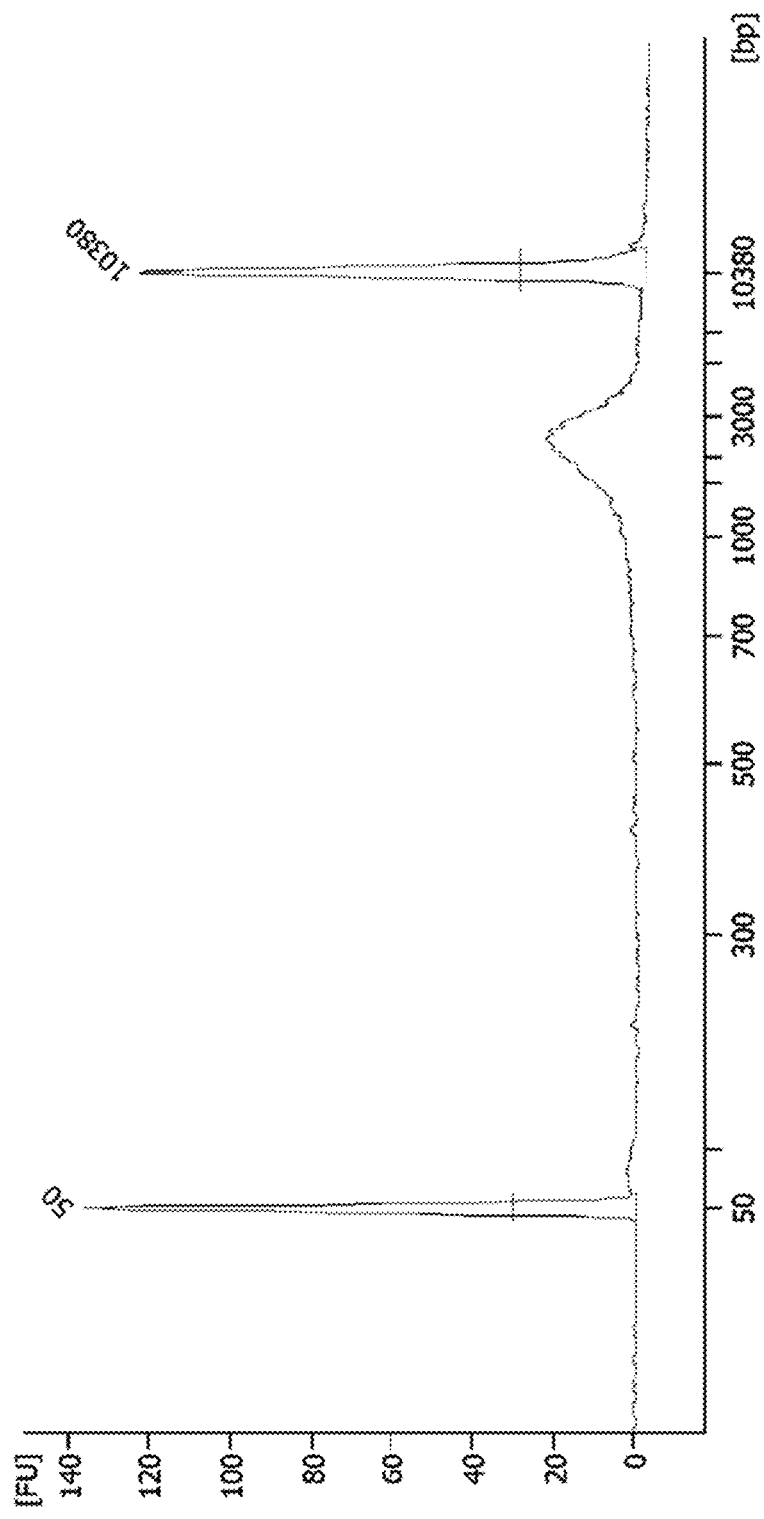
FIG. 66 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 9-base random primer.
Figure 67:
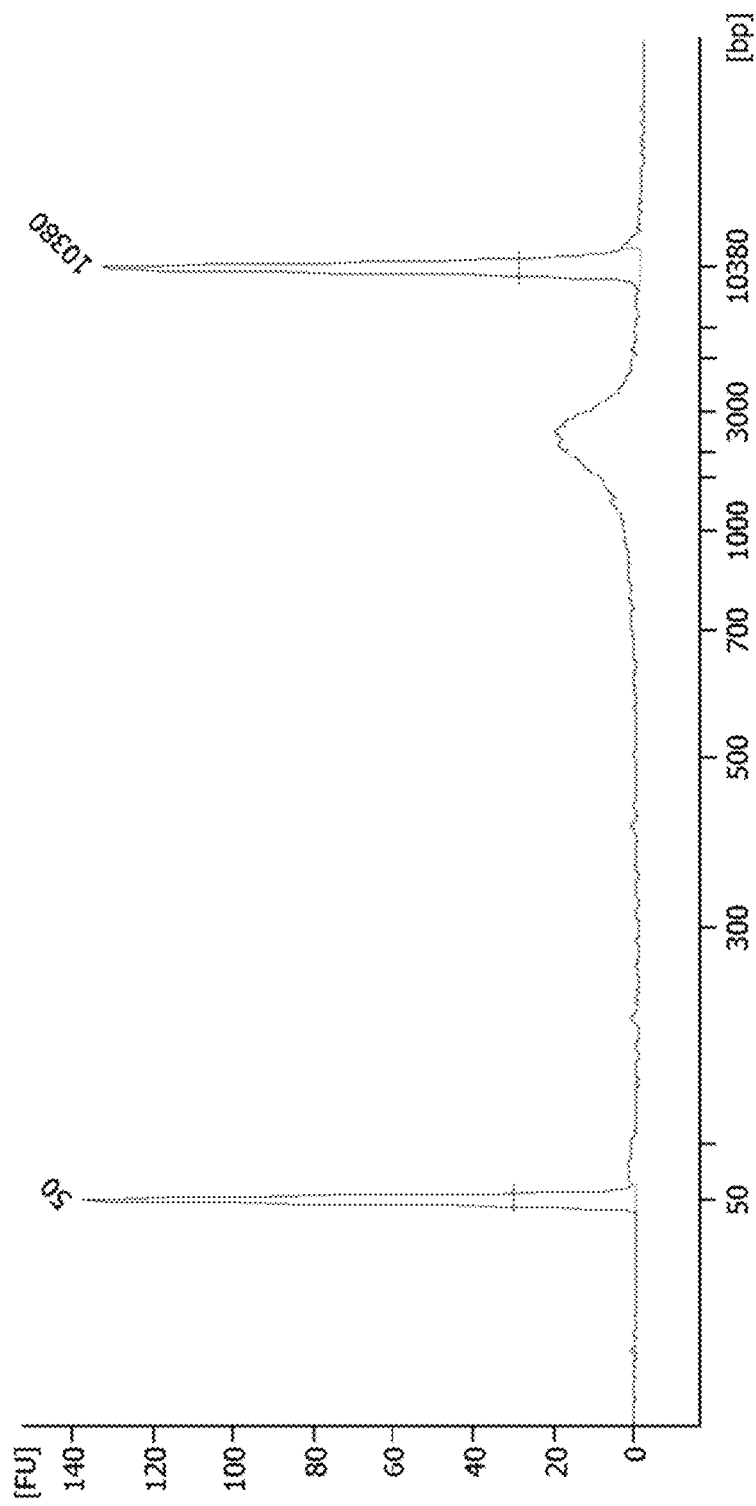
FIG. 67 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 9-base random primer.
Figure 68:
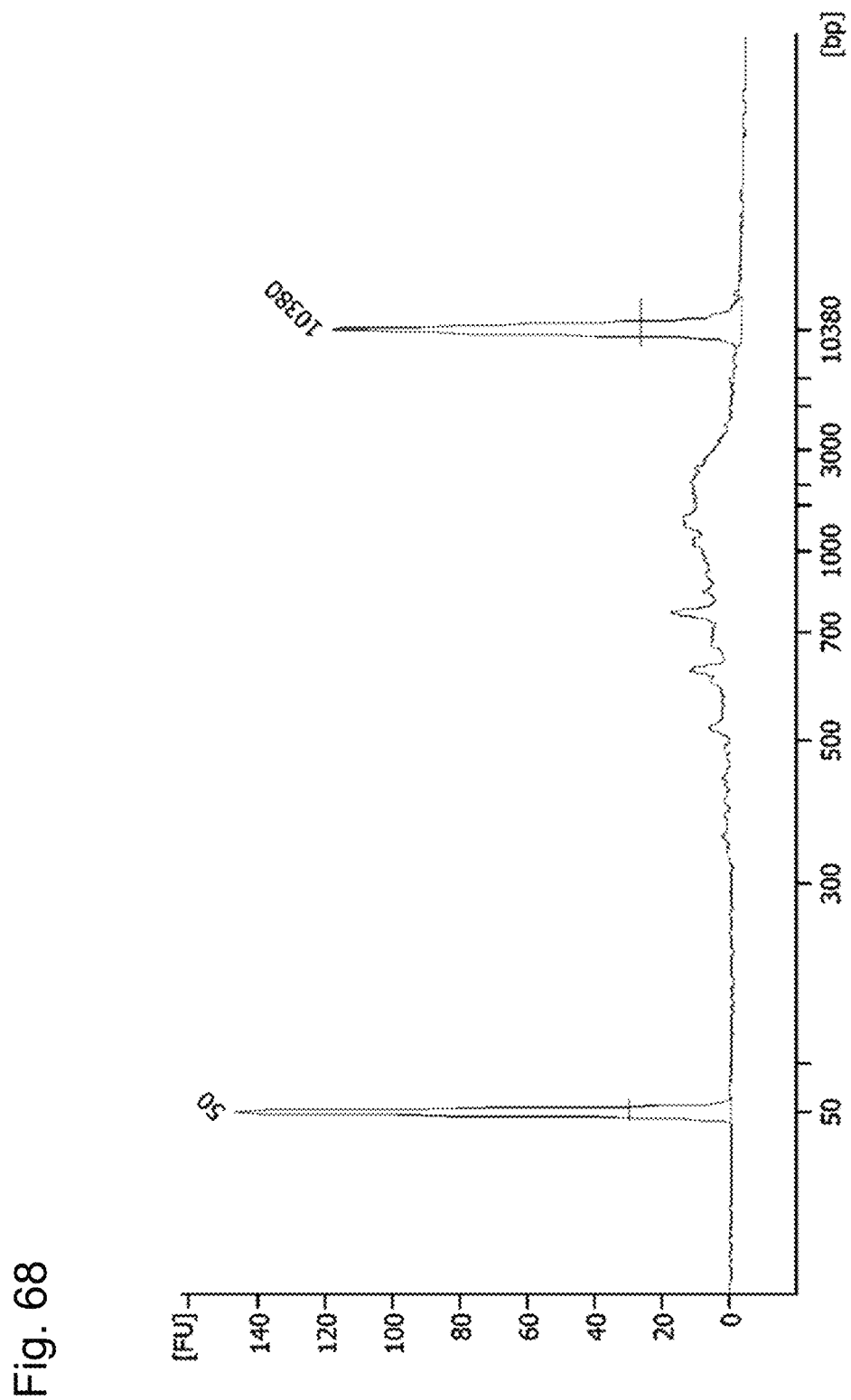
FIG. 68 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer.
Figure 69:
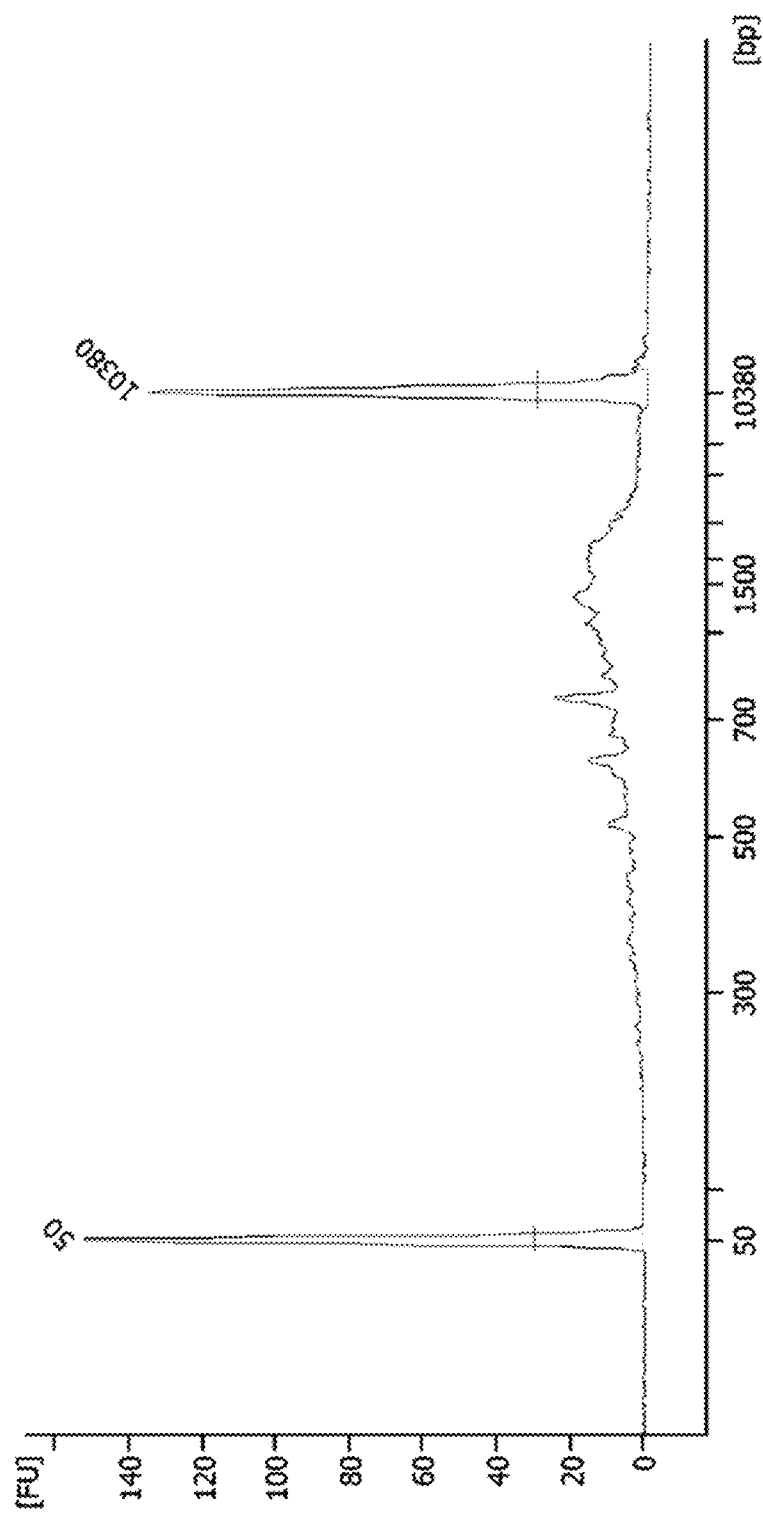
FIG. 69 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer.
Figure 70:
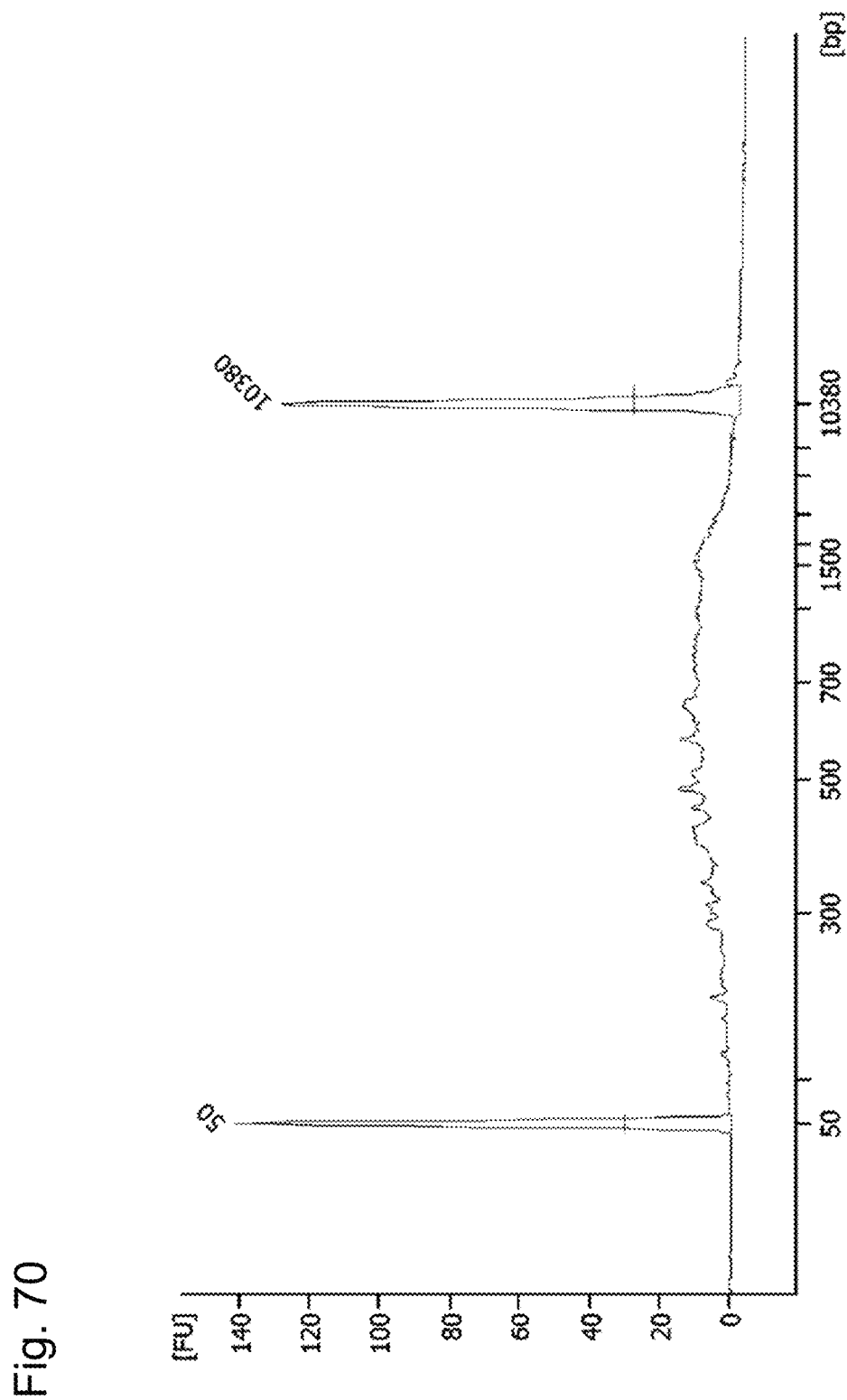
FIG. 70 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 11-base random primer.
Figure 71:
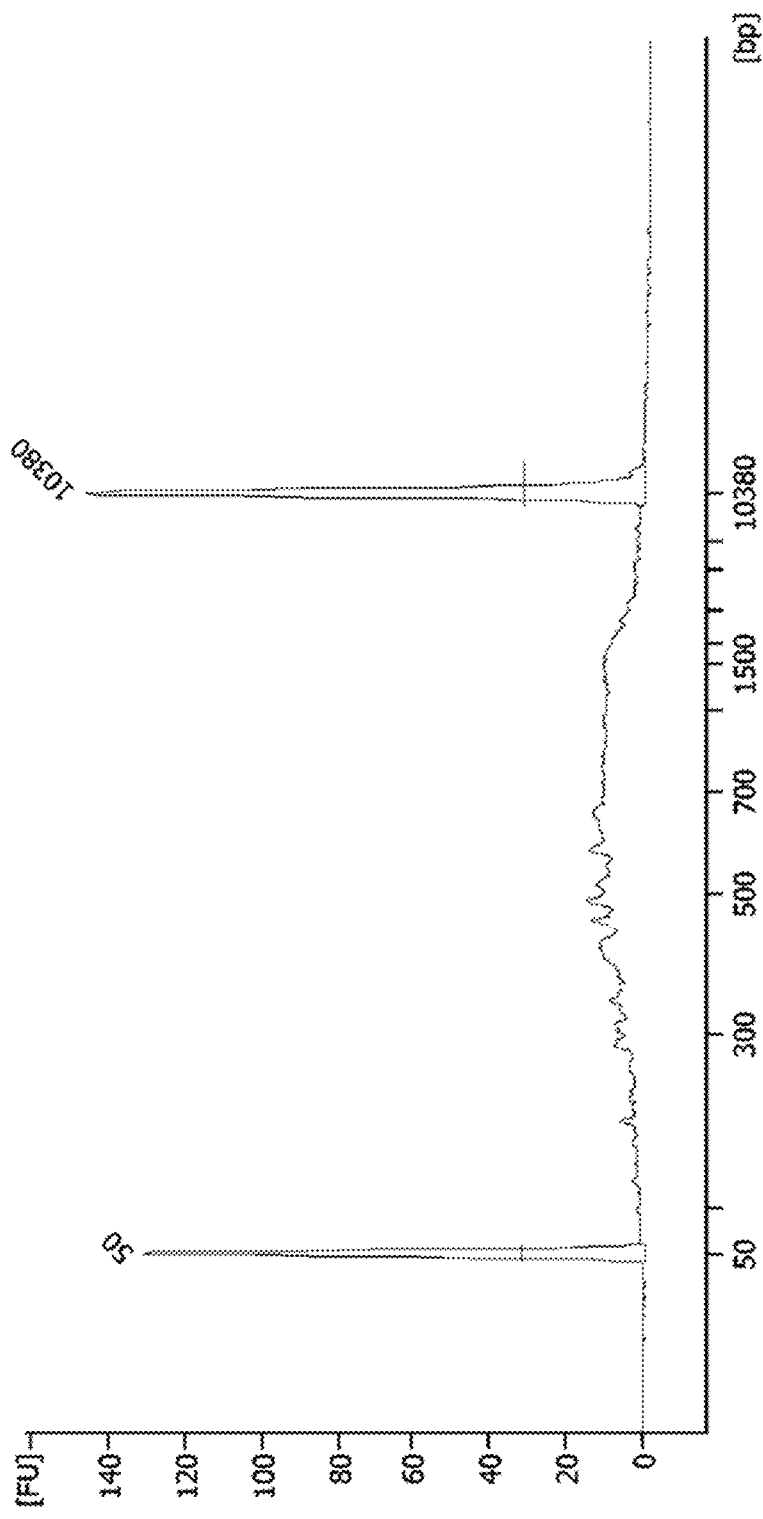
FIG. 71 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 11-base random primer.
Figure 72:
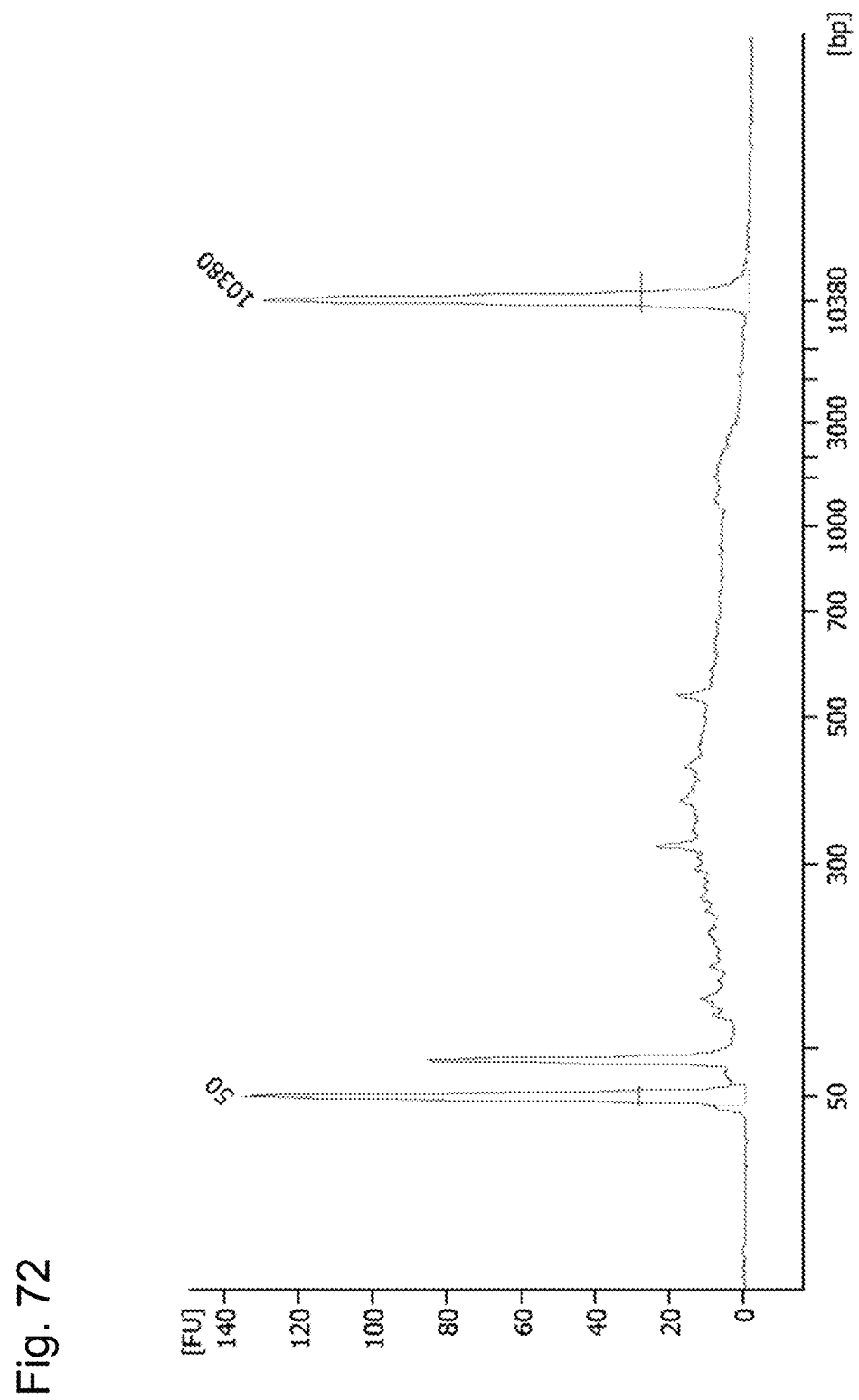
FIG. 72 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 12-base random primer.
Figure 73:
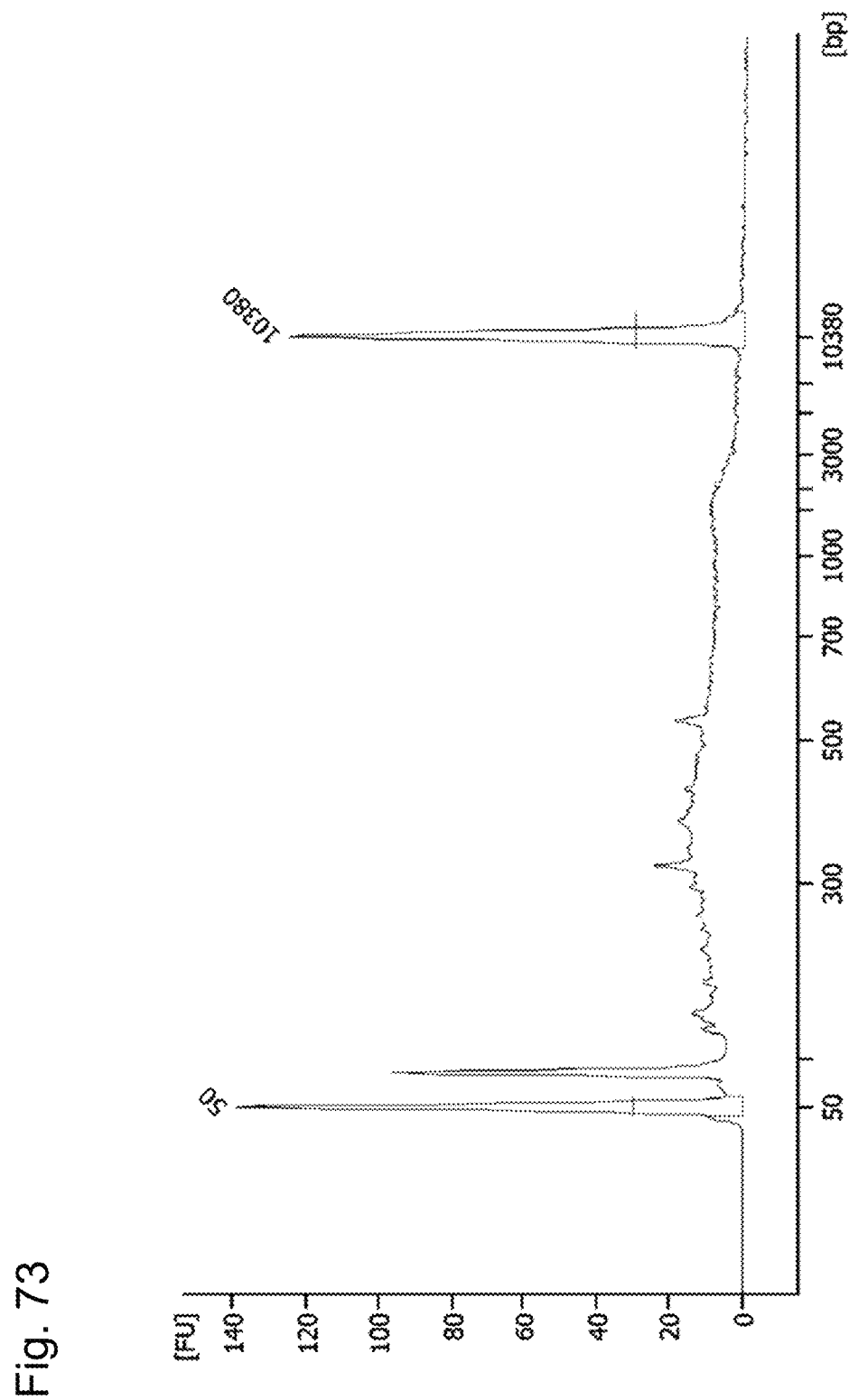
FIG. 73 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 12-base random primer.
Figure 74:
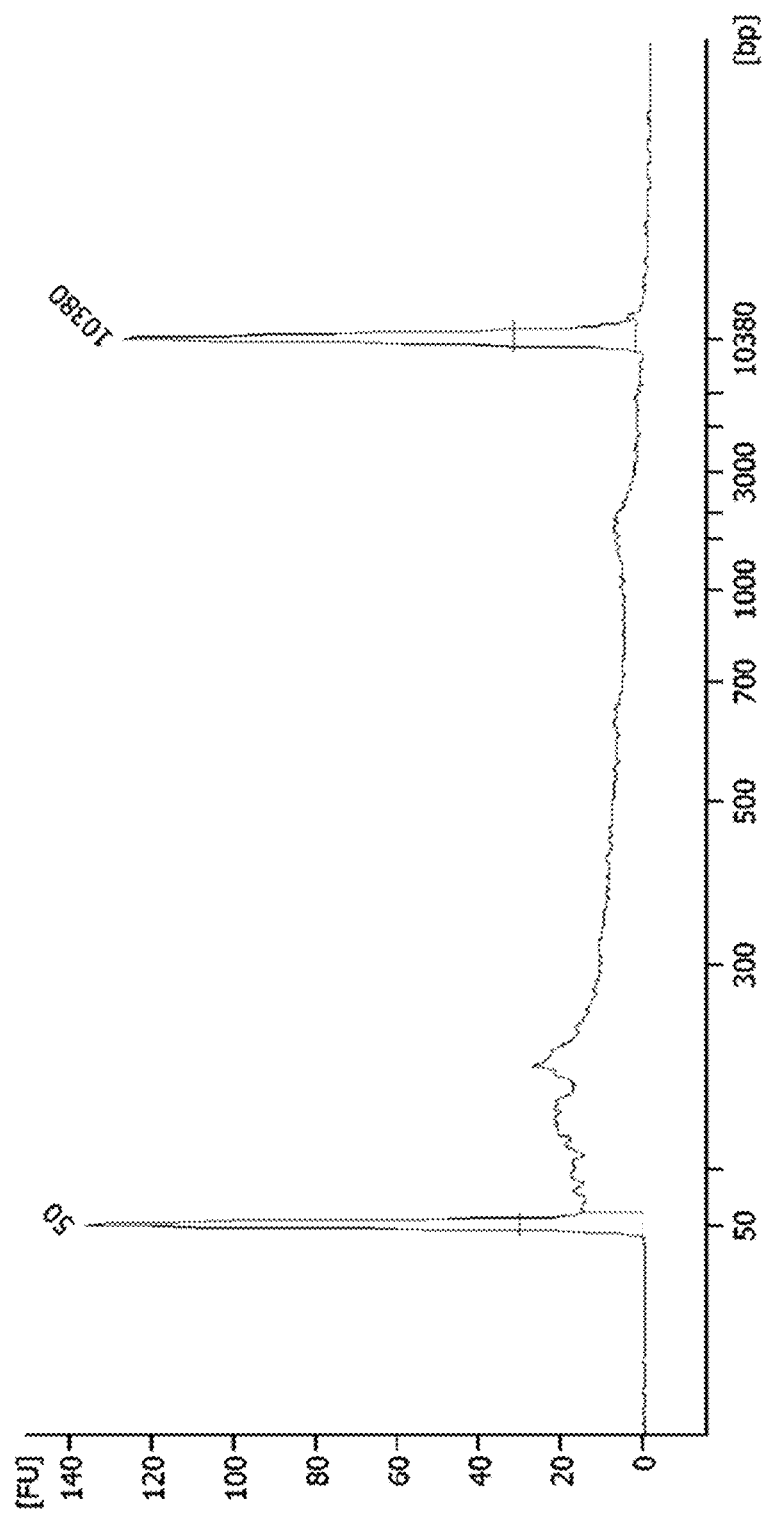
FIG. 74 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 14-base random primer.
Figure 75:
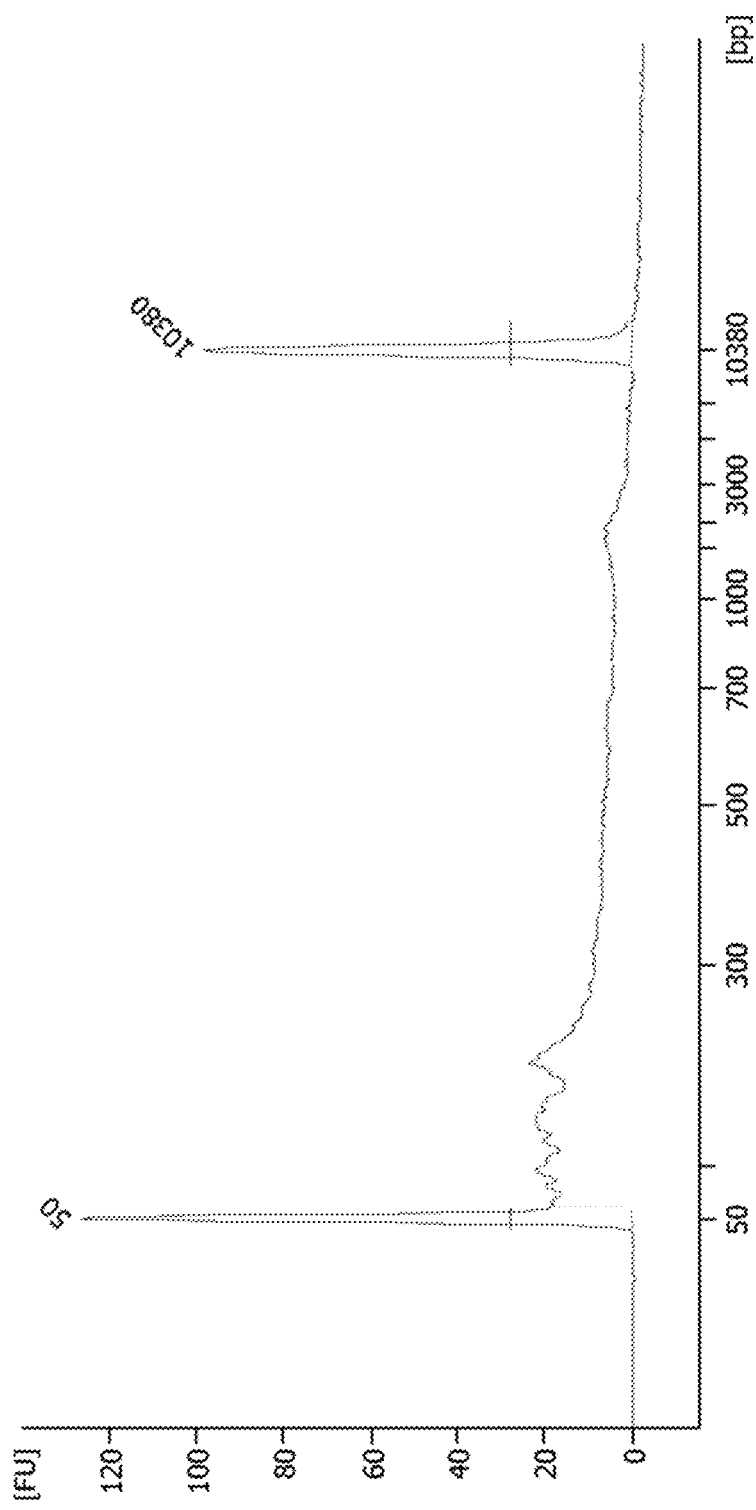
FIG. 75 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 14-base random primer.
Figure 76:
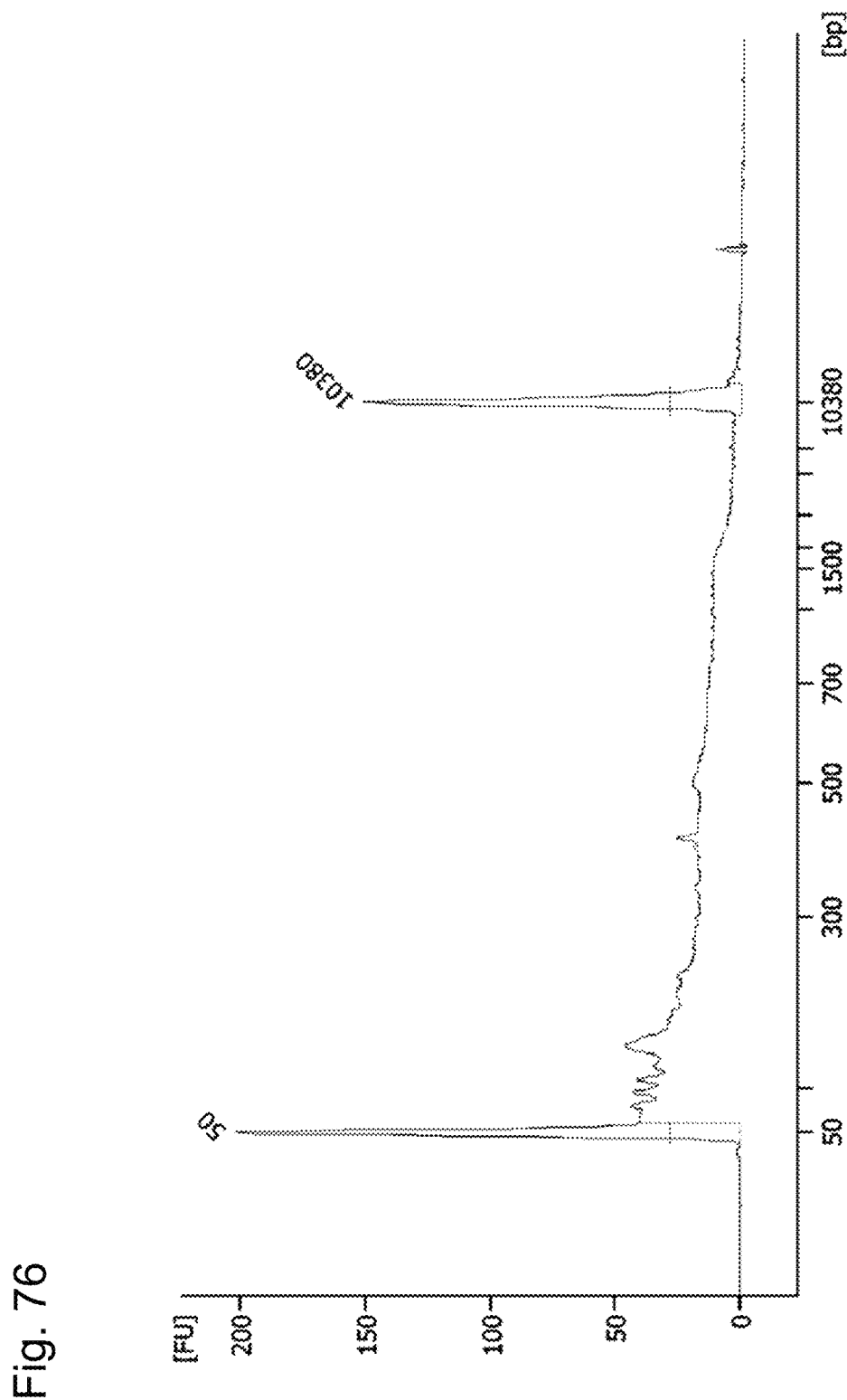
FIG. 76 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 16-base random primer.
Figure 77:
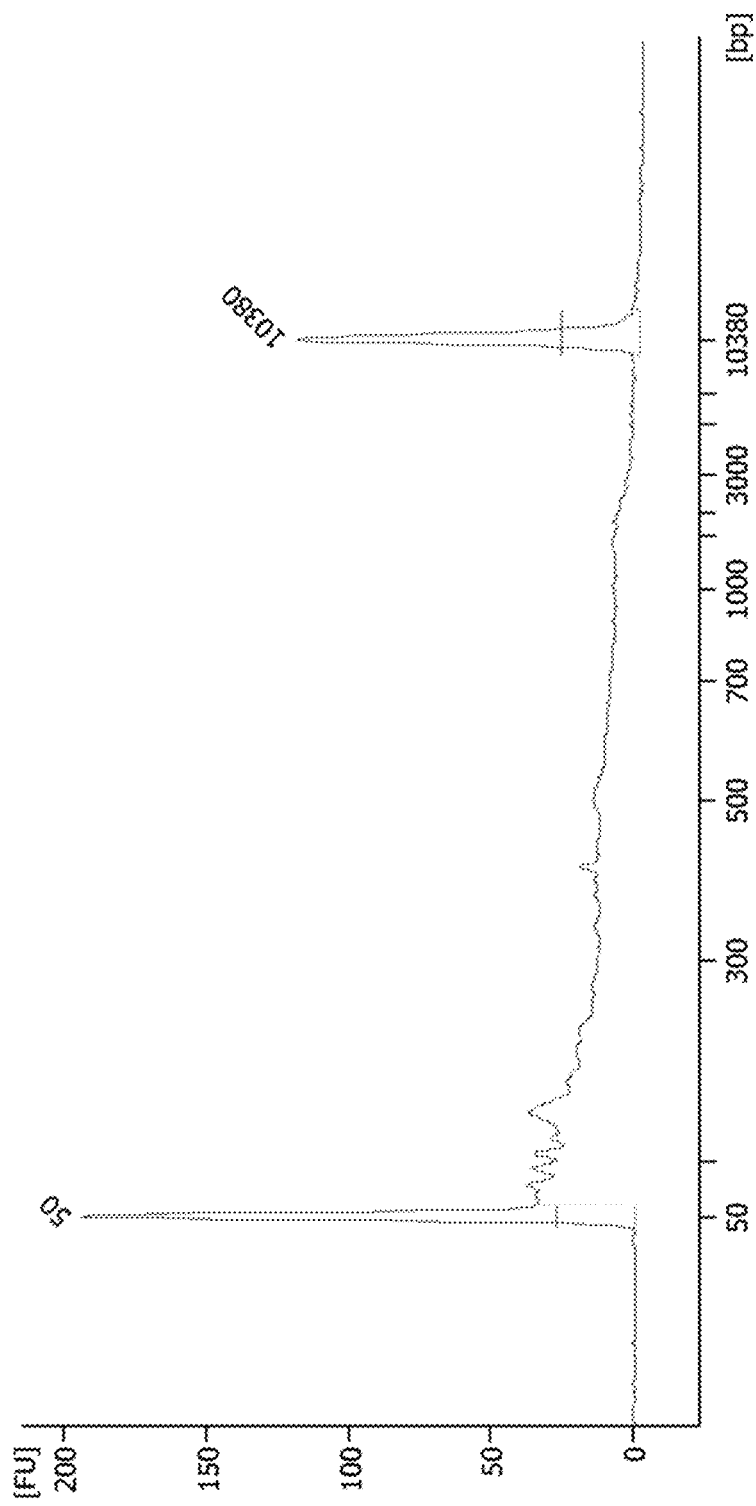
FIG. 77 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 16-base random primer.
Figure 78:
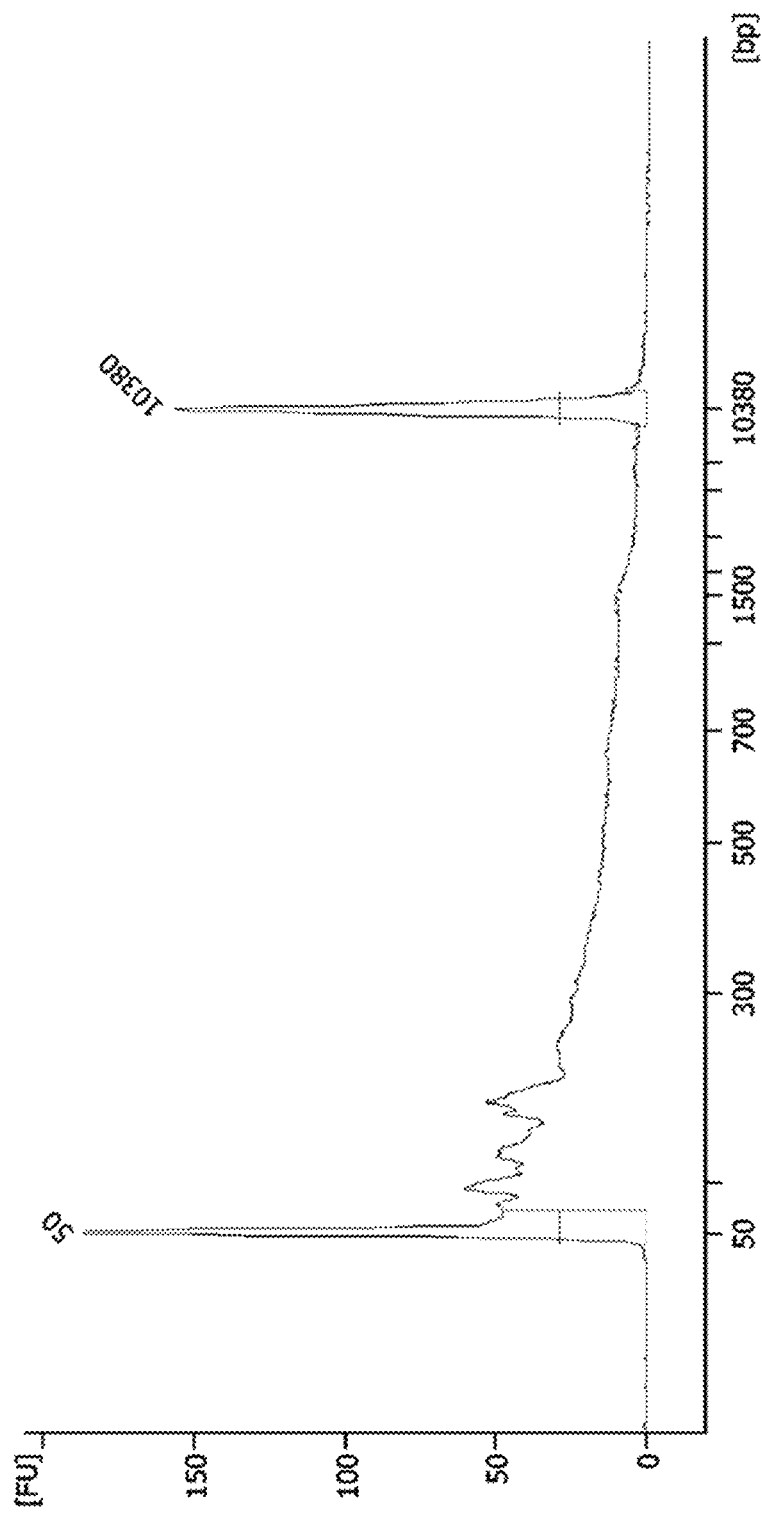
FIG. 78 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 18-base random primer.
Figure 79:
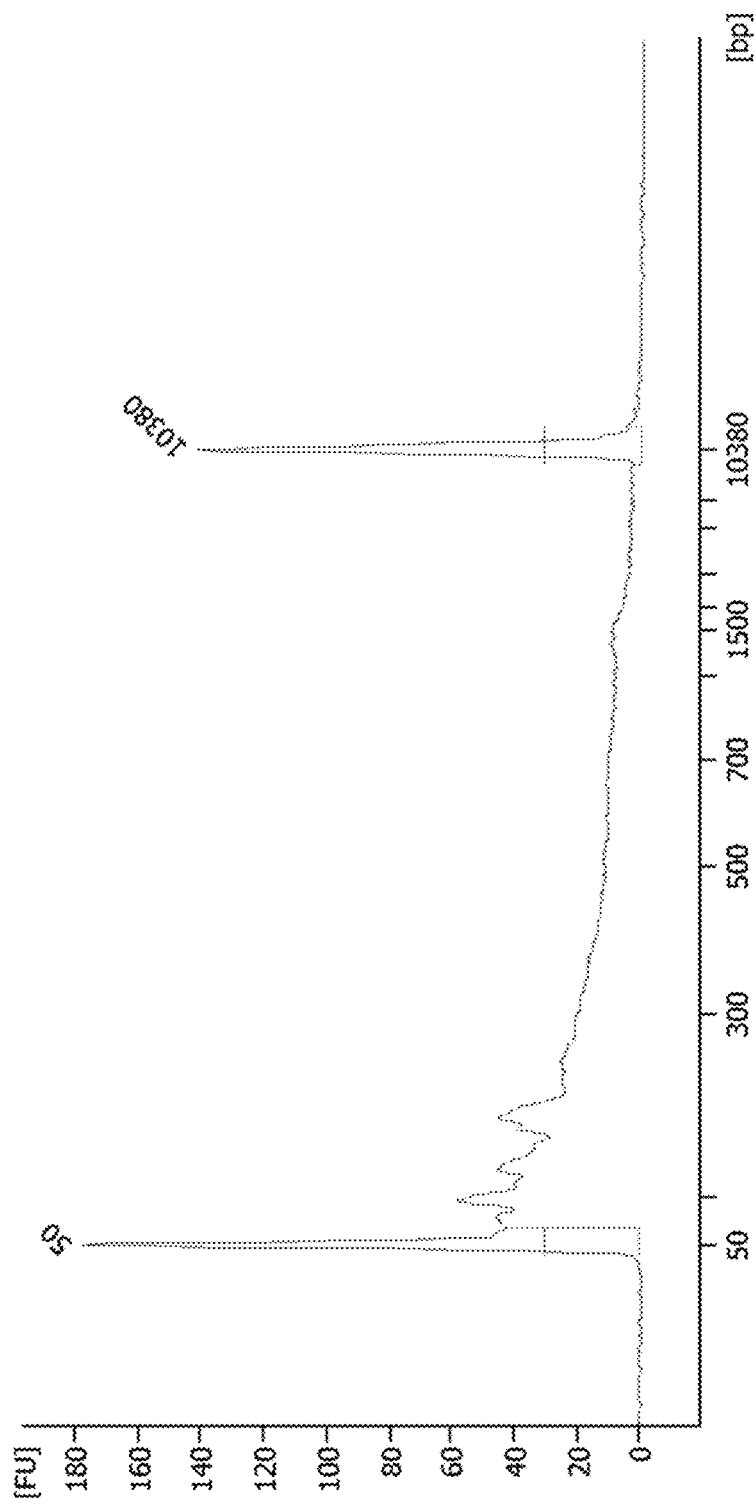
FIG. 79 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 18-base random primer.
Figure 80:
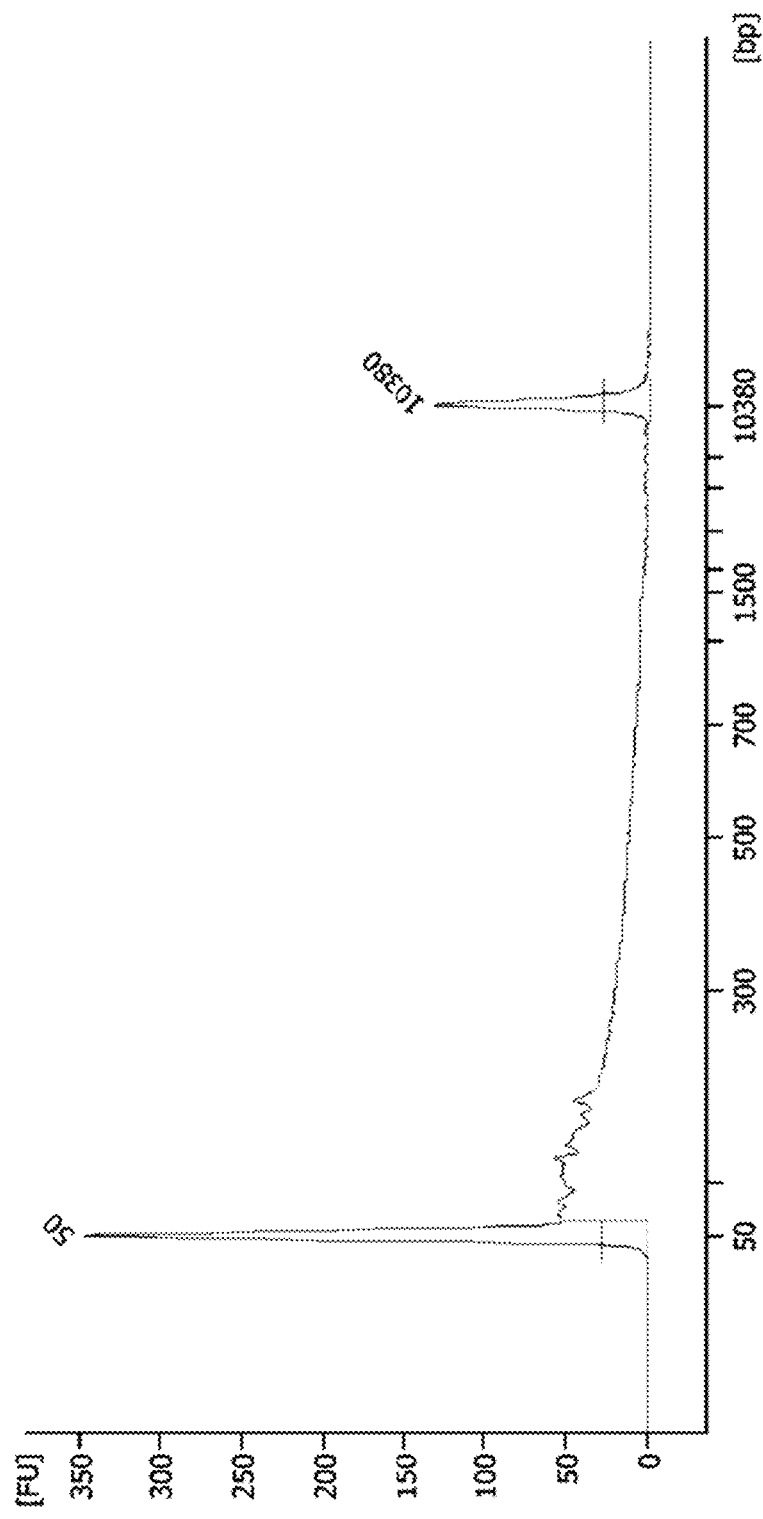
FIG. 80 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 20-base random primer.
Figure 81:
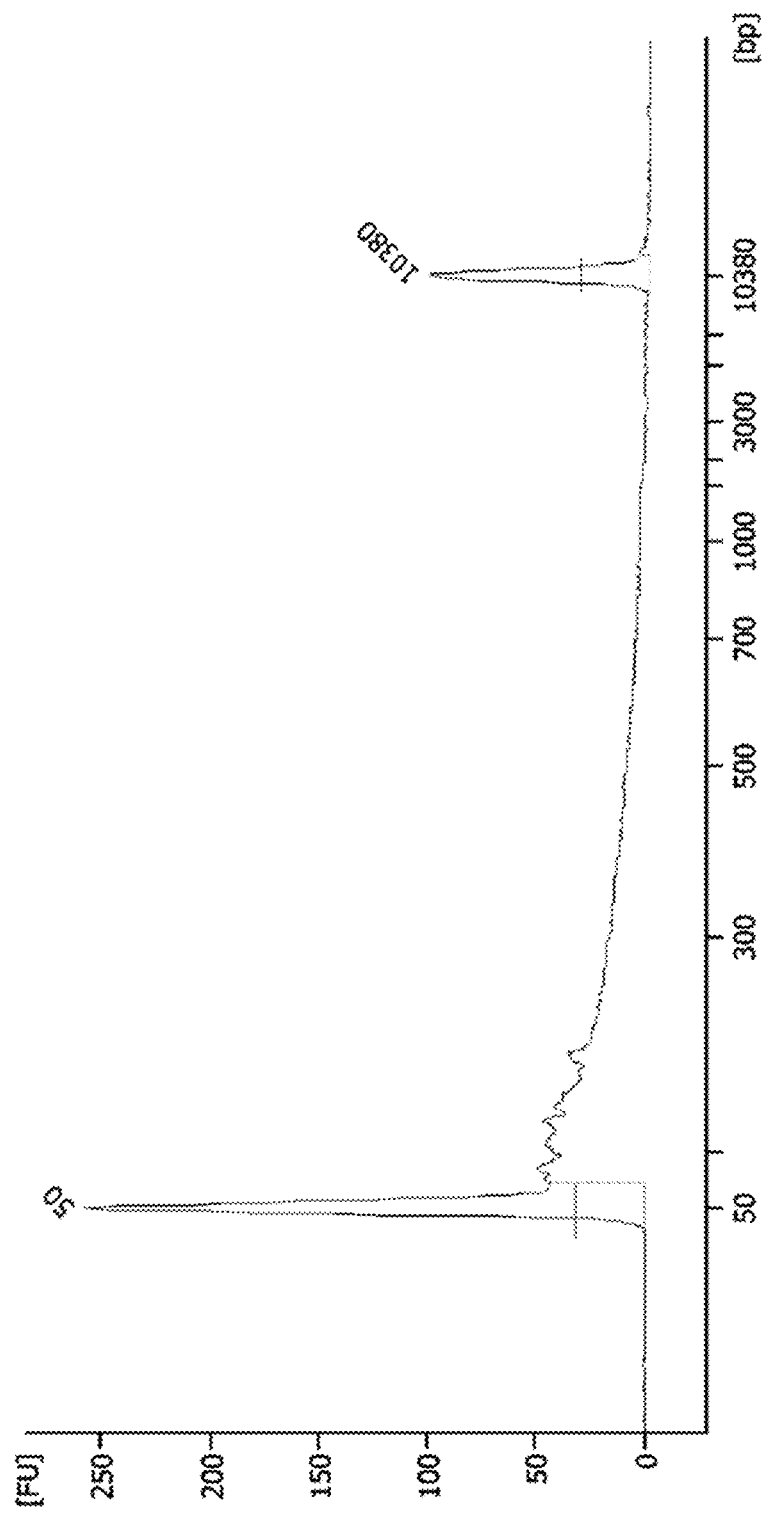
FIG. 81 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 20-base random primer.

| Random primer length | Repeat | FIG. No. | Correlational coefficient (ρ) |
|---|---|---|---|
| 9 | First | FIG. 66 | 0.981 |
|  | Second | FIG. 67 |  |
| 10 | First | FIG. 68 | 0.979 |
|  | Second | FIG. 69 |  |
| 11 | First | FIG. 70 | 0.914 |
|  | Second | FIG. 71 |  |
| 12 | First | FIG. 72 | 0.957 |
|  | Second | FIG. 73 |  |
| 14 | First | FIG. 74 | 0.984 |
|  | Second | FIG. 75 |  |
| 16 | First | FIG. 76 | 0.989 |
|  | Second | FIG. 77 |  |
| 18 | First | FIG. 78 | 0.995 |
|  | Second | FIG. 79 |  |
| 20 | First | FIG. 80 | 0.999 |
|  | Second | FIG. 81 |  |

When random primers were used at high concentration of 10.0 microM, which is 13.3 times greater than the usual level, as shown in FIGS. 66 to 81, it was found that a low-molecular-weight DNA fragment could be amplified using 9- to 20-base random primers while achieving very high reproducibility. As the base length of a random primer increased (12 bases or more, in particular), the molecular weight of the amplified fragment was likely to decrease. When a 9-base random primer was used, the amount of the DNA fragment amplified was increased by setting the annealing temperature at 37 degrees C.

In order to elucidate the correlation between the concentration and the length of random primers, as described in 3.6.2 above, PCR was carried out with the use of 8- to 35-base random primers at the concentration of 0.6 to 300 microM, so as to prepare a DNA library. The results are shown in Table 28.

TABLE 28

Correlation between concentration and length of random primer relative to DNA library

| Primer µM | Conc. relative to standard | Primer length | | | | | | | | | | | | | | |
|---|---|---|---|---|---|---|---|---|---|---|---|---|---|---|---|---|
|  |  | 8 | 9 | 10 | 11 | 12 | 14 | 16 | 18 | 20 | 22 | 24 | 26 | 28 | 29 | 30 | 35 |
| 0.6 | Standard | x | x | x | x | x | x | x | x | x | x | x | x | x | x | x | x |
| 2 | 3.3x | x | x | x | x | x | x | x | x | x | x | x | x | x | x | x | x |
| 4 | 6.7x | x | x | x | x | x | o | o | o | o | o | o | o | o | x | x | x |
| 6 | 10.0x | x | x | x | x | x | o | o | o | o | o | o | o | o | o | o | x |
| 8 | 13.3x | x | x | x | x | o | o | o | o | o | o | o | o | o | o | x | x |
| 10 | 16.7x | x | x | x | x | o | o | o | o | o | o | o | o | o | o | x | x |
| 20 | 33.3x | x | x | x | o | o | o | o | o | o | o | o | x | x | x | x | x |
| 40 | 66.7x | x | o | o | o | o | o | o | o | o | x | x | x | x | x | x | x |
| 60 | 100.0x | x | o | o | o | o | o | o | o | o | x | x | x | x | x | x | x |
| 100 | 166.7x | — | x | o | o | o | o | o | o | x | — | — | — | — | — | — | — |
| 200 | 333.3x | — | x | o | o | x | x | x | x | x | — | — | — | — | — | — | — |
| 300 | 500.0x | — | x | x | x | x | x | x | x | x | — | — | — | — | — | — | — | o: DNA library covering 100 to 500 bases is amplified with good reproducibility (ρ > 0.9)

x: DNA library not covering 100 to 500 bases or reproducibility being poor (ρ ≤ 0.9)

—: Unperformed

As shown in Table 28, it was found that a low-molecular-weight (100 to 500 bases) DNA fragment could be amplified with high reproducibility with the use of 9- to 30-base random primers at the concentration of 4.0 to 200 microM. In particular, it was confirmed that low-molecular-weight (100 to 500 bases) DNA fragments could be amplified with certainty and high reproducibility with the use of 9- to 30-base random primers at the concentration of 4.0 to 100 microM.

Figure 82:
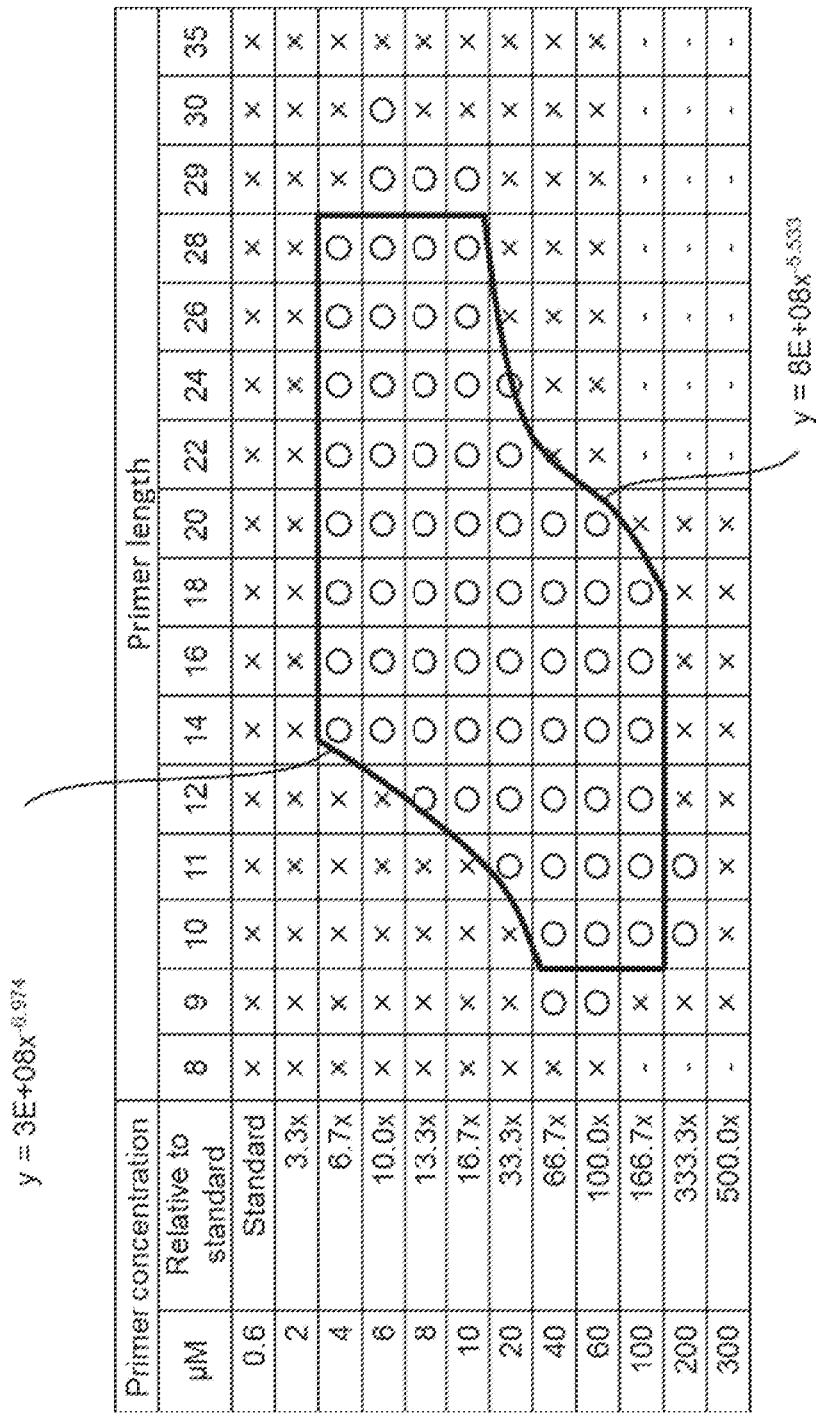
FIG. 82 shows a characteristic diagram demonstrating the results of investigating the reproducibility of the DNA library amplified using DNA of the sugarcane variety NiF8 as a template and 8- to 35-base random primers at a concentration of 0.6 to 300 microM.

The results shown in Table 28 are examined in greater detail. As a result, the correlation between the length and the concentration of random primers is found to be preferably within a range surrounded by a frame, as shown in FIG. 82. More specifically, the random primer concentration is preferably 40 to 60 microM when the random primers comprise 9 to 10 bases. It is preferable that a random primer concentration satisfy the condition represented by an inequation: $y > 3E+08x^{-6.974}$ ($r=0.985$), provided that the base length of the random primer is represented by x and the random primer concentration is represented by y, and 100 microM or lower, when the random primer comprises 10 to 14 bases. The random primer concentration is preferably 4 to 100 mM when the random primer comprises 14 to 18 bases. When a random primer comprises 18 to 28 bases, it is preferable that the random primer concentration be 4 microM or higher and the condition represented by an inequation: $y < 8E+08x^{-5.533}$ ($r=0.967$) be satisfied. When a random primer comprises 28 to 29 bases, the random primer concentration is preferably 4 to 10 microM. The inequations $y > 3E+08x^{-6.974}$ and $y < 8E+08x^{-5.533}$ are determined on the basis of the Microsoft Excel power approximation. In the Microsoft Excel power approximation, "r" (rho) represents a rank correlation coefficient.

By prescribing the number of bases and the concentration of random primers within given ranges as described above, it was found that low-molecular-weight (100 to 500 bases) DNA fragments could be amplified with high reproducibility. For example, the accuracy of the data obtained via analysis of high-molecular-weight DNA fragments with the use of a next-generation sequencer is known to deteriorate to a significant extent. As described in this example, the number of bases and the concentration of random primers may be prescribed within given ranges, so that a DNA library with a molecular size suitable for analysis with a next-generation sequencer can be prepared with satisfactory reproducibility, and such DNA library can be suitable for marker analysis with the use of a next-generation sequencer.

4.7 Number of Random Primers

As described in 3.7 above, 1, 2, 3, 12, 24, or 48 types of random primers (concentration: 60 microM) were used to prepare a DNA library, and the results are shown in FIGS. 83 to 94. The results are summarized in Table 29.

TABLE 29

Figure 83:
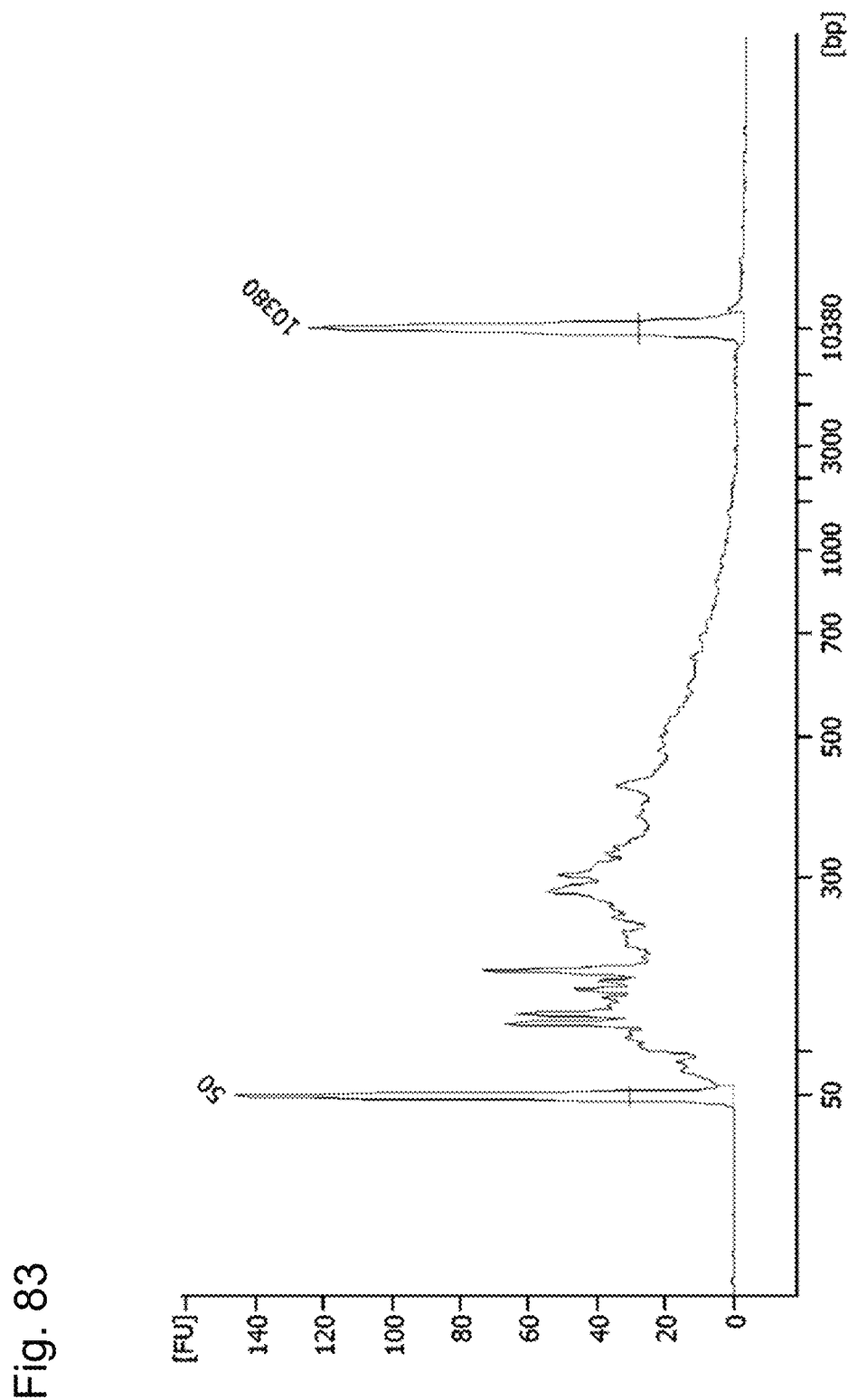
FIG. 83 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a single type of random primer.
Figure 84:
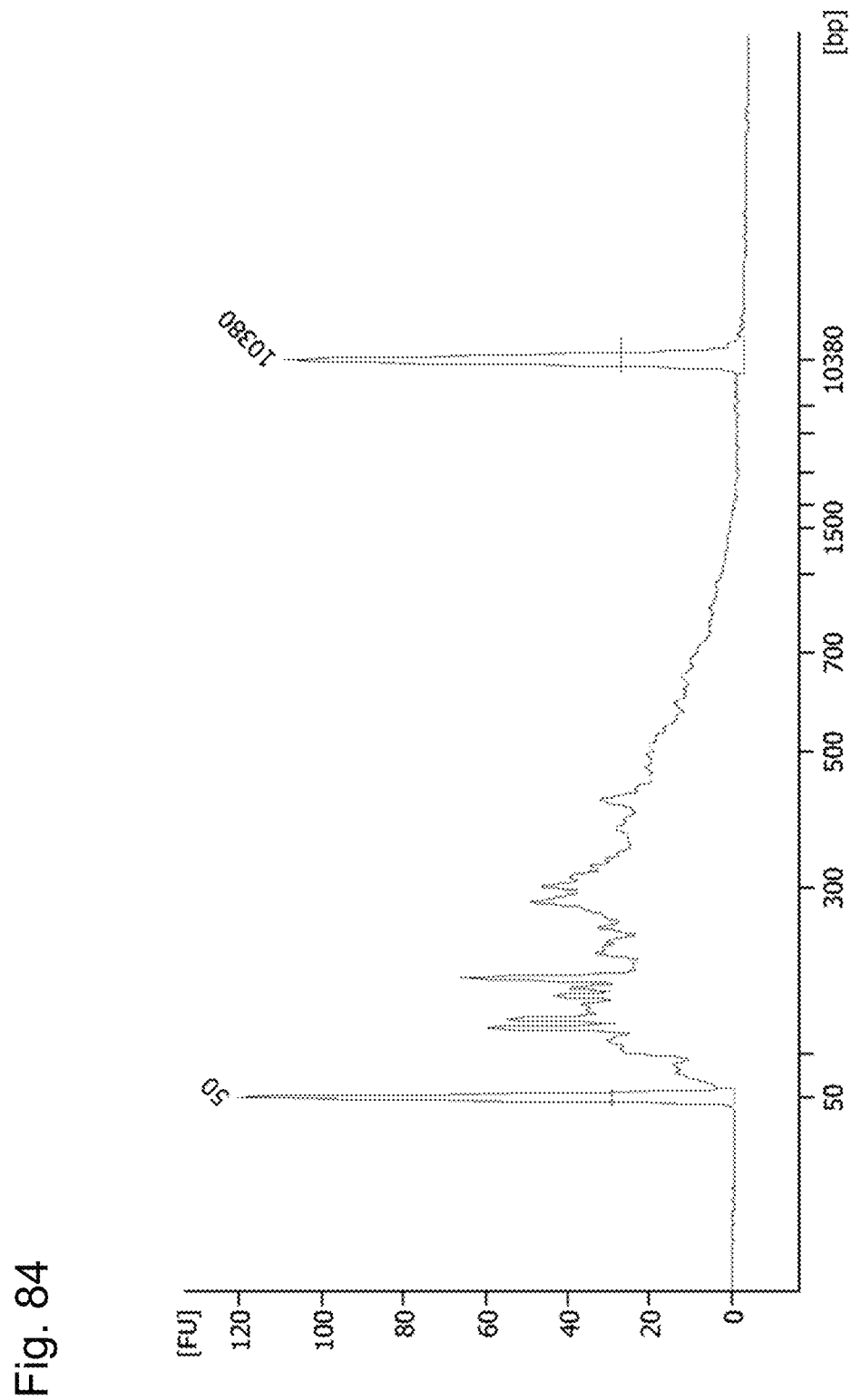
FIG. 84 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a single type of random primer.
Figure 85:
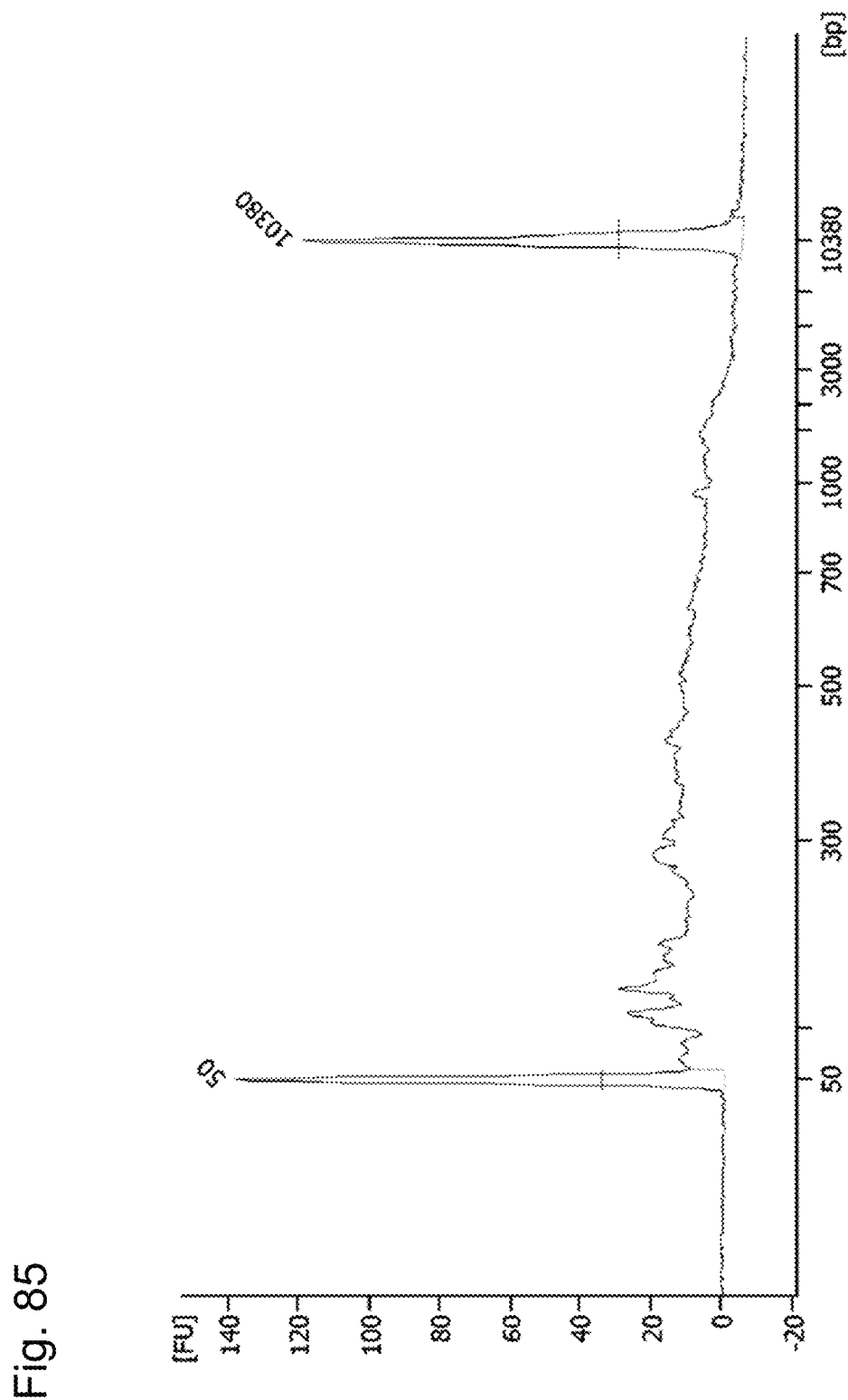
FIG. 85 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and 2 types of random primers.
Figure 86:
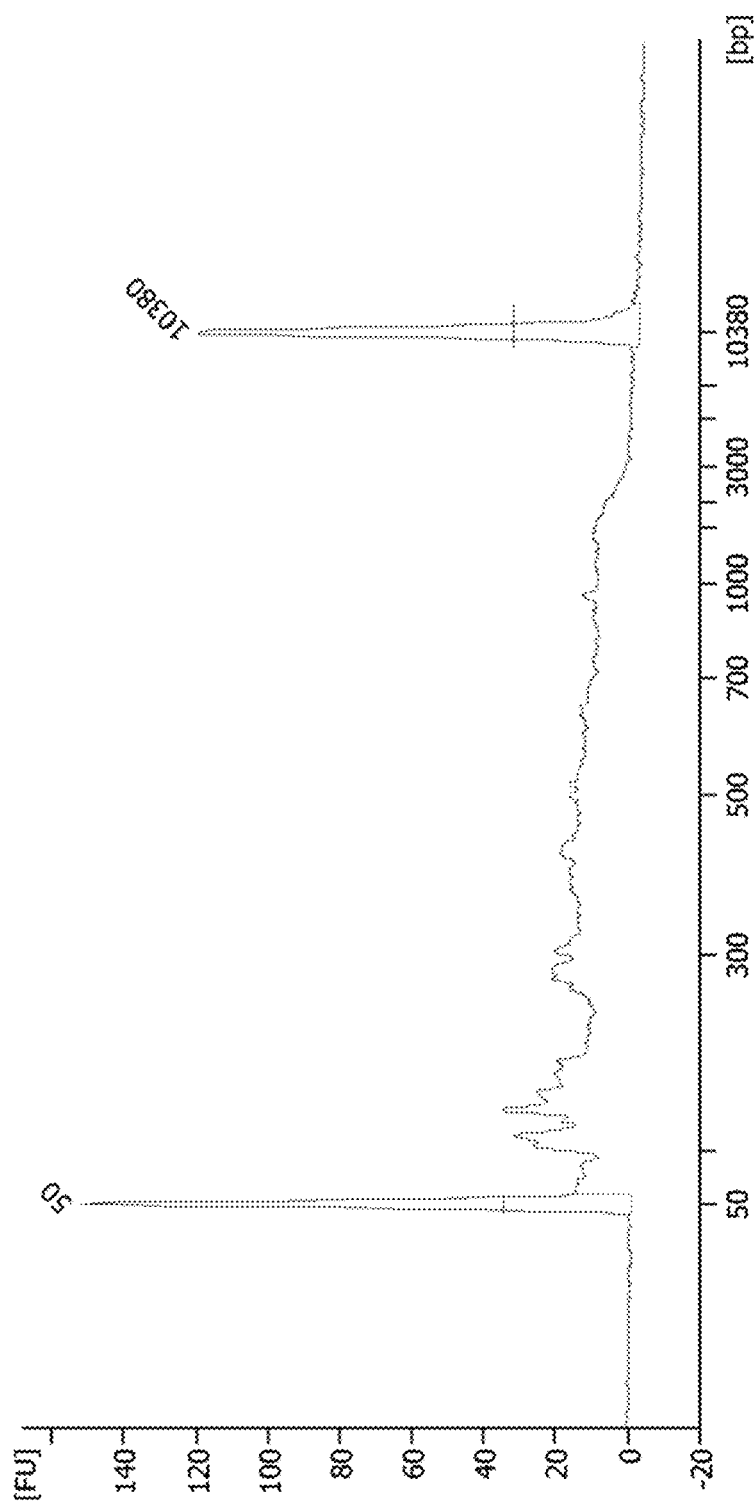
FIG. 86 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and 2 types of random primers.
Figure 87:
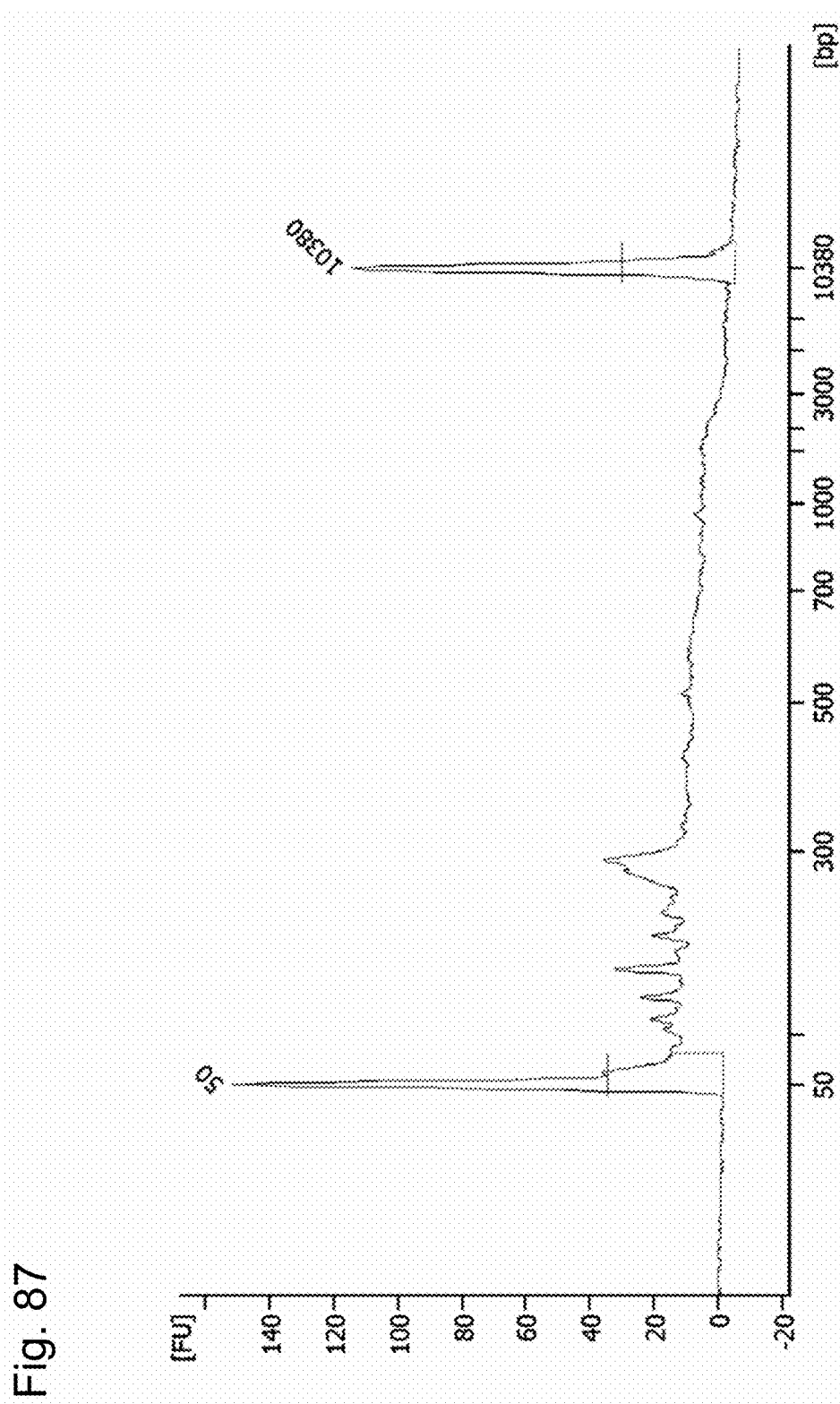
FIG. 87 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and 3 types of random primers.
Figure 88:
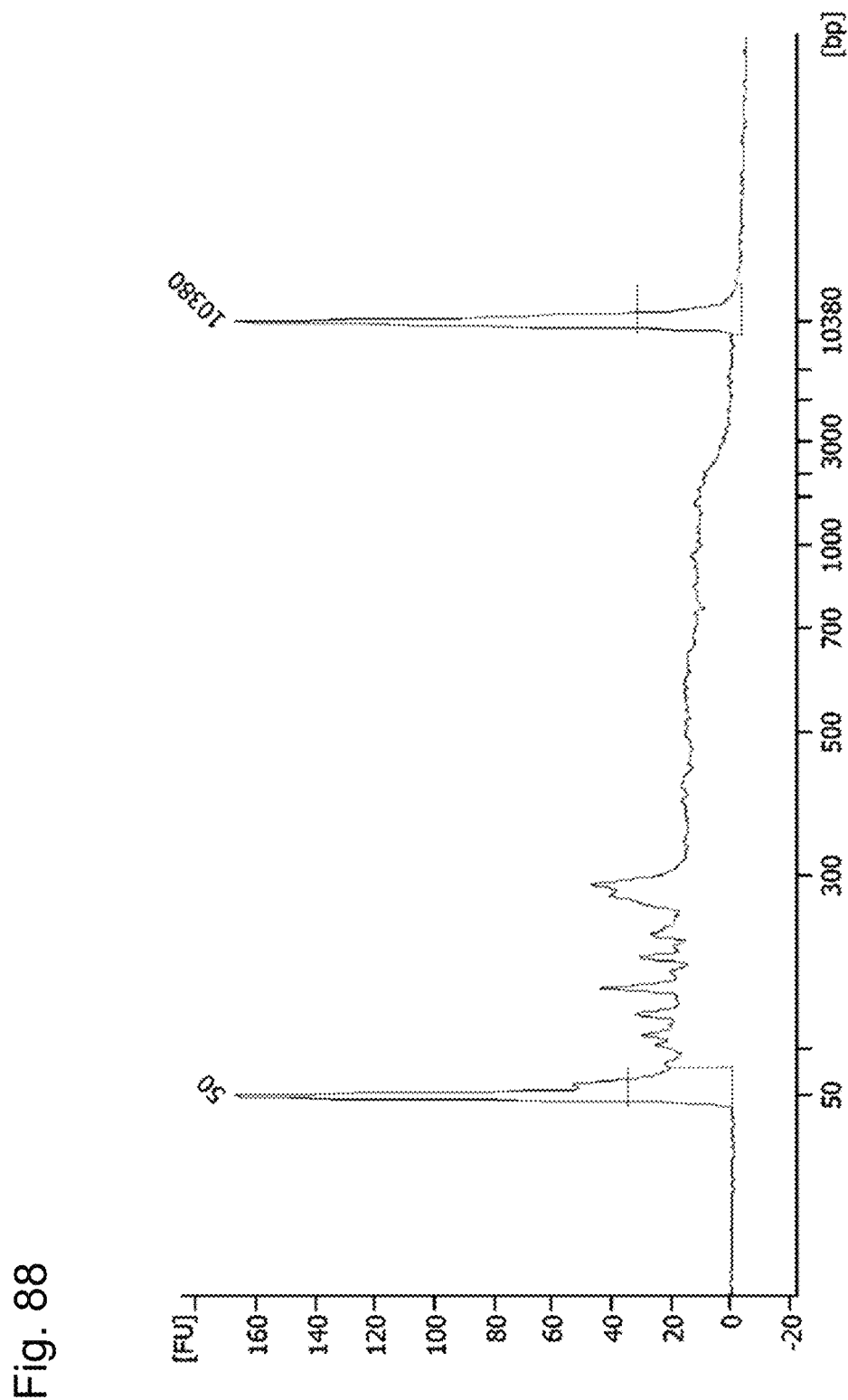
FIG. 88 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and 3 types of random primers.
Figure 89:
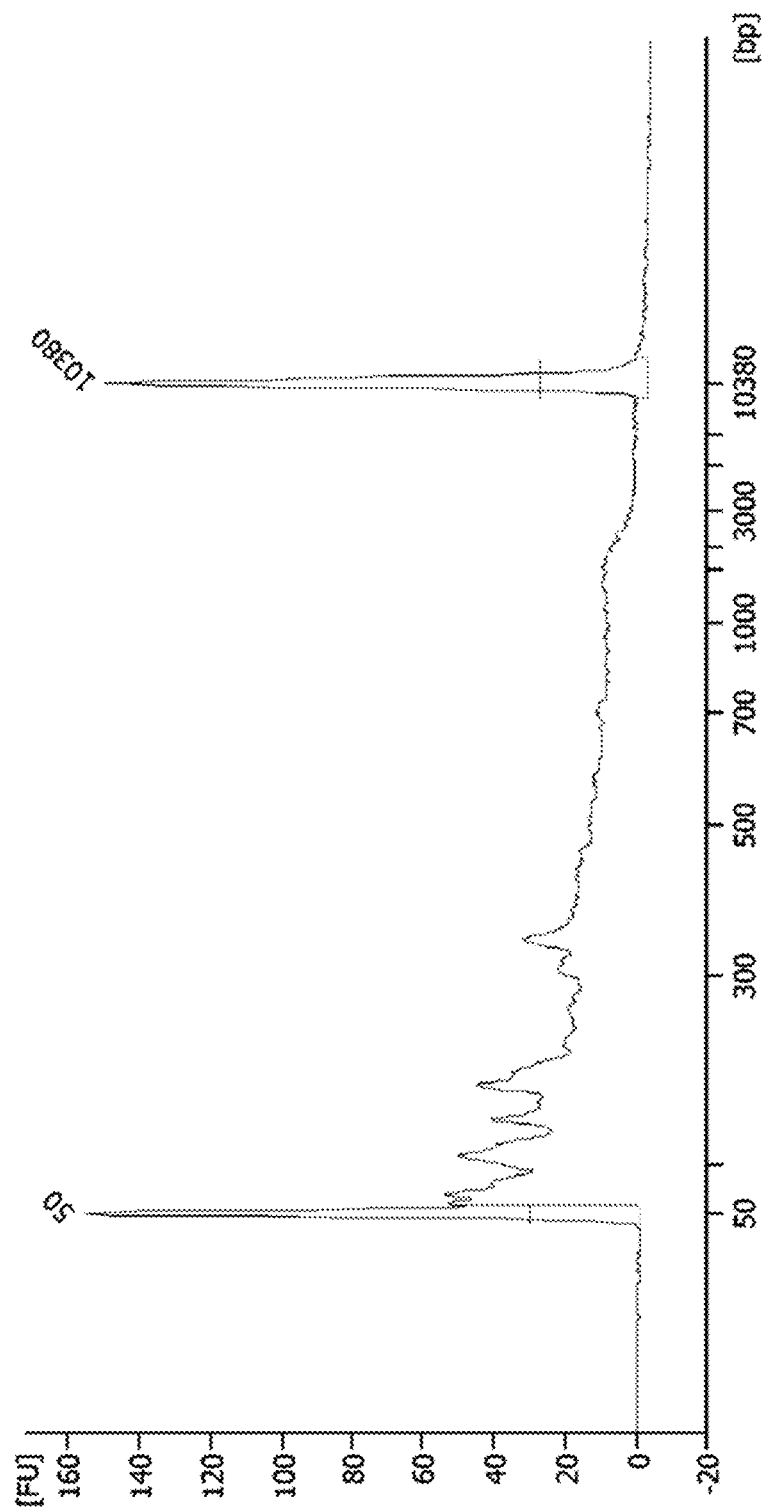
FIG. 89 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and 12 types of random primers.
Figure 90:
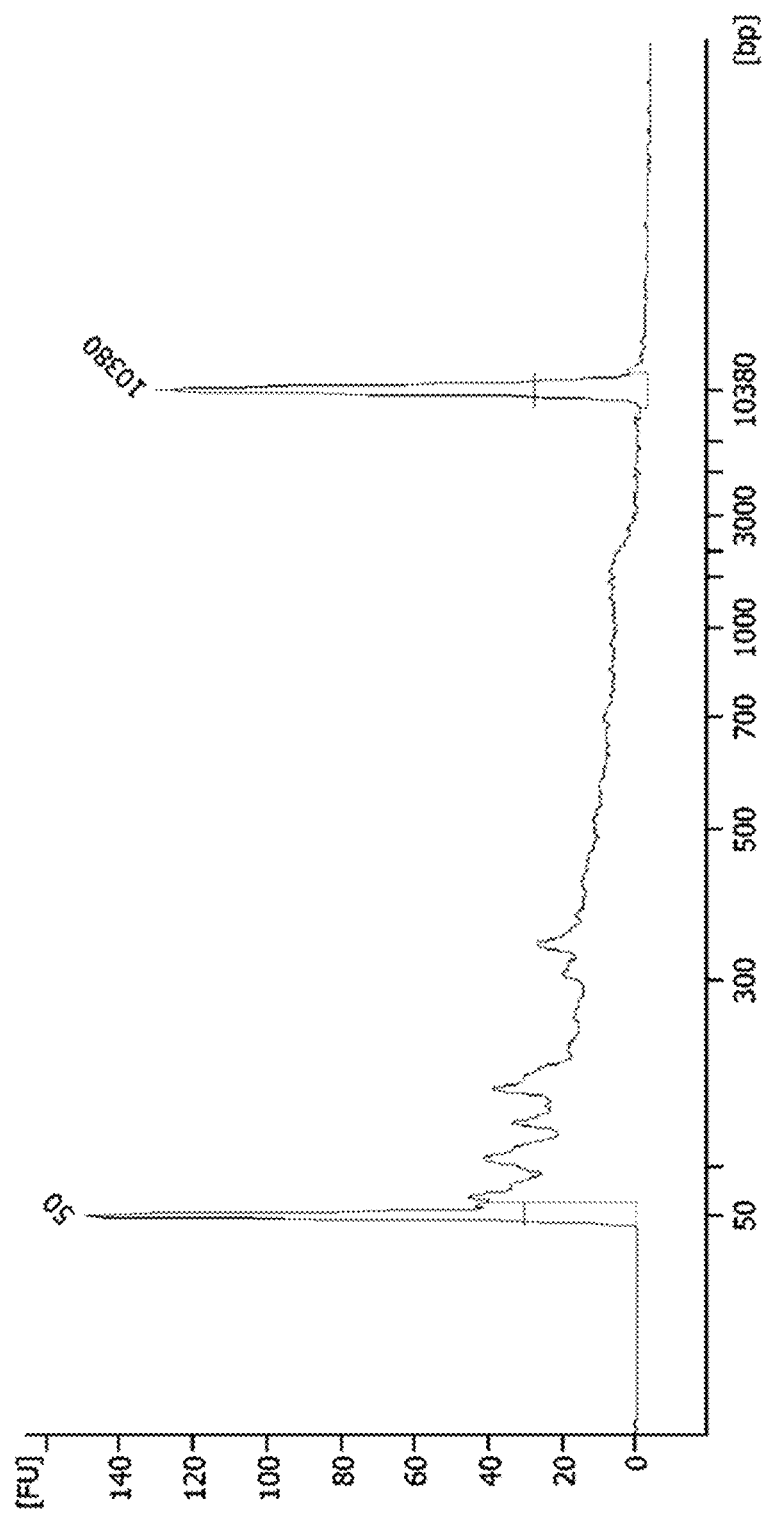
FIG. 90 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and 12 types of random primers.
Figure 91:
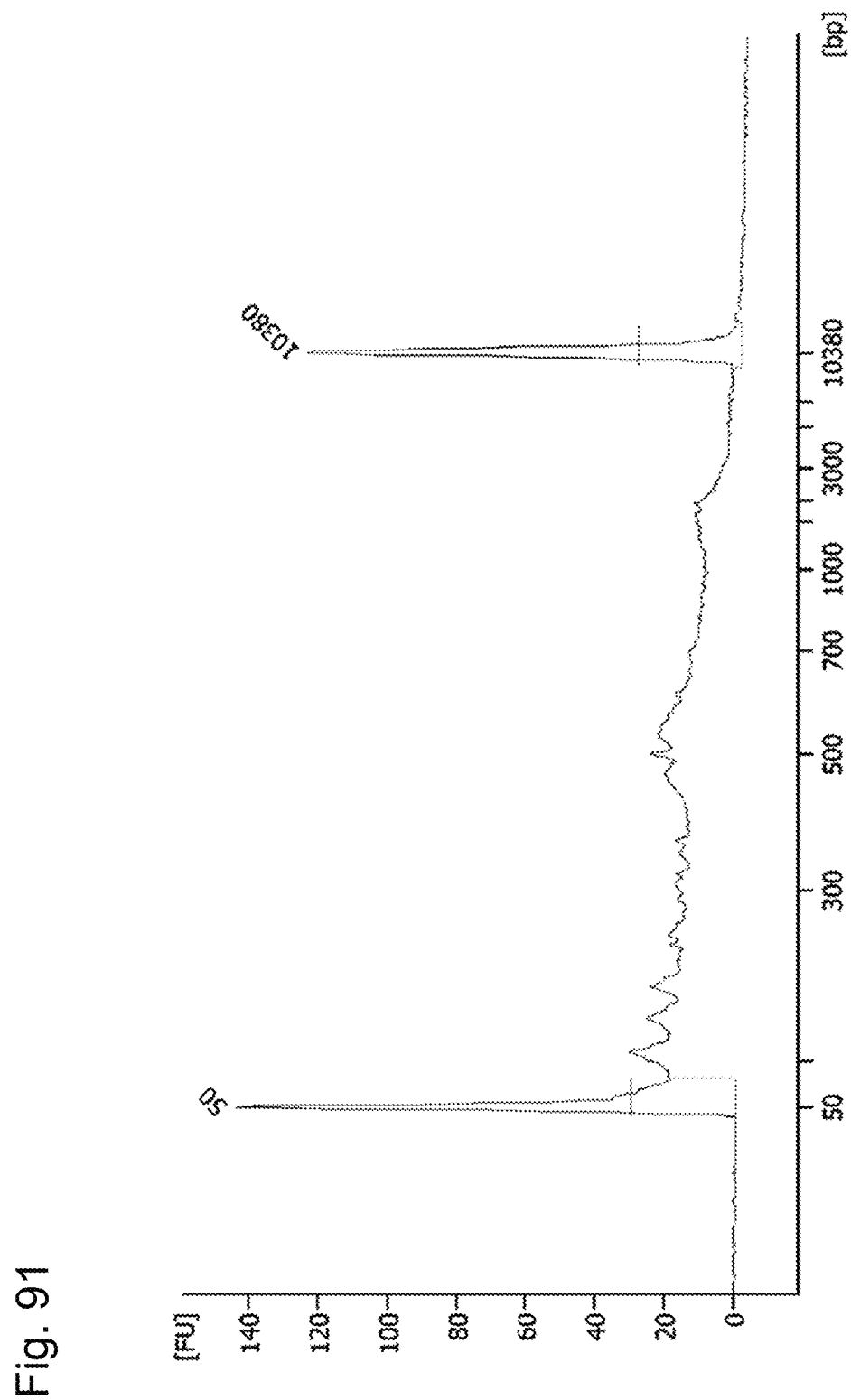
FIG. 91 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and 24 types of random primers.
Figure 92:
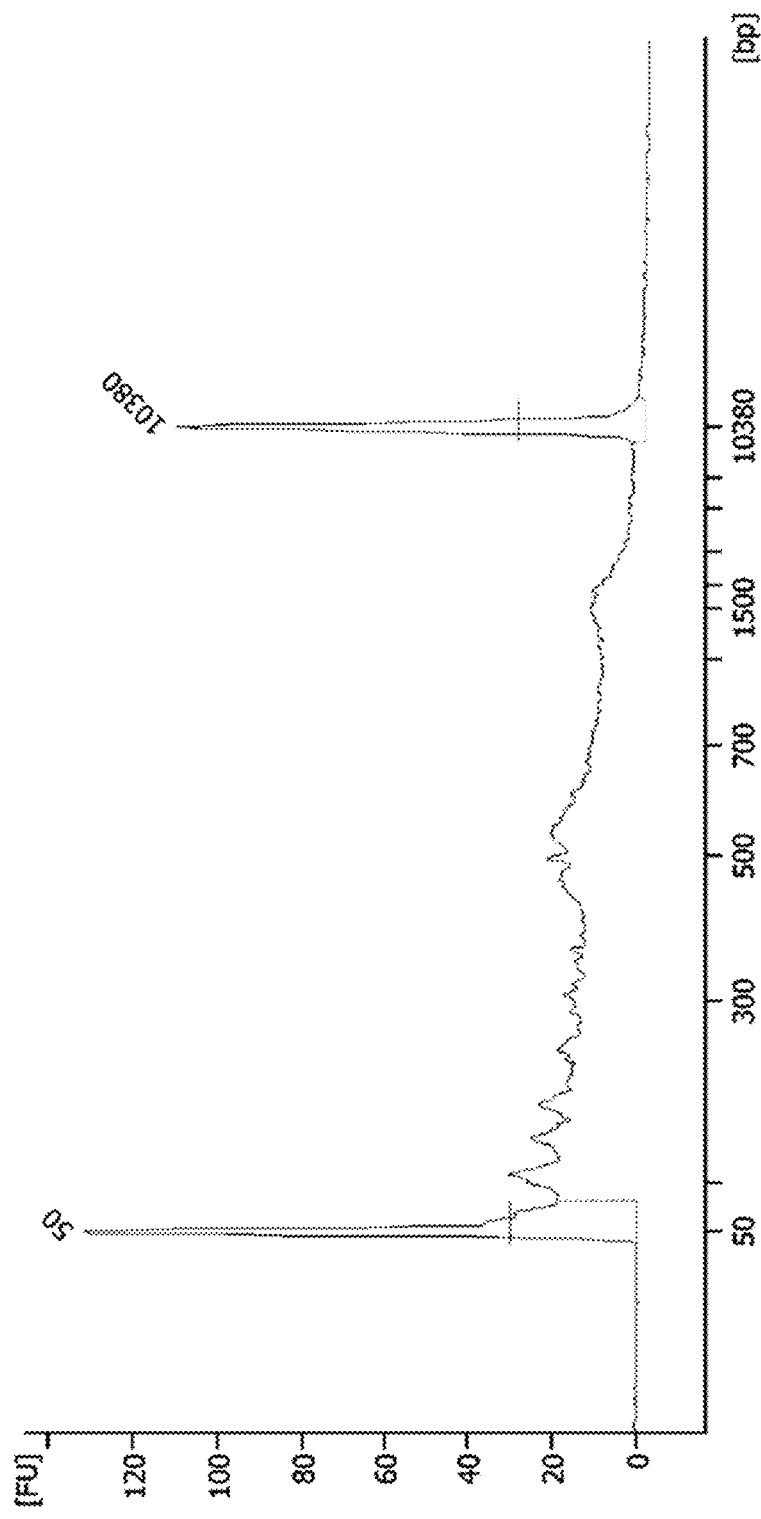
FIG. 92 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and 24 types of random primers.
Figure 93:
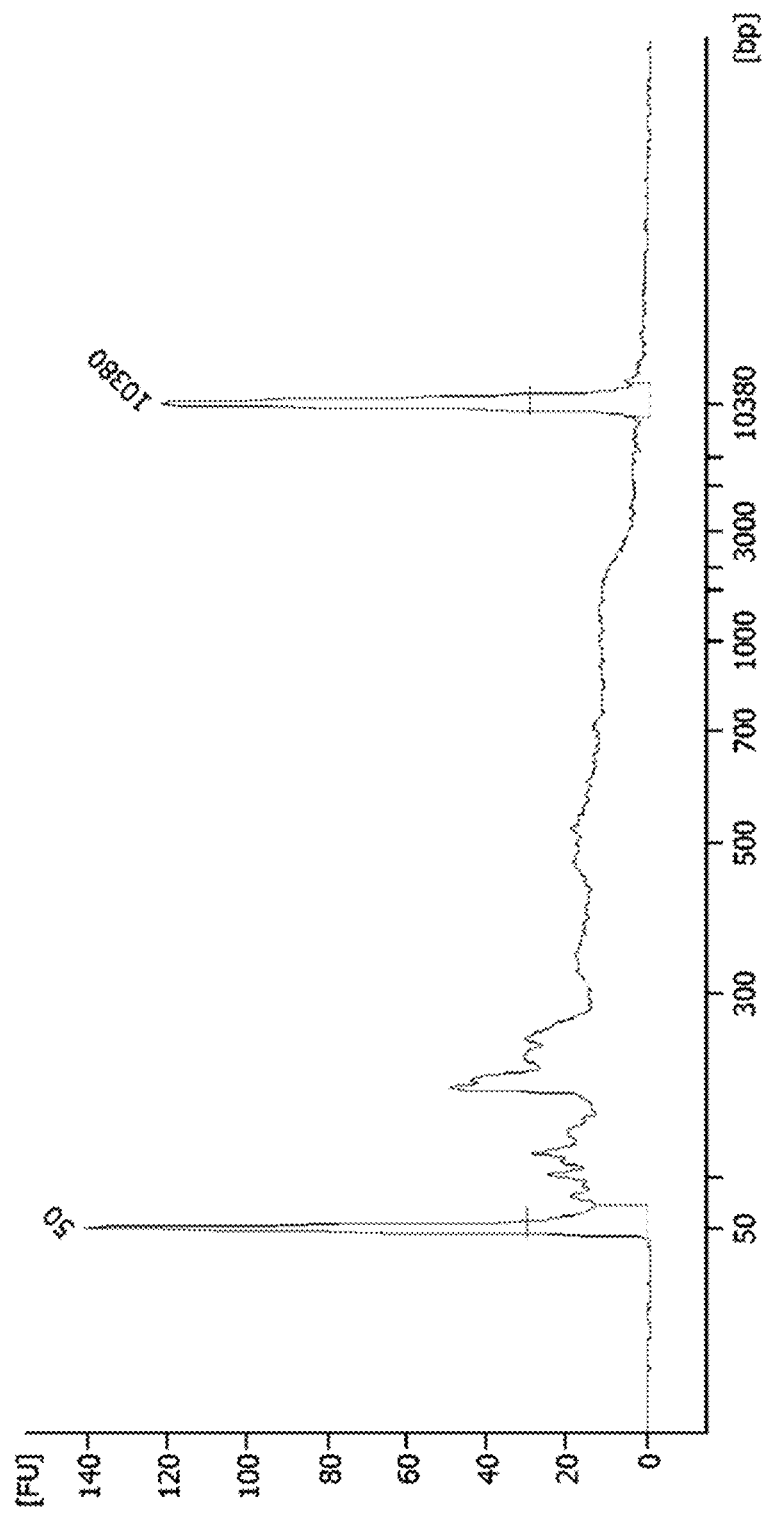
FIG. 93 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and 48 types of random primers.
Figure 94:
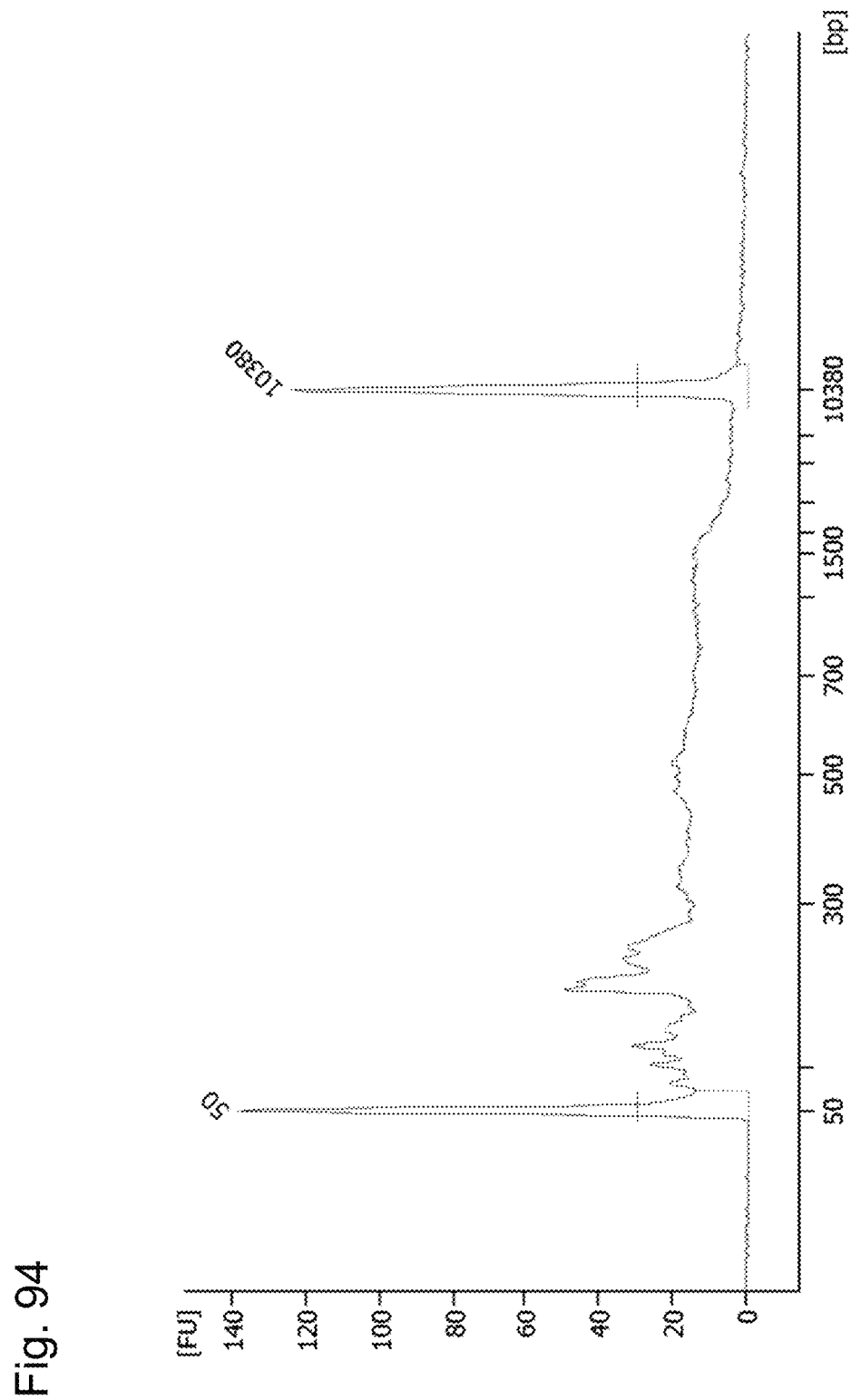
FIG. 94 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and 48 types of random primers.

| Number of random primers | Repeat | FIG. No. | Correlational coefficient (ρ) |
|---|---|---|---|
| 1 | First | FIG. 83 | 0.984 |
|   | Second | FIG. 84 |  |
| 2 | First | FIG. 85 | 0.968 |
|   | Second | FIG. 86 |  |
| 3 | First | FIG. 87 | 0.974 |
|   | Second | FIG. 88 |  |
| 12 | First | FIG. 89 | 0.993 |
|    | Second | FIG. 90 |  |
| 24 | First | FIG. 91 | 0.986 |
|    | Second | FIG. 92 |  |
| 48 | First | FIG. 93 | 0.978 |
|    | Second | FIG. 94 |  |

As shown in FIGS. 83 to 94, it was found that low-molecular-weight DNA fragments could be amplified using any of 1, 2, 3, 12, 24, or 48 types of random primers while achieving very high reproducibility. As the number of types of random primers increases, in particular, a peak in the electrophoretic pattern lowers, and a deviation is likely to disappear.

4.8 Random Primer Sequence

As described in 3.8 above, DNA libraries were prepared with the use of sets of random primers shown in Tables 4 to 8 (i.e., 10-base primer B, 10-base primer C, 10-base primer D, 10-base primer E, and 10-base primer F), and the results are shown in FIGS. 95 to 104. The results are summarized in Table 30.

TABLE 30

Figure 95:
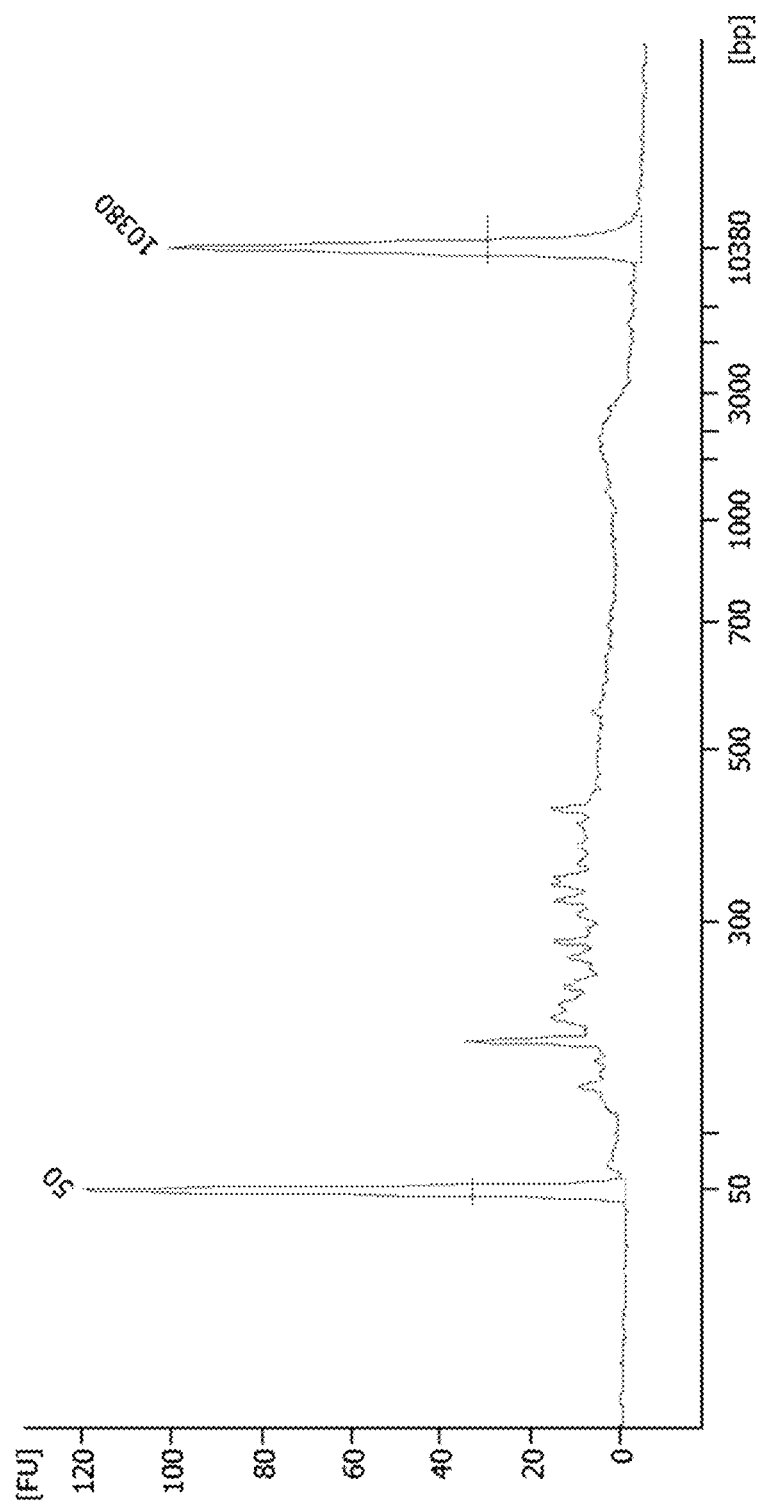
FIG. 95 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer B.
Figure 96:
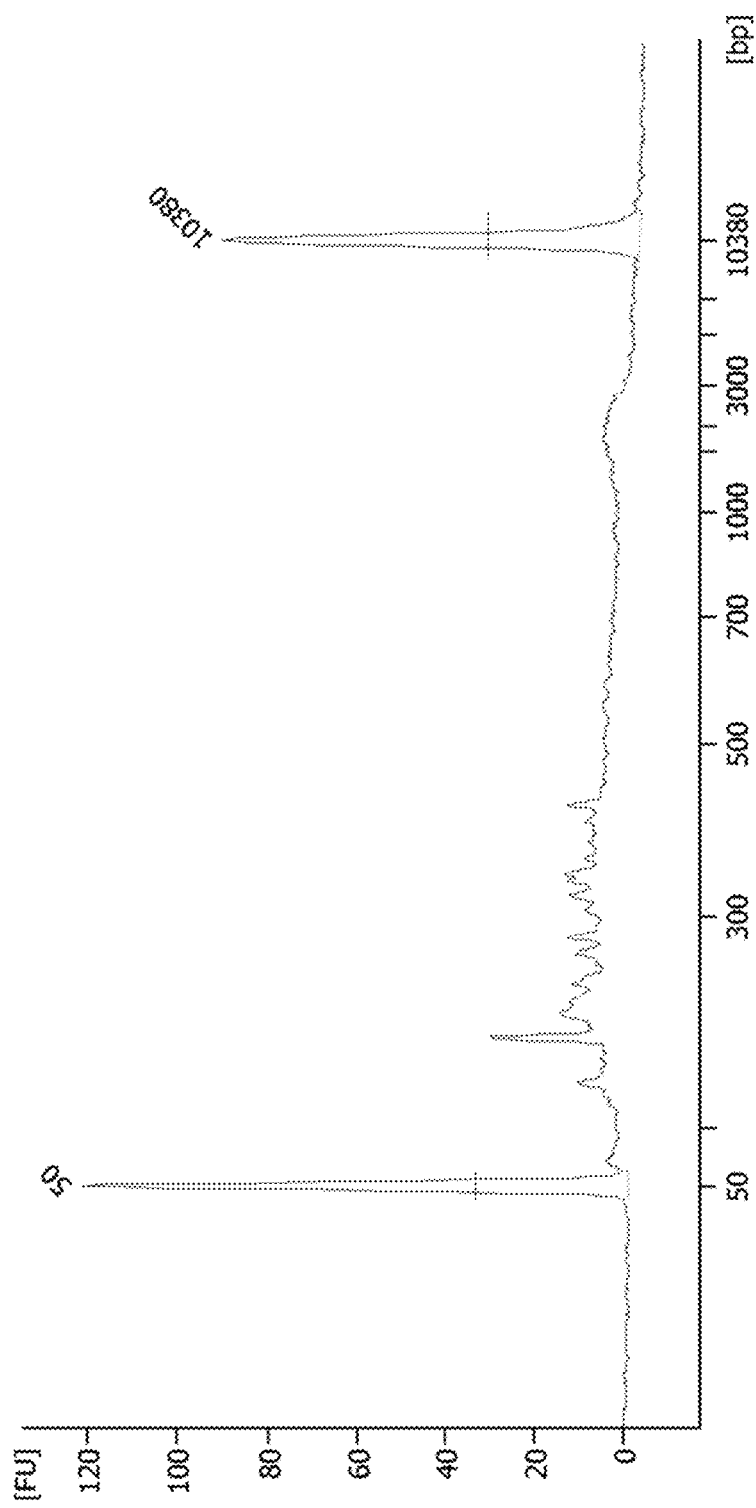
FIG. 96 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer B.
Figure 97:
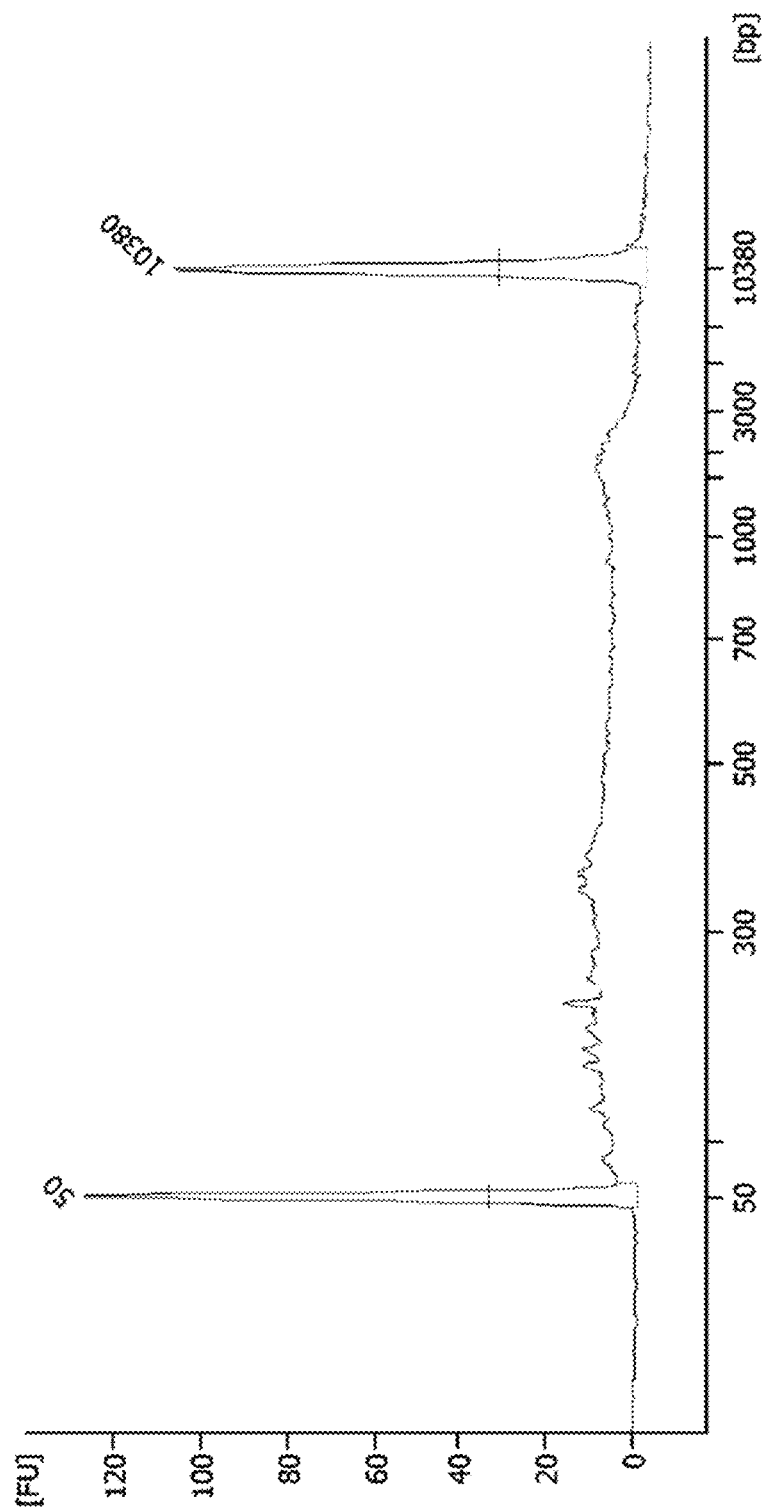
FIG. 97 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer C.
Figure 98:
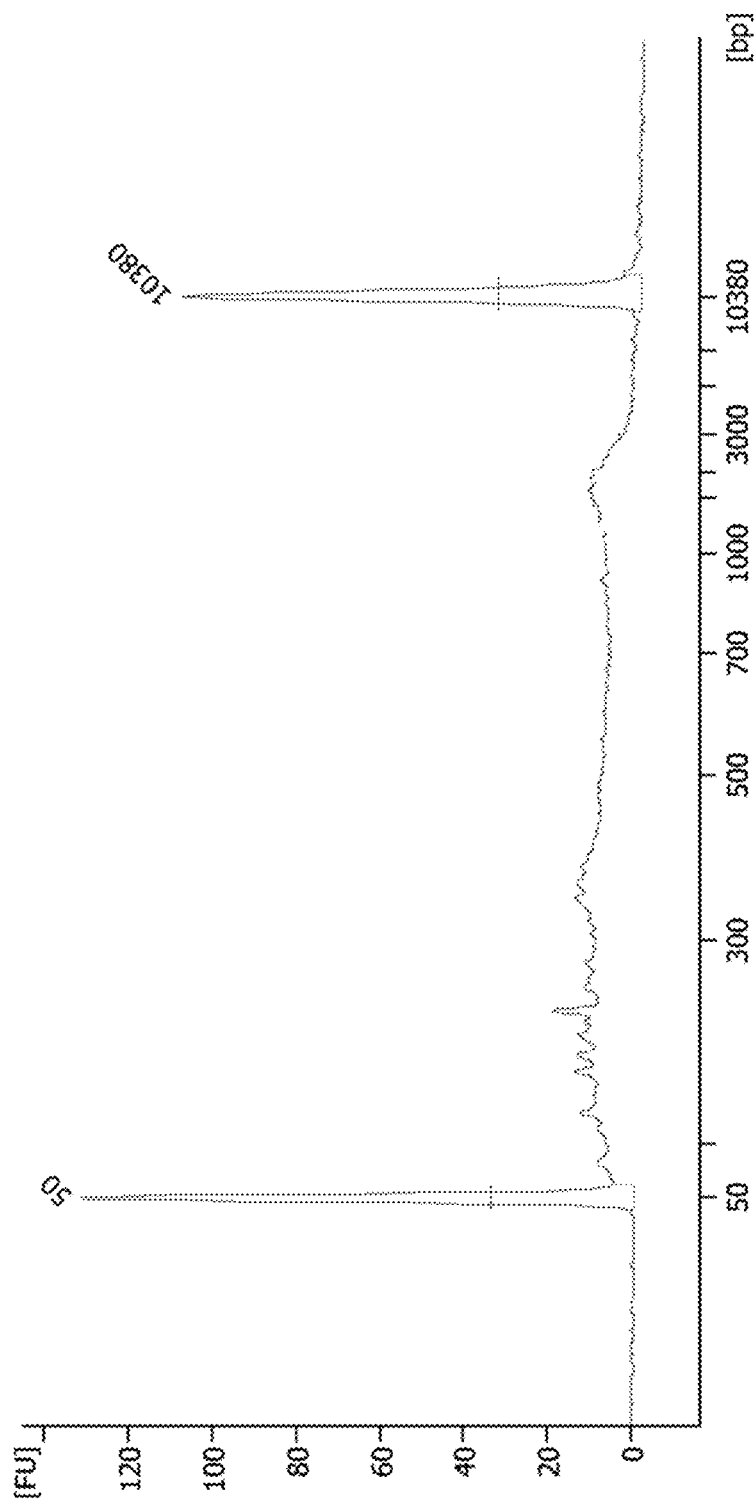
FIG. 98 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer C.
Figure 99:
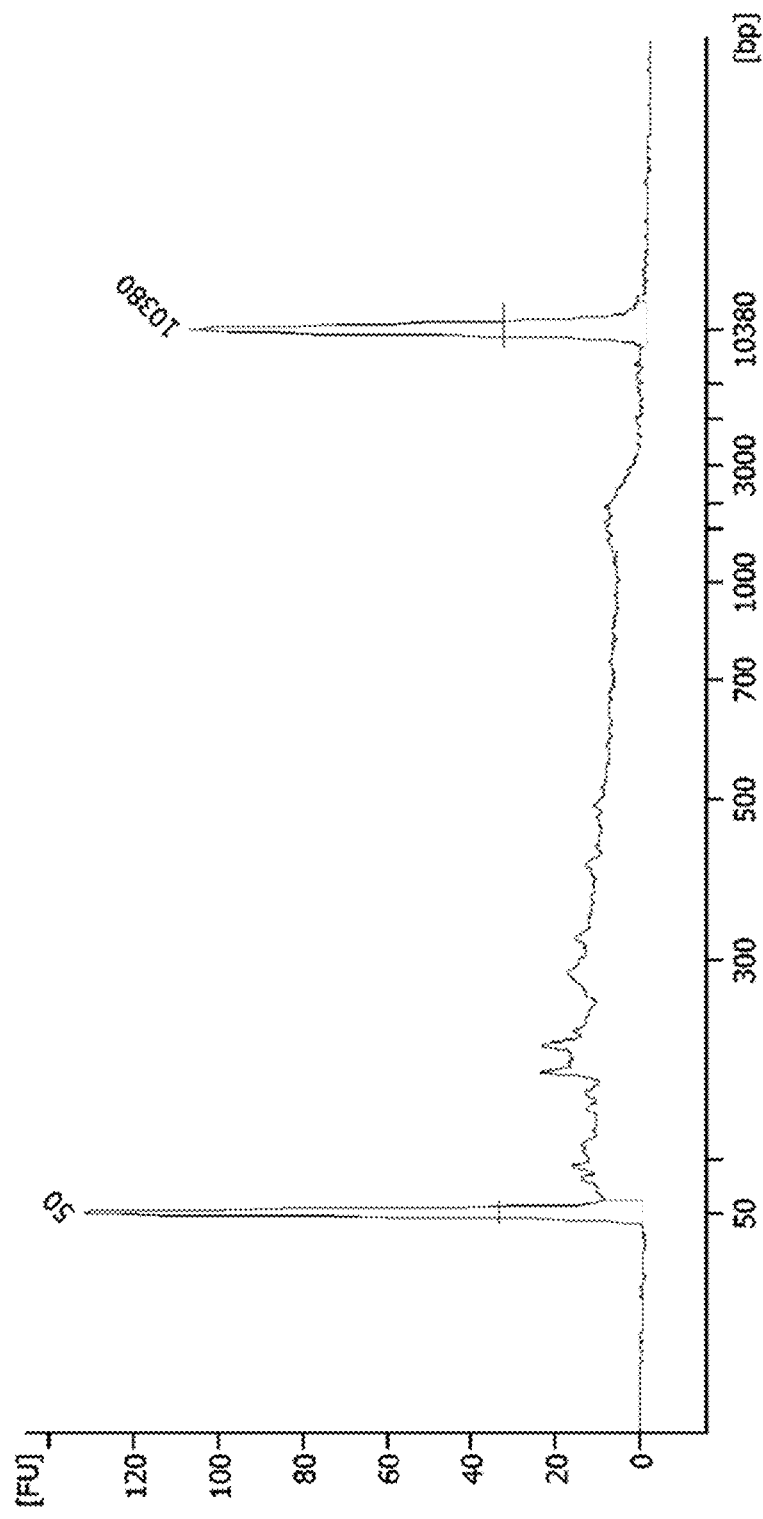
FIG. 99 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer D.
Figure 100:
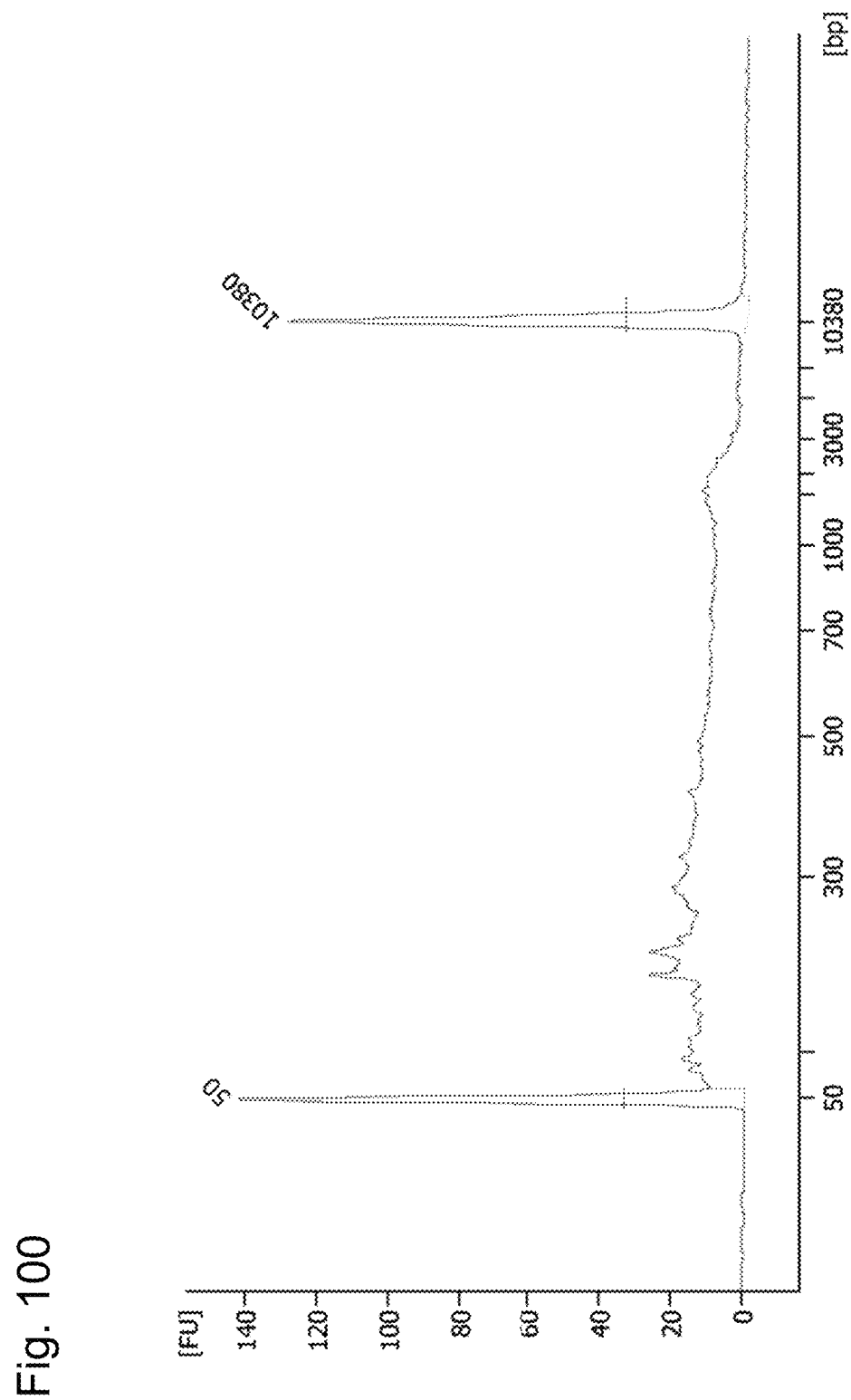
FIG. 100 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer D.
Figure 101:
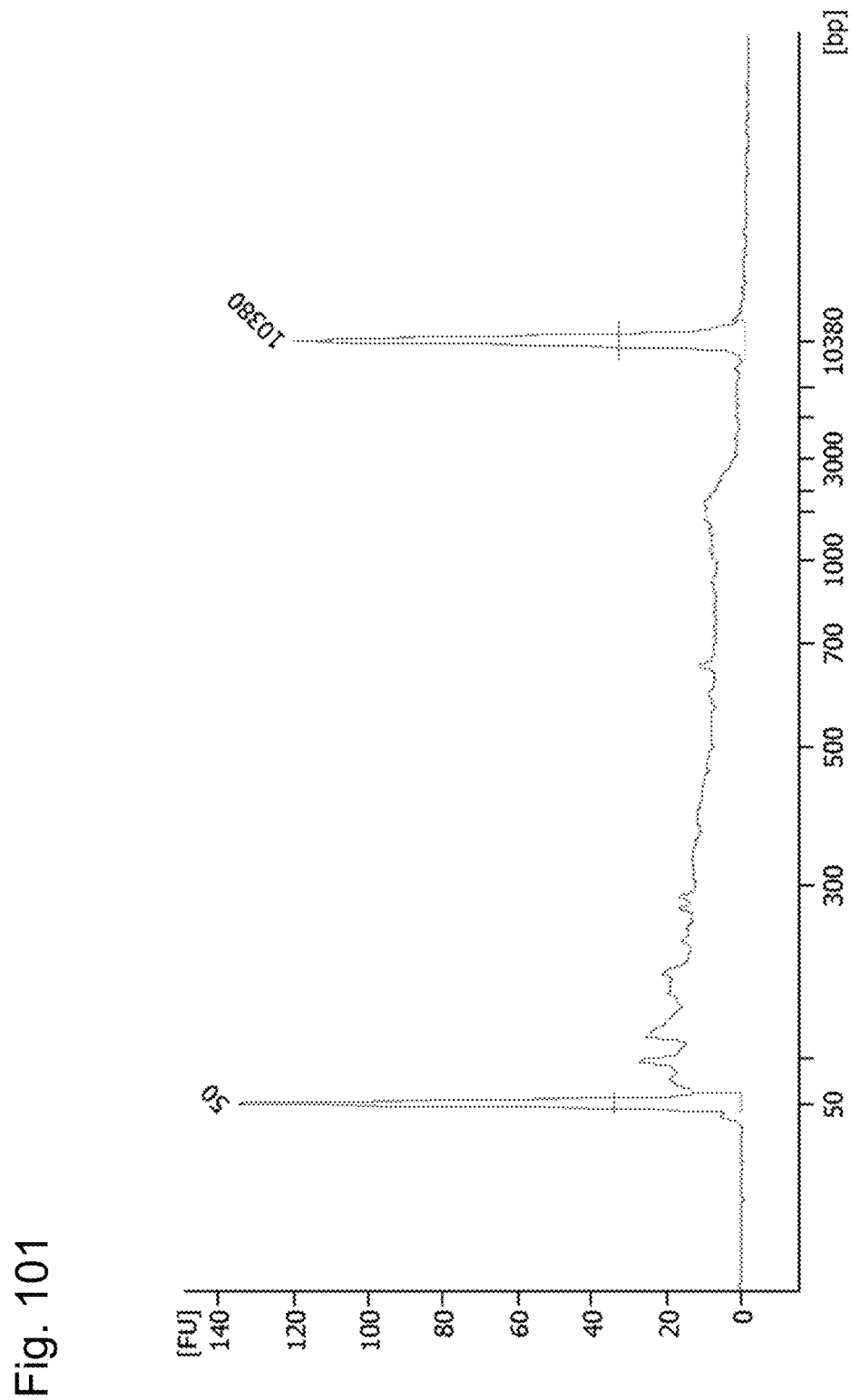
FIG. 101 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer E.
Figure 102:
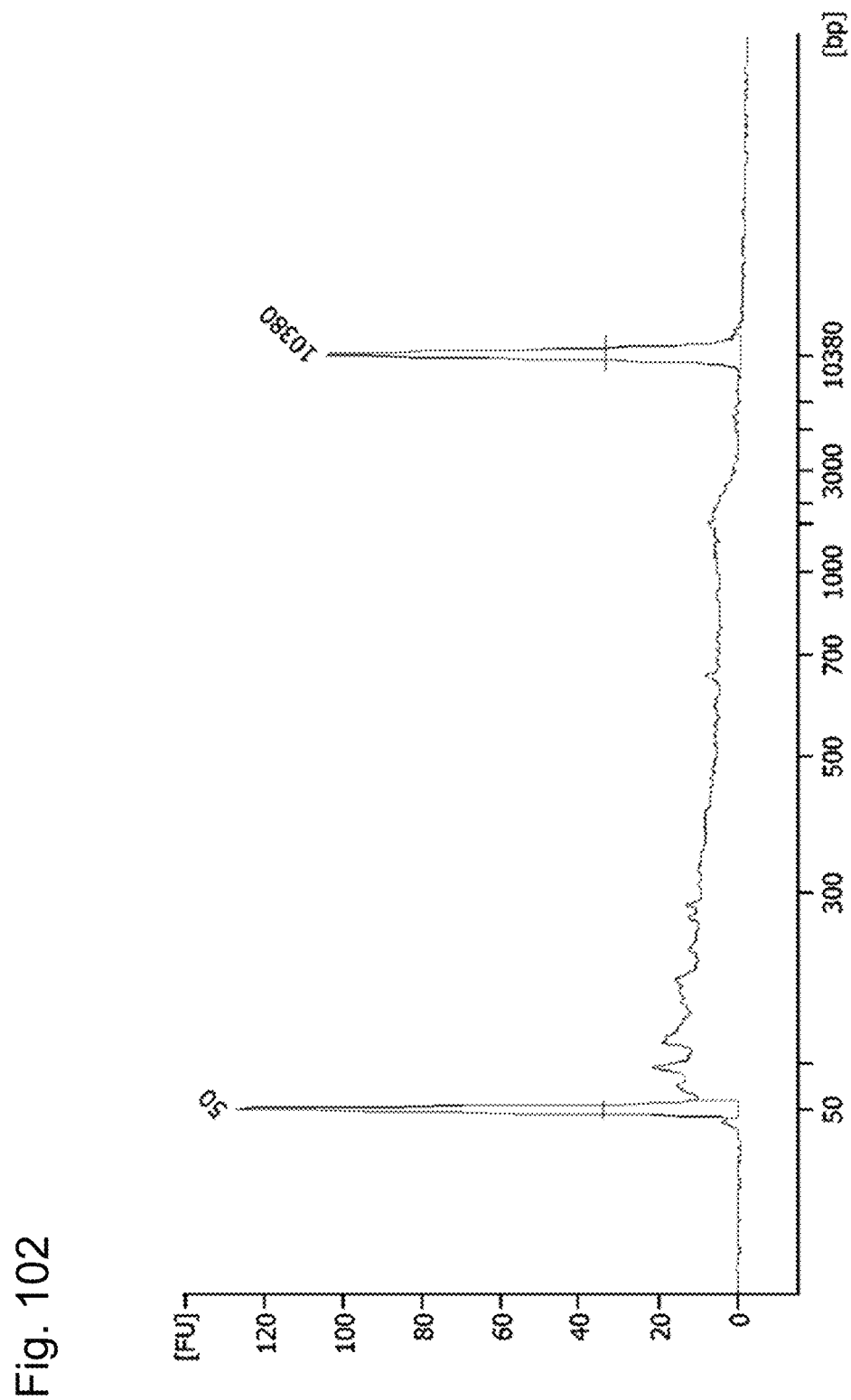
FIG. 102 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer E.
Figure 103:
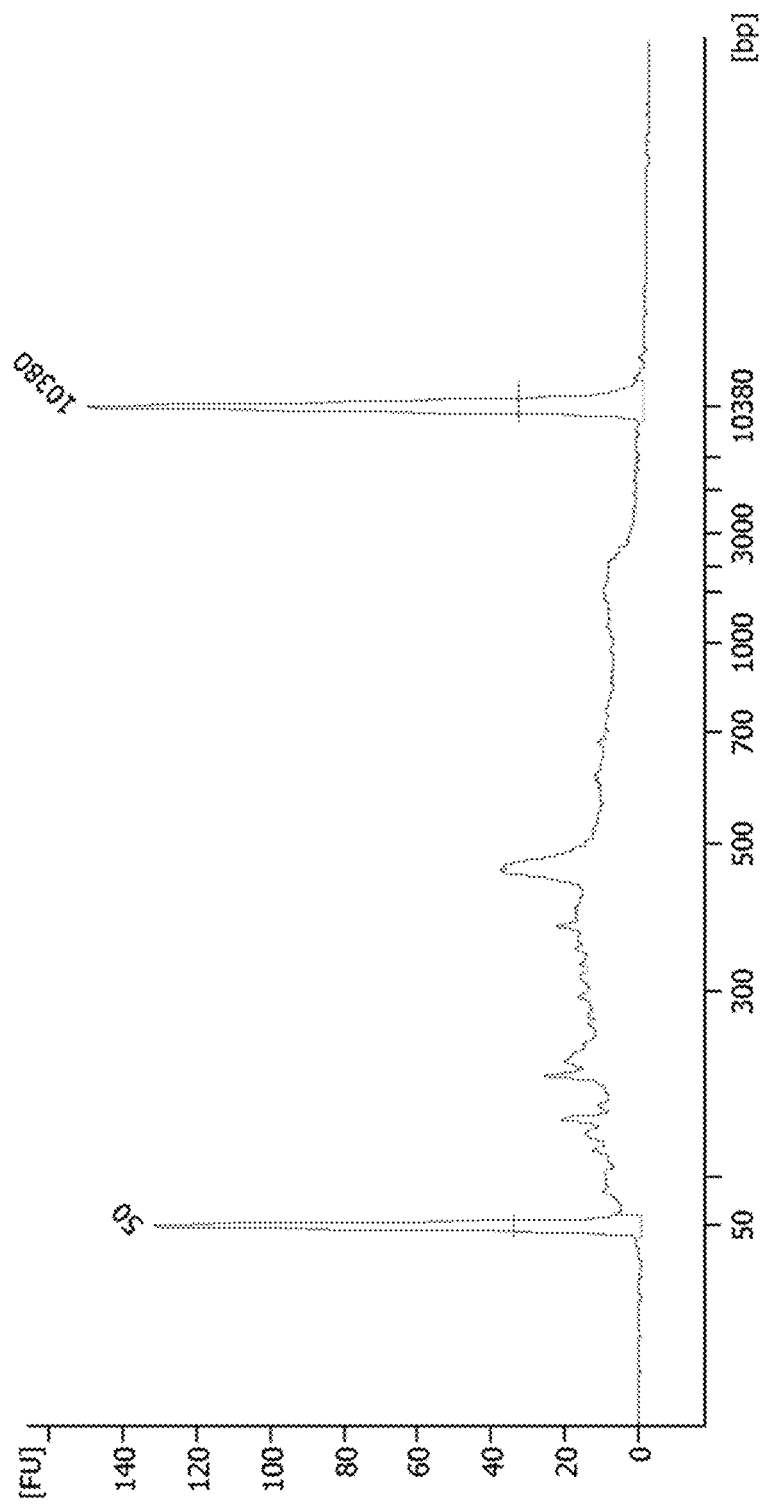
FIG. 103 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer F.
Figure 104:
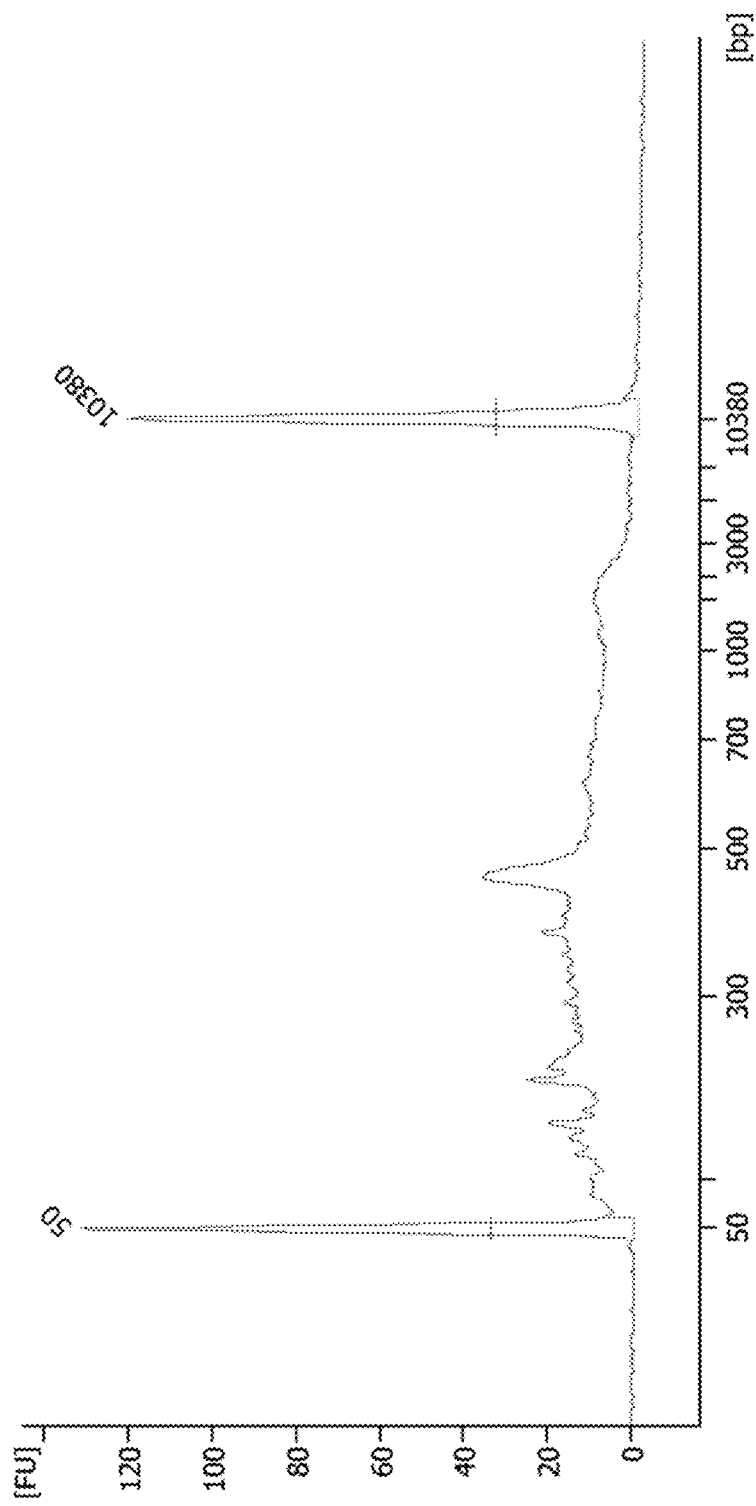
FIG. 104 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer F.

| Set of random primers | Repeat | FIG. No. | Correlational coefficient (ρ) |
|---|---|---|---|
| 10-base primers B | First | FIG. 95 | 0.916 |
|   | Second | FIG. 96 |  |
| 10-base primers C | First | FIG. 97 | 0.965 |
|   | Second | FIG. 98 |  |
| 10-base primers D | First | FIG. 99 | 0.986 |
|   | Second | FIG. 100 |  |
| 10-base primers E | First | FIG. 101 | 0.983 |
|   | Second | FIG. 102 |  |
| 10-base primers F | First | FIG. 103 | 0.988 |
|   | Second | FIG. 104 |  |

As shown in FIGS. 95 to 104, it was found that low-molecular-weight DNA fragments could be amplified using any sets of 10-base primer B, 10-base primer C, 10-base primer D, 10-base primer E, or 10-base primer F while achieving very high reproducibility.

4.9 Production of Human DNA Library

Figure 105:
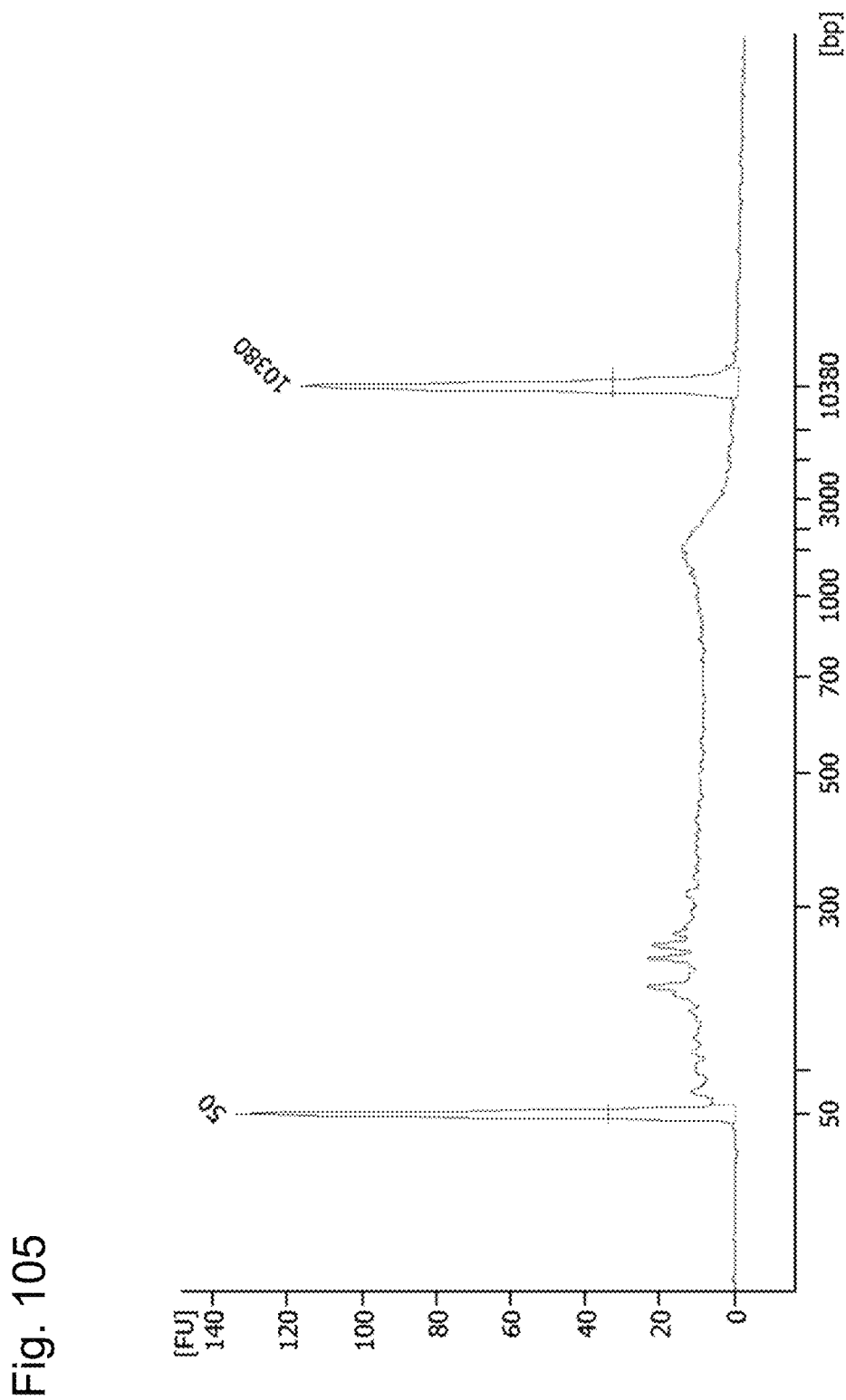
FIG. 105 shows a characteristic diagram demonstrating a correlation between an amplified fragment length and a fluorescence unit (FU) in which the amplified fragment length is determined based on an electrophoretic pattern (appeared for the first time) of the DNA library amplified using human genomic DNA as a template and a 10-base random primer A.
Figure 106:
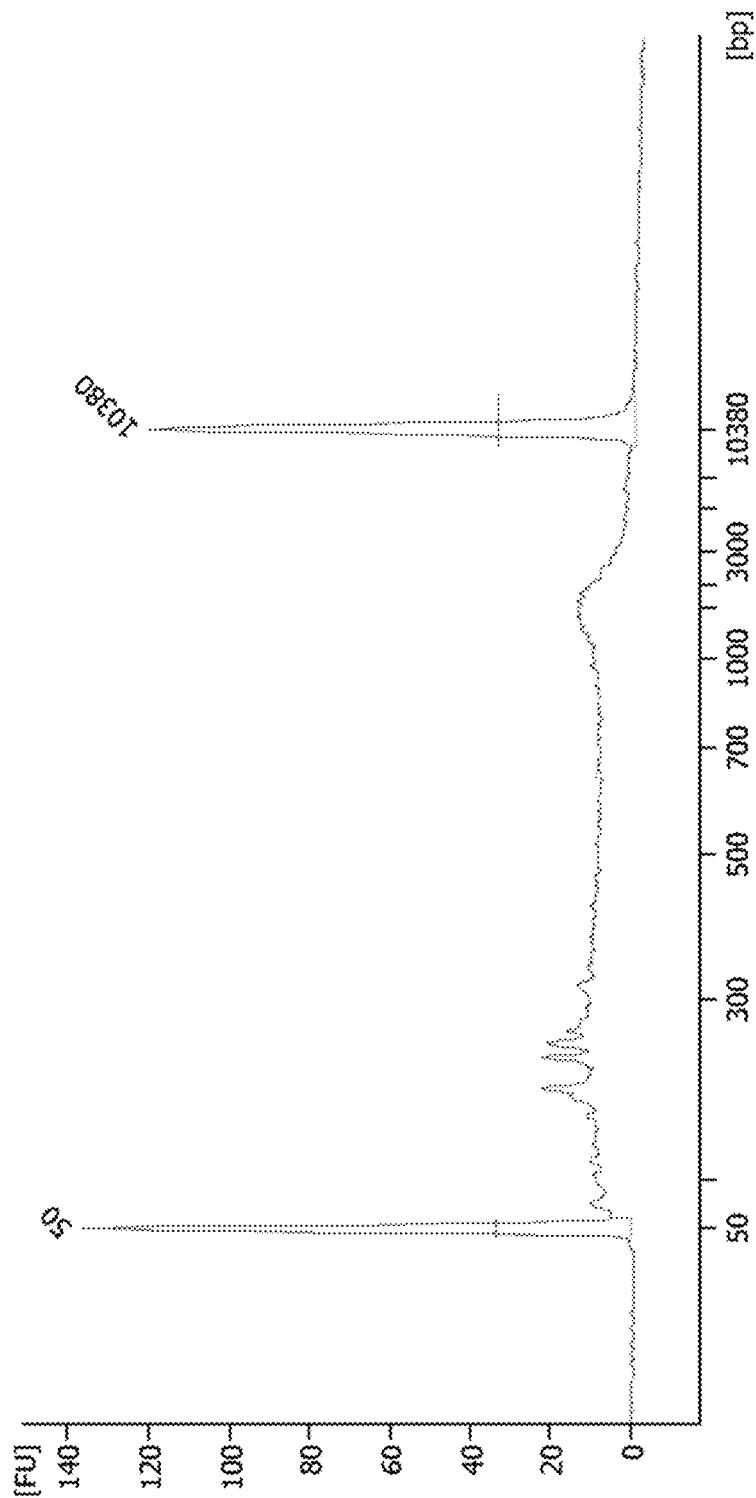
FIG. 106 shows a characteristic diagram demonstrating a correlation between an amplified fragment length and a fluorescence unit (FU) in which the amplified fragment length is determined based on an electrophoretic pattern (appeared for the second time) of the DNA library amplified using human genomic DNA as a template and a 10-base random primer A.

As described in 3.9 above, a DNA library was prepared with the use of human-derived genomic DNA and random primers at a final concentration of 60 microM (10-base primer A), and the results are shown in FIGS. 105 and 106. FIG. 105 shows the results of the first repeated experiment, and FIG. 106 shows the results of the second repeated experiment. As shown in FIGS. 105 and 106, it was found that low-molecular-weight DNA fragments could be amplified while achieving very high reproducibility even if human-derived genomic DNA was used.

Example 2

1. Flow Chart

Figure 107:
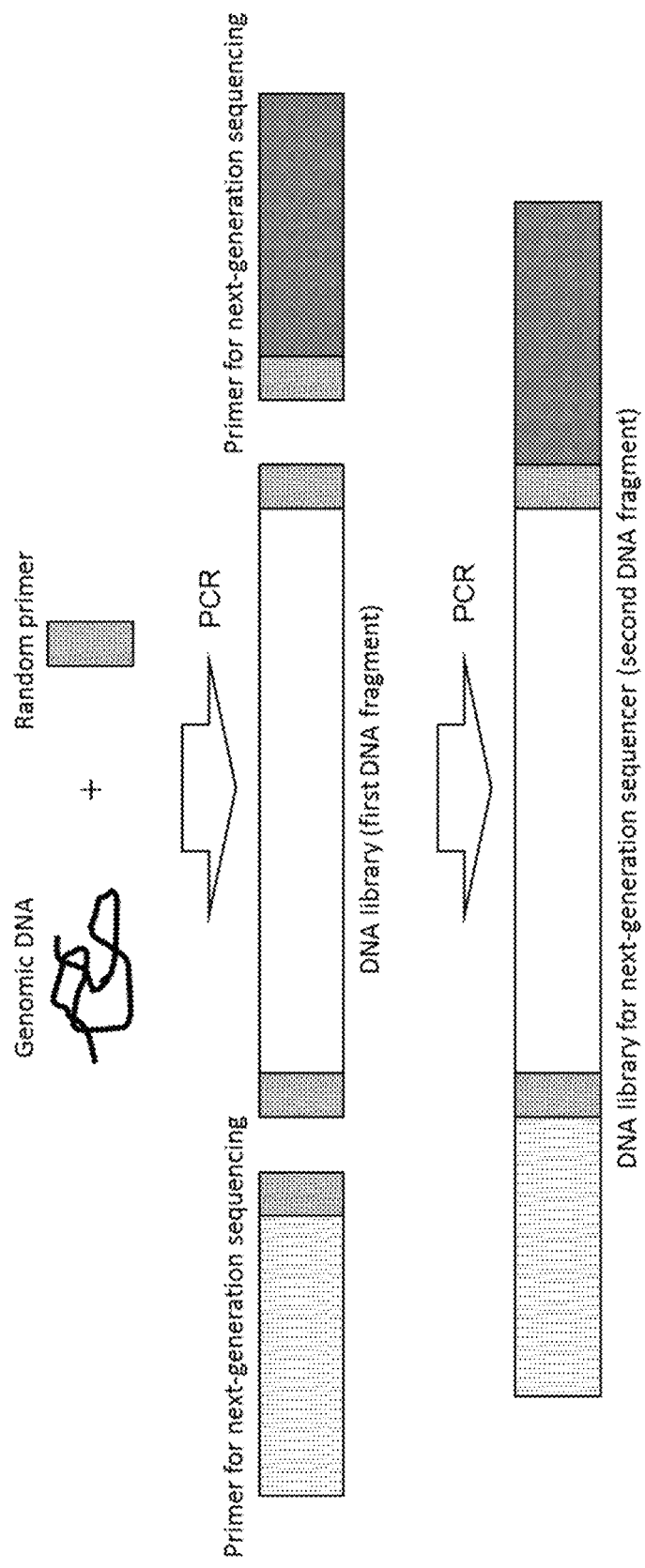
FIG. 107 shows a characteristic diagram schematically demonstrating a method for preparing a DNA library applied to a next-generation sequencer.
Figure 108:
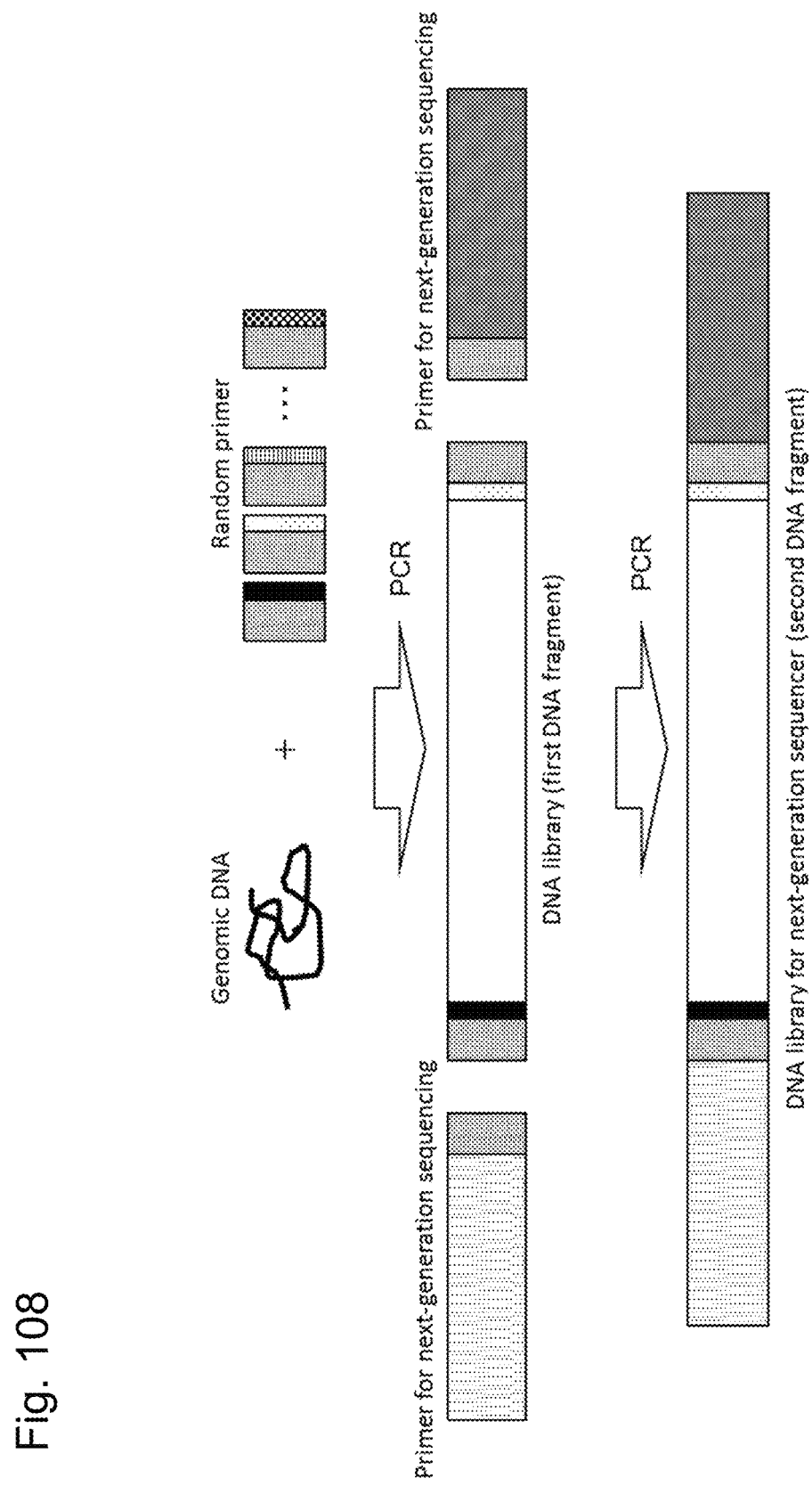
FIG. 108 shows a characteristic diagram schematically demonstrating a method for preparing a DNA library applied to a next-generation sequencer.

In this example, the first DNA fragment was prepared via PCR using genomic DNA as a template and a random primer in accordance with the schematic diagrams shown in FIGS. 107 and 108, and the second DNA fragment was then prepared via PCR using the prepared first DNA fragment as a template and a primer for the next-generation sequencer. With the use of the prepared second DNA fragment as a library for the sequencer, sequence analysis was performed with the use of a so-called next-generation sequencer, and the genotype was analyzed based on the obtained read data.

2. Materials

In this example, genomic DNAs were extracted from the sugarcane variety NiF8 and the rice variety Nipponbare using the DNeasy Plant Mini kit (QIAGEN), and the extracted genomic DNAs were purified. The purified genomic DNAs were used as NiF8-derived genomic DNA and Nipponbare-derived genomic DNA, respectively.

3. Method

3.1 Examination of Sugarcane Variety NiF8

3.1.1 Designing of Random Primer and Primer for the Next-Generation Sequencer In this example, a random primer was designed based on 10 bases at the 3' terminus of the Nextera adapter sequence for the next-generation sequencer (Illumina). In this example, specifically, GTTACACACG (SEQ ID NO: 2041, 10-base primer G) was used as a random primer. The primer for the next-generation sequencer was also designed based on the sequence information of the Nextera adaptor (Illumina) (Table 31).

TABLE 31

| No | Primer sequence | SEQ ID NO: |
|----|-----------------|------------|
| 1 | AATGATACGGCGACCACCGAGATCTAC ACCTCTCTATTCGTCGGCAGCGTCAGA TGTGTATAAGAGACAG | 2042 |
| 2 | CAAGCAGAAGACGGCATACGAGATTAA GGCGAGTCTCGTGGGCTCGGAGATGTG TATAAGAGACAG | 2043 |

3.1.2 Preparation of DNA Library

To NiF8-derived genomic DNA (30 ng) described in 2. above, a 0.2 mM dNTP mixture, 1.0 mM MgCl$_2$, 1.25 units of DNA polymerase (PrimeSTAR, TAKARA), and a 60 microM random primer (10-base primer G) at final concentration were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. Thus, a DNA library (the first DNA fragment) was prepared.

3.1.3 Purification and Electrophoresis

The DNA library obtained in 3.1.2 above was purified with the use of the MinElute PCR Purification Kit (QIAGEN) and subjected to electrophoresis with the use of the Agilent 2100 bioanalyzer (Agilent Technologies) to obtain a fluorescence unit (FU). Also, the reproducibility of the repeated data was evaluated on the basis of the Spearman's rank correlation (rho>0.9).

3.1.4 Preparation of DNA Library for Next-Generation Sequencer

To the first DNA fragment (100 ng) purified in 3.1.3 above, a 0.2 mM dNTP mixture, 1.0 mM MgCl$_2$, 1.25 units of DNA Polymerase (PrimeSTAR, TAKARA), a 0.5 microM primer for the next-generation sequencer at final concentration were added, and a reaction solution was prepared while adjusting the final reaction level to 50 microliters. The resultant was subjected to PCR under thermal cycling conditions comprising 95 degrees C. for 2 minutes, 25 cycles of 98 degrees C. for 15 seconds, 55 degrees C. for 15 seconds, and 72 degrees C. for 20 seconds, and 72 degrees C. for 1 minute, followed by storage at 4 degrees C. Thus, a DNA library (the second DNA fragment) for the next-generation sequencer was prepared. The DNA library for the next-generation sequencer was subjected to purification and electrophoresis in the same manner as in 3.1.3.

3.1.5 MiSeq Analysis

With the use of the MiSeq Reagent Kit V2 500 Cycle (Illumina), the DNA library for the next-generation sequencer obtained in 3.1.4 (the second DNA fragment) was analyzed via 100 base paired-end sequencing.

3.1.6 Read Data Analysis

The read patterns were identified on the basis of the read data obtained in 3.1.5. The number of reads was counted for each read pattern, the numbers of reads of the repeated analyses were compared, and the reproducibility was evaluated in terms of the correlational coefficient.

3.2 Analysis of Rice Variety Nipponbare

3.3.1 Designing of Random Primer and Primer for the Next-Generation Sequencer In this example, a random primer was designed based on 10 bases at the 3' terminus of the Nextera adapter sequence for the next-generation sequencer (Illumina). In this example, specifically, 16 types of nucleotide sequences comprising a total of 12 bases; that is, 10 bases at the 3' terminus of the Nextera adapter sequence and arbitrary 2 bases added to the 3' terminus of the 10-base sequence, were designed as random primers (Table 32, 12-base primer B).

TABLE 32

| No | Primer sequence | SEQ ID NO: |
|----|-----------------|------------|
| 1 | TAAGAGACAGAA | 2044 |
| 2 | TAAGAGACAGAT | 2045 |
| 3 | TAAGAGACAGAC | 2046 |
| 4 | TAAGAGACAGAG | 2047 |
| 5 | TAAGAGACAGTA | 2048 |
| 6 | TAAGAGACAGTT | 2049 |
| 7 | TAAGAGACAGTC | 2050 |
| 8 | TAAGAGACAGTG | 2051 |
| 9 | TAAGAGACAGCA | 2052 |
| 10 | TAAGAGACAGCT | 2053 |
| 11 | TAAGAGACAGCC | 2054 |
| 12 | TAAGAGACAGCG | 2055 |
| 13 | TAAGAGACAGGA | 2056 |
| 14 | TAAGAGACAGGT | 2057 |
| 15 | TAAGAGACAGGC | 2058 |
| 16 | TAAGAGACAGGG | 2059 |

In this example, the primer for the next-generation sequencer designed based on the sequence information of the Nextera adaptor sequence (Illumina) was used as in 3.1.1 above.

3.2.2 Preparation of DNA Library

To the Nipponbare-derived genomic DNA (30 ng) described in 2. above, a 0.2 mM dNTP mixture, 1.0 mM MgCl$_2$, 1.25 units of DNA polymerase (PrimeSTAR, TAKARA), and a 40 microM random primer (12-base primer B) at final concentration were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. Thus, a DNA library (the first DNA fragment) was prepared.

3.2.3 Purification and Electrophoresis

The DNA library obtained in 3.2.2 above was purified with the use of the MinElute PCR Purification Kit (QIAGEN) and subjected to electrophoresis with the use of the Agilent 2100 bioanalyzer (Agilent Technologies) to obtain a fluorescence unit (FU). Also, the reproducibility of the repeated data was evaluated on the basis of the Spearman's rank correlation (rho>0.9).

3.2.4 Preparation of DNA Library for Next-Generation Sequencer

To the first DNA fragment (100 ng) purified in 3.2.3 above, a 0.2 mM dNTP mixture, 1.0 mM $MgCl_2$, 1.25 units of DNA Polymerase (PrimeSTAR, TAKARA), and a 0.5 microM primer for the next-generation sequencer at final concentration were added, and a reaction solution was prepared while adjusting the final reaction level to 50 microliters. The resultant was subjected to PCR under thermal cycling conditions comprising 95 degrees C. for 2 minutes, 25 cycles of 98 degrees C. for 15 seconds, 55 degrees C. for 15 seconds, and 72 degrees C. for 20 seconds, and 72 degrees C. for 1 minute, followed by storage at 4 degrees C. Thus, a DNA library for the next-generation sequencer (the second DNA fragment) was prepared. The DNA library for the next-generation sequencer was subjected to purification and electrophoresis in the same manner as in 3.1.3.

3.2.5 MiSeq Analysis

With the use of the MiSeq Reagent Kit V2 500 Cycle (Illumina), the DNA library for the next-generation sequencer obtained in 3.2.4 (the second DNA fragment) was analyzed via 100 base paired-end sequencing.

3.2.6 Read Data Analysis

The read patterns obtained in 3.2.5 were mapped to the genomic information of Nipponbare (NC_008394 to NC_008405) with Bowtie2, and the extent of concordance between the random primer sequence and genomic DNA was inspected. Also, the read patterns were identified on the basis of the read data obtained in 3.2.5. The number of reads was counted for each read pattern, the numbers of reads of the repeated analyses were compared, and the reproducibility was evaluated in terms of the correlational coefficient.

4. Results and Discussion

4.1 Results of Examination of Sugarcane Variety NiF8

Figure 109:
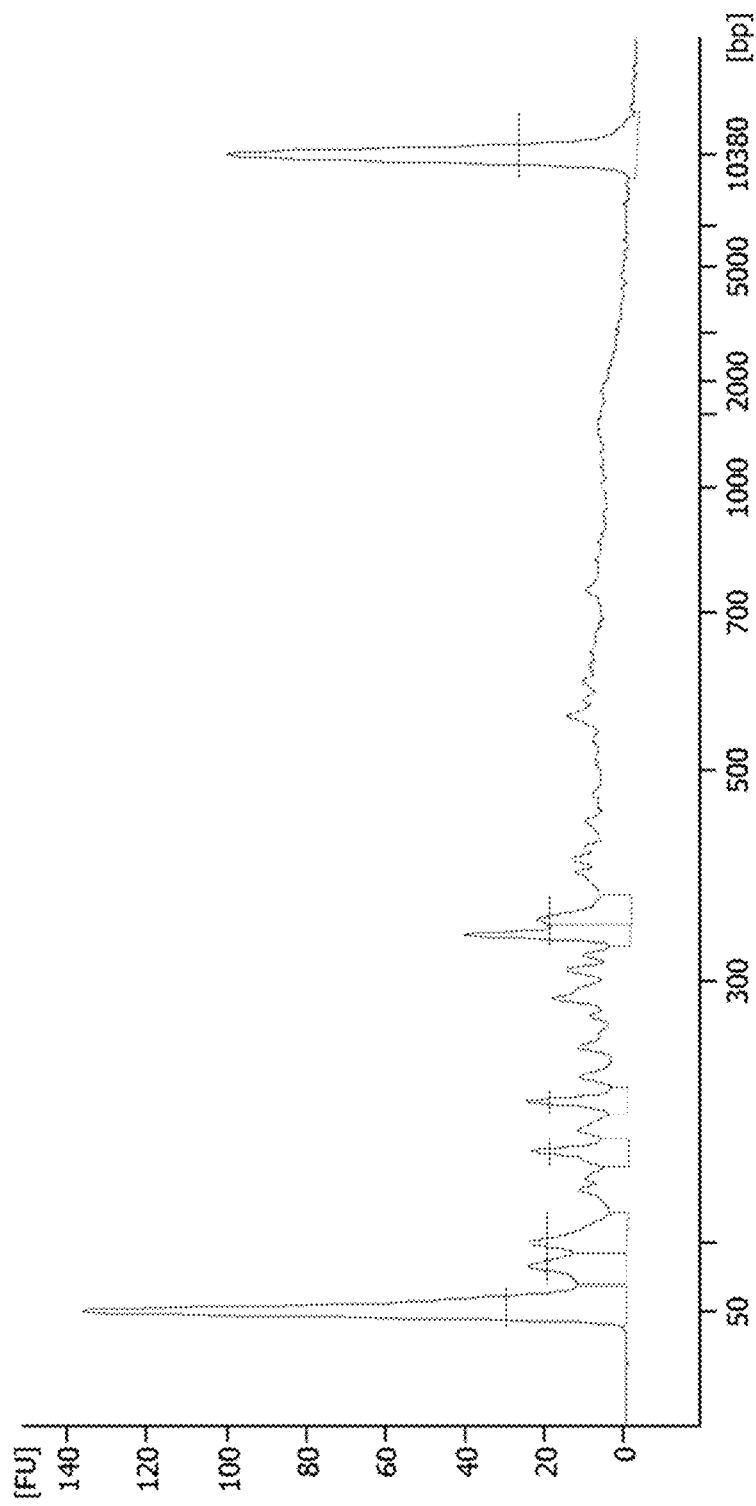
FIG. 109 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the sugarcane variety NiF8 as a template and a 10-base random primer G.
Figure 110:
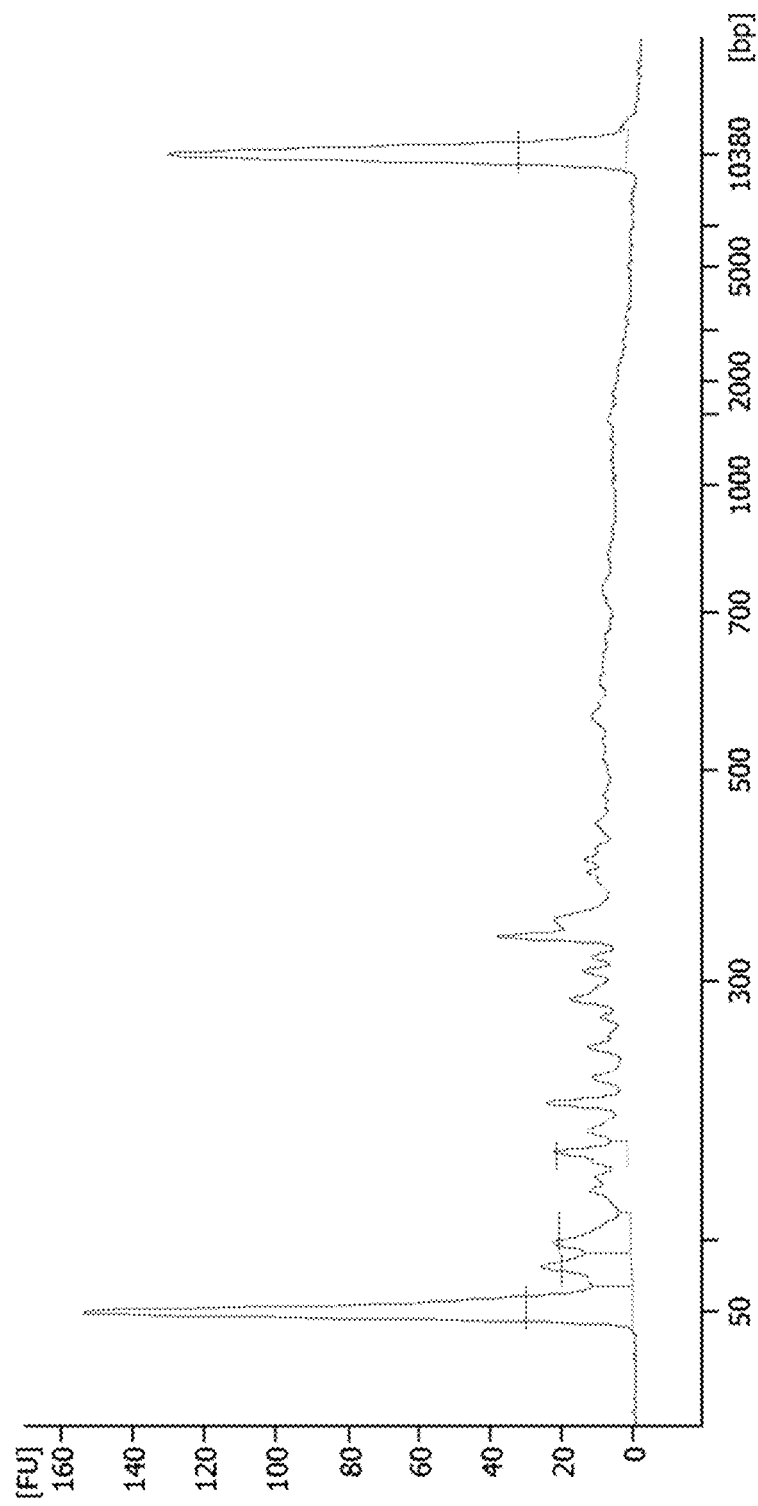
FIG. 110 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the sugarcane variety NiF8 as a template and a 10-base random primer G.

FIG. 109 and FIG. 110 show the results of electrophoresis when PCR was carried out using a 10-base random primer at the 3' terminus of the Nextera adapter for the next-generation sequencer (Illumina) (10-base primer G) at high concentration of 60 microliters. As shown in FIG. 109 and FIG. 110, amplification was observed in a wide range of area including 100 bp to 500 bp (the first DNA fragment). It was considered that amplification was observed in a wide range of area because amplification was also observed in areas other than the genomic DNA region corresponding to the random primer. Since the rank correlation coefficient among the repeated data was not less than 0.9 (i.e., 0.957), high reproducibility was observed in amplification patterns.

Figure 111:
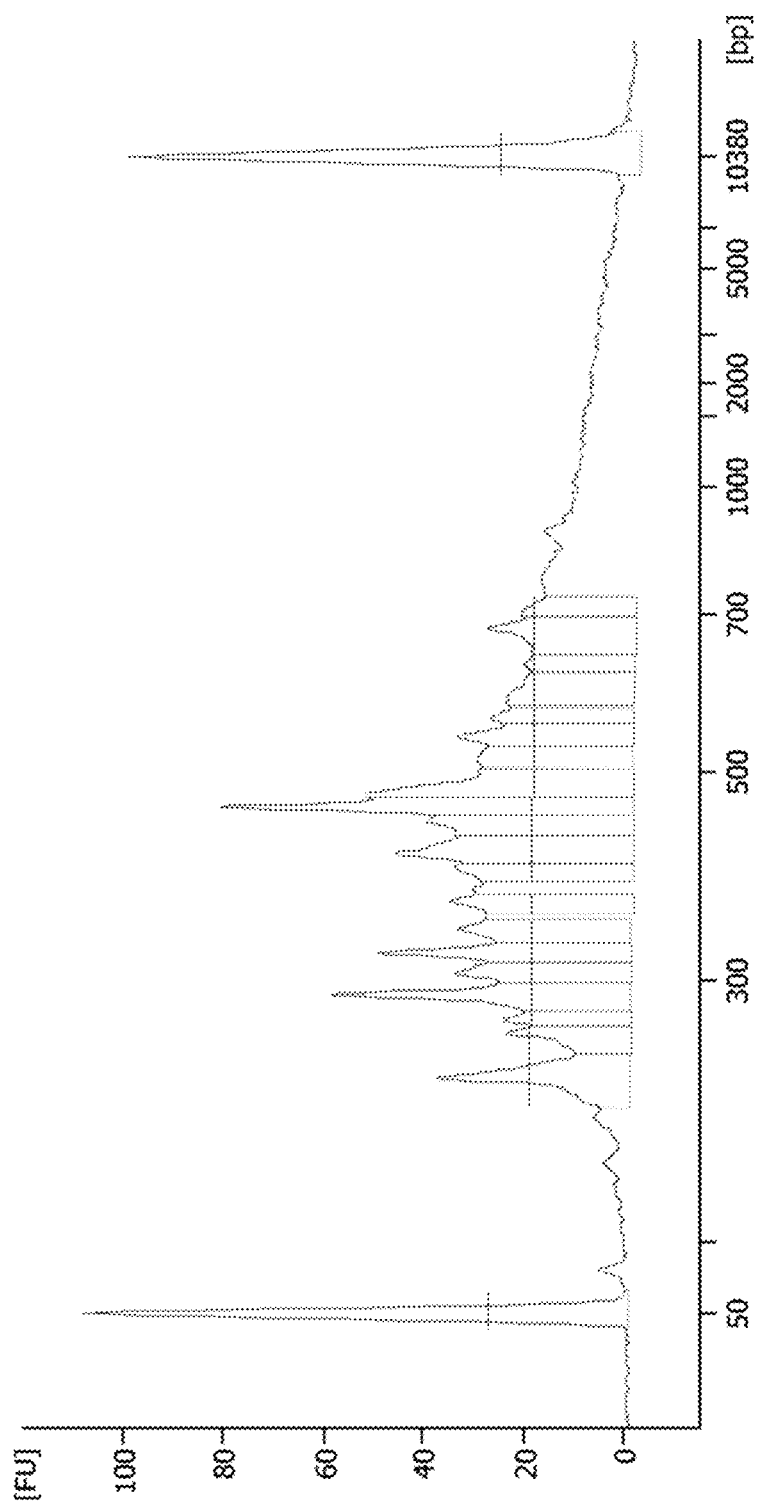
FIG. 111 shows a characteristic diagram demonstrating a correlation between an amplified fragment length and a fluorescence unit (FU) in which the amplified fragment length is determined based on an electrophoretic pattern (appeared for the first time) of the DNA library amplified using, as a template, the DNA library of the sugarcane variety NiF8 prepared using a 10-base random primer G and a primer for the next-generation sequencer.
Figure 112:
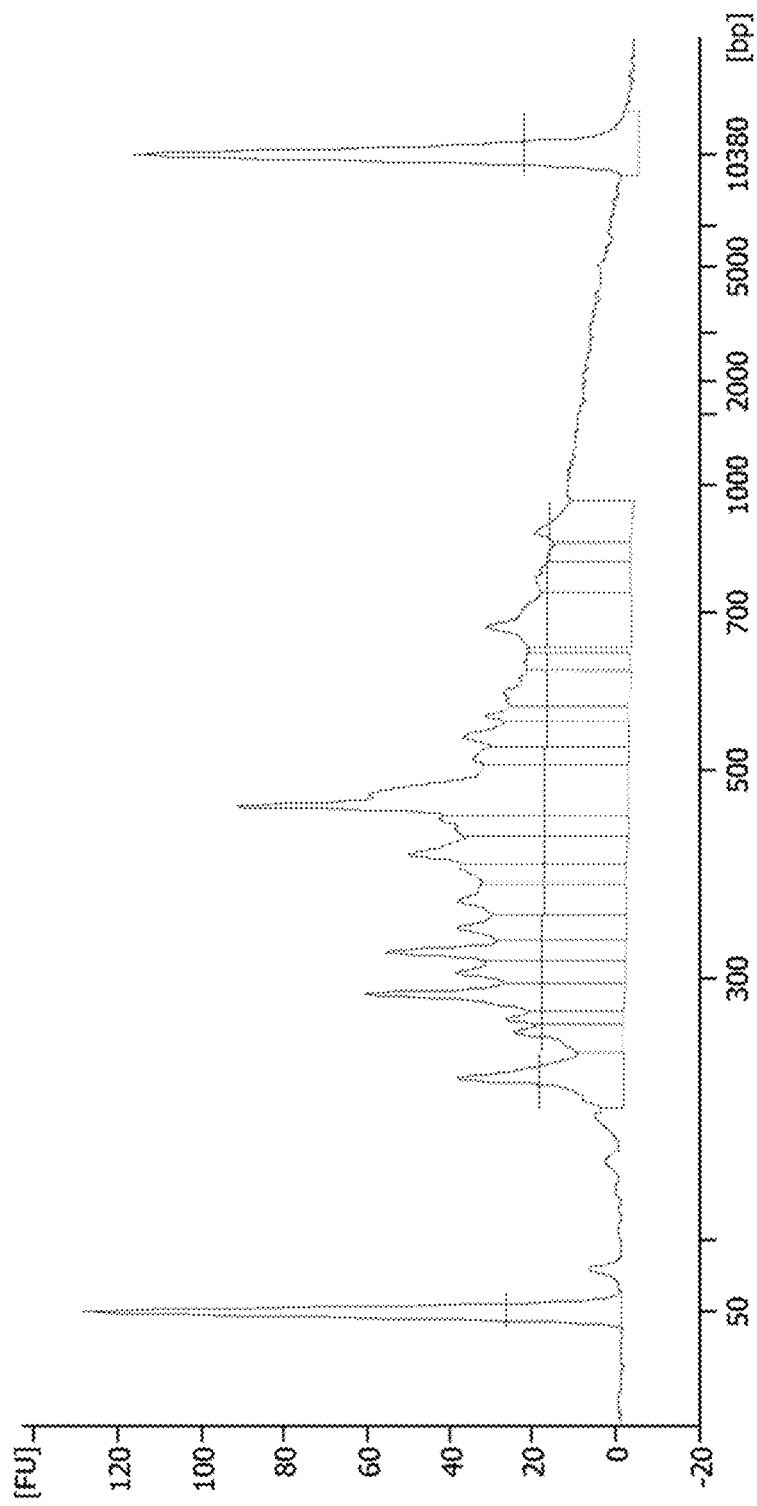
FIG. 112 shows a characteristic diagram demonstrating a correlation between an amplified fragment length and a fluorescence unit (FU) in which the amplified fragment length is determined based on an electrophoretic pattern (appeared for the second time) of the DNA library amplified using, as a template, the DNA library of the sugarcane variety NiF8 prepared using a 10-base random primer G and a primer for the next-generation sequencer.

FIG. 111 and FIG. 112 show the results of electrophoresis when PCR was carried out using the primer for the next-generation sequencer as described in 3.1.4. In order to prepare a DNA library (the second DNA fragment) comprising the Nextera adaptor of the next-generation ligated thereto, specifically, PCR was carried out using the first DNA fragment as a template and the primer for the next-generation sequencer comprising the Nextera adaptor sequence (Illumina). When the DNA library includes numerous short fragments of 100 bp or smaller or long fragments of 1 kbp or longer, the accuracy of analysis of the next-generation sequencer (Illumina) is drastically deteriorated. The DNA library for the next-generation sequencer prepared in this example (the second DNA fragment) showed a distribution in a range primarily from 150 bp to 1 kbp with the peak at approximately 500 bp as shown in FIG. 111 and FIG. 112. Accordingly, such DNA library was considered suitable for its application as the DNA library for the next-generation sequencer. Since the rank correlation coefficient among the repeated data was not less than 0.9 (i.e., 0.989), high reproducibility was observed in amplification patterns.

Figure 113:
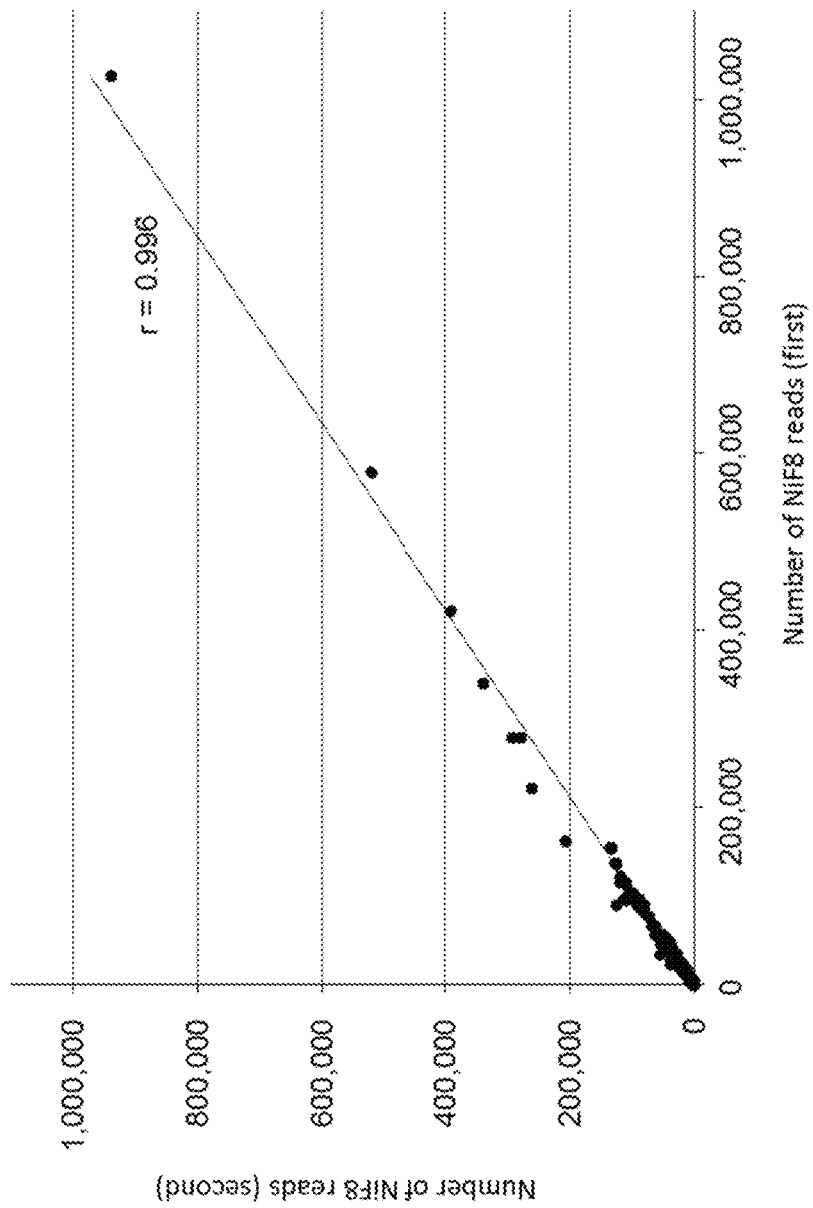
FIG. 113 shows a characteristic diagram demonstrating the results of MiSeq analysis of the DNA library amplified using DNA of the sugarcane variety NiF8 as a template and a 10-base random primer G.

The resulting DNA library (the second DNA fragment) was subjected to MiSeq analysis using the next-generation sequencer, and the read data of 3.5 Gbp and 3.6 Gbp were obtained as a consequence. The values of >=Q30 indicating a precision of the MiSeq data were 93.3% and 93.1%. Since the read data of 3.0 Gbp or greater and the >=Q30 value of 85.0% or greater were recommended by the manufacturer, the DNA library of the next-generation sequencer prepared in this example (the second DNA fragment) was considered to be applicable to analysis using the next-generation sequencer. In order to inspect the reproducibility, the number of reads of the repeated analyses was compared concerning the 34,613 read patterns obtained via MiSeq analysis. The results are shown in FIG. 113. As shown in FIG. 113, as with the case of electrophoresis, the number of reads was found to be highly correlated among the repeated analyses (i.e., r=0.996).

As described above, a DNA library (the first DNA fragment) was obtained via PCR using a 10-base random primer at the 3' terminus of the Nextera adapter for the next-generation sequencer (Illumina) at high concentration, and PCR was further carried out using the primer for the next-generation sequencer comprising the Nextera Adaptor sequence. Thus, the DNA library (the second DNA fragment) for the next-generation sequencer comprising numerous fragments was prepared in a convenient and highly reproducible manner.

4.2 Results of Examination of Rice Variety Nipponbare

Figure 114:
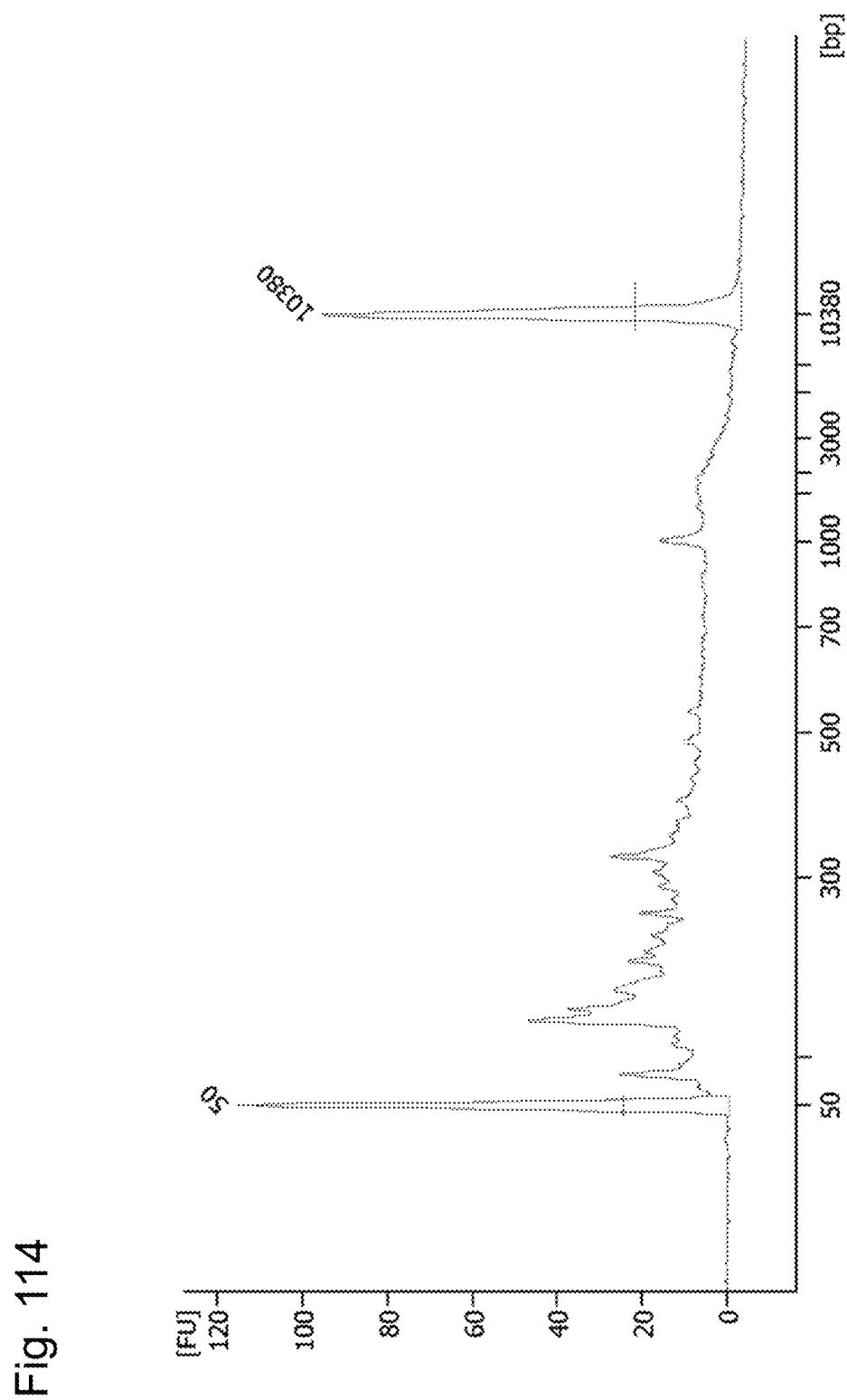
FIG. 114 shows a characteristic diagram demonstrating a correlation between an amplified fragment length and a fluorescence unit (FU) in which the amplified fragment length is determined based on an electrophoretic pattern (appeared for the first time) of the DNA library amplified using DNA of the rice variety Nipponbare as a template and a 12-base random primer B.
Figure 115:
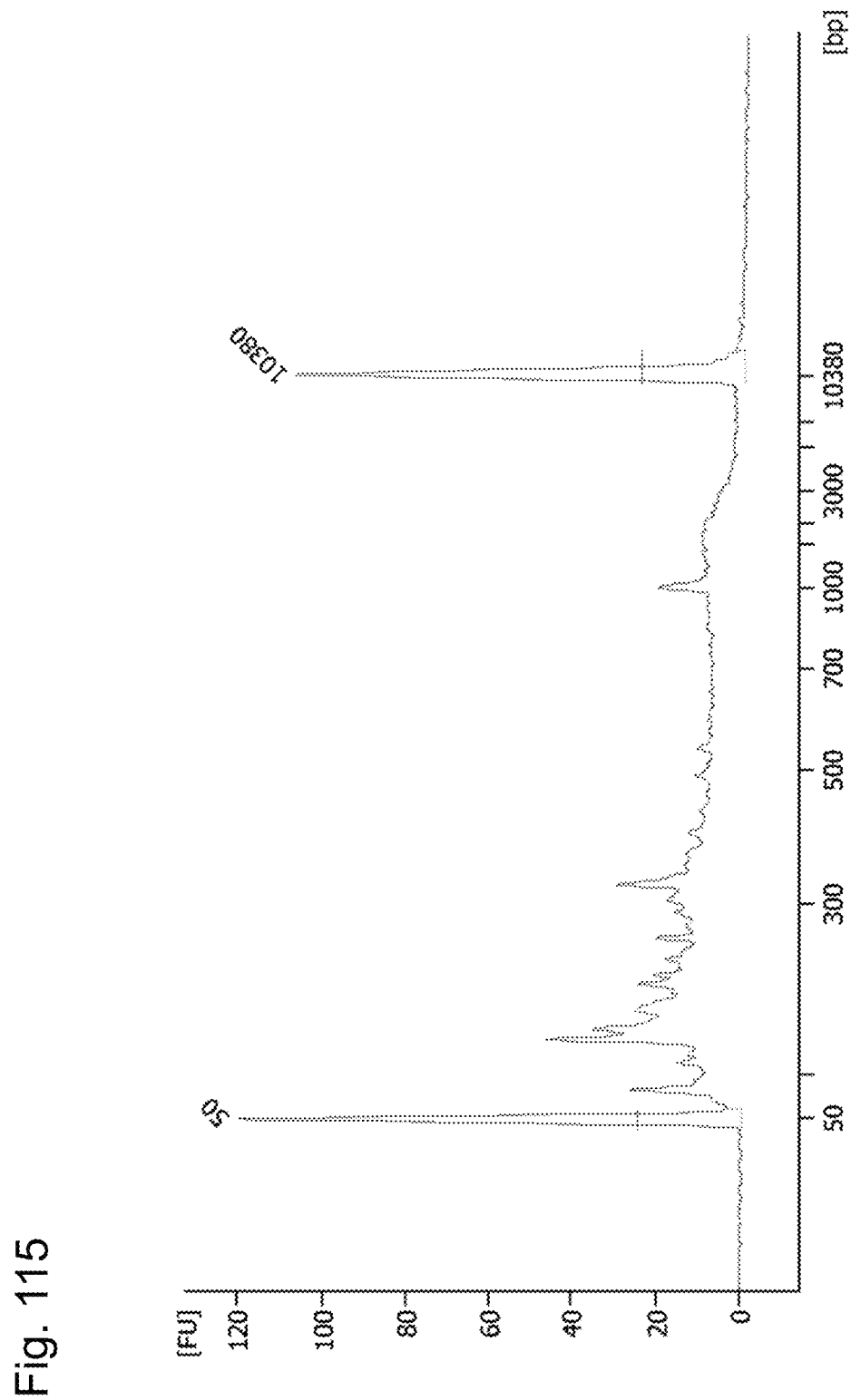
FIG. 115 shows a characteristic diagram demonstrating a correlation between an amplified fragment length and a fluorescence unit (FU) in which the amplified fragment length is determined based on an electrophoretic pattern (appeared for the second time) of the DNA library amplified using DNA of the rice variety Nipponbare as a template and a 12-base random primer B.

FIG. 114 and FIG. 115 show the results of electrophoresis when PCR was carried out using 16 types of random primers (12-base primer B) each comprising a total of 12 bases; that is, 10 bases at the 3' terminus of the Nextera adapter sequence for the next-generation sequencer (Illumina) and arbitrary 2 bases added to the 3' terminus thereof, at high concentration of 40 microliters. As shown in FIG. 114 and FIG. 115, amplification was observed in a wide range of area including 100 bp to 500 bp (the first DNA fragment). It was considered that amplification was observed in a wide range of area because amplification was also observed in areas other than the genomic DNA region concordant with the random primer, as with the case of 4.1. Since the rank correlation coefficient was not less than 0.9 (i.e., 0.950), high reproducibility was observed in amplification patterns.

Figure 116:
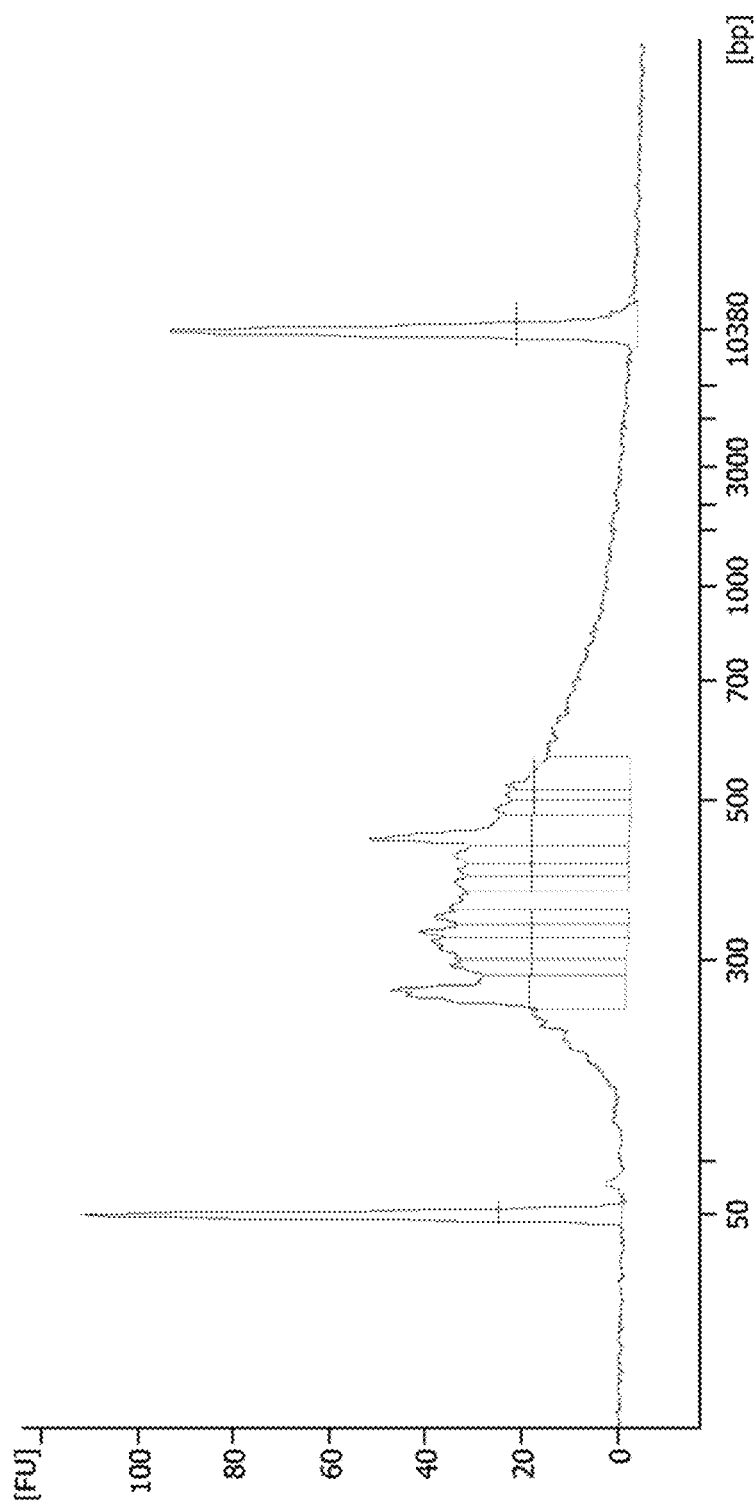
FIG. 116 shows a characteristic diagram demonstrating a correlation between an amplified fragment length and a fluorescence unit (FU) in which the amplified fragment length is determined based on an electrophoretic pattern (appeared for the first time) of the DNA library amplified using, as a template, the DNA library of the rice variety Nipponbare prepared using a 12-base random primer B and a primer for a next-generation sequencer.
Figure 117:
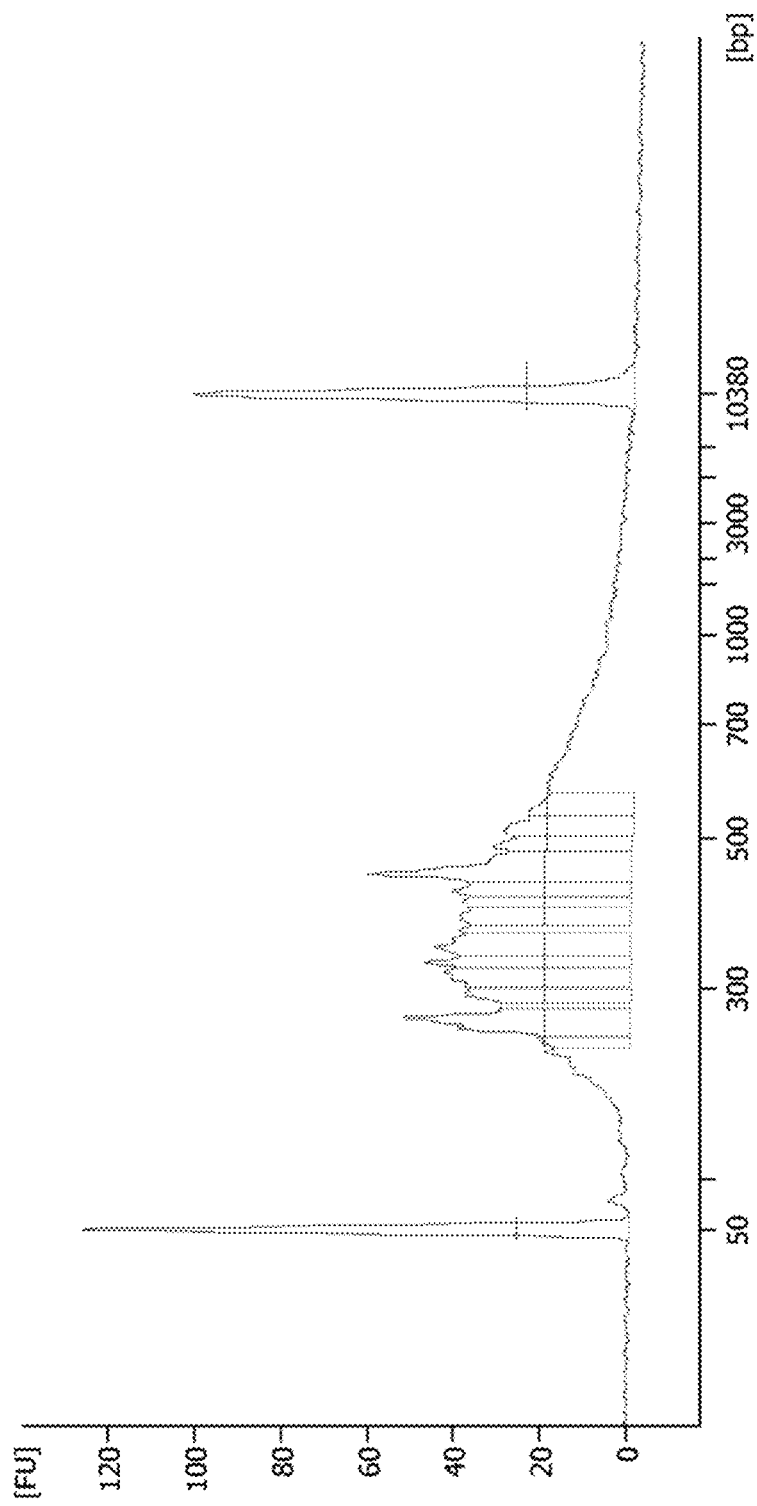
FIG. 117 shows a characteristic diagram demonstrating a correlation between an amplified fragment length and a fluorescence unit (FU) in which the amplified fragment length is determined based on an electrophoretic pattern (appeared for the second time) of the DNA library amplified using, as a template, the DNA library of the rice variety Nipponbare using a 12-base random primer B and a primer for a next-generation sequencer.

FIG. 116 and FIG. 117 show the results of electrophoresis when PCR was carried out using the primer for the next-generation sequencer as described in 3.2.4. In order to prepare a DNA library (the second DNA fragment) comprising the Nextera adaptor of the next-generation ligated thereto, specifically, PCR was carried out using the first DNA fragment as a template and the primer for the next-generation sequencer comprising the Nextera adaptor sequence (Illumina). As a result, the DNA library for the next-generation sequencer prepared in this example (the second DNA fragment) was found to show a distribution in a range primarily from 150 bp to 1 kbp with the peak at approximately 300 bp as shown in FIG. 116 and FIG. 117.

Accordingly, such DNA library was considered suitable for its application as the DNA library for the next-generation sequencer. Since the rank correlation coefficient among the repeated data was not less than 0.9 (i.e., 0.992), high reproducibility was observed in amplification patterns.

Figure 118:
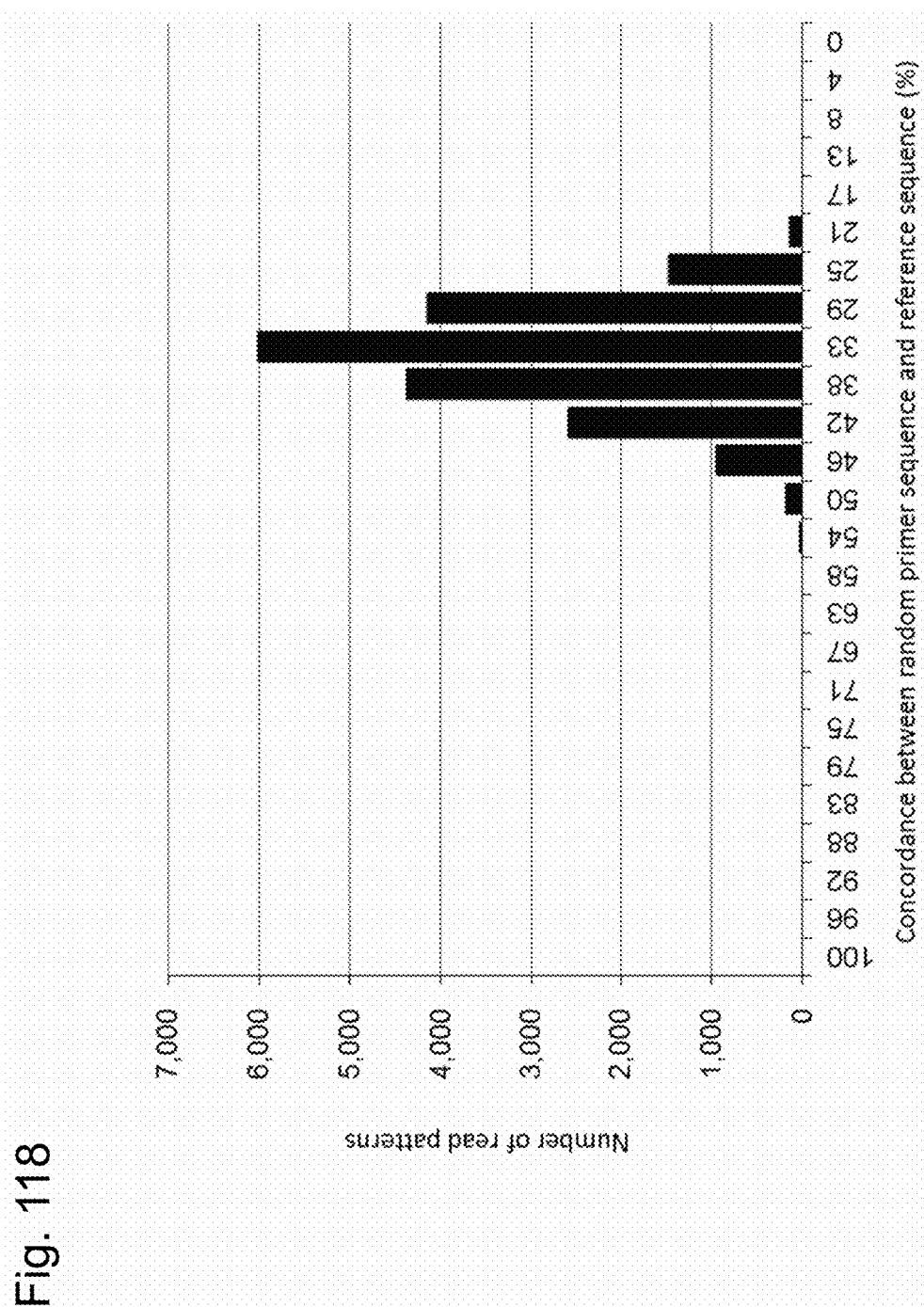
FIG. 118 shows a characteristic diagram demonstrating a distribution of the number of read patterns obtained via MiSeq analysis of the DNA library amplified using DNA of the rice variety Nipponbare as a template and a 12-base random primer B and an extent of concordance between the random primer and the reference sequence of the rice variety Nipponbare.
Figure 119:
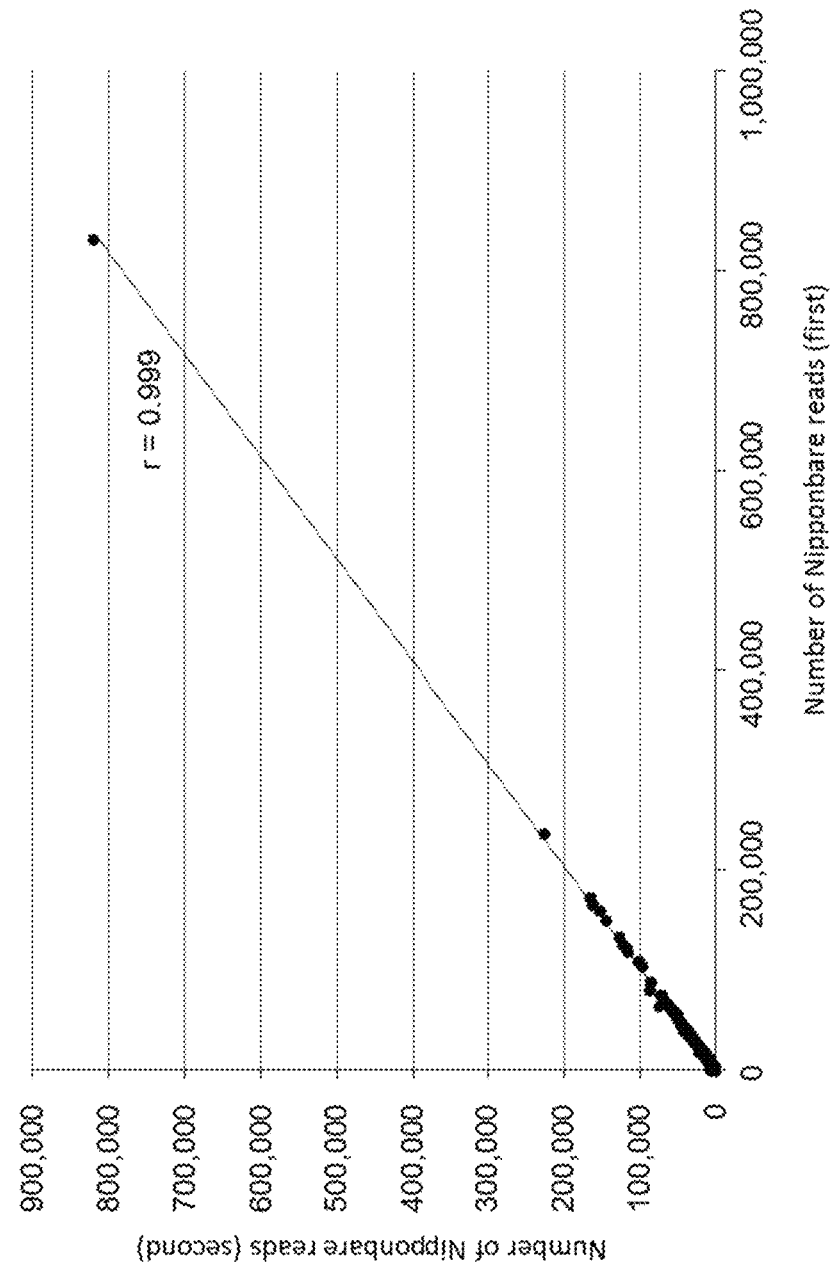
FIG. 119 shows a characteristic diagram demonstrating the results of MiSeq analysis of the DNA library amplified using DNA of the rice variety Nipponbare as a template and a 12-base random primer B.

The resulting DNA library (the second DNA fragment) was subjected to MiSeq analysis using the next-generation sequencer, and the read data of 4.0 Gbp and 3.8 Gbp were obtained as a consequence. The values of >=Q30 indicating a precision of the MiSeq data were 94.0% and 95.3%. The results demonstrate that the DNA library for the next-generation sequencer prepared in this example (the second DNA fragment) is applicable to analysis using the next-generation sequencer as described in 4.1.1 above. FIG. 118 demonstrates the results of comparison between a random primer sequence and the Nipponbare reference sequence, so as to evaluate the extent of concordance between the random primer sequence and the genome concerning the 19,849 read patterns obtained via MiSeq analysis. As shown in FIG. 118, the average extent of concordance between the random primer sequence and the Nipponbare reference sequence was 34.5%. Since there were no read patterns that were completely concordant between the random primer sequence and the Nipponbare reference sequence, in particular, all the read patterns were considered to result from binding of a random primer to a sequence that is not concordant therewith. Such results were considered to be concordant with the results attained with the use of the bioanalyzer. In order to examine the reproducibility of read patterns, the number of reads was compared among the repeated data. The results are shown in FIG. 119. As shown in FIG. 119, as with the case of electrophoresis, the number of reads was found to be highly correlated among the repeated analyses (i.e., r=0.999).

As described above, a DNA library (the first DNA fragment) was obtained via PCR using 16 types of 12-base random primers in total; i.e., 10 bases at the 3' terminus of the Nextera adapter for the next-generation sequencer (Illumina) and arbitrary 2 bases added to the 3' terminus thereof, at high concentration, and PCR was further performed using a primer comprising the Nextera Adaptor sequence. Thus, a DNA library (the second DNA fragment) for the next-generation sequencer comprising numerous fragments was prepared in a convenient and highly reproducible manner.

Example 3

1. Flow Chart

In this example, the first DNA fragment was prepared via PCR using genomic DNA as a template and a random primer in the same manner as in Example 2, and the second DNA fragment was then prepared via PCR using the prepared first DNA fragment as a template and a primer for the next-generation sequencer. With the use of the prepared second DNA fragment as a library for the sequencer, sequence analysis was performed with the use of a so-called next-generation sequencer, and the genotype was analyzed based on the read data. In this example, in particular, whether or not amplification of a DNA fragment derived from the chloroplast genome could be suppressed depending on a type of a random primer used was examined. 2. Materials In this example, genomic DNA was extracted from the rice variety Nipponbare using the DNeasy Plant Mini kit (QIAGEN), and the extracted genomic DNA was purified. The purified genomic DNA was used as rice-derived genomic DNA. Genomic DNAs of corn, potato, and soybean used in this example were purchased from Cosmo Bio Co., Ltd. (Product Numbers: D1634330, D1634350, and D1634370).

3. Method 3.1 Designing of Random Primers

As random primers, 64 types of nucleotide sequences each comprising 13 bases in total; i.e., 10 bases (TAAGAGACAG) at the 3' terminus of the Nextera adapter sequence for the next-generation sequencer (Illumina) and arbitrary 3 bases added to the 3' terminus thereof, were designed (Table 33). Sets of 64, 63, 60, 40, 20, and 10 random primers (sets of random primers A to F) were prepared. Also, 16 types of nucleotide sequences each comprising 12 bases in total; i.e., 10 bases (TAAGAGACAG) and arbitrary 2 bases added to the 3' terminus thereof, were designed (Table 34, Set G). The primer for the next-generation sequencer was also designed on the basis of the sequence information of the Nextera adaptor (Illumina) (Table 35).

TABLE 33

Primer information for sets of random primers (13-base primers)*

| SEQ ID NO: | Sequence | Set of random primers (the number of primers) | | | | | |
|---|---|---|---|---|---|---|---|
| | | A (64) | B (63) | C (60) | D (40) | E (20) | F (10) |
| 2080 | TAAGAGACAGAAA | ○ | ○ | ○ | ○ | — | — |
| 2081 | TAAGAGACAGAAC | ○ | ○ | ○ | ○ | — | — |
| 2082 | TAAGAGACAGAAG | ○ | ○ | ○ | — | ○ | — |
| 2083 | TAAGAGACAGAAT | ○ | ○ | ○ | ○ | — | — |
| 2084 | TAAGAGACAGACA | ○ | ○ | ○ | ○ | — | — |
| 2085 | TAAGAGACAGACC | ○ | ○ | ○ | — | ○ | ○ |
| 2086 | TAAGAGACAGACG | ○ | ○ | ○ | ○ | — | — |
| 2087 | TAAGAGACAGACT | ○ | ○ | ○ | ○ | — | — |
| 2088 | TAAGAGACAGAGA | ○ | ○ | ○ | — | ○ | — |
| 2089 | TAAGAGACAGAGC | ○ | ○ | ○ | — | — | ○ |
| 2090 | TAAGAGACAGAGG | ○ | ○ | ○ | — | ○ | — |
| 2091 | TAAGAGACAGAGT | ○ | ○ | ○ | ○ | — | — |
| 2092 | TAAGAGACAGATA | ○ | ○ | ○ | ○ | — | — |
| 2093 | TAAGAGACAGATC | ○ | ○ | ○ | ○ | — | — |
| 2094 | TAAGAGACAGATG | ○ | ○ | ○ | — | ○ | — |
| 2095 | TAAGAGACAGATT | ○ | ○ | ○ | ○ | — | — |

TABLE 33-continued

Primer information for sets of random primers (13-base primers)*

| SEQ ID NO: | Sequence | Set of random primers (the number of primers) | | | | | |
|---|---|---|---|---|---|---|---|
| | | A (64) | B (63) | C (60) | D (40) | E (20) | F (10) |
| 2096 | TAAGAGACAGCAA | ○ | ○ | ○ | – | ○ | ○ |
| 2097 | TAAGAGACAGCAC | ○ | ○ | ○ | ○ | – | – |
| 2098 | TAAGAGACAGCAG | ○ | ○ | – | ○ | – | – |
| 2099 | TAAGAGACAGCAT | ○ | ○ | ○ | – | ○ | ○ |
| 2100 | TAAGAGACAGCCA | ○ | ○ | ○ | – | ○ | – |
| 2101 | TAAGAGACAGCCC | ○ | ○ | – | – | ○ | – |
| 2102 | TAAGAGACAGCCG | ○ | ○ | ○ | ○ | – | – |
| 2103 | TAAGAGACAGCCT | ○ | ○ | ○ | – | ○ | – |
| 2104 | TAAGAGACAGCGA | ○ | ○ | ○ | ○ | – | – |
| 2105 | TAAGAGACAGCGC | ○ | ○ | ○ | ○ | – | – |
| 2106 | TAAGAGACAGCGG | ○ | ○ | ○ | – | ○ | – |
| 2107 | TAAGAGACAGCGT | ○ | ○ | ○ | ○ | – | – |
| 2108 | TAAGAGACAGCTA | ○ | ○ | ○ | ○ | – | – |
| 2109 | TAAGAGACAGCTC | ○ | ○ | ○ | – | ○ | – |
| 2110 | TAAGAGACAGCTG | ○ | ○ | ○ | ○ | – | ○ |
| 2111 | TAAGAGACAGCTT | ○ | ○ | ○ | ○ | – | – |
| 2112 | TAAGAGACAGGAA | ○ | ○ | ○ | – | ○ | – |
| 2113 | TAAGAGACAGGAC | ○ | ○ | ○ | ○ | – | – |
| 2114 | TAAGAGACAGGAG | ○ | ○ | ○ | ○ | – | – |
| 2115 | TAAGAGACAGGAT | ○ | ○ | ○ | ○ | – | – |
| 2116 | TAAGAGACAGGCA | ○ | ○ | ○ | ○ | – | ○ |
| 2117 | TAAGAGACAGGCC | ○ | ○ | ○ | ○ | – | – |
| 2118 | TAAGAGACAGGCG | ○ | ○ | ○ | ○ | – | – |
| 2119 | TAAGAGACAGGCT | ○ | ○ | ○ | ○ | – | – |
| 2120 | TAAGAGACAGGGA | ○ | ○ | ○ | ○ | – | – |
| 2121 | TAAGAGACAGGGC | ○ | ○ | ○ | ○ | – | – |
| 2122 | TAAGAGACAGGGG | ○ | ○ | – | ○ | – | – |
| 2123 | TAAGAGACAGGGT | ○ | ○ | ○ | ○ | – | – |
| 2124 | TAAGAGACAGGTA | ○ | ○ | ○ | ○ | – | – |
| 2125 | TAAGAGACAGGTC | ○ | ○ | ○ | ○ | – | – |
| 2126 | TAAGAGACAGGTG | ○ | ○ | ○ | – | ○ | ○ |
| 2127 | TAAGAGACAGGTT | ○ | ○ | ○ | ○ | – | – |
| 2128 | TAAGAGACAGTAA | ○ | ○ | ○ | ○ | – | – |
| 2129 | TAAGAGACAGTAC | ○ | ○ | ○ | ○ | – | – |
| 2130 | TAAGAGACAGTAG | ○ | ○ | ○ | ○ | – | – |
| 2131 | TAAGAGACAGTAT | ○ | ○ | ○ | ○ | – | – |
| 2132 | TAAGAGACAGTCA | ○ | ○ | ○ | – | ○ | – |
| 2133 | TAAGAGACAGTCC | ○ | ○ | ○ | – | ○ | – |
| 2134 | TAAGAGACAGTCG | ○ | ○ | ○ | – | – | ○ |
| 2135 | TAAGAGACAGTCT | ○ | ○ | ○ | ○ | – | – |
| 2136 | TAAGAGACAGTGA | ○ | ○ | ○ | – | ○ | – |
| 2064 | TAAGAGACAGTGC | ○ | – | – | – | – | – |
| 2137 | TAAGAGACAGTGG | ○ | ○ | ○ | ○ | – | ○ |
| 2138 | TAAGAGACAGTGT | ○ | ○ | ○ | – | ○ | – |
| 2139 | TAAGAGACAGTTA | ○ | ○ | ○ | ○ | – | – |
| 2140 | TAAGAGACAGTTC | ○ | ○ | ○ | ○ | – | – |

TABLE 33-continued

Primer information for sets of random primers (13-base primers)*

| SEQ ID NO: | Sequence | A (64) | B (63) | C (60) | D (40) | E (20) | F (10) |
|---|---|---|---|---|---|---|---|
| 2141 | TAAGAGACAGTTG | ○ | ○ | ○ | — | ○ | — |
| 2142 | TAAGAGACAGTTT | ○ | ○ | ○ | ○ | — | — |

Primer indicated by "○" is used

TABLE 34

Primer information for set of random primers G (12-base primers)

| SEQ ID NO: | Sequence |
|---|---|
| 2065 | TAAGAGACAGAA |
| 2066 | TAAGAGACAGAT |
| 2067 | TAAGAGACAGAC |
| 2068 | TAAGAGACAGAG |
| 2069 | TAAGAGACAGTA |
| 2070 | TAAGAGACAGTT |
| 2071 | TAAGAGACAGTC |
| 2063 | TAAGAGACAGTG |
| 2072 | TAAGAGACAGCA |
| 2073 | TAAGAGACAGCT |
| 2074 | TAAGAGACAGCC |
| 2075 | TAAGAGACAGCG |
| 2076 | TAAGAGACAGGA |
| 2077 | TAAGAGACAGGT |
| 2078 | TAAGAGACAGGC |
| 2079 | TAAGAGACAGGG |

TABLE 35

Primer information for sequencer

| No | Type | Sequence | SEQ ID NO: |
|---|---|---|---|
| 1 | P5 | AATGATACGGCGACCACCGAGATCTACACGTCGTGCATCGTCGGCAGCGTCAGATGTGTATAAGAGACAG | 2143 |
| 2 | | AATGATACGGCGACCACCGAGATCTACACTCGCTGCATCGTCGGCAGCGTCAGATGTGTATAAGAGACAG | 2144 |
| 3 | | AATGATACGGCGACCACCGAGATCTACACCACAGTAGTCGTCGGCAGCGTCAGATGTGTATAAGAGACAG | 2145 |
| 4 | | AATGATACGGCGACCACCGAGATCTACACTGCTCGATTCGTCGGCAGCGTCAGATGTGTATAAGAGACAG | 2146 |
| 5 | | AATGATACGGCGACCACCGAGATCTACACTGACGAGTTCGTCGGCAGCGTCAGATGTGTATAAGAGACAG | 2147 |
| 6 | | AATGATACGGCGACCACCGAGATCTACACGCATATGTTCGTCGGCAGCGTCAGATGTGTATAAGAGACAG | 2148 |
| 7 | P7 | CAAGCAGAAGACGGCATACGAGATAAGAGGCAGTCTCGTGGGCTCGGAGATGTGTATAAGAGACAG | 2149 |
| 8 | | CAAGCAGAAGACGGCATACGAGATAGGAGTCCGTCTCGTGGGCTCGGAGATGTGTATAAGAGACAG | 2150 |
| 9 | | CAAGCAGAAGACGGCATACGAGATGTAGAGAGGTCTCGTGGGCTCGGAGATGTGTATAAGAGACAG | 2151 |
| 10 | | CAAGCAGAAGACGGCATACGAGATCCTCTCTGGTCTCGTGGGCTCGGAGATGTGTATAAGAGACAG | 2152 |

3.2 Preparation of DNA Library

To genomic DNA (15 ng) described in 2. above, a 0.2 mM dNTP mixture, 1.0 mM MgCl$_2$, 0.625 units of DNA polymerase (PrimeSTAR, TAKARA), and a 40 microM random primer at final concentration were added, and a reaction solution was prepared while adjusting the final reaction level to 25 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. Thus, a DNA library (the first DNA fragment) was prepared.

3.3 Preparation of DNA Library for Next-Generation Sequencer

To 1 microliter of the DNA library (the first DNA fragment) prepared in 3.2 above, a 0.2 mM dNTP mixture, 1.0 mM MgCl$_2$, 1.25 units of DNA Polymerase (PrimeSTAR, TAKARA), and a 0.25 microM primer for the next-generation sequencer at final concentration were added, and a reaction solution was prepared while adjusting the final reaction level to 50 microliters. The resultant was subjected to PCR under thermal cycling conditions comprising 95 degrees C. for 2 minutes, 25 cycles of 98 degrees C. for 15 seconds, 55 degrees C. for 15 seconds, and 72 degrees C. for 20 seconds, and 72 degrees C. for 1 minute, followed by storage at 4 degrees C. Thus, a DNA library for the next-generation sequencer (the second DNA fragment) was prepared. The DNA library was subjected to purification with the MinElute PCR Purification Kit (QIAGEN) and electrophoresis with the Agilent 2100 bioanalyzer (Agilent Technologies), and the waveforms thereof were examined.

3.4 Analysis Using Next-Generation Sequencer

With the use of the MiSeq Reagent Kit V2 500 Cycle (Illumina), the DNA library (the second DNA fragment) obtained in 3.3 was analyzed via 100 base paired-end sequencing. 3.5 Analysis of nucleotide sequence information The read data obtained in 3.4 were mapped to the nucleotide sequence information of the chloroplast genomes from the relevant plants (corn: NC_001666.2 *Zea mays* chloroplast, complete genome; rice: NC_001320.1 *Oryza sativa* japonica group plastid, complete genome; potato: NC_008096.2 *Solanum tuberosum* chloroplast, complete genome; soybean: NC_007942.1 *Glycine max* chloroplast, complete genome) with Bowtie2, and the read data derived from the chloroplast genomes and the regions thereof were identified.

4. Results 4.1 Analysis of Read Data Derived From the Chloroplast Genome 4.1.1 Mapping to the Chloroplast Genome Table 36 shows the results of MiSeq analysis of the DNA library prepared with the use of the set of random primers A shown in Table 33.

TABLE 36

Read data derived from chloroplast genome of each plant (set A)

| | Corn | Rice | Potato | Soybean |
|---|---|---|---|---|
| Total number of reads | 436,442 | 414,826 | 465,639 | 462,796 |
| Chloroplast* | 9,725 | 37,355 | 131,558 | 134,709 |
| Percentage (%) | 2.2% | 9.0% | 28.3% | 29.1% |

*Number of reads mapped to chloroplast genome

As shown in Table 36, 410,000 or more read data were obtained for corn, rice, potato, and soybean with the use of the set of random primers A. The obtained read data were mapped to the nucleotide sequence information of the chloroplast genomes from plants, and 9,725 to 134,709 read data were mapped to the chloroplast genome, as shown in Table 36. In particular, 28.3% and 29.1% of the obtained read data concerning the potato and the soybean were considered to be derived from the chloroplast genomes. When the set of random primers A was used, accordingly, it was concluded that data loss in the analysis of the nuclear genome was significant.

4.1.2 Particular Region of Chloroplast Genome

In order to identify the position of the chloroplast genome to which large quantities of read data had mapped in 4.1.1, from among the read data that had mapped to the chloroplast genome, a region to which 1% or more thereof had mapped was designated as a "particular region." Table 37 shows the results summarizing the number of reads mapped to the particular region of the chloroplast genome from corn. Table 38 shows the results summarizing the number of reads mapped to the particular region of the chloroplast genome from rice. Table 39 shows the results summarizing the number of reads mapped to the particular region of the chloroplast genome from potato. Table 40 shows the results summarizing the number of reads mapped to the particular region of the chloroplast genome from soybean.

TABLE 37

Number of reads mapped to particular region in chloroplast genome of corn

| Region | Position (bp) | Length (bp) | Number of reads | Percentage |
|---|---|---|---|---|
| Region_1_1 | 100,794 | 349 | 1,617 | 16.6% |
| Region_1_2 | 101,027 | 116 | 2,331 | 24.0% |
| Region_2_1 | 121,595 | 349 | 2,175 | 22.4% |
| Region_2_2 | 121,595 | 116 | 3,246 | 33.4% |
| Total | | | 9,369 | 96.3% |

TABLE 38

Number of reads mapped to particular region in chloroplast genome of rice

| Region | Position (bp) | Length (bp) | Number of reads | Percentage |
|---|---|---|---|---|
| Region_1_1 | 96,947 | 348 | 5,342 | 14.3% |
| Region_1_2 | 97,179 | 116 | 5,437 | 14.6% |
| Region_2_1 | 117,824 | 348 | 7,394 | 19.8% |
| Region_2_2 | 117,824 | 116 | 7,448 | 19.9% |
| Region_3_1 | 32,151 | 114 | 3,248 | 8.7% |
| Region_3_2 | 32,165 | 87 | 7,467 | 20.0% |
| Total | | | 36,336 | 97.3% |

TABLE 39

Number of reads mapped to particular region in chloroplast genome of potato

| Region | Position (bp) | Length (bp) | Number of reads | Percentage |
|---|---|---|---|---|
| Region_1_1 | 107,147 | 348 | 5,367 | 4.1% |
| Region_1_2 | 107,379 | 116 | 50,443 | 38.3% |
| Region_2_1 | 133,540 | 348 | 7,592 | 5.8% |
| Region_2_2 | 133,540 | 116 | 67,416 | 51.2% |
| Total | | | 130,818 | 99.4% |

TABLE 40

Number of reads mapped to particular region
in chloroplast genome of soybean

| Region | Position (bp) | Length (bp) | Number of reads | Percentage |
|---|---|---|---|---|
| Region_1_1 | 105,184 | 348 | 3,995 | 3.0% |
| Region_1_2 | 105,416 | 116 | 52,251 | 38.8% |
| Region_2_1 | 129,863 | 348 | 5,512 | 4.1% |
| Region_2_2 | 129,863 | 116 | 69,814 | 51.8% |
| Total | | | 131,572 | 97.7% |

As shown in Tables 37 to 40, 4 particular regions were observed in corn, potato, and soybean, and 6 particular regions were observed in rice. The percentage of the reads mapped to these particular regions was as high as 96.3% to 99.4% relative to the reads mapped to the chloroplast genome, and most of the reads was considered to be derived from these particular regions.

FIGS. 120-1 and 120-2 show the results of comparison of nucleotide sequences of Region_1_1 and Region_2_1 from among the particular regions shown in Tables 37 to 40. In FIGS. 120-1 and 120-2, particular regions found in corn are indicated as Region_1_1_Corn and Region_2_1_Corn, particular regions found in rice are indicated as Region_1_1_Oryza and Region_2_1_Oryza, particular regions found in potato are indicated as Region_1_1_Potato and Region_2_1_Poteto, and particular regions found in soybean are indicated as Region_1_1_Soybean and Region_2_1_Soybean. SEQ ID NO: 2153 shows the nucleotide sequence of Region_1_1_Corn, SEQ ID NO: 2154 shows the nucleotide sequence of Region_1_1_Oryza, SEQ ID NO: 2155 shows the nucleotide sequence of Region_1_1_Potato, SEQ ID NO: 2156 shows the nucleotide sequence of Region_1_1_Soybean, SEQ ID NO: 2157 shows the nucleotide sequence of Region_2_1_Corn, SEQ ID NO: 2158 shows the nucleotide sequence of Region_2_1_Oryza, SEQ ID NO: 2159 shows the nucleotide sequence of Region_2_1_Potato, and SEQ ID NO: 2160 shows the nucleotide sequence of Region_2_1_Soybean.

As a result of comparison of nucleotide sequences of particular regions, as shown in FIGS. 120-1 and 120-2, 4 regions (i.e., Region_1_1, Region_1_2, Region_2_1, and Region_2_2) were very similar among all the plants, and these regions were thus considered to be common thereamong. Region_1_2 and Region_2_2 (indicated as "Region_*_2" in FIGS. 120-1 and 120-2) were present in the regions of Region_1_1 and Region_2_1, respectively, and a complementary strand of Region_1_1 was similar to that of Region_2_1. It was thus considered that palindromes were formed.

The terminal sequences of these 4 regions could be roughly classified into 3 types, and, in particular, a sequence of 110 bases in each of such regions was common among 4 regions. On the basis of the sequence information of these regions, it was considered that a region of interest would be amplified with the aid of a random primer selected from among the set of random primers A, which comprises "TAAGAGACAG" and "TGC," "GGA," "GGG," or "GTG" ligated to the 3' terminus thereof. In particular, the sequence "TAAGAGACAGTGC" was considered to be a random primer associated with amplification of all such regions.

FIG. 121 shows the results of comparison of Region_3_1 and Region_3_2 among the particular regions found in rice (indicated as "Region_3_1_Oryza" and "Region_3_2_Oryza," respectively). SEQ ID NO: 2161 and SEQ ID NO: 2162 show the nucleotide sequences of Region_3_1_Oryza and Region_3_2_Oryza, respectively. As shown in FIG. 121, Region_3_2 was the internal sequence of Region_3_1. The results of analysis demonstrate that a region of interest was amplified with the aid of a random primer comprising a sequence composed of "TAAGAGACAG" and "TGC," "GTA," "ATA," or "CCA" ligated to the 3' terminus thereof.

4.2 Selection of Random Primer

The results of analysis in 4.1.2 demonstrate that amplification of the DNA fragment derived from the chloroplast genome is significantly associated with the random primer "TAAGAGACAGTGC" among the set of random primers A. Thus, 5 sets of 63-base, 60-base, 40-base, 20-base, and 10-base random primers other than the random primer "TAAGAGACAGTGC" were selected (Table 33, Sets of random primers B to F).

4.3 Analysis of Selected Sets of Random Primers

With the use of the 5 sets of random primers (Sets of random primers B to F) selected in 4.2, corn, rice, potato, and soybean were analyzed in the same manner as with the method involving the use of the set of random primers A. Table 41 shows the results attained with the use of the set of random primers B, Table 42 shows the results attained with the use of the set of random primers C, Table 43 shows the results attained with the use of the set of random primers D, Table 44 shows the results attained with the use of the set of random primers E, and Table 45 shows the results attained with the use of the set of random primers F.

TABLE 41

Read data derived from chloroplast genome of each plant (set B)

| | Corn | Rice | Potato | Soybean |
|---|---|---|---|---|
| Total number of reads | 387,025 | 336,103 | 395,188 | 376,049 |
| Chloroplast* | 1,004 | 1,981 | 2,189 | 12,488 |
| Percentage (%) | 0.3% | 0.6% | 0.6% | 3.3% |

*Number of reads mapped to chloroplast genome

TABLE 42

Read data derived from chloroplast genome of each plant (set C)

| | Corn | Rice | Potato | Soybean |
|---|---|---|---|---|
| Total number of reads | 539,769 | 477,714 | 524,522 | 520,182 |
| Chloroplast* | 2,190 | 4,074 | 2,132 | 14,191 |
| Percentage (%) | 0.4% | 0.9% | 0.4% | 2.7% |

*Number of reads mapped to chloroplast genome

TABLE 43

Read data derived from chloroplast genome of each plant (set D)

| | Corn | Rice | Potato | Soybean |
|---|---|---|---|---|
| Total number of reads | 426,523 | 406,970 | 434,928 | 424,31 |
| Chloroplast* | 776 | 1,466 | 3,093 | 4,476 |
| Percentage (%) | 0.2% | 0.4% | 0.7% | 1.1% |

*Number of reads mapped to chloroplast genome

TABLE 44

Read data derived from chloroplast genome of each plant (set E)

|  | Corn | Rice | Potato | Soybean |
|---|---|---|---|---|
| Total number of reads | 479,090 | 390,738 | 392,798 | 381,038 |
| Chloroplast* | 2,192 | 13,961 | 2,999 | 34,104 |
| Percentage (%) | 0.5% | 3.6% | 0.8% | 9.0% |

*Number of reads mapped to chloroplast genome

TABLE 45

Read data derived from chloroplast genome of each plant (set F)

|  | Corn | Rice | Potato | Soybean |
|---|---|---|---|---|
| Total number of reads | 406,309 | 416,556 | 397,316 | 422,655 |
| Chloroplast* | 735 | 1,175 | 2,892 | 7,400 |
| Percentage (%) | 0.2% | 0.3% | 0.7% | 1.8% |

*Number of reads mapped to chloroplast genome

FIG. 122 shows the results shown in Tables 41 to 45 in combination with the results shown in Table 36. The results demonstrated in Tables 41 to 45 and in FIG. 122 demonstrate that the proportion of the read data mapped to the chloroplast genome would be reduced to at least a half of the usual level with the use of the sets of random primers B to F that do not comprise TAAGAGACAGTGC. With the use of the set of random primers B prepared by removing a random primer "TAAGAGACAGTGC" from the set of random primers A, the proportion of such read data was reduced to a significant extent (i.e., 0.3% to 3.3% of the usual level). With the use of the set of 10 random primers, also, the proportion of such read data was reduced to a significant extent (i.e., 0.2% to 1.8% of the usual level).

The results demonstrate that a random primer may be selected on the basis of the sequence information of a particular region in the chloroplast genome found in this example, so that the read data derived from the chloroplast genome can be reduced to a significant extent.

4.4 Analysis of Set of Random Primers G

In order to inspect the correlation between the particular region found in 4.1.2 and the random primer length, in this example, the genome of the rice variety Nipponbare was analyzed with the use of the set of 12-base random primers G (Table 34). Table 46 shows the results of analysis.

TABLE 46

Number of reads mapped to particular region in chloroplast genome of rice (set G)

| Region | Position (bp) | Length (bp) | Number of reads | Percentage |
|---|---|---|---|---|
| Region_1_1 | 96,947 | 348 | 20,830 | 2.3% |
| Region_1_2 | 97,179 | 116 | 179,845 | 19.6% |
| Region_2_1 | 117,824 | 348 | 38,743 | 4.2% |
| Region_2_2 | 117,824 | 116 | 298,605 | 32.6% |
| Region_3_1 | 32,151 | 114 | 359,157 | 39.2% |
| Region_3_2 | 32,165 | 87 | — | — |

As shown in Table 46, 97.9% of the reads mapped to the chloroplast genome were mapped to 5 regions other than Region_3_2. The results demonstrate that a majority of the reads mapped to the chloroplast genome was derived from such particular regions, regardless of the random primer length. In addition, it was considered that these regions were amplified by random primers comprising "TG" at the 3' terminus of "TAAGAGACAG."

5. Examination

As described in this example, the read data obtained using the next-generation sequencer with the use of a set of random primers comprising TAAGAGACAG at its 5' terminus were analyzed. As a result of analysis, all the plant species were found to include large quantities of read data derived from the chloroplast genome and approximately 30% of the read data obtained from certain types of plant species was derived from the chloroplast genome. Since the performance of the analysis involving the use of a next-generation sequencer significantly varies depending on the amount of read data, it is critical to improve the yield of the target read data. When the nuclear genome is to be analyzed, in general, the read data of the chloroplast genome are not necessary, and a reduction thereof was an issue of concern.

As is apparent from the examples above, a majority of the read data mapped to the chloroplast genome was derived from a particular region. As described in the examples above, also, the read data derived from a particular region of the chloroplast genome can be reduced to a significant extent with the use of the set of random primers excluding particular random primers. Specifically, 5 sets of random primers excluding "TAAGAGACAGTGC" were selected on the basis of the sequence information of the particular region. With the use of any sets of primers, the read data derived from the chloroplast genome was reduced to at least a half of the usual level. With the use of the set of primers B prepared by removing "TAAGAGACAGTGC" or the set of 10 random primers F, in particular, a significant reduction was observed. On the basis of the results demonstrated above, a set of random primers capable of preventing the DNA fragment derived from a particular region from amplification may be designed, and the read data derived from the chloroplast genome may then be reduced to a significant extent, regardless of the number of random primers in the set of random primers.

The invention claimed is:

1. A method for preparing a DNA library, said method comprising: conducting a nucleic acid amplification reaction in a reaction solution, wherein said reaction solution contains genomic DNA from a plant or algae, and further contains a single primer set that amplifies DNA fragments using said genomic DNA as a template in the nucleic acid amplification reaction, wherein
   (a) said single primer set consists of at least one primer selected from the group consisting of nucleic acid sequences SEQ ID NOs: 2065-2079; or
   (b) said single primer set consists of at least one primer selected from the group consisting of nucleic acid sequences SEQ ID NOs: 2080-2142, and
   wherein a concentration of said single primer set in said reaction solution is between 4 micromolar (μM) and 100 μM.

2. The method according to claim 1, wherein when said reaction solution contains said single primer set that consists of at least one primer selected from the group consisting of nucleic acid sequences SEQ ID NOs: 2065-2079, said reaction solution contains one of:

(i) a primer consisting of nucleic acid sequence SEQ ID NO: 2079 in combination with at least one primer selected from the group consisting of nucleic acid sequences SEQ ID NOs: 2065-2078;

(ii) a primer consisting of nucleic acid sequence SEQ ID NO: 2077 in combination with at least one primer selected from the group consisting of nucleic acid sequences SEQ ID NOS: 2065-2076 and 2078-2079;

(iii) a primer consisting of nucleic acid sequence SEQ ID NO: 2066 in combination with at least one primer selected from the group consisting of nucleic acid sequences SEQ ID NOS: 2065 and 2067-2079; or (iv) a primer consisting of nucleic acid sequence SEQ ID NO: 2074 in combination with at least one primer selected from the group consisting of nucleic acid sequences SEQ ID NOs: 2065-2073 and 2075-2079.

3. The method according to claim 1, wherein when said reaction solution contains said single primer set that consists of at least one primer selected from the group consisting of nucleic acid sequences SEQ ID NOs: 2080-2142, said reaction solution contains one of:

(i) a primer consisting of nucleic acid sequence SEQ ID NO: 2120 in combination with at least one primer selected from the group consisting of nucleic acid sequences SEQ ID NOs: 2080-2119 and 2121-2142;

(ii) a primer consisting of nucleic acid sequence SEQ ID NO: 2122 in combination with at least one primer selected from the group consisting of nucleic acid sequences SEQ ID NOs: 2080-2121 and 2123-2142;

(iii) a primer consisting of nucleic acid sequence SEQ ID NO: 2126 in combination with at least one primer selected from the group consisting of nucleic acid sequences SEQ ID NOs: 2080-2125 and 2127-2142;

(iv) a primer consisting of nucleic acid sequence SEQ ID NO: 2124 in combination with at least one primer selected from the group consisting of nucleic acid sequences SEQ ID NOS: 2080-2123 and 2125-2142;

(v) a primer consisting of nucleic acid sequence SEQ IN NO: 2092 in combination with at least one primer selected from the group consisting of nucleic acid sequences SEQ IN NOs: 2080-2091 and 2093-2142; or (vi) a primer consisting of nucleic acid sequence SEQ ID NO: 2100 in combination with at least one primer selected from the group consisting of nucleic acid sequences SEQ IN NOs: 2080-2099 and 2101-2142.

4. The method according to claim 1, wherein: (a) said single primer set consists of at least 5 different primers selected from the group consisting of nucleic acid sequences SEQ ID NOs: 2065-2079; or wherein (b) said single primer set consists of at least 5 different primers selected from the group consisting of nucleic acid sequences SEQ ID NOs: 2080-2142.

5. The method according to claim 1, wherein: (a) said single primer set consists of at least 10 different primers selected from the group consisting of nucleic acid sequences SEQ ID NOs: 2065-2079;

or wherein (b) said single primer set consists of at least 10 different primers selected from the group consisting of nucleic acid sequences SEQ ID NOs: 2080-2142.

* * * * *

SEQUENCE LISTING

<160> NUMBER OF SEQ ID NOS: 2162

<210> SEQ ID NO 1
<211> LENGTH: 10
<212> TYPE: DNA
<213> ORGANISM: Artificial
<220> FEATURE:
<223> OTHER INFORMATION: synthetic DNA

```
<400> SEQUENCE: 1
agacgtcgtt                                                              10

<210> SEQ ID NO 2
<211> LENGTH: 10
<212> TYPE: DNA
<213> ORGANISM: Artificial
<220> FEATURE:
<223> OTHER INFORMATION: synthetic DNA

<400> SEQUENCE: 2
gaggcgatat                                                              10

<210> SEQ ID NO 3
<211> LENGTH: 10
<212> TYPE: DNA
<213> ORGANISM: Artificial
<220> FEATURE:
<223> OTHER INFORMATION: synthetic DNA

<400> SEQUENCE: 3
gtgcgaacgt                                                              10

<210> SEQ ID NO 4
<211> LENGTH: 10
<212> TYPE: DNA
<213> ORGANISM: Artificial
<220> FEATURE:
<223> OTHER INFORMATION: synthetic DNA

<400> SEQUENCE: 4
ttatactgcc                                                              10

<210> SEQ ID NO 5
<211> LENGTH: 10
<212> TYPE: DNA
<213> ORGANISM: Artificial
<220> FEATURE:
<223> OTHER INFORMATION: synthetic DNA

<400> SEQUENCE: 5
caagttcgca                                                              10

<210> SEQ ID NO 6
<211> LENGTH: 10
<212> TYPE: DNA
<213> ORGANISM: Artificial
<220> FEATURE:
<223> OTHER INFORMATION: synthetic DNA

<400> SEQUENCE: 6
acaaggtagt                                                              10

<210> SEQ ID NO 7
<211> LENGTH: 10
<212> TYPE: DNA
<213> ORGANISM: Artificial
<220> FEATURE:
<223> OTHER INFORMATION: synthetic DNA

<400> SEQUENCE: 7
acacagcgac                                                              10

<210> SEQ ID NO 8
```

-continued

<211> LENGTH: 10
<212> TYPE: DNA
<213> ORGANISM: Artificial
<220> FEATURE:
<223> OTHER INFORMATION: synthetic DNA

<400> SEQUENCE: 8
ttaccgatgt                                                              10

<210> SEQ ID NO 9
<211> LENGTH: 10
<212> TYPE: DNA
<213> ORGANISM: Artificial
<220> FEATURE:
<223> OTHER INFORMATION: synthetic DNA

<400> SEQUENCE: 9
cacagagtcg                                                              10

<210> SEQ ID NO 10
<211> LENGTH: 10
<212> TYPE: DNA
<213> ORGANISM: Artificial
<220> FEATURE:
<223> OTHER INFORMATION: synthetic DNA

<400> SEQUENCE: 10
ttcagcgcgt                                                              10

<210> SEQ ID NO 11
<211> LENGTH: 10
<212> TYPE: DNA
<213> ORGANISM: Artificial
<220> FEATURE:
<223> OTHER INFORMATION: synthetic DNA

<400> SEQUENCE: 11
aggaccgtga                                                              10

<210> SEQ ID NO 12
<211> LENGTH: 10
<212> TYPE: DNA
<213> ORGANISM: Artificial
<220> FEATURE:
<223> OTHER INFORMATION: synthetic DNA

<400> SEQUENCE: 12
gtctgttcgc                                                              10

<210> SEQ ID NO 13
<211> LENGTH: 10
<212> TYPE: DNA
<213> ORGANISM: Artificial
<220> FEATURE:
<223> OTHER INFORMATION: synthetic DNA

<400> SEQUENCE: 13
acctgtccac                                                              10

<210> SEQ ID NO 14
<211> LENGTH: 10
<212> TYPE: DNA
<213> ORGANISM: Artificial
<220> FEATURE:
<223> OTHER INFORMATION: synthetic DNA

<400> SEQUENCE: 14

```
<210> SEQ ID NO 15
<211> LENGTH: 10
<212> TYPE: DNA
<213> ORGANISM: Artificial
<220> FEATURE:
<223> OTHER INFORMATION: synthetic DNA

<400> SEQUENCE: 15
ctgccgatca                                                                10

<210> SEQ ID NO 16
<211> LENGTH: 10
<212> TYPE: DNA
<213> ORGANISM: Artificial
<220> FEATURE:
<223> OTHER INFORMATION: synthetic DNA

<400> SEQUENCE: 16
tacacggagc                                                                10

<210> SEQ ID NO 17
<211> LENGTH: 10
<212> TYPE: DNA
<213> ORGANISM: Artificial
<220> FEATURE:
<223> OTHER INFORMATION: synthetic DNA

<400> SEQUENCE: 17
ccgcattcat                                                                10

<210> SEQ ID NO 18
<211> LENGTH: 10
<212> TYPE: DNA
<213> ORGANISM: Artificial
<220> FEATURE:
<223> OTHER INFORMATION: synthetic DNA

<400> SEQUENCE: 18
gactctagac                                                                10

<210> SEQ ID NO 19
<211> LENGTH: 10
<212> TYPE: DNA
<213> ORGANISM: Artificial
<220> FEATURE:
<223> OTHER INFORMATION: synthetic DNA

<400> SEQUENCE: 19
ggagaactta                                                                10

<210> SEQ ID NO 20
<211> LENGTH: 10
<212> TYPE: DNA
<213> ORGANISM: Artificial
<220> FEATURE:
<223> OTHER INFORMATION: synthetic DNA

<400> SEQUENCE: 20
tccggtatgc                                                                10

<210> SEQ ID NO 21
<211> LENGTH: 10
<212> TYPE: DNA
```
ccgcaatgac                                                                10

```
<213> ORGANISM: Artificial
<220> FEATURE:
<223> OTHER INFORMATION: synthetic DNA

<400> SEQUENCE: 21
ggtcaggagt                                                            10

<210> SEQ ID NO 22
<211> LENGTH: 10
<212> TYPE: DNA
<213> ORGANISM: Artificial
<220> FEATURE:
<223> OTHER INFORMATION: synthetic DNA

<400> SEQUENCE: 22
acattggcag                                                            10

<210> SEQ ID NO 23
<211> LENGTH: 10
<212> TYPE: DNA
<213> ORGANISM: Artificial
<220> FEATURE:
<223> OTHER INFORMATION: synthetic DNA

<400> SEQUENCE: 23
cgtagactgc                                                            10

<210> SEQ ID NO 24
<211> LENGTH: 10
<212> TYPE: DNA
<213> ORGANISM: Artificial
<220> FEATURE:
<223> OTHER INFORMATION: synthetic DNA

<400> SEQUENCE: 24
agactgtact                                                            10

<210> SEQ ID NO 25
<211> LENGTH: 10
<212> TYPE: DNA
<213> ORGANISM: Artificial
<220> FEATURE:
<223> OTHER INFORMATION: synthetic DNA

<400> SEQUENCE: 25
tagacgcagt                                                            10

<210> SEQ ID NO 26
<211> LENGTH: 10
<212> TYPE: DNA
<213> ORGANISM: Artificial
<220> FEATURE:
<223> OTHER INFORMATION: synthetic DNA

<400> SEQUENCE: 26
ccgataatct                                                            10

<210> SEQ ID NO 27
<211> LENGTH: 10
<212> TYPE: DNA
<213> ORGANISM: Artificial
<220> FEATURE:
<223> OTHER INFORMATION: synthetic DNA

<400> SEQUENCE: 27
gagagctagt                                                            10
```

```
<210> SEQ ID NO 28
<211> LENGTH: 10
<212> TYPE: DNA
<213> ORGANISM: Artificial
<220> FEATURE:
<223> OTHER INFORMATION: synthetic DNA

<400> SEQUENCE: 28
gtaccgcgtt                                                          10

<210> SEQ ID NO 29
<211> LENGTH: 10
<212> TYPE: DNA
<213> ORGANISM: Artificial
<220> FEATURE:
<223> OTHER INFORMATION: synthetic DNA

<400> SEQUENCE: 29
gacttgcgca                                                          10

<210> SEQ ID NO 30
<211> LENGTH: 10
<212> TYPE: DNA
<213> ORGANISM: Artificial
<220> FEATURE:
<223> OTHER INFORMATION: synthetic DNA

<400> SEQUENCE: 30
cgtgattgcg                                                          10

<210> SEQ ID NO 31
<211> LENGTH: 10
<212> TYPE: DNA
<213> ORGANISM: Artificial
<220> FEATURE:
<223> OTHER INFORMATION: synthetic DNA

<400> SEQUENCE: 31
atcgtctctg                                                          10

<210> SEQ ID NO 32
<211> LENGTH: 10
<212> TYPE: DNA
<213> ORGANISM: Artificial
<220> FEATURE:
<223> OTHER INFORMATION: synthetic DNA

<400> SEQUENCE: 32
cgtagctacg                                                          10

<210> SEQ ID NO 33
<211> LENGTH: 10
<212> TYPE: DNA
<213> ORGANISM: Artificial
<220> FEATURE:
<223> OTHER INFORMATION: synthetic DNA

<400> SEQUENCE: 33
gccgaatagt                                                          10

<210> SEQ ID NO 34
<211> LENGTH: 10
<212> TYPE: DNA
<213> ORGANISM: Artificial
<220> FEATURE:
```

<223> OTHER INFORMATION: synthetic DNA

<400> SEQUENCE: 34
gtacctaggc                                                                          10

<210> SEQ ID NO 35
<211> LENGTH: 10
<212> TYPE: DNA
<213> ORGANISM: Artificial
<220> FEATURE:
<223> OTHER INFORMATION: synthetic DNA

<400> SEQUENCE: 35
gcttacatga                                                                          10

<210> SEQ ID NO 36
<211> LENGTH: 10
<212> TYPE: DNA
<213> ORGANISM: Artificial
<220> FEATURE:
<223> OTHER INFORMATION: synthetic DNA

<400> SEQUENCE: 36
tccacgtagt                                                                          10

<210> SEQ ID NO 37
<211> LENGTH: 10
<212> TYPE: DNA
<213> ORGANISM: Artificial
<220> FEATURE:
<223> OTHER INFORMATION: synthetic DNA

<400> SEQUENCE: 37
agaggccatc                                                                          10

<210> SEQ ID NO 38
<211> LENGTH: 10
<212> TYPE: DNA
<213> ORGANISM: Artificial
<220> FEATURE:
<223> OTHER INFORMATION: synthetic DNA

<400> SEQUENCE: 38
cggtgatgct                                                                          10

<210> SEQ ID NO 39
<211> LENGTH: 10
<212> TYPE: DNA
<213> ORGANISM: Artificial
<220> FEATURE:
<223> OTHER INFORMATION: synthetic DNA

<400> SEQUENCE: 39
cactgtgctt                                                                          10

<210> SEQ ID NO 40
<211> LENGTH: 10
<212> TYPE: DNA
<213> ORGANISM: Artificial
<220> FEATURE:
<223> OTHER INFORMATION: synthetic DNA

<400> SEQUENCE: 40
catgatggct                                                                          10

```
<210> SEQ ID NO 41
<211> LENGTH: 10
<212> TYPE: DNA
<213> ORGANISM: Artificial
<220> FEATURE:
<223> OTHER INFORMATION: synthetic DNA

<400> SEQUENCE: 41
gccacacatg                                                          10

<210> SEQ ID NO 42
<211> LENGTH: 10
<212> TYPE: DNA
<213> ORGANISM: Artificial
<220> FEATURE:
<223> OTHER INFORMATION: synthetic DNA

<400> SEQUENCE: 42
cacacactgt                                                          10

<210> SEQ ID NO 43
<211> LENGTH: 10
<212> TYPE: DNA
<213> ORGANISM: Artificial
<220> FEATURE:
<223> OTHER INFORMATION: synthetic DNA

<400> SEQUENCE: 43
cagaatcata                                                          10

<210> SEQ ID NO 44
<211> LENGTH: 10
<212> TYPE: DNA
<213> ORGANISM: Artificial
<220> FEATURE:
<223> OTHER INFORMATION: synthetic DNA

<400> SEQUENCE: 44
atcgtctacg                                                          10

<210> SEQ ID NO 45
<211> LENGTH: 10
<212> TYPE: DNA
<213> ORGANISM: Artificial
<220> FEATURE:
<223> OTHER INFORMATION: synthetic DNA

<400> SEQUENCE: 45
cgagcaatac                                                          10

<210> SEQ ID NO 46
<211> LENGTH: 10
<212> TYPE: DNA
<213> ORGANISM: Artificial
<220> FEATURE:
<223> OTHER INFORMATION: synthetic DNA

<400> SEQUENCE: 46
acaagcgcac                                                          10

<210> SEQ ID NO 47
<211> LENGTH: 10
<212> TYPE: DNA
<213> ORGANISM: Artificial
<220> FEATURE:
<223> OTHER INFORMATION: synthetic DNA
```

```
<400> SEQUENCE: 47
gcttagatgt                                                              10

<210> SEQ ID NO 48
<211> LENGTH: 10
<212> TYPE: DNA
<213> ORGANISM: Artificial
<220> FEATURE:
<223> OTHER INFORMATION: synthetic DNA

<400> SEQUENCE: 48
tgcattctgg                                                              10

<210> SEQ ID NO 49
<211> LENGTH: 10
<212> TYPE: DNA
<213> ORGANISM: Artificial
<220> FEATURE:
<223> OTHER INFORMATION: synthetic DNA

<400> SEQUENCE: 49
tgtcggacca                                                              10

<210> SEQ ID NO 50
<211> LENGTH: 10
<212> TYPE: DNA
<213> ORGANISM: Artificial
<220> FEATURE:
<223> OTHER INFORMATION: synthetic DNA

<400> SEQUENCE: 50
aggcactcgt                                                              10

<210> SEQ ID NO 51
<211> LENGTH: 10
<212> TYPE: DNA
<213> ORGANISM: Artificial
<220> FEATURE:
<223> OTHER INFORMATION: synthetic DNA

<400> SEQUENCE: 51
ctgcatgtga                                                              10

<210> SEQ ID NO 52
<211> LENGTH: 10
<212> TYPE: DNA
<213> ORGANISM: Artificial
<220> FEATURE:
<223> OTHER INFORMATION: synthetic DNA

<400> SEQUENCE: 52
accacgccta                                                              10

<210> SEQ ID NO 53
<211> LENGTH: 10
<212> TYPE: DNA
<213> ORGANISM: Artificial
<220> FEATURE:
<223> OTHER INFORMATION: synthetic DNA

<400> SEQUENCE: 53
gaggtcgtac                                                              10

<210> SEQ ID NO 54
<211> LENGTH: 10
```

```
<212> TYPE: DNA
<213> ORGANISM: Artificial
<220> FEATURE:
<223> OTHER INFORMATION: synthetic DNA

<400> SEQUENCE: 54
aatactctgt                                                          10

<210> SEQ ID NO 55
<211> LENGTH: 10
<212> TYPE: DNA
<213> ORGANISM: Artificial
<220> FEATURE:
<223> OTHER INFORMATION: synthetic DNA

<400> SEQUENCE: 55
tgccaactga                                                          10

<210> SEQ ID NO 56
<211> LENGTH: 10
<212> TYPE: DNA
<213> ORGANISM: Artificial
<220> FEATURE:
<223> OTHER INFORMATION: synthetic DNA

<400> SEQUENCE: 56
cctgttcggt                                                          10

<210> SEQ ID NO 57
<211> LENGTH: 10
<212> TYPE: DNA
<213> ORGANISM: Artificial
<220> FEATURE:
<223> OTHER INFORMATION: synthetic DNA

<400> SEQUENCE: 57
gtagagagtt                                                          10

<210> SEQ ID NO 58
<211> LENGTH: 10
<212> TYPE: DNA
<213> ORGANISM: Artificial
<220> FEATURE:
<223> OTHER INFORMATION: synthetic DNA

<400> SEQUENCE: 58
tacagcgtaa                                                          10

<210> SEQ ID NO 59
<211> LENGTH: 10
<212> TYPE: DNA
<213> ORGANISM: Artificial
<220> FEATURE:
<223> OTHER INFORMATION: synthetic DNA

<400> SEQUENCE: 59
tgacgtgatg                                                          10

<210> SEQ ID NO 60
<211> LENGTH: 10
<212> TYPE: DNA
<213> ORGANISM: Artificial
<220> FEATURE:
<223> OTHER INFORMATION: synthetic DNA

<400> SEQUENCE: 60
```
agacgtcggt                                                              10

<210> SEQ ID NO 61
<211> LENGTH: 10
<212> TYPE: DNA
<213> ORGANISM: Artificial
<220> FEATURE:
<223> OTHER INFORMATION: synthetic DNA

<400> SEQUENCE: 61
cgctaggttc                                                              10

<210> SEQ ID NO 62
<211> LENGTH: 10
<212> TYPE: DNA
<213> ORGANISM: Artificial
<220> FEATURE:
<223> OTHER INFORMATION: synthetic DNA

<400> SEQUENCE: 62
gccttatagc                                                              10

<210> SEQ ID NO 63
<211> LENGTH: 10
<212> TYPE: DNA
<213> ORGANISM: Artificial
<220> FEATURE:
<223> OTHER INFORMATION: synthetic DNA

<400> SEQUENCE: 63
ccttcgatct                                                              10

<210> SEQ ID NO 64
<211> LENGTH: 10
<212> TYPE: DNA
<213> ORGANISM: Artificial
<220> FEATURE:
<223> OTHER INFORMATION: synthetic DNA

<400> SEQUENCE: 64
aggcaacgtg                                                              10

<210> SEQ ID NO 65
<211> LENGTH: 10
<212> TYPE: DNA
<213> ORGANISM: Artificial
<220> FEATURE:
<223> OTHER INFORMATION: synthetic DNA

<400> SEQUENCE: 65
tgagcggtgt                                                              10

<210> SEQ ID NO 66
<211> LENGTH: 10
<212> TYPE: DNA
<213> ORGANISM: Artificial
<220> FEATURE:
<223> OTHER INFORMATION: synthetic DNA

<400> SEQUENCE: 66
gtgtcgaacg                                                              10

<210> SEQ ID NO 67
<211> LENGTH: 10
<212> TYPE: DNA
<213> ORGANISM: Artificial

```
<220> FEATURE:
<223> OTHER INFORMATION: synthetic DNA

<400> SEQUENCE: 67
cgatgttgcg                                                          10

<210> SEQ ID NO 68
<211> LENGTH: 10
<212> TYPE: DNA
<213> ORGANISM: Artificial
<220> FEATURE:
<223> OTHER INFORMATION: synthetic DNA

<400> SEQUENCE: 68
aacaagacac                                                          10

<210> SEQ ID NO 69
<211> LENGTH: 10
<212> TYPE: DNA
<213> ORGANISM: Artificial
<220> FEATURE:
<223> OTHER INFORMATION: synthetic DNA

<400> SEQUENCE: 69
gatgctggtt                                                          10

<210> SEQ ID NO 70
<211> LENGTH: 10
<212> TYPE: DNA
<213> ORGANISM: Artificial
<220> FEATURE:
<223> OTHER INFORMATION: synthetic DNA

<400> SEQUENCE: 70
accggtagtc                                                          10

<210> SEQ ID NO 71
<211> LENGTH: 10
<212> TYPE: DNA
<213> ORGANISM: Artificial
<220> FEATURE:
<223> OTHER INFORMATION: synthetic DNA

<400> SEQUENCE: 71
gtgactagca                                                          10

<210> SEQ ID NO 72
<211> LENGTH: 10
<212> TYPE: DNA
<213> ORGANISM: Artificial
<220> FEATURE:
<223> OTHER INFORMATION: synthetic DNA

<400> SEQUENCE: 72
agcctatatt                                                          10

<210> SEQ ID NO 73
<211> LENGTH: 10
<212> TYPE: DNA
<213> ORGANISM: Artificial
<220> FEATURE:
<223> OTHER INFORMATION: synthetic DNA

<400> SEQUENCE: 73
tcgtgagctt                                                          10
```

<210> SEQ ID NO 74
<211> LENGTH: 10
<212> TYPE: DNA
<213> ORGANISM: Artificial
<220> FEATURE:
<223> OTHER INFORMATION: synthetic DNA

<400> SEQUENCE: 74
acactatggc                                                            10

<210> SEQ ID NO 75
<211> LENGTH: 10
<212> TYPE: DNA
<213> ORGANISM: Artificial
<220> FEATURE:
<223> OTHER INFORMATION: synthetic DNA

<400> SEQUENCE: 75
gactctgtcg                                                            10

<210> SEQ ID NO 76
<211> LENGTH: 10
<212> TYPE: DNA
<213> ORGANISM: Artificial
<220> FEATURE:
<223> OTHER INFORMATION: synthetic DNA

<400> SEQUENCE: 76
tcgatgatgc                                                            10

<210> SEQ ID NO 77
<211> LENGTH: 10
<212> TYPE: DNA
<213> ORGANISM: Artificial
<220> FEATURE:
<223> OTHER INFORMATION: synthetic DNA

<400> SEQUENCE: 77
cttggacact                                                            10

<210> SEQ ID NO 78
<211> LENGTH: 10
<212> TYPE: DNA
<213> ORGANISM: Artificial
<220> FEATURE:
<223> OTHER INFORMATION: synthetic DNA

<400> SEQUENCE: 78
ggctgatcgt                                                            10

<210> SEQ ID NO 79
<211> LENGTH: 10
<212> TYPE: DNA
<213> ORGANISM: Artificial
<220> FEATURE:
<223> OTHER INFORMATION: synthetic DNA

<400> SEQUENCE: 79
actcacaggc                                                            10

<210> SEQ ID NO 80
<211> LENGTH: 10
<212> TYPE: DNA
<213> ORGANISM: Artificial
<220> FEATURE:
<223> OTHER INFORMATION: synthetic DNA

```
<400> SEQUENCE: 80
atgtgcgtac                                                              10

<210> SEQ ID NO 81
<211> LENGTH: 10
<212> TYPE: DNA
<213> ORGANISM: Artificial
<220> FEATURE:
<223> OTHER INFORMATION: synthetic DNA

<400> SEQUENCE: 81
caccatcgat                                                              10

<210> SEQ ID NO 82
<211> LENGTH: 10
<212> TYPE: DNA
<213> ORGANISM: Artificial
<220> FEATURE:
<223> OTHER INFORMATION: synthetic DNA

<400> SEQUENCE: 82
agccattaac                                                              10

<210> SEQ ID NO 83
<211> LENGTH: 10
<212> TYPE: DNA
<213> ORGANISM: Artificial
<220> FEATURE:
<223> OTHER INFORMATION: synthetic DNA

<400> SEQUENCE: 83
aatcgactgt                                                              10

<210> SEQ ID NO 84
<211> LENGTH: 10
<212> TYPE: DNA
<213> ORGANISM: Artificial
<220> FEATURE:
<223> OTHER INFORMATION: synthetic DNA

<400> SEQUENCE: 84
aatactagcg                                                              10

<210> SEQ ID NO 85
<211> LENGTH: 10
<212> TYPE: DNA
<213> ORGANISM: Artificial
<220> FEATURE:
<223> OTHER INFORMATION: synthetic DNA

<400> SEQUENCE: 85
tcgtcactga                                                              10

<210> SEQ ID NO 86
<211> LENGTH: 10
<212> TYPE: DNA
<213> ORGANISM: Artificial
<220> FEATURE:
<223> OTHER INFORMATION: synthetic DNA

<400> SEQUENCE: 86
caggctctta                                                              10

<210> SEQ ID NO 87
```

-continued

```
<211> LENGTH: 10
<212> TYPE: DNA
<213> ORGANISM: Artificial
<220> FEATURE:
<223> OTHER INFORMATION: synthetic DNA

<400> SEQUENCE: 87
ggtcggtgat                                                                10

<210> SEQ ID NO 88
<211> LENGTH: 10
<212> TYPE: DNA
<213> ORGANISM: Artificial
<220> FEATURE:
<223> OTHER INFORMATION: synthetic DNA

<400> SEQUENCE: 88
cattaggcgt                                                                10

<210> SEQ ID NO 89
<211> LENGTH: 10
<212> TYPE: DNA
<213> ORGANISM: Artificial
<220> FEATURE:
<223> OTHER INFORMATION: synthetic DNA

<400> SEQUENCE: 89
actcgcgagt                                                                10

<210> SEQ ID NO 90
<211> LENGTH: 10
<212> TYPE: DNA
<213> ORGANISM: Artificial
<220> FEATURE:
<223> OTHER INFORMATION: synthetic DNA

<400> SEQUENCE: 90
ttccgaataa                                                                10

<210> SEQ ID NO 91
<211> LENGTH: 10
<212> TYPE: DNA
<213> ORGANISM: Artificial
<220> FEATURE:
<223> OTHER INFORMATION: synthetic DNA

<400> SEQUENCE: 91
tgagcatcgt                                                                10

<210> SEQ ID NO 92
<211> LENGTH: 10
<212> TYPE: DNA
<213> ORGANISM: Artificial
<220> FEATURE:
<223> OTHER INFORMATION: synthetic DNA

<400> SEQUENCE: 92
gccacgtaac                                                                10

<210> SEQ ID NO 93
<211> LENGTH: 10
<212> TYPE: DNA
<213> ORGANISM: Artificial
<220> FEATURE:
<223> OTHER INFORMATION: synthetic DNA

<400> SEQUENCE: 93
```
gaactacatg                                                                    10

<210> SEQ ID NO 94
<211> LENGTH: 10
<212> TYPE: DNA
<213> ORGANISM: Artificial
<220> FEATURE:
<223> OTHER INFORMATION: synthetic DNA

<400> SEQUENCE: 94
tcgtgaggac                                                                    10

<210> SEQ ID NO 95
<211> LENGTH: 10
<212> TYPE: DNA
<213> ORGANISM: Artificial
<220> FEATURE:
<223> OTHER INFORMATION: synthetic DNA

<400> SEQUENCE: 95
gcggccttaa                                                                    10

<210> SEQ ID NO 96
<211> LENGTH: 10
<212> TYPE: DNA
<213> ORGANISM: Artificial
<220> FEATURE:
<223> OTHER INFORMATION: synthetic DNA

<400> SEQUENCE: 96
gctaaggacc                                                                    10

<210> SEQ ID NO 97
<211> LENGTH: 10
<212> TYPE: DNA
<213> ORGANISM: Artificial
<220> FEATURE:
<223> OTHER INFORMATION: synthetic DNA

<400> SEQUENCE: 97
atagccatta                                                                    10

<210> SEQ ID NO 98
<211> LENGTH: 10
<212> TYPE: DNA
<213> ORGANISM: Artificial
<220> FEATURE:
<223> OTHER INFORMATION: synthetic DNA

<400> SEQUENCE: 98
cagtaatcat                                                                    10

<210> SEQ ID NO 99
<211> LENGTH: 10
<212> TYPE: DNA
<213> ORGANISM: Artificial
<220> FEATURE:
<223> OTHER INFORMATION: synthetic DNA

<400> SEQUENCE: 99
actccttaat                                                                    10

<210> SEQ ID NO 100
<211> LENGTH: 10
<212> TYPE: DNA

```
<213> ORGANISM: Artificial
<220> FEATURE:
<223> OTHER INFORMATION: synthetic DNA

<400> SEQUENCE: 100
tcgaacatta                                                          10

<210> SEQ ID NO 101
<211> LENGTH: 10
<212> TYPE: DNA
<213> ORGANISM: Artificial
<220> FEATURE:
<223> OTHER INFORMATION: synthetic DNA

<400> SEQUENCE: 101
attatgaggt                                                          10

<210> SEQ ID NO 102
<211> LENGTH: 10
<212> TYPE: DNA
<213> ORGANISM: Artificial
<220> FEATURE:
<223> OTHER INFORMATION: synthetic DNA

<400> SEQUENCE: 102
aatcttagag                                                          10

<210> SEQ ID NO 103
<211> LENGTH: 10
<212> TYPE: DNA
<213> ORGANISM: Artificial
<220> FEATURE:
<223> OTHER INFORMATION: synthetic DNA

<400> SEQUENCE: 103
ttagatgatg                                                          10

<210> SEQ ID NO 104
<211> LENGTH: 10
<212> TYPE: DNA
<213> ORGANISM: Artificial
<220> FEATURE:
<223> OTHER INFORMATION: synthetic DNA

<400> SEQUENCE: 104
tacatatctg                                                          10

<210> SEQ ID NO 105
<211> LENGTH: 10
<212> TYPE: DNA
<213> ORGANISM: Artificial
<220> FEATURE:
<223> OTHER INFORMATION: synthetic DNA

<400> SEQUENCE: 105
tccttaatca                                                          10

<210> SEQ ID NO 106
<211> LENGTH: 10
<212> TYPE: DNA
<213> ORGANISM: Artificial
<220> FEATURE:
<223> OTHER INFORMATION: synthetic DNA

<400> SEQUENCE: 106
gttgagatta                                                          10
```

<210> SEQ ID NO 107
<211> LENGTH: 10
<212> TYPE: DNA
<213> ORGANISM: Artificial
<220> FEATURE:
<223> OTHER INFORMATION: synthetic DNA

<400> SEQUENCE: 107
tgttaacgta                                                          10

<210> SEQ ID NO 108
<211> LENGTH: 10
<212> TYPE: DNA
<213> ORGANISM: Artificial
<220> FEATURE:
<223> OTHER INFORMATION: synthetic DNA

<400> SEQUENCE: 108
catacagtaa                                                          10

<210> SEQ ID NO 109
<211> LENGTH: 10
<212> TYPE: DNA
<213> ORGANISM: Artificial
<220> FEATURE:
<223> OTHER INFORMATION: synthetic DNA

<400> SEQUENCE: 109
cttatacgaa                                                          10

<210> SEQ ID NO 110
<211> LENGTH: 10
<212> TYPE: DNA
<213> ORGANISM: Artificial
<220> FEATURE:
<223> OTHER INFORMATION: synthetic DNA

<400> SEQUENCE: 110
agatctatgt                                                          10

<210> SEQ ID NO 111
<211> LENGTH: 10
<212> TYPE: DNA
<213> ORGANISM: Artificial
<220> FEATURE:
<223> OTHER INFORMATION: synthetic DNA

<400> SEQUENCE: 111
aagacttagt                                                          10

<210> SEQ ID NO 112
<211> LENGTH: 10
<212> TYPE: DNA
<213> ORGANISM: Artificial
<220> FEATURE:
<223> OTHER INFORMATION: synthetic DNA

<400> SEQUENCE: 112
tgcgcaataa                                                          10

<210> SEQ ID NO 113
<211> LENGTH: 10
<212> TYPE: DNA
<213> ORGANISM: Artificial
<220> FEATURE:

<223> OTHER INFORMATION: synthetic DNA

<400> SEQUENCE: 113
ttggccatat                                                            10

<210> SEQ ID NO 114
<211> LENGTH: 10
<212> TYPE: DNA
<213> ORGANISM: Artificial
<220> FEATURE:
<223> OTHER INFORMATION: synthetic DNA

<400> SEQUENCE: 114
tattacgagg                                                            10

<210> SEQ ID NO 115
<211> LENGTH: 10
<212> TYPE: DNA
<213> ORGANISM: Artificial
<220> FEATURE:
<223> OTHER INFORMATION: synthetic DNA

<400> SEQUENCE: 115
ttatgatcgc                                                            10

<210> SEQ ID NO 116
<211> LENGTH: 10
<212> TYPE: DNA
<213> ORGANISM: Artificial
<220> FEATURE:
<223> OTHER INFORMATION: synthetic DNA

<400> SEQUENCE: 116
aacttaggag                                                            10

<210> SEQ ID NO 117
<211> LENGTH: 10
<212> TYPE: DNA
<213> ORGANISM: Artificial
<220> FEATURE:
<223> OTHER INFORMATION: synthetic DNA

<400> SEQUENCE: 117
tcacaatcgt                                                            10

<210> SEQ ID NO 118
<211> LENGTH: 10
<212> TYPE: DNA
<213> ORGANISM: Artificial
<220> FEATURE:
<223> OTHER INFORMATION: synthetic DNA

<400> SEQUENCE: 118
gagtatatgg                                                            10

<210> SEQ ID NO 119
<211> LENGTH: 10
<212> TYPE: DNA
<213> ORGANISM: Artificial
<220> FEATURE:
<223> OTHER INFORMATION: synthetic DNA

<400> SEQUENCE: 119
atcaggacaa                                                            10

```
<210> SEQ ID NO 120
<211> LENGTH: 10
<212> TYPE: DNA
<213> ORGANISM: Artificial
<220> FEATURE:
<223> OTHER INFORMATION: synthetic DNA

<400> SEQUENCE: 120
gtactgatag                                                          10

<210> SEQ ID NO 121
<211> LENGTH: 10
<212> TYPE: DNA
<213> ORGANISM: Artificial
<220> FEATURE:
<223> OTHER INFORMATION: synthetic DNA

<400> SEQUENCE: 121
cttatactcg                                                          10

<210> SEQ ID NO 122
<211> LENGTH: 10
<212> TYPE: DNA
<213> ORGANISM: Artificial
<220> FEATURE:
<223> OTHER INFORMATION: synthetic DNA

<400> SEQUENCE: 122
taacggacta                                                          10

<210> SEQ ID NO 123
<211> LENGTH: 10
<212> TYPE: DNA
<213> ORGANISM: Artificial
<220> FEATURE:
<223> OTHER INFORMATION: synthetic DNA

<400> SEQUENCE: 123
gcgttgtata                                                          10

<210> SEQ ID NO 124
<211> LENGTH: 10
<212> TYPE: DNA
<213> ORGANISM: Artificial
<220> FEATURE:
<223> OTHER INFORMATION: synthetic DNA

<400> SEQUENCE: 124
cttaagtgct                                                          10

<210> SEQ ID NO 125
<211> LENGTH: 10
<212> TYPE: DNA
<213> ORGANISM: Artificial
<220> FEATURE:
<223> OTHER INFORMATION: synthetic DNA

<400> SEQUENCE: 125
atacgactgt                                                          10

<210> SEQ ID NO 126
<211> LENGTH: 10
<212> TYPE: DNA
<213> ORGANISM: Artificial
<220> FEATURE:
<223> OTHER INFORMATION: synthetic DNA
```

```
<400> SEQUENCE: 126
actgttatcg                                                          10

<210> SEQ ID NO 127
<211> LENGTH: 10
<212> TYPE: DNA
<213> ORGANISM: Artificial
<220> FEATURE:
<223> OTHER INFORMATION: synthetic DNA

<400> SEQUENCE: 127
aatcttgacg                                                          10

<210> SEQ ID NO 128
<211> LENGTH: 10
<212> TYPE: DNA
<213> ORGANISM: Artificial
<220> FEATURE:
<223> OTHER INFORMATION: synthetic DNA

<400> SEQUENCE: 128
acatcacctt                                                          10

<210> SEQ ID NO 129
<211> LENGTH: 10
<212> TYPE: DNA
<213> ORGANISM: Artificial
<220> FEATURE:
<223> OTHER INFORMATION: synthetic DNA

<400> SEQUENCE: 129
ggtatagtac                                                          10

<210> SEQ ID NO 130
<211> LENGTH: 10
<212> TYPE: DNA
<213> ORGANISM: Artificial
<220> FEATURE:
<223> OTHER INFORMATION: synthetic DNA

<400> SEQUENCE: 130
ctaatccaca                                                          10

<210> SEQ ID NO 131
<211> LENGTH: 10
<212> TYPE: DNA
<213> ORGANISM: Artificial
<220> FEATURE:
<223> OTHER INFORMATION: synthetic DNA

<400> SEQUENCE: 131
gcaccttatt                                                          10

<210> SEQ ID NO 132
<211> LENGTH: 10
<212> TYPE: DNA
<213> ORGANISM: Artificial
<220> FEATURE:
<223> OTHER INFORMATION: synthetic DNA

<400> SEQUENCE: 132
attgacggta                                                          10

<210> SEQ ID NO 133
<211> LENGTH: 10
```

```
<212> TYPE: DNA
<213> ORGANISM: Artificial
<220> FEATURE:
<223> OTHER INFORMATION: synthetic DNA

<400> SEQUENCE: 133
gacatatggt                                                             10

<210> SEQ ID NO 134
<211> LENGTH: 10
<212> TYPE: DNA
<213> ORGANISM: Artificial
<220> FEATURE:
<223> OTHER INFORMATION: synthetic DNA

<400> SEQUENCE: 134
gatagtcgta                                                             10

<210> SEQ ID NO 135
<211> LENGTH: 10
<212> TYPE: DNA
<213> ORGANISM: Artificial
<220> FEATURE:
<223> OTHER INFORMATION: synthetic DNA

<400> SEQUENCE: 135
caattatcgc                                                             10

<210> SEQ ID NO 136
<211> LENGTH: 10
<212> TYPE: DNA
<213> ORGANISM: Artificial
<220> FEATURE:
<223> OTHER INFORMATION: synthetic DNA

<400> SEQUENCE: 136
cttaggtgat                                                             10

<210> SEQ ID NO 137
<211> LENGTH: 10
<212> TYPE: DNA
<213> ORGANISM: Artificial
<220> FEATURE:
<223> OTHER INFORMATION: synthetic DNA

<400> SEQUENCE: 137
catactactg                                                             10

<210> SEQ ID NO 138
<211> LENGTH: 10
<212> TYPE: DNA
<213> ORGANISM: Artificial
<220> FEATURE:
<223> OTHER INFORMATION: synthetic DNA

<400> SEQUENCE: 138
taacgcgaat                                                             10

<210> SEQ ID NO 139
<211> LENGTH: 10
<212> TYPE: DNA
<213> ORGANISM: Artificial
<220> FEATURE:
<223> OTHER INFORMATION: synthetic DNA

<400> SEQUENCE: 139
```

-continued caagttacga                                                        10

<210> SEQ ID NO 140
<211> LENGTH: 10
<212> TYPE: DNA
<213> ORGANISM: Artificial
<220> FEATURE:
<223> OTHER INFORMATION: synthetic DNA

<400> SEQUENCE: 140
aatctcaagg                                                        10

<210> SEQ ID NO 141
<211> LENGTH: 10
<212> TYPE: DNA
<213> ORGANISM: Artificial
<220> FEATURE:
<223> OTHER INFORMATION: synthetic DNA

<400> SEQUENCE: 141
gcaatcatca                                                        10

<210> SEQ ID NO 142
<211> LENGTH: 10
<212> TYPE: DNA
<213> ORGANISM: Artificial
<220> FEATURE:
<223> OTHER INFORMATION: synthetic DNA

<400> SEQUENCE: 142
tgtaacgttc                                                        10

<210> SEQ ID NO 143
<211> LENGTH: 10
<212> TYPE: DNA
<213> ORGANISM: Artificial
<220> FEATURE:
<223> OTHER INFORMATION: synthetic DNA

<400> SEQUENCE: 143
tatcgttggt                                                        10

<210> SEQ ID NO 144
<211> LENGTH: 10
<212> TYPE: DNA
<213> ORGANISM: Artificial
<220> FEATURE:
<223> OTHER INFORMATION: synthetic DNA

<400> SEQUENCE: 144
cgcttaagat                                                        10

<210> SEQ ID NO 145
<211> LENGTH: 10
<212> TYPE: DNA
<213> ORGANISM: Artificial
<220> FEATURE:
<223> OTHER INFORMATION: synthetic DNA

<400> SEQUENCE: 145
ttagaactgg                                                        10

<210> SEQ ID NO 146
<211> LENGTH: 10
<212> TYPE: DNA
<213> ORGANISM: Artificial

```
<220> FEATURE:
<223> OTHER INFORMATION: synthetic DNA

<400> SEQUENCE: 146
gtcataacgt                                                              10

<210> SEQ ID NO 147
<211> LENGTH: 10
<212> TYPE: DNA
<213> ORGANISM: Artificial
<220> FEATURE:
<223> OTHER INFORMATION: synthetic DNA

<400> SEQUENCE: 147
agagcagtat                                                              10

<210> SEQ ID NO 148
<211> LENGTH: 10
<212> TYPE: DNA
<213> ORGANISM: Artificial
<220> FEATURE:
<223> OTHER INFORMATION: synthetic DNA

<400> SEQUENCE: 148
caacatcact                                                              10

<210> SEQ ID NO 149
<211> LENGTH: 10
<212> TYPE: DNA
<213> ORGANISM: Artificial
<220> FEATURE:
<223> OTHER INFORMATION: synthetic DNA

<400> SEQUENCE: 149
cagaagctta                                                              10

<210> SEQ ID NO 150
<211> LENGTH: 10
<212> TYPE: DNA
<213> ORGANISM: Artificial
<220> FEATURE:
<223> OTHER INFORMATION: synthetic DNA

<400> SEQUENCE: 150
aactaacgtg                                                              10

<210> SEQ ID NO 151
<211> LENGTH: 10
<212> TYPE: DNA
<213> ORGANISM: Artificial
<220> FEATURE:
<223> OTHER INFORMATION: synthetic DNA

<400> SEQUENCE: 151
ttataccgct                                                              10

<210> SEQ ID NO 152
<211> LENGTH: 10
<212> TYPE: DNA
<213> ORGANISM: Artificial
<220> FEATURE:
<223> OTHER INFORMATION: synthetic DNA

<400> SEQUENCE: 152
gaattcgaga                                                              10
```

```
<210> SEQ ID NO 153
<211> LENGTH: 10
<212> TYPE: DNA
<213> ORGANISM: Artificial
<220> FEATURE:
<223> OTHER INFORMATION: synthetic DNA

<400> SEQUENCE: 153
ttacgtaacc                                                            10

<210> SEQ ID NO 154
<211> LENGTH: 10
<212> TYPE: DNA
<213> ORGANISM: Artificial
<220> FEATURE:
<223> OTHER INFORMATION: synthetic DNA

<400> SEQUENCE: 154
gcatggttaa                                                            10

<210> SEQ ID NO 155
<211> LENGTH: 10
<212> TYPE: DNA
<213> ORGANISM: Artificial
<220> FEATURE:
<223> OTHER INFORMATION: synthetic DNA

<400> SEQUENCE: 155
gcacctaatt                                                            10

<210> SEQ ID NO 156
<211> LENGTH: 10
<212> TYPE: DNA
<213> ORGANISM: Artificial
<220> FEATURE:
<223> OTHER INFORMATION: synthetic DNA

<400> SEQUENCE: 156
tgtaggttgt                                                            10

<210> SEQ ID NO 157
<211> LENGTH: 10
<212> TYPE: DNA
<213> ORGANISM: Artificial
<220> FEATURE:
<223> OTHER INFORMATION: synthetic DNA

<400> SEQUENCE: 157
ccatctggaa                                                            10

<210> SEQ ID NO 158
<211> LENGTH: 10
<212> TYPE: DNA
<213> ORGANISM: Artificial
<220> FEATURE:
<223> OTHER INFORMATION: synthetic DNA

<400> SEQUENCE: 158
ttcgcgttga                                                            10

<210> SEQ ID NO 159
<211> LENGTH: 10
<212> TYPE: DNA
<213> ORGANISM: Artificial
<220> FEATURE:
<223> OTHER INFORMATION: synthetic DNA
```

```
<400> SEQUENCE: 159
aaccgaggtt                                                                  10

<210> SEQ ID NO 160
<211> LENGTH: 10
<212> TYPE: DNA
<213> ORGANISM: Artificial
<220> FEATURE:
<223> OTHER INFORMATION: synthetic DNA

<400> SEQUENCE: 160
gtacgctgtt                                                                  10

<210> SEQ ID NO 161
<211> LENGTH: 10
<212> TYPE: DNA
<213> ORGANISM: Artificial
<220> FEATURE:
<223> OTHER INFORMATION: synthetic DNA

<400> SEQUENCE: 161
agtatcctgg                                                                  10

<210> SEQ ID NO 162
<211> LENGTH: 10
<212> TYPE: DNA
<213> ORGANISM: Artificial
<220> FEATURE:
<223> OTHER INFORMATION: synthetic DNA

<400> SEQUENCE: 162
ggttgtacag                                                                  10

<210> SEQ ID NO 163
<211> LENGTH: 10
<212> TYPE: DNA
<213> ORGANISM: Artificial
<220> FEATURE:
<223> OTHER INFORMATION: synthetic DNA

<400> SEQUENCE: 163
acgtacacca                                                                  10

<210> SEQ ID NO 164
<211> LENGTH: 10
<212> TYPE: DNA
<213> ORGANISM: Artificial
<220> FEATURE:
<223> OTHER INFORMATION: synthetic DNA

<400> SEQUENCE: 164
tgtcgagcaa                                                                  10

<210> SEQ ID NO 165
<211> LENGTH: 10
<212> TYPE: DNA
<213> ORGANISM: Artificial
<220> FEATURE:
<223> OTHER INFORMATION: synthetic DNA

<400> SEQUENCE: 165
gtcgtgttac                                                                  10

<210> SEQ ID NO 166
```

-continued

```
<211> LENGTH: 10
<212> TYPE: DNA
<213> ORGANISM: Artificial
<220> FEATURE:
<223> OTHER INFORMATION: synthetic DNA

<400> SEQUENCE: 166
gtgcaatagg                                                          10

<210> SEQ ID NO 167
<211> LENGTH: 10
<212> TYPE: DNA
<213> ORGANISM: Artificial
<220> FEATURE:
<223> OTHER INFORMATION: synthetic DNA

<400> SEQUENCE: 167
actcgatgct                                                          10

<210> SEQ ID NO 168
<211> LENGTH: 10
<212> TYPE: DNA
<213> ORGANISM: Artificial
<220> FEATURE:
<223> OTHER INFORMATION: synthetic DNA

<400> SEQUENCE: 168
gaatcgcgta                                                          10

<210> SEQ ID NO 169
<211> LENGTH: 10
<212> TYPE: DNA
<213> ORGANISM: Artificial
<220> FEATURE:
<223> OTHER INFORMATION: synthetic DNA

<400> SEQUENCE: 169
cggtcattgt                                                          10

<210> SEQ ID NO 170
<211> LENGTH: 10
<212> TYPE: DNA
<213> ORGANISM: Artificial
<220> FEATURE:
<223> OTHER INFORMATION: synthetic DNA

<400> SEQUENCE: 170
atcaggcgat                                                          10

<210> SEQ ID NO 171
<211> LENGTH: 10
<212> TYPE: DNA
<213> ORGANISM: Artificial
<220> FEATURE:
<223> OTHER INFORMATION: synthetic DNA

<400> SEQUENCE: 171
gtaagatgcg                                                          10

<210> SEQ ID NO 172
<211> LENGTH: 10
<212> TYPE: DNA
<213> ORGANISM: Artificial
<220> FEATURE:
<223> OTHER INFORMATION: synthetic DNA

<400> SEQUENCE: 172
```
ggtctcttga    10

<210> SEQ ID NO 173
<211> LENGTH: 10
<212> TYPE: DNA
<213> ORGANISM: Artificial
<220> FEATURE:
<223> OTHER INFORMATION: synthetic DNA

<400> SEQUENCE: 173
tcctcgctaa    10

<210> SEQ ID NO 174
<211> LENGTH: 10
<212> TYPE: DNA
<213> ORGANISM: Artificial
<220> FEATURE:
<223> OTHER INFORMATION: synthetic DNA

<400> SEQUENCE: 174
ctgcgtgata    10

<210> SEQ ID NO 175
<211> LENGTH: 10
<212> TYPE: DNA
<213> ORGANISM: Artificial
<220> FEATURE:
<223> OTHER INFORMATION: synthetic DNA

<400> SEQUENCE: 175
catactcgtc    10

<210> SEQ ID NO 176
<211> LENGTH: 10
<212> TYPE: DNA
<213> ORGANISM: Artificial
<220> FEATURE:
<223> OTHER INFORMATION: synthetic DNA

<400> SEQUENCE: 176
atctgagctc    10

<210> SEQ ID NO 177
<211> LENGTH: 10
<212> TYPE: DNA
<213> ORGANISM: Artificial
<220> FEATURE:
<223> OTHER INFORMATION: synthetic DNA

<400> SEQUENCE: 177
acggatagtg    10

<210> SEQ ID NO 178
<211> LENGTH: 10
<212> TYPE: DNA
<213> ORGANISM: Artificial
<220> FEATURE:
<223> OTHER INFORMATION: synthetic DNA

<400> SEQUENCE: 178
actgcaatgc    10

<210> SEQ ID NO 179
<211> LENGTH: 10
<212> TYPE: DNA

```
<213> ORGANISM: Artificial
<220> FEATURE:
<223> OTHER INFORMATION: synthetic DNA

<400> SEQUENCE: 179
taacgacgtg                                                           10

<210> SEQ ID NO 180
<211> LENGTH: 10
<212> TYPE: DNA
<213> ORGANISM: Artificial
<220> FEATURE:
<223> OTHER INFORMATION: synthetic DNA

<400> SEQUENCE: 180
tagactgtcg                                                           10

<210> SEQ ID NO 181
<211> LENGTH: 10
<212> TYPE: DNA
<213> ORGANISM: Artificial
<220> FEATURE:
<223> OTHER INFORMATION: synthetic DNA

<400> SEQUENCE: 181
cagcacttca                                                           10

<210> SEQ ID NO 182
<211> LENGTH: 10
<212> TYPE: DNA
<213> ORGANISM: Artificial
<220> FEATURE:
<223> OTHER INFORMATION: synthetic DNA

<400> SEQUENCE: 182
aacattcgcc                                                           10

<210> SEQ ID NO 183
<211> LENGTH: 10
<212> TYPE: DNA
<213> ORGANISM: Artificial
<220> FEATURE:
<223> OTHER INFORMATION: synthetic DNA

<400> SEQUENCE: 183
actagtgcgt                                                           10

<210> SEQ ID NO 184
<211> LENGTH: 10
<212> TYPE: DNA
<213> ORGANISM: Artificial
<220> FEATURE:
<223> OTHER INFORMATION: synthetic DNA

<400> SEQUENCE: 184
acgctgttct                                                           10

<210> SEQ ID NO 185
<211> LENGTH: 10
<212> TYPE: DNA
<213> ORGANISM: Artificial
<220> FEATURE:
<223> OTHER INFORMATION: synthetic DNA

<400> SEQUENCE: 185
cgtcgaatgc                                                           10
```

```
<210> SEQ ID NO 186
<211> LENGTH: 10
<212> TYPE: DNA
<213> ORGANISM: Artificial
<220> FEATURE:
<223> OTHER INFORMATION: synthetic DNA

<400> SEQUENCE: 186
ctctgacggt                                                              10

<210> SEQ ID NO 187
<211> LENGTH: 10
<212> TYPE: DNA
<213> ORGANISM: Artificial
<220> FEATURE:
<223> OTHER INFORMATION: synthetic DNA

<400> SEQUENCE: 187
gtcgccatgt                                                              10

<210> SEQ ID NO 188
<211> LENGTH: 10
<212> TYPE: DNA
<213> ORGANISM: Artificial
<220> FEATURE:
<223> OTHER INFORMATION: synthetic DNA

<400> SEQUENCE: 188
ggtccacgtt                                                              10

<210> SEQ ID NO 189
<211> LENGTH: 10
<212> TYPE: DNA
<213> ORGANISM: Artificial
<220> FEATURE:
<223> OTHER INFORMATION: synthetic DNA

<400> SEQUENCE: 189
cgagcgactt                                                              10

<210> SEQ ID NO 190
<211> LENGTH: 10
<212> TYPE: DNA
<213> ORGANISM: Artificial
<220> FEATURE:
<223> OTHER INFORMATION: synthetic DNA

<400> SEQUENCE: 190
ttgacgcgtg                                                              10

<210> SEQ ID NO 191
<211> LENGTH: 10
<212> TYPE: DNA
<213> ORGANISM: Artificial
<220> FEATURE:
<223> OTHER INFORMATION: synthetic DNA

<400> SEQUENCE: 191
ctgagagcct                                                              10

<210> SEQ ID NO 192
<211> LENGTH: 10
<212> TYPE: DNA
<213> ORGANISM: Artificial
<220> FEATURE:
```

<223> OTHER INFORMATION: synthetic DNA

<400> SEQUENCE: 192
cgcgctaact                                                          10

<210> SEQ ID NO 193
<211> LENGTH: 10
<212> TYPE: DNA
<213> ORGANISM: Artificial
<220> FEATURE:
<223> OTHER INFORMATION: synthetic DNA

<400> SEQUENCE: 193
ggtcgtcaag                                                          10

<210> SEQ ID NO 194
<211> LENGTH: 10
<212> TYPE: DNA
<213> ORGANISM: Artificial
<220> FEATURE:
<223> OTHER INFORMATION: synthetic DNA

<400> SEQUENCE: 194
aggttgacca                                                          10

<210> SEQ ID NO 195
<211> LENGTH: 10
<212> TYPE: DNA
<213> ORGANISM: Artificial
<220> FEATURE:
<223> OTHER INFORMATION: synthetic DNA

<400> SEQUENCE: 195
taacggcaac                                                          10

<210> SEQ ID NO 196
<211> LENGTH: 10
<212> TYPE: DNA
<213> ORGANISM: Artificial
<220> FEATURE:
<223> OTHER INFORMATION: synthetic DNA

<400> SEQUENCE: 196
gaggctggat                                                          10

<210> SEQ ID NO 197
<211> LENGTH: 10
<212> TYPE: DNA
<213> ORGANISM: Artificial
<220> FEATURE:
<223> OTHER INFORMATION: synthetic DNA

<400> SEQUENCE: 197
gtgcacacct                                                          10

<210> SEQ ID NO 198
<211> LENGTH: 10
<212> TYPE: DNA
<213> ORGANISM: Artificial
<220> FEATURE:
<223> OTHER INFORMATION: synthetic DNA

<400> SEQUENCE: 198
tgaggaccag                                                          10

```
<210> SEQ ID NO 199
<211> LENGTH: 10
<212> TYPE: DNA
<213> ORGANISM: Artificial
<220> FEATURE:
<223> OTHER INFORMATION: synthetic DNA

<400> SEQUENCE: 199
tacttgcgag                                                           10

<210> SEQ ID NO 200
<211> LENGTH: 10
<212> TYPE: DNA
<213> ORGANISM: Artificial
<220> FEATURE:
<223> OTHER INFORMATION: synthetic DNA

<400> SEQUENCE: 200
aactgtgaga                                                           10

<210> SEQ ID NO 201
<211> LENGTH: 10
<212> TYPE: DNA
<213> ORGANISM: Artificial
<220> FEATURE:
<223> OTHER INFORMATION: synthetic DNA

<400> SEQUENCE: 201
ctccatcaac                                                           10

<210> SEQ ID NO 202
<211> LENGTH: 10
<212> TYPE: DNA
<213> ORGANISM: Artificial
<220> FEATURE:
<223> OTHER INFORMATION: synthetic DNA

<400> SEQUENCE: 202
cggactgtta                                                           10

<210> SEQ ID NO 203
<211> LENGTH: 10
<212> TYPE: DNA
<213> ORGANISM: Artificial
<220> FEATURE:
<223> OTHER INFORMATION: synthetic DNA

<400> SEQUENCE: 203
taggacagtc                                                           10

<210> SEQ ID NO 204
<211> LENGTH: 10
<212> TYPE: DNA
<213> ORGANISM: Artificial
<220> FEATURE:
<223> OTHER INFORMATION: synthetic DNA

<400> SEQUENCE: 204
agaggacaca                                                           10

<210> SEQ ID NO 205
<211> LENGTH: 10
<212> TYPE: DNA
<213> ORGANISM: Artificial
<220> FEATURE:
<223> OTHER INFORMATION: synthetic DNA
```

```
<400> SEQUENCE: 205
acattcgcgg                                                          10

<210> SEQ ID NO 206
<211> LENGTH: 10
<212> TYPE: DNA
<213> ORGANISM: Artificial
<220> FEATURE:
<223> OTHER INFORMATION: synthetic DNA

<400> SEQUENCE: 206
gcttactgca                                                          10

<210> SEQ ID NO 207
<211> LENGTH: 10
<212> TYPE: DNA
<213> ORGANISM: Artificial
<220> FEATURE:
<223> OTHER INFORMATION: synthetic DNA

<400> SEQUENCE: 207
caatacgtaa                                                          10

<210> SEQ ID NO 208
<211> LENGTH: 10
<212> TYPE: DNA
<213> ORGANISM: Artificial
<220> FEATURE:
<223> OTHER INFORMATION: synthetic DNA

<400> SEQUENCE: 208
agacttgcgc                                                          10

<210> SEQ ID NO 209
<211> LENGTH: 10
<212> TYPE: DNA
<213> ORGANISM: Artificial
<220> FEATURE:
<223> OTHER INFORMATION: synthetic DNA

<400> SEQUENCE: 209
gagcggtgtt                                                          10

<210> SEQ ID NO 210
<211> LENGTH: 10
<212> TYPE: DNA
<213> ORGANISM: Artificial
<220> FEATURE:
<223> OTHER INFORMATION: synthetic DNA

<400> SEQUENCE: 210
cgtgagaggt                                                          10

<210> SEQ ID NO 211
<211> LENGTH: 10
<212> TYPE: DNA
<213> ORGANISM: Artificial
<220> FEATURE:
<223> OTHER INFORMATION: synthetic DNA

<400> SEQUENCE: 211
aatccgtcag                                                          10

<210> SEQ ID NO 212
<211> LENGTH: 10
```

```
<212> TYPE: DNA
<213> ORGANISM: Artificial
<220> FEATURE:
<223> OTHER INFORMATION: synthetic DNA

<400> SEQUENCE: 212
atacgtaccg                                                          10

<210> SEQ ID NO 213
<211> LENGTH: 10
<212> TYPE: DNA
<213> ORGANISM: Artificial
<220> FEATURE:
<223> OTHER INFORMATION: synthetic DNA

<400> SEQUENCE: 213
aactgattcc                                                          10

<210> SEQ ID NO 214
<211> LENGTH: 10
<212> TYPE: DNA
<213> ORGANISM: Artificial
<220> FEATURE:
<223> OTHER INFORMATION: synthetic DNA

<400> SEQUENCE: 214
ctgagcgtac                                                          10

<210> SEQ ID NO 215
<211> LENGTH: 10
<212> TYPE: DNA
<213> ORGANISM: Artificial
<220> FEATURE:
<223> OTHER INFORMATION: synthetic DNA

<400> SEQUENCE: 215
gtcggattcg                                                          10

<210> SEQ ID NO 216
<211> LENGTH: 10
<212> TYPE: DNA
<213> ORGANISM: Artificial
<220> FEATURE:
<223> OTHER INFORMATION: synthetic DNA

<400> SEQUENCE: 216
gccgaccata                                                          10

<210> SEQ ID NO 217
<211> LENGTH: 10
<212> TYPE: DNA
<213> ORGANISM: Artificial
<220> FEATURE:
<223> OTHER INFORMATION: synthetic DNA

<400> SEQUENCE: 217
gcagaactaa                                                          10

<210> SEQ ID NO 218
<211> LENGTH: 10
<212> TYPE: DNA
<213> ORGANISM: Artificial
<220> FEATURE:
<223> OTHER INFORMATION: synthetic DNA

<400> SEQUENCE: 218
```
ctaacgaccg                                                                  10

<210> SEQ ID NO 219
<211> LENGTH: 10
<212> TYPE: DNA
<213> ORGANISM: Artificial
<220> FEATURE:
<223> OTHER INFORMATION: synthetic DNA

<400> SEQUENCE: 219
gctggaccat                                                                  10

<210> SEQ ID NO 220
<211> LENGTH: 10
<212> TYPE: DNA
<213> ORGANISM: Artificial
<220> FEATURE:
<223> OTHER INFORMATION: synthetic DNA

<400> SEQUENCE: 220
gacgcggtta                                                                  10

<210> SEQ ID NO 221
<211> LENGTH: 10
<212> TYPE: DNA
<213> ORGANISM: Artificial
<220> FEATURE:
<223> OTHER INFORMATION: synthetic DNA

<400> SEQUENCE: 221
agtggtgagc                                                                  10

<210> SEQ ID NO 222
<211> LENGTH: 10
<212> TYPE: DNA
<213> ORGANISM: Artificial
<220> FEATURE:
<223> OTHER INFORMATION: synthetic DNA

<400> SEQUENCE: 222
caggcagtca                                                                  10

<210> SEQ ID NO 223
<211> LENGTH: 10
<212> TYPE: DNA
<213> ORGANISM: Artificial
<220> FEATURE:
<223> OTHER INFORMATION: synthetic DNA

<400> SEQUENCE: 223
tctgacgtca                                                                  10

<210> SEQ ID NO 224
<211> LENGTH: 10
<212> TYPE: DNA
<213> ORGANISM: Artificial
<220> FEATURE:
<223> OTHER INFORMATION: synthetic DNA

<400> SEQUENCE: 224
tacatgacgt                                                                  10

<210> SEQ ID NO 225
<211> LENGTH: 10
<212> TYPE: DNA
<213> ORGANISM: Artificial

<220> FEATURE:
<223> OTHER INFORMATION: synthetic DNA

<400> SEQUENCE: 225
tgaggcaacc                                                          10

<210> SEQ ID NO 226
<211> LENGTH: 10
<212> TYPE: DNA
<213> ORGANISM: Artificial
<220> FEATURE:
<223> OTHER INFORMATION: synthetic DNA

<400> SEQUENCE: 226
caactgcagt                                                          10

<210> SEQ ID NO 227
<211> LENGTH: 10
<212> TYPE: DNA
<213> ORGANISM: Artificial
<220> FEATURE:
<223> OTHER INFORMATION: synthetic DNA

<400> SEQUENCE: 227
cggagatacg                                                          10

<210> SEQ ID NO 228
<211> LENGTH: 10
<212> TYPE: DNA
<213> ORGANISM: Artificial
<220> FEATURE:
<223> OTHER INFORMATION: synthetic DNA

<400> SEQUENCE: 228
cttcgcaagt                                                          10

<210> SEQ ID NO 229
<211> LENGTH: 10
<212> TYPE: DNA
<213> ORGANISM: Artificial
<220> FEATURE:
<223> OTHER INFORMATION: synthetic DNA

<400> SEQUENCE: 229
ctggcatacg                                                          10

<210> SEQ ID NO 230
<211> LENGTH: 10
<212> TYPE: DNA
<213> ORGANISM: Artificial
<220> FEATURE:
<223> OTHER INFORMATION: synthetic DNA

<400> SEQUENCE: 230
taacgttcgc                                                          10

<210> SEQ ID NO 231
<211> LENGTH: 10
<212> TYPE: DNA
<213> ORGANISM: Artificial
<220> FEATURE:
<223> OTHER INFORMATION: synthetic DNA

<400> SEQUENCE: 231
ccggcgttaa                                                          10

```
<210> SEQ ID NO 232
<211> LENGTH: 10
<212> TYPE: DNA
<213> ORGANISM: Artificial
<220> FEATURE:
<223> OTHER INFORMATION: synthetic DNA

<400> SEQUENCE: 232
acaagacgcc                                                              10

<210> SEQ ID NO 233
<211> LENGTH: 10
<212> TYPE: DNA
<213> ORGANISM: Artificial
<220> FEATURE:
<223> OTHER INFORMATION: synthetic DNA

<400> SEQUENCE: 233
ccattagact                                                              10

<210> SEQ ID NO 234
<211> LENGTH: 10
<212> TYPE: DNA
<213> ORGANISM: Artificial
<220> FEATURE:
<223> OTHER INFORMATION: synthetic DNA

<400> SEQUENCE: 234
gtctgtgaca                                                              10

<210> SEQ ID NO 235
<211> LENGTH: 10
<212> TYPE: DNA
<213> ORGANISM: Artificial
<220> FEATURE:
<223> OTHER INFORMATION: synthetic DNA

<400> SEQUENCE: 235
ggcattggac                                                              10

<210> SEQ ID NO 236
<211> LENGTH: 10
<212> TYPE: DNA
<213> ORGANISM: Artificial
<220> FEATURE:
<223> OTHER INFORMATION: synthetic DNA

<400> SEQUENCE: 236
tcttcgcacg                                                              10

<210> SEQ ID NO 237
<211> LENGTH: 10
<212> TYPE: DNA
<213> ORGANISM: Artificial
<220> FEATURE:
<223> OTHER INFORMATION: synthetic DNA

<400> SEQUENCE: 237
tagcctgtgc                                                              10

<210> SEQ ID NO 238
<211> LENGTH: 10
<212> TYPE: DNA
<213> ORGANISM: Artificial
<220> FEATURE:
<223> OTHER INFORMATION: synthetic DNA
```

```
<400> SEQUENCE: 238
cactgaccta                                                             10

<210> SEQ ID NO 239
<211> LENGTH: 10
<212> TYPE: DNA
<213> ORGANISM: Artificial
<220> FEATURE:
<223> OTHER INFORMATION: synthetic DNA

<400> SEQUENCE: 239
ccgcacgatt                                                             10

<210> SEQ ID NO 240
<211> LENGTH: 10
<212> TYPE: DNA
<213> ORGANISM: Artificial
<220> FEATURE:
<223> OTHER INFORMATION: synthetic DNA

<400> SEQUENCE: 240
atagcacacg                                                             10

<210> SEQ ID NO 241
<211> LENGTH: 10
<212> TYPE: DNA
<213> ORGANISM: Artificial
<220> FEATURE:
<223> OTHER INFORMATION: synthetic DNA

<400> SEQUENCE: 241
gcacgtcata                                                             10

<210> SEQ ID NO 242
<211> LENGTH: 10
<212> TYPE: DNA
<213> ORGANISM: Artificial
<220> FEATURE:
<223> OTHER INFORMATION: synthetic DNA

<400> SEQUENCE: 242
aagccgttgg                                                             10

<210> SEQ ID NO 243
<211> LENGTH: 10
<212> TYPE: DNA
<213> ORGANISM: Artificial
<220> FEATURE:
<223> OTHER INFORMATION: synthetic DNA

<400> SEQUENCE: 243
cggaccgtta                                                             10

<210> SEQ ID NO 244
<211> LENGTH: 10
<212> TYPE: DNA
<213> ORGANISM: Artificial
<220> FEATURE:
<223> OTHER INFORMATION: synthetic DNA

<400> SEQUENCE: 244
tacacagcgt                                                             10

<210> SEQ ID NO 245
```

```
<211> LENGTH: 10
<212> TYPE: DNA
<213> ORGANISM: Artificial
<220> FEATURE:
<223> OTHER INFORMATION: synthetic DNA

<400> SEQUENCE: 245
cggacttcag                                                          10

<210> SEQ ID NO 246
<211> LENGTH: 10
<212> TYPE: DNA
<213> ORGANISM: Artificial
<220> FEATURE:
<223> OTHER INFORMATION: synthetic DNA

<400> SEQUENCE: 246
tagaacgtca                                                          10

<210> SEQ ID NO 247
<211> LENGTH: 10
<212> TYPE: DNA
<213> ORGANISM: Artificial
<220> FEATURE:
<223> OTHER INFORMATION: synthetic DNA

<400> SEQUENCE: 247
ggcattggag                                                          10

<210> SEQ ID NO 248
<211> LENGTH: 10
<212> TYPE: DNA
<213> ORGANISM: Artificial
<220> FEATURE:
<223> OTHER INFORMATION: synthetic DNA

<400> SEQUENCE: 248
ggcactcgtt                                                          10

<210> SEQ ID NO 249
<211> LENGTH: 10
<212> TYPE: DNA
<213> ORGANISM: Artificial
<220> FEATURE:
<223> OTHER INFORMATION: synthetic DNA

<400> SEQUENCE: 249
gtaccgttaa                                                          10

<210> SEQ ID NO 250
<211> LENGTH: 10
<212> TYPE: DNA
<213> ORGANISM: Artificial
<220> FEATURE:
<223> OTHER INFORMATION: synthetic DNA

<400> SEQUENCE: 250
aatacgtgtc                                                          10

<210> SEQ ID NO 251
<211> LENGTH: 10
<212> TYPE: DNA
<213> ORGANISM: Artificial
<220> FEATURE:
<223> OTHER INFORMATION: synthetic DNA

<400> SEQUENCE: 251
```

```
ccattgacgt                                                               10

<210> SEQ ID NO 252
<211> LENGTH: 10
<212> TYPE: DNA
<213> ORGANISM: Artificial
<220> FEATURE:
<223> OTHER INFORMATION: synthetic DNA

<400> SEQUENCE: 252
cgtgaatcgc                                                               10

<210> SEQ ID NO 253
<211> LENGTH: 10
<212> TYPE: DNA
<213> ORGANISM: Artificial
<220> FEATURE:
<223> OTHER INFORMATION: synthetic DNA

<400> SEQUENCE: 253
atcaacgcgg                                                               10

<210> SEQ ID NO 254
<211> LENGTH: 10
<212> TYPE: DNA
<213> ORGANISM: Artificial
<220> FEATURE:
<223> OTHER INFORMATION: synthetic DNA

<400> SEQUENCE: 254
cgccaaggta                                                               10

<210> SEQ ID NO 255
<211> LENGTH: 10
<212> TYPE: DNA
<213> ORGANISM: Artificial
<220> FEATURE:
<223> OTHER INFORMATION: synthetic DNA

<400> SEQUENCE: 255
agaagacgcc                                                               10

<210> SEQ ID NO 256
<211> LENGTH: 10
<212> TYPE: DNA
<213> ORGANISM: Artificial
<220> FEATURE:
<223> OTHER INFORMATION: synthetic DNA

<400> SEQUENCE: 256
ccgcatagtc                                                               10

<210> SEQ ID NO 257
<211> LENGTH: 10
<212> TYPE: DNA
<213> ORGANISM: Artificial
<220> FEATURE:
<223> OTHER INFORMATION: synthetic DNA

<400> SEQUENCE: 257
cttatatgtg                                                               10

<210> SEQ ID NO 258
<211> LENGTH: 10
<212> TYPE: DNA
```

```
<213> ORGANISM: Artificial
<220> FEATURE:
<223> OTHER INFORMATION: synthetic DNA

<400> SEQUENCE: 258
ggtctcatcg                                                              10

<210> SEQ ID NO 259
<211> LENGTH: 10
<212> TYPE: DNA
<213> ORGANISM: Artificial
<220> FEATURE:
<223> OTHER INFORMATION: synthetic DNA

<400> SEQUENCE: 259
ccaccatgtc                                                              10

<210> SEQ ID NO 260
<211> LENGTH: 10
<212> TYPE: DNA
<213> ORGANISM: Artificial
<220> FEATURE:
<223> OTHER INFORMATION: synthetic DNA

<400> SEQUENCE: 260
acgaatgtgt                                                              10

<210> SEQ ID NO 261
<211> LENGTH: 10
<212> TYPE: DNA
<213> ORGANISM: Artificial
<220> FEATURE:
<223> OTHER INFORMATION: synthetic DNA

<400> SEQUENCE: 261
ggtagtaaca                                                              10

<210> SEQ ID NO 262
<211> LENGTH: 10
<212> TYPE: DNA
<213> ORGANISM: Artificial
<220> FEATURE:
<223> OTHER INFORMATION: synthetic DNA

<400> SEQUENCE: 262
gccacttaat                                                              10

<210> SEQ ID NO 263
<211> LENGTH: 10
<212> TYPE: DNA
<213> ORGANISM: Artificial
<220> FEATURE:
<223> OTHER INFORMATION: synthetic DNA

<400> SEQUENCE: 263
atattgcgcc                                                              10

<210> SEQ ID NO 264
<211> LENGTH: 10
<212> TYPE: DNA
<213> ORGANISM: Artificial
<220> FEATURE:
<223> OTHER INFORMATION: synthetic DNA

<400> SEQUENCE: 264
gaccaatagt                                                              10
```

```
<210> SEQ ID NO 265
<211> LENGTH: 10
<212> TYPE: DNA
<213> ORGANISM: Artificial
<220> FEATURE:
<223> OTHER INFORMATION: synthetic DNA

<400> SEQUENCE: 265
aacaacacgg                                                              10

<210> SEQ ID NO 266
<211> LENGTH: 10
<212> TYPE: DNA
<213> ORGANISM: Artificial
<220> FEATURE:
<223> OTHER INFORMATION: synthetic DNA

<400> SEQUENCE: 266
atagccgatg                                                              10

<210> SEQ ID NO 267
<211> LENGTH: 10
<212> TYPE: DNA
<213> ORGANISM: Artificial
<220> FEATURE:
<223> OTHER INFORMATION: synthetic DNA

<400> SEQUENCE: 267
cgagagcata                                                              10

<210> SEQ ID NO 268
<211> LENGTH: 10
<212> TYPE: DNA
<213> ORGANISM: Artificial
<220> FEATURE:
<223> OTHER INFORMATION: synthetic DNA

<400> SEQUENCE: 268
cgagacatga                                                              10

<210> SEQ ID NO 269
<211> LENGTH: 10
<212> TYPE: DNA
<213> ORGANISM: Artificial
<220> FEATURE:
<223> OTHER INFORMATION: synthetic DNA

<400> SEQUENCE: 269
cgccaagtta                                                              10

<210> SEQ ID NO 270
<211> LENGTH: 10
<212> TYPE: DNA
<213> ORGANISM: Artificial
<220> FEATURE:
<223> OTHER INFORMATION: synthetic DNA

<400> SEQUENCE: 270
ttataatcgc                                                              10

<210> SEQ ID NO 271
<211> LENGTH: 10
<212> TYPE: DNA
<213> ORGANISM: Artificial
<220> FEATURE:
```

<223> OTHER INFORMATION: synthetic DNA

<400> SEQUENCE: 271
tagaagtgca                                                          10

<210> SEQ ID NO 272
<211> LENGTH: 10
<212> TYPE: DNA
<213> ORGANISM: Artificial
<220> FEATURE:
<223> OTHER INFORMATION: synthetic DNA

<400> SEQUENCE: 272
ggaggcatgt                                                          10

<210> SEQ ID NO 273
<211> LENGTH: 10
<212> TYPE: DNA
<213> ORGANISM: Artificial
<220> FEATURE:
<223> OTHER INFORMATION: synthetic DNA

<400> SEQUENCE: 273
gccacttcga                                                          10

<210> SEQ ID NO 274
<211> LENGTH: 10
<212> TYPE: DNA
<213> ORGANISM: Artificial
<220> FEATURE:
<223> OTHER INFORMATION: synthetic DNA

<400> SEQUENCE: 274
tccacggtac                                                          10

<210> SEQ ID NO 275
<211> LENGTH: 10
<212> TYPE: DNA
<213> ORGANISM: Artificial
<220> FEATURE:
<223> OTHER INFORMATION: synthetic DNA

<400> SEQUENCE: 275
caactatgca                                                          10

<210> SEQ ID NO 276
<211> LENGTH: 10
<212> TYPE: DNA
<213> ORGANISM: Artificial
<220> FEATURE:
<223> OTHER INFORMATION: synthetic DNA

<400> SEQUENCE: 276
caaggaggac                                                          10

<210> SEQ ID NO 277
<211> LENGTH: 10
<212> TYPE: DNA
<213> ORGANISM: Artificial
<220> FEATURE:
<223> OTHER INFORMATION: synthetic DNA

<400> SEQUENCE: 277
gaggtaccta                                                          10

```
<210> SEQ ID NO 278
<211> LENGTH: 10
<212> TYPE: DNA
<213> ORGANISM: Artificial
<220> FEATURE:
<223> OTHER INFORMATION: synthetic DNA

<400> SEQUENCE: 278
gagcgcataa                                                            10

<210> SEQ ID NO 279
<211> LENGTH: 10
<212> TYPE: DNA
<213> ORGANISM: Artificial
<220> FEATURE:
<223> OTHER INFORMATION: synthetic DNA

<400> SEQUENCE: 279
tcgtcacgtg                                                            10

<210> SEQ ID NO 280
<211> LENGTH: 10
<212> TYPE: DNA
<213> ORGANISM: Artificial
<220> FEATURE:
<223> OTHER INFORMATION: synthetic DNA

<400> SEQUENCE: 280
aactgtgaca                                                            10

<210> SEQ ID NO 281
<211> LENGTH: 10
<212> TYPE: DNA
<213> ORGANISM: Artificial
<220> FEATURE:
<223> OTHER INFORMATION: synthetic DNA

<400> SEQUENCE: 281
tccacgtgag                                                            10

<210> SEQ ID NO 282
<211> LENGTH: 10
<212> TYPE: DNA
<213> ORGANISM: Artificial
<220> FEATURE:
<223> OTHER INFORMATION: synthetic DNA

<400> SEQUENCE: 282
acactgctct                                                            10

<210> SEQ ID NO 283
<211> LENGTH: 10
<212> TYPE: DNA
<213> ORGANISM: Artificial
<220> FEATURE:
<223> OTHER INFORMATION: synthetic DNA

<400> SEQUENCE: 283
tacggtgagc                                                            10

<210> SEQ ID NO 284
<211> LENGTH: 10
<212> TYPE: DNA
<213> ORGANISM: Artificial
<220> FEATURE:
<223> OTHER INFORMATION: synthetic DNA
```

```
<400> SEQUENCE: 284
cggactaagt                                                          10

<210> SEQ ID NO 285
<211> LENGTH: 10
<212> TYPE: DNA
<213> ORGANISM: Artificial
<220> FEATURE:
<223> OTHER INFORMATION: synthetic DNA

<400> SEQUENCE: 285
aagccacgtt                                                          10

<210> SEQ ID NO 286
<211> LENGTH: 10
<212> TYPE: DNA
<213> ORGANISM: Artificial
<220> FEATURE:
<223> OTHER INFORMATION: synthetic DNA

<400> SEQUENCE: 286
caattactcg                                                          10

<210> SEQ ID NO 287
<211> LENGTH: 10
<212> TYPE: DNA
<213> ORGANISM: Artificial
<220> FEATURE:
<223> OTHER INFORMATION: synthetic DNA

<400> SEQUENCE: 287
tctggccata                                                          10

<210> SEQ ID NO 288
<211> LENGTH: 10
<212> TYPE: DNA
<213> ORGANISM: Artificial
<220> FEATURE:
<223> OTHER INFORMATION: synthetic DNA

<400> SEQUENCE: 288
tcaggctagt                                                          10

<210> SEQ ID NO 289
<211> LENGTH: 10
<212> TYPE: DNA
<213> ORGANISM: Artificial
<220> FEATURE:
<223> OTHER INFORMATION: synthetic DNA

<400> SEQUENCE: 289
ttgacccgga                                                          10

<210> SEQ ID NO 290
<211> LENGTH: 10
<212> TYPE: DNA
<213> ORGANISM: Artificial
<220> FEATURE:
<223> OTHER INFORMATION: synthetic DNA

<400> SEQUENCE: 290
tttttatggt                                                          10

<210> SEQ ID NO 291
<211> LENGTH: 10
```

```
<212> TYPE: DNA
<213> ORGANISM: Artificial
<220> FEATURE:
<223> OTHER INFORMATION: synthetic DNA

<400> SEQUENCE: 291
atgtggtgcg                                                              10

<210> SEQ ID NO 292
<211> LENGTH: 10
<212> TYPE: DNA
<213> ORGANISM: Artificial
<220> FEATURE:
<223> OTHER INFORMATION: synthetic DNA

<400> SEQUENCE: 292
aaggcgctag                                                              10

<210> SEQ ID NO 293
<211> LENGTH: 10
<212> TYPE: DNA
<213> ORGANISM: Artificial
<220> FEATURE:
<223> OTHER INFORMATION: synthetic DNA

<400> SEQUENCE: 293
tccaactttg                                                              10

<210> SEQ ID NO 294
<211> LENGTH: 10
<212> TYPE: DNA
<213> ORGANISM: Artificial
<220> FEATURE:
<223> OTHER INFORMATION: synthetic DNA

<400> SEQUENCE: 294
ccatcccatc                                                              10

<210> SEQ ID NO 295
<211> LENGTH: 10
<212> TYPE: DNA
<213> ORGANISM: Artificial
<220> FEATURE:
<223> OTHER INFORMATION: synthetic DNA

<400> SEQUENCE: 295
caatacgagg                                                              10

<210> SEQ ID NO 296
<211> LENGTH: 10
<212> TYPE: DNA
<213> ORGANISM: Artificial
<220> FEATURE:
<223> OTHER INFORMATION: synthetic DNA

<400> SEQUENCE: 296
gagtgttacc                                                              10

<210> SEQ ID NO 297
<211> LENGTH: 10
<212> TYPE: DNA
<213> ORGANISM: Artificial
<220> FEATURE:
<223> OTHER INFORMATION: synthetic DNA

<400> SEQUENCE: 297
```
gcctcctgta                                                              10

<210> SEQ ID NO 298
<211> LENGTH: 10
<212> TYPE: DNA
<213> ORGANISM: Artificial
<220> FEATURE:
<223> OTHER INFORMATION: synthetic DNA

<400> SEQUENCE: 298
cgaaggttgc                                                              10

<210> SEQ ID NO 299
<211> LENGTH: 10
<212> TYPE: DNA
<213> ORGANISM: Artificial
<220> FEATURE:
<223> OTHER INFORMATION: synthetic DNA

<400> SEQUENCE: 299
gaggtgctat                                                              10

<210> SEQ ID NO 300
<211> LENGTH: 10
<212> TYPE: DNA
<213> ORGANISM: Artificial
<220> FEATURE:
<223> OTHER INFORMATION: synthetic DNA

<400> SEQUENCE: 300
taggataatt                                                              10

<210> SEQ ID NO 301
<211> LENGTH: 10
<212> TYPE: DNA
<213> ORGANISM: Artificial
<220> FEATURE:
<223> OTHER INFORMATION: synthetic DNA

<400> SEQUENCE: 301
cgttgtcctc                                                              10

<210> SEQ ID NO 302
<211> LENGTH: 10
<212> TYPE: DNA
<213> ORGANISM: Artificial
<220> FEATURE:
<223> OTHER INFORMATION: synthetic DNA

<400> SEQUENCE: 302
tgagaccagc                                                              10

<210> SEQ ID NO 303
<211> LENGTH: 10
<212> TYPE: DNA
<213> ORGANISM: Artificial
<220> FEATURE:
<223> OTHER INFORMATION: synthetic DNA

<400> SEQUENCE: 303
tgcccaagct                                                              10

<210> SEQ ID NO 304
<211> LENGTH: 10
<212> TYPE: DNA
<213> ORGANISM: Artificial

```
<220> FEATURE:
<223> OTHER INFORMATION: synthetic DNA

<400> SEQUENCE: 304
tactgaatcg                                                         10

<210> SEQ ID NO 305
<211> LENGTH: 10
<212> TYPE: DNA
<213> ORGANISM: Artificial
<220> FEATURE:
<223> OTHER INFORMATION: synthetic DNA

<400> SEQUENCE: 305
ttacatagtc                                                         10

<210> SEQ ID NO 306
<211> LENGTH: 10
<212> TYPE: DNA
<213> ORGANISM: Artificial
<220> FEATURE:
<223> OTHER INFORMATION: synthetic DNA

<400> SEQUENCE: 306
acaaaggaaa                                                         10

<210> SEQ ID NO 307
<211> LENGTH: 10
<212> TYPE: DNA
<213> ORGANISM: Artificial
<220> FEATURE:
<223> OTHER INFORMATION: synthetic DNA

<400> SEQUENCE: 307
ctcgcttggg                                                         10

<210> SEQ ID NO 308
<211> LENGTH: 10
<212> TYPE: DNA
<213> ORGANISM: Artificial
<220> FEATURE:
<223> OTHER INFORMATION: synthetic DNA

<400> SEQUENCE: 308
ccttgcgtca                                                         10

<210> SEQ ID NO 309
<211> LENGTH: 10
<212> TYPE: DNA
<213> ORGANISM: Artificial
<220> FEATURE:
<223> OTHER INFORMATION: synthetic DNA

<400> SEQUENCE: 309
taattccgaa                                                         10

<210> SEQ ID NO 310
<211> LENGTH: 10
<212> TYPE: DNA
<213> ORGANISM: Artificial
<220> FEATURE:
<223> OTHER INFORMATION: synthetic DNA

<400> SEQUENCE: 310
gtgagcttga                                                         10
```

```
<210> SEQ ID NO 311
<211> LENGTH: 10
<212> TYPE: DNA
<213> ORGANISM: Artificial
<220> FEATURE:
<223> OTHER INFORMATION: synthetic DNA

<400> SEQUENCE: 311
atgccgattc                                                          10

<210> SEQ ID NO 312
<211> LENGTH: 10
<212> TYPE: DNA
<213> ORGANISM: Artificial
<220> FEATURE:
<223> OTHER INFORMATION: synthetic DNA

<400> SEQUENCE: 312
gcttgggctt                                                          10

<210> SEQ ID NO 313
<211> LENGTH: 10
<212> TYPE: DNA
<213> ORGANISM: Artificial
<220> FEATURE:
<223> OTHER INFORMATION: synthetic DNA

<400> SEQUENCE: 313
acaaagcgcc                                                          10

<210> SEQ ID NO 314
<211> LENGTH: 10
<212> TYPE: DNA
<213> ORGANISM: Artificial
<220> FEATURE:
<223> OTHER INFORMATION: synthetic DNA

<400> SEQUENCE: 314
gaaagctcta                                                          10

<210> SEQ ID NO 315
<211> LENGTH: 10
<212> TYPE: DNA
<213> ORGANISM: Artificial
<220> FEATURE:
<223> OTHER INFORMATION: synthetic DNA

<400> SEQUENCE: 315
taccgaccgt                                                          10

<210> SEQ ID NO 316
<211> LENGTH: 10
<212> TYPE: DNA
<213> ORGANISM: Artificial
<220> FEATURE:
<223> OTHER INFORMATION: synthetic DNA

<400> SEQUENCE: 316
tcgaagagac                                                          10

<210> SEQ ID NO 317
<211> LENGTH: 10
<212> TYPE: DNA
<213> ORGANISM: Artificial
<220> FEATURE:
<223> OTHER INFORMATION: synthetic DNA
```

```
<400> SEQUENCE: 317
gtcgcttacg                                                          10

<210> SEQ ID NO 318
<211> LENGTH: 10
<212> TYPE: DNA
<213> ORGANISM: Artificial
<220> FEATURE:
<223> OTHER INFORMATION: synthetic DNA

<400> SEQUENCE: 318
gggctctcca                                                          10

<210> SEQ ID NO 319
<211> LENGTH: 10
<212> TYPE: DNA
<213> ORGANISM: Artificial
<220> FEATURE:
<223> OTHER INFORMATION: synthetic DNA

<400> SEQUENCE: 319
gcgcccttgt                                                          10

<210> SEQ ID NO 320
<211> LENGTH: 10
<212> TYPE: DNA
<213> ORGANISM: Artificial
<220> FEATURE:
<223> OTHER INFORMATION: synthetic DNA

<400> SEQUENCE: 320
ggcaataggc                                                          10

<210> SEQ ID NO 321
<211> LENGTH: 10
<212> TYPE: DNA
<213> ORGANISM: Artificial
<220> FEATURE:
<223> OTHER INFORMATION: synthetic DNA

<400> SEQUENCE: 321
caagtcagga                                                          10

<210> SEQ ID NO 322
<211> LENGTH: 10
<212> TYPE: DNA
<213> ORGANISM: Artificial
<220> FEATURE:
<223> OTHER INFORMATION: synthetic DNA

<400> SEQUENCE: 322
gggtcgcaat                                                          10

<210> SEQ ID NO 323
<211> LENGTH: 10
<212> TYPE: DNA
<213> ORGANISM: Artificial
<220> FEATURE:
<223> OTHER INFORMATION: synthetic DNA

<400> SEQUENCE: 323
cagcaaccta                                                          10

<210> SEQ ID NO 324
```

```
<211> LENGTH: 10
<212> TYPE: DNA
<213> ORGANISM: Artificial
<220> FEATURE:
<223> OTHER INFORMATION: synthetic DNA

<400> SEQUENCE: 324
ttcccgccac                                                                10

<210> SEQ ID NO 325
<211> LENGTH: 10
<212> TYPE: DNA
<213> ORGANISM: Artificial
<220> FEATURE:
<223> OTHER INFORMATION: synthetic DNA

<400> SEQUENCE: 325
tgtgcatttt                                                                10

<210> SEQ ID NO 326
<211> LENGTH: 10
<212> TYPE: DNA
<213> ORGANISM: Artificial
<220> FEATURE:
<223> OTHER INFORMATION: synthetic DNA

<400> SEQUENCE: 326
atcaacgacg                                                                10

<210> SEQ ID NO 327
<211> LENGTH: 10
<212> TYPE: DNA
<213> ORGANISM: Artificial
<220> FEATURE:
<223> OTHER INFORMATION: synthetic DNA

<400> SEQUENCE: 327
gtgacgtcca                                                                10

<210> SEQ ID NO 328
<211> LENGTH: 10
<212> TYPE: DNA
<213> ORGANISM: Artificial
<220> FEATURE:
<223> OTHER INFORMATION: synthetic DNA

<400> SEQUENCE: 328
cgatctagtc                                                                10

<210> SEQ ID NO 329
<211> LENGTH: 10
<212> TYPE: DNA
<213> ORGANISM: Artificial
<220> FEATURE:
<223> OTHER INFORMATION: synthetic DNA

<400> SEQUENCE: 329
ttacatcctg                                                                10

<210> SEQ ID NO 330
<211> LENGTH: 10
<212> TYPE: DNA
<213> ORGANISM: Artificial
<220> FEATURE:
<223> OTHER INFORMATION: synthetic DNA

<400> SEQUENCE: 330
```
agccttcaat                                                            10

<210> SEQ ID NO 331
<211> LENGTH: 10
<212> TYPE: DNA
<213> ORGANISM: Artificial
<220> FEATURE:
<223> OTHER INFORMATION: synthetic DNA

<400> SEQUENCE: 331
tccatccgat                                                            10

<210> SEQ ID NO 332
<211> LENGTH: 10
<212> TYPE: DNA
<213> ORGANISM: Artificial
<220> FEATURE:
<223> OTHER INFORMATION: synthetic DNA

<400> SEQUENCE: 332
gactgggtct                                                            10

<210> SEQ ID NO 333
<211> LENGTH: 10
<212> TYPE: DNA
<213> ORGANISM: Artificial
<220> FEATURE:
<223> OTHER INFORMATION: synthetic DNA

<400> SEQUENCE: 333
ttcggtggag                                                            10

<210> SEQ ID NO 334
<211> LENGTH: 10
<212> TYPE: DNA
<213> ORGANISM: Artificial
<220> FEATURE:
<223> OTHER INFORMATION: synthetic DNA

<400> SEQUENCE: 334
gaccagcaca                                                            10

<210> SEQ ID NO 335
<211> LENGTH: 10
<212> TYPE: DNA
<213> ORGANISM: Artificial
<220> FEATURE:
<223> OTHER INFORMATION: synthetic DNA

<400> SEQUENCE: 335
cattaacgga                                                            10

<210> SEQ ID NO 336
<211> LENGTH: 10
<212> TYPE: DNA
<213> ORGANISM: Artificial
<220> FEATURE:
<223> OTHER INFORMATION: synthetic DNA

<400> SEQUENCE: 336
tttttcttga                                                            10

<210> SEQ ID NO 337
<211> LENGTH: 10
<212> TYPE: DNA

```
<213> ORGANISM: Artificial
<220> FEATURE:
<223> OTHER INFORMATION: synthetic DNA

<400> SEQUENCE: 337
cattgcactg                                                            10

<210> SEQ ID NO 338
<211> LENGTH: 10
<212> TYPE: DNA
<213> ORGANISM: Artificial
<220> FEATURE:
<223> OTHER INFORMATION: synthetic DNA

<400> SEQUENCE: 338
tgcggcgatc                                                            10

<210> SEQ ID NO 339
<211> LENGTH: 10
<212> TYPE: DNA
<213> ORGANISM: Artificial
<220> FEATURE:
<223> OTHER INFORMATION: synthetic DNA

<400> SEQUENCE: 339
atattgcggt                                                            10

<210> SEQ ID NO 340
<211> LENGTH: 10
<212> TYPE: DNA
<213> ORGANISM: Artificial
<220> FEATURE:
<223> OTHER INFORMATION: synthetic DNA

<400> SEQUENCE: 340
gacgtcgctc                                                            10

<210> SEQ ID NO 341
<211> LENGTH: 10
<212> TYPE: DNA
<213> ORGANISM: Artificial
<220> FEATURE:
<223> OTHER INFORMATION: synthetic DNA

<400> SEQUENCE: 341
tcgcttatcg                                                            10

<210> SEQ ID NO 342
<211> LENGTH: 10
<212> TYPE: DNA
<213> ORGANISM: Artificial
<220> FEATURE:
<223> OTHER INFORMATION: synthetic DNA

<400> SEQUENCE: 342
gcgcagacac                                                            10

<210> SEQ ID NO 343
<211> LENGTH: 10
<212> TYPE: DNA
<213> ORGANISM: Artificial
<220> FEATURE:
<223> OTHER INFORMATION: synthetic DNA

<400> SEQUENCE: 343
catgtattgt                                                            10
```

<210> SEQ ID NO 344
<211> LENGTH: 10
<212> TYPE: DNA
<213> ORGANISM: Artificial
<220> FEATURE:
<223> OTHER INFORMATION: synthetic DNA

<400> SEQUENCE: 344
tctataacct                                                          10

<210> SEQ ID NO 345
<211> LENGTH: 10
<212> TYPE: DNA
<213> ORGANISM: Artificial
<220> FEATURE:
<223> OTHER INFORMATION: synthetic DNA

<400> SEQUENCE: 345
gtggagacaa                                                          10

<210> SEQ ID NO 346
<211> LENGTH: 10
<212> TYPE: DNA
<213> ORGANISM: Artificial
<220> FEATURE:
<223> OTHER INFORMATION: synthetic DNA

<400> SEQUENCE: 346
cgaagattat                                                          10

<210> SEQ ID NO 347
<211> LENGTH: 10
<212> TYPE: DNA
<213> ORGANISM: Artificial
<220> FEATURE:
<223> OTHER INFORMATION: synthetic DNA

<400> SEQUENCE: 347
tagcaactgc                                                          10

<210> SEQ ID NO 348
<211> LENGTH: 10
<212> TYPE: DNA
<213> ORGANISM: Artificial
<220> FEATURE:
<223> OTHER INFORMATION: synthetic DNA

<400> SEQUENCE: 348
ataatcggta                                                          10

<210> SEQ ID NO 349
<211> LENGTH: 10
<212> TYPE: DNA
<213> ORGANISM: Artificial
<220> FEATURE:
<223> OTHER INFORMATION: synthetic DNA

<400> SEQUENCE: 349
caggatgggt                                                          10

<210> SEQ ID NO 350
<211> LENGTH: 10
<212> TYPE: DNA
<213> ORGANISM: Artificial
<220> FEATURE:

<223> OTHER INFORMATION: synthetic DNA

<400> SEQUENCE: 350
gacgattccc                                                                10

<210> SEQ ID NO 351
<211> LENGTH: 10
<212> TYPE: DNA
<213> ORGANISM: Artificial
<220> FEATURE:
<223> OTHER INFORMATION: synthetic DNA

<400> SEQUENCE: 351
cacgccttac                                                                10

<210> SEQ ID NO 352
<211> LENGTH: 10
<212> TYPE: DNA
<213> ORGANISM: Artificial
<220> FEATURE:
<223> OTHER INFORMATION: synthetic DNA

<400> SEQUENCE: 352
agttggttcc                                                                10

<210> SEQ ID NO 353
<211> LENGTH: 10
<212> TYPE: DNA
<213> ORGANISM: Artificial
<220> FEATURE:
<223> OTHER INFORMATION: synthetic DNA

<400> SEQUENCE: 353
tcttatcagg                                                                10

<210> SEQ ID NO 354
<211> LENGTH: 10
<212> TYPE: DNA
<213> ORGANISM: Artificial
<220> FEATURE:
<223> OTHER INFORMATION: synthetic DNA

<400> SEQUENCE: 354
cgagaagttc                                                                10

<210> SEQ ID NO 355
<211> LENGTH: 10
<212> TYPE: DNA
<213> ORGANISM: Artificial
<220> FEATURE:
<223> OTHER INFORMATION: synthetic DNA

<400> SEQUENCE: 355
gtggtagaat                                                                10

<210> SEQ ID NO 356
<211> LENGTH: 10
<212> TYPE: DNA
<213> ORGANISM: Artificial
<220> FEATURE:
<223> OTHER INFORMATION: synthetic DNA

<400> SEQUENCE: 356
taggcttgtg                                                                10

<210> SEQ ID NO 357
<211> LENGTH: 10
<212> TYPE: DNA
<213> ORGANISM: Artificial
<220> FEATURE:
<223> OTHER INFORMATION: synthetic DNA

<400> SEQUENCE: 357 atgcgttacg					10

<210> SEQ ID NO 358
<211> LENGTH: 10
<212> TYPE: DNA
<213> ORGANISM: Artificial
<220> FEATURE:
<223> OTHER INFORMATION: synthetic DNA

<400> SEQUENCE: 358 actaccgagg					10

<210> SEQ ID NO 359
<211> LENGTH: 10
<212> TYPE: DNA
<213> ORGANISM: Artificial
<220> FEATURE:
<223> OTHER INFORMATION: synthetic DNA

<400> SEQUENCE: 359 cgagttggtg					10

<210> SEQ ID NO 360
<211> LENGTH: 10
<212> TYPE: DNA
<213> ORGANISM: Artificial
<220> FEATURE:
<223> OTHER INFORMATION: synthetic DNA

<400> SEQUENCE: 360 ggacgatcaa					10

<210> SEQ ID NO 361
<211> LENGTH: 10
<212> TYPE: DNA
<213> ORGANISM: Artificial
<220> FEATURE:
<223> OTHER INFORMATION: synthetic DNA

<400> SEQUENCE: 361 aacagtatgc					10

<210> SEQ ID NO 362
<211> LENGTH: 10
<212> TYPE: DNA
<213> ORGANISM: Artificial
<220> FEATURE:
<223> OTHER INFORMATION: synthetic DNA

<400> SEQUENCE: 362 ttggctgatc					10

<210> SEQ ID NO 363
<211> LENGTH: 10
<212> TYPE: DNA
<213> ORGANISM: Artificial
<220> FEATURE:
<223> OTHER INFORMATION: synthetic DNA

```
<400> SEQUENCE: 363
aggattggaa                                                              10

<210> SEQ ID NO 364
<211> LENGTH: 10
<212> TYPE: DNA
<213> ORGANISM: Artificial
<220> FEATURE:
<223> OTHER INFORMATION: synthetic DNA

<400> SEQUENCE: 364
catatggaga                                                              10

<210> SEQ ID NO 365
<211> LENGTH: 10
<212> TYPE: DNA
<213> ORGANISM: Artificial
<220> FEATURE:
<223> OTHER INFORMATION: synthetic DNA

<400> SEQUENCE: 365
ctgcaggttt                                                              10

<210> SEQ ID NO 366
<211> LENGTH: 10
<212> TYPE: DNA
<213> ORGANISM: Artificial
<220> FEATURE:
<223> OTHER INFORMATION: synthetic DNA

<400> SEQUENCE: 366
ctctcttttt                                                              10

<210> SEQ ID NO 367
<211> LENGTH: 10
<212> TYPE: DNA
<213> ORGANISM: Artificial
<220> FEATURE:
<223> OTHER INFORMATION: synthetic DNA

<400> SEQUENCE: 367
agtagggtc                                                               10

<210> SEQ ID NO 368
<211> LENGTH: 10
<212> TYPE: DNA
<213> ORGANISM: Artificial
<220> FEATURE:
<223> OTHER INFORMATION: synthetic DNA

<400> SEQUENCE: 368
acaccgcaag                                                              10

<210> SEQ ID NO 369
<211> LENGTH: 10
<212> TYPE: DNA
<213> ORGANISM: Artificial
<220> FEATURE:
<223> OTHER INFORMATION: synthetic DNA

<400> SEQUENCE: 369
gaagcgggag                                                              10

<210> SEQ ID NO 370
<211> LENGTH: 10
```

```
<212> TYPE: DNA
<213> ORGANISM: Artificial
<220> FEATURE:
<223> OTHER INFORMATION: synthetic DNA

<400> SEQUENCE: 370
gatacggact                                                            10

<210> SEQ ID NO 371
<211> LENGTH: 10
<212> TYPE: DNA
<213> ORGANISM: Artificial
<220> FEATURE:
<223> OTHER INFORMATION: synthetic DNA

<400> SEQUENCE: 371
tacgacgtgt                                                            10

<210> SEQ ID NO 372
<211> LENGTH: 10
<212> TYPE: DNA
<213> ORGANISM: Artificial
<220> FEATURE:
<223> OTHER INFORMATION: synthetic DNA

<400> SEQUENCE: 372
gtgcctcctt                                                            10

<210> SEQ ID NO 373
<211> LENGTH: 10
<212> TYPE: DNA
<213> ORGANISM: Artificial
<220> FEATURE:
<223> OTHER INFORMATION: synthetic DNA

<400> SEQUENCE: 373
ggtgactgat                                                            10

<210> SEQ ID NO 374
<211> LENGTH: 10
<212> TYPE: DNA
<213> ORGANISM: Artificial
<220> FEATURE:
<223> OTHER INFORMATION: synthetic DNA

<400> SEQUENCE: 374
atatcttacg                                                            10

<210> SEQ ID NO 375
<211> LENGTH: 10
<212> TYPE: DNA
<213> ORGANISM: Artificial
<220> FEATURE:
<223> OTHER INFORMATION: synthetic DNA

<400> SEQUENCE: 375
aatcatacgg                                                            10

<210> SEQ ID NO 376
<211> LENGTH: 10
<212> TYPE: DNA
<213> ORGANISM: Artificial
<220> FEATURE:
<223> OTHER INFORMATION: synthetic DNA

<400> SEQUENCE: 376
```
ctcttgggac 10

<210> SEQ ID NO 377
<211> LENGTH: 10
<212> TYPE: DNA
<213> ORGANISM: Artificial
<220> FEATURE:
<223> OTHER INFORMATION: synthetic DNA

<400> SEQUENCE: 377
gacgacaaat 10

<210> SEQ ID NO 378
<211> LENGTH: 10
<212> TYPE: DNA
<213> ORGANISM: Artificial
<220> FEATURE:
<223> OTHER INFORMATION: synthetic DNA

<400> SEQUENCE: 378
gttgcgaggt 10

<210> SEQ ID NO 379
<211> LENGTH: 10
<212> TYPE: DNA
<213> ORGANISM: Artificial
<220> FEATURE:
<223> OTHER INFORMATION: synthetic DNA

<400> SEQUENCE: 379
aaaccgcacc 10

<210> SEQ ID NO 380
<211> LENGTH: 10
<212> TYPE: DNA
<213> ORGANISM: Artificial
<220> FEATURE:
<223> OTHER INFORMATION: synthetic DNA

<400> SEQUENCE: 380
gctaacacgt 10

<210> SEQ ID NO 381
<211> LENGTH: 10
<212> TYPE: DNA
<213> ORGANISM: Artificial
<220> FEATURE:
<223> OTHER INFORMATION: synthetic DNA

<400> SEQUENCE: 381
atcatgaggg 10

<210> SEQ ID NO 382
<211> LENGTH: 10
<212> TYPE: DNA
<213> ORGANISM: Artificial
<220> FEATURE:
<223> OTHER INFORMATION: synthetic DNA

<400> SEQUENCE: 382
gattcacgta 10

<210> SEQ ID NO 383
<211> LENGTH: 10
<212> TYPE: DNA
<213> ORGANISM: Artificial

<220> FEATURE:
<223> OTHER INFORMATION: synthetic DNA

<400> SEQUENCE: 383
tctcgaaaag                                                                10

<210> SEQ ID NO 384
<211> LENGTH: 10
<212> TYPE: DNA
<213> ORGANISM: Artificial
<220> FEATURE:
<223> OTHER INFORMATION: synthetic DNA

<400> SEQUENCE: 384
ctcgtaacca                                                                10

<210> SEQ ID NO 385
<211> LENGTH: 10
<212> TYPE: DNA
<213> ORGANISM: Artificial
<220> FEATURE:
<223> OTHER INFORMATION: synthetic DNA

<400> SEQUENCE: 385
gttacacacg                                                                10

<210> SEQ ID NO 386
<211> LENGTH: 10
<212> TYPE: DNA
<213> ORGANISM: Artificial
<220> FEATURE:
<223> OTHER INFORMATION: synthetic DNA

<400> SEQUENCE: 386
cgtgaagggt                                                                10

<210> SEQ ID NO 387
<211> LENGTH: 10
<212> TYPE: DNA
<213> ORGANISM: Artificial
<220> FEATURE:
<223> OTHER INFORMATION: synthetic DNA

<400> SEQUENCE: 387
acgagcatct                                                                10

<210> SEQ ID NO 388
<211> LENGTH: 10
<212> TYPE: DNA
<213> ORGANISM: Artificial
<220> FEATURE:
<223> OTHER INFORMATION: synthetic DNA

<400> SEQUENCE: 388
acgagggatt                                                                10

<210> SEQ ID NO 389
<211> LENGTH: 10
<212> TYPE: DNA
<213> ORGANISM: Artificial
<220> FEATURE:
<223> OTHER INFORMATION: synthetic DNA

<400> SEQUENCE: 389
gcaacgtcgg                                                                10

<210> SEQ ID NO 390
<211> LENGTH: 10
<212> TYPE: DNA
<213> ORGANISM: Artificial
<220> FEATURE:
<223> OTHER INFORMATION: synthetic DNA

<400> SEQUENCE: 390
cacggctagg                                                              10

<210> SEQ ID NO 391
<211> LENGTH: 10
<212> TYPE: DNA
<213> ORGANISM: Artificial
<220> FEATURE:
<223> OTHER INFORMATION: synthetic DNA

<400> SEQUENCE: 391
cgtgactctc                                                              10

<210> SEQ ID NO 392
<211> LENGTH: 10
<212> TYPE: DNA
<213> ORGANISM: Artificial
<220> FEATURE:
<223> OTHER INFORMATION: synthetic DNA

<400> SEQUENCE: 392
tctagacgca                                                              10

<210> SEQ ID NO 393
<211> LENGTH: 10
<212> TYPE: DNA
<213> ORGANISM: Artificial
<220> FEATURE:
<223> OTHER INFORMATION: synthetic DNA

<400> SEQUENCE: 393
ctgcgcacat                                                              10

<210> SEQ ID NO 394
<211> LENGTH: 10
<212> TYPE: DNA
<213> ORGANISM: Artificial
<220> FEATURE:
<223> OTHER INFORMATION: synthetic DNA

<400> SEQUENCE: 394
atgcttgaca                                                              10

<210> SEQ ID NO 395
<211> LENGTH: 10
<212> TYPE: DNA
<213> ORGANISM: Artificial
<220> FEATURE:
<223> OTHER INFORMATION: synthetic DNA

<400> SEQUENCE: 395
tttgtcgaca                                                              10

<210> SEQ ID NO 396
<211> LENGTH: 10
<212> TYPE: DNA
<213> ORGANISM: Artificial
<220> FEATURE:
<223> OTHER INFORMATION: synthetic DNA

<400> SEQUENCE: 396
acgtgtcagc                                                          10

<210> SEQ ID NO 397
<211> LENGTH: 10
<212> TYPE: DNA
<213> ORGANISM: Artificial
<220> FEATURE:
<223> OTHER INFORMATION: synthetic DNA

<400> SEQUENCE: 397
gaaaacatta                                                          10

<210> SEQ ID NO 398
<211> LENGTH: 10
<212> TYPE: DNA
<213> ORGANISM: Artificial
<220> FEATURE:
<223> OTHER INFORMATION: synthetic DNA

<400> SEQUENCE: 398
acattaacgg                                                          10

<210> SEQ ID NO 399
<211> LENGTH: 10
<212> TYPE: DNA
<213> ORGANISM: Artificial
<220> FEATURE:
<223> OTHER INFORMATION: synthetic DNA

<400> SEQUENCE: 399
gtacaggtcc                                                          10

<210> SEQ ID NO 400
<211> LENGTH: 10
<212> TYPE: DNA
<213> ORGANISM: Artificial
<220> FEATURE:
<223> OTHER INFORMATION: synthetic DNA

<400> SEQUENCE: 400
ctatgtgtac                                                          10

<210> SEQ ID NO 401
<211> LENGTH: 10
<212> TYPE: DNA
<213> ORGANISM: Artificial
<220> FEATURE:
<223> OTHER INFORMATION: synthetic DNA

<400> SEQUENCE: 401
gcgtacatta                                                          10

<210> SEQ ID NO 402
<211> LENGTH: 10
<212> TYPE: DNA
<213> ORGANISM: Artificial
<220> FEATURE:
<223> OTHER INFORMATION: synthetic DNA

<400> SEQUENCE: 402
gatttgtggc                                                          10

<210> SEQ ID NO 403

```
<211> LENGTH: 10
<212> TYPE: DNA
<213> ORGANISM: Artificial
<220> FEATURE:
<223> OTHER INFORMATION: synthetic DNA

<400> SEQUENCE: 403
tcgcgcgcta                                                          10

<210> SEQ ID NO 404
<211> LENGTH: 10
<212> TYPE: DNA
<213> ORGANISM: Artificial
<220> FEATURE:
<223> OTHER INFORMATION: synthetic DNA

<400> SEQUENCE: 404
acaagggcga                                                          10

<210> SEQ ID NO 405
<211> LENGTH: 10
<212> TYPE: DNA
<213> ORGANISM: Artificial
<220> FEATURE:
<223> OTHER INFORMATION: synthetic DNA

<400> SEQUENCE: 405
aacgcgcgat                                                          10

<210> SEQ ID NO 406
<211> LENGTH: 10
<212> TYPE: DNA
<213> ORGANISM: Artificial
<220> FEATURE:
<223> OTHER INFORMATION: synthetic DNA

<400> SEQUENCE: 406
cgtaaatgcg                                                          10

<210> SEQ ID NO 407
<211> LENGTH: 10
<212> TYPE: DNA
<213> ORGANISM: Artificial
<220> FEATURE:
<223> OTHER INFORMATION: synthetic DNA

<400> SEQUENCE: 407
taggcactac                                                          10

<210> SEQ ID NO 408
<211> LENGTH: 10
<212> TYPE: DNA
<213> ORGANISM: Artificial
<220> FEATURE:
<223> OTHER INFORMATION: synthetic DNA

<400> SEQUENCE: 408
gcgaggatcg                                                          10

<210> SEQ ID NO 409
<211> LENGTH: 10
<212> TYPE: DNA
<213> ORGANISM: Artificial
<220> FEATURE:
<223> OTHER INFORMATION: synthetic DNA

<400> SEQUENCE: 409
```
cacgtttact                                                              10

<210> SEQ ID NO 410
<211> LENGTH: 10
<212> TYPE: DNA
<213> ORGANISM: Artificial
<220> FEATURE:
<223> OTHER INFORMATION: synthetic DNA

<400> SEQUENCE: 410
taccaccacg                                                              10

<210> SEQ ID NO 411
<211> LENGTH: 10
<212> TYPE: DNA
<213> ORGANISM: Artificial
<220> FEATURE:
<223> OTHER INFORMATION: synthetic DNA

<400> SEQUENCE: 411
ttaacaggac                                                              10

<210> SEQ ID NO 412
<211> LENGTH: 10
<212> TYPE: DNA
<213> ORGANISM: Artificial
<220> FEATURE:
<223> OTHER INFORMATION: synthetic DNA

<400> SEQUENCE: 412
gctgtataac                                                              10

<210> SEQ ID NO 413
<211> LENGTH: 10
<212> TYPE: DNA
<213> ORGANISM: Artificial
<220> FEATURE:
<223> OTHER INFORMATION: synthetic DNA

<400> SEQUENCE: 413
gttgctggca                                                              10

<210> SEQ ID NO 414
<211> LENGTH: 10
<212> TYPE: DNA
<213> ORGANISM: Artificial
<220> FEATURE:
<223> OTHER INFORMATION: synthetic DNA

<400> SEQUENCE: 414
agtgtggcca                                                              10

<210> SEQ ID NO 415
<211> LENGTH: 10
<212> TYPE: DNA
<213> ORGANISM: Artificial
<220> FEATURE:
<223> OTHER INFORMATION: synthetic DNA

<400> SEQUENCE: 415
ctgcggttgt                                                              10

<210> SEQ ID NO 416
<211> LENGTH: 10
<212> TYPE: DNA

```
<213> ORGANISM: Artificial
<220> FEATURE:
<223> OTHER INFORMATION: synthetic DNA

<400> SEQUENCE: 416
tagatcagcg                                                          10

<210> SEQ ID NO 417
<211> LENGTH: 10
<212> TYPE: DNA
<213> ORGANISM: Artificial
<220> FEATURE:
<223> OTHER INFORMATION: synthetic DNA

<400> SEQUENCE: 417
ttccggttat                                                          10

<210> SEQ ID NO 418
<211> LENGTH: 10
<212> TYPE: DNA
<213> ORGANISM: Artificial
<220> FEATURE:
<223> OTHER INFORMATION: synthetic DNA

<400> SEQUENCE: 418
gataaactgt                                                          10

<210> SEQ ID NO 419
<211> LENGTH: 10
<212> TYPE: DNA
<213> ORGANISM: Artificial
<220> FEATURE:
<223> OTHER INFORMATION: synthetic DNA

<400> SEQUENCE: 419
tacagttgcc                                                          10

<210> SEQ ID NO 420
<211> LENGTH: 10
<212> TYPE: DNA
<213> ORGANISM: Artificial
<220> FEATURE:
<223> OTHER INFORMATION: synthetic DNA

<400> SEQUENCE: 420
cgatggcgaa                                                          10

<210> SEQ ID NO 421
<211> LENGTH: 10
<212> TYPE: DNA
<213> ORGANISM: Artificial
<220> FEATURE:
<223> OTHER INFORMATION: synthetic DNA

<400> SEQUENCE: 421
ccgacgtcag                                                          10

<210> SEQ ID NO 422
<211> LENGTH: 10
<212> TYPE: DNA
<213> ORGANISM: Artificial
<220> FEATURE:
<223> OTHER INFORMATION: synthetic DNA

<400> SEQUENCE: 422
tatggtgcaa                                                          10
```

<210> SEQ ID NO 423
<211> LENGTH: 10
<212> TYPE: DNA
<213> ORGANISM: Artificial
<220> FEATURE:
<223> OTHER INFORMATION: synthetic DNA

<400> SEQUENCE: 423
gacgacagtc                                                          10

<210> SEQ ID NO 424
<211> LENGTH: 10
<212> TYPE: DNA
<213> ORGANISM: Artificial
<220> FEATURE:
<223> OTHER INFORMATION: synthetic DNA

<400> SEQUENCE: 424
gtcaccgtcc                                                          10

<210> SEQ ID NO 425
<211> LENGTH: 10
<212> TYPE: DNA
<213> ORGANISM: Artificial
<220> FEATURE:
<223> OTHER INFORMATION: synthetic DNA

<400> SEQUENCE: 425
ggttttaaca                                                          10

<210> SEQ ID NO 426
<211> LENGTH: 10
<212> TYPE: DNA
<213> ORGANISM: Artificial
<220> FEATURE:
<223> OTHER INFORMATION: synthetic DNA

<400> SEQUENCE: 426
gaggacagta                                                          10

<210> SEQ ID NO 427
<211> LENGTH: 10
<212> TYPE: DNA
<213> ORGANISM: Artificial
<220> FEATURE:
<223> OTHER INFORMATION: synthetic DNA

<400> SEQUENCE: 427
gttacctaag                                                          10

<210> SEQ ID NO 428
<211> LENGTH: 10
<212> TYPE: DNA
<213> ORGANISM: Artificial
<220> FEATURE:
<223> OTHER INFORMATION: synthetic DNA

<400> SEQUENCE: 428
atcacgtgtt                                                          10

<210> SEQ ID NO 429
<211> LENGTH: 10
<212> TYPE: DNA
<213> ORGANISM: Artificial
<220> FEATURE:

<223> OTHER INFORMATION: synthetic DNA

<400> SEQUENCE: 429
taaggcctgg                                                                                  10

<210> SEQ ID NO 430
<211> LENGTH: 10
<212> TYPE: DNA
<213> ORGANISM: Artificial
<220> FEATURE:
<223> OTHER INFORMATION: synthetic DNA

<400> SEQUENCE: 430
tgttcgtagc                                                                                  10

<210> SEQ ID NO 431
<211> LENGTH: 10
<212> TYPE: DNA
<213> ORGANISM: Artificial
<220> FEATURE:
<223> OTHER INFORMATION: synthetic DNA

<400> SEQUENCE: 431
tgaggacgtg                                                                                  10

<210> SEQ ID NO 432
<211> LENGTH: 10
<212> TYPE: DNA
<213> ORGANISM: Artificial
<220> FEATURE:
<223> OTHER INFORMATION: synthetic DNA

<400> SEQUENCE: 432
gtgctgtgta                                                                                  10

<210> SEQ ID NO 433
<211> LENGTH: 10
<212> TYPE: DNA
<213> ORGANISM: Artificial
<220> FEATURE:
<223> OTHER INFORMATION: synthetic DNA

<400> SEQUENCE: 433
gagggtacgc                                                                                  10

<210> SEQ ID NO 434
<211> LENGTH: 10
<212> TYPE: DNA
<213> ORGANISM: Artificial
<220> FEATURE:
<223> OTHER INFORMATION: synthetic DNA

<400> SEQUENCE: 434
ccgtgattgt                                                                                  10

<210> SEQ ID NO 435
<211> LENGTH: 10
<212> TYPE: DNA
<213> ORGANISM: Artificial
<220> FEATURE:
<223> OTHER INFORMATION: synthetic DNA

<400> SEQUENCE: 435
aaaatcgcct                                                                                  10

```
<210> SEQ ID NO 436
<211> LENGTH: 10
<212> TYPE: DNA
<213> ORGANISM: Artificial
<220> FEATURE:
<223> OTHER INFORMATION: synthetic DNA

<400> SEQUENCE: 436
cgatcgcagt                                                          10

<210> SEQ ID NO 437
<211> LENGTH: 10
<212> TYPE: DNA
<213> ORGANISM: Artificial
<220> FEATURE:
<223> OTHER INFORMATION: synthetic DNA

<400> SEQUENCE: 437
acgcaataag                                                          10

<210> SEQ ID NO 438
<211> LENGTH: 10
<212> TYPE: DNA
<213> ORGANISM: Artificial
<220> FEATURE:
<223> OTHER INFORMATION: synthetic DNA

<400> SEQUENCE: 438
aaggtgcatc                                                          10

<210> SEQ ID NO 439
<211> LENGTH: 10
<212> TYPE: DNA
<213> ORGANISM: Artificial
<220> FEATURE:
<223> OTHER INFORMATION: synthetic DNA

<400> SEQUENCE: 439
cgcgtagata                                                          10

<210> SEQ ID NO 440
<211> LENGTH: 10
<212> TYPE: DNA
<213> ORGANISM: Artificial
<220> FEATURE:
<223> OTHER INFORMATION: synthetic DNA

<400> SEQUENCE: 440
cgagcagtgc                                                          10

<210> SEQ ID NO 441
<211> LENGTH: 10
<212> TYPE: DNA
<213> ORGANISM: Artificial
<220> FEATURE:
<223> OTHER INFORMATION: synthetic DNA

<400> SEQUENCE: 441
atacgtgacg                                                          10

<210> SEQ ID NO 442
<211> LENGTH: 10
<212> TYPE: DNA
<213> ORGANISM: Artificial
<220> FEATURE:
<223> OTHER INFORMATION: synthetic DNA
```

<400> SEQUENCE: 442
agattgcgcg                                                              10

<210> SEQ ID NO 443
<211> LENGTH: 10
<212> TYPE: DNA
<213> ORGANISM: Artificial
<220> FEATURE:
<223> OTHER INFORMATION: synthetic DNA

<400> SEQUENCE: 443
acgtgatgcc                                                              10

<210> SEQ ID NO 444
<211> LENGTH: 10
<212> TYPE: DNA
<213> ORGANISM: Artificial
<220> FEATURE:
<223> OTHER INFORMATION: synthetic DNA

<400> SEQUENCE: 444
gtacgcatcg                                                              10

<210> SEQ ID NO 445
<211> LENGTH: 10
<212> TYPE: DNA
<213> ORGANISM: Artificial
<220> FEATURE:
<223> OTHER INFORMATION: synthetic DNA

<400> SEQUENCE: 445
tcccgactta                                                              10

<210> SEQ ID NO 446
<211> LENGTH: 10
<212> TYPE: DNA
<213> ORGANISM: Artificial
<220> FEATURE:
<223> OTHER INFORMATION: synthetic DNA

<400> SEQUENCE: 446
gtttttacac                                                              10

<210> SEQ ID NO 447
<211> LENGTH: 10
<212> TYPE: DNA
<213> ORGANISM: Artificial
<220> FEATURE:
<223> OTHER INFORMATION: synthetic DNA

<400> SEQUENCE: 447
cctgagcgtg                                                              10

<210> SEQ ID NO 448
<211> LENGTH: 10
<212> TYPE: DNA
<213> ORGANISM: Artificial
<220> FEATURE:
<223> OTHER INFORMATION: synthetic DNA

<400> SEQUENCE: 448
cggcattgta                                                              10

<210> SEQ ID NO 449
<211> LENGTH: 10

```
<212> TYPE: DNA
<213> ORGANISM: Artificial
<220> FEATURE:
<223> OTHER INFORMATION: synthetic DNA

<400> SEQUENCE: 449
tagagtgcgt                                                              10

<210> SEQ ID NO 450
<211> LENGTH: 10
<212> TYPE: DNA
<213> ORGANISM: Artificial
<220> FEATURE:
<223> OTHER INFORMATION: synthetic DNA

<400> SEQUENCE: 450
atggccagac                                                              10

<210> SEQ ID NO 451
<211> LENGTH: 10
<212> TYPE: DNA
<213> ORGANISM: Artificial
<220> FEATURE:
<223> OTHER INFORMATION: synthetic DNA

<400> SEQUENCE: 451
cttagcatgc                                                              10

<210> SEQ ID NO 452
<211> LENGTH: 10
<212> TYPE: DNA
<213> ORGANISM: Artificial
<220> FEATURE:
<223> OTHER INFORMATION: synthetic DNA

<400> SEQUENCE: 452
acaacacctg                                                              10

<210> SEQ ID NO 453
<211> LENGTH: 10
<212> TYPE: DNA
<213> ORGANISM: Artificial
<220> FEATURE:
<223> OTHER INFORMATION: synthetic DNA

<400> SEQUENCE: 453
agtgactatc                                                              10

<210> SEQ ID NO 454
<211> LENGTH: 10
<212> TYPE: DNA
<213> ORGANISM: Artificial
<220> FEATURE:
<223> OTHER INFORMATION: synthetic DNA

<400> SEQUENCE: 454
catgctacac                                                              10

<210> SEQ ID NO 455
<211> LENGTH: 10
<212> TYPE: DNA
<213> ORGANISM: Artificial
<220> FEATURE:
<223> OTHER INFORMATION: synthetic DNA

<400> SEQUENCE: 455
```
aaagcgggcg                                                                         10

<210> SEQ ID NO 456
<211> LENGTH: 10
<212> TYPE: DNA
<213> ORGANISM: Artificial
<220> FEATURE:
<223> OTHER INFORMATION: synthetic DNA

<400> SEQUENCE: 456
agatcgccgt                                                                         10

<210> SEQ ID NO 457
<211> LENGTH: 10
<212> TYPE: DNA
<213> ORGANISM: Artificial
<220> FEATURE:
<223> OTHER INFORMATION: synthetic DNA

<400> SEQUENCE: 457
cgtagatatt                                                                         10

<210> SEQ ID NO 458
<211> LENGTH: 10
<212> TYPE: DNA
<213> ORGANISM: Artificial
<220> FEATURE:
<223> OTHER INFORMATION: synthetic DNA

<400> SEQUENCE: 458
aatggcagac                                                                         10

<210> SEQ ID NO 459
<211> LENGTH: 10
<212> TYPE: DNA
<213> ORGANISM: Artificial
<220> FEATURE:
<223> OTHER INFORMATION: synthetic DNA

<400> SEQUENCE: 459
gtataacgtg                                                                         10

<210> SEQ ID NO 460
<211> LENGTH: 10
<212> TYPE: DNA
<213> ORGANISM: Artificial
<220> FEATURE:
<223> OTHER INFORMATION: synthetic DNA

<400> SEQUENCE: 460
atgtgcgtca                                                                         10

<210> SEQ ID NO 461
<211> LENGTH: 10
<212> TYPE: DNA
<213> ORGANISM: Artificial
<220> FEATURE:
<223> OTHER INFORMATION: synthetic DNA

<400> SEQUENCE: 461
cctgccaact                                                                         10

<210> SEQ ID NO 462
<211> LENGTH: 10
<212> TYPE: DNA
<213> ORGANISM: Artificial

```
<220> FEATURE:
<223> OTHER INFORMATION: synthetic DNA

<400> SEQUENCE: 462
tttataactc                                                          10

<210> SEQ ID NO 463
<211> LENGTH: 10
<212> TYPE: DNA
<213> ORGANISM: Artificial
<220> FEATURE:
<223> OTHER INFORMATION: synthetic DNA

<400> SEQUENCE: 463
acggttacgc                                                          10

<210> SEQ ID NO 464
<211> LENGTH: 10
<212> TYPE: DNA
<213> ORGANISM: Artificial
<220> FEATURE:
<223> OTHER INFORMATION: synthetic DNA

<400> SEQUENCE: 464
tagcctcttg                                                          10

<210> SEQ ID NO 465
<211> LENGTH: 10
<212> TYPE: DNA
<213> ORGANISM: Artificial
<220> FEATURE:
<223> OTHER INFORMATION: synthetic DNA

<400> SEQUENCE: 465
tcgcgaagtt                                                          10

<210> SEQ ID NO 466
<211> LENGTH: 10
<212> TYPE: DNA
<213> ORGANISM: Artificial
<220> FEATURE:
<223> OTHER INFORMATION: synthetic DNA

<400> SEQUENCE: 466
gtctacaacc                                                          10

<210> SEQ ID NO 467
<211> LENGTH: 10
<212> TYPE: DNA
<213> ORGANISM: Artificial
<220> FEATURE:
<223> OTHER INFORMATION: synthetic DNA

<400> SEQUENCE: 467
gtctactgcg                                                          10

<210> SEQ ID NO 468
<211> LENGTH: 10
<212> TYPE: DNA
<213> ORGANISM: Artificial
<220> FEATURE:
<223> OTHER INFORMATION: synthetic DNA

<400> SEQUENCE: 468
gttgcgtctc                                                          10
```

```
<210> SEQ ID NO 469
<211> LENGTH: 10
<212> TYPE: DNA
<213> ORGANISM: Artificial
<220> FEATURE:
<223> OTHER INFORMATION: synthetic DNA

<400> SEQUENCE: 469
gggccgctaa                                                          10

<210> SEQ ID NO 470
<211> LENGTH: 10
<212> TYPE: DNA
<213> ORGANISM: Artificial
<220> FEATURE:
<223> OTHER INFORMATION: synthetic DNA

<400> SEQUENCE: 470
gtacgtcgga                                                          10

<210> SEQ ID NO 471
<211> LENGTH: 10
<212> TYPE: DNA
<213> ORGANISM: Artificial
<220> FEATURE:
<223> OTHER INFORMATION: synthetic DNA

<400> SEQUENCE: 471
agcgagagac                                                          10

<210> SEQ ID NO 472
<211> LENGTH: 10
<212> TYPE: DNA
<213> ORGANISM: Artificial
<220> FEATURE:
<223> OTHER INFORMATION: synthetic DNA

<400> SEQUENCE: 472
tggctacggt                                                          10

<210> SEQ ID NO 473
<211> LENGTH: 10
<212> TYPE: DNA
<213> ORGANISM: Artificial
<220> FEATURE:
<223> OTHER INFORMATION: synthetic DNA

<400> SEQUENCE: 473
aggcatcacg                                                          10

<210> SEQ ID NO 474
<211> LENGTH: 10
<212> TYPE: DNA
<213> ORGANISM: Artificial
<220> FEATURE:
<223> OTHER INFORMATION: synthetic DNA

<400> SEQUENCE: 474
tagctcctcg                                                          10

<210> SEQ ID NO 475
<211> LENGTH: 10
<212> TYPE: DNA
<213> ORGANISM: Artificial
<220> FEATURE:
<223> OTHER INFORMATION: synthetic DNA
```

```
<400> SEQUENCE: 475
ggctagtcag                                                              10

<210> SEQ ID NO 476
<211> LENGTH: 10
<212> TYPE: DNA
<213> ORGANISM: Artificial
<220> FEATURE:
<223> OTHER INFORMATION: synthetic DNA

<400> SEQUENCE: 476
ctcactttat                                                              10

<210> SEQ ID NO 477
<211> LENGTH: 10
<212> TYPE: DNA
<213> ORGANISM: Artificial
<220> FEATURE:
<223> OTHER INFORMATION: synthetic DNA

<400> SEQUENCE: 477
acggccacgt                                                              10

<210> SEQ ID NO 478
<211> LENGTH: 10
<212> TYPE: DNA
<213> ORGANISM: Artificial
<220> FEATURE:
<223> OTHER INFORMATION: synthetic DNA

<400> SEQUENCE: 478
agcgtatatc                                                              10

<210> SEQ ID NO 479
<211> LENGTH: 10
<212> TYPE: DNA
<213> ORGANISM: Artificial
<220> FEATURE:
<223> OTHER INFORMATION: synthetic DNA

<400> SEQUENCE: 479
gacacgtcta                                                              10

<210> SEQ ID NO 480
<211> LENGTH: 10
<212> TYPE: DNA
<213> ORGANISM: Artificial
<220> FEATURE:
<223> OTHER INFORMATION: synthetic DNA

<400> SEQUENCE: 480
gccagcgtac                                                              10

<210> SEQ ID NO 481
<211> LENGTH: 10
<212> TYPE: DNA
<213> ORGANISM: Artificial
<220> FEATURE:
<223> OTHER INFORMATION: synthetic DNA

<400> SEQUENCE: 481
aacattagcg                                                              10

<210> SEQ ID NO 482
```

```
<211> LENGTH: 10
<212> TYPE: DNA
<213> ORGANISM: Artificial
<220> FEATURE:
<223> OTHER INFORMATION: synthetic DNA

<400> SEQUENCE: 482
agtgtgctat                                                          10

<210> SEQ ID NO 483
<211> LENGTH: 10
<212> TYPE: DNA
<213> ORGANISM: Artificial
<220> FEATURE:
<223> OTHER INFORMATION: synthetic DNA

<400> SEQUENCE: 483
cacgagcgtt                                                          10

<210> SEQ ID NO 484
<211> LENGTH: 10
<212> TYPE: DNA
<213> ORGANISM: Artificial
<220> FEATURE:
<223> OTHER INFORMATION: synthetic DNA

<400> SEQUENCE: 484
gtaacgccta                                                          10

<210> SEQ ID NO 485
<211> LENGTH: 10
<212> TYPE: DNA
<213> ORGANISM: Artificial
<220> FEATURE:
<223> OTHER INFORMATION: synthetic DNA

<400> SEQUENCE: 485
cacatagtac                                                          10

<210> SEQ ID NO 486
<211> LENGTH: 10
<212> TYPE: DNA
<213> ORGANISM: Artificial
<220> FEATURE:
<223> OTHER INFORMATION: synthetic DNA

<400> SEQUENCE: 486
cgcgatatcg                                                          10

<210> SEQ ID NO 487
<211> LENGTH: 10
<212> TYPE: DNA
<213> ORGANISM: Artificial
<220> FEATURE:
<223> OTHER INFORMATION: synthetic DNA

<400> SEQUENCE: 487
cgttctgtgc                                                          10

<210> SEQ ID NO 488
<211> LENGTH: 10
<212> TYPE: DNA
<213> ORGANISM: Artificial
<220> FEATURE:
<223> OTHER INFORMATION: synthetic DNA

<400> SEQUENCE: 488
```
ctgatcgcat                                                          10

<210> SEQ ID NO 489
<211> LENGTH: 10
<212> TYPE: DNA
<213> ORGANISM: Artificial
<220> FEATURE:
<223> OTHER INFORMATION: synthetic DNA

<400> SEQUENCE: 489
tggcgtgaga                                                          10

<210> SEQ ID NO 490
<211> LENGTH: 10
<212> TYPE: DNA
<213> ORGANISM: Artificial
<220> FEATURE:
<223> OTHER INFORMATION: synthetic DNA

<400> SEQUENCE: 490
ttgccaggct                                                          10

<210> SEQ ID NO 491
<211> LENGTH: 10
<212> TYPE: DNA
<213> ORGANISM: Artificial
<220> FEATURE:
<223> OTHER INFORMATION: synthetic DNA

<400> SEQUENCE: 491
gttatacaca                                                          10

<210> SEQ ID NO 492
<211> LENGTH: 10
<212> TYPE: DNA
<213> ORGANISM: Artificial
<220> FEATURE:
<223> OTHER INFORMATION: synthetic DNA

<400> SEQUENCE: 492
agtgccaact                                                          10

<210> SEQ ID NO 493
<211> LENGTH: 10
<212> TYPE: DNA
<213> ORGANISM: Artificial
<220> FEATURE:
<223> OTHER INFORMATION: synthetic DNA

<400> SEQUENCE: 493
tcacgtagca                                                          10

<210> SEQ ID NO 494
<211> LENGTH: 10
<212> TYPE: DNA
<213> ORGANISM: Artificial
<220> FEATURE:
<223> OTHER INFORMATION: synthetic DNA

<400> SEQUENCE: 494
taattcagcg                                                          10

<210> SEQ ID NO 495
<211> LENGTH: 10
<212> TYPE: DNA

```
<213> ORGANISM: Artificial
<220> FEATURE:
<223> OTHER INFORMATION: synthetic DNA

<400> SEQUENCE: 495
aagtatcgtc                                                          10

<210> SEQ ID NO 496
<211> LENGTH: 10
<212> TYPE: DNA
<213> ORGANISM: Artificial
<220> FEATURE:
<223> OTHER INFORMATION: synthetic DNA

<400> SEQUENCE: 496
cacagttact                                                          10

<210> SEQ ID NO 497
<211> LENGTH: 10
<212> TYPE: DNA
<213> ORGANISM: Artificial
<220> FEATURE:
<223> OTHER INFORMATION: synthetic DNA

<400> SEQUENCE: 497
ccttaccgtg                                                          10

<210> SEQ ID NO 498
<211> LENGTH: 10
<212> TYPE: DNA
<213> ORGANISM: Artificial
<220> FEATURE:
<223> OTHER INFORMATION: synthetic DNA

<400> SEQUENCE: 498
acggtgtcgt                                                          10

<210> SEQ ID NO 499
<211> LENGTH: 10
<212> TYPE: DNA
<213> ORGANISM: Artificial
<220> FEATURE:
<223> OTHER INFORMATION: synthetic DNA

<400> SEQUENCE: 499
cgcgtaagac                                                          10

<210> SEQ ID NO 500
<211> LENGTH: 10
<212> TYPE: DNA
<213> ORGANISM: Artificial
<220> FEATURE:
<223> OTHER INFORMATION: synthetic DNA

<400> SEQUENCE: 500
ttcgcaccag                                                          10

<210> SEQ ID NO 501
<211> LENGTH: 10
<212> TYPE: DNA
<213> ORGANISM: Artificial
<220> FEATURE:
<223> OTHER INFORMATION: synthetic DNA

<400> SEQUENCE: 501
cacgaacaga                                                          10
```

```
<210> SEQ ID NO 502
<211> LENGTH: 10
<212> TYPE: DNA
<213> ORGANISM: Artificial
<220> FEATURE:
<223> OTHER INFORMATION: synthetic DNA

<400> SEQUENCE: 502
gttggacatt                                                          10

<210> SEQ ID NO 503
<211> LENGTH: 10
<212> TYPE: DNA
<213> ORGANISM: Artificial
<220> FEATURE:
<223> OTHER INFORMATION: synthetic DNA

<400> SEQUENCE: 503
ggtgcttaag                                                          10

<210> SEQ ID NO 504
<211> LENGTH: 10
<212> TYPE: DNA
<213> ORGANISM: Artificial
<220> FEATURE:
<223> OTHER INFORMATION: synthetic DNA

<400> SEQUENCE: 504
tcggtctcgt                                                          10

<210> SEQ ID NO 505
<211> LENGTH: 10
<212> TYPE: DNA
<213> ORGANISM: Artificial
<220> FEATURE:
<223> OTHER INFORMATION: synthetic DNA

<400> SEQUENCE: 505
tctagtacgc                                                          10

<210> SEQ ID NO 506
<211> LENGTH: 10
<212> TYPE: DNA
<213> ORGANISM: Artificial
<220> FEATURE:
<223> OTHER INFORMATION: synthetic DNA

<400> SEQUENCE: 506
ttaggccgag                                                          10

<210> SEQ ID NO 507
<211> LENGTH: 10
<212> TYPE: DNA
<213> ORGANISM: Artificial
<220> FEATURE:
<223> OTHER INFORMATION: synthetic DNA

<400> SEQUENCE: 507
cgtcaagagc                                                          10

<210> SEQ ID NO 508
<211> LENGTH: 10
<212> TYPE: DNA
<213> ORGANISM: Artificial
<220> FEATURE:
```

<223> OTHER INFORMATION: synthetic DNA

<400> SEQUENCE: 508
acatgtctac                                                          10

<210> SEQ ID NO 509
<211> LENGTH: 10
<212> TYPE: DNA
<213> ORGANISM: Artificial
<220> FEATURE:
<223> OTHER INFORMATION: synthetic DNA

<400> SEQUENCE: 509
atcgttacgt                                                          10

<210> SEQ ID NO 510
<211> LENGTH: 10
<212> TYPE: DNA
<213> ORGANISM: Artificial
<220> FEATURE:
<223> OTHER INFORMATION: synthetic DNA

<400> SEQUENCE: 510
acggatcgtt                                                          10

<210> SEQ ID NO 511
<211> LENGTH: 10
<212> TYPE: DNA
<213> ORGANISM: Artificial
<220> FEATURE:
<223> OTHER INFORMATION: synthetic DNA

<400> SEQUENCE: 511
aatcttggcg                                                          10

<210> SEQ ID NO 512
<211> LENGTH: 10
<212> TYPE: DNA
<213> ORGANISM: Artificial
<220> FEATURE:
<223> OTHER INFORMATION: synthetic DNA

<400> SEQUENCE: 512
agtatctggt                                                          10

<210> SEQ ID NO 513
<211> LENGTH: 10
<212> TYPE: DNA
<213> ORGANISM: Artificial
<220> FEATURE:
<223> OTHER INFORMATION: synthetic DNA

<400> SEQUENCE: 513
caaccgacgt                                                          10

<210> SEQ ID NO 514
<211> LENGTH: 10
<212> TYPE: DNA
<213> ORGANISM: Artificial
<220> FEATURE:
<223> OTHER INFORMATION: synthetic DNA

<400> SEQUENCE: 514
tggtaacgcg                                                          10

```
<210> SEQ ID NO 515
<211> LENGTH: 10
<212> TYPE: DNA
<213> ORGANISM: Artificial
<220> FEATURE:
<223> OTHER INFORMATION: synthetic DNA

<400> SEQUENCE: 515
gtgcagacat                                                            10

<210> SEQ ID NO 516
<211> LENGTH: 10
<212> TYPE: DNA
<213> ORGANISM: Artificial
<220> FEATURE:
<223> OTHER INFORMATION: synthetic DNA

<400> SEQUENCE: 516
gtctagttgc                                                            10

<210> SEQ ID NO 517
<211> LENGTH: 10
<212> TYPE: DNA
<213> ORGANISM: Artificial
<220> FEATURE:
<223> OTHER INFORMATION: synthetic DNA

<400> SEQUENCE: 517
caattcgacg                                                            10

<210> SEQ ID NO 518
<211> LENGTH: 10
<212> TYPE: DNA
<213> ORGANISM: Artificial
<220> FEATURE:
<223> OTHER INFORMATION: synthetic DNA

<400> SEQUENCE: 518
cttagcacct                                                            10

<210> SEQ ID NO 519
<211> LENGTH: 10
<212> TYPE: DNA
<213> ORGANISM: Artificial
<220> FEATURE:
<223> OTHER INFORMATION: synthetic DNA

<400> SEQUENCE: 519
taatgtcgca                                                            10

<210> SEQ ID NO 520
<211> LENGTH: 10
<212> TYPE: DNA
<213> ORGANISM: Artificial
<220> FEATURE:
<223> OTHER INFORMATION: synthetic DNA

<400> SEQUENCE: 520
caatcggtac                                                            10

<210> SEQ ID NO 521
<211> LENGTH: 10
<212> TYPE: DNA
<213> ORGANISM: Artificial
<220> FEATURE:
<223> OTHER INFORMATION: synthetic DNA
```

```
<400> SEQUENCE: 521
agcacgcatt                                                          10

<210> SEQ ID NO 522
<211> LENGTH: 10
<212> TYPE: DNA
<213> ORGANISM: Artificial
<220> FEATURE:
<223> OTHER INFORMATION: synthetic DNA

<400> SEQUENCE: 522
aggtcctcgt                                                          10

<210> SEQ ID NO 523
<211> LENGTH: 10
<212> TYPE: DNA
<213> ORGANISM: Artificial
<220> FEATURE:
<223> OTHER INFORMATION: synthetic DNA

<400> SEQUENCE: 523
ttgtgcctgc                                                          10

<210> SEQ ID NO 524
<211> LENGTH: 10
<212> TYPE: DNA
<213> ORGANISM: Artificial
<220> FEATURE:
<223> OTHER INFORMATION: synthetic DNA

<400> SEQUENCE: 524
accgcctgta                                                          10

<210> SEQ ID NO 525
<211> LENGTH: 10
<212> TYPE: DNA
<213> ORGANISM: Artificial
<220> FEATURE:
<223> OTHER INFORMATION: synthetic DNA

<400> SEQUENCE: 525
gtacgtcagg                                                          10

<210> SEQ ID NO 526
<211> LENGTH: 10
<212> TYPE: DNA
<213> ORGANISM: Artificial
<220> FEATURE:
<223> OTHER INFORMATION: synthetic DNA

<400> SEQUENCE: 526
gcacacaact                                                          10

<210> SEQ ID NO 527
<211> LENGTH: 10
<212> TYPE: DNA
<213> ORGANISM: Artificial
<220> FEATURE:
<223> OTHER INFORMATION: synthetic DNA

<400> SEQUENCE: 527
tgagcactta                                                          10

<210> SEQ ID NO 528
<211> LENGTH: 10
```

```
<212> TYPE: DNA
<213> ORGANISM: Artificial
<220> FEATURE:
<223> OTHER INFORMATION: synthetic DNA

<400> SEQUENCE: 528
gtgccgcata                                                          10

<210> SEQ ID NO 529
<211> LENGTH: 10
<212> TYPE: DNA
<213> ORGANISM: Artificial
<220> FEATURE:
<223> OTHER INFORMATION: synthetic DNA

<400> SEQUENCE: 529
atgttttcgc                                                          10

<210> SEQ ID NO 530
<211> LENGTH: 10
<212> TYPE: DNA
<213> ORGANISM: Artificial
<220> FEATURE:
<223> OTHER INFORMATION: synthetic DNA

<400> SEQUENCE: 530
acacttaggt                                                          10

<210> SEQ ID NO 531
<211> LENGTH: 10
<212> TYPE: DNA
<213> ORGANISM: Artificial
<220> FEATURE:
<223> OTHER INFORMATION: synthetic DNA

<400> SEQUENCE: 531
cgtgccgtga                                                          10

<210> SEQ ID NO 532
<211> LENGTH: 10
<212> TYPE: DNA
<213> ORGANISM: Artificial
<220> FEATURE:
<223> OTHER INFORMATION: synthetic DNA

<400> SEQUENCE: 532
ttactaatca                                                          10

<210> SEQ ID NO 533
<211> LENGTH: 10
<212> TYPE: DNA
<213> ORGANISM: Artificial
<220> FEATURE:
<223> OTHER INFORMATION: synthetic DNA

<400> SEQUENCE: 533
gtggcaggta                                                          10

<210> SEQ ID NO 534
<211> LENGTH: 10
<212> TYPE: DNA
<213> ORGANISM: Artificial
<220> FEATURE:
<223> OTHER INFORMATION: synthetic DNA

<400> SEQUENCE: 534
```
gcgcgatatg                                                                10

<210> SEQ ID NO 535
<211> LENGTH: 10
<212> TYPE: DNA
<213> ORGANISM: Artificial
<220> FEATURE:
<223> OTHER INFORMATION: synthetic DNA

<400> SEQUENCE: 535
gaacgacgtt                                                                10

<210> SEQ ID NO 536
<211> LENGTH: 10
<212> TYPE: DNA
<213> ORGANISM: Artificial
<220> FEATURE:
<223> OTHER INFORMATION: synthetic DNA

<400> SEQUENCE: 536
atcaggagtg                                                                10

<210> SEQ ID NO 537
<211> LENGTH: 10
<212> TYPE: DNA
<213> ORGANISM: Artificial
<220> FEATURE:
<223> OTHER INFORMATION: synthetic DNA

<400> SEQUENCE: 537
gccagtaagt                                                                10

<210> SEQ ID NO 538
<211> LENGTH: 10
<212> TYPE: DNA
<213> ORGANISM: Artificial
<220> FEATURE:
<223> OTHER INFORMATION: synthetic DNA

<400> SEQUENCE: 538
gcaagaagca                                                                10

<210> SEQ ID NO 539
<211> LENGTH: 10
<212> TYPE: DNA
<213> ORGANISM: Artificial
<220> FEATURE:
<223> OTHER INFORMATION: synthetic DNA

<400> SEQUENCE: 539
aactccgcca                                                                10

<210> SEQ ID NO 540
<211> LENGTH: 10
<212> TYPE: DNA
<213> ORGANISM: Artificial
<220> FEATURE:
<223> OTHER INFORMATION: synthetic DNA

<400> SEQUENCE: 540
acttgagcct                                                                10

<210> SEQ ID NO 541
<211> LENGTH: 10
<212> TYPE: DNA
<213> ORGANISM: Artificial

<220> FEATURE:
<223> OTHER INFORMATION: synthetic DNA

<400> SEQUENCE: 541
cgtgatcgtg                                                          10

<210> SEQ ID NO 542
<211> LENGTH: 10
<212> TYPE: DNA
<213> ORGANISM: Artificial
<220> FEATURE:
<223> OTHER INFORMATION: synthetic DNA

<400> SEQUENCE: 542
aattagcgaa                                                          10

<210> SEQ ID NO 543
<211> LENGTH: 10
<212> TYPE: DNA
<213> ORGANISM: Artificial
<220> FEATURE:
<223> OTHER INFORMATION: synthetic DNA

<400> SEQUENCE: 543
acttccttag                                                          10

<210> SEQ ID NO 544
<211> LENGTH: 10
<212> TYPE: DNA
<213> ORGANISM: Artificial
<220> FEATURE:
<223> OTHER INFORMATION: synthetic DNA

<400> SEQUENCE: 544
tgtgctgata                                                          10

<210> SEQ ID NO 545
<211> LENGTH: 10
<212> TYPE: DNA
<213> ORGANISM: Artificial
<220> FEATURE:
<223> OTHER INFORMATION: synthetic DNA

<400> SEQUENCE: 545
aggcggctga                                                          10

<210> SEQ ID NO 546
<211> LENGTH: 10
<212> TYPE: DNA
<213> ORGANISM: Artificial
<220> FEATURE:
<223> OTHER INFORMATION: synthetic DNA

<400> SEQUENCE: 546
cgtttagagc                                                          10

<210> SEQ ID NO 547
<211> LENGTH: 10
<212> TYPE: DNA
<213> ORGANISM: Artificial
<220> FEATURE:
<223> OTHER INFORMATION: synthetic DNA

<400> SEQUENCE: 547
acgcgtctaa                                                          10

```
<210> SEQ ID NO 548
<211> LENGTH: 10
<212> TYPE: DNA
<213> ORGANISM: Artificial
<220> FEATURE:
<223> OTHER INFORMATION: synthetic DNA

<400> SEQUENCE: 548
gcgaatgtac                                                          10

<210> SEQ ID NO 549
<211> LENGTH: 10
<212> TYPE: DNA
<213> ORGANISM: Artificial
<220> FEATURE:
<223> OTHER INFORMATION: synthetic DNA

<400> SEQUENCE: 549
cgtgatccaa                                                          10

<210> SEQ ID NO 550
<211> LENGTH: 10
<212> TYPE: DNA
<213> ORGANISM: Artificial
<220> FEATURE:
<223> OTHER INFORMATION: synthetic DNA

<400> SEQUENCE: 550
caaccagatg                                                          10

<210> SEQ ID NO 551
<211> LENGTH: 10
<212> TYPE: DNA
<213> ORGANISM: Artificial
<220> FEATURE:
<223> OTHER INFORMATION: synthetic DNA

<400> SEQUENCE: 551
accattaacc                                                          10

<210> SEQ ID NO 552
<211> LENGTH: 10
<212> TYPE: DNA
<213> ORGANISM: Artificial
<220> FEATURE:
<223> OTHER INFORMATION: synthetic DNA

<400> SEQUENCE: 552
cgattcacgt                                                          10

<210> SEQ ID NO 553
<211> LENGTH: 10
<212> TYPE: DNA
<213> ORGANISM: Artificial
<220> FEATURE:
<223> OTHER INFORMATION: synthetic DNA

<400> SEQUENCE: 553
ctagaacctg                                                          10

<210> SEQ ID NO 554
<211> LENGTH: 10
<212> TYPE: DNA
<213> ORGANISM: Artificial
<220> FEATURE:
<223> OTHER INFORMATION: synthetic DNA
```

```
<400> SEQUENCE: 554
cctaacgaca                                                              10

<210> SEQ ID NO 555
<211> LENGTH: 10
<212> TYPE: DNA
<213> ORGANISM: Artificial
<220> FEATURE:
<223> OTHER INFORMATION: synthetic DNA

<400> SEQUENCE: 555
gacgtgcatg                                                              10

<210> SEQ ID NO 556
<211> LENGTH: 10
<212> TYPE: DNA
<213> ORGANISM: Artificial
<220> FEATURE:
<223> OTHER INFORMATION: synthetic DNA

<400> SEQUENCE: 556
atgtaacctt                                                              10

<210> SEQ ID NO 557
<211> LENGTH: 10
<212> TYPE: DNA
<213> ORGANISM: Artificial
<220> FEATURE:
<223> OTHER INFORMATION: synthetic DNA

<400> SEQUENCE: 557
gatacagtcg                                                              10

<210> SEQ ID NO 558
<211> LENGTH: 10
<212> TYPE: DNA
<213> ORGANISM: Artificial
<220> FEATURE:
<223> OTHER INFORMATION: synthetic DNA

<400> SEQUENCE: 558
cgtatgtctc                                                              10

<210> SEQ ID NO 559
<211> LENGTH: 10
<212> TYPE: DNA
<213> ORGANISM: Artificial
<220> FEATURE:
<223> OTHER INFORMATION: synthetic DNA

<400> SEQUENCE: 559
agattatcga                                                              10

<210> SEQ ID NO 560
<211> LENGTH: 10
<212> TYPE: DNA
<213> ORGANISM: Artificial
<220> FEATURE:
<223> OTHER INFORMATION: synthetic DNA

<400> SEQUENCE: 560
atactggtaa                                                              10

<210> SEQ ID NO 561
```

```
<211> LENGTH: 10
<212> TYPE: DNA
<213> ORGANISM: Artificial
<220> FEATURE:
<223> OTHER INFORMATION: synthetic DNA

<400> SEQUENCE: 561
gttgagtagc                                                          10

<210> SEQ ID NO 562
<211> LENGTH: 10
<212> TYPE: DNA
<213> ORGANISM: Artificial
<220> FEATURE:
<223> OTHER INFORMATION: synthetic DNA

<400> SEQUENCE: 562
accattatca                                                          10

<210> SEQ ID NO 563
<211> LENGTH: 10
<212> TYPE: DNA
<213> ORGANISM: Artificial
<220> FEATURE:
<223> OTHER INFORMATION: synthetic DNA

<400> SEQUENCE: 563
cacacttcag                                                          10

<210> SEQ ID NO 564
<211> LENGTH: 10
<212> TYPE: DNA
<213> ORGANISM: Artificial
<220> FEATURE:
<223> OTHER INFORMATION: synthetic DNA

<400> SEQUENCE: 564
gactagcggt                                                          10

<210> SEQ ID NO 565
<211> LENGTH: 10
<212> TYPE: DNA
<213> ORGANISM: Artificial
<220> FEATURE:
<223> OTHER INFORMATION: synthetic DNA

<400> SEQUENCE: 565
aattgtcgag                                                          10

<210> SEQ ID NO 566
<211> LENGTH: 10
<212> TYPE: DNA
<213> ORGANISM: Artificial
<220> FEATURE:
<223> OTHER INFORMATION: synthetic DNA

<400> SEQUENCE: 566
ctaaggacgt                                                          10

<210> SEQ ID NO 567
<211> LENGTH: 10
<212> TYPE: DNA
<213> ORGANISM: Artificial
<220> FEATURE:
<223> OTHER INFORMATION: synthetic DNA

<400> SEQUENCE: 567
```

```
attacgatga                                                          10
```

<210> SEQ ID NO 568
<211> LENGTH: 10
<212> TYPE: DNA
<213> ORGANISM: Artificial
<220> FEATURE:
<223> OTHER INFORMATION: synthetic DNA

<400> SEQUENCE: 568

```
attgaagact                                                          10
```

<210> SEQ ID NO 569
<211> LENGTH: 10
<212> TYPE: DNA
<213> ORGANISM: Artificial
<220> FEATURE:
<223> OTHER INFORMATION: synthetic DNA

<400> SEQUENCE: 569

```
gcttgtacgt                                                          10
```

<210> SEQ ID NO 570
<211> LENGTH: 10
<212> TYPE: DNA
<213> ORGANISM: Artificial
<220> FEATURE:
<223> OTHER INFORMATION: synthetic DNA

<400> SEQUENCE: 570

```
cctacgtcac                                                          10
```

<210> SEQ ID NO 571
<211> LENGTH: 10
<212> TYPE: DNA
<213> ORGANISM: Artificial
<220> FEATURE:
<223> OTHER INFORMATION: synthetic DNA

<400> SEQUENCE: 571

```
cacaacttag                                                          10
```

<210> SEQ ID NO 572
<211> LENGTH: 10
<212> TYPE: DNA
<213> ORGANISM: Artificial
<220> FEATURE:
<223> OTHER INFORMATION: synthetic DNA

<400> SEQUENCE: 572

```
gcggttcatc                                                          10
```

<210> SEQ ID NO 573
<211> LENGTH: 10
<212> TYPE: DNA
<213> ORGANISM: Artificial
<220> FEATURE:
<223> OTHER INFORMATION: synthetic DNA

<400> SEQUENCE: 573

```
gtactcatct                                                          10
```

<210> SEQ ID NO 574
<211> LENGTH: 10
<212> TYPE: DNA

```
<213> ORGANISM: Artificial
<220> FEATURE:
<223> OTHER INFORMATION: synthetic DNA

<400> SEQUENCE: 574
gtgcatcagt                                                          10

<210> SEQ ID NO 575
<211> LENGTH: 10
<212> TYPE: DNA
<213> ORGANISM: Artificial
<220> FEATURE:
<223> OTHER INFORMATION: synthetic DNA

<400> SEQUENCE: 575
tcacatccta                                                          10

<210> SEQ ID NO 576
<211> LENGTH: 10
<212> TYPE: DNA
<213> ORGANISM: Artificial
<220> FEATURE:
<223> OTHER INFORMATION: synthetic DNA

<400> SEQUENCE: 576
cacgcgctat                                                          10

<210> SEQ ID NO 577
<211> LENGTH: 8
<212> TYPE: DNA
<213> ORGANISM: Artificial
<220> FEATURE:
<223> OTHER INFORMATION: synthetic DNA

<400> SEQUENCE: 577 ctatcttg                                                             8

<210> SEQ ID NO 578
<211> LENGTH: 8
<212> TYPE: DNA
<213> ORGANISM: Artificial
<220> FEATURE:
<223> OTHER INFORMATION: synthetic DNA

<400> SEQUENCE: 578 aagtgcgt                                                             8

<210> SEQ ID NO 579
<211> LENGTH: 8
<212> TYPE: DNA
<213> ORGANISM: Artificial
<220> FEATURE:
<223> OTHER INFORMATION: synthetic DNA

<400> SEQUENCE: 579 acatgcga                                                             8

<210> SEQ ID NO 580
<211> LENGTH: 8
<212> TYPE: DNA
<213> ORGANISM: Artificial
<220> FEATURE:
<223> OTHER INFORMATION: synthetic DNA

<400> SEQUENCE: 580 accaatgg                                                             8
```

```
<210> SEQ ID NO 581
<211> LENGTH: 8
<212> TYPE: DNA
<213> ORGANISM: Artificial
<220> FEATURE:
<223> OTHER INFORMATION: synthetic DNA

<400> SEQUENCE: 581 tgcgttga                                                              8

<210> SEQ ID NO 582
<211> LENGTH: 8
<212> TYPE: DNA
<213> ORGANISM: Artificial
<220> FEATURE:
<223> OTHER INFORMATION: synthetic DNA

<400> SEQUENCE: 582 gacatgtc                                                              8

<210> SEQ ID NO 583
<211> LENGTH: 8
<212> TYPE: DNA
<213> ORGANISM: Artificial
<220> FEATURE:
<223> OTHER INFORMATION: synthetic DNA

<400> SEQUENCE: 583 ttgtgcgt                                                              8

<210> SEQ ID NO 584
<211> LENGTH: 8
<212> TYPE: DNA
<213> ORGANISM: Artificial
<220> FEATURE:
<223> OTHER INFORMATION: synthetic DNA

<400> SEQUENCE: 584 acatcgca                                                              8

<210> SEQ ID NO 585
<211> LENGTH: 8
<212> TYPE: DNA
<213> ORGANISM: Artificial
<220> FEATURE:
<223> OTHER INFORMATION: synthetic DNA

<400> SEQUENCE: 585 gaagacga                                                              8

<210> SEQ ID NO 586
<211> LENGTH: 8
<212> TYPE: DNA
<213> ORGANISM: Artificial
<220> FEATURE:
<223> OTHER INFORMATION: synthetic DNA

<400> SEQUENCE: 586 tcgataga                                                              8

<210> SEQ ID NO 587
<211> LENGTH: 8
<212> TYPE: DNA
<213> ORGANISM: Artificial
<220> FEATURE:
```

<223> OTHER INFORMATION: synthetic DNA

<400> SEQUENCE: 587 tcttgcaa                                                                    8

<210> SEQ ID NO 588
<211> LENGTH: 8
<212> TYPE: DNA
<213> ORGANISM: Artificial
<220> FEATURE:
<223> OTHER INFORMATION: synthetic DNA

<400> SEQUENCE: 588 agcaagtt                                                                    8

<210> SEQ ID NO 589
<211> LENGTH: 8
<212> TYPE: DNA
<213> ORGANISM: Artificial
<220> FEATURE:
<223> OTHER INFORMATION: synthetic DNA

<400> SEQUENCE: 589 ttcatgga                                                                    8

<210> SEQ ID NO 590
<211> LENGTH: 8
<212> TYPE: DNA
<213> ORGANISM: Artificial
<220> FEATURE:
<223> OTHER INFORMATION: synthetic DNA

<400> SEQUENCE: 590 tcaattcg                                                                    8

<210> SEQ ID NO 591
<211> LENGTH: 8
<212> TYPE: DNA
<213> ORGANISM: Artificial
<220> FEATURE:
<223> OTHER INFORMATION: synthetic DNA

<400> SEQUENCE: 591 cggtatgt                                                                    8

<210> SEQ ID NO 592
<211> LENGTH: 8
<212> TYPE: DNA
<213> ORGANISM: Artificial
<220> FEATURE:
<223> OTHER INFORMATION: synthetic DNA

<400> SEQUENCE: 592 accactac                                                                    8

<210> SEQ ID NO 593
<211> LENGTH: 8
<212> TYPE: DNA
<213> ORGANISM: Artificial
<220> FEATURE:
<223> OTHER INFORMATION: synthetic DNA

<400> SEQUENCE: 593 tcgcttat                                                                    8

-continued

```
<210> SEQ ID NO 594
<211> LENGTH: 8
<212> TYPE: DNA
<213> ORGANISM: Artificial
<220> FEATURE:
<223> OTHER INFORMATION: synthetic DNA

<400> SEQUENCE: 594 tctcgact                                                                   8

<210> SEQ ID NO 595
<211> LENGTH: 8
<212> TYPE: DNA
<213> ORGANISM: Artificial
<220> FEATURE:
<223> OTHER INFORMATION: synthetic DNA

<400> SEQUENCE: 595 gaatcggt                                                                   8

<210> SEQ ID NO 596
<211> LENGTH: 8
<212> TYPE: DNA
<213> ORGANISM: Artificial
<220> FEATURE:
<223> OTHER INFORMATION: synthetic DNA

<400> SEQUENCE: 596 gttacaag                                                                   8

<210> SEQ ID NO 597
<211> LENGTH: 8
<212> TYPE: DNA
<213> ORGANISM: Artificial
<220> FEATURE:
<223> OTHER INFORMATION: synthetic DNA

<400> SEQUENCE: 597 ctgtgtag                                                                   8

<210> SEQ ID NO 598
<211> LENGTH: 8
<212> TYPE: DNA
<213> ORGANISM: Artificial
<220> FEATURE:
<223> OTHER INFORMATION: synthetic DNA

<400> SEQUENCE: 598 tggtagaa                                                                   8

<210> SEQ ID NO 599
<211> LENGTH: 8
<212> TYPE: DNA
<213> ORGANISM: Artificial
<220> FEATURE:
<223> OTHER INFORMATION: synthetic DNA

<400> SEQUENCE: 599 atactgcg                                                                   8

<210> SEQ ID NO 600
<211> LENGTH: 8
<212> TYPE: DNA
<213> ORGANISM: Artificial
<220> FEATURE:
<223> OTHER INFORMATION: synthetic DNA
```

```
<400> SEQUENCE: 600 aactcgtc                                                             8

<210> SEQ ID NO 601
<211> LENGTH: 8
<212> TYPE: DNA
<213> ORGANISM: Artificial
<220> FEATURE:
<223> OTHER INFORMATION: synthetic DNA

<400> SEQUENCE: 601 atatgtgc                                                             8

<210> SEQ ID NO 602
<211> LENGTH: 8
<212> TYPE: DNA
<213> ORGANISM: Artificial
<220> FEATURE:
<223> OTHER INFORMATION: synthetic DNA

<400> SEQUENCE: 602 aagttgcg                                                             8

<210> SEQ ID NO 603
<211> LENGTH: 8
<212> TYPE: DNA
<213> ORGANISM: Artificial
<220> FEATURE:
<223> OTHER INFORMATION: synthetic DNA

<400> SEQUENCE: 603 gatcatgt                                                             8

<210> SEQ ID NO 604
<211> LENGTH: 8
<212> TYPE: DNA
<213> ORGANISM: Artificial
<220> FEATURE:
<223> OTHER INFORMATION: synthetic DNA

<400> SEQUENCE: 604 ttgttgct                                                             8

<210> SEQ ID NO 605
<211> LENGTH: 8
<212> TYPE: DNA
<213> ORGANISM: Artificial
<220> FEATURE:
<223> OTHER INFORMATION: synthetic DNA

<400> SEQUENCE: 605 cctcttag                                                             8

<210> SEQ ID NO 606
<211> LENGTH: 8
<212> TYPE: DNA
<213> ORGANISM: Artificial
<220> FEATURE:
<223> OTHER INFORMATION: synthetic DNA

<400> SEQUENCE: 606 tcacagct                                                             8

<210> SEQ ID NO 607
<211> LENGTH: 8
```

```
<212> TYPE: DNA
<213> ORGANISM: Artificial
<220> FEATURE:
<223> OTHER INFORMATION: synthetic DNA

<400> SEQUENCE: 607 agattgac                                                                 8

<210> SEQ ID NO 608
<211> LENGTH: 8
<212> TYPE: DNA
<213> ORGANISM: Artificial
<220> FEATURE:
<223> OTHER INFORMATION: synthetic DNA

<400> SEQUENCE: 608 agcctgat                                                                 8

<210> SEQ ID NO 609
<211> LENGTH: 8
<212> TYPE: DNA
<213> ORGANISM: Artificial
<220> FEATURE:
<223> OTHER INFORMATION: synthetic DNA

<400> SEQUENCE: 609 cgtcaagt                                                                 8

<210> SEQ ID NO 610
<211> LENGTH: 8
<212> TYPE: DNA
<213> ORGANISM: Artificial
<220> FEATURE:
<223> OTHER INFORMATION: synthetic DNA

<400> SEQUENCE: 610 aagtagac                                                                 8

<210> SEQ ID NO 611
<211> LENGTH: 8
<212> TYPE: DNA
<213> ORGANISM: Artificial
<220> FEATURE:
<223> OTHER INFORMATION: synthetic DNA

<400> SEQUENCE: 611 tcagacaa                                                                 8

<210> SEQ ID NO 612
<211> LENGTH: 8
<212> TYPE: DNA
<213> ORGANISM: Artificial
<220> FEATURE:
<223> OTHER INFORMATION: synthetic DNA

<400> SEQUENCE: 612 tccttgac                                                                 8

<210> SEQ ID NO 613
<211> LENGTH: 8
<212> TYPE: DNA
<213> ORGANISM: Artificial
<220> FEATURE:
<223> OTHER INFORMATION: synthetic DNA

<400> SEQUENCE: 613
``` gtagctgt 8

<210> SEQ ID NO 614
<211> LENGTH: 8
<212> TYPE: DNA
<213> ORGANISM: Artificial
<220> FEATURE:
<223> OTHER INFORMATION: synthetic DNA

<400> SEQUENCE: 614 cgtcgtaa 8

<210> SEQ ID NO 615
<211> LENGTH: 8
<212> TYPE: DNA
<213> ORGANISM: Artificial
<220> FEATURE:
<223> OTHER INFORMATION: synthetic DNA

<400> SEQUENCE: 615 ccaatgga 8

<210> SEQ ID NO 616
<211> LENGTH: 8
<212> TYPE: DNA
<213> ORGANISM: Artificial
<220> FEATURE:
<223> OTHER INFORMATION: synthetic DNA

<400> SEQUENCE: 616 ttgagaga 8

<210> SEQ ID NO 617
<211> LENGTH: 8
<212> TYPE: DNA
<213> ORGANISM: Artificial
<220> FEATURE:
<223> OTHER INFORMATION: synthetic DNA

<400> SEQUENCE: 617 acaacacc 8

<210> SEQ ID NO 618
<211> LENGTH: 8
<212> TYPE: DNA
<213> ORGANISM: Artificial
<220> FEATURE:
<223> OTHER INFORMATION: synthetic DNA

<400> SEQUENCE: 618 tctagtac 8

<210> SEQ ID NO 619
<211> LENGTH: 8
<212> TYPE: DNA
<213> ORGANISM: Artificial
<220> FEATURE:
<223> OTHER INFORMATION: synthetic DNA

<400> SEQUENCE: 619 gaggaagt 8

<210> SEQ ID NO 620
<211> LENGTH: 8
<212> TYPE: DNA
<213> ORGANISM: Artificial

```
<220> FEATURE:
<223> OTHER INFORMATION: synthetic DNA

<400> SEQUENCE: 620 gcgtattg                                                                 8

<210> SEQ ID NO 621
<211> LENGTH: 8
<212> TYPE: DNA
<213> ORGANISM: Artificial
<220> FEATURE:
<223> OTHER INFORMATION: synthetic DNA

<400> SEQUENCE: 621 aagtagct                                                                 8

<210> SEQ ID NO 622
<211> LENGTH: 8
<212> TYPE: DNA
<213> ORGANISM: Artificial
<220> FEATURE:
<223> OTHER INFORMATION: synthetic DNA

<400> SEQUENCE: 622 tgaacctt                                                                 8

<210> SEQ ID NO 623
<211> LENGTH: 8
<212> TYPE: DNA
<213> ORGANISM: Artificial
<220> FEATURE:
<223> OTHER INFORMATION: synthetic DNA

<400> SEQUENCE: 623 tgtgttac                                                                 8

<210> SEQ ID NO 624
<211> LENGTH: 8
<212> TYPE: DNA
<213> ORGANISM: Artificial
<220> FEATURE:
<223> OTHER INFORMATION: synthetic DNA

<400> SEQUENCE: 624 taacctga                                                                 8

<210> SEQ ID NO 625
<211> LENGTH: 8
<212> TYPE: DNA
<213> ORGANISM: Artificial
<220> FEATURE:
<223> OTHER INFORMATION: synthetic DNA

<400> SEQUENCE: 625 gctattcc                                                                 8

<210> SEQ ID NO 626
<211> LENGTH: 8
<212> TYPE: DNA
<213> ORGANISM: Artificial
<220> FEATURE:
<223> OTHER INFORMATION: synthetic DNA

<400> SEQUENCE: 626 gttagatg                                                                 8
```

```
<210> SEQ ID NO 627
<211> LENGTH: 8
<212> TYPE: DNA
<213> ORGANISM: Artificial
<220> FEATURE:
<223> OTHER INFORMATION: synthetic DNA

<400> SEQUENCE: 627 caggataa                                                                8

<210> SEQ ID NO 628
<211> LENGTH: 8
<212> TYPE: DNA
<213> ORGANISM: Artificial
<220> FEATURE:
<223> OTHER INFORMATION: synthetic DNA

<400> SEQUENCE: 628 accgtagt                                                                8

<210> SEQ ID NO 629
<211> LENGTH: 8
<212> TYPE: DNA
<213> ORGANISM: Artificial
<220> FEATURE:
<223> OTHER INFORMATION: synthetic DNA

<400> SEQUENCE: 629 ccgtgtat                                                                8

<210> SEQ ID NO 630
<211> LENGTH: 8
<212> TYPE: DNA
<213> ORGANISM: Artificial
<220> FEATURE:
<223> OTHER INFORMATION: synthetic DNA

<400> SEQUENCE: 630 tccactct                                                                8

<210> SEQ ID NO 631
<211> LENGTH: 8
<212> TYPE: DNA
<213> ORGANISM: Artificial
<220> FEATURE:
<223> OTHER INFORMATION: synthetic DNA

<400> SEQUENCE: 631 tagctcat                                                                8

<210> SEQ ID NO 632
<211> LENGTH: 8
<212> TYPE: DNA
<213> ORGANISM: Artificial
<220> FEATURE:
<223> OTHER INFORMATION: synthetic DNA

<400> SEQUENCE: 632 cgctaata                                                                8

<210> SEQ ID NO 633
<211> LENGTH: 8
<212> TYPE: DNA
<213> ORGANISM: Artificial
<220> FEATURE:
<223> OTHER INFORMATION: synthetic DNA
```

```
<400> SEQUENCE: 633 tacctctg                                                              8

<210> SEQ ID NO 634
<211> LENGTH: 8
<212> TYPE: DNA
<213> ORGANISM: Artificial
<220> FEATURE:
<223> OTHER INFORMATION: synthetic DNA

<400> SEQUENCE: 634 tgcactac                                                              8

<210> SEQ ID NO 635
<211> LENGTH: 8
<212> TYPE: DNA
<213> ORGANISM: Artificial
<220> FEATURE:
<223> OTHER INFORMATION: synthetic DNA

<400> SEQUENCE: 635 cttggaag                                                              8

<210> SEQ ID NO 636
<211> LENGTH: 8
<212> TYPE: DNA
<213> ORGANISM: Artificial
<220> FEATURE:
<223> OTHER INFORMATION: synthetic DNA

<400> SEQUENCE: 636 aatgcacg                                                              8

<210> SEQ ID NO 637
<211> LENGTH: 8
<212> TYPE: DNA
<213> ORGANISM: Artificial
<220> FEATURE:
<223> OTHER INFORMATION: synthetic DNA

<400> SEQUENCE: 637 cactgtta                                                              8

<210> SEQ ID NO 638
<211> LENGTH: 8
<212> TYPE: DNA
<213> ORGANISM: Artificial
<220> FEATURE:
<223> OTHER INFORMATION: synthetic DNA

<400> SEQUENCE: 638 tcgactag                                                              8

<210> SEQ ID NO 639
<211> LENGTH: 8
<212> TYPE: DNA
<213> ORGANISM: Artificial
<220> FEATURE:
<223> OTHER INFORMATION: synthetic DNA

<400> SEQUENCE: 639 ctaggtta                                                              8

<210> SEQ ID NO 640
```

```
<211> LENGTH: 8
<212> TYPE: DNA
<213> ORGANISM: Artificial
<220> FEATURE:
<223> OTHER INFORMATION: synthetic DNA

<400> SEQUENCE: 640 gcagatgt                                                                   8

<210> SEQ ID NO 641
<211> LENGTH: 8
<212> TYPE: DNA
<213> ORGANISM: Artificial
<220> FEATURE:
<223> OTHER INFORMATION: synthetic DNA

<400> SEQUENCE: 641 agttcaga                                                                   8

<210> SEQ ID NO 642
<211> LENGTH: 8
<212> TYPE: DNA
<213> ORGANISM: Artificial
<220> FEATURE:
<223> OTHER INFORMATION: synthetic DNA

<400> SEQUENCE: 642 ctccatca                                                                   8

<210> SEQ ID NO 643
<211> LENGTH: 8
<212> TYPE: DNA
<213> ORGANISM: Artificial
<220> FEATURE:
<223> OTHER INFORMATION: synthetic DNA

<400> SEQUENCE: 643 tggttacg                                                                   8

<210> SEQ ID NO 644
<211> LENGTH: 8
<212> TYPE: DNA
<213> ORGANISM: Artificial
<220> FEATURE:
<223> OTHER INFORMATION: synthetic DNA

<400> SEQUENCE: 644 acgtagca                                                                   8

<210> SEQ ID NO 645
<211> LENGTH: 8
<212> TYPE: DNA
<213> ORGANISM: Artificial
<220> FEATURE:
<223> OTHER INFORMATION: synthetic DNA

<400> SEQUENCE: 645 ctcttcca                                                                   8

<210> SEQ ID NO 646
<211> LENGTH: 8
<212> TYPE: DNA
<213> ORGANISM: Artificial
<220> FEATURE:
<223> OTHER INFORMATION: synthetic DNA

<400> SEQUENCE: 646
``` cgtcagat                                                                8

<210> SEQ ID NO 647
<211> LENGTH: 8
<212> TYPE: DNA
<213> ORGANISM: Artificial
<220> FEATURE:
<223> OTHER INFORMATION: synthetic DNA

<400> SEQUENCE: 647 tggatcat                                                                8

<210> SEQ ID NO 648
<211> LENGTH: 8
<212> TYPE: DNA
<213> ORGANISM: Artificial
<220> FEATURE:
<223> OTHER INFORMATION: synthetic DNA

<400> SEQUENCE: 648 atatcgac                                                                8

<210> SEQ ID NO 649
<211> LENGTH: 8
<212> TYPE: DNA
<213> ORGANISM: Artificial
<220> FEATURE:
<223> OTHER INFORMATION: synthetic DNA

<400> SEQUENCE: 649 ttgtggag                                                                8

<210> SEQ ID NO 650
<211> LENGTH: 8
<212> TYPE: DNA
<213> ORGANISM: Artificial
<220> FEATURE:
<223> OTHER INFORMATION: synthetic DNA

<400> SEQUENCE: 650 ttagagca                                                                8

<210> SEQ ID NO 651
<211> LENGTH: 8
<212> TYPE: DNA
<213> ORGANISM: Artificial
<220> FEATURE:
<223> OTHER INFORMATION: synthetic DNA

<400> SEQUENCE: 651 taactacc                                                                8

<210> SEQ ID NO 652
<211> LENGTH: 8
<212> TYPE: DNA
<213> ORGANISM: Artificial
<220> FEATURE:
<223> OTHER INFORMATION: synthetic DNA

<400> SEQUENCE: 652 ctatgagg                                                                8

<210> SEQ ID NO 653
<211> LENGTH: 8
<212> TYPE: DNA

```
<213> ORGANISM: Artificial
<220> FEATURE:
<223> OTHER INFORMATION: synthetic DNA

<400> SEQUENCE: 653 cttctcac                                                                8

<210> SEQ ID NO 654
<211> LENGTH: 8
<212> TYPE: DNA
<213> ORGANISM: Artificial
<220> FEATURE:
<223> OTHER INFORMATION: synthetic DNA

<400> SEQUENCE: 654 cgttctct                                                                8

<210> SEQ ID NO 655
<211> LENGTH: 8
<212> TYPE: DNA
<213> ORGANISM: Artificial
<220> FEATURE:
<223> OTHER INFORMATION: synthetic DNA

<400> SEQUENCE: 655 gtcactat                                                                8

<210> SEQ ID NO 656
<211> LENGTH: 8
<212> TYPE: DNA
<213> ORGANISM: Artificial
<220> FEATURE:
<223> OTHER INFORMATION: synthetic DNA

<400> SEQUENCE: 656 tcgttagc                                                                8

<210> SEQ ID NO 657
<211> LENGTH: 8
<212> TYPE: DNA
<213> ORGANISM: Artificial
<220> FEATURE:
<223> OTHER INFORMATION: synthetic DNA

<400> SEQUENCE: 657 atcgtgta                                                                8

<210> SEQ ID NO 658
<211> LENGTH: 8
<212> TYPE: DNA
<213> ORGANISM: Artificial
<220> FEATURE:
<223> OTHER INFORMATION: synthetic DNA

<400> SEQUENCE: 658 gagagcaa                                                                8

<210> SEQ ID NO 659
<211> LENGTH: 8
<212> TYPE: DNA
<213> ORGANISM: Artificial
<220> FEATURE:
<223> OTHER INFORMATION: synthetic DNA

<400> SEQUENCE: 659 agacgcaa                                                                8
```

<210> SEQ ID NO 660
<211> LENGTH: 8
<212> TYPE: DNA
<213> ORGANISM: Artificial
<220> FEATURE:
<223> OTHER INFORMATION: synthetic DNA

<400> SEQUENCE: 660 tccagtta                                                                8

<210> SEQ ID NO 661
<211> LENGTH: 8
<212> TYPE: DNA
<213> ORGANISM: Artificial
<220> FEATURE:
<223> OTHER INFORMATION: synthetic DNA

<400> SEQUENCE: 661 aatgccac                                                                8

<210> SEQ ID NO 662
<211> LENGTH: 8
<212> TYPE: DNA
<213> ORGANISM: Artificial
<220> FEATURE:
<223> OTHER INFORMATION: synthetic DNA

<400> SEQUENCE: 662 atcacgtg                                                                8

<210> SEQ ID NO 663
<211> LENGTH: 8
<212> TYPE: DNA
<213> ORGANISM: Artificial
<220> FEATURE:
<223> OTHER INFORMATION: synthetic DNA

<400> SEQUENCE: 663 actgtgca                                                                8

<210> SEQ ID NO 664
<211> LENGTH: 8
<212> TYPE: DNA
<213> ORGANISM: Artificial
<220> FEATURE:
<223> OTHER INFORMATION: synthetic DNA

<400> SEQUENCE: 664 tcactgca                                                                8

<210> SEQ ID NO 665
<211> LENGTH: 8
<212> TYPE: DNA
<213> ORGANISM: Artificial
<220> FEATURE:
<223> OTHER INFORMATION: synthetic DNA

<400> SEQUENCE: 665 gcatccaa                                                                8

<210> SEQ ID NO 666
<211> LENGTH: 8
<212> TYPE: DNA
<213> ORGANISM: Artificial
<220> FEATURE:

<223> OTHER INFORMATION: synthetic DNA

<400> SEQUENCE: 666 agcactat                                                                  8

<210> SEQ ID NO 667
<211> LENGTH: 8
<212> TYPE: DNA
<213> ORGANISM: Artificial
<220> FEATURE:
<223> OTHER INFORMATION: synthetic DNA

<400> SEQUENCE: 667 cgaaggat                                                                  8

<210> SEQ ID NO 668
<211> LENGTH: 8
<212> TYPE: DNA
<213> ORGANISM: Artificial
<220> FEATURE:
<223> OTHER INFORMATION: synthetic DNA

<400> SEQUENCE: 668 ccttgtgt                                                                  8

<210> SEQ ID NO 669
<211> LENGTH: 8
<212> TYPE: DNA
<213> ORGANISM: Artificial
<220> FEATURE:
<223> OTHER INFORMATION: synthetic DNA

<400> SEQUENCE: 669 tgcggata                                                                  8

<210> SEQ ID NO 670
<211> LENGTH: 8
<212> TYPE: DNA
<213> ORGANISM: Artificial
<220> FEATURE:
<223> OTHER INFORMATION: synthetic DNA

<400> SEQUENCE: 670 aggaatgg                                                                  8

<210> SEQ ID NO 671
<211> LENGTH: 8
<212> TYPE: DNA
<213> ORGANISM: Artificial
<220> FEATURE:
<223> OTHER INFORMATION: synthetic DNA

<400> SEQUENCE: 671 atcgtaac                                                                  8

<210> SEQ ID NO 672
<211> LENGTH: 8
<212> TYPE: DNA
<213> ORGANISM: Artificial
<220> FEATURE:
<223> OTHER INFORMATION: synthetic DNA

<400> SEQUENCE: 672 gaatgtct                                                                  8

```
<210> SEQ ID NO 673
<211> LENGTH: 9
<212> TYPE: DNA
<213> ORGANISM: Artificial
<220> FEATURE:
<223> OTHER INFORMATION: synthetic DNA

<400> SEQUENCE: 673 ttgctacat                                                              9

<210> SEQ ID NO 674
<211> LENGTH: 9
<212> TYPE: DNA
<213> ORGANISM: Artificial
<220> FEATURE:
<223> OTHER INFORMATION: synthetic DNA

<400> SEQUENCE: 674 taacgtatg                                                              9

<210> SEQ ID NO 675
<211> LENGTH: 9
<212> TYPE: DNA
<213> ORGANISM: Artificial
<220> FEATURE:
<223> OTHER INFORMATION: synthetic DNA

<400> SEQUENCE: 675 cagtatgta                                                              9

<210> SEQ ID NO 676
<211> LENGTH: 9
<212> TYPE: DNA
<213> ORGANISM: Artificial
<220> FEATURE:
<223> OTHER INFORMATION: synthetic DNA

<400> SEQUENCE: 676 tcaataacg                                                              9

<210> SEQ ID NO 677
<211> LENGTH: 9
<212> TYPE: DNA
<213> ORGANISM: Artificial
<220> FEATURE:
<223> OTHER INFORMATION: synthetic DNA

<400> SEQUENCE: 677 cacacttat                                                              9

<210> SEQ ID NO 678
<211> LENGTH: 9
<212> TYPE: DNA
<213> ORGANISM: Artificial
<220> FEATURE:
<223> OTHER INFORMATION: synthetic DNA

<400> SEQUENCE: 678 gactgtaat                                                              9

<210> SEQ ID NO 679
<211> LENGTH: 9
<212> TYPE: DNA
<213> ORGANISM: Artificial
<220> FEATURE:
<223> OTHER INFORMATION: synthetic DNA
```

<400> SEQUENCE: 679 tatacactg                                                                9

<210> SEQ ID NO 680
<211> LENGTH: 9
<212> TYPE: DNA
<213> ORGANISM: Artificial
<220> FEATURE:
<223> OTHER INFORMATION: synthetic DNA

<400> SEQUENCE: 680 actgcatta                                                                9

<210> SEQ ID NO 681
<211> LENGTH: 9
<212> TYPE: DNA
<213> ORGANISM: Artificial
<220> FEATURE:
<223> OTHER INFORMATION: synthetic DNA

<400> SEQUENCE: 681 acattaagc                                                                9

<210> SEQ ID NO 682
<211> LENGTH: 9
<212> TYPE: DNA
<213> ORGANISM: Artificial
<220> FEATURE:
<223> OTHER INFORMATION: synthetic DNA

<400> SEQUENCE: 682 catattacg                                                                9

<210> SEQ ID NO 683
<211> LENGTH: 9
<212> TYPE: DNA
<213> ORGANISM: Artificial
<220> FEATURE:
<223> OTHER INFORMATION: synthetic DNA

<400> SEQUENCE: 683 atatctacg                                                                9

<210> SEQ ID NO 684
<211> LENGTH: 9
<212> TYPE: DNA
<213> ORGANISM: Artificial
<220> FEATURE:
<223> OTHER INFORMATION: synthetic DNA

<400> SEQUENCE: 684 agtaactgt                                                                9

<210> SEQ ID NO 685
<211> LENGTH: 9
<212> TYPE: DNA
<213> ORGANISM: Artificial
<220> FEATURE:
<223> OTHER INFORMATION: synthetic DNA

<400> SEQUENCE: 685 atgacgtta                                                                9

<210> SEQ ID NO 686
<211> LENGTH: 9

```
<212> TYPE: DNA
<213> ORGANISM: Artificial
<220> FEATURE:
<223> OTHER INFORMATION: synthetic DNA

<400> SEQUENCE: 686 attatgcga                                                               9

<210> SEQ ID NO 687
<211> LENGTH: 9
<212> TYPE: DNA
<213> ORGANISM: Artificial
<220> FEATURE:
<223> OTHER INFORMATION: synthetic DNA

<400> SEQUENCE: 687 agtatacac                                                               9

<210> SEQ ID NO 688
<211> LENGTH: 9
<212> TYPE: DNA
<213> ORGANISM: Artificial
<220> FEATURE:
<223> OTHER INFORMATION: synthetic DNA

<400> SEQUENCE: 688 ttagcgtta                                                               9

<210> SEQ ID NO 689
<211> LENGTH: 9
<212> TYPE: DNA
<213> ORGANISM: Artificial
<220> FEATURE:
<223> OTHER INFORMATION: synthetic DNA

<400> SEQUENCE: 689 tatgacact                                                               9

<210> SEQ ID NO 690
<211> LENGTH: 9
<212> TYPE: DNA
<213> ORGANISM: Artificial
<220> FEATURE:
<223> OTHER INFORMATION: synthetic DNA

<400> SEQUENCE: 690 attaacgct                                                               9

<210> SEQ ID NO 691
<211> LENGTH: 9
<212> TYPE: DNA
<213> ORGANISM: Artificial
<220> FEATURE:
<223> OTHER INFORMATION: synthetic DNA

<400> SEQUENCE: 691 taggacaat                                                               9

<210> SEQ ID NO 692
<211> LENGTH: 9
<212> TYPE: DNA
<213> ORGANISM: Artificial
<220> FEATURE:
<223> OTHER INFORMATION: synthetic DNA

<400> SEQUENCE: 692
``` aagacgtta 9

<210> SEQ ID NO 693
<211> LENGTH: 9
<212> TYPE: DNA
<213> ORGANISM: Artificial
<220> FEATURE:
<223> OTHER INFORMATION: synthetic DNA

<400> SEQUENCE: 693 tataagcgt 9

<210> SEQ ID NO 694
<211> LENGTH: 9
<212> TYPE: DNA
<213> ORGANISM: Artificial
<220> FEATURE:
<223> OTHER INFORMATION: synthetic DNA

<400> SEQUENCE: 694 atacctggc 9

<210> SEQ ID NO 695
<211> LENGTH: 9
<212> TYPE: DNA
<213> ORGANISM: Artificial
<220> FEATURE:
<223> OTHER INFORMATION: synthetic DNA

<400> SEQUENCE: 695 ctcgagatc 9

<210> SEQ ID NO 696
<211> LENGTH: 9
<212> TYPE: DNA
<213> ORGANISM: Artificial
<220> FEATURE:
<223> OTHER INFORMATION: synthetic DNA

<400> SEQUENCE: 696 atggtgagg 9

<210> SEQ ID NO 697
<211> LENGTH: 9
<212> TYPE: DNA
<213> ORGANISM: Artificial
<220> FEATURE:
<223> OTHER INFORMATION: synthetic DNA

<400> SEQUENCE: 697 atgtcgacg 9

<210> SEQ ID NO 698
<211> LENGTH: 9
<212> TYPE: DNA
<213> ORGANISM: Artificial
<220> FEATURE:
<223> OTHER INFORMATION: synthetic DNA

<400> SEQUENCE: 698 gacgtctga 9

<210> SEQ ID NO 699
<211> LENGTH: 9
<212> TYPE: DNA
<213> ORGANISM: Artificial

```
<220> FEATURE:
<223> OTHER INFORMATION: synthetic DNA

<400> SEQUENCE: 699 tacactgcg                                                                    9

<210> SEQ ID NO 700
<211> LENGTH: 9
<212> TYPE: DNA
<213> ORGANISM: Artificial
<220> FEATURE:
<223> OTHER INFORMATION: synthetic DNA

<400> SEQUENCE: 700 atcgtcagg                                                                    9

<210> SEQ ID NO 701
<211> LENGTH: 9
<212> TYPE: DNA
<213> ORGANISM: Artificial
<220> FEATURE:
<223> OTHER INFORMATION: synthetic DNA

<400> SEQUENCE: 701 tgcacgtac                                                                    9

<210> SEQ ID NO 702
<211> LENGTH: 9
<212> TYPE: DNA
<213> ORGANISM: Artificial
<220> FEATURE:
<223> OTHER INFORMATION: synthetic DNA

<400> SEQUENCE: 702 gtcgtgcat                                                                    9

<210> SEQ ID NO 703
<211> LENGTH: 9
<212> TYPE: DNA
<213> ORGANISM: Artificial
<220> FEATURE:
<223> OTHER INFORMATION: synthetic DNA

<400> SEQUENCE: 703 gagtgttac                                                                    9

<210> SEQ ID NO 704
<211> LENGTH: 9
<212> TYPE: DNA
<213> ORGANISM: Artificial
<220> FEATURE:
<223> OTHER INFORMATION: synthetic DNA

<400> SEQUENCE: 704 agactgtac                                                                    9

<210> SEQ ID NO 705
<211> LENGTH: 9
<212> TYPE: DNA
<213> ORGANISM: Artificial
<220> FEATURE:
<223> OTHER INFORMATION: synthetic DNA

<400> SEQUENCE: 705 tgcgactta                                                                    9
```

<210> SEQ ID NO 706
<211> LENGTH: 9
<212> TYPE: DNA
<213> ORGANISM: Artificial
<220> FEATURE:
<223> OTHER INFORMATION: synthetic DNA

<400> SEQUENCE: 706 tgtccgtaa                                                                 9

<210> SEQ ID NO 707
<211> LENGTH: 9
<212> TYPE: DNA
<213> ORGANISM: Artificial
<220> FEATURE:
<223> OTHER INFORMATION: synthetic DNA

<400> SEQUENCE: 707 gtaatcgag                                                                 9

<210> SEQ ID NO 708
<211> LENGTH: 9
<212> TYPE: DNA
<213> ORGANISM: Artificial
<220> FEATURE:
<223> OTHER INFORMATION: synthetic DNA

<400> SEQUENCE: 708 gtaccttag                                                                 9

<210> SEQ ID NO 709
<211> LENGTH: 9
<212> TYPE: DNA
<213> ORGANISM: Artificial
<220> FEATURE:
<223> OTHER INFORMATION: synthetic DNA

<400> SEQUENCE: 709 atcacgtgt                                                                 9

<210> SEQ ID NO 710
<211> LENGTH: 9
<212> TYPE: DNA
<213> ORGANISM: Artificial
<220> FEATURE:
<223> OTHER INFORMATION: synthetic DNA

<400> SEQUENCE: 710 acttagcgt                                                                 9

<210> SEQ ID NO 711
<211> LENGTH: 9
<212> TYPE: DNA
<213> ORGANISM: Artificial
<220> FEATURE:
<223> OTHER INFORMATION: synthetic DNA

<400> SEQUENCE: 711 gtaatcgtg                                                                 9

<210> SEQ ID NO 712
<211> LENGTH: 9
<212> TYPE: DNA
<213> ORGANISM: Artificial
<220> FEATURE:
<223> OTHER INFORMATION: synthetic DNA

```
<400> SEQUENCE: 712 atgccgtta                                                          9

<210> SEQ ID NO 713
<211> LENGTH: 9
<212> TYPE: DNA
<213> ORGANISM: Artificial
<220> FEATURE:
<223> OTHER INFORMATION: synthetic DNA

<400> SEQUENCE: 713 ataacgtgc                                                          9

<210> SEQ ID NO 714
<211> LENGTH: 9
<212> TYPE: DNA
<213> ORGANISM: Artificial
<220> FEATURE:
<223> OTHER INFORMATION: synthetic DNA

<400> SEQUENCE: 714 ctacgttgt                                                          9

<210> SEQ ID NO 715
<211> LENGTH: 9
<212> TYPE: DNA
<213> ORGANISM: Artificial
<220> FEATURE:
<223> OTHER INFORMATION: synthetic DNA

<400> SEQUENCE: 715 tatgacgca                                                          9

<210> SEQ ID NO 716
<211> LENGTH: 9
<212> TYPE: DNA
<213> ORGANISM: Artificial
<220> FEATURE:
<223> OTHER INFORMATION: synthetic DNA

<400> SEQUENCE: 716 ccgataaca                                                          9

<210> SEQ ID NO 717
<211> LENGTH: 9
<212> TYPE: DNA
<213> ORGANISM: Artificial
<220> FEATURE:
<223> OTHER INFORMATION: synthetic DNA

<400> SEQUENCE: 717 atgcgcata                                                          9

<210> SEQ ID NO 718
<211> LENGTH: 9
<212> TYPE: DNA
<213> ORGANISM: Artificial
<220> FEATURE:
<223> OTHER INFORMATION: synthetic DNA

<400> SEQUENCE: 718 gataagcgt                                                          9

<210> SEQ ID NO 719
```

```
<211> LENGTH: 9
<212> TYPE: DNA
<213> ORGANISM: Artificial
<220> FEATURE:
<223> OTHER INFORMATION: synthetic DNA

<400> SEQUENCE: 719 atatctgcg                                                                 9

<210> SEQ ID NO 720
<211> LENGTH: 9
<212> TYPE: DNA
<213> ORGANISM: Artificial
<220> FEATURE:
<223> OTHER INFORMATION: synthetic DNA

<400> SEQUENCE: 720 acttagacg                                                                 9

<210> SEQ ID NO 721
<211> LENGTH: 9
<212> TYPE: DNA
<213> ORGANISM: Artificial
<220> FEATURE:
<223> OTHER INFORMATION: synthetic DNA

<400> SEQUENCE: 721 atcaccgta                                                                 9

<210> SEQ ID NO 722
<211> LENGTH: 9
<212> TYPE: DNA
<213> ORGANISM: Artificial
<220> FEATURE:
<223> OTHER INFORMATION: synthetic DNA

<400> SEQUENCE: 722 taagacacg                                                                 9

<210> SEQ ID NO 723
<211> LENGTH: 9
<212> TYPE: DNA
<213> ORGANISM: Artificial
<220> FEATURE:
<223> OTHER INFORMATION: synthetic DNA

<400> SEQUENCE: 723 aatgccgta                                                                 9

<210> SEQ ID NO 724
<211> LENGTH: 9
<212> TYPE: DNA
<213> ORGANISM: Artificial
<220> FEATURE:
<223> OTHER INFORMATION: synthetic DNA

<400> SEQUENCE: 724 aatcacgtg                                                                 9

<210> SEQ ID NO 725
<211> LENGTH: 9
<212> TYPE: DNA
<213> ORGANISM: Artificial
<220> FEATURE:
<223> OTHER INFORMATION: synthetic DNA

<400> SEQUENCE: 725
```

```
tcgttagtc                                                             9

<210> SEQ ID NO 726
<211> LENGTH: 9
<212> TYPE: DNA
<213> ORGANISM: Artificial
<220> FEATURE:
<223> OTHER INFORMATION: synthetic DNA

<400> SEQUENCE: 726 catcatgtc                                                             9

<210> SEQ ID NO 727
<211> LENGTH: 9
<212> TYPE: DNA
<213> ORGANISM: Artificial
<220> FEATURE:
<223> OTHER INFORMATION: synthetic DNA

<400> SEQUENCE: 727 taagacggt                                                             9

<210> SEQ ID NO 728
<211> LENGTH: 9
<212> TYPE: DNA
<213> ORGANISM: Artificial
<220> FEATURE:
<223> OTHER INFORMATION: synthetic DNA

<400> SEQUENCE: 728 tgcatagtg                                                             9

<210> SEQ ID NO 729
<211> LENGTH: 9
<212> TYPE: DNA
<213> ORGANISM: Artificial
<220> FEATURE:
<223> OTHER INFORMATION: synthetic DNA

<400> SEQUENCE: 729 gagcgttat                                                             9

<210> SEQ ID NO 730
<211> LENGTH: 9
<212> TYPE: DNA
<213> ORGANISM: Artificial
<220> FEATURE:
<223> OTHER INFORMATION: synthetic DNA

<400> SEQUENCE: 730 tgccttaca                                                             9

<210> SEQ ID NO 731
<211> LENGTH: 9
<212> TYPE: DNA
<213> ORGANISM: Artificial
<220> FEATURE:
<223> OTHER INFORMATION: synthetic DNA

<400> SEQUENCE: 731 ttcgcgtta                                                             9

<210> SEQ ID NO 732
<211> LENGTH: 9
<212> TYPE: DNA
```

```
<213> ORGANISM: Artificial
<220> FEATURE:
<223> OTHER INFORMATION: synthetic DNA

<400> SEQUENCE: 732 gtgttaacg                                                           9

<210> SEQ ID NO 733
<211> LENGTH: 9
<212> TYPE: DNA
<213> ORGANISM: Artificial
<220> FEATURE:
<223> OTHER INFORMATION: synthetic DNA

<400> SEQUENCE: 733 gacactgaa                                                           9

<210> SEQ ID NO 734
<211> LENGTH: 9
<212> TYPE: DNA
<213> ORGANISM: Artificial
<220> FEATURE:
<223> OTHER INFORMATION: synthetic DNA

<400> SEQUENCE: 734 ctgttatcg                                                           9

<210> SEQ ID NO 735
<211> LENGTH: 9
<212> TYPE: DNA
<213> ORGANISM: Artificial
<220> FEATURE:
<223> OTHER INFORMATION: synthetic DNA

<400> SEQUENCE: 735 ggtcgttat                                                           9

<210> SEQ ID NO 736
<211> LENGTH: 9
<212> TYPE: DNA
<213> ORGANISM: Artificial
<220> FEATURE:
<223> OTHER INFORMATION: synthetic DNA

<400> SEQUENCE: 736 cgagagtat                                                           9

<210> SEQ ID NO 737
<211> LENGTH: 9
<212> TYPE: DNA
<213> ORGANISM: Artificial
<220> FEATURE:
<223> OTHER INFORMATION: synthetic DNA

<400> SEQUENCE: 737 atacagtcc                                                           9

<210> SEQ ID NO 738
<211> LENGTH: 9
<212> TYPE: DNA
<213> ORGANISM: Artificial
<220> FEATURE:
<223> OTHER INFORMATION: synthetic DNA

<400> SEQUENCE: 738 aattcacgc                                                           9
```

```
<210> SEQ ID NO 739
<211> LENGTH: 9
<212> TYPE: DNA
<213> ORGANISM: Artificial
<220> FEATURE:
<223> OTHER INFORMATION: synthetic DNA

<400> SEQUENCE: 739 tatgtgcac                                                                9

<210> SEQ ID NO 740
<211> LENGTH: 9
<212> TYPE: DNA
<213> ORGANISM: Artificial
<220> FEATURE:
<223> OTHER INFORMATION: synthetic DNA

<400> SEQUENCE: 740 gatgacgta                                                                9

<210> SEQ ID NO 741
<211> LENGTH: 9
<212> TYPE: DNA
<213> ORGANISM: Artificial
<220> FEATURE:
<223> OTHER INFORMATION: synthetic DNA

<400> SEQUENCE: 741 gatgcgata                                                                9

<210> SEQ ID NO 742
<211> LENGTH: 9
<212> TYPE: DNA
<213> ORGANISM: Artificial
<220> FEATURE:
<223> OTHER INFORMATION: synthetic DNA

<400> SEQUENCE: 742 gagcgatta                                                                9

<210> SEQ ID NO 743
<211> LENGTH: 9
<212> TYPE: DNA
<213> ORGANISM: Artificial
<220> FEATURE:
<223> OTHER INFORMATION: synthetic DNA

<400> SEQUENCE: 743 tgtcacaga                                                                9

<210> SEQ ID NO 744
<211> LENGTH: 9
<212> TYPE: DNA
<213> ORGANISM: Artificial
<220> FEATURE:
<223> OTHER INFORMATION: synthetic DNA

<400> SEQUENCE: 744 tactaaccg                                                                9

<210> SEQ ID NO 745
<211> LENGTH: 9
<212> TYPE: DNA
<213> ORGANISM: Artificial
<220> FEATURE:
```

```
<223> OTHER INFORMATION: synthetic DNA

<400> SEQUENCE: 745 cataacgag                                                                  9

<210> SEQ ID NO 746
<211> LENGTH: 9
<212> TYPE: DNA
<213> ORGANISM: Artificial
<220> FEATURE:
<223> OTHER INFORMATION: synthetic DNA

<400> SEQUENCE: 746 cgtatacct                                                                  9

<210> SEQ ID NO 747
<211> LENGTH: 9
<212> TYPE: DNA
<213> ORGANISM: Artificial
<220> FEATURE:
<223> OTHER INFORMATION: synthetic DNA

<400> SEQUENCE: 747 tatcacgtg                                                                  9

<210> SEQ ID NO 748
<211> LENGTH: 9
<212> TYPE: DNA
<213> ORGANISM: Artificial
<220> FEATURE:
<223> OTHER INFORMATION: synthetic DNA

<400> SEQUENCE: 748 gaacgttac                                                                  9

<210> SEQ ID NO 749
<211> LENGTH: 9
<212> TYPE: DNA
<213> ORGANISM: Artificial
<220> FEATURE:
<223> OTHER INFORMATION: synthetic DNA

<400> SEQUENCE: 749 gtcgtatac                                                                  9

<210> SEQ ID NO 750
<211> LENGTH: 9
<212> TYPE: DNA
<213> ORGANISM: Artificial
<220> FEATURE:
<223> OTHER INFORMATION: synthetic DNA

<400> SEQUENCE: 750 atgtcgaca                                                                  9

<210> SEQ ID NO 751
<211> LENGTH: 9
<212> TYPE: DNA
<213> ORGANISM: Artificial
<220> FEATURE:
<223> OTHER INFORMATION: synthetic DNA

<400> SEQUENCE: 751 atacagcac                                                                  9
```

```
<210> SEQ ID NO 752
<211> LENGTH: 9
<212> TYPE: DNA
<213> ORGANISM: Artificial
<220> FEATURE:
<223> OTHER INFORMATION: synthetic DNA

<400> SEQUENCE: 752 tacttacgc                                                                 9

<210> SEQ ID NO 753
<211> LENGTH: 9
<212> TYPE: DNA
<213> ORGANISM: Artificial
<220> FEATURE:
<223> OTHER INFORMATION: synthetic DNA

<400> SEQUENCE: 753 aactacggt                                                                 9

<210> SEQ ID NO 754
<211> LENGTH: 9
<212> TYPE: DNA
<213> ORGANISM: Artificial
<220> FEATURE:
<223> OTHER INFORMATION: synthetic DNA

<400> SEQUENCE: 754 tagaacggt                                                                 9

<210> SEQ ID NO 755
<211> LENGTH: 9
<212> TYPE: DNA
<213> ORGANISM: Artificial
<220> FEATURE:
<223> OTHER INFORMATION: synthetic DNA

<400> SEQUENCE: 755 gaatgtcac                                                                 9

<210> SEQ ID NO 756
<211> LENGTH: 9
<212> TYPE: DNA
<213> ORGANISM: Artificial
<220> FEATURE:
<223> OTHER INFORMATION: synthetic DNA

<400> SEQUENCE: 756 tgtacgtct                                                                 9

<210> SEQ ID NO 757
<211> LENGTH: 9
<212> TYPE: DNA
<213> ORGANISM: Artificial
<220> FEATURE:
<223> OTHER INFORMATION: synthetic DNA

<400> SEQUENCE: 757 aacattgcg                                                                 9

<210> SEQ ID NO 758
<211> LENGTH: 9
<212> TYPE: DNA
<213> ORGANISM: Artificial
<220> FEATURE:
<223> OTHER INFORMATION: synthetic DNA
```

```
<400> SEQUENCE: 758 ttgaacgct                                                                9

<210> SEQ ID NO 759
<211> LENGTH: 9
<212> TYPE: DNA
<213> ORGANISM: Artificial
<220> FEATURE:
<223> OTHER INFORMATION: synthetic DNA

<400> SEQUENCE: 759 aatcaggac                                                                9

<210> SEQ ID NO 760
<211> LENGTH: 9
<212> TYPE: DNA
<213> ORGANISM: Artificial
<220> FEATURE:
<223> OTHER INFORMATION: synthetic DNA

<400> SEQUENCE: 760 attcgcaca                                                                9

<210> SEQ ID NO 761
<211> LENGTH: 9
<212> TYPE: DNA
<213> ORGANISM: Artificial
<220> FEATURE:
<223> OTHER INFORMATION: synthetic DNA

<400> SEQUENCE: 761 ccatgtact                                                                9

<210> SEQ ID NO 762
<211> LENGTH: 9
<212> TYPE: DNA
<213> ORGANISM: Artificial
<220> FEATURE:
<223> OTHER INFORMATION: synthetic DNA

<400> SEQUENCE: 762 tgtcctgtt                                                                9

<210> SEQ ID NO 763
<211> LENGTH: 9
<212> TYPE: DNA
<213> ORGANISM: Artificial
<220> FEATURE:
<223> OTHER INFORMATION: synthetic DNA

<400> SEQUENCE: 763 taattgcgc                                                                9

<210> SEQ ID NO 764
<211> LENGTH: 9
<212> TYPE: DNA
<213> ORGANISM: Artificial
<220> FEATURE:
<223> OTHER INFORMATION: synthetic DNA

<400> SEQUENCE: 764 gatagtgtg                                                                9

<210> SEQ ID NO 765
<211> LENGTH: 9
```

-continued

```
<212> TYPE: DNA
<213> ORGANISM: Artificial
<220> FEATURE:
<223> OTHER INFORMATION: synthetic DNA

<400> SEQUENCE: 765 atagacgca                                                            9

<210> SEQ ID NO 766
<211> LENGTH: 9
<212> TYPE: DNA
<213> ORGANISM: Artificial
<220> FEATURE:
<223> OTHER INFORMATION: synthetic DNA

<400> SEQUENCE: 766 tgtaccgtt                                                            9

<210> SEQ ID NO 767
<211> LENGTH: 9
<212> TYPE: DNA
<213> ORGANISM: Artificial
<220> FEATURE:
<223> OTHER INFORMATION: synthetic DNA

<400> SEQUENCE: 767 attgtcgca                                                            9

<210> SEQ ID NO 768
<211> LENGTH: 9
<212> TYPE: DNA
<213> ORGANISM: Artificial
<220> FEATURE:
<223> OTHER INFORMATION: synthetic DNA

<400> SEQUENCE: 768 gtcacgtaa                                                            9

<210> SEQ ID NO 769
<211> LENGTH: 11
<212> TYPE: DNA
<213> ORGANISM: Artificial
<220> FEATURE:
<223> OTHER INFORMATION: synthetic DNA

<400> SEQUENCE: 769
ttacactatg c                                                        11

<210> SEQ ID NO 770
<211> LENGTH: 11
<212> TYPE: DNA
<213> ORGANISM: Artificial
<220> FEATURE:
<223> OTHER INFORMATION: synthetic DNA

<400> SEQUENCE: 770
gcgatagtcg t                                                        11

<210> SEQ ID NO 771
<211> LENGTH: 11
<212> TYPE: DNA
<213> ORGANISM: Artificial
<220> FEATURE:
<223> OTHER INFORMATION: synthetic DNA

<400> SEQUENCE: 771
```
ctattcacag t                                                           11

<210> SEQ ID NO 772
<211> LENGTH: 11
<212> TYPE: DNA
<213> ORGANISM: Artificial
<220> FEATURE:
<223> OTHER INFORMATION: synthetic DNA

<400> SEQUENCE: 772
agagtcactg t                                                           11

<210> SEQ ID NO 773
<211> LENGTH: 11
<212> TYPE: DNA
<213> ORGANISM: Artificial
<220> FEATURE:
<223> OTHER INFORMATION: synthetic DNA

<400> SEQUENCE: 773
agagtcgaag c                                                           11

<210> SEQ ID NO 774
<211> LENGTH: 11
<212> TYPE: DNA
<213> ORGANISM: Artificial
<220> FEATURE:
<223> OTHER INFORMATION: synthetic DNA

<400> SEQUENCE: 774
ctgaatatgt g                                                           11

<210> SEQ ID NO 775
<211> LENGTH: 11
<212> TYPE: DNA
<213> ORGANISM: Artificial
<220> FEATURE:
<223> OTHER INFORMATION: synthetic DNA

<400> SEQUENCE: 775
actccacagg a                                                           11

<210> SEQ ID NO 776
<211> LENGTH: 11
<212> TYPE: DNA
<213> ORGANISM: Artificial
<220> FEATURE:
<223> OTHER INFORMATION: synthetic DNA

<400> SEQUENCE: 776
atcctcgtaa g                                                           11

<210> SEQ ID NO 777
<211> LENGTH: 11
<212> TYPE: DNA
<213> ORGANISM: Artificial
<220> FEATURE:
<223> OTHER INFORMATION: synthetic DNA

<400> SEQUENCE: 777
taccatcgcc t                                                           11

<210> SEQ ID NO 778
<211> LENGTH: 11
<212> TYPE: DNA
<213> ORGANISM: Artificial

```
<220> FEATURE:
<223> OTHER INFORMATION: synthetic DNA

<400> SEQUENCE: 778
aacgcctata a                                                          11

<210> SEQ ID NO 779
<211> LENGTH: 11
<212> TYPE: DNA
<213> ORGANISM: Artificial
<220> FEATURE:
<223> OTHER INFORMATION: synthetic DNA

<400> SEQUENCE: 779
ctgtcgaact t                                                          11

<210> SEQ ID NO 780
<211> LENGTH: 11
<212> TYPE: DNA
<213> ORGANISM: Artificial
<220> FEATURE:
<223> OTHER INFORMATION: synthetic DNA

<400> SEQUENCE: 780
tcagatgtcc g                                                          11

<210> SEQ ID NO 781
<211> LENGTH: 11
<212> TYPE: DNA
<213> ORGANISM: Artificial
<220> FEATURE:
<223> OTHER INFORMATION: synthetic DNA

<400> SEQUENCE: 781
ctgcttatcg t                                                          11

<210> SEQ ID NO 782
<211> LENGTH: 11
<212> TYPE: DNA
<213> ORGANISM: Artificial
<220> FEATURE:
<223> OTHER INFORMATION: synthetic DNA

<400> SEQUENCE: 782
acattcgcac a                                                          11

<210> SEQ ID NO 783
<211> LENGTH: 11
<212> TYPE: DNA
<213> ORGANISM: Artificial
<220> FEATURE:
<223> OTHER INFORMATION: synthetic DNA

<400> SEQUENCE: 783
ccttaatgca t                                                          11

<210> SEQ ID NO 784
<211> LENGTH: 11
<212> TYPE: DNA
<213> ORGANISM: Artificial
<220> FEATURE:
<223> OTHER INFORMATION: synthetic DNA

<400> SEQUENCE: 784
ggctagctac t                                                          11
```

```
<210> SEQ ID NO 785
<211> LENGTH: 11
<212> TYPE: DNA
<213> ORGANISM: Artificial
<220> FEATURE:
<223> OTHER INFORMATION: synthetic DNA

<400> SEQUENCE: 785
ttccagttgg c                                                            11

<210> SEQ ID NO 786
<211> LENGTH: 11
<212> TYPE: DNA
<213> ORGANISM: Artificial
<220> FEATURE:
<223> OTHER INFORMATION: synthetic DNA

<400> SEQUENCE: 786
gagtcacaag g                                                            11

<210> SEQ ID NO 787
<211> LENGTH: 11
<212> TYPE: DNA
<213> ORGANISM: Artificial
<220> FEATURE:
<223> OTHER INFORMATION: synthetic DNA

<400> SEQUENCE: 787
cagaaggttc a                                                            11

<210> SEQ ID NO 788
<211> LENGTH: 11
<212> TYPE: DNA
<213> ORGANISM: Artificial
<220> FEATURE:
<223> OTHER INFORMATION: synthetic DNA

<400> SEQUENCE: 788
tcaacgtgca g                                                            11

<210> SEQ ID NO 789
<211> LENGTH: 11
<212> TYPE: DNA
<213> ORGANISM: Artificial
<220> FEATURE:
<223> OTHER INFORMATION: synthetic DNA

<400> SEQUENCE: 789
caagcttact a                                                            11

<210> SEQ ID NO 790
<211> LENGTH: 11
<212> TYPE: DNA
<213> ORGANISM: Artificial
<220> FEATURE:
<223> OTHER INFORMATION: synthetic DNA

<400> SEQUENCE: 790
agaactcgtt g                                                            11

<210> SEQ ID NO 791
<211> LENGTH: 11
<212> TYPE: DNA
<213> ORGANISM: Artificial
<220> FEATURE:
<223> OTHER INFORMATION: synthetic DNA
```

```
<400> SEQUENCE: 791
ccgatacaga g                                                              11

<210> SEQ ID NO 792
<211> LENGTH: 11
<212> TYPE: DNA
<213> ORGANISM: Artificial
<220> FEATURE:
<223> OTHER INFORMATION: synthetic DNA

<400> SEQUENCE: 792
gtacgctgat c                                                              11

<210> SEQ ID NO 793
<211> LENGTH: 11
<212> TYPE: DNA
<213> ORGANISM: Artificial
<220> FEATURE:
<223> OTHER INFORMATION: synthetic DNA

<400> SEQUENCE: 793
tcctcagtga a                                                              11

<210> SEQ ID NO 794
<211> LENGTH: 11
<212> TYPE: DNA
<213> ORGANISM: Artificial
<220> FEATURE:
<223> OTHER INFORMATION: synthetic DNA

<400> SEQUENCE: 794
gagccaacat t                                                              11

<210> SEQ ID NO 795
<211> LENGTH: 11
<212> TYPE: DNA
<213> ORGANISM: Artificial
<220> FEATURE:
<223> OTHER INFORMATION: synthetic DNA

<400> SEQUENCE: 795
gagatcgatg g                                                              11

<210> SEQ ID NO 796
<211> LENGTH: 11
<212> TYPE: DNA
<213> ORGANISM: Artificial
<220> FEATURE:
<223> OTHER INFORMATION: synthetic DNA

<400> SEQUENCE: 796
atcgtcagct g                                                              11

<210> SEQ ID NO 797
<211> LENGTH: 11
<212> TYPE: DNA
<213> ORGANISM: Artificial
<220> FEATURE:
<223> OTHER INFORMATION: synthetic DNA

<400> SEQUENCE: 797
gaagcacacg t                                                              11

<210> SEQ ID NO 798
```

```
<211> LENGTH: 11
<212> TYPE: DNA
<213> ORGANISM: Artificial
<220> FEATURE:
<223> OTHER INFORMATION: synthetic DNA

<400> SEQUENCE: 798
atcacgcaac c                                                          11

<210> SEQ ID NO 799
<211> LENGTH: 11
<212> TYPE: DNA
<213> ORGANISM: Artificial
<220> FEATURE:
<223> OTHER INFORMATION: synthetic DNA

<400> SEQUENCE: 799
tcgaatagtc g                                                          11

<210> SEQ ID NO 800
<211> LENGTH: 11
<212> TYPE: DNA
<213> ORGANISM: Artificial
<220> FEATURE:
<223> OTHER INFORMATION: synthetic DNA

<400> SEQUENCE: 800
tattaccgtc t                                                          11

<210> SEQ ID NO 801
<211> LENGTH: 11
<212> TYPE: DNA
<213> ORGANISM: Artificial
<220> FEATURE:
<223> OTHER INFORMATION: synthetic DNA

<400> SEQUENCE: 801
cagtcacgac a                                                          11

<210> SEQ ID NO 802
<211> LENGTH: 11
<212> TYPE: DNA
<213> ORGANISM: Artificial
<220> FEATURE:
<223> OTHER INFORMATION: synthetic DNA

<400> SEQUENCE: 802
ttactcgacg t                                                          11

<210> SEQ ID NO 803
<211> LENGTH: 11
<212> TYPE: DNA
<213> ORGANISM: Artificial
<220> FEATURE:
<223> OTHER INFORMATION: synthetic DNA

<400> SEQUENCE: 803
gcaatgttga a                                                          11

<210> SEQ ID NO 804
<211> LENGTH: 11
<212> TYPE: DNA
<213> ORGANISM: Artificial
<220> FEATURE:
<223> OTHER INFORMATION: synthetic DNA

<400> SEQUENCE: 804
```
gacacgagca a                                      11

<210> SEQ ID NO 805
<211> LENGTH: 11
<212> TYPE: DNA
<213> ORGANISM: Artificial
<220> FEATURE:
<223> OTHER INFORMATION: synthetic DNA

<400> SEQUENCE: 805
cgagattaca a                                      11

<210> SEQ ID NO 806
<211> LENGTH: 11
<212> TYPE: DNA
<213> ORGANISM: Artificial
<220> FEATURE:
<223> OTHER INFORMATION: synthetic DNA

<400> SEQUENCE: 806
taccgactac a                                      11

<210> SEQ ID NO 807
<211> LENGTH: 11
<212> TYPE: DNA
<213> ORGANISM: Artificial
<220> FEATURE:
<223> OTHER INFORMATION: synthetic DNA

<400> SEQUENCE: 807
accgttgcca t                                      11

<210> SEQ ID NO 808
<211> LENGTH: 11
<212> TYPE: DNA
<213> ORGANISM: Artificial
<220> FEATURE:
<223> OTHER INFORMATION: synthetic DNA

<400> SEQUENCE: 808
atgtaatcgc c                                      11

<210> SEQ ID NO 809
<211> LENGTH: 11
<212> TYPE: DNA
<213> ORGANISM: Artificial
<220> FEATURE:
<223> OTHER INFORMATION: synthetic DNA

<400> SEQUENCE: 809
aagcctgatg t                                      11

<210> SEQ ID NO 810
<211> LENGTH: 11
<212> TYPE: DNA
<213> ORGANISM: Artificial
<220> FEATURE:
<223> OTHER INFORMATION: synthetic DNA

<400> SEQUENCE: 810
aagtaacgtg g                                      11

<210> SEQ ID NO 811
<211> LENGTH: 11
<212> TYPE: DNA

```
<213> ORGANISM: Artificial
<220> FEATURE:
<223> OTHER INFORMATION: synthetic DNA

<400> SEQUENCE: 811
gtagaggttg g                                                          11

<210> SEQ ID NO 812
<211> LENGTH: 11
<212> TYPE: DNA
<213> ORGANISM: Artificial
<220> FEATURE:
<223> OTHER INFORMATION: synthetic DNA

<400> SEQUENCE: 812
ctcttgcctc a                                                          11

<210> SEQ ID NO 813
<211> LENGTH: 11
<212> TYPE: DNA
<213> ORGANISM: Artificial
<220> FEATURE:
<223> OTHER INFORMATION: synthetic DNA

<400> SEQUENCE: 813
atcgtgaagt g                                                          11

<210> SEQ ID NO 814
<211> LENGTH: 11
<212> TYPE: DNA
<213> ORGANISM: Artificial
<220> FEATURE:
<223> OTHER INFORMATION: synthetic DNA

<400> SEQUENCE: 814
accagcacta t                                                          11

<210> SEQ ID NO 815
<211> LENGTH: 11
<212> TYPE: DNA
<213> ORGANISM: Artificial
<220> FEATURE:
<223> OTHER INFORMATION: synthetic DNA

<400> SEQUENCE: 815
caccagaatg t                                                          11

<210> SEQ ID NO 816
<211> LENGTH: 11
<212> TYPE: DNA
<213> ORGANISM: Artificial
<220> FEATURE:
<223> OTHER INFORMATION: synthetic DNA

<400> SEQUENCE: 816
gagtgaacaa c                                                          11

<210> SEQ ID NO 817
<211> LENGTH: 11
<212> TYPE: DNA
<213> ORGANISM: Artificial
<220> FEATURE:
<223> OTHER INFORMATION: synthetic DNA

<400> SEQUENCE: 817
taacgttacg c                                                          11
```

<210> SEQ ID NO 818
<211> LENGTH: 11
<212> TYPE: DNA
<213> ORGANISM: Artificial
<220> FEATURE:
<223> OTHER INFORMATION: synthetic DNA

<400> SEQUENCE: 818
cttggatctt g                                                          11

<210> SEQ ID NO 819
<211> LENGTH: 11
<212> TYPE: DNA
<213> ORGANISM: Artificial
<220> FEATURE:
<223> OTHER INFORMATION: synthetic DNA

<400> SEQUENCE: 819
gttccaacgt t                                                          11

<210> SEQ ID NO 820
<211> LENGTH: 11
<212> TYPE: DNA
<213> ORGANISM: Artificial
<220> FEATURE:
<223> OTHER INFORMATION: synthetic DNA

<400> SEQUENCE: 820
caaggaccgt a                                                          11

<210> SEQ ID NO 821
<211> LENGTH: 11
<212> TYPE: DNA
<213> ORGANISM: Artificial
<220> FEATURE:
<223> OTHER INFORMATION: synthetic DNA

<400> SEQUENCE: 821
gacttcacgc a                                                          11

<210> SEQ ID NO 822
<211> LENGTH: 11
<212> TYPE: DNA
<213> ORGANISM: Artificial
<220> FEATURE:
<223> OTHER INFORMATION: synthetic DNA

<400> SEQUENCE: 822
cacactactg g                                                          11

<210> SEQ ID NO 823
<211> LENGTH: 11
<212> TYPE: DNA
<213> ORGANISM: Artificial
<220> FEATURE:
<223> OTHER INFORMATION: synthetic DNA

<400> SEQUENCE: 823
tcagatgaat c                                                          11

<210> SEQ ID NO 824
<211> LENGTH: 11
<212> TYPE: DNA
<213> ORGANISM: Artificial
<220> FEATURE:

<223> OTHER INFORMATION: synthetic DNA

<400> SEQUENCE: 824
tatggatctg g                                                                                11

<210> SEQ ID NO 825
<211> LENGTH: 11
<212> TYPE: DNA
<213> ORGANISM: Artificial
<220> FEATURE:
<223> OTHER INFORMATION: synthetic DNA

<400> SEQUENCE: 825
tcttaggtgt g                                                                                11

<210> SEQ ID NO 826
<211> LENGTH: 11
<212> TYPE: DNA
<213> ORGANISM: Artificial
<220> FEATURE:
<223> OTHER INFORMATION: synthetic DNA

<400> SEQUENCE: 826
tgtcagcgtc a                                                                                11

<210> SEQ ID NO 827
<211> LENGTH: 11
<212> TYPE: DNA
<213> ORGANISM: Artificial
<220> FEATURE:
<223> OTHER INFORMATION: synthetic DNA

<400> SEQUENCE: 827
gtctaggaca g                                                                                11

<210> SEQ ID NO 828
<211> LENGTH: 11
<212> TYPE: DNA
<213> ORGANISM: Artificial
<220> FEATURE:
<223> OTHER INFORMATION: synthetic DNA

<400> SEQUENCE: 828
gcctcttcat a                                                                                11

<210> SEQ ID NO 829
<211> LENGTH: 11
<212> TYPE: DNA
<213> ORGANISM: Artificial
<220> FEATURE:
<223> OTHER INFORMATION: synthetic DNA

<400> SEQUENCE: 829
agaagtgtta c                                                                                11

<210> SEQ ID NO 830
<211> LENGTH: 11
<212> TYPE: DNA
<213> ORGANISM: Artificial
<220> FEATURE:
<223> OTHER INFORMATION: synthetic DNA

<400> SEQUENCE: 830
catgaggctt g                                                                                11

```
<210> SEQ ID NO 831
<211> LENGTH: 11
<212> TYPE: DNA
<213> ORGANISM: Artificial
<220> FEATURE:
<223> OTHER INFORMATION: synthetic DNA

<400> SEQUENCE: 831
tggattgctc a                                                             11

<210> SEQ ID NO 832
<211> LENGTH: 11
<212> TYPE: DNA
<213> ORGANISM: Artificial
<220> FEATURE:
<223> OTHER INFORMATION: synthetic DNA

<400> SEQUENCE: 832
atctacctaa g                                                             11

<210> SEQ ID NO 833
<211> LENGTH: 11
<212> TYPE: DNA
<213> ORGANISM: Artificial
<220> FEATURE:
<223> OTHER INFORMATION: synthetic DNA

<400> SEQUENCE: 833
atgagcagtg a                                                             11

<210> SEQ ID NO 834
<211> LENGTH: 11
<212> TYPE: DNA
<213> ORGANISM: Artificial
<220> FEATURE:
<223> OTHER INFORMATION: synthetic DNA

<400> SEQUENCE: 834
ccaggagata c                                                             11

<210> SEQ ID NO 835
<211> LENGTH: 11
<212> TYPE: DNA
<213> ORGANISM: Artificial
<220> FEATURE:
<223> OTHER INFORMATION: synthetic DNA

<400> SEQUENCE: 835
ccgttatact t                                                             11

<210> SEQ ID NO 836
<211> LENGTH: 11
<212> TYPE: DNA
<213> ORGANISM: Artificial
<220> FEATURE:
<223> OTHER INFORMATION: synthetic DNA

<400> SEQUENCE: 836
ctcagtacaa g                                                             11

<210> SEQ ID NO 837
<211> LENGTH: 11
<212> TYPE: DNA
<213> ORGANISM: Artificial
<220> FEATURE:
<223> OTHER INFORMATION: synthetic DNA
```

<400> SEQUENCE: 837
ggtgatcgta g                                                          11

<210> SEQ ID NO 838
<211> LENGTH: 11
<212> TYPE: DNA
<213> ORGANISM: Artificial
<220> FEATURE:
<223> OTHER INFORMATION: synthetic DNA

<400> SEQUENCE: 838
cgaacgagac a                                                          11

<210> SEQ ID NO 839
<211> LENGTH: 11
<212> TYPE: DNA
<213> ORGANISM: Artificial
<220> FEATURE:
<223> OTHER INFORMATION: synthetic DNA

<400> SEQUENCE: 839
actacgagct t                                                          11

<210> SEQ ID NO 840
<211> LENGTH: 11
<212> TYPE: DNA
<213> ORGANISM: Artificial
<220> FEATURE:
<223> OTHER INFORMATION: synthetic DNA

<400> SEQUENCE: 840
ttgccacagc a                                                          11

<210> SEQ ID NO 841
<211> LENGTH: 11
<212> TYPE: DNA
<213> ORGANISM: Artificial
<220> FEATURE:
<223> OTHER INFORMATION: synthetic DNA

<400> SEQUENCE: 841
gtcaactcta c                                                          11

<210> SEQ ID NO 842
<211> LENGTH: 11
<212> TYPE: DNA
<213> ORGANISM: Artificial
<220> FEATURE:
<223> OTHER INFORMATION: synthetic DNA

<400> SEQUENCE: 842
tggactgtgt c                                                          11

<210> SEQ ID NO 843
<211> LENGTH: 11
<212> TYPE: DNA
<213> ORGANISM: Artificial
<220> FEATURE:
<223> OTHER INFORMATION: synthetic DNA

<400> SEQUENCE: 843
ggaatggact t                                                          11

<210> SEQ ID NO 844
<211> LENGTH: 11

```
<212> TYPE: DNA
<213> ORGANISM: Artificial
<220> FEATURE:
<223> OTHER INFORMATION: synthetic DNA

<400> SEQUENCE: 844
cgagaacata a                                                        11

<210> SEQ ID NO 845
<211> LENGTH: 11
<212> TYPE: DNA
<213> ORGANISM: Artificial
<220> FEATURE:
<223> OTHER INFORMATION: synthetic DNA

<400> SEQUENCE: 845
acctggtcag t                                                        11

<210> SEQ ID NO 846
<211> LENGTH: 11
<212> TYPE: DNA
<213> ORGANISM: Artificial
<220> FEATURE:
<223> OTHER INFORMATION: synthetic DNA

<400> SEQUENCE: 846
cgaacgacac a                                                        11

<210> SEQ ID NO 847
<211> LENGTH: 11
<212> TYPE: DNA
<213> ORGANISM: Artificial
<220> FEATURE:
<223> OTHER INFORMATION: synthetic DNA

<400> SEQUENCE: 847
agtctagcca t                                                        11

<210> SEQ ID NO 848
<211> LENGTH: 11
<212> TYPE: DNA
<213> ORGANISM: Artificial
<220> FEATURE:
<223> OTHER INFORMATION: synthetic DNA

<400> SEQUENCE: 848
aggcctagat g                                                        11

<210> SEQ ID NO 849
<211> LENGTH: 11
<212> TYPE: DNA
<213> ORGANISM: Artificial
<220> FEATURE:
<223> OTHER INFORMATION: synthetic DNA

<400> SEQUENCE: 849
ggtgcgttag t                                                        11

<210> SEQ ID NO 850
<211> LENGTH: 11
<212> TYPE: DNA
<213> ORGANISM: Artificial
<220> FEATURE:
<223> OTHER INFORMATION: synthetic DNA

<400> SEQUENCE: 850
```
attgtgtccg a						11

<210> SEQ ID NO 851
<211> LENGTH: 11
<212> TYPE: DNA
<213> ORGANISM: Artificial
<220> FEATURE:
<223> OTHER INFORMATION: synthetic DNA

<400> SEQUENCE: 851
gcagacatta a						11

<210> SEQ ID NO 852
<211> LENGTH: 11
<212> TYPE: DNA
<213> ORGANISM: Artificial
<220> FEATURE:
<223> OTHER INFORMATION: synthetic DNA

<400> SEQUENCE: 852
attggctcat g						11

<210> SEQ ID NO 853
<211> LENGTH: 11
<212> TYPE: DNA
<213> ORGANISM: Artificial
<220> FEATURE:
<223> OTHER INFORMATION: synthetic DNA

<400> SEQUENCE: 853
gaggttacat g						11

<210> SEQ ID NO 854
<211> LENGTH: 11
<212> TYPE: DNA
<213> ORGANISM: Artificial
<220> FEATURE:
<223> OTHER INFORMATION: synthetic DNA

<400> SEQUENCE: 854
cctataggac c						11

<210> SEQ ID NO 855
<211> LENGTH: 11
<212> TYPE: DNA
<213> ORGANISM: Artificial
<220> FEATURE:
<223> OTHER INFORMATION: synthetic DNA

<400> SEQUENCE: 855
ttagacggtc t						11

<210> SEQ ID NO 856
<211> LENGTH: 11
<212> TYPE: DNA
<213> ORGANISM: Artificial
<220> FEATURE:
<223> OTHER INFORMATION: synthetic DNA

<400> SEQUENCE: 856
gattgacgca c						11

<210> SEQ ID NO 857
<211> LENGTH: 11
<212> TYPE: DNA
<213> ORGANISM: Artificial

```
<220> FEATURE:
<223> OTHER INFORMATION: synthetic DNA

<400> SEQUENCE: 857
aagacacctc g                                                          11

<210> SEQ ID NO 858
<211> LENGTH: 11
<212> TYPE: DNA
<213> ORGANISM: Artificial
<220> FEATURE:
<223> OTHER INFORMATION: synthetic DNA

<400> SEQUENCE: 858
tcgaataatc g                                                          11

<210> SEQ ID NO 859
<211> LENGTH: 11
<212> TYPE: DNA
<213> ORGANISM: Artificial
<220> FEATURE:
<223> OTHER INFORMATION: synthetic DNA

<400> SEQUENCE: 859
tctatgtcgg a                                                          11

<210> SEQ ID NO 860
<211> LENGTH: 11
<212> TYPE: DNA
<213> ORGANISM: Artificial
<220> FEATURE:
<223> OTHER INFORMATION: synthetic DNA

<400> SEQUENCE: 860
tcgcatgaac c                                                          11

<210> SEQ ID NO 861
<211> LENGTH: 11
<212> TYPE: DNA
<213> ORGANISM: Artificial
<220> FEATURE:
<223> OTHER INFORMATION: synthetic DNA

<400> SEQUENCE: 861
tgttatgtct c                                                          11

<210> SEQ ID NO 862
<211> LENGTH: 11
<212> TYPE: DNA
<213> ORGANISM: Artificial
<220> FEATURE:
<223> OTHER INFORMATION: synthetic DNA

<400> SEQUENCE: 862
tggatcctac a                                                          11

<210> SEQ ID NO 863
<211> LENGTH: 11
<212> TYPE: DNA
<213> ORGANISM: Artificial
<220> FEATURE:
<223> OTHER INFORMATION: synthetic DNA

<400> SEQUENCE: 863
atcgttcagc c                                                          11
```

<210> SEQ ID NO 864
<211> LENGTH: 11
<212> TYPE: DNA
<213> ORGANISM: Artificial
<220> FEATURE:
<223> OTHER INFORMATION: synthetic DNA

<400> SEQUENCE: 864
taccgcaagc a                                                          11

<210> SEQ ID NO 865
<211> LENGTH: 12
<212> TYPE: DNA
<213> ORGANISM: Artificial
<220> FEATURE:
<223> OTHER INFORMATION: synthetic DNA

<400> SEQUENCE: 865
gctgttgaac cg                                                         12

<210> SEQ ID NO 866
<211> LENGTH: 12
<212> TYPE: DNA
<213> ORGANISM: Artificial
<220> FEATURE:
<223> OTHER INFORMATION: synthetic DNA

<400> SEQUENCE: 866
atactccgag at                                                         12

<210> SEQ ID NO 867
<211> LENGTH: 12
<212> TYPE: DNA
<213> ORGANISM: Artificial
<220> FEATURE:
<223> OTHER INFORMATION: synthetic DNA

<400> SEQUENCE: 867
cttaaggagc gc                                                         12

<210> SEQ ID NO 868
<211> LENGTH: 12
<212> TYPE: DNA
<213> ORGANISM: Artificial
<220> FEATURE:
<223> OTHER INFORMATION: synthetic DNA

<400> SEQUENCE: 868
tatactacaa gc                                                         12

<210> SEQ ID NO 869
<211> LENGTH: 12
<212> TYPE: DNA
<213> ORGANISM: Artificial
<220> FEATURE:
<223> OTHER INFORMATION: synthetic DNA

<400> SEQUENCE: 869
tagtggtcgt ca                                                         12

<210> SEQ ID NO 870
<211> LENGTH: 12
<212> TYPE: DNA
<213> ORGANISM: Artificial
<220> FEATURE:
<223> OTHER INFORMATION: synthetic DNA

```
<400> SEQUENCE: 870
gtgcttcagg ag                                                          12

<210> SEQ ID NO 871
<211> LENGTH: 12
<212> TYPE: DNA
<213> ORGANISM: Artificial
<220> FEATURE:
<223> OTHER INFORMATION: synthetic DNA

<400> SEQUENCE: 871
gacgcatacc tc                                                          12

<210> SEQ ID NO 872
<211> LENGTH: 12
<212> TYPE: DNA
<213> ORGANISM: Artificial
<220> FEATURE:
<223> OTHER INFORMATION: synthetic DNA

<400> SEQUENCE: 872
cctacctgtg ga                                                          12

<210> SEQ ID NO 873
<211> LENGTH: 12
<212> TYPE: DNA
<213> ORGANISM: Artificial
<220> FEATURE:
<223> OTHER INFORMATION: synthetic DNA

<400> SEQUENCE: 873
gcggtcacat at                                                          12

<210> SEQ ID NO 874
<211> LENGTH: 12
<212> TYPE: DNA
<213> ORGANISM: Artificial
<220> FEATURE:
<223> OTHER INFORMATION: synthetic DNA

<400> SEQUENCE: 874
ctgcattcac ga                                                          12

<210> SEQ ID NO 875
<211> LENGTH: 12
<212> TYPE: DNA
<213> ORGANISM: Artificial
<220> FEATURE:
<223> OTHER INFORMATION: synthetic DNA

<400> SEQUENCE: 875
tggatccttc at                                                          12

<210> SEQ ID NO 876
<211> LENGTH: 12
<212> TYPE: DNA
<213> ORGANISM: Artificial
<220> FEATURE:
<223> OTHER INFORMATION: synthetic DNA

<400> SEQUENCE: 876
ttgtgctgga ct                                                          12

<210> SEQ ID NO 877
```

```
<211> LENGTH: 12
<212> TYPE: DNA
<213> ORGANISM: Artificial
<220> FEATURE:
<223> OTHER INFORMATION: synthetic DNA

<400> SEQUENCE: 877
attgagagct at                                                               12

<210> SEQ ID NO 878
<211> LENGTH: 12
<212> TYPE: DNA
<213> ORGANISM: Artificial
<220> FEATURE:
<223> OTHER INFORMATION: synthetic DNA

<400> SEQUENCE: 878
tcgctaatgt ag                                                               12

<210> SEQ ID NO 879
<211> LENGTH: 12
<212> TYPE: DNA
<213> ORGANISM: Artificial
<220> FEATURE:
<223> OTHER INFORMATION: synthetic DNA

<400> SEQUENCE: 879
ctactggcac aa                                                               12

<210> SEQ ID NO 880
<211> LENGTH: 12
<212> TYPE: DNA
<213> ORGANISM: Artificial
<220> FEATURE:
<223> OTHER INFORMATION: synthetic DNA

<400> SEQUENCE: 880
agagccagtc gt                                                               12

<210> SEQ ID NO 881
<211> LENGTH: 12
<212> TYPE: DNA
<213> ORGANISM: Artificial
<220> FEATURE:
<223> OTHER INFORMATION: synthetic DNA

<400> SEQUENCE: 881
aatactggct aa                                                               12

<210> SEQ ID NO 882
<211> LENGTH: 12
<212> TYPE: DNA
<213> ORGANISM: Artificial
<220> FEATURE:
<223> OTHER INFORMATION: synthetic DNA

<400> SEQUENCE: 882
ctgcatgcat aa                                                               12

<210> SEQ ID NO 883
<211> LENGTH: 12
<212> TYPE: DNA
<213> ORGANISM: Artificial
<220> FEATURE:
<223> OTHER INFORMATION: synthetic DNA

<400> SEQUENCE: 883
```
ttgtcacaac tc                                                            12

<210> SEQ ID NO 884
<211> LENGTH: 12
<212> TYPE: DNA
<213> ORGANISM: Artificial
<220> FEATURE:
<223> OTHER INFORMATION: synthetic DNA

<400> SEQUENCE: 884
tgctaactct cc                                                            12

<210> SEQ ID NO 885
<211> LENGTH: 12
<212> TYPE: DNA
<213> ORGANISM: Artificial
<220> FEATURE:
<223> OTHER INFORMATION: synthetic DNA

<400> SEQUENCE: 885
tctctagttc gg                                                            12

<210> SEQ ID NO 886
<211> LENGTH: 12
<212> TYPE: DNA
<213> ORGANISM: Artificial
<220> FEATURE:
<223> OTHER INFORMATION: synthetic DNA

<400> SEQUENCE: 886
ttacgtccgc aa                                                            12

<210> SEQ ID NO 887
<211> LENGTH: 12
<212> TYPE: DNA
<213> ORGANISM: Artificial
<220> FEATURE:
<223> OTHER INFORMATION: synthetic DNA

<400> SEQUENCE: 887
gtgttgctac ca                                                            12

<210> SEQ ID NO 888
<211> LENGTH: 12
<212> TYPE: DNA
<213> ORGANISM: Artificial
<220> FEATURE:
<223> OTHER INFORMATION: synthetic DNA

<400> SEQUENCE: 888
cgcatgtatg cc                                                            12

<210> SEQ ID NO 889
<211> LENGTH: 12
<212> TYPE: DNA
<213> ORGANISM: Artificial
<220> FEATURE:
<223> OTHER INFORMATION: synthetic DNA

<400> SEQUENCE: 889
cctgttctga tt                                                            12

<210> SEQ ID NO 890
<211> LENGTH: 12
<212> TYPE: DNA

```
<213> ORGANISM: Artificial
<220> FEATURE:
<223> OTHER INFORMATION: synthetic DNA

<400> SEQUENCE: 890
taagatgctt ga                                                              12

<210> SEQ ID NO 891
<211> LENGTH: 12
<212> TYPE: DNA
<213> ORGANISM: Artificial
<220> FEATURE:
<223> OTHER INFORMATION: synthetic DNA

<400> SEQUENCE: 891
atatatctca gc                                                              12

<210> SEQ ID NO 892
<211> LENGTH: 12
<212> TYPE: DNA
<213> ORGANISM: Artificial
<220> FEATURE:
<223> OTHER INFORMATION: synthetic DNA

<400> SEQUENCE: 892
ttcctcgtgg tt                                                              12

<210> SEQ ID NO 893
<211> LENGTH: 12
<212> TYPE: DNA
<213> ORGANISM: Artificial
<220> FEATURE:
<223> OTHER INFORMATION: synthetic DNA

<400> SEQUENCE: 893
atgtcgatct ag                                                              12

<210> SEQ ID NO 894
<211> LENGTH: 12
<212> TYPE: DNA
<213> ORGANISM: Artificial
<220> FEATURE:
<223> OTHER INFORMATION: synthetic DNA

<400> SEQUENCE: 894
catccactaa tc                                                              12

<210> SEQ ID NO 895
<211> LENGTH: 12
<212> TYPE: DNA
<213> ORGANISM: Artificial
<220> FEATURE:
<223> OTHER INFORMATION: synthetic DNA

<400> SEQUENCE: 895
gcctctggta ac                                                              12

<210> SEQ ID NO 896
<211> LENGTH: 12
<212> TYPE: DNA
<213> ORGANISM: Artificial
<220> FEATURE:
<223> OTHER INFORMATION: synthetic DNA

<400> SEQUENCE: 896
agtcaagaga tt                                                              12
```

<210> SEQ ID NO 897
<211> LENGTH: 12
<212> TYPE: DNA
<213> ORGANISM: Artificial
<220> FEATURE:
<223> OTHER INFORMATION: synthetic DNA

<400> SEQUENCE: 897
actgaggcgt tc                                                          12

<210> SEQ ID NO 898
<211> LENGTH: 12
<212> TYPE: DNA
<213> ORGANISM: Artificial
<220> FEATURE:
<223> OTHER INFORMATION: synthetic DNA

<400> SEQUENCE: 898
taaggctgac at                                                          12

<210> SEQ ID NO 899
<211> LENGTH: 12
<212> TYPE: DNA
<213> ORGANISM: Artificial
<220> FEATURE:
<223> OTHER INFORMATION: synthetic DNA

<400> SEQUENCE: 899
agttcgcata ca                                                          12

<210> SEQ ID NO 900
<211> LENGTH: 12
<212> TYPE: DNA
<213> ORGANISM: Artificial
<220> FEATURE:
<223> OTHER INFORMATION: synthetic DNA

<400> SEQUENCE: 900
gcagaattgc ga                                                          12

<210> SEQ ID NO 901
<211> LENGTH: 12
<212> TYPE: DNA
<213> ORGANISM: Artificial
<220> FEATURE:
<223> OTHER INFORMATION: synthetic DNA

<400> SEQUENCE: 901
ggttatgaag aa                                                          12

<210> SEQ ID NO 902
<211> LENGTH: 12
<212> TYPE: DNA
<213> ORGANISM: Artificial
<220> FEATURE:
<223> OTHER INFORMATION: synthetic DNA

<400> SEQUENCE: 902
agaagtcgcc tc                                                          12

<210> SEQ ID NO 903
<211> LENGTH: 12
<212> TYPE: DNA
<213> ORGANISM: Artificial
<220> FEATURE:

<223> OTHER INFORMATION: synthetic DNA

<400> SEQUENCE: 903
ttcgcgttat tg                                                          12

<210> SEQ ID NO 904
<211> LENGTH: 12
<212> TYPE: DNA
<213> ORGANISM: Artificial
<220> FEATURE:
<223> OTHER INFORMATION: synthetic DNA

<400> SEQUENCE: 904
tacctggtcg gt                                                          12

<210> SEQ ID NO 905
<211> LENGTH: 12
<212> TYPE: DNA
<213> ORGANISM: Artificial
<220> FEATURE:
<223> OTHER INFORMATION: synthetic DNA

<400> SEQUENCE: 905
ggttaccgag ga                                                          12

<210> SEQ ID NO 906
<211> LENGTH: 12
<212> TYPE: DNA
<213> ORGANISM: Artificial
<220> FEATURE:
<223> OTHER INFORMATION: synthetic DNA

<400> SEQUENCE: 906
acacacttct ag                                                          12

<210> SEQ ID NO 907
<211> LENGTH: 12
<212> TYPE: DNA
<213> ORGANISM: Artificial
<220> FEATURE:
<223> OTHER INFORMATION: synthetic DNA

<400> SEQUENCE: 907
ggaagtgatt aa                                                          12

<210> SEQ ID NO 908
<211> LENGTH: 12
<212> TYPE: DNA
<213> ORGANISM: Artificial
<220> FEATURE:
<223> OTHER INFORMATION: synthetic DNA

<400> SEQUENCE: 908
tccatcagat aa                                                          12

<210> SEQ ID NO 909
<211> LENGTH: 12
<212> TYPE: DNA
<213> ORGANISM: Artificial
<220> FEATURE:
<223> OTHER INFORMATION: synthetic DNA

<400> SEQUENCE: 909
tgtctgtatc at                                                          12

```
<210> SEQ ID NO 910
<211> LENGTH: 12
<212> TYPE: DNA
<213> ORGANISM: Artificial
<220> FEATURE:
<223> OTHER INFORMATION: synthetic DNA

<400> SEQUENCE: 910
aattggctat ag                                                         12

<210> SEQ ID NO 911
<211> LENGTH: 12
<212> TYPE: DNA
<213> ORGANISM: Artificial
<220> FEATURE:
<223> OTHER INFORMATION: synthetic DNA

<400> SEQUENCE: 911
acgtcggaag gt                                                         12

<210> SEQ ID NO 912
<211> LENGTH: 12
<212> TYPE: DNA
<213> ORGANISM: Artificial
<220> FEATURE:
<223> OTHER INFORMATION: synthetic DNA

<400> SEQUENCE: 912
aggcatccgt tg                                                         12

<210> SEQ ID NO 913
<211> LENGTH: 12
<212> TYPE: DNA
<213> ORGANISM: Artificial
<220> FEATURE:
<223> OTHER INFORMATION: synthetic DNA

<400> SEQUENCE: 913
accgtcgctt ga                                                         12

<210> SEQ ID NO 914
<211> LENGTH: 12
<212> TYPE: DNA
<213> ORGANISM: Artificial
<220> FEATURE:
<223> OTHER INFORMATION: synthetic DNA

<400> SEQUENCE: 914
taccgtcaag tg                                                         12

<210> SEQ ID NO 915
<211> LENGTH: 12
<212> TYPE: DNA
<213> ORGANISM: Artificial
<220> FEATURE:
<223> OTHER INFORMATION: synthetic DNA

<400> SEQUENCE: 915
ctcgatatag tt                                                         12

<210> SEQ ID NO 916
<211> LENGTH: 12
<212> TYPE: DNA
<213> ORGANISM: Artificial
<220> FEATURE:
<223> OTHER INFORMATION: synthetic DNA
```

```
<400> SEQUENCE: 916
cgtcaacgtg gt                                                          12

<210> SEQ ID NO 917
<211> LENGTH: 12
<212> TYPE: DNA
<213> ORGANISM: Artificial
<220> FEATURE:
<223> OTHER INFORMATION: synthetic DNA

<400> SEQUENCE: 917
tagtcaacgt ag                                                          12

<210> SEQ ID NO 918
<211> LENGTH: 12
<212> TYPE: DNA
<213> ORGANISM: Artificial
<220> FEATURE:
<223> OTHER INFORMATION: synthetic DNA

<400> SEQUENCE: 918
tgagtaggtc ag                                                          12

<210> SEQ ID NO 919
<211> LENGTH: 12
<212> TYPE: DNA
<213> ORGANISM: Artificial
<220> FEATURE:
<223> OTHER INFORMATION: synthetic DNA

<400> SEQUENCE: 919
cttggcatgt ac                                                          12

<210> SEQ ID NO 920
<211> LENGTH: 12
<212> TYPE: DNA
<213> ORGANISM: Artificial
<220> FEATURE:
<223> OTHER INFORMATION: synthetic DNA

<400> SEQUENCE: 920
tgccgagact tc                                                          12

<210> SEQ ID NO 921
<211> LENGTH: 12
<212> TYPE: DNA
<213> ORGANISM: Artificial
<220> FEATURE:
<223> OTHER INFORMATION: synthetic DNA

<400> SEQUENCE: 921
ctaagactta ag                                                          12

<210> SEQ ID NO 922
<211> LENGTH: 12
<212> TYPE: DNA
<213> ORGANISM: Artificial
<220> FEATURE:
<223> OTHER INFORMATION: synthetic DNA

<400> SEQUENCE: 922
ttctcgtgtg cg                                                          12

<210> SEQ ID NO 923
<211> LENGTH: 12
```

```
<212> TYPE: DNA
<213> ORGANISM: Artificial
<220> FEATURE:
<223> OTHER INFORMATION: synthetic DNA

<400> SEQUENCE: 923
cacctgcacg at                                                         12

<210> SEQ ID NO 924
<211> LENGTH: 12
<212> TYPE: DNA
<213> ORGANISM: Artificial
<220> FEATURE:
<223> OTHER INFORMATION: synthetic DNA

<400> SEQUENCE: 924
attaagccta ag                                                         12

<210> SEQ ID NO 925
<211> LENGTH: 12
<212> TYPE: DNA
<213> ORGANISM: Artificial
<220> FEATURE:
<223> OTHER INFORMATION: synthetic DNA

<400> SEQUENCE: 925
ggtggaacca tg                                                         12

<210> SEQ ID NO 926
<211> LENGTH: 12
<212> TYPE: DNA
<213> ORGANISM: Artificial
<220> FEATURE:
<223> OTHER INFORMATION: synthetic DNA

<400> SEQUENCE: 926
actaacgcga ct                                                         12

<210> SEQ ID NO 927
<211> LENGTH: 12
<212> TYPE: DNA
<213> ORGANISM: Artificial
<220> FEATURE:
<223> OTHER INFORMATION: synthetic DNA

<400> SEQUENCE: 927
cagttgtgct at                                                         12

<210> SEQ ID NO 928
<211> LENGTH: 12
<212> TYPE: DNA
<213> ORGANISM: Artificial
<220> FEATURE:
<223> OTHER INFORMATION: synthetic DNA

<400> SEQUENCE: 928
acgctgttag ca                                                         12

<210> SEQ ID NO 929
<211> LENGTH: 12
<212> TYPE: DNA
<213> ORGANISM: Artificial
<220> FEATURE:
<223> OTHER INFORMATION: synthetic DNA

<400> SEQUENCE: 929
```
gtcaacgcta ag					12

<210> SEQ ID NO 930
<211> LENGTH: 12
<212> TYPE: DNA
<213> ORGANISM: Artificial
<220> FEATURE:
<223> OTHER INFORMATION: synthetic DNA

<400> SEQUENCE: 930
agcttaggta tg					12

<210> SEQ ID NO 931
<211> LENGTH: 12
<212> TYPE: DNA
<213> ORGANISM: Artificial
<220> FEATURE:
<223> OTHER INFORMATION: synthetic DNA

<400> SEQUENCE: 931
cgcaggacga tt					12

<210> SEQ ID NO 932
<211> LENGTH: 12
<212> TYPE: DNA
<213> ORGANISM: Artificial
<220> FEATURE:
<223> OTHER INFORMATION: synthetic DNA

<400> SEQUENCE: 932
aaccggctgt ct					12

<210> SEQ ID NO 933
<211> LENGTH: 12
<212> TYPE: DNA
<213> ORGANISM: Artificial
<220> FEATURE:
<223> OTHER INFORMATION: synthetic DNA

<400> SEQUENCE: 933
gttgctcacg tg					12

<210> SEQ ID NO 934
<211> LENGTH: 12
<212> TYPE: DNA
<213> ORGANISM: Artificial
<220> FEATURE:
<223> OTHER INFORMATION: synthetic DNA

<400> SEQUENCE: 934
gaatcttccg cg					12

<210> SEQ ID NO 935
<211> LENGTH: 12
<212> TYPE: DNA
<213> ORGANISM: Artificial
<220> FEATURE:
<223> OTHER INFORMATION: synthetic DNA

<400> SEQUENCE: 935
agagcgtaca cg					12

<210> SEQ ID NO 936
<211> LENGTH: 12
<212> TYPE: DNA
<213> ORGANISM: Artificial

```
<220> FEATURE:
<223> OTHER INFORMATION: synthetic DNA

<400> SEQUENCE: 936
aaggctaatg tc                                                              12

<210> SEQ ID NO 937
<211> LENGTH: 12
<212> TYPE: DNA
<213> ORGANISM: Artificial
<220> FEATURE:
<223> OTHER INFORMATION: synthetic DNA

<400> SEQUENCE: 937
tctatgtaga cg                                                              12

<210> SEQ ID NO 938
<211> LENGTH: 12
<212> TYPE: DNA
<213> ORGANISM: Artificial
<220> FEATURE:
<223> OTHER INFORMATION: synthetic DNA

<400> SEQUENCE: 938
agacggtcta gt                                                              12

<210> SEQ ID NO 939
<211> LENGTH: 12
<212> TYPE: DNA
<213> ORGANISM: Artificial
<220> FEATURE:
<223> OTHER INFORMATION: synthetic DNA

<400> SEQUENCE: 939
ttggtcacac gc                                                              12

<210> SEQ ID NO 940
<211> LENGTH: 12
<212> TYPE: DNA
<213> ORGANISM: Artificial
<220> FEATURE:
<223> OTHER INFORMATION: synthetic DNA

<400> SEQUENCE: 940
gtcgatatat gg                                                              12

<210> SEQ ID NO 941
<211> LENGTH: 12
<212> TYPE: DNA
<213> ORGANISM: Artificial
<220> FEATURE:
<223> OTHER INFORMATION: synthetic DNA

<400> SEQUENCE: 941
aacatggata cg                                                              12

<210> SEQ ID NO 942
<211> LENGTH: 12
<212> TYPE: DNA
<213> ORGANISM: Artificial
<220> FEATURE:
<223> OTHER INFORMATION: synthetic DNA

<400> SEQUENCE: 942
ttcgcagttc ct                                                              12
```

<210> SEQ ID NO 943
<211> LENGTH: 12
<212> TYPE: DNA
<213> ORGANISM: Artificial
<220> FEATURE:
<223> OTHER INFORMATION: synthetic DNA

<400> SEQUENCE: 943
cgcatgttgt gc                                                          12

<210> SEQ ID NO 944
<211> LENGTH: 12
<212> TYPE: DNA
<213> ORGANISM: Artificial
<220> FEATURE:
<223> OTHER INFORMATION: synthetic DNA

<400> SEQUENCE: 944
tgttaagttg ga                                                          12

<210> SEQ ID NO 945
<211> LENGTH: 12
<212> TYPE: DNA
<213> ORGANISM: Artificial
<220> FEATURE:
<223> OTHER INFORMATION: synthetic DNA

<400> SEQUENCE: 945
caagtgtgat ga                                                          12

<210> SEQ ID NO 946
<211> LENGTH: 12
<212> TYPE: DNA
<213> ORGANISM: Artificial
<220> FEATURE:
<223> OTHER INFORMATION: synthetic DNA

<400> SEQUENCE: 946
ctggtaccac gt                                                          12

<210> SEQ ID NO 947
<211> LENGTH: 12
<212> TYPE: DNA
<213> ORGANISM: Artificial
<220> FEATURE:
<223> OTHER INFORMATION: synthetic DNA

<400> SEQUENCE: 947
cgctaggatc ac                                                          12

<210> SEQ ID NO 948
<211> LENGTH: 12
<212> TYPE: DNA
<213> ORGANISM: Artificial
<220> FEATURE:
<223> OTHER INFORMATION: synthetic DNA

<400> SEQUENCE: 948
tgctcattac gg                                                          12

<210> SEQ ID NO 949
<211> LENGTH: 12
<212> TYPE: DNA
<213> ORGANISM: Artificial
<220> FEATURE:
<223> OTHER INFORMATION: synthetic DNA

<400> SEQUENCE: 949
tgctcagtaa ca                                                         12

<210> SEQ ID NO 950
<211> LENGTH: 12
<212> TYPE: DNA
<213> ORGANISM: Artificial
<220> FEATURE:
<223> OTHER INFORMATION: synthetic DNA

<400> SEQUENCE: 950
acgatcatag cc                                                         12

<210> SEQ ID NO 951
<211> LENGTH: 12
<212> TYPE: DNA
<213> ORGANISM: Artificial
<220> FEATURE:
<223> OTHER INFORMATION: synthetic DNA

<400> SEQUENCE: 951
acgatacgtg ga                                                         12

<210> SEQ ID NO 952
<211> LENGTH: 12
<212> TYPE: DNA
<213> ORGANISM: Artificial
<220> FEATURE:
<223> OTHER INFORMATION: synthetic DNA

<400> SEQUENCE: 952
gttcgatgat gg                                                         12

<210> SEQ ID NO 953
<211> LENGTH: 12
<212> TYPE: DNA
<213> ORGANISM: Artificial
<220> FEATURE:
<223> OTHER INFORMATION: synthetic DNA

<400> SEQUENCE: 953
aagagctgtg cc                                                         12

<210> SEQ ID NO 954
<211> LENGTH: 12
<212> TYPE: DNA
<213> ORGANISM: Artificial
<220> FEATURE:
<223> OTHER INFORMATION: synthetic DNA

<400> SEQUENCE: 954
ggttggatca ac                                                         12

<210> SEQ ID NO 955
<211> LENGTH: 12
<212> TYPE: DNA
<213> ORGANISM: Artificial
<220> FEATURE:
<223> OTHER INFORMATION: synthetic DNA

<400> SEQUENCE: 955
gcgcgcttat ga                                                         12

<210> SEQ ID NO 956

```
<211> LENGTH: 12
<212> TYPE: DNA
<213> ORGANISM: Artificial
<220> FEATURE:
<223> OTHER INFORMATION: synthetic DNA

<400> SEQUENCE: 956
cgtcgatcat ca                                                              12

<210> SEQ ID NO 957
<211> LENGTH: 12
<212> TYPE: DNA
<213> ORGANISM: Artificial
<220> FEATURE:
<223> OTHER INFORMATION: synthetic DNA

<400> SEQUENCE: 957
gagactgcac tc                                                              12

<210> SEQ ID NO 958
<211> LENGTH: 12
<212> TYPE: DNA
<213> ORGANISM: Artificial
<220> FEATURE:
<223> OTHER INFORMATION: synthetic DNA

<400> SEQUENCE: 958
gatagatcgc at                                                              12

<210> SEQ ID NO 959
<211> LENGTH: 12
<212> TYPE: DNA
<213> ORGANISM: Artificial
<220> FEATURE:
<223> OTHER INFORMATION: synthetic DNA

<400> SEQUENCE: 959
ggccatcatc ag                                                              12

<210> SEQ ID NO 960
<211> LENGTH: 12
<212> TYPE: DNA
<213> ORGANISM: Artificial
<220> FEATURE:
<223> OTHER INFORMATION: synthetic DNA

<400> SEQUENCE: 960
ggtgttccac tg                                                              12

<210> SEQ ID NO 961
<211> LENGTH: 14
<212> TYPE: DNA
<213> ORGANISM: Artificial
<220> FEATURE:
<223> OTHER INFORMATION: synthetic DNA

<400> SEQUENCE: 961
agctatacag aggt                                                            14

<210> SEQ ID NO 962
<211> LENGTH: 14
<212> TYPE: DNA
<213> ORGANISM: Artificial
<220> FEATURE:
<223> OTHER INFORMATION: synthetic DNA

<400> SEQUENCE: 962
```

```
aggccgttct gtct                                                      14

<210> SEQ ID NO 963
<211> LENGTH: 14
<212> TYPE: DNA
<213> ORGANISM: Artificial
<220> FEATURE:
<223> OTHER INFORMATION: synthetic DNA

<400> SEQUENCE: 963
cattggtctg ctat                                                      14

<210> SEQ ID NO 964
<211> LENGTH: 14
<212> TYPE: DNA
<213> ORGANISM: Artificial
<220> FEATURE:
<223> OTHER INFORMATION: synthetic DNA

<400> SEQUENCE: 964
ctacatacgc gcca                                                      14

<210> SEQ ID NO 965
<211> LENGTH: 14
<212> TYPE: DNA
<213> ORGANISM: Artificial
<220> FEATURE:
<223> OTHER INFORMATION: synthetic DNA

<400> SEQUENCE: 965
gcttaacggc gctt                                                      14

<210> SEQ ID NO 966
<211> LENGTH: 14
<212> TYPE: DNA
<213> ORGANISM: Artificial
<220> FEATURE:
<223> OTHER INFORMATION: synthetic DNA

<400> SEQUENCE: 966
tacgatactc cacc                                                      14

<210> SEQ ID NO 967
<211> LENGTH: 14
<212> TYPE: DNA
<213> ORGANISM: Artificial
<220> FEATURE:
<223> OTHER INFORMATION: synthetic DNA

<400> SEQUENCE: 967
accggcataa gaag                                                      14

<210> SEQ ID NO 968
<211> LENGTH: 14
<212> TYPE: DNA
<213> ORGANISM: Artificial
<220> FEATURE:
<223> OTHER INFORMATION: synthetic DNA

<400> SEQUENCE: 968
ggatgcttcg ataa                                                      14

<210> SEQ ID NO 969
<211> LENGTH: 14
<212> TYPE: DNA
```

```
<213> ORGANISM: Artificial
<220> FEATURE:
<223> OTHER INFORMATION: synthetic DNA

<400> SEQUENCE: 969
gtgtacctga atgt                                                    14

<210> SEQ ID NO 970
<211> LENGTH: 14
<212> TYPE: DNA
<213> ORGANISM: Artificial
<220> FEATURE:
<223> OTHER INFORMATION: synthetic DNA

<400> SEQUENCE: 970
cgcggataca caga                                                    14

<210> SEQ ID NO 971
<211> LENGTH: 14
<212> TYPE: DNA
<213> ORGANISM: Artificial
<220> FEATURE:
<223> OTHER INFORMATION: synthetic DNA

<400> SEQUENCE: 971
ttccacggca ctgt                                                    14

<210> SEQ ID NO 972
<211> LENGTH: 14
<212> TYPE: DNA
<213> ORGANISM: Artificial
<220> FEATURE:
<223> OTHER INFORMATION: synthetic DNA

<400> SEQUENCE: 972
tagccaggca acaa                                                    14

<210> SEQ ID NO 973
<211> LENGTH: 14
<212> TYPE: DNA
<213> ORGANISM: Artificial
<220> FEATURE:
<223> OTHER INFORMATION: synthetic DNA

<400> SEQUENCE: 973
agcgtcaaca cgta                                                    14

<210> SEQ ID NO 974
<211> LENGTH: 14
<212> TYPE: DNA
<213> ORGANISM: Artificial
<220> FEATURE:
<223> OTHER INFORMATION: synthetic DNA

<400> SEQUENCE: 974
taacgctact cgcg                                                    14

<210> SEQ ID NO 975
<211> LENGTH: 14
<212> TYPE: DNA
<213> ORGANISM: Artificial
<220> FEATURE:
<223> OTHER INFORMATION: synthetic DNA

<400> SEQUENCE: 975
tagatagacg atct                                                    14
```

```
<210> SEQ ID NO 976
<211> LENGTH: 14
<212> TYPE: DNA
<213> ORGANISM: Artificial
<220> FEATURE:
<223> OTHER INFORMATION: synthetic DNA

<400> SEQUENCE: 976
actcttgcaa tgct                                                       14

<210> SEQ ID NO 977
<211> LENGTH: 14
<212> TYPE: DNA
<213> ORGANISM: Artificial
<220> FEATURE:
<223> OTHER INFORMATION: synthetic DNA

<400> SEQUENCE: 977
actcggttag gtcg                                                       14

<210> SEQ ID NO 978
<211> LENGTH: 14
<212> TYPE: DNA
<213> ORGANISM: Artificial
<220> FEATURE:
<223> OTHER INFORMATION: synthetic DNA

<400> SEQUENCE: 978
cattatctac gcat                                                       14

<210> SEQ ID NO 979
<211> LENGTH: 14
<212> TYPE: DNA
<213> ORGANISM: Artificial
<220> FEATURE:
<223> OTHER INFORMATION: synthetic DNA

<400> SEQUENCE: 979
cacaccggcg atta                                                       14

<210> SEQ ID NO 980
<211> LENGTH: 14
<212> TYPE: DNA
<213> ORGANISM: Artificial
<220> FEATURE:
<223> OTHER INFORMATION: synthetic DNA

<400> SEQUENCE: 980
tacgcagtac tgtg                                                       14

<210> SEQ ID NO 981
<211> LENGTH: 14
<212> TYPE: DNA
<213> ORGANISM: Artificial
<220> FEATURE:
<223> OTHER INFORMATION: synthetic DNA

<400> SEQUENCE: 981
caagcgcgtg aatg                                                       14

<210> SEQ ID NO 982
<211> LENGTH: 14
<212> TYPE: DNA
<213> ORGANISM: Artificial
<220> FEATURE:
```

<223> OTHER INFORMATION: synthetic DNA

<400> SEQUENCE: 982
gaatggactg acga                                                        14

<210> SEQ ID NO 983
<211> LENGTH: 14
<212> TYPE: DNA
<213> ORGANISM: Artificial
<220> FEATURE:
<223> OTHER INFORMATION: synthetic DNA

<400> SEQUENCE: 983
ctagcgctga agtt                                                        14

<210> SEQ ID NO 984
<211> LENGTH: 14
<212> TYPE: DNA
<213> ORGANISM: Artificial
<220> FEATURE:
<223> OTHER INFORMATION: synthetic DNA

<400> SEQUENCE: 984
tgcggcagac caat                                                        14

<210> SEQ ID NO 985
<211> LENGTH: 14
<212> TYPE: DNA
<213> ORGANISM: Artificial
<220> FEATURE:
<223> OTHER INFORMATION: synthetic DNA

<400> SEQUENCE: 985
aaggcataga gatt                                                        14

<210> SEQ ID NO 986
<211> LENGTH: 14
<212> TYPE: DNA
<213> ORGANISM: Artificial
<220> FEATURE:
<223> OTHER INFORMATION: synthetic DNA

<400> SEQUENCE: 986
ttctcctcgc catg                                                        14

<210> SEQ ID NO 987
<211> LENGTH: 14
<212> TYPE: DNA
<213> ORGANISM: Artificial
<220> FEATURE:
<223> OTHER INFORMATION: synthetic DNA

<400> SEQUENCE: 987
tcattggtcg tgaa                                                        14

<210> SEQ ID NO 988
<211> LENGTH: 14
<212> TYPE: DNA
<213> ORGANISM: Artificial
<220> FEATURE:
<223> OTHER INFORMATION: synthetic DNA

<400> SEQUENCE: 988
attacgctat acga                                                        14

```
<210> SEQ ID NO 989
<211> LENGTH: 14
<212> TYPE: DNA
<213> ORGANISM: Artificial
<220> FEATURE:
<223> OTHER INFORMATION: synthetic DNA

<400> SEQUENCE: 989
atgatcctcc acgg                                                     14

<210> SEQ ID NO 990
<211> LENGTH: 14
<212> TYPE: DNA
<213> ORGANISM: Artificial
<220> FEATURE:
<223> OTHER INFORMATION: synthetic DNA

<400> SEQUENCE: 990
cgtcgttagt aatc                                                     14

<210> SEQ ID NO 991
<211> LENGTH: 14
<212> TYPE: DNA
<213> ORGANISM: Artificial
<220> FEATURE:
<223> OTHER INFORMATION: synthetic DNA

<400> SEQUENCE: 991
tgcacatagt ctca                                                     14

<210> SEQ ID NO 992
<211> LENGTH: 14
<212> TYPE: DNA
<213> ORGANISM: Artificial
<220> FEATURE:
<223> OTHER INFORMATION: synthetic DNA

<400> SEQUENCE: 992
gtcaaggagt cacg                                                     14

<210> SEQ ID NO 993
<211> LENGTH: 14
<212> TYPE: DNA
<213> ORGANISM: Artificial
<220> FEATURE:
<223> OTHER INFORMATION: synthetic DNA

<400> SEQUENCE: 993
ggttggaatc ttgc                                                     14

<210> SEQ ID NO 994
<211> LENGTH: 14
<212> TYPE: DNA
<213> ORGANISM: Artificial
<220> FEATURE:
<223> OTHER INFORMATION: synthetic DNA

<400> SEQUENCE: 994
catcggtgca ctca                                                     14

<210> SEQ ID NO 995
<211> LENGTH: 14
<212> TYPE: DNA
<213> ORGANISM: Artificial
<220> FEATURE:
<223> OTHER INFORMATION: synthetic DNA
```

```
<400> SEQUENCE: 995
aatgcactag acgt                                                       14

<210> SEQ ID NO 996
<211> LENGTH: 14
<212> TYPE: DNA
<213> ORGANISM: Artificial
<220> FEATURE:
<223> OTHER INFORMATION: synthetic DNA

<400> SEQUENCE: 996
tacagtcagg ctcg                                                       14

<210> SEQ ID NO 997
<211> LENGTH: 14
<212> TYPE: DNA
<213> ORGANISM: Artificial
<220> FEATURE:
<223> OTHER INFORMATION: synthetic DNA

<400> SEQUENCE: 997
agagaagctt agcc                                                       14

<210> SEQ ID NO 998
<211> LENGTH: 14
<212> TYPE: DNA
<213> ORGANISM: Artificial
<220> FEATURE:
<223> OTHER INFORMATION: synthetic DNA

<400> SEQUENCE: 998
ccataggatc gtat                                                       14

<210> SEQ ID NO 999
<211> LENGTH: 14
<212> TYPE: DNA
<213> ORGANISM: Artificial
<220> FEATURE:
<223> OTHER INFORMATION: synthetic DNA

<400> SEQUENCE: 999
ttgtgctaca cctg                                                       14

<210> SEQ ID NO 1000
<211> LENGTH: 14
<212> TYPE: DNA
<213> ORGANISM: Artificial
<220> FEATURE:
<223> OTHER INFORMATION: synthetic DNA

<400> SEQUENCE: 1000
ctccagtaat acta                                                       14

<210> SEQ ID NO 1001
<211> LENGTH: 14
<212> TYPE: DNA
<213> ORGANISM: Artificial
<220> FEATURE:
<223> OTHER INFORMATION: synthetic DNA

<400> SEQUENCE: 1001
tgatgccgat gtgg                                                       14

<210> SEQ ID NO 1002
<211> LENGTH: 14
```

```
<212> TYPE: DNA
<213> ORGANISM: Artificial
<220> FEATURE:
<223> OTHER INFORMATION: synthetic DNA

<400> SEQUENCE: 1002
gtcataccgc ttaa                                                       14

<210> SEQ ID NO 1003
<211> LENGTH: 14
<212> TYPE: DNA
<213> ORGANISM: Artificial
<220> FEATURE:
<223> OTHER INFORMATION: synthetic DNA

<400> SEQUENCE: 1003
acgttctctt gaga                                                       14

<210> SEQ ID NO 1004
<211> LENGTH: 14
<212> TYPE: DNA
<213> ORGANISM: Artificial
<220> FEATURE:
<223> OTHER INFORMATION: synthetic DNA

<400> SEQUENCE: 1004
cagccatatc gtgt                                                       14

<210> SEQ ID NO 1005
<211> LENGTH: 14
<212> TYPE: DNA
<213> ORGANISM: Artificial
<220> FEATURE:
<223> OTHER INFORMATION: synthetic DNA

<400> SEQUENCE: 1005
ttgaacgtag caat                                                       14

<210> SEQ ID NO 1006
<211> LENGTH: 14
<212> TYPE: DNA
<213> ORGANISM: Artificial
<220> FEATURE:
<223> OTHER INFORMATION: synthetic DNA

<400> SEQUENCE: 1006
acaatcgcgg taat                                                       14

<210> SEQ ID NO 1007
<211> LENGTH: 14
<212> TYPE: DNA
<213> ORGANISM: Artificial
<220> FEATURE:
<223> OTHER INFORMATION: synthetic DNA

<400> SEQUENCE: 1007
gttcctgtag atcc                                                       14

<210> SEQ ID NO 1008
<211> LENGTH: 14
<212> TYPE: DNA
<213> ORGANISM: Artificial
<220> FEATURE:
<223> OTHER INFORMATION: synthetic DNA

<400> SEQUENCE: 1008
```
agagccttac ggca                                                        14

<210> SEQ ID NO 1009
<211> LENGTH: 14
<212> TYPE: DNA
<213> ORGANISM: Artificial
<220> FEATURE:
<223> OTHER INFORMATION: synthetic DNA

<400> SEQUENCE: 1009
aatatggcgc cacc                                                        14

<210> SEQ ID NO 1010
<211> LENGTH: 14
<212> TYPE: DNA
<213> ORGANISM: Artificial
<220> FEATURE:
<223> OTHER INFORMATION: synthetic DNA

<400> SEQUENCE: 1010
accatatagg ttcg                                                        14

<210> SEQ ID NO 1011
<211> LENGTH: 14
<212> TYPE: DNA
<213> ORGANISM: Artificial
<220> FEATURE:
<223> OTHER INFORMATION: synthetic DNA

<400> SEQUENCE: 1011
atgcaccaca gctg                                                        14

<210> SEQ ID NO 1012
<211> LENGTH: 14
<212> TYPE: DNA
<213> ORGANISM: Artificial
<220> FEATURE:
<223> OTHER INFORMATION: synthetic DNA

<400> SEQUENCE: 1012
ctactattga acag                                                        14

<210> SEQ ID NO 1013
<211> LENGTH: 14
<212> TYPE: DNA
<213> ORGANISM: Artificial
<220> FEATURE:
<223> OTHER INFORMATION: synthetic DNA

<400> SEQUENCE: 1013
tgccatcact ctag                                                        14

<210> SEQ ID NO 1014
<211> LENGTH: 14
<212> TYPE: DNA
<213> ORGANISM: Artificial
<220> FEATURE:
<223> OTHER INFORMATION: synthetic DNA

<400> SEQUENCE: 1014
gcgaacgaga atcg                                                        14

<210> SEQ ID NO 1015
<211> LENGTH: 14
<212> TYPE: DNA
<213> ORGANISM: Artificial
<220> FEATURE:
<223> OTHER INFORMATION: synthetic DNA

<400> SEQUENCE: 1015
gaatcaagga gacc                                                        14

<210> SEQ ID NO 1016
<211> LENGTH: 14
<212> TYPE: DNA
<213> ORGANISM: Artificial
<220> FEATURE:
<223> OTHER INFORMATION: synthetic DNA

<400> SEQUENCE: 1016
caacatctat gcag                                                        14

<210> SEQ ID NO 1017
<211> LENGTH: 14
<212> TYPE: DNA
<213> ORGANISM: Artificial
<220> FEATURE:
<223> OTHER INFORMATION: synthetic DNA

<400> SEQUENCE: 1017
caatccgtca tgga                                                        14

<210> SEQ ID NO 1018
<211> LENGTH: 14
<212> TYPE: DNA
<213> ORGANISM: Artificial
<220> FEATURE:
<223> OTHER INFORMATION: synthetic DNA

<400> SEQUENCE: 1018
agctcttagc cata                                                        14

<210> SEQ ID NO 1019
<211> LENGTH: 14
<212> TYPE: DNA
<213> ORGANISM: Artificial
<220> FEATURE:
<223> OTHER INFORMATION: synthetic DNA

<400> SEQUENCE: 1019
aacaaggcaa ctgg                                                        14

<210> SEQ ID NO 1020
<211> LENGTH: 14
<212> TYPE: DNA
<213> ORGANISM: Artificial
<220> FEATURE:
<223> OTHER INFORMATION: synthetic DNA

<400> SEQUENCE: 1020
gtcgtcgctc ctat                                                        14

<210> SEQ ID NO 1021
<211> LENGTH: 14
<212> TYPE: DNA
<213> ORGANISM: Artificial
<220> FEATURE:
<223> OTHER INFORMATION: synthetic DNA

<400> SEQUENCE: 1021
gtcatcatta gatg                                                        14

```
<210> SEQ ID NO 1022
<211> LENGTH: 14
<212> TYPE: DNA
<213> ORGANISM: Artificial
<220> FEATURE:
<223> OTHER INFORMATION: synthetic DNA

<400> SEQUENCE: 1022
gcactaagta gcag                                                        14

<210> SEQ ID NO 1023
<211> LENGTH: 14
<212> TYPE: DNA
<213> ORGANISM: Artificial
<220> FEATURE:
<223> OTHER INFORMATION: synthetic DNA

<400> SEQUENCE: 1023
accttaccgg acct                                                        14

<210> SEQ ID NO 1024
<211> LENGTH: 14
<212> TYPE: DNA
<213> ORGANISM: Artificial
<220> FEATURE:
<223> OTHER INFORMATION: synthetic DNA

<400> SEQUENCE: 1024
gctcaggtat gtca                                                        14

<210> SEQ ID NO 1025
<211> LENGTH: 14
<212> TYPE: DNA
<213> ORGANISM: Artificial
<220> FEATURE:
<223> OTHER INFORMATION: synthetic DNA

<400> SEQUENCE: 1025
tgtcacgagt tagt                                                        14

<210> SEQ ID NO 1026
<211> LENGTH: 14
<212> TYPE: DNA
<213> ORGANISM: Artificial
<220> FEATURE:
<223> OTHER INFORMATION: synthetic DNA

<400> SEQUENCE: 1026
cagatgactt acgt                                                        14

<210> SEQ ID NO 1027
<211> LENGTH: 14
<212> TYPE: DNA
<213> ORGANISM: Artificial
<220> FEATURE:
<223> OTHER INFORMATION: synthetic DNA

<400> SEQUENCE: 1027
gaagtagcga ttga                                                        14

<210> SEQ ID NO 1028
<211> LENGTH: 14
<212> TYPE: DNA
<213> ORGANISM: Artificial
<220> FEATURE:
<223> OTHER INFORMATION: synthetic DNA
```

<400> SEQUENCE: 1028
gcaggcaatc tgta                                                14

<210> SEQ ID NO 1029
<211> LENGTH: 14
<212> TYPE: DNA
<213> ORGANISM: Artificial
<220> FEATURE:
<223> OTHER INFORMATION: synthetic DNA

<400> SEQUENCE: 1029
ccttatacaa caag                                                14

<210> SEQ ID NO 1030
<211> LENGTH: 14
<212> TYPE: DNA
<213> ORGANISM: Artificial
<220> FEATURE:
<223> OTHER INFORMATION: synthetic DNA

<400> SEQUENCE: 1030
ccttagattg attg                                                14

<210> SEQ ID NO 1031
<211> LENGTH: 14
<212> TYPE: DNA
<213> ORGANISM: Artificial
<220> FEATURE:
<223> OTHER INFORMATION: synthetic DNA

<400> SEQUENCE: 1031
agccacgagt gata                                                14

<210> SEQ ID NO 1032
<211> LENGTH: 14
<212> TYPE: DNA
<213> ORGANISM: Artificial
<220> FEATURE:
<223> OTHER INFORMATION: synthetic DNA

<400> SEQUENCE: 1032
ggatgactcg tgac                                                14

<210> SEQ ID NO 1033
<211> LENGTH: 14
<212> TYPE: DNA
<213> ORGANISM: Artificial
<220> FEATURE:
<223> OTHER INFORMATION: synthetic DNA

<400> SEQUENCE: 1033
cttcgttcgc catt                                                14

<210> SEQ ID NO 1034
<211> LENGTH: 14
<212> TYPE: DNA
<213> ORGANISM: Artificial
<220> FEATURE:
<223> OTHER INFORMATION: synthetic DNA

<400> SEQUENCE: 1034
tcttgcgtat tgat                                                14

<210> SEQ ID NO 1035

```
<211> LENGTH: 14
<212> TYPE: DNA
<213> ORGANISM: Artificial
<220> FEATURE:
<223> OTHER INFORMATION: synthetic DNA

<400> SEQUENCE: 1035
cttaacgtgg tggc                                                       14

<210> SEQ ID NO 1036
<211> LENGTH: 14
<212> TYPE: DNA
<213> ORGANISM: Artificial
<220> FEATURE:
<223> OTHER INFORMATION: synthetic DNA

<400> SEQUENCE: 1036
tgctgttacg gaag                                                       14

<210> SEQ ID NO 1037
<211> LENGTH: 14
<212> TYPE: DNA
<213> ORGANISM: Artificial
<220> FEATURE:
<223> OTHER INFORMATION: synthetic DNA

<400> SEQUENCE: 1037
ctgaattagt tctc                                                       14

<210> SEQ ID NO 1038
<211> LENGTH: 14
<212> TYPE: DNA
<213> ORGANISM: Artificial
<220> FEATURE:
<223> OTHER INFORMATION: synthetic DNA

<400> SEQUENCE: 1038
cctccaagta caga                                                       14

<210> SEQ ID NO 1039
<211> LENGTH: 14
<212> TYPE: DNA
<213> ORGANISM: Artificial
<220> FEATURE:
<223> OTHER INFORMATION: synthetic DNA

<400> SEQUENCE: 1039
ctggtaattc gcgg                                                       14

<210> SEQ ID NO 1040
<211> LENGTH: 14
<212> TYPE: DNA
<213> ORGANISM: Artificial
<220> FEATURE:
<223> OTHER INFORMATION: synthetic DNA

<400> SEQUENCE: 1040
cgactgcaat ctgg                                                       14

<210> SEQ ID NO 1041
<211> LENGTH: 14
<212> TYPE: DNA
<213> ORGANISM: Artificial
<220> FEATURE:
<223> OTHER INFORMATION: synthetic DNA

<400> SEQUENCE: 1041
```
tggatcgcga ttgg                                                            14

<210> SEQ ID NO 1042
<211> LENGTH: 14
<212> TYPE: DNA
<213> ORGANISM: Artificial
<220> FEATURE:
<223> OTHER INFORMATION: synthetic DNA

<400> SEQUENCE: 1042
cgactattcc tgcg                                                            14

<210> SEQ ID NO 1043
<211> LENGTH: 14
<212> TYPE: DNA
<213> ORGANISM: Artificial
<220> FEATURE:
<223> OTHER INFORMATION: synthetic DNA

<400> SEQUENCE: 1043
caagtaggtc cgtc                                                            14

<210> SEQ ID NO 1044
<211> LENGTH: 14
<212> TYPE: DNA
<213> ORGANISM: Artificial
<220> FEATURE:
<223> OTHER INFORMATION: synthetic DNA

<400> SEQUENCE: 1044
agtaatcagt gttc                                                            14

<210> SEQ ID NO 1045
<211> LENGTH: 14
<212> TYPE: DNA
<213> ORGANISM: Artificial
<220> FEATURE:
<223> OTHER INFORMATION: synthetic DNA

<400> SEQUENCE: 1045
ttattctcac tacg                                                            14

<210> SEQ ID NO 1046
<211> LENGTH: 14
<212> TYPE: DNA
<213> ORGANISM: Artificial
<220> FEATURE:
<223> OTHER INFORMATION: synthetic DNA

<400> SEQUENCE: 1046
catgtcttct tcgt                                                            14

<210> SEQ ID NO 1047
<211> LENGTH: 14
<212> TYPE: DNA
<213> ORGANISM: Artificial
<220> FEATURE:
<223> OTHER INFORMATION: synthetic DNA

<400> SEQUENCE: 1047
aggcacatac catc                                                            14

<210> SEQ ID NO 1048
<211> LENGTH: 14
<212> TYPE: DNA

```
<213> ORGANISM: Artificial
<220> FEATURE:
<223> OTHER INFORMATION: synthetic DNA

<400> SEQUENCE: 1048
aggttagagg atgt                                                  14

<210> SEQ ID NO 1049
<211> LENGTH: 14
<212> TYPE: DNA
<213> ORGANISM: Artificial
<220> FEATURE:
<223> OTHER INFORMATION: synthetic DNA

<400> SEQUENCE: 1049
caactggcaa gtgc                                                  14

<210> SEQ ID NO 1050
<211> LENGTH: 14
<212> TYPE: DNA
<213> ORGANISM: Artificial
<220> FEATURE:
<223> OTHER INFORMATION: synthetic DNA

<400> SEQUENCE: 1050
cgctcacata gagg                                                  14

<210> SEQ ID NO 1051
<211> LENGTH: 14
<212> TYPE: DNA
<213> ORGANISM: Artificial
<220> FEATURE:
<223> OTHER INFORMATION: synthetic DNA

<400> SEQUENCE: 1051
gcaatgtcga gatc                                                  14

<210> SEQ ID NO 1052
<211> LENGTH: 14
<212> TYPE: DNA
<213> ORGANISM: Artificial
<220> FEATURE:
<223> OTHER INFORMATION: synthetic DNA

<400> SEQUENCE: 1052
gttctgtggt gctc                                                  14

<210> SEQ ID NO 1053
<211> LENGTH: 14
<212> TYPE: DNA
<213> ORGANISM: Artificial
<220> FEATURE:
<223> OTHER INFORMATION: synthetic DNA

<400> SEQUENCE: 1053
aagtgatcag acta                                                  14

<210> SEQ ID NO 1054
<211> LENGTH: 14
<212> TYPE: DNA
<213> ORGANISM: Artificial
<220> FEATURE:
<223> OTHER INFORMATION: synthetic DNA

<400> SEQUENCE: 1054
attgaaggat tcca                                                  14
```

<210> SEQ ID NO 1055
<211> LENGTH: 14
<212> TYPE: DNA
<213> ORGANISM: Artificial
<220> FEATURE:
<223> OTHER INFORMATION: synthetic DNA

<400> SEQUENCE: 1055
acgccatgct acta                                                         14

<210> SEQ ID NO 1056
<211> LENGTH: 14
<212> TYPE: DNA
<213> ORGANISM: Artificial
<220> FEATURE:
<223> OTHER INFORMATION: synthetic DNA

<400> SEQUENCE: 1056
ctgaagatgt ctgc                                                         14

<210> SEQ ID NO 1057
<211> LENGTH: 16
<212> TYPE: DNA
<213> ORGANISM: Artificial
<220> FEATURE:
<223> OTHER INFORMATION: synthetic DNA

<400> SEQUENCE: 1057
gacaatctct gccgat                                                       16

<210> SEQ ID NO 1058
<211> LENGTH: 16
<212> TYPE: DNA
<213> ORGANISM: Artificial
<220> FEATURE:
<223> OTHER INFORMATION: synthetic DNA

<400> SEQUENCE: 1058
ggtccgccta atgtaa                                                       16

<210> SEQ ID NO 1059
<211> LENGTH: 16
<212> TYPE: DNA
<213> ORGANISM: Artificial
<220> FEATURE:
<223> OTHER INFORMATION: synthetic DNA

<400> SEQUENCE: 1059
agccacaggc aattcc                                                       16

<210> SEQ ID NO 1060
<211> LENGTH: 16
<212> TYPE: DNA
<213> ORGANISM: Artificial
<220> FEATURE:
<223> OTHER INFORMATION: synthetic DNA

<400> SEQUENCE: 1060
atctcaagtt ctcaac                                                       16

<210> SEQ ID NO 1061
<211> LENGTH: 16
<212> TYPE: DNA
<213> ORGANISM: Artificial
<220> FEATURE:

```
<223> OTHER INFORMATION: synthetic DNA

<400> SEQUENCE: 1061
tgtaacgcat acgacg                                              16

<210> SEQ ID NO 1062
<211> LENGTH: 16
<212> TYPE: DNA
<213> ORGANISM: Artificial
<220> FEATURE:
<223> OTHER INFORMATION: synthetic DNA

<400> SEQUENCE: 1062
tatctcgaat accagc                                              16

<210> SEQ ID NO 1063
<211> LENGTH: 16
<212> TYPE: DNA
<213> ORGANISM: Artificial
<220> FEATURE:
<223> OTHER INFORMATION: synthetic DNA

<400> SEQUENCE: 1063
accgcaacac aggcaa                                              16

<210> SEQ ID NO 1064
<211> LENGTH: 16
<212> TYPE: DNA
<213> ORGANISM: Artificial
<220> FEATURE:
<223> OTHER INFORMATION: synthetic DNA

<400> SEQUENCE: 1064
ggccagtaac atgact                                              16

<210> SEQ ID NO 1065
<211> LENGTH: 16
<212> TYPE: DNA
<213> ORGANISM: Artificial
<220> FEATURE:
<223> OTHER INFORMATION: synthetic DNA

<400> SEQUENCE: 1065
gtgaacagtt aaggtg                                              16

<210> SEQ ID NO 1066
<211> LENGTH: 16
<212> TYPE: DNA
<213> ORGANISM: Artificial
<220> FEATURE:
<223> OTHER INFORMATION: synthetic DNA

<400> SEQUENCE: 1066
ccaggatccg tattgc                                              16

<210> SEQ ID NO 1067
<211> LENGTH: 16
<212> TYPE: DNA
<213> ORGANISM: Artificial
<220> FEATURE:
<223> OTHER INFORMATION: synthetic DNA

<400> SEQUENCE: 1067
gacctagcac tagacc                                              16
```

```
<210> SEQ ID NO 1068
<211> LENGTH: 16
<212> TYPE: DNA
<213> ORGANISM: Artificial
<220> FEATURE:
<223> OTHER INFORMATION: synthetic DNA

<400> SEQUENCE: 1068
cgccatccta ttcacg                                                    16

<210> SEQ ID NO 1069
<211> LENGTH: 16
<212> TYPE: DNA
<213> ORGANISM: Artificial
<220> FEATURE:
<223> OTHER INFORMATION: synthetic DNA

<400> SEQUENCE: 1069
aagtgcagta atggaa                                                    16

<210> SEQ ID NO 1070
<211> LENGTH: 16
<212> TYPE: DNA
<213> ORGANISM: Artificial
<220> FEATURE:
<223> OTHER INFORMATION: synthetic DNA

<400> SEQUENCE: 1070
tcaacgcgtt cgtcta                                                    16

<210> SEQ ID NO 1071
<211> LENGTH: 16
<212> TYPE: DNA
<213> ORGANISM: Artificial
<220> FEATURE:
<223> OTHER INFORMATION: synthetic DNA

<400> SEQUENCE: 1071
agcggccact atctaa                                                    16

<210> SEQ ID NO 1072
<211> LENGTH: 16
<212> TYPE: DNA
<213> ORGANISM: Artificial
<220> FEATURE:
<223> OTHER INFORMATION: synthetic DNA

<400> SEQUENCE: 1072
ctcggcgcca tataga                                                    16

<210> SEQ ID NO 1073
<211> LENGTH: 16
<212> TYPE: DNA
<213> ORGANISM: Artificial
<220> FEATURE:
<223> OTHER INFORMATION: synthetic DNA

<400> SEQUENCE: 1073
cgataactta gaagaa                                                    16

<210> SEQ ID NO 1074
<211> LENGTH: 16
<212> TYPE: DNA
<213> ORGANISM: Artificial
<220> FEATURE:
<223> OTHER INFORMATION: synthetic DNA
```

<400> SEQUENCE: 1074
cataggatgt gacgcc    16

<210> SEQ ID NO 1075
<211> LENGTH: 16
<212> TYPE: DNA
<213> ORGANISM: Artificial
<220> FEATURE:
<223> OTHER INFORMATION: synthetic DNA

<400> SEQUENCE: 1075
ggcttgtcgt cgtatc    16

<210> SEQ ID NO 1076
<211> LENGTH: 16
<212> TYPE: DNA
<213> ORGANISM: Artificial
<220> FEATURE:
<223> OTHER INFORMATION: synthetic DNA

<400> SEQUENCE: 1076
cttgtctgaa tattag    16

<210> SEQ ID NO 1077
<211> LENGTH: 16
<212> TYPE: DNA
<213> ORGANISM: Artificial
<220> FEATURE:
<223> OTHER INFORMATION: synthetic DNA

<400> SEQUENCE: 1077
acagttcgag tgtcgg    16

<210> SEQ ID NO 1078
<211> LENGTH: 16
<212> TYPE: DNA
<213> ORGANISM: Artificial
<220> FEATURE:
<223> OTHER INFORMATION: synthetic DNA

<400> SEQUENCE: 1078
ctctaacctg tgacgt    16

<210> SEQ ID NO 1079
<211> LENGTH: 16
<212> TYPE: DNA
<213> ORGANISM: Artificial
<220> FEATURE:
<223> OTHER INFORMATION: synthetic DNA

<400> SEQUENCE: 1079
cgcgctaatt caacaa    16

<210> SEQ ID NO 1080
<211> LENGTH: 16
<212> TYPE: DNA
<213> ORGANISM: Artificial
<220> FEATURE:
<223> OTHER INFORMATION: synthetic DNA

<400> SEQUENCE: 1080
actcacgaat gcggca    16

<210> SEQ ID NO 1081
<211> LENGTH: 16

```
<212> TYPE: DNA
<213> ORGANISM: Artificial
<220> FEATURE:
<223> OTHER INFORMATION: synthetic DNA

<400> SEQUENCE: 1081
aatcttcggc attcat                                              16

<210> SEQ ID NO 1082
<211> LENGTH: 16
<212> TYPE: DNA
<213> ORGANISM: Artificial
<220> FEATURE:
<223> OTHER INFORMATION: synthetic DNA

<400> SEQUENCE: 1082
aagtatcagg atcgcg                                              16

<210> SEQ ID NO 1083
<211> LENGTH: 16
<212> TYPE: DNA
<213> ORGANISM: Artificial
<220> FEATURE:
<223> OTHER INFORMATION: synthetic DNA

<400> SEQUENCE: 1083
agtaactctg cagaca                                              16

<210> SEQ ID NO 1084
<211> LENGTH: 16
<212> TYPE: DNA
<213> ORGANISM: Artificial
<220> FEATURE:
<223> OTHER INFORMATION: synthetic DNA

<400> SEQUENCE: 1084
ggattgaaca ttgtgc                                              16

<210> SEQ ID NO 1085
<211> LENGTH: 16
<212> TYPE: DNA
<213> ORGANISM: Artificial
<220> FEATURE:
<223> OTHER INFORMATION: synthetic DNA

<400> SEQUENCE: 1085
gtgatgctca cgcatc                                              16

<210> SEQ ID NO 1086
<211> LENGTH: 16
<212> TYPE: DNA
<213> ORGANISM: Artificial
<220> FEATURE:
<223> OTHER INFORMATION: synthetic DNA

<400> SEQUENCE: 1086
cgtagcgtaa cggata                                              16

<210> SEQ ID NO 1087
<211> LENGTH: 16
<212> TYPE: DNA
<213> ORGANISM: Artificial
<220> FEATURE:
<223> OTHER INFORMATION: synthetic DNA

<400> SEQUENCE: 1087
```

```
tgcgatgcac cgttag                                              16

<210> SEQ ID NO 1088
<211> LENGTH: 16
<212> TYPE: DNA
<213> ORGANISM: Artificial
<220> FEATURE:
<223> OTHER INFORMATION: synthetic DNA

<400> SEQUENCE: 1088
ccagtatgct ctcagg                                              16

<210> SEQ ID NO 1089
<211> LENGTH: 16
<212> TYPE: DNA
<213> ORGANISM: Artificial
<220> FEATURE:
<223> OTHER INFORMATION: synthetic DNA

<400> SEQUENCE: 1089
aatgacgttg aagcct                                              16

<210> SEQ ID NO 1090
<211> LENGTH: 16
<212> TYPE: DNA
<213> ORGANISM: Artificial
<220> FEATURE:
<223> OTHER INFORMATION: synthetic DNA

<400> SEQUENCE: 1090
tcgattctat aggagt                                              16

<210> SEQ ID NO 1091
<211> LENGTH: 16
<212> TYPE: DNA
<213> ORGANISM: Artificial
<220> FEATURE:
<223> OTHER INFORMATION: synthetic DNA

<400> SEQUENCE: 1091
cgataggttc agctat                                              16

<210> SEQ ID NO 1092
<211> LENGTH: 16
<212> TYPE: DNA
<213> ORGANISM: Artificial
<220> FEATURE:
<223> OTHER INFORMATION: synthetic DNA

<400> SEQUENCE: 1092
ccatgttgat agaata                                              16

<210> SEQ ID NO 1093
<211> LENGTH: 16
<212> TYPE: DNA
<213> ORGANISM: Artificial
<220> FEATURE:
<223> OTHER INFORMATION: synthetic DNA

<400> SEQUENCE: 1093
gagccacttc tacagg                                              16

<210> SEQ ID NO 1094
<211> LENGTH: 16
<212> TYPE: DNA
<213> ORGANISM: Artificial
```

```
<220> FEATURE:
<223> OTHER INFORMATION: synthetic DNA

<400> SEQUENCE: 1094
gcgaactctc ggtaat                                                    16

<210> SEQ ID NO 1095
<211> LENGTH: 16
<212> TYPE: DNA
<213> ORGANISM: Artificial
<220> FEATURE:
<223> OTHER INFORMATION: synthetic DNA

<400> SEQUENCE: 1095
gacctgagta gctggt                                                    16

<210> SEQ ID NO 1096
<211> LENGTH: 16
<212> TYPE: DNA
<213> ORGANISM: Artificial
<220> FEATURE:
<223> OTHER INFORMATION: synthetic DNA

<400> SEQUENCE: 1096
cgagtctatt agcctg                                                    16

<210> SEQ ID NO 1097
<211> LENGTH: 16
<212> TYPE: DNA
<213> ORGANISM: Artificial
<220> FEATURE:
<223> OTHER INFORMATION: synthetic DNA

<400> SEQUENCE: 1097
gtagtgccat acacct                                                    16

<210> SEQ ID NO 1098
<211> LENGTH: 16
<212> TYPE: DNA
<213> ORGANISM: Artificial
<220> FEATURE:
<223> OTHER INFORMATION: synthetic DNA

<400> SEQUENCE: 1098
ccagtggtct atagca                                                    16

<210> SEQ ID NO 1099
<211> LENGTH: 16
<212> TYPE: DNA
<213> ORGANISM: Artificial
<220> FEATURE:
<223> OTHER INFORMATION: synthetic DNA

<400> SEQUENCE: 1099
gtcagtgcgt tattgc                                                    16

<210> SEQ ID NO 1100
<211> LENGTH: 16
<212> TYPE: DNA
<213> ORGANISM: Artificial
<220> FEATURE:
<223> OTHER INFORMATION: synthetic DNA

<400> SEQUENCE: 1100
agtgtcggag tgacga                                                    16
```

```
<210> SEQ ID NO 1101
<211> LENGTH: 16
<212> TYPE: DNA
<213> ORGANISM: Artificial
<220> FEATURE:
<223> OTHER INFORMATION: synthetic DNA

<400> SEQUENCE: 1101
aatctccgct atagtt                                                     16

<210> SEQ ID NO 1102
<211> LENGTH: 16
<212> TYPE: DNA
<213> ORGANISM: Artificial
<220> FEATURE:
<223> OTHER INFORMATION: synthetic DNA

<400> SEQUENCE: 1102
cgagtaggtc tgactt                                                     16

<210> SEQ ID NO 1103
<211> LENGTH: 16
<212> TYPE: DNA
<213> ORGANISM: Artificial
<220> FEATURE:
<223> OTHER INFORMATION: synthetic DNA

<400> SEQUENCE: 1103
ctgtcgctct aataac                                                     16

<210> SEQ ID NO 1104
<211> LENGTH: 16
<212> TYPE: DNA
<213> ORGANISM: Artificial
<220> FEATURE:
<223> OTHER INFORMATION: synthetic DNA

<400> SEQUENCE: 1104
gctgtcaata taactg                                                     16

<210> SEQ ID NO 1105
<211> LENGTH: 16
<212> TYPE: DNA
<213> ORGANISM: Artificial
<220> FEATURE:
<223> OTHER INFORMATION: synthetic DNA

<400> SEQUENCE: 1105
agctcaagtt gaatcc                                                     16

<210> SEQ ID NO 1106
<211> LENGTH: 16
<212> TYPE: DNA
<213> ORGANISM: Artificial
<220> FEATURE:
<223> OTHER INFORMATION: synthetic DNA

<400> SEQUENCE: 1106
aattcatgct cctaac                                                     16

<210> SEQ ID NO 1107
<211> LENGTH: 16
<212> TYPE: DNA
<213> ORGANISM: Artificial
<220> FEATURE:
<223> OTHER INFORMATION: synthetic DNA
```

```
<400> SEQUENCE: 1107
ccaaggtctg gtgata                                                    16

<210> SEQ ID NO 1108
<211> LENGTH: 16
<212> TYPE: DNA
<213> ORGANISM: Artificial
<220> FEATURE:
<223> OTHER INFORMATION: synthetic DNA

<400> SEQUENCE: 1108
ctccacgtat cttgaa                                                    16

<210> SEQ ID NO 1109
<211> LENGTH: 16
<212> TYPE: DNA
<213> ORGANISM: Artificial
<220> FEATURE:
<223> OTHER INFORMATION: synthetic DNA

<400> SEQUENCE: 1109
tagccgaaca acactt                                                    16

<210> SEQ ID NO 1110
<211> LENGTH: 16
<212> TYPE: DNA
<213> ORGANISM: Artificial
<220> FEATURE:
<223> OTHER INFORMATION: synthetic DNA

<400> SEQUENCE: 1110
agtacacgac atatgc                                                    16

<210> SEQ ID NO 1111
<211> LENGTH: 16
<212> TYPE: DNA
<213> ORGANISM: Artificial
<220> FEATURE:
<223> OTHER INFORMATION: synthetic DNA

<400> SEQUENCE: 1111
acgttctaga ctcctg                                                    16

<210> SEQ ID NO 1112
<211> LENGTH: 16
<212> TYPE: DNA
<213> ORGANISM: Artificial
<220> FEATURE:
<223> OTHER INFORMATION: synthetic DNA

<400> SEQUENCE: 1112
cgactcaagc actgct                                                    16

<210> SEQ ID NO 1113
<211> LENGTH: 16
<212> TYPE: DNA
<213> ORGANISM: Artificial
<220> FEATURE:
<223> OTHER INFORMATION: synthetic DNA

<400> SEQUENCE: 1113
tgaagctcac gattaa                                                    16

<210> SEQ ID NO 1114
```

```
<211> LENGTH: 16
<212> TYPE: DNA
<213> ORGANISM: Artificial
<220> FEATURE:
<223> OTHER INFORMATION: synthetic DNA

<400> SEQUENCE: 1114
tatctaacgt atggta                                                         16

<210> SEQ ID NO 1115
<211> LENGTH: 16
<212> TYPE: DNA
<213> ORGANISM: Artificial
<220> FEATURE:
<223> OTHER INFORMATION: synthetic DNA

<400> SEQUENCE: 1115
tataccatgt tccttg                                                         16

<210> SEQ ID NO 1116
<211> LENGTH: 16
<212> TYPE: DNA
<213> ORGANISM: Artificial
<220> FEATURE:
<223> OTHER INFORMATION: synthetic DNA

<400> SEQUENCE: 1116
ttcctacgat gacttc                                                         16

<210> SEQ ID NO 1117
<211> LENGTH: 16
<212> TYPE: DNA
<213> ORGANISM: Artificial
<220> FEATURE:
<223> OTHER INFORMATION: synthetic DNA

<400> SEQUENCE: 1117
ctctccaata tgtgcc                                                         16

<210> SEQ ID NO 1118
<211> LENGTH: 16
<212> TYPE: DNA
<213> ORGANISM: Artificial
<220> FEATURE:
<223> OTHER INFORMATION: synthetic DNA

<400> SEQUENCE: 1118
gagtagagtc ttgcca                                                         16

<210> SEQ ID NO 1119
<211> LENGTH: 16
<212> TYPE: DNA
<213> ORGANISM: Artificial
<220> FEATURE:
<223> OTHER INFORMATION: synthetic DNA

<400> SEQUENCE: 1119
gcgagatgtg gtccta                                                         16

<210> SEQ ID NO 1120
<211> LENGTH: 16
<212> TYPE: DNA
<213> ORGANISM: Artificial
<220> FEATURE:
<223> OTHER INFORMATION: synthetic DNA

<400> SEQUENCE: 1120
```
aagctacacg gaccac                                                    16

<210> SEQ ID NO 1121
<211> LENGTH: 16
<212> TYPE: DNA
<213> ORGANISM: Artificial
<220> FEATURE:
<223> OTHER INFORMATION: synthetic DNA

<400> SEQUENCE: 1121
atacaactgg caaccg                                                    16

<210> SEQ ID NO 1122
<211> LENGTH: 16
<212> TYPE: DNA
<213> ORGANISM: Artificial
<220> FEATURE:
<223> OTHER INFORMATION: synthetic DNA

<400> SEQUENCE: 1122
cggtagatgc tatgct                                                    16

<210> SEQ ID NO 1123
<211> LENGTH: 16
<212> TYPE: DNA
<213> ORGANISM: Artificial
<220> FEATURE:
<223> OTHER INFORMATION: synthetic DNA

<400> SEQUENCE: 1123
tcttgaccgg tcatca                                                    16

<210> SEQ ID NO 1124
<211> LENGTH: 16
<212> TYPE: DNA
<213> ORGANISM: Artificial
<220> FEATURE:
<223> OTHER INFORMATION: synthetic DNA

<400> SEQUENCE: 1124
agatcgtgca tgcgat                                                    16

<210> SEQ ID NO 1125
<211> LENGTH: 16
<212> TYPE: DNA
<213> ORGANISM: Artificial
<220> FEATURE:
<223> OTHER INFORMATION: synthetic DNA

<400> SEQUENCE: 1125
tcctcgagac agcctt                                                    16

<210> SEQ ID NO 1126
<211> LENGTH: 16
<212> TYPE: DNA
<213> ORGANISM: Artificial
<220> FEATURE:
<223> OTHER INFORMATION: synthetic DNA

<400> SEQUENCE: 1126
tagccggtac cactta                                                    16

<210> SEQ ID NO 1127
<211> LENGTH: 16
<212> TYPE: DNA

```
<213> ORGANISM: Artificial
<220> FEATURE:
<223> OTHER INFORMATION: synthetic DNA

<400> SEQUENCE: 1127
gtaaggcagc gtgcaa                                                 16

<210> SEQ ID NO 1128
<211> LENGTH: 16
<212> TYPE: DNA
<213> ORGANISM: Artificial
<220> FEATURE:
<223> OTHER INFORMATION: synthetic DNA

<400> SEQUENCE: 1128
tagtctgctc ctggtc                                                 16

<210> SEQ ID NO 1129
<211> LENGTH: 16
<212> TYPE: DNA
<213> ORGANISM: Artificial
<220> FEATURE:
<223> OTHER INFORMATION: synthetic DNA

<400> SEQUENCE: 1129
tggattatag cagcag                                                 16

<210> SEQ ID NO 1130
<211> LENGTH: 16
<212> TYPE: DNA
<213> ORGANISM: Artificial
<220> FEATURE:
<223> OTHER INFORMATION: synthetic DNA

<400> SEQUENCE: 1130
aagaatgatc agacat                                                 16

<210> SEQ ID NO 1131
<211> LENGTH: 16
<212> TYPE: DNA
<213> ORGANISM: Artificial
<220> FEATURE:
<223> OTHER INFORMATION: synthetic DNA

<400> SEQUENCE: 1131
cagcgctata tacctc                                                 16

<210> SEQ ID NO 1132
<211> LENGTH: 16
<212> TYPE: DNA
<213> ORGANISM: Artificial
<220> FEATURE:
<223> OTHER INFORMATION: synthetic DNA

<400> SEQUENCE: 1132
gagtagtacc tccacc                                                 16

<210> SEQ ID NO 1133
<211> LENGTH: 16
<212> TYPE: DNA
<213> ORGANISM: Artificial
<220> FEATURE:
<223> OTHER INFORMATION: synthetic DNA

<400> SEQUENCE: 1133
gacgtgatcc tctaga                                                 16
```

<210> SEQ ID NO 1134
<211> LENGTH: 16
<212> TYPE: DNA
<213> ORGANISM: Artificial
<220> FEATURE:
<223> OTHER INFORMATION: synthetic DNA

<400> SEQUENCE: 1134
gttccgttca ctacga                                                 16

<210> SEQ ID NO 1135
<211> LENGTH: 16
<212> TYPE: DNA
<213> ORGANISM: Artificial
<220> FEATURE:
<223> OTHER INFORMATION: synthetic DNA

<400> SEQUENCE: 1135
tgcaagcacc aggatg                                                 16

<210> SEQ ID NO 1136
<211> LENGTH: 16
<212> TYPE: DNA
<213> ORGANISM: Artificial
<220> FEATURE:
<223> OTHER INFORMATION: synthetic DNA

<400> SEQUENCE: 1136
ttagttggcg gctgag                                                 16

<210> SEQ ID NO 1137
<211> LENGTH: 16
<212> TYPE: DNA
<213> ORGANISM: Artificial
<220> FEATURE:
<223> OTHER INFORMATION: synthetic DNA

<400> SEQUENCE: 1137
cagatgcaga catacg                                                 16

<210> SEQ ID NO 1138
<211> LENGTH: 16
<212> TYPE: DNA
<213> ORGANISM: Artificial
<220> FEATURE:
<223> OTHER INFORMATION: synthetic DNA

<400> SEQUENCE: 1138
gacgcttgat gattat                                                 16

<210> SEQ ID NO 1139
<211> LENGTH: 16
<212> TYPE: DNA
<213> ORGANISM: Artificial
<220> FEATURE:
<223> OTHER INFORMATION: synthetic DNA

<400> SEQUENCE: 1139
tggatcacga ctagga                                                 16

<210> SEQ ID NO 1140
<211> LENGTH: 16
<212> TYPE: DNA
<213> ORGANISM: Artificial
<220> FEATURE:

<223> OTHER INFORMATION: synthetic DNA

<400> SEQUENCE: 1140
ctcgtcggta taacgc                                                      16

<210> SEQ ID NO 1141
<211> LENGTH: 16
<212> TYPE: DNA
<213> ORGANISM: Artificial
<220> FEATURE:
<223> OTHER INFORMATION: synthetic DNA

<400> SEQUENCE: 1141
aagcacggat gcgatt                                                      16

<210> SEQ ID NO 1142
<211> LENGTH: 16
<212> TYPE: DNA
<213> ORGANISM: Artificial
<220> FEATURE:
<223> OTHER INFORMATION: synthetic DNA

<400> SEQUENCE: 1142
agatcttccg gtgaac                                                      16

<210> SEQ ID NO 1143
<211> LENGTH: 16
<212> TYPE: DNA
<213> ORGANISM: Artificial
<220> FEATURE:
<223> OTHER INFORMATION: synthetic DNA

<400> SEQUENCE: 1143
ggacaatagc aacctg                                                      16

<210> SEQ ID NO 1144
<211> LENGTH: 16
<212> TYPE: DNA
<213> ORGANISM: Artificial
<220> FEATURE:
<223> OTHER INFORMATION: synthetic DNA

<400> SEQUENCE: 1144
gataatcggt tccaat                                                      16

<210> SEQ ID NO 1145
<211> LENGTH: 16
<212> TYPE: DNA
<213> ORGANISM: Artificial
<220> FEATURE:
<223> OTHER INFORMATION: synthetic DNA

<400> SEQUENCE: 1145
ctcaagctac agttgt                                                      16

<210> SEQ ID NO 1146
<211> LENGTH: 16
<212> TYPE: DNA
<213> ORGANISM: Artificial
<220> FEATURE:
<223> OTHER INFORMATION: synthetic DNA

<400> SEQUENCE: 1146
gttggcatga tgtaga                                                      16

```
<210> SEQ ID NO 1147
<211> LENGTH: 16
<212> TYPE: DNA
<213> ORGANISM: Artificial
<220> FEATURE:
<223> OTHER INFORMATION: synthetic DNA

<400> SEQUENCE: 1147
cagcatgagg taagtg                                                    16

<210> SEQ ID NO 1148
<211> LENGTH: 16
<212> TYPE: DNA
<213> ORGANISM: Artificial
<220> FEATURE:
<223> OTHER INFORMATION: synthetic DNA

<400> SEQUENCE: 1148
gcctcatcac acgtca                                                    16

<210> SEQ ID NO 1149
<211> LENGTH: 16
<212> TYPE: DNA
<213> ORGANISM: Artificial
<220> FEATURE:
<223> OTHER INFORMATION: synthetic DNA

<400> SEQUENCE: 1149
tcgatactac acatcg                                                    16

<210> SEQ ID NO 1150
<211> LENGTH: 16
<212> TYPE: DNA
<213> ORGANISM: Artificial
<220> FEATURE:
<223> OTHER INFORMATION: synthetic DNA

<400> SEQUENCE: 1150
tacacgaggc ttgatc                                                    16

<210> SEQ ID NO 1151
<211> LENGTH: 16
<212> TYPE: DNA
<213> ORGANISM: Artificial
<220> FEATURE:
<223> OTHER INFORMATION: synthetic DNA

<400> SEQUENCE: 1151
ttctcgtgtc cgcatt                                                    16

<210> SEQ ID NO 1152
<211> LENGTH: 16
<212> TYPE: DNA
<213> ORGANISM: Artificial
<220> FEATURE:
<223> OTHER INFORMATION: synthetic DNA

<400> SEQUENCE: 1152
ggtgaagcaa cagcat                                                    16

<210> SEQ ID NO 1153
<211> LENGTH: 18
<212> TYPE: DNA
<213> ORGANISM: Artificial
<220> FEATURE:
<223> OTHER INFORMATION: synthetic DNA
```

```
<400> SEQUENCE: 1153
cgaaccgact gtacagtt                                                    18

<210> SEQ ID NO 1154
<211> LENGTH: 18
<212> TYPE: DNA
<213> ORGANISM: Artificial
<220> FEATURE:
<223> OTHER INFORMATION: synthetic DNA

<400> SEQUENCE: 1154
ccgactgcgg ataagtta                                                    18

<210> SEQ ID NO 1155
<211> LENGTH: 18
<212> TYPE: DNA
<213> ORGANISM: Artificial
<220> FEATURE:
<223> OTHER INFORMATION: synthetic DNA

<400> SEQUENCE: 1155
cgacaggtag gtaagcag                                                    18

<210> SEQ ID NO 1156
<211> LENGTH: 18
<212> TYPE: DNA
<213> ORGANISM: Artificial
<220> FEATURE:
<223> OTHER INFORMATION: synthetic DNA

<400> SEQUENCE: 1156
tgatacgttg gtatacag                                                    18

<210> SEQ ID NO 1157
<211> LENGTH: 18
<212> TYPE: DNA
<213> ORGANISM: Artificial
<220> FEATURE:
<223> OTHER INFORMATION: synthetic DNA

<400> SEQUENCE: 1157
ctactataga atacgtag                                                    18

<210> SEQ ID NO 1158
<211> LENGTH: 18
<212> TYPE: DNA
<213> ORGANISM: Artificial
<220> FEATURE:
<223> OTHER INFORMATION: synthetic DNA

<400> SEQUENCE: 1158
agactgtggc aatggcat                                                    18

<210> SEQ ID NO 1159
<211> LENGTH: 18
<212> TYPE: DNA
<213> ORGANISM: Artificial
<220> FEATURE:
<223> OTHER INFORMATION: synthetic DNA

<400> SEQUENCE: 1159
ggaagactga tacaacga                                                    18

<210> SEQ ID NO 1160
<211> LENGTH: 18
```

```
<212> TYPE: DNA
<213> ORGANISM: Artificial
<220> FEATURE:
<223> OTHER INFORMATION: synthetic DNA

<400> SEQUENCE: 1160
tatgcacata tagcgctt                                                   18

<210> SEQ ID NO 1161
<211> LENGTH: 18
<212> TYPE: DNA
<213> ORGANISM: Artificial
<220> FEATURE:
<223> OTHER INFORMATION: synthetic DNA

<400> SEQUENCE: 1161
catggtaatc gaccgagg                                                   18

<210> SEQ ID NO 1162
<211> LENGTH: 18
<212> TYPE: DNA
<213> ORGANISM: Artificial
<220> FEATURE:
<223> OTHER INFORMATION: synthetic DNA

<400> SEQUENCE: 1162
gtcattgccg tcattgcc                                                   18

<210> SEQ ID NO 1163
<211> LENGTH: 18
<212> TYPE: DNA
<213> ORGANISM: Artificial
<220> FEATURE:
<223> OTHER INFORMATION: synthetic DNA

<400> SEQUENCE: 1163
cctaagaact ccgaagct                                                   18

<210> SEQ ID NO 1164
<211> LENGTH: 18
<212> TYPE: DNA
<213> ORGANISM: Artificial
<220> FEATURE:
<223> OTHER INFORMATION: synthetic DNA

<400> SEQUENCE: 1164
tcgctcaccg tactagga                                                   18

<210> SEQ ID NO 1165
<211> LENGTH: 18
<212> TYPE: DNA
<213> ORGANISM: Artificial
<220> FEATURE:
<223> OTHER INFORMATION: synthetic DNA

<400> SEQUENCE: 1165
tattactgtc acagcagg                                                   18

<210> SEQ ID NO 1166
<211> LENGTH: 18
<212> TYPE: DNA
<213> ORGANISM: Artificial
<220> FEATURE:
<223> OTHER INFORMATION: synthetic DNA

<400> SEQUENCE: 1166
```
tgagacaggc tacgagtc                                               18

<210> SEQ ID NO 1167
<211> LENGTH: 18
<212> TYPE: DNA
<213> ORGANISM: Artificial
<220> FEATURE:
<223> OTHER INFORMATION: synthetic DNA

<400> SEQUENCE: 1167
aagctatgcg aacacgtt                                               18

<210> SEQ ID NO 1168
<211> LENGTH: 18
<212> TYPE: DNA
<213> ORGANISM: Artificial
<220> FEATURE:
<223> OTHER INFORMATION: synthetic DNA

<400> SEQUENCE: 1168
aacggaggag tgagccaa                                               18

<210> SEQ ID NO 1169
<211> LENGTH: 18
<212> TYPE: DNA
<213> ORGANISM: Artificial
<220> FEATURE:
<223> OTHER INFORMATION: synthetic DNA

<400> SEQUENCE: 1169
ccactatgga catcatgg                                               18

<210> SEQ ID NO 1170
<211> LENGTH: 18
<212> TYPE: DNA
<213> ORGANISM: Artificial
<220> FEATURE:
<223> OTHER INFORMATION: synthetic DNA

<400> SEQUENCE: 1170
atggtggtgg atagctcg                                               18

<210> SEQ ID NO 1171
<211> LENGTH: 18
<212> TYPE: DNA
<213> ORGANISM: Artificial
<220> FEATURE:
<223> OTHER INFORMATION: synthetic DNA

<400> SEQUENCE: 1171
tcaccggtta cacatcgc                                               18

<210> SEQ ID NO 1172
<211> LENGTH: 18
<212> TYPE: DNA
<213> ORGANISM: Artificial
<220> FEATURE:
<223> OTHER INFORMATION: synthetic DNA

<400> SEQUENCE: 1172
aagatactga gatatgga                                               18

<210> SEQ ID NO 1173
<211> LENGTH: 18
<212> TYPE: DNA
<213> ORGANISM: Artificial

```
<220> FEATURE:
<223> OTHER INFORMATION: synthetic DNA

<400> SEQUENCE: 1173
gacctgttct tgaactag                                               18

<210> SEQ ID NO 1174
<211> LENGTH: 18
<212> TYPE: DNA
<213> ORGANISM: Artificial
<220> FEATURE:
<223> OTHER INFORMATION: synthetic DNA

<400> SEQUENCE: 1174
aagtagagct ctcggtta                                               18

<210> SEQ ID NO 1175
<211> LENGTH: 18
<212> TYPE: DNA
<213> ORGANISM: Artificial
<220> FEATURE:
<223> OTHER INFORMATION: synthetic DNA

<400> SEQUENCE: 1175
ctatgttctt actctctt                                               18

<210> SEQ ID NO 1176
<211> LENGTH: 18
<212> TYPE: DNA
<213> ORGANISM: Artificial
<220> FEATURE:
<223> OTHER INFORMATION: synthetic DNA

<400> SEQUENCE: 1176
caaggctata agcggtta                                               18

<210> SEQ ID NO 1177
<211> LENGTH: 18
<212> TYPE: DNA
<213> ORGANISM: Artificial
<220> FEATURE:
<223> OTHER INFORMATION: synthetic DNA

<400> SEQUENCE: 1177
gaagctaatt aaccgata                                               18

<210> SEQ ID NO 1178
<211> LENGTH: 18
<212> TYPE: DNA
<213> ORGANISM: Artificial
<220> FEATURE:
<223> OTHER INFORMATION: synthetic DNA

<400> SEQUENCE: 1178
ttcacgtctg ccaagcac                                               18

<210> SEQ ID NO 1179
<211> LENGTH: 18
<212> TYPE: DNA
<213> ORGANISM: Artificial
<220> FEATURE:
<223> OTHER INFORMATION: synthetic DNA

<400> SEQUENCE: 1179
atcgtataga tcgagaca                                               18
```

<210> SEQ ID NO 1180
<211> LENGTH: 18
<212> TYPE: DNA
<213> ORGANISM: Artificial
<220> FEATURE:
<223> OTHER INFORMATION: synthetic DNA

<400> SEQUENCE: 1180
gtcacagatt cacatcat                                            18

<210> SEQ ID NO 1181
<211> LENGTH: 18
<212> TYPE: DNA
<213> ORGANISM: Artificial
<220> FEATURE:
<223> OTHER INFORMATION: synthetic DNA

<400> SEQUENCE: 1181
gtgcctgtga actatcag                                            18

<210> SEQ ID NO 1182
<211> LENGTH: 18
<212> TYPE: DNA
<213> ORGANISM: Artificial
<220> FEATURE:
<223> OTHER INFORMATION: synthetic DNA

<400> SEQUENCE: 1182
cagcgtacaa gatagtcg                                            18

<210> SEQ ID NO 1183
<211> LENGTH: 18
<212> TYPE: DNA
<213> ORGANISM: Artificial
<220> FEATURE:
<223> OTHER INFORMATION: synthetic DNA

<400> SEQUENCE: 1183
gcatggcatg gtagacct                                            18

<210> SEQ ID NO 1184
<211> LENGTH: 18
<212> TYPE: DNA
<213> ORGANISM: Artificial
<220> FEATURE:
<223> OTHER INFORMATION: synthetic DNA

<400> SEQUENCE: 1184
ggtatgctac tcttcgca                                            18

<210> SEQ ID NO 1185
<211> LENGTH: 18
<212> TYPE: DNA
<213> ORGANISM: Artificial
<220> FEATURE:
<223> OTHER INFORMATION: synthetic DNA

<400> SEQUENCE: 1185
atgttcagtc acaagcga                                            18

<210> SEQ ID NO 1186
<211> LENGTH: 18
<212> TYPE: DNA
<213> ORGANISM: Artificial
<220> FEATURE:
<223> OTHER INFORMATION: synthetic DNA

```
<400> SEQUENCE: 1186
taggaagtgt gtaatagc                                                  18

<210> SEQ ID NO 1187
<211> LENGTH: 18
<212> TYPE: DNA
<213> ORGANISM: Artificial
<220> FEATURE:
<223> OTHER INFORMATION: synthetic DNA

<400> SEQUENCE: 1187
aatccatgta gctgtacg                                                  18

<210> SEQ ID NO 1188
<211> LENGTH: 18
<212> TYPE: DNA
<213> ORGANISM: Artificial
<220> FEATURE:
<223> OTHER INFORMATION: synthetic DNA

<400> SEQUENCE: 1188
ccagattcac tggcatag                                                  18

<210> SEQ ID NO 1189
<211> LENGTH: 18
<212> TYPE: DNA
<213> ORGANISM: Artificial
<220> FEATURE:
<223> OTHER INFORMATION: synthetic DNA

<400> SEQUENCE: 1189
ttgtctctac gtaatatc                                                  18

<210> SEQ ID NO 1190
<211> LENGTH: 18
<212> TYPE: DNA
<213> ORGANISM: Artificial
<220> FEATURE:
<223> OTHER INFORMATION: synthetic DNA

<400> SEQUENCE: 1190
gtggtgcttg tgacaatt                                                  18

<210> SEQ ID NO 1191
<211> LENGTH: 18
<212> TYPE: DNA
<213> ORGANISM: Artificial
<220> FEATURE:
<223> OTHER INFORMATION: synthetic DNA

<400> SEQUENCE: 1191
cagcctactt ggctgaga                                                  18

<210> SEQ ID NO 1192
<211> LENGTH: 18
<212> TYPE: DNA
<213> ORGANISM: Artificial
<220> FEATURE:
<223> OTHER INFORMATION: synthetic DNA

<400> SEQUENCE: 1192
tactcaatgc atctgtgt                                                  18

<210> SEQ ID NO 1193
```

```
<211> LENGTH: 18
<212> TYPE: DNA
<213> ORGANISM: Artificial
<220> FEATURE:
<223> OTHER INFORMATION: synthetic DNA

<400> SEQUENCE: 1193
tgtagagaga cgaatata                                              18

<210> SEQ ID NO 1194
<211> LENGTH: 18
<212> TYPE: DNA
<213> ORGANISM: Artificial
<220> FEATURE:
<223> OTHER INFORMATION: synthetic DNA

<400> SEQUENCE: 1194
gcctacaacc atcctact                                              18

<210> SEQ ID NO 1195
<211> LENGTH: 18
<212> TYPE: DNA
<213> ORGANISM: Artificial
<220> FEATURE:
<223> OTHER INFORMATION: synthetic DNA

<400> SEQUENCE: 1195
gcgtggcatt gagattca                                              18

<210> SEQ ID NO 1196
<211> LENGTH: 18
<212> TYPE: DNA
<213> ORGANISM: Artificial
<220> FEATURE:
<223> OTHER INFORMATION: synthetic DNA

<400> SEQUENCE: 1196
gcatgccagc taactgag                                              18

<210> SEQ ID NO 1197
<211> LENGTH: 18
<212> TYPE: DNA
<213> ORGANISM: Artificial
<220> FEATURE:
<223> OTHER INFORMATION: synthetic DNA

<400> SEQUENCE: 1197
gcgagtaatc cggttgga                                              18

<210> SEQ ID NO 1198
<211> LENGTH: 18
<212> TYPE: DNA
<213> ORGANISM: Artificial
<220> FEATURE:
<223> OTHER INFORMATION: synthetic DNA

<400> SEQUENCE: 1198
gcctctacca gaacgtca                                              18

<210> SEQ ID NO 1199
<211> LENGTH: 18
<212> TYPE: DNA
<213> ORGANISM: Artificial
<220> FEATURE:
<223> OTHER INFORMATION: synthetic DNA

<400> SEQUENCE: 1199
```

```
gtcagcagaa gactgacc                                                    18

<210> SEQ ID NO 1200
<211> LENGTH: 18
<212> TYPE: DNA
<213> ORGANISM: Artificial
<220> FEATURE:
<223> OTHER INFORMATION: synthetic DNA

<400> SEQUENCE: 1200
gataacagac gtagcagg                                                    18

<210> SEQ ID NO 1201
<211> LENGTH: 18
<212> TYPE: DNA
<213> ORGANISM: Artificial
<220> FEATURE:
<223> OTHER INFORMATION: synthetic DNA

<400> SEQUENCE: 1201
caggagatcg catgtcgt                                                    18

<210> SEQ ID NO 1202
<211> LENGTH: 18
<212> TYPE: DNA
<213> ORGANISM: Artificial
<220> FEATURE:
<223> OTHER INFORMATION: synthetic DNA

<400> SEQUENCE: 1202
ctggaaggaa tggagcca                                                    18

<210> SEQ ID NO 1203
<211> LENGTH: 18
<212> TYPE: DNA
<213> ORGANISM: Artificial
<220> FEATURE:
<223> OTHER INFORMATION: synthetic DNA

<400> SEQUENCE: 1203
attggttctc taccacaa                                                    18

<210> SEQ ID NO 1204
<211> LENGTH: 18
<212> TYPE: DNA
<213> ORGANISM: Artificial
<220> FEATURE:
<223> OTHER INFORMATION: synthetic DNA

<400> SEQUENCE: 1204
ctcattgttg acggctca                                                    18

<210> SEQ ID NO 1205
<211> LENGTH: 18
<212> TYPE: DNA
<213> ORGANISM: Artificial
<220> FEATURE:
<223> OTHER INFORMATION: synthetic DNA

<400> SEQUENCE: 1205
ttcaggactg tagttcat                                                    18

<210> SEQ ID NO 1206
<211> LENGTH: 18
<212> TYPE: DNA
```

```
<213> ORGANISM: Artificial
<220> FEATURE:
<223> OTHER INFORMATION: synthetic DNA

<400> SEQUENCE: 1206
agaccgcact aactcaag                                                 18

<210> SEQ ID NO 1207
<211> LENGTH: 18
<212> TYPE: DNA
<213> ORGANISM: Artificial
<220> FEATURE:
<223> OTHER INFORMATION: synthetic DNA

<400> SEQUENCE: 1207
ggaatattgt gcagaccg                                                 18

<210> SEQ ID NO 1208
<211> LENGTH: 18
<212> TYPE: DNA
<213> ORGANISM: Artificial
<220> FEATURE:
<223> OTHER INFORMATION: synthetic DNA

<400> SEQUENCE: 1208
cctattacta atagctca                                                 18

<210> SEQ ID NO 1209
<211> LENGTH: 18
<212> TYPE: DNA
<213> ORGANISM: Artificial
<220> FEATURE:
<223> OTHER INFORMATION: synthetic DNA

<400> SEQUENCE: 1209
atggcatgag tacttcgg                                                 18

<210> SEQ ID NO 1210
<211> LENGTH: 18
<212> TYPE: DNA
<213> ORGANISM: Artificial
<220> FEATURE:
<223> OTHER INFORMATION: synthetic DNA

<400> SEQUENCE: 1210
gacacgtatg cgtctagc                                                 18

<210> SEQ ID NO 1211
<211> LENGTH: 18
<212> TYPE: DNA
<213> ORGANISM: Artificial
<220> FEATURE:
<223> OTHER INFORMATION: synthetic DNA

<400> SEQUENCE: 1211
gaaggtacgg aatctgtt                                                 18

<210> SEQ ID NO 1212
<211> LENGTH: 18
<212> TYPE: DNA
<213> ORGANISM: Artificial
<220> FEATURE:
<223> OTHER INFORMATION: synthetic DNA

<400> SEQUENCE: 1212
tataacgtcc gacactgt                                                 18
```

<210> SEQ ID NO 1213
<211> LENGTH: 18
<212> TYPE: DNA
<213> ORGANISM: Artificial
<220> FEATURE:
<223> OTHER INFORMATION: synthetic DNA

<400> SEQUENCE: 1213
gctaatacat taccgccg                                              18

<210> SEQ ID NO 1214
<211> LENGTH: 18
<212> TYPE: DNA
<213> ORGANISM: Artificial
<220> FEATURE:
<223> OTHER INFORMATION: synthetic DNA

<400> SEQUENCE: 1214
gaagccaaca ctcctgac                                              18

<210> SEQ ID NO 1215
<211> LENGTH: 18
<212> TYPE: DNA
<213> ORGANISM: Artificial
<220> FEATURE:
<223> OTHER INFORMATION: synthetic DNA

<400> SEQUENCE: 1215
cgaataacga gctgtgat                                              18

<210> SEQ ID NO 1216
<211> LENGTH: 18
<212> TYPE: DNA
<213> ORGANISM: Artificial
<220> FEATURE:
<223> OTHER INFORMATION: synthetic DNA

<400> SEQUENCE: 1216
gcctaccgat cgcactta                                              18

<210> SEQ ID NO 1217
<211> LENGTH: 18
<212> TYPE: DNA
<213> ORGANISM: Artificial
<220> FEATURE:
<223> OTHER INFORMATION: synthetic DNA

<400> SEQUENCE: 1217
ctgaggagaa tagcctgc                                              18

<210> SEQ ID NO 1218
<211> LENGTH: 18
<212> TYPE: DNA
<213> ORGANISM: Artificial
<220> FEATURE:
<223> OTHER INFORMATION: synthetic DNA

<400> SEQUENCE: 1218
cagcatggac agtacttc                                              18

<210> SEQ ID NO 1219
<211> LENGTH: 18
<212> TYPE: DNA
<213> ORGANISM: Artificial
<220> FEATURE:

<223> OTHER INFORMATION: synthetic DNA

<400> SEQUENCE: 1219
ggtatagagc cttcctta                                                18

<210> SEQ ID NO 1220
<211> LENGTH: 18
<212> TYPE: DNA
<213> ORGANISM: Artificial
<220> FEATURE:
<223> OTHER INFORMATION: synthetic DNA

<400> SEQUENCE: 1220
cgctctgcat atatagca                                                18

<210> SEQ ID NO 1221
<211> LENGTH: 18
<212> TYPE: DNA
<213> ORGANISM: Artificial
<220> FEATURE:
<223> OTHER INFORMATION: synthetic DNA

<400> SEQUENCE: 1221
cggctctact atgctcgt                                                18

<210> SEQ ID NO 1222
<211> LENGTH: 18
<212> TYPE: DNA
<213> ORGANISM: Artificial
<220> FEATURE:
<223> OTHER INFORMATION: synthetic DNA

<400> SEQUENCE: 1222
cctaatgcga agctcacc                                                18

<210> SEQ ID NO 1223
<211> LENGTH: 18
<212> TYPE: DNA
<213> ORGANISM: Artificial
<220> FEATURE:
<223> OTHER INFORMATION: synthetic DNA

<400> SEQUENCE: 1223
acaaccggtg aggcagta                                                18

<210> SEQ ID NO 1224
<211> LENGTH: 18
<212> TYPE: DNA
<213> ORGANISM: Artificial
<220> FEATURE:
<223> OTHER INFORMATION: synthetic DNA

<400> SEQUENCE: 1224
ttggttcgaa ccaaccgc                                                18

<210> SEQ ID NO 1225
<211> LENGTH: 18
<212> TYPE: DNA
<213> ORGANISM: Artificial
<220> FEATURE:
<223> OTHER INFORMATION: synthetic DNA

<400> SEQUENCE: 1225
atactaggtt gaactaag                                                18

```
<210> SEQ ID NO 1226
<211> LENGTH: 18
<212> TYPE: DNA
<213> ORGANISM: Artificial
<220> FEATURE:
<223> OTHER INFORMATION: synthetic DNA

<400> SEQUENCE: 1226
gcgttgagag taacatat                                                    18

<210> SEQ ID NO 1227
<211> LENGTH: 18
<212> TYPE: DNA
<213> ORGANISM: Artificial
<220> FEATURE:
<223> OTHER INFORMATION: synthetic DNA

<400> SEQUENCE: 1227
agttgtataa taagcgtc                                                    18

<210> SEQ ID NO 1228
<211> LENGTH: 18
<212> TYPE: DNA
<213> ORGANISM: Artificial
<220> FEATURE:
<223> OTHER INFORMATION: synthetic DNA

<400> SEQUENCE: 1228
gtatgatgcc gtccaatt                                                    18

<210> SEQ ID NO 1229
<211> LENGTH: 18
<212> TYPE: DNA
<213> ORGANISM: Artificial
<220> FEATURE:
<223> OTHER INFORMATION: synthetic DNA

<400> SEQUENCE: 1229
ggactctctg aagagtct                                                    18

<210> SEQ ID NO 1230
<211> LENGTH: 18
<212> TYPE: DNA
<213> ORGANISM: Artificial
<220> FEATURE:
<223> OTHER INFORMATION: synthetic DNA

<400> SEQUENCE: 1230
ggactctctt gacttgaa                                                    18

<210> SEQ ID NO 1231
<211> LENGTH: 18
<212> TYPE: DNA
<213> ORGANISM: Artificial
<220> FEATURE:
<223> OTHER INFORMATION: synthetic DNA

<400> SEQUENCE: 1231
gataacagtg cttcgtcc                                                    18

<210> SEQ ID NO 1232
<211> LENGTH: 18
<212> TYPE: DNA
<213> ORGANISM: Artificial
<220> FEATURE:
<223> OTHER INFORMATION: synthetic DNA
```

```
<400> SEQUENCE: 1232
ggccattata gatgaact                                                  18

<210> SEQ ID NO 1233
<211> LENGTH: 18
<212> TYPE: DNA
<213> ORGANISM: Artificial
<220> FEATURE:
<223> OTHER INFORMATION: synthetic DNA

<400> SEQUENCE: 1233
atagagagca cagagcag                                                  18

<210> SEQ ID NO 1234
<211> LENGTH: 18
<212> TYPE: DNA
<213> ORGANISM: Artificial
<220> FEATURE:
<223> OTHER INFORMATION: synthetic DNA

<400> SEQUENCE: 1234
gtgtgagtgt atcataac                                                  18

<210> SEQ ID NO 1235
<211> LENGTH: 18
<212> TYPE: DNA
<213> ORGANISM: Artificial
<220> FEATURE:
<223> OTHER INFORMATION: synthetic DNA

<400> SEQUENCE: 1235
ataaccttag tgcgcgtc                                                  18

<210> SEQ ID NO 1236
<211> LENGTH: 18
<212> TYPE: DNA
<213> ORGANISM: Artificial
<220> FEATURE:
<223> OTHER INFORMATION: synthetic DNA

<400> SEQUENCE: 1236
ccgactgata tgcatgga                                                  18

<210> SEQ ID NO 1237
<211> LENGTH: 18
<212> TYPE: DNA
<213> ORGANISM: Artificial
<220> FEATURE:
<223> OTHER INFORMATION: synthetic DNA

<400> SEQUENCE: 1237
ggatatctga tcgcatca                                                  18

<210> SEQ ID NO 1238
<211> LENGTH: 18
<212> TYPE: DNA
<213> ORGANISM: Artificial
<220> FEATURE:
<223> OTHER INFORMATION: synthetic DNA

<400> SEQUENCE: 1238
cagcattaac gaggcgaa                                                  18

<210> SEQ ID NO 1239
<211> LENGTH: 18
```

```
<212> TYPE: DNA
<213> ORGANISM: Artificial
<220> FEATURE:
<223> OTHER INFORMATION: synthetic DNA

<400> SEQUENCE: 1239
gcgaggccta catattcg                                                  18

<210> SEQ ID NO 1240
<211> LENGTH: 18
<212> TYPE: DNA
<213> ORGANISM: Artificial
<220> FEATURE:
<223> OTHER INFORMATION: synthetic DNA

<400> SEQUENCE: 1240
cgataagtgg taaggtct                                                  18

<210> SEQ ID NO 1241
<211> LENGTH: 18
<212> TYPE: DNA
<213> ORGANISM: Artificial
<220> FEATURE:
<223> OTHER INFORMATION: synthetic DNA

<400> SEQUENCE: 1241
agatcctgag tcgagcaa                                                  18

<210> SEQ ID NO 1242
<211> LENGTH: 18
<212> TYPE: DNA
<213> ORGANISM: Artificial
<220> FEATURE:
<223> OTHER INFORMATION: synthetic DNA

<400> SEQUENCE: 1242
aagatataac gagaccga                                                  18

<210> SEQ ID NO 1243
<211> LENGTH: 18
<212> TYPE: DNA
<213> ORGANISM: Artificial
<220> FEATURE:
<223> OTHER INFORMATION: synthetic DNA

<400> SEQUENCE: 1243
ccgactgatt gagaacgt                                                  18

<210> SEQ ID NO 1244
<211> LENGTH: 18
<212> TYPE: DNA
<213> ORGANISM: Artificial
<220> FEATURE:
<223> OTHER INFORMATION: synthetic DNA

<400> SEQUENCE: 1244
tcggcttata tgacacgt                                                  18

<210> SEQ ID NO 1245
<211> LENGTH: 18
<212> TYPE: DNA
<213> ORGANISM: Artificial
<220> FEATURE:
<223> OTHER INFORMATION: synthetic DNA

<400> SEQUENCE: 1245
```
aataacgtac gccggagg                                              18

<210> SEQ ID NO 1246
<211> LENGTH: 18
<212> TYPE: DNA
<213> ORGANISM: Artificial
<220> FEATURE:
<223> OTHER INFORMATION: synthetic DNA

<400> SEQUENCE: 1246
aacacagcat tgcgcacg                                              18

<210> SEQ ID NO 1247
<211> LENGTH: 18
<212> TYPE: DNA
<213> ORGANISM: Artificial
<220> FEATURE:
<223> OTHER INFORMATION: synthetic DNA

<400> SEQUENCE: 1247
gtagtctgac agcaacaa                                              18

<210> SEQ ID NO 1248
<211> LENGTH: 18
<212> TYPE: DNA
<213> ORGANISM: Artificial
<220> FEATURE:
<223> OTHER INFORMATION: synthetic DNA

<400> SEQUENCE: 1248
agaatgactt gagctgct                                              18

<210> SEQ ID NO 1249
<211> LENGTH: 20
<212> TYPE: DNA
<213> ORGANISM: Artificial
<220> FEATURE:
<223> OTHER INFORMATION: synthetic DNA

<400> SEQUENCE: 1249
actggtagta acgtccacct                                            20

<210> SEQ ID NO 1250
<211> LENGTH: 20
<212> TYPE: DNA
<213> ORGANISM: Artificial
<220> FEATURE:
<223> OTHER INFORMATION: synthetic DNA

<400> SEQUENCE: 1250
agactggttg ttattcgcct                                            20

<210> SEQ ID NO 1251
<211> LENGTH: 20
<212> TYPE: DNA
<213> ORGANISM: Artificial
<220> FEATURE:
<223> OTHER INFORMATION: synthetic DNA

<400> SEQUENCE: 1251
tatcattgac agcgagctca                                            20

<210> SEQ ID NO 1252
<211> LENGTH: 20
<212> TYPE: DNA
<213> ORGANISM: Artificial

```
<220> FEATURE:
<223> OTHER INFORMATION: synthetic DNA

<400> SEQUENCE: 1252
tggagtctga agaaggactc                                                 20

<210> SEQ ID NO 1253
<211> LENGTH: 20
<212> TYPE: DNA
<213> ORGANISM: Artificial
<220> FEATURE:
<223> OTHER INFORMATION: synthetic DNA

<400> SEQUENCE: 1253
catctggact acggcaacga                                                 20

<210> SEQ ID NO 1254
<211> LENGTH: 20
<212> TYPE: DNA
<213> ORGANISM: Artificial
<220> FEATURE:
<223> OTHER INFORMATION: synthetic DNA

<400> SEQUENCE: 1254
aactgtcata agacagacaa                                                 20

<210> SEQ ID NO 1255
<211> LENGTH: 20
<212> TYPE: DNA
<213> ORGANISM: Artificial
<220> FEATURE:
<223> OTHER INFORMATION: synthetic DNA

<400> SEQUENCE: 1255
cctcaacatg acatacaccg                                                 20

<210> SEQ ID NO 1256
<211> LENGTH: 20
<212> TYPE: DNA
<213> ORGANISM: Artificial
<220> FEATURE:
<223> OTHER INFORMATION: synthetic DNA

<400> SEQUENCE: 1256
caataccgtt cgcgattcta                                                 20

<210> SEQ ID NO 1257
<211> LENGTH: 20
<212> TYPE: DNA
<213> ORGANISM: Artificial
<220> FEATURE:
<223> OTHER INFORMATION: synthetic DNA

<400> SEQUENCE: 1257
gcgtctacgt tgattcggcc                                                 20

<210> SEQ ID NO 1258
<211> LENGTH: 20
<212> TYPE: DNA
<213> ORGANISM: Artificial
<220> FEATURE:
<223> OTHER INFORMATION: synthetic DNA

<400> SEQUENCE: 1258
tgaacagagg cacttgcagg                                                 20
```

<210> SEQ ID NO 1259
<211> LENGTH: 20
<212> TYPE: DNA
<213> ORGANISM: Artificial
<220> FEATURE:
<223> OTHER INFORMATION: synthetic DNA

<400> SEQUENCE: 1259
cgactagaac ctactactgc                                            20

<210> SEQ ID NO 1260
<211> LENGTH: 20
<212> TYPE: DNA
<213> ORGANISM: Artificial
<220> FEATURE:
<223> OTHER INFORMATION: synthetic DNA

<400> SEQUENCE: 1260
gcaccgcacg tggagagata                                            20

<210> SEQ ID NO 1261
<211> LENGTH: 20
<212> TYPE: DNA
<213> ORGANISM: Artificial
<220> FEATURE:
<223> OTHER INFORMATION: synthetic DNA

<400> SEQUENCE: 1261
ctgagagacc gactgatgcg                                            20

<210> SEQ ID NO 1262
<211> LENGTH: 20
<212> TYPE: DNA
<213> ORGANISM: Artificial
<220> FEATURE:
<223> OTHER INFORMATION: synthetic DNA

<400> SEQUENCE: 1262
tcgtccttct acttaatgat                                            20

<210> SEQ ID NO 1263
<211> LENGTH: 20
<212> TYPE: DNA
<213> ORGANISM: Artificial
<220> FEATURE:
<223> OTHER INFORMATION: synthetic DNA

<400> SEQUENCE: 1263
caagctatac catccgaatt                                            20

<210> SEQ ID NO 1264
<211> LENGTH: 20
<212> TYPE: DNA
<213> ORGANISM: Artificial
<220> FEATURE:
<223> OTHER INFORMATION: synthetic DNA

<400> SEQUENCE: 1264
caatacgtat agtcttagat                                            20

<210> SEQ ID NO 1265
<211> LENGTH: 20
<212> TYPE: DNA
<213> ORGANISM: Artificial
<220> FEATURE:
<223> OTHER INFORMATION: synthetic DNA

<400> SEQUENCE: 1265
ccatccacag tgacctatgt                                               20

<210> SEQ ID NO 1266
<211> LENGTH: 20
<212> TYPE: DNA
<213> ORGANISM: Artificial
<220> FEATURE:
<223> OTHER INFORMATION: synthetic DNA

<400> SEQUENCE: 1266
tatccgttgg agaaggttca                                               20

<210> SEQ ID NO 1267
<211> LENGTH: 20
<212> TYPE: DNA
<213> ORGANISM: Artificial
<220> FEATURE:
<223> OTHER INFORMATION: synthetic DNA

<400> SEQUENCE: 1267
cgcctaggta cctgagtacg                                               20

<210> SEQ ID NO 1268
<211> LENGTH: 20
<212> TYPE: DNA
<213> ORGANISM: Artificial
<220> FEATURE:
<223> OTHER INFORMATION: synthetic DNA

<400> SEQUENCE: 1268
cagagtgctc gtgttcgcga                                               20

<210> SEQ ID NO 1269
<211> LENGTH: 20
<212> TYPE: DNA
<213> ORGANISM: Artificial
<220> FEATURE:
<223> OTHER INFORMATION: synthetic DNA

<400> SEQUENCE: 1269
cgcttggaca tccttaagaa                                               20

<210> SEQ ID NO 1270
<211> LENGTH: 20
<212> TYPE: DNA
<213> ORGANISM: Artificial
<220> FEATURE:
<223> OTHER INFORMATION: synthetic DNA

<400> SEQUENCE: 1270
gaccgcatga ttagtcttac                                               20

<210> SEQ ID NO 1271
<211> LENGTH: 20
<212> TYPE: DNA
<213> ORGANISM: Artificial
<220> FEATURE:
<223> OTHER INFORMATION: synthetic DNA

<400> SEQUENCE: 1271
cttggccgta gtcactcagt                                               20

<210> SEQ ID NO 1272

-continued

```
<211> LENGTH: 20
<212> TYPE: DNA
<213> ORGANISM: Artificial
<220> FEATURE:
<223> OTHER INFORMATION: synthetic DNA

<400> SEQUENCE: 1272
gatagcgata ttcagttcgc                                               20

<210> SEQ ID NO 1273
<211> LENGTH: 20
<212> TYPE: DNA
<213> ORGANISM: Artificial
<220> FEATURE:
<223> OTHER INFORMATION: synthetic DNA

<400> SEQUENCE: 1273
atccaacact aagacaacca                                               20

<210> SEQ ID NO 1274
<211> LENGTH: 20
<212> TYPE: DNA
<213> ORGANISM: Artificial
<220> FEATURE:
<223> OTHER INFORMATION: synthetic DNA

<400> SEQUENCE: 1274
ccattctgtt gcgtgtcctc                                               20

<210> SEQ ID NO 1275
<211> LENGTH: 20
<212> TYPE: DNA
<213> ORGANISM: Artificial
<220> FEATURE:
<223> OTHER INFORMATION: synthetic DNA

<400> SEQUENCE: 1275
acattctgta cgcttgcagc                                               20

<210> SEQ ID NO 1276
<211> LENGTH: 20
<212> TYPE: DNA
<213> ORGANISM: Artificial
<220> FEATURE:
<223> OTHER INFORMATION: synthetic DNA

<400> SEQUENCE: 1276
tgctgaacgc caatcgctta                                               20

<210> SEQ ID NO 1277
<211> LENGTH: 20
<212> TYPE: DNA
<213> ORGANISM: Artificial
<220> FEATURE:
<223> OTHER INFORMATION: synthetic DNA

<400> SEQUENCE: 1277
tcctctacaa gaatattgcg                                               20

<210> SEQ ID NO 1278
<211> LENGTH: 20
<212> TYPE: DNA
<213> ORGANISM: Artificial
<220> FEATURE:
<223> OTHER INFORMATION: synthetic DNA

<400> SEQUENCE: 1278
```
cgaccaacgc agcctgattc                                                      20

<210> SEQ ID NO 1279
<211> LENGTH: 20
<212> TYPE: DNA
<213> ORGANISM: Artificial
<220> FEATURE:
<223> OTHER INFORMATION: synthetic DNA

<400> SEQUENCE: 1279
attgcgagct tgagtagcgc                                                      20

<210> SEQ ID NO 1280
<211> LENGTH: 20
<212> TYPE: DNA
<213> ORGANISM: Artificial
<220> FEATURE:
<223> OTHER INFORMATION: synthetic DNA

<400> SEQUENCE: 1280
aaggtgcgag cataggaatc                                                      20

<210> SEQ ID NO 1281
<211> LENGTH: 20
<212> TYPE: DNA
<213> ORGANISM: Artificial
<220> FEATURE:
<223> OTHER INFORMATION: synthetic DNA

<400> SEQUENCE: 1281
cacttaagtg tgatatagat                                                      20

<210> SEQ ID NO 1282
<211> LENGTH: 20
<212> TYPE: DNA
<213> ORGANISM: Artificial
<220> FEATURE:
<223> OTHER INFORMATION: synthetic DNA

<400> SEQUENCE: 1282
atcggtatgc tgacctagac                                                      20

<210> SEQ ID NO 1283
<211> LENGTH: 20
<212> TYPE: DNA
<213> ORGANISM: Artificial
<220> FEATURE:
<223> OTHER INFORMATION: synthetic DNA

<400> SEQUENCE: 1283
tacaatctcg aatgcaggat                                                      20

<210> SEQ ID NO 1284
<211> LENGTH: 20
<212> TYPE: DNA
<213> ORGANISM: Artificial
<220> FEATURE:
<223> OTHER INFORMATION: synthetic DNA

<400> SEQUENCE: 1284
ccatatgaag cgcagccgtc                                                      20

<210> SEQ ID NO 1285
<211> LENGTH: 20
<212> TYPE: DNA

```
<213> ORGANISM: Artificial
<220> FEATURE:
<223> OTHER INFORMATION: synthetic DNA

<400> SEQUENCE: 1285
cgtctcgtgg acattcgagg                                                  20

<210> SEQ ID NO 1286
<211> LENGTH: 20
<212> TYPE: DNA
<213> ORGANISM: Artificial
<220> FEATURE:
<223> OTHER INFORMATION: synthetic DNA

<400> SEQUENCE: 1286
ccgagtacag aagcgtggaa                                                  20

<210> SEQ ID NO 1287
<211> LENGTH: 20
<212> TYPE: DNA
<213> ORGANISM: Artificial
<220> FEATURE:
<223> OTHER INFORMATION: synthetic DNA

<400> SEQUENCE: 1287
ttacgtggtc gacaggcagt                                                  20

<210> SEQ ID NO 1288
<211> LENGTH: 20
<212> TYPE: DNA
<213> ORGANISM: Artificial
<220> FEATURE:
<223> OTHER INFORMATION: synthetic DNA

<400> SEQUENCE: 1288
agctgcaatc tgcatgatta                                                  20

<210> SEQ ID NO 1289
<211> LENGTH: 20
<212> TYPE: DNA
<213> ORGANISM: Artificial
<220> FEATURE:
<223> OTHER INFORMATION: synthetic DNA

<400> SEQUENCE: 1289
acctgccgaa gcagcctaca                                                  20

<210> SEQ ID NO 1290
<211> LENGTH: 20
<212> TYPE: DNA
<213> ORGANISM: Artificial
<220> FEATURE:
<223> OTHER INFORMATION: synthetic DNA

<400> SEQUENCE: 1290
aacatgataa ccacatggtt                                                  20

<210> SEQ ID NO 1291
<211> LENGTH: 20
<212> TYPE: DNA
<213> ORGANISM: Artificial
<220> FEATURE:
<223> OTHER INFORMATION: synthetic DNA

<400> SEQUENCE: 1291
atccgactga ttgaattacc                                                  20
```

<210> SEQ ID NO 1292
<211> LENGTH: 20
<212> TYPE: DNA
<213> ORGANISM: Artificial
<220> FEATURE:
<223> OTHER INFORMATION: synthetic DNA

<400> SEQUENCE: 1292
tcacgctgac tcttatcagg                                               20

<210> SEQ ID NO 1293
<211> LENGTH: 20
<212> TYPE: DNA
<213> ORGANISM: Artificial
<220> FEATURE:
<223> OTHER INFORMATION: synthetic DNA

<400> SEQUENCE: 1293
gcgcgctcga agtacaacat                                               20

<210> SEQ ID NO 1294
<211> LENGTH: 20
<212> TYPE: DNA
<213> ORGANISM: Artificial
<220> FEATURE:
<223> OTHER INFORMATION: synthetic DNA

<400> SEQUENCE: 1294
acagccagat gcgttgttcc                                               20

<210> SEQ ID NO 1295
<211> LENGTH: 20
<212> TYPE: DNA
<213> ORGANISM: Artificial
<220> FEATURE:
<223> OTHER INFORMATION: synthetic DNA

<400> SEQUENCE: 1295
ggagctctga cctgcaagaa                                               20

<210> SEQ ID NO 1296
<211> LENGTH: 20
<212> TYPE: DNA
<213> ORGANISM: Artificial
<220> FEATURE:
<223> OTHER INFORMATION: synthetic DNA

<400> SEQUENCE: 1296
aacattagcc tcaagtaaga                                               20

<210> SEQ ID NO 1297
<211> LENGTH: 20
<212> TYPE: DNA
<213> ORGANISM: Artificial
<220> FEATURE:
<223> OTHER INFORMATION: synthetic DNA

<400> SEQUENCE: 1297
tgtgattatg ccgaatgagg                                               20

<210> SEQ ID NO 1298
<211> LENGTH: 20
<212> TYPE: DNA
<213> ORGANISM: Artificial
<220> FEATURE:

<223> OTHER INFORMATION: synthetic DNA

<400> SEQUENCE: 1298
gagtaataat ccaatcagta                                              20

<210> SEQ ID NO 1299
<211> LENGTH: 20
<212> TYPE: DNA
<213> ORGANISM: Artificial
<220> FEATURE:
<223> OTHER INFORMATION: synthetic DNA

<400> SEQUENCE: 1299
ctccttggcg acagctgaac                                              20

<210> SEQ ID NO 1300
<211> LENGTH: 20
<212> TYPE: DNA
<213> ORGANISM: Artificial
<220> FEATURE:
<223> OTHER INFORMATION: synthetic DNA

<400> SEQUENCE: 1300
ttacgcacac atacacagac                                              20

<210> SEQ ID NO 1301
<211> LENGTH: 20
<212> TYPE: DNA
<213> ORGANISM: Artificial
<220> FEATURE:
<223> OTHER INFORMATION: synthetic DNA

<400> SEQUENCE: 1301
acgccgtatg gcgacttagg                                              20

<210> SEQ ID NO 1302
<211> LENGTH: 20
<212> TYPE: DNA
<213> ORGANISM: Artificial
<220> FEATURE:
<223> OTHER INFORMATION: synthetic DNA

<400> SEQUENCE: 1302
agaacgacaa ttacgatggc                                              20

<210> SEQ ID NO 1303
<211> LENGTH: 20
<212> TYPE: DNA
<213> ORGANISM: Artificial
<220> FEATURE:
<223> OTHER INFORMATION: synthetic DNA

<400> SEQUENCE: 1303
tgctaacgta ccactgccac                                              20

<210> SEQ ID NO 1304
<211> LENGTH: 20
<212> TYPE: DNA
<213> ORGANISM: Artificial
<220> FEATURE:
<223> OTHER INFORMATION: synthetic DNA

<400> SEQUENCE: 1304
catccagaat gtctatcata                                              20

```
<210> SEQ ID NO 1305
<211> LENGTH: 20
<212> TYPE: DNA
<213> ORGANISM: Artificial
<220> FEATURE:
<223> OTHER INFORMATION: synthetic DNA

<400> SEQUENCE: 1305
ggagaacgcc tatagcactc                                               20

<210> SEQ ID NO 1306
<211> LENGTH: 20
<212> TYPE: DNA
<213> ORGANISM: Artificial
<220> FEATURE:
<223> OTHER INFORMATION: synthetic DNA

<400> SEQUENCE: 1306
acctcttgtg acggccagtc                                               20

<210> SEQ ID NO 1307
<211> LENGTH: 20
<212> TYPE: DNA
<213> ORGANISM: Artificial
<220> FEATURE:
<223> OTHER INFORMATION: synthetic DNA

<400> SEQUENCE: 1307
tgccataact tggcataaga                                               20

<210> SEQ ID NO 1308
<211> LENGTH: 20
<212> TYPE: DNA
<213> ORGANISM: Artificial
<220> FEATURE:
<223> OTHER INFORMATION: synthetic DNA

<400> SEQUENCE: 1308
acaattgtct gaccacgctc                                               20

<210> SEQ ID NO 1309
<211> LENGTH: 20
<212> TYPE: DNA
<213> ORGANISM: Artificial
<220> FEATURE:
<223> OTHER INFORMATION: synthetic DNA

<400> SEQUENCE: 1309
tcgtcacctt cacagaacga                                               20

<210> SEQ ID NO 1310
<211> LENGTH: 20
<212> TYPE: DNA
<213> ORGANISM: Artificial
<220> FEATURE:
<223> OTHER INFORMATION: synthetic DNA

<400> SEQUENCE: 1310
agcagcagat gatgatccaa                                               20

<210> SEQ ID NO 1311
<211> LENGTH: 20
<212> TYPE: DNA
<213> ORGANISM: Artificial
<220> FEATURE:
<223> OTHER INFORMATION: synthetic DNA
```

```
<400> SEQUENCE: 1311
tcgtgccttg gattccagga                                          20

<210> SEQ ID NO 1312
<211> LENGTH: 20
<212> TYPE: DNA
<213> ORGANISM: Artificial
<220> FEATURE:
<223> OTHER INFORMATION: synthetic DNA

<400> SEQUENCE: 1312
tgttatagcc acgatactat                                          20

<210> SEQ ID NO 1313
<211> LENGTH: 20
<212> TYPE: DNA
<213> ORGANISM: Artificial
<220> FEATURE:
<223> OTHER INFORMATION: synthetic DNA

<400> SEQUENCE: 1313
aatctcacct gtaccttccg                                          20

<210> SEQ ID NO 1314
<211> LENGTH: 20
<212> TYPE: DNA
<213> ORGANISM: Artificial
<220> FEATURE:
<223> OTHER INFORMATION: synthetic DNA

<400> SEQUENCE: 1314
gagtagcgga agcgttagcg                                          20

<210> SEQ ID NO 1315
<211> LENGTH: 20
<212> TYPE: DNA
<213> ORGANISM: Artificial
<220> FEATURE:
<223> OTHER INFORMATION: synthetic DNA

<400> SEQUENCE: 1315
aatactccgg cgaggtatac                                          20

<210> SEQ ID NO 1316
<211> LENGTH: 20
<212> TYPE: DNA
<213> ORGANISM: Artificial
<220> FEATURE:
<223> OTHER INFORMATION: synthetic DNA

<400> SEQUENCE: 1316
ttcgcatcct tgcacgaaca                                          20

<210> SEQ ID NO 1317
<211> LENGTH: 20
<212> TYPE: DNA
<213> ORGANISM: Artificial
<220> FEATURE:
<223> OTHER INFORMATION: synthetic DNA

<400> SEQUENCE: 1317
aaccggctaa tactactggc                                          20

<210> SEQ ID NO 1318
<211> LENGTH: 20
```

```
<212> TYPE: DNA
<213> ORGANISM: Artificial
<220> FEATURE:
<223> OTHER INFORMATION: synthetic DNA

<400> SEQUENCE: 1318
ctagcatctt agacaccaga                                          20

<210> SEQ ID NO 1319
<211> LENGTH: 20
<212> TYPE: DNA
<213> ORGANISM: Artificial
<220> FEATURE:
<223> OTHER INFORMATION: synthetic DNA

<400> SEQUENCE: 1319
tagttgcgtg atacaagata                                          20

<210> SEQ ID NO 1320
<211> LENGTH: 20
<212> TYPE: DNA
<213> ORGANISM: Artificial
<220> FEATURE:
<223> OTHER INFORMATION: synthetic DNA

<400> SEQUENCE: 1320
tcgtctcgac acagttggtc                                          20

<210> SEQ ID NO 1321
<211> LENGTH: 20
<212> TYPE: DNA
<213> ORGANISM: Artificial
<220> FEATURE:
<223> OTHER INFORMATION: synthetic DNA

<400> SEQUENCE: 1321
tccgttcgcg tgcgaactga                                          20

<210> SEQ ID NO 1322
<211> LENGTH: 20
<212> TYPE: DNA
<213> ORGANISM: Artificial
<220> FEATURE:
<223> OTHER INFORMATION: synthetic DNA

<400> SEQUENCE: 1322
tctgactctg gtgtacagtc                                          20

<210> SEQ ID NO 1323
<211> LENGTH: 20
<212> TYPE: DNA
<213> ORGANISM: Artificial
<220> FEATURE:
<223> OTHER INFORMATION: synthetic DNA

<400> SEQUENCE: 1323
acagcgcaat tatatcctgt                                          20

<210> SEQ ID NO 1324
<211> LENGTH: 20
<212> TYPE: DNA
<213> ORGANISM: Artificial
<220> FEATURE:
<223> OTHER INFORMATION: synthetic DNA

<400> SEQUENCE: 1324
```
agatccgtac gtgagactag                                              20

<210> SEQ ID NO 1325
<211> LENGTH: 20
<212> TYPE: DNA
<213> ORGANISM: Artificial
<220> FEATURE:
<223> OTHER INFORMATION: synthetic DNA

<400> SEQUENCE: 1325
tacattgaag catccgaaca                                              20

<210> SEQ ID NO 1326
<211> LENGTH: 20
<212> TYPE: DNA
<213> ORGANISM: Artificial
<220> FEATURE:
<223> OTHER INFORMATION: synthetic DNA

<400> SEQUENCE: 1326
ctcctgagag atcaacgcca                                              20

<210> SEQ ID NO 1327
<211> LENGTH: 20
<212> TYPE: DNA
<213> ORGANISM: Artificial
<220> FEATURE:
<223> OTHER INFORMATION: synthetic DNA

<400> SEQUENCE: 1327
tcacctcgaa tgagttcgtt                                              20

<210> SEQ ID NO 1328
<211> LENGTH: 20
<212> TYPE: DNA
<213> ORGANISM: Artificial
<220> FEATURE:
<223> OTHER INFORMATION: synthetic DNA

<400> SEQUENCE: 1328
tagcgactta aggtccaagc                                              20

<210> SEQ ID NO 1329
<211> LENGTH: 20
<212> TYPE: DNA
<213> ORGANISM: Artificial
<220> FEATURE:
<223> OTHER INFORMATION: synthetic DNA

<400> SEQUENCE: 1329
agtacgtatt gccgtgcaag                                              20

<210> SEQ ID NO 1330
<211> LENGTH: 20
<212> TYPE: DNA
<213> ORGANISM: Artificial
<220> FEATURE:
<223> OTHER INFORMATION: synthetic DNA

<400> SEQUENCE: 1330
agccacgaac cgacgtcata                                              20

<210> SEQ ID NO 1331
<211> LENGTH: 20
<212> TYPE: DNA
<213> ORGANISM: Artificial

```
<220> FEATURE:
<223> OTHER INFORMATION: synthetic DNA

<400> SEQUENCE: 1331
tgatgtgtac gctactacta                                                20

<210> SEQ ID NO 1332
<211> LENGTH: 20
<212> TYPE: DNA
<213> ORGANISM: Artificial
<220> FEATURE:
<223> OTHER INFORMATION: synthetic DNA

<400> SEQUENCE: 1332
ccactgtgtg cagcagacga                                                20

<210> SEQ ID NO 1333
<211> LENGTH: 20
<212> TYPE: DNA
<213> ORGANISM: Artificial
<220> FEATURE:
<223> OTHER INFORMATION: synthetic DNA

<400> SEQUENCE: 1333
ctattgtaca gcgaacgctg                                                20

<210> SEQ ID NO 1334
<211> LENGTH: 20
<212> TYPE: DNA
<213> ORGANISM: Artificial
<220> FEATURE:
<223> OTHER INFORMATION: synthetic DNA

<400> SEQUENCE: 1334
ctccgatatc gcacggatcg                                                20

<210> SEQ ID NO 1335
<211> LENGTH: 20
<212> TYPE: DNA
<213> ORGANISM: Artificial
<220> FEATURE:
<223> OTHER INFORMATION: synthetic DNA

<400> SEQUENCE: 1335
aacttatcgt cggacgcatg                                                20

<210> SEQ ID NO 1336
<211> LENGTH: 20
<212> TYPE: DNA
<213> ORGANISM: Artificial
<220> FEATURE:
<223> OTHER INFORMATION: synthetic DNA

<400> SEQUENCE: 1336
tatcctaatt cgtgccggtc                                                20

<210> SEQ ID NO 1337
<211> LENGTH: 20
<212> TYPE: DNA
<213> ORGANISM: Artificial
<220> FEATURE:
<223> OTHER INFORMATION: synthetic DNA

<400> SEQUENCE: 1337
acagccttcc tgtgtggact                                                20
```

```
<210> SEQ ID NO 1338
<211> LENGTH: 20
<212> TYPE: DNA
<213> ORGANISM: Artificial
<220> FEATURE:
<223> OTHER INFORMATION: synthetic DNA

<400> SEQUENCE: 1338
cctccgtgag gatcgtacca                                               20

<210> SEQ ID NO 1339
<211> LENGTH: 20
<212> TYPE: DNA
<213> ORGANISM: Artificial
<220> FEATURE:
<223> OTHER INFORMATION: synthetic DNA

<400> SEQUENCE: 1339
gctctaagta acagaactaa                                               20

<210> SEQ ID NO 1340
<211> LENGTH: 20
<212> TYPE: DNA
<213> ORGANISM: Artificial
<220> FEATURE:
<223> OTHER INFORMATION: synthetic DNA

<400> SEQUENCE: 1340
gacttaccgc gcgttctggt                                               20

<210> SEQ ID NO 1341
<211> LENGTH: 20
<212> TYPE: DNA
<213> ORGANISM: Artificial
<220> FEATURE:
<223> OTHER INFORMATION: synthetic DNA

<400> SEQUENCE: 1341
tctgaggata cacatgtgga                                               20

<210> SEQ ID NO 1342
<211> LENGTH: 20
<212> TYPE: DNA
<213> ORGANISM: Artificial
<220> FEATURE:
<223> OTHER INFORMATION: synthetic DNA

<400> SEQUENCE: 1342
tgtaatcaca ctggtgtcgg                                               20

<210> SEQ ID NO 1343
<211> LENGTH: 20
<212> TYPE: DNA
<213> ORGANISM: Artificial
<220> FEATURE:
<223> OTHER INFORMATION: synthetic DNA

<400> SEQUENCE: 1343
cactaggcgg cagacataca                                               20

<210> SEQ ID NO 1344
<211> LENGTH: 20
<212> TYPE: DNA
<213> ORGANISM: Artificial
<220> FEATURE:
<223> OTHER INFORMATION: synthetic DNA
```

```
<400> SEQUENCE: 1344
ctagagcaca gtaccacgtt                                              20

<210> SEQ ID NO 1345
<211> LENGTH: 22
<212> TYPE: DNA
<213> ORGANISM: Artificial
<220> FEATURE:
<223> OTHER INFORMATION: synthetic DNA

<400> SEQUENCE: 1345
ttcagaggtc tacgcttccg gt                                           22

<210> SEQ ID NO 1346
<211> LENGTH: 22
<212> TYPE: DNA
<213> ORGANISM: Artificial
<220> FEATURE:
<223> OTHER INFORMATION: synthetic DNA

<400> SEQUENCE: 1346
aacacagact gcgttatgcc aa                                           22

<210> SEQ ID NO 1347
<211> LENGTH: 22
<212> TYPE: DNA
<213> ORGANISM: Artificial
<220> FEATURE:
<223> OTHER INFORMATION: synthetic DNA

<400> SEQUENCE: 1347
tgctgagttc tatacagcag tg                                           22

<210> SEQ ID NO 1348
<211> LENGTH: 22
<212> TYPE: DNA
<213> ORGANISM: Artificial
<220> FEATURE:
<223> OTHER INFORMATION: synthetic DNA

<400> SEQUENCE: 1348
acctattata tgatagcgtc at                                           22

<210> SEQ ID NO 1349
<211> LENGTH: 22
<212> TYPE: DNA
<213> ORGANISM: Artificial
<220> FEATURE:
<223> OTHER INFORMATION: synthetic DNA

<400> SEQUENCE: 1349
atcgtgagct acagtgaatg ca                                           22

<210> SEQ ID NO 1350
<211> LENGTH: 22
<212> TYPE: DNA
<213> ORGANISM: Artificial
<220> FEATURE:
<223> OTHER INFORMATION: synthetic DNA

<400> SEQUENCE: 1350
cgtgatgtat ccggccttgc ag                                           22

<210> SEQ ID NO 1351
```

```
<211> LENGTH: 22
<212> TYPE: DNA
<213> ORGANISM: Artificial
<220> FEATURE:
<223> OTHER INFORMATION: synthetic DNA

<400> SEQUENCE: 1351
tcttctggtc ctagagttgt gc                                              22

<210> SEQ ID NO 1352
<211> LENGTH: 22
<212> TYPE: DNA
<213> ORGANISM: Artificial
<220> FEATURE:
<223> OTHER INFORMATION: synthetic DNA

<400> SEQUENCE: 1352
tgatgtcggc ggcggatcag at                                              22

<210> SEQ ID NO 1353
<211> LENGTH: 22
<212> TYPE: DNA
<213> ORGANISM: Artificial
<220> FEATURE:
<223> OTHER INFORMATION: synthetic DNA

<400> SEQUENCE: 1353
tcggccttag cgttcagcat cc                                              22

<210> SEQ ID NO 1354
<211> LENGTH: 22
<212> TYPE: DNA
<213> ORGANISM: Artificial
<220> FEATURE:
<223> OTHER INFORMATION: synthetic DNA

<400> SEQUENCE: 1354
ttaagtaggt cagccactgc ac                                              22

<210> SEQ ID NO 1355
<211> LENGTH: 22
<212> TYPE: DNA
<213> ORGANISM: Artificial
<220> FEATURE:
<223> OTHER INFORMATION: synthetic DNA

<400> SEQUENCE: 1355
ccaggtgagt tgatctgaca cc                                              22

<210> SEQ ID NO 1356
<211> LENGTH: 22
<212> TYPE: DNA
<213> ORGANISM: Artificial
<220> FEATURE:
<223> OTHER INFORMATION: synthetic DNA

<400> SEQUENCE: 1356
tatactatta ctgtgttcga tc                                              22

<210> SEQ ID NO 1357
<211> LENGTH: 22
<212> TYPE: DNA
<213> ORGANISM: Artificial
<220> FEATURE:
<223> OTHER INFORMATION: synthetic DNA

<400> SEQUENCE: 1357
```

```
ccgcagtatg tctagtgttg tc                                              22
```

<210> SEQ ID NO 1358
<211> LENGTH: 22
<212> TYPE: DNA
<213> ORGANISM: Artificial
<220> FEATURE:
<223> OTHER INFORMATION: synthetic DNA

<400> SEQUENCE: 1358

```
gtctaccgcg tacgaagctc tc                                              22
```

<210> SEQ ID NO 1359
<211> LENGTH: 22
<212> TYPE: DNA
<213> ORGANISM: Artificial
<220> FEATURE:
<223> OTHER INFORMATION: synthetic DNA

<400> SEQUENCE: 1359

```
atgcgagtcc gtggtcgatc ct                                              22
```

<210> SEQ ID NO 1360
<211> LENGTH: 22
<212> TYPE: DNA
<213> ORGANISM: Artificial
<220> FEATURE:
<223> OTHER INFORMATION: synthetic DNA

<400> SEQUENCE: 1360

```
tggtagattg gtgtgagaac ta                                              22
```

<210> SEQ ID NO 1361
<211> LENGTH: 22
<212> TYPE: DNA
<213> ORGANISM: Artificial
<220> FEATURE:
<223> OTHER INFORMATION: synthetic DNA

<400> SEQUENCE: 1361

```
aggttcgtcg atcaactgct aa                                              22
```

<210> SEQ ID NO 1362
<211> LENGTH: 22
<212> TYPE: DNA
<213> ORGANISM: Artificial
<220> FEATURE:
<223> OTHER INFORMATION: synthetic DNA

<400> SEQUENCE: 1362

```
acgacaagca tcctgcgata tc                                              22
```

<210> SEQ ID NO 1363
<211> LENGTH: 22
<212> TYPE: DNA
<213> ORGANISM: Artificial
<220> FEATURE:
<223> OTHER INFORMATION: synthetic DNA

<400> SEQUENCE: 1363

```
ttgaatcaca gagagcgtga tt                                              22
```

<210> SEQ ID NO 1364
<211> LENGTH: 22
<212> TYPE: DNA

```
<213> ORGANISM: Artificial
<220> FEATURE:
<223> OTHER INFORMATION: synthetic DNA

<400> SEQUENCE: 1364
gtacttagtg cttacgtcag ct                                              22

<210> SEQ ID NO 1365
<211> LENGTH: 22
<212> TYPE: DNA
<213> ORGANISM: Artificial
<220> FEATURE:
<223> OTHER INFORMATION: synthetic DNA

<400> SEQUENCE: 1365
gattattaag gccaagctca ta                                              22

<210> SEQ ID NO 1366
<211> LENGTH: 22
<212> TYPE: DNA
<213> ORGANISM: Artificial
<220> FEATURE:
<223> OTHER INFORMATION: synthetic DNA

<400> SEQUENCE: 1366
gcatgcagag acgtactcat cg                                              22

<210> SEQ ID NO 1367
<211> LENGTH: 22
<212> TYPE: DNA
<213> ORGANISM: Artificial
<220> FEATURE:
<223> OTHER INFORMATION: synthetic DNA

<400> SEQUENCE: 1367
tagcggatgg tgtcctggca ct                                              22

<210> SEQ ID NO 1368
<211> LENGTH: 22
<212> TYPE: DNA
<213> ORGANISM: Artificial
<220> FEATURE:
<223> OTHER INFORMATION: synthetic DNA

<400> SEQUENCE: 1368
tacggctgcc aacttaataa ct                                              22

<210> SEQ ID NO 1369
<211> LENGTH: 22
<212> TYPE: DNA
<213> ORGANISM: Artificial
<220> FEATURE:
<223> OTHER INFORMATION: synthetic DNA

<400> SEQUENCE: 1369
ctcatatgac aacttctata gt                                              22

<210> SEQ ID NO 1370
<211> LENGTH: 22
<212> TYPE: DNA
<213> ORGANISM: Artificial
<220> FEATURE:
<223> OTHER INFORMATION: synthetic DNA

<400> SEQUENCE: 1370
caagcaatag ttgtcggcca cc                                              22
```

```
<210> SEQ ID NO 1371
<211> LENGTH: 22
<212> TYPE: DNA
<213> ORGANISM: Artificial
<220> FEATURE:
<223> OTHER INFORMATION: synthetic DNA

<400> SEQUENCE: 1371
ttcagcaatc cgtactgcta ga                                            22

<210> SEQ ID NO 1372
<211> LENGTH: 22
<212> TYPE: DNA
<213> ORGANISM: Artificial
<220> FEATURE:
<223> OTHER INFORMATION: synthetic DNA

<400> SEQUENCE: 1372
tgagacgttg ctgacattct cc                                            22

<210> SEQ ID NO 1373
<211> LENGTH: 22
<212> TYPE: DNA
<213> ORGANISM: Artificial
<220> FEATURE:
<223> OTHER INFORMATION: synthetic DNA

<400> SEQUENCE: 1373
gttccgatga gttagatgta ta                                            22

<210> SEQ ID NO 1374
<211> LENGTH: 22
<212> TYPE: DNA
<213> ORGANISM: Artificial
<220> FEATURE:
<223> OTHER INFORMATION: synthetic DNA

<400> SEQUENCE: 1374
ttgacgcttg gaggagtaca ag                                            22

<210> SEQ ID NO 1375
<211> LENGTH: 22
<212> TYPE: DNA
<213> ORGANISM: Artificial
<220> FEATURE:
<223> OTHER INFORMATION: synthetic DNA

<400> SEQUENCE: 1375
ttcatgttac ctccacattg tg                                            22

<210> SEQ ID NO 1376
<211> LENGTH: 22
<212> TYPE: DNA
<213> ORGANISM: Artificial
<220> FEATURE:
<223> OTHER INFORMATION: synthetic DNA

<400> SEQUENCE: 1376
gagcacgtgc cagattgcaa cc                                            22

<210> SEQ ID NO 1377
<211> LENGTH: 22
<212> TYPE: DNA
<213> ORGANISM: Artificial
<220> FEATURE:
```

<223> OTHER INFORMATION: synthetic DNA

<400> SEQUENCE: 1377
ggtcgacaag cacaagcctt ct                                    22

<210> SEQ ID NO 1378
<211> LENGTH: 22
<212> TYPE: DNA
<213> ORGANISM: Artificial
<220> FEATURE:
<223> OTHER INFORMATION: synthetic DNA

<400> SEQUENCE: 1378
taggcaggta agatgaccga ct                                    22

<210> SEQ ID NO 1379
<211> LENGTH: 22
<212> TYPE: DNA
<213> ORGANISM: Artificial
<220> FEATURE:
<223> OTHER INFORMATION: synthetic DNA

<400> SEQUENCE: 1379
cgaggcatgc caagtcgcca at                                    22

<210> SEQ ID NO 1380
<211> LENGTH: 22
<212> TYPE: DNA
<213> ORGANISM: Artificial
<220> FEATURE:
<223> OTHER INFORMATION: synthetic DNA

<400> SEQUENCE: 1380
agtgttgata ggcggatgag ag                                    22

<210> SEQ ID NO 1381
<211> LENGTH: 22
<212> TYPE: DNA
<213> ORGANISM: Artificial
<220> FEATURE:
<223> OTHER INFORMATION: synthetic DNA

<400> SEQUENCE: 1381
ttcggtctag acctctcaca at                                    22

<210> SEQ ID NO 1382
<211> LENGTH: 22
<212> TYPE: DNA
<213> ORGANISM: Artificial
<220> FEATURE:
<223> OTHER INFORMATION: synthetic DNA

<400> SEQUENCE: 1382
gtgacgctca tatcttgcca cc                                    22

<210> SEQ ID NO 1383
<211> LENGTH: 22
<212> TYPE: DNA
<213> ORGANISM: Artificial
<220> FEATURE:
<223> OTHER INFORMATION: synthetic DNA

<400> SEQUENCE: 1383
gatgtaattc tacgcgcgga ct                                    22

<210> SEQ ID NO 1384
<211> LENGTH: 22
<212> TYPE: DNA
<213> ORGANISM: Artificial
<220> FEATURE:
<223> OTHER INFORMATION: synthetic DNA

<400> SEQUENCE: 1384
gatggcgatg ttgcattaca tg                                              22

<210> SEQ ID NO 1385
<211> LENGTH: 22
<212> TYPE: DNA
<213> ORGANISM: Artificial
<220> FEATURE:
<223> OTHER INFORMATION: synthetic DNA

<400> SEQUENCE: 1385
tatgctctga attaacgtag aa                                              22

<210> SEQ ID NO 1386
<211> LENGTH: 22
<212> TYPE: DNA
<213> ORGANISM: Artificial
<220> FEATURE:
<223> OTHER INFORMATION: synthetic DNA

<400> SEQUENCE: 1386
aggcaatatg gtgatccgta gc                                              22

<210> SEQ ID NO 1387
<211> LENGTH: 22
<212> TYPE: DNA
<213> ORGANISM: Artificial
<220> FEATURE:
<223> OTHER INFORMATION: synthetic DNA

<400> SEQUENCE: 1387
tgacagcgat gcatacagta gt                                              22

<210> SEQ ID NO 1388
<211> LENGTH: 22
<212> TYPE: DNA
<213> ORGANISM: Artificial
<220> FEATURE:
<223> OTHER INFORMATION: synthetic DNA

<400> SEQUENCE: 1388
ttctgctaac ggtatccaat ac                                              22

<210> SEQ ID NO 1389
<211> LENGTH: 22
<212> TYPE: DNA
<213> ORGANISM: Artificial
<220> FEATURE:
<223> OTHER INFORMATION: synthetic DNA

<400> SEQUENCE: 1389
gagtcgtcca tacgatctag ga                                              22

<210> SEQ ID NO 1390
<211> LENGTH: 22
<212> TYPE: DNA
<213> ORGANISM: Artificial
<220> FEATURE:
<223> OTHER INFORMATION: synthetic DNA

```
<400> SEQUENCE: 1390
agacggactc aacgccaatt cc                                              22

<210> SEQ ID NO 1391
<211> LENGTH: 22
<212> TYPE: DNA
<213> ORGANISM: Artificial
<220> FEATURE:
<223> OTHER INFORMATION: synthetic DNA

<400> SEQUENCE: 1391
gtagtgttga gcggaccgag ct                                              22

<210> SEQ ID NO 1392
<211> LENGTH: 22
<212> TYPE: DNA
<213> ORGANISM: Artificial
<220> FEATURE:
<223> OTHER INFORMATION: synthetic DNA

<400> SEQUENCE: 1392
aatataacta gatcatagcc ag                                              22

<210> SEQ ID NO 1393
<211> LENGTH: 22
<212> TYPE: DNA
<213> ORGANISM: Artificial
<220> FEATURE:
<223> OTHER INFORMATION: synthetic DNA

<400> SEQUENCE: 1393
tcaatcggag aatacagaac gt                                              22

<210> SEQ ID NO 1394
<211> LENGTH: 22
<212> TYPE: DNA
<213> ORGANISM: Artificial
<220> FEATURE:
<223> OTHER INFORMATION: synthetic DNA

<400> SEQUENCE: 1394
atctccgtcg tccgaaccaa ca                                              22

<210> SEQ ID NO 1395
<211> LENGTH: 22
<212> TYPE: DNA
<213> ORGANISM: Artificial
<220> FEATURE:
<223> OTHER INFORMATION: synthetic DNA

<400> SEQUENCE: 1395
taggcgttca gcggtatgct ta                                              22

<210> SEQ ID NO 1396
<211> LENGTH: 22
<212> TYPE: DNA
<213> ORGANISM: Artificial
<220> FEATURE:
<223> OTHER INFORMATION: synthetic DNA

<400> SEQUENCE: 1396
tgcgtgctat acaacctata cg                                              22

<210> SEQ ID NO 1397
<211> LENGTH: 22
```

<212> TYPE: DNA
<213> ORGANISM: Artificial
<220> FEATURE:
<223> OTHER INFORMATION: synthetic DNA

<400> SEQUENCE: 1397
atggccggca tacatctgta tg                                                22

<210> SEQ ID NO 1398
<211> LENGTH: 22
<212> TYPE: DNA
<213> ORGANISM: Artificial
<220> FEATURE:
<223> OTHER INFORMATION: synthetic DNA

<400> SEQUENCE: 1398
tgatgctgac ataacactga at                                                22

<210> SEQ ID NO 1399
<211> LENGTH: 22
<212> TYPE: DNA
<213> ORGANISM: Artificial
<220> FEATURE:
<223> OTHER INFORMATION: synthetic DNA

<400> SEQUENCE: 1399
atccaaggta cctgaacatc ct                                                22

<210> SEQ ID NO 1400
<211> LENGTH: 22
<212> TYPE: DNA
<213> ORGANISM: Artificial
<220> FEATURE:
<223> OTHER INFORMATION: synthetic DNA

<400> SEQUENCE: 1400
tagtgacgac caggtgagcc tc                                                22

<210> SEQ ID NO 1401
<211> LENGTH: 22
<212> TYPE: DNA
<213> ORGANISM: Artificial
<220> FEATURE:
<223> OTHER INFORMATION: synthetic DNA

<400> SEQUENCE: 1401
aggaggatcc gtcaagtcga cc                                                22

<210> SEQ ID NO 1402
<211> LENGTH: 22
<212> TYPE: DNA
<213> ORGANISM: Artificial
<220> FEATURE:
<223> OTHER INFORMATION: synthetic DNA

<400> SEQUENCE: 1402
agagtatgcc agatcgtgag gc                                                22

<210> SEQ ID NO 1403
<211> LENGTH: 22
<212> TYPE: DNA
<213> ORGANISM: Artificial
<220> FEATURE:
<223> OTHER INFORMATION: synthetic DNA

<400> SEQUENCE: 1403
ccactcacta ggatggctgc gt    22

<210> SEQ ID NO 1404
<211> LENGTH: 22
<212> TYPE: DNA
<213> ORGANISM: Artificial
<220> FEATURE:
<223> OTHER INFORMATION: synthetic DNA

<400> SEQUENCE: 1404
tatccaacct gttatagcga tt    22

<210> SEQ ID NO 1405
<211> LENGTH: 22
<212> TYPE: DNA
<213> ORGANISM: Artificial
<220> FEATURE:
<223> OTHER INFORMATION: synthetic DNA

<400> SEQUENCE: 1405
tcttgcagtg agttgagtct gc    22

<210> SEQ ID NO 1406
<211> LENGTH: 22
<212> TYPE: DNA
<213> ORGANISM: Artificial
<220> FEATURE:
<223> OTHER INFORMATION: synthetic DNA

<400> SEQUENCE: 1406
ccactgttgt acatacacct gg    22

<210> SEQ ID NO 1407
<211> LENGTH: 22
<212> TYPE: DNA
<213> ORGANISM: Artificial
<220> FEATURE:
<223> OTHER INFORMATION: synthetic DNA

<400> SEQUENCE: 1407
atgcgcgtag gccactaagt cc    22

<210> SEQ ID NO 1408
<211> LENGTH: 22
<212> TYPE: DNA
<213> ORGANISM: Artificial
<220> FEATURE:
<223> OTHER INFORMATION: synthetic DNA

<400> SEQUENCE: 1408
acagcggtct acaaccgact gc    22

<210> SEQ ID NO 1409
<211> LENGTH: 22
<212> TYPE: DNA
<213> ORGANISM: Artificial
<220> FEATURE:
<223> OTHER INFORMATION: synthetic DNA

<400> SEQUENCE: 1409
tcgcgctcca gacaattgca gc    22

<210> SEQ ID NO 1410
<211> LENGTH: 22
<212> TYPE: DNA
<213> ORGANISM: Artificial

```
<220> FEATURE:
<223> OTHER INFORMATION: synthetic DNA

<400> SEQUENCE: 1410
ccggtagacc aggagtggtc at                                              22

<210> SEQ ID NO 1411
<211> LENGTH: 22
<212> TYPE: DNA
<213> ORGANISM: Artificial
<220> FEATURE:
<223> OTHER INFORMATION: synthetic DNA

<400> SEQUENCE: 1411
atctcctaac ctagagccat ct                                              22

<210> SEQ ID NO 1412
<211> LENGTH: 22
<212> TYPE: DNA
<213> ORGANISM: Artificial
<220> FEATURE:
<223> OTHER INFORMATION: synthetic DNA

<400> SEQUENCE: 1412
ccacatcgaa tctaacaact ac                                              22

<210> SEQ ID NO 1413
<211> LENGTH: 22
<212> TYPE: DNA
<213> ORGANISM: Artificial
<220> FEATURE:
<223> OTHER INFORMATION: synthetic DNA

<400> SEQUENCE: 1413
tagtcttatt gaatacgtcc ta                                              22

<210> SEQ ID NO 1414
<211> LENGTH: 22
<212> TYPE: DNA
<213> ORGANISM: Artificial
<220> FEATURE:
<223> OTHER INFORMATION: synthetic DNA

<400> SEQUENCE: 1414
tccttaagcc ttggaactgg cg                                              22

<210> SEQ ID NO 1415
<211> LENGTH: 22
<212> TYPE: DNA
<213> ORGANISM: Artificial
<220> FEATURE:
<223> OTHER INFORMATION: synthetic DNA

<400> SEQUENCE: 1415
ccgtgatgga ttgacgtaga gg                                              22

<210> SEQ ID NO 1416
<211> LENGTH: 22
<212> TYPE: DNA
<213> ORGANISM: Artificial
<220> FEATURE:
<223> OTHER INFORMATION: synthetic DNA

<400> SEQUENCE: 1416
gcctggataa cagatgtctt ag                                              22
```

```
<210> SEQ ID NO 1417
<211> LENGTH: 22
<212> TYPE: DNA
<213> ORGANISM: Artificial
<220> FEATURE:
<223> OTHER INFORMATION: synthetic DNA

<400> SEQUENCE: 1417
ctcgacctat aatcttctgc ca                                              22

<210> SEQ ID NO 1418
<211> LENGTH: 22
<212> TYPE: DNA
<213> ORGANISM: Artificial
<220> FEATURE:
<223> OTHER INFORMATION: synthetic DNA

<400> SEQUENCE: 1418
agctacttct ccttcctaat ca                                              22

<210> SEQ ID NO 1419
<211> LENGTH: 22
<212> TYPE: DNA
<213> ORGANISM: Artificial
<220> FEATURE:
<223> OTHER INFORMATION: synthetic DNA

<400> SEQUENCE: 1419
acacgctatt gccttccagt ta                                              22

<210> SEQ ID NO 1420
<211> LENGTH: 22
<212> TYPE: DNA
<213> ORGANISM: Artificial
<220> FEATURE:
<223> OTHER INFORMATION: synthetic DNA

<400> SEQUENCE: 1420
aagcctgtgc atgcaatgag aa                                              22

<210> SEQ ID NO 1421
<211> LENGTH: 22
<212> TYPE: DNA
<213> ORGANISM: Artificial
<220> FEATURE:
<223> OTHER INFORMATION: synthetic DNA

<400> SEQUENCE: 1421
tcgttggtta tagcacaact tc                                              22

<210> SEQ ID NO 1422
<211> LENGTH: 22
<212> TYPE: DNA
<213> ORGANISM: Artificial
<220> FEATURE:
<223> OTHER INFORMATION: synthetic DNA

<400> SEQUENCE: 1422
gcgatgcctt ccaacatacc aa                                              22

<210> SEQ ID NO 1423
<211> LENGTH: 22
<212> TYPE: DNA
<213> ORGANISM: Artificial
<220> FEATURE:
<223> OTHER INFORMATION: synthetic DNA
```

<400> SEQUENCE: 1423
ccaccgttag cacgtgctac gt                                    22

<210> SEQ ID NO 1424
<211> LENGTH: 22
<212> TYPE: DNA
<213> ORGANISM: Artificial
<220> FEATURE:
<223> OTHER INFORMATION: synthetic DNA

<400> SEQUENCE: 1424
gttaccacaa tgccgccatc aa                                    22

<210> SEQ ID NO 1425
<211> LENGTH: 22
<212> TYPE: DNA
<213> ORGANISM: Artificial
<220> FEATURE:
<223> OTHER INFORMATION: synthetic DNA

<400> SEQUENCE: 1425
ggtgcattaa gaacgaacta cc                                    22

<210> SEQ ID NO 1426
<211> LENGTH: 22
<212> TYPE: DNA
<213> ORGANISM: Artificial
<220> FEATURE:
<223> OTHER INFORMATION: synthetic DNA

<400> SEQUENCE: 1426
tccttccgga taatgccgat tc                                    22

<210> SEQ ID NO 1427
<211> LENGTH: 22
<212> TYPE: DNA
<213> ORGANISM: Artificial
<220> FEATURE:
<223> OTHER INFORMATION: synthetic DNA

<400> SEQUENCE: 1427
aaccgcaact tctagcggaa ga                                    22

<210> SEQ ID NO 1428
<211> LENGTH: 22
<212> TYPE: DNA
<213> ORGANISM: Artificial
<220> FEATURE:
<223> OTHER INFORMATION: synthetic DNA

<400> SEQUENCE: 1428
tccttaagca gttgaaccta gg                                    22

<210> SEQ ID NO 1429
<211> LENGTH: 22
<212> TYPE: DNA
<213> ORGANISM: Artificial
<220> FEATURE:
<223> OTHER INFORMATION: synthetic DNA

<400> SEQUENCE: 1429
tactaagtca gataagatca ga                                    22

<210> SEQ ID NO 1430

```
<211> LENGTH: 22
<212> TYPE: DNA
<213> ORGANISM: Artificial
<220> FEATURE:
<223> OTHER INFORMATION: synthetic DNA

<400> SEQUENCE: 1430
ttcgccataa ctagatgaat gc                                              22

<210> SEQ ID NO 1431
<211> LENGTH: 22
<212> TYPE: DNA
<213> ORGANISM: Artificial
<220> FEATURE:
<223> OTHER INFORMATION: synthetic DNA

<400> SEQUENCE: 1431
aagaagttag acgcggtggc tg                                              22

<210> SEQ ID NO 1432
<211> LENGTH: 22
<212> TYPE: DNA
<213> ORGANISM: Artificial
<220> FEATURE:
<223> OTHER INFORMATION: synthetic DNA

<400> SEQUENCE: 1432
gtatctgatc gaagagcggt gg                                              22

<210> SEQ ID NO 1433
<211> LENGTH: 22
<212> TYPE: DNA
<213> ORGANISM: Artificial
<220> FEATURE:
<223> OTHER INFORMATION: synthetic DNA

<400> SEQUENCE: 1433
tcaagagcta cgaagtaagt cc                                              22

<210> SEQ ID NO 1434
<211> LENGTH: 22
<212> TYPE: DNA
<213> ORGANISM: Artificial
<220> FEATURE:
<223> OTHER INFORMATION: synthetic DNA

<400> SEQUENCE: 1434
cgagtacaca gcagcatacc ta                                              22

<210> SEQ ID NO 1435
<211> LENGTH: 22
<212> TYPE: DNA
<213> ORGANISM: Artificial
<220> FEATURE:
<223> OTHER INFORMATION: synthetic DNA

<400> SEQUENCE: 1435
ctcgataagt tactctgcta ga                                              22

<210> SEQ ID NO 1436
<211> LENGTH: 22
<212> TYPE: DNA
<213> ORGANISM: Artificial
<220> FEATURE:
<223> OTHER INFORMATION: synthetic DNA

<400> SEQUENCE: 1436
```

```
atggtgctgg ttctccgtct gt                                              22

<210> SEQ ID NO 1437
<211> LENGTH: 22
<212> TYPE: DNA
<213> ORGANISM: Artificial
<220> FEATURE:
<223> OTHER INFORMATION: synthetic DNA

<400> SEQUENCE: 1437
tcaagcggtc caaggctgag ac                                              22

<210> SEQ ID NO 1438
<211> LENGTH: 22
<212> TYPE: DNA
<213> ORGANISM: Artificial
<220> FEATURE:
<223> OTHER INFORMATION: synthetic DNA

<400> SEQUENCE: 1438
tgtcctgctc tgttgctacc gt                                              22

<210> SEQ ID NO 1439
<211> LENGTH: 22
<212> TYPE: DNA
<213> ORGANISM: Artificial
<220> FEATURE:
<223> OTHER INFORMATION: synthetic DNA

<400> SEQUENCE: 1439
agtcatatcg cgtcacacgt tg                                              22

<210> SEQ ID NO 1440
<211> LENGTH: 22
<212> TYPE: DNA
<213> ORGANISM: Artificial
<220> FEATURE:
<223> OTHER INFORMATION: synthetic DNA

<400> SEQUENCE: 1440
ggtgaataag gacatgagaa gc                                              22

<210> SEQ ID NO 1441
<211> LENGTH: 24
<212> TYPE: DNA
<213> ORGANISM: Artificial
<220> FEATURE:
<223> OTHER INFORMATION: synthetic DNA

<400> SEQUENCE: 1441
cctgatctta tctagtagag actc                                            24

<210> SEQ ID NO 1442
<211> LENGTH: 24
<212> TYPE: DNA
<213> ORGANISM: Artificial
<220> FEATURE:
<223> OTHER INFORMATION: synthetic DNA

<400> SEQUENCE: 1442
ttctgtgtag gtgtgccaat cacc                                            24

<210> SEQ ID NO 1443
<211> LENGTH: 24
<212> TYPE: DNA
```

<213> ORGANISM: Artificial
<220> FEATURE:
<223> OTHER INFORMATION: synthetic DNA

<400> SEQUENCE: 1443
gacttccaga tgcttaagac gaca                                      24

<210> SEQ ID NO 1444
<211> LENGTH: 24
<212> TYPE: DNA
<213> ORGANISM: Artificial
<220> FEATURE:
<223> OTHER INFORMATION: synthetic DNA

<400> SEQUENCE: 1444
gtccttcgac ggagaacatc cgag                                      24

<210> SEQ ID NO 1445
<211> LENGTH: 24
<212> TYPE: DNA
<213> ORGANISM: Artificial
<220> FEATURE:
<223> OTHER INFORMATION: synthetic DNA

<400> SEQUENCE: 1445
cttggttagt gtaccgtcaa cgtc                                      24

<210> SEQ ID NO 1446
<211> LENGTH: 24
<212> TYPE: DNA
<213> ORGANISM: Artificial
<220> FEATURE:
<223> OTHER INFORMATION: synthetic DNA

<400> SEQUENCE: 1446
aagcggcatg tgcctaatcg acgt                                      24

<210> SEQ ID NO 1447
<211> LENGTH: 24
<212> TYPE: DNA
<213> ORGANISM: Artificial
<220> FEATURE:
<223> OTHER INFORMATION: synthetic DNA

<400> SEQUENCE: 1447
cgaccgtcgt tacacggaat ccga                                      24

<210> SEQ ID NO 1448
<211> LENGTH: 24
<212> TYPE: DNA
<213> ORGANISM: Artificial
<220> FEATURE:
<223> OTHER INFORMATION: synthetic DNA

<400> SEQUENCE: 1448
tcgcaagtgt gccgttctgt tcat                                      24

<210> SEQ ID NO 1449
<211> LENGTH: 24
<212> TYPE: DNA
<213> ORGANISM: Artificial
<220> FEATURE:
<223> OTHER INFORMATION: synthetic DNA

<400> SEQUENCE: 1449
cgtactgaag ttcggagtcg ccgt                                      24

<210> SEQ ID NO 1450
<211> LENGTH: 24
<212> TYPE: DNA
<213> ORGANISM: Artificial
<220> FEATURE:
<223> OTHER INFORMATION: synthetic DNA

<400> SEQUENCE: 1450
ccactacaga atggtagcag atca                                          24

<210> SEQ ID NO 1451
<211> LENGTH: 24
<212> TYPE: DNA
<213> ORGANISM: Artificial
<220> FEATURE:
<223> OTHER INFORMATION: synthetic DNA

<400> SEQUENCE: 1451
agtaggagag aggcctacac aaca                                          24

<210> SEQ ID NO 1452
<211> LENGTH: 24
<212> TYPE: DNA
<213> ORGANISM: Artificial
<220> FEATURE:
<223> OTHER INFORMATION: synthetic DNA

<400> SEQUENCE: 1452
agccaagata ctcgttcggt atgg                                          24

<210> SEQ ID NO 1453
<211> LENGTH: 24
<212> TYPE: DNA
<213> ORGANISM: Artificial
<220> FEATURE:
<223> OTHER INFORMATION: synthetic DNA

<400> SEQUENCE: 1453
gttccgagta cattgaatcc tggc                                          24

<210> SEQ ID NO 1454
<211> LENGTH: 24
<212> TYPE: DNA
<213> ORGANISM: Artificial
<220> FEATURE:
<223> OTHER INFORMATION: synthetic DNA

<400> SEQUENCE: 1454
aggcgtacga gttattgcca gagg                                          24

<210> SEQ ID NO 1455
<211> LENGTH: 24
<212> TYPE: DNA
<213> ORGANISM: Artificial
<220> FEATURE:
<223> OTHER INFORMATION: synthetic DNA

<400> SEQUENCE: 1455
gtggcatcac acatatctca gcat                                          24

<210> SEQ ID NO 1456
<211> LENGTH: 24
<212> TYPE: DNA
<213> ORGANISM: Artificial
<220> FEATURE:

```
<223> OTHER INFORMATION: synthetic DNA

<400> SEQUENCE: 1456
gagaccgata tgttgatgcc agaa                                              24

<210> SEQ ID NO 1457
<211> LENGTH: 24
<212> TYPE: DNA
<213> ORGANISM: Artificial
<220> FEATURE:
<223> OTHER INFORMATION: synthetic DNA

<400> SEQUENCE: 1457
caactgtagc cagtcgattg ctat                                              24

<210> SEQ ID NO 1458
<211> LENGTH: 24
<212> TYPE: DNA
<213> ORGANISM: Artificial
<220> FEATURE:
<223> OTHER INFORMATION: synthetic DNA

<400> SEQUENCE: 1458
tatcaatgca atgagaggat gcag                                              24

<210> SEQ ID NO 1459
<211> LENGTH: 24
<212> TYPE: DNA
<213> ORGANISM: Artificial
<220> FEATURE:
<223> OTHER INFORMATION: synthetic DNA

<400> SEQUENCE: 1459
gtatgctcgg ctccaagtac tgtt                                              24

<210> SEQ ID NO 1460
<211> LENGTH: 24
<212> TYPE: DNA
<213> ORGANISM: Artificial
<220> FEATURE:
<223> OTHER INFORMATION: synthetic DNA

<400> SEQUENCE: 1460
agagactctt ataggcttga cgga                                              24

<210> SEQ ID NO 1461
<211> LENGTH: 24
<212> TYPE: DNA
<213> ORGANISM: Artificial
<220> FEATURE:
<223> OTHER INFORMATION: synthetic DNA

<400> SEQUENCE: 1461
acttaacaga tatggatcat cgcc                                              24

<210> SEQ ID NO 1462
<211> LENGTH: 24
<212> TYPE: DNA
<213> ORGANISM: Artificial
<220> FEATURE:
<223> OTHER INFORMATION: synthetic DNA

<400> SEQUENCE: 1462
aatcagagcg agtctcgctt cagg                                              24
```

```
<210> SEQ ID NO 1463
<211> LENGTH: 24
<212> TYPE: DNA
<213> ORGANISM: Artificial
<220> FEATURE:
<223> OTHER INFORMATION: synthetic DNA

<400> SEQUENCE: 1463
accaccgagg aacaggtgcg acaa                                           24

<210> SEQ ID NO 1464
<211> LENGTH: 24
<212> TYPE: DNA
<213> ORGANISM: Artificial
<220> FEATURE:
<223> OTHER INFORMATION: synthetic DNA

<400> SEQUENCE: 1464
tggtacatgt caaccgtaag cctg                                           24

<210> SEQ ID NO 1465
<211> LENGTH: 24
<212> TYPE: DNA
<213> ORGANISM: Artificial
<220> FEATURE:
<223> OTHER INFORMATION: synthetic DNA

<400> SEQUENCE: 1465
cgtgccgcgg tgttcttgta tatg                                           24

<210> SEQ ID NO 1466
<211> LENGTH: 24
<212> TYPE: DNA
<213> ORGANISM: Artificial
<220> FEATURE:
<223> OTHER INFORMATION: synthetic DNA

<400> SEQUENCE: 1466
gacaagcgcg cgtgagacat atca                                           24

<210> SEQ ID NO 1467
<211> LENGTH: 24
<212> TYPE: DNA
<213> ORGANISM: Artificial
<220> FEATURE:
<223> OTHER INFORMATION: synthetic DNA

<400> SEQUENCE: 1467
agtgcactcc gaacaagagt tagt                                           24

<210> SEQ ID NO 1468
<211> LENGTH: 24
<212> TYPE: DNA
<213> ORGANISM: Artificial
<220> FEATURE:
<223> OTHER INFORMATION: synthetic DNA

<400> SEQUENCE: 1468
cctcattacc gcgttaggag tccg                                           24

<210> SEQ ID NO 1469
<211> LENGTH: 24
<212> TYPE: DNA
<213> ORGANISM: Artificial
<220> FEATURE:
<223> OTHER INFORMATION: synthetic DNA
```

```
<400> SEQUENCE: 1469
tgcttattgc ttagttgcta tctc                                          24

<210> SEQ ID NO 1470
<211> LENGTH: 24
<212> TYPE: DNA
<213> ORGANISM: Artificial
<220> FEATURE:
<223> OTHER INFORMATION: synthetic DNA

<400> SEQUENCE: 1470
gcgtgatcct gttctattcg ttag                                          24

<210> SEQ ID NO 1471
<211> LENGTH: 24
<212> TYPE: DNA
<213> ORGANISM: Artificial
<220> FEATURE:
<223> OTHER INFORMATION: synthetic DNA

<400> SEQUENCE: 1471
ggccagaact atgacgagta taag                                          24

<210> SEQ ID NO 1472
<211> LENGTH: 24
<212> TYPE: DNA
<213> ORGANISM: Artificial
<220> FEATURE:
<223> OTHER INFORMATION: synthetic DNA

<400> SEQUENCE: 1472
gatggcgact atctaattgc aatg                                          24

<210> SEQ ID NO 1473
<211> LENGTH: 24
<212> TYPE: DNA
<213> ORGANISM: Artificial
<220> FEATURE:
<223> OTHER INFORMATION: synthetic DNA

<400> SEQUENCE: 1473
tagtaaccat agctctgtac aact                                          24

<210> SEQ ID NO 1474
<211> LENGTH: 24
<212> TYPE: DNA
<213> ORGANISM: Artificial
<220> FEATURE:
<223> OTHER INFORMATION: synthetic DNA

<400> SEQUENCE: 1474
cgtgatcgcc aatacacatg tcgc                                          24

<210> SEQ ID NO 1475
<211> LENGTH: 24
<212> TYPE: DNA
<213> ORGANISM: Artificial
<220> FEATURE:
<223> OTHER INFORMATION: synthetic DNA

<400> SEQUENCE: 1475
taataacgga tcgatatgca cgcg                                          24

<210> SEQ ID NO 1476
<211> LENGTH: 24
```

```
<212> TYPE: DNA
<213> ORGANISM: Artificial
<220> FEATURE:
<223> OTHER INFORMATION: synthetic DNA

<400> SEQUENCE: 1476
atcatcgcgc taatactatc tgaa                                          24

<210> SEQ ID NO 1477
<211> LENGTH: 24
<212> TYPE: DNA
<213> ORGANISM: Artificial
<220> FEATURE:
<223> OTHER INFORMATION: synthetic DNA

<400> SEQUENCE: 1477
cacgtgcgtg caggtcacta gtat                                          24

<210> SEQ ID NO 1478
<211> LENGTH: 24
<212> TYPE: DNA
<213> ORGANISM: Artificial
<220> FEATURE:
<223> OTHER INFORMATION: synthetic DNA

<400> SEQUENCE: 1478
aggtccaatg ccgagcgatc agaa                                          24

<210> SEQ ID NO 1479
<211> LENGTH: 24
<212> TYPE: DNA
<213> ORGANISM: Artificial
<220> FEATURE:
<223> OTHER INFORMATION: synthetic DNA

<400> SEQUENCE: 1479
cagcataaca acgagccagg tcag                                          24

<210> SEQ ID NO 1480
<211> LENGTH: 24
<212> TYPE: DNA
<213> ORGANISM: Artificial
<220> FEATURE:
<223> OTHER INFORMATION: synthetic DNA

<400> SEQUENCE: 1480
atggcgtcca atactccgac ctat                                          24

<210> SEQ ID NO 1481
<211> LENGTH: 24
<212> TYPE: DNA
<213> ORGANISM: Artificial
<220> FEATURE:
<223> OTHER INFORMATION: synthetic DNA

<400> SEQUENCE: 1481
aggaacatcg tgaataatga agac                                          24

<210> SEQ ID NO 1482
<211> LENGTH: 24
<212> TYPE: DNA
<213> ORGANISM: Artificial
<220> FEATURE:
<223> OTHER INFORMATION: synthetic DNA

<400> SEQUENCE: 1482
```
tctcgacgtt catgtaatta agga                                          24

<210> SEQ ID NO 1483
<211> LENGTH: 24
<212> TYPE: DNA
<213> ORGANISM: Artificial
<220> FEATURE:
<223> OTHER INFORMATION: synthetic DNA

<400> SEQUENCE: 1483
tcgcggttaa ccttacttag acga                                          24

<210> SEQ ID NO 1484
<211> LENGTH: 24
<212> TYPE: DNA
<213> ORGANISM: Artificial
<220> FEATURE:
<223> OTHER INFORMATION: synthetic DNA

<400> SEQUENCE: 1484
atcatatcta cggctctggc gccg                                          24

<210> SEQ ID NO 1485
<211> LENGTH: 24
<212> TYPE: DNA
<213> ORGANISM: Artificial
<220> FEATURE:
<223> OTHER INFORMATION: synthetic DNA

<400> SEQUENCE: 1485
gcagatggag accagaggta cagg                                          24

<210> SEQ ID NO 1486
<211> LENGTH: 24
<212> TYPE: DNA
<213> ORGANISM: Artificial
<220> FEATURE:
<223> OTHER INFORMATION: synthetic DNA

<400> SEQUENCE: 1486
agacagaaga ttaccacgtg ctat                                          24

<210> SEQ ID NO 1487
<211> LENGTH: 24
<212> TYPE: DNA
<213> ORGANISM: Artificial
<220> FEATURE:
<223> OTHER INFORMATION: synthetic DNA

<400> SEQUENCE: 1487
ccacggacaa catgccgctt aact                                          24

<210> SEQ ID NO 1488
<211> LENGTH: 24
<212> TYPE: DNA
<213> ORGANISM: Artificial
<220> FEATURE:
<223> OTHER INFORMATION: synthetic DNA

<400> SEQUENCE: 1488
cttgaagtct caagctatga gaga                                          24

<210> SEQ ID NO 1489
<211> LENGTH: 24
<212> TYPE: DNA
<213> ORGANISM: Artificial

```
<220> FEATURE:
<223> OTHER INFORMATION: synthetic DNA

<400> SEQUENCE: 1489
acagcagtcg tgcttaggtc actg                                              24

<210> SEQ ID NO 1490
<211> LENGTH: 24
<212> TYPE: DNA
<213> ORGANISM: Artificial
<220> FEATURE:
<223> OTHER INFORMATION: synthetic DNA

<400> SEQUENCE: 1490
aggtgttaat gaacgtaggt gaga                                              24

<210> SEQ ID NO 1491
<211> LENGTH: 24
<212> TYPE: DNA
<213> ORGANISM: Artificial
<220> FEATURE:
<223> OTHER INFORMATION: synthetic DNA

<400> SEQUENCE: 1491
agccactatg ttcaaggctg agcc                                              24

<210> SEQ ID NO 1492
<211> LENGTH: 24
<212> TYPE: DNA
<213> ORGANISM: Artificial
<220> FEATURE:
<223> OTHER INFORMATION: synthetic DNA

<400> SEQUENCE: 1492
gcaggcggtg tcgtgtgaca atga                                              24

<210> SEQ ID NO 1493
<211> LENGTH: 24
<212> TYPE: DNA
<213> ORGANISM: Artificial
<220> FEATURE:
<223> OTHER INFORMATION: synthetic DNA

<400> SEQUENCE: 1493
agccattgct acagaggtta ctta                                              24

<210> SEQ ID NO 1494
<211> LENGTH: 24
<212> TYPE: DNA
<213> ORGANISM: Artificial
<220> FEATURE:
<223> OTHER INFORMATION: synthetic DNA

<400> SEQUENCE: 1494
acaatcgaac ctacactgag tccg                                              24

<210> SEQ ID NO 1495
<211> LENGTH: 24
<212> TYPE: DNA
<213> ORGANISM: Artificial
<220> FEATURE:
<223> OTHER INFORMATION: synthetic DNA

<400> SEQUENCE: 1495
ccgatctcaa taggtaccac gaac                                              24
```

```
<210> SEQ ID NO 1496
<211> LENGTH: 24
<212> TYPE: DNA
<213> ORGANISM: Artificial
<220> FEATURE:
<223> OTHER INFORMATION: synthetic DNA

<400> SEQUENCE: 1496
gatacgtggc gctatgctaa ttaa                                           24

<210> SEQ ID NO 1497
<211> LENGTH: 24
<212> TYPE: DNA
<213> ORGANISM: Artificial
<220> FEATURE:
<223> OTHER INFORMATION: synthetic DNA

<400> SEQUENCE: 1497
agagagatgg cacacattga cgtc                                           24

<210> SEQ ID NO 1498
<211> LENGTH: 24
<212> TYPE: DNA
<213> ORGANISM: Artificial
<220> FEATURE:
<223> OTHER INFORMATION: synthetic DNA

<400> SEQUENCE: 1498
ctcaactcat ccttgtagcc gatg                                           24

<210> SEQ ID NO 1499
<211> LENGTH: 24
<212> TYPE: DNA
<213> ORGANISM: Artificial
<220> FEATURE:
<223> OTHER INFORMATION: synthetic DNA

<400> SEQUENCE: 1499
gtggaataac gcgatacgac tctt                                           24

<210> SEQ ID NO 1500
<211> LENGTH: 24
<212> TYPE: DNA
<213> ORGANISM: Artificial
<220> FEATURE:
<223> OTHER INFORMATION: synthetic DNA

<400> SEQUENCE: 1500
atctaccatg cgaatgctct ctag                                           24

<210> SEQ ID NO 1501
<211> LENGTH: 24
<212> TYPE: DNA
<213> ORGANISM: Artificial
<220> FEATURE:
<223> OTHER INFORMATION: synthetic DNA

<400> SEQUENCE: 1501
atacgcacgc ctgacacaag gacc                                           24

<210> SEQ ID NO 1502
<211> LENGTH: 24
<212> TYPE: DNA
<213> ORGANISM: Artificial
<220> FEATURE:
<223> OTHER INFORMATION: synthetic DNA
```

<400> SEQUENCE: 1502
gtccactctc agtgtgtaga gtcc                                          24

<210> SEQ ID NO 1503
<211> LENGTH: 24
<212> TYPE: DNA
<213> ORGANISM: Artificial
<220> FEATURE:
<223> OTHER INFORMATION: synthetic DNA

<400> SEQUENCE: 1503
aatatatcca gattctctgt gcag                                          24

<210> SEQ ID NO 1504
<211> LENGTH: 24
<212> TYPE: DNA
<213> ORGANISM: Artificial
<220> FEATURE:
<223> OTHER INFORMATION: synthetic DNA

<400> SEQUENCE: 1504
ccttccgcca catgttcgac aagg                                          24

<210> SEQ ID NO 1505
<211> LENGTH: 24
<212> TYPE: DNA
<213> ORGANISM: Artificial
<220> FEATURE:
<223> OTHER INFORMATION: synthetic DNA

<400> SEQUENCE: 1505
actgtgccat catccgagga gcca                                          24

<210> SEQ ID NO 1506
<211> LENGTH: 24
<212> TYPE: DNA
<213> ORGANISM: Artificial
<220> FEATURE:
<223> OTHER INFORMATION: synthetic DNA

<400> SEQUENCE: 1506
tctatgccgc tatggcgtcg tgta                                          24

<210> SEQ ID NO 1507
<211> LENGTH: 24
<212> TYPE: DNA
<213> ORGANISM: Artificial
<220> FEATURE:
<223> OTHER INFORMATION: synthetic DNA

<400> SEQUENCE: 1507
cgtaacctaa ggtaatatgt ctgc                                          24

<210> SEQ ID NO 1508
<211> LENGTH: 24
<212> TYPE: DNA
<213> ORGANISM: Artificial
<220> FEATURE:
<223> OTHER INFORMATION: synthetic DNA

<400> SEQUENCE: 1508
tactgaccgt atcaagatta ctaa                                          24

<210> SEQ ID NO 1509

<211> LENGTH: 24
<212> TYPE: DNA
<213> ORGANISM: Artificial
<220> FEATURE:
<223> OTHER INFORMATION: synthetic DNA

<400> SEQUENCE: 1509
tcatcggagc gccatacggt acgt                                         24

<210> SEQ ID NO 1510
<211> LENGTH: 24
<212> TYPE: DNA
<213> ORGANISM: Artificial
<220> FEATURE:
<223> OTHER INFORMATION: synthetic DNA

<400> SEQUENCE: 1510
gcaagaggaa tgaacgaagt gatt                                         24

<210> SEQ ID NO 1511
<211> LENGTH: 24
<212> TYPE: DNA
<213> ORGANISM: Artificial
<220> FEATURE:
<223> OTHER INFORMATION: synthetic DNA

<400> SEQUENCE: 1511
ggctgattga catcctgact tagt                                         24

<210> SEQ ID NO 1512
<211> LENGTH: 24
<212> TYPE: DNA
<213> ORGANISM: Artificial
<220> FEATURE:
<223> OTHER INFORMATION: synthetic DNA

<400> SEQUENCE: 1512
aaggcgctag attggattaa cgta                                         24

<210> SEQ ID NO 1513
<211> LENGTH: 24
<212> TYPE: DNA
<213> ORGANISM: Artificial
<220> FEATURE:
<223> OTHER INFORMATION: synthetic DNA

<400> SEQUENCE: 1513
gctagctaga agaataggat tcgt                                         24

<210> SEQ ID NO 1514
<211> LENGTH: 24
<212> TYPE: DNA
<213> ORGANISM: Artificial
<220> FEATURE:
<223> OTHER INFORMATION: synthetic DNA

<400> SEQUENCE: 1514
caggtgacgg cctctataac tcat                                         24

<210> SEQ ID NO 1515
<211> LENGTH: 24
<212> TYPE: DNA
<213> ORGANISM: Artificial
<220> FEATURE:
<223> OTHER INFORMATION: synthetic DNA

<400> SEQUENCE: 1515
caggttacac ataccactat cttc                                          24

<210> SEQ ID NO 1516
<211> LENGTH: 24
<212> TYPE: DNA
<213> ORGANISM: Artificial
<220> FEATURE:
<223> OTHER INFORMATION: synthetic DNA

<400> SEQUENCE: 1516
ttgctacgta ccgtcttaat ccgt                                          24

<210> SEQ ID NO 1517
<211> LENGTH: 24
<212> TYPE: DNA
<213> ORGANISM: Artificial
<220> FEATURE:
<223> OTHER INFORMATION: synthetic DNA

<400> SEQUENCE: 1517
ctcaacatgt cttgcaagct tcga                                          24

<210> SEQ ID NO 1518
<211> LENGTH: 24
<212> TYPE: DNA
<213> ORGANISM: Artificial
<220> FEATURE:
<223> OTHER INFORMATION: synthetic DNA

<400> SEQUENCE: 1518
ggtgcggtac gtagaaccag atca                                          24

<210> SEQ ID NO 1519
<211> LENGTH: 24
<212> TYPE: DNA
<213> ORGANISM: Artificial
<220> FEATURE:
<223> OTHER INFORMATION: synthetic DNA

<400> SEQUENCE: 1519
aatgctctcc aagatcctga ccta                                          24

<210> SEQ ID NO 1520
<211> LENGTH: 24
<212> TYPE: DNA
<213> ORGANISM: Artificial
<220> FEATURE:
<223> OTHER INFORMATION: synthetic DNA

<400> SEQUENCE: 1520
gcttcgcagg tctggatgat ggag                                          24

<210> SEQ ID NO 1521
<211> LENGTH: 24
<212> TYPE: DNA
<213> ORGANISM: Artificial
<220> FEATURE:
<223> OTHER INFORMATION: synthetic DNA

<400> SEQUENCE: 1521
acattgacca gacagcacct tgcg                                          24

<210> SEQ ID NO 1522
<211> LENGTH: 24
<212> TYPE: DNA

```
<213> ORGANISM: Artificial
<220> FEATURE:
<223> OTHER INFORMATION: synthetic DNA

<400> SEQUENCE: 1522
aggtatcaat gtgcttaata ggcg                                              24

<210> SEQ ID NO 1523
<211> LENGTH: 24
<212> TYPE: DNA
<213> ORGANISM: Artificial
<220> FEATURE:
<223> OTHER INFORMATION: synthetic DNA

<400> SEQUENCE: 1523
tccggacaca cgattagtaa cgga                                              24

<210> SEQ ID NO 1524
<211> LENGTH: 24
<212> TYPE: DNA
<213> ORGANISM: Artificial
<220> FEATURE:
<223> OTHER INFORMATION: synthetic DNA

<400> SEQUENCE: 1524
tacgaagtac tacagatcgg tcag                                              24

<210> SEQ ID NO 1525
<211> LENGTH: 24
<212> TYPE: DNA
<213> ORGANISM: Artificial
<220> FEATURE:
<223> OTHER INFORMATION: synthetic DNA

<400> SEQUENCE: 1525
aattgtcaga cgaatactgc tgga                                              24

<210> SEQ ID NO 1526
<211> LENGTH: 24
<212> TYPE: DNA
<213> ORGANISM: Artificial
<220> FEATURE:
<223> OTHER INFORMATION: synthetic DNA

<400> SEQUENCE: 1526
tgaatcatga gccagaggtt atgc                                              24

<210> SEQ ID NO 1527
<211> LENGTH: 24
<212> TYPE: DNA
<213> ORGANISM: Artificial
<220> FEATURE:
<223> OTHER INFORMATION: synthetic DNA

<400> SEQUENCE: 1527
cacaagacac gtcattaaca tcaa                                              24

<210> SEQ ID NO 1528
<211> LENGTH: 24
<212> TYPE: DNA
<213> ORGANISM: Artificial
<220> FEATURE:
<223> OTHER INFORMATION: synthetic DNA

<400> SEQUENCE: 1528
gaatgactac attactccgc cagg                                              24
```

<210> SEQ ID NO 1529
<211> LENGTH: 24
<212> TYPE: DNA
<213> ORGANISM: Artificial
<220> FEATURE:
<223> OTHER INFORMATION: synthetic DNA

<400> SEQUENCE: 1529
agccagagat actggaactt gact                                      24

<210> SEQ ID NO 1530
<211> LENGTH: 24
<212> TYPE: DNA
<213> ORGANISM: Artificial
<220> FEATURE:
<223> OTHER INFORMATION: synthetic DNA

<400> SEQUENCE: 1530
tatcagacac atcacaatgg atac                                      24

<210> SEQ ID NO 1531
<211> LENGTH: 24
<212> TYPE: DNA
<213> ORGANISM: Artificial
<220> FEATURE:
<223> OTHER INFORMATION: synthetic DNA

<400> SEQUENCE: 1531
ctaggacacc gctagtcggt tgaa                                      24

<210> SEQ ID NO 1532
<211> LENGTH: 24
<212> TYPE: DNA
<213> ORGANISM: Artificial
<220> FEATURE:
<223> OTHER INFORMATION: synthetic DNA

<400> SEQUENCE: 1532
gtataactgc gtgtcctggt gtat                                      24

<210> SEQ ID NO 1533
<211> LENGTH: 24
<212> TYPE: DNA
<213> ORGANISM: Artificial
<220> FEATURE:
<223> OTHER INFORMATION: synthetic DNA

<400> SEQUENCE: 1533
atgcaatact aaggtggacc tccg                                      24

<210> SEQ ID NO 1534
<211> LENGTH: 24
<212> TYPE: DNA
<213> ORGANISM: Artificial
<220> FEATURE:
<223> OTHER INFORMATION: synthetic DNA

<400> SEQUENCE: 1534
atgcagacgc ttgcgataag tcat                                      24

<210> SEQ ID NO 1535
<211> LENGTH: 24
<212> TYPE: DNA
<213> ORGANISM: Artificial
<220> FEATURE:

<223> OTHER INFORMATION: synthetic DNA

<400> SEQUENCE: 1535
ttgctcgata cacgtagacc agtg                                   24

<210> SEQ ID NO 1536
<211> LENGTH: 24
<212> TYPE: DNA
<213> ORGANISM: Artificial
<220> FEATURE:
<223> OTHER INFORMATION: synthetic DNA

<400> SEQUENCE: 1536
tactggagga cgattgtcta tcat                                   24

<210> SEQ ID NO 1537
<211> LENGTH: 26
<212> TYPE: DNA
<213> ORGANISM: Artificial
<220> FEATURE:
<223> OTHER INFORMATION: synthetic DNA

<400> SEQUENCE: 1537
actaaggcac gctgattcga gcatta                                 26

<210> SEQ ID NO 1538
<211> LENGTH: 26
<212> TYPE: DNA
<213> ORGANISM: Artificial
<220> FEATURE:
<223> OTHER INFORMATION: synthetic DNA

<400> SEQUENCE: 1538
cggattctgg cacgtacaag tagcag                                 26

<210> SEQ ID NO 1539
<211> LENGTH: 26
<212> TYPE: DNA
<213> ORGANISM: Artificial
<220> FEATURE:
<223> OTHER INFORMATION: synthetic DNA

<400> SEQUENCE: 1539
ttatggctcc agatctagtc accagc                                 26

<210> SEQ ID NO 1540
<211> LENGTH: 26
<212> TYPE: DNA
<213> ORGANISM: Artificial
<220> FEATURE:
<223> OTHER INFORMATION: synthetic DNA

<400> SEQUENCE: 1540
catacactcc aggcatgtat gatagg                                 26

<210> SEQ ID NO 1541
<211> LENGTH: 26
<212> TYPE: DNA
<213> ORGANISM: Artificial
<220> FEATURE:
<223> OTHER INFORMATION: synthetic DNA

<400> SEQUENCE: 1541
agttgtaagc caacgagtgt agcgta                                 26

```
<210> SEQ ID NO 1542
<211> LENGTH: 26
<212> TYPE: DNA
<213> ORGANISM: Artificial
<220> FEATURE:
<223> OTHER INFORMATION: synthetic DNA

<400> SEQUENCE: 1542
gtatcagctc cttcctctga ttccgg                                          26

<210> SEQ ID NO 1543
<211> LENGTH: 26
<212> TYPE: DNA
<213> ORGANISM: Artificial
<220> FEATURE:
<223> OTHER INFORMATION: synthetic DNA

<400> SEQUENCE: 1543
aacatacaga atgtctatgg tcagct                                          26

<210> SEQ ID NO 1544
<211> LENGTH: 26
<212> TYPE: DNA
<213> ORGANISM: Artificial
<220> FEATURE:
<223> OTHER INFORMATION: synthetic DNA

<400> SEQUENCE: 1544
gactcatatt catgttcagt atagag                                          26

<210> SEQ ID NO 1545
<211> LENGTH: 26
<212> TYPE: DNA
<213> ORGANISM: Artificial
<220> FEATURE:
<223> OTHER INFORMATION: synthetic DNA

<400> SEQUENCE: 1545
agagtgaacg aacgtgaccg acgctc                                          26

<210> SEQ ID NO 1546
<211> LENGTH: 26
<212> TYPE: DNA
<213> ORGANISM: Artificial
<220> FEATURE:
<223> OTHER INFORMATION: synthetic DNA

<400> SEQUENCE: 1546
aattggcgtc cttgccacaa catctt                                          26

<210> SEQ ID NO 1547
<211> LENGTH: 26
<212> TYPE: DNA
<213> ORGANISM: Artificial
<220> FEATURE:
<223> OTHER INFORMATION: synthetic DNA

<400> SEQUENCE: 1547
tcgtagacgc ctcgtacatc cgagat                                          26

<210> SEQ ID NO 1548
<211> LENGTH: 26
<212> TYPE: DNA
<213> ORGANISM: Artificial
<220> FEATURE:
<223> OTHER INFORMATION: synthetic DNA
```

```
<400> SEQUENCE: 1548
ccggctcgtg aggcgataat catata                                              26

<210> SEQ ID NO 1549
<211> LENGTH: 26
<212> TYPE: DNA
<213> ORGANISM: Artificial
<220> FEATURE:
<223> OTHER INFORMATION: synthetic DNA

<400> SEQUENCE: 1549
agtcctgatc acgaccacga ctcacg                                              26

<210> SEQ ID NO 1550
<211> LENGTH: 26
<212> TYPE: DNA
<213> ORGANISM: Artificial
<220> FEATURE:
<223> OTHER INFORMATION: synthetic DNA

<400> SEQUENCE: 1550
ggcactcaat cctccatgga gaagct                                              26

<210> SEQ ID NO 1551
<211> LENGTH: 26
<212> TYPE: DNA
<213> ORGANISM: Artificial
<220> FEATURE:
<223> OTHER INFORMATION: synthetic DNA

<400> SEQUENCE: 1551
tcatcattcc tcacgttcac cggtga                                              26

<210> SEQ ID NO 1552
<211> LENGTH: 26
<212> TYPE: DNA
<213> ORGANISM: Artificial
<220> FEATURE:
<223> OTHER INFORMATION: synthetic DNA

<400> SEQUENCE: 1552
tcaactctgt gctaaccggt cgtaca                                              26

<210> SEQ ID NO 1553
<211> LENGTH: 26
<212> TYPE: DNA
<213> ORGANISM: Artificial
<220> FEATURE:
<223> OTHER INFORMATION: synthetic DNA

<400> SEQUENCE: 1553
tgttcttatg cattaatgcc aggctt                                              26

<210> SEQ ID NO 1554
<211> LENGTH: 26
<212> TYPE: DNA
<213> ORGANISM: Artificial
<220> FEATURE:
<223> OTHER INFORMATION: synthetic DNA

<400> SEQUENCE: 1554
gattcacgac ctcaacagca tcactc                                              26

<210> SEQ ID NO 1555
<211> LENGTH: 26
```

```
<212> TYPE: DNA
<213> ORGANISM: Artificial
<220> FEATURE:
<223> OTHER INFORMATION: synthetic DNA

<400> SEQUENCE: 1555
ggcgagttcg accagaatgc tggaca                                          26

<210> SEQ ID NO 1556
<211> LENGTH: 26
<212> TYPE: DNA
<213> ORGANISM: Artificial
<220> FEATURE:
<223> OTHER INFORMATION: synthetic DNA

<400> SEQUENCE: 1556
ttccgtatac aatgcgatta agatct                                          26

<210> SEQ ID NO 1557
<211> LENGTH: 26
<212> TYPE: DNA
<213> ORGANISM: Artificial
<220> FEATURE:
<223> OTHER INFORMATION: synthetic DNA

<400> SEQUENCE: 1557
gagtaatccg taaccggcca acgttg                                          26

<210> SEQ ID NO 1558
<211> LENGTH: 26
<212> TYPE: DNA
<213> ORGANISM: Artificial
<220> FEATURE:
<223> OTHER INFORMATION: synthetic DNA

<400> SEQUENCE: 1558
cgcttccatc atggtacggt acgtat                                          26

<210> SEQ ID NO 1559
<211> LENGTH: 26
<212> TYPE: DNA
<213> ORGANISM: Artificial
<220> FEATURE:
<223> OTHER INFORMATION: synthetic DNA

<400> SEQUENCE: 1559
ccgtcgtggt gtgttgactg gtcaac                                          26

<210> SEQ ID NO 1560
<211> LENGTH: 26
<212> TYPE: DNA
<213> ORGANISM: Artificial
<220> FEATURE:
<223> OTHER INFORMATION: synthetic DNA

<400> SEQUENCE: 1560
tattcgcatc tccgtattag ttgtag                                          26

<210> SEQ ID NO 1561
<211> LENGTH: 26
<212> TYPE: DNA
<213> ORGANISM: Artificial
<220> FEATURE:
<223> OTHER INFORMATION: synthetic DNA

<400> SEQUENCE: 1561
```
tattattgta ttctaggcgg tgcaac					26

<210> SEQ ID NO 1562
<211> LENGTH: 26
<212> TYPE: DNA
<213> ORGANISM: Artificial
<220> FEATURE:
<223> OTHER INFORMATION: synthetic DNA

<400> SEQUENCE: 1562
aggctgccta cttcctcgtc atctcg					26

<210> SEQ ID NO 1563
<211> LENGTH: 26
<212> TYPE: DNA
<213> ORGANISM: Artificial
<220> FEATURE:
<223> OTHER INFORMATION: synthetic DNA

<400> SEQUENCE: 1563
gtaacatacg gctcatcgaa tgcatc					26

<210> SEQ ID NO 1564
<211> LENGTH: 26
<212> TYPE: DNA
<213> ORGANISM: Artificial
<220> FEATURE:
<223> OTHER INFORMATION: synthetic DNA

<400> SEQUENCE: 1564
ttatggcacg gatattaccg tacgcc					26

<210> SEQ ID NO 1565
<211> LENGTH: 26
<212> TYPE: DNA
<213> ORGANISM: Artificial
<220> FEATURE:
<223> OTHER INFORMATION: synthetic DNA

<400> SEQUENCE: 1565
atagcacttc ctctaatgct ctgctg					26

<210> SEQ ID NO 1566
<211> LENGTH: 26
<212> TYPE: DNA
<213> ORGANISM: Artificial
<220> FEATURE:
<223> OTHER INFORMATION: synthetic DNA

<400> SEQUENCE: 1566
tcacaggcaa tagcctaata ttatat					26

<210> SEQ ID NO 1567
<211> LENGTH: 26
<212> TYPE: DNA
<213> ORGANISM: Artificial
<220> FEATURE:
<223> OTHER INFORMATION: synthetic DNA

<400> SEQUENCE: 1567
ggcggatgtt cgttaatatt ataagg					26

<210> SEQ ID NO 1568
<211> LENGTH: 26
<212> TYPE: DNA
<213> ORGANISM: Artificial

```
<220> FEATURE:
<223> OTHER INFORMATION: synthetic DNA

<400> SEQUENCE: 1568
tgcaatagcc gttgtctctg ccagcg                                         26

<210> SEQ ID NO 1569
<211> LENGTH: 26
<212> TYPE: DNA
<213> ORGANISM: Artificial
<220> FEATURE:
<223> OTHER INFORMATION: synthetic DNA

<400> SEQUENCE: 1569
tacagcgcgt tggcgagtac tgatag                                         26

<210> SEQ ID NO 1570
<211> LENGTH: 26
<212> TYPE: DNA
<213> ORGANISM: Artificial
<220> FEATURE:
<223> OTHER INFORMATION: synthetic DNA

<400> SEQUENCE: 1570
tgcagttagt accttctcac gccaac                                         26

<210> SEQ ID NO 1571
<211> LENGTH: 26
<212> TYPE: DNA
<213> ORGANISM: Artificial
<220> FEATURE:
<223> OTHER INFORMATION: synthetic DNA

<400> SEQUENCE: 1571
ccattggcta cctagcagac tctacc                                         26

<210> SEQ ID NO 1572
<211> LENGTH: 26
<212> TYPE: DNA
<213> ORGANISM: Artificial
<220> FEATURE:
<223> OTHER INFORMATION: synthetic DNA

<400> SEQUENCE: 1572
aacagtagct cgcgtcttgc tctcgt                                         26

<210> SEQ ID NO 1573
<211> LENGTH: 26
<212> TYPE: DNA
<213> ORGANISM: Artificial
<220> FEATURE:
<223> OTHER INFORMATION: synthetic DNA

<400> SEQUENCE: 1573
gcagtccatc agctctcgct tataga                                         26

<210> SEQ ID NO 1574
<211> LENGTH: 26
<212> TYPE: DNA
<213> ORGANISM: Artificial
<220> FEATURE:
<223> OTHER INFORMATION: synthetic DNA

<400> SEQUENCE: 1574
tatctctctg tcgccagctt gaccaa                                         26
```

<210> SEQ ID NO 1575
<211> LENGTH: 26
<212> TYPE: DNA
<213> ORGANISM: Artificial
<220> FEATURE:
<223> OTHER INFORMATION: synthetic DNA

<400> SEQUENCE: 1575
cagactgttc aagcttgctg taggag                                          26

<210> SEQ ID NO 1576
<211> LENGTH: 26
<212> TYPE: DNA
<213> ORGANISM: Artificial
<220> FEATURE:
<223> OTHER INFORMATION: synthetic DNA

<400> SEQUENCE: 1576
taaccggaac tcgttcagca acattc                                          26

<210> SEQ ID NO 1577
<211> LENGTH: 26
<212> TYPE: DNA
<213> ORGANISM: Artificial
<220> FEATURE:
<223> OTHER INFORMATION: synthetic DNA

<400> SEQUENCE: 1577
tcaattatgc atgtcgtccg atctct                                          26

<210> SEQ ID NO 1578
<211> LENGTH: 26
<212> TYPE: DNA
<213> ORGANISM: Artificial
<220> FEATURE:
<223> OTHER INFORMATION: synthetic DNA

<400> SEQUENCE: 1578
ttgtctaagt caacctgtgg ataatc                                          26

<210> SEQ ID NO 1579
<211> LENGTH: 26
<212> TYPE: DNA
<213> ORGANISM: Artificial
<220> FEATURE:
<223> OTHER INFORMATION: synthetic DNA

<400> SEQUENCE: 1579
tctaagagtg gtatgaccag gagtcc                                          26

<210> SEQ ID NO 1580
<211> LENGTH: 26
<212> TYPE: DNA
<213> ORGANISM: Artificial
<220> FEATURE:
<223> OTHER INFORMATION: synthetic DNA

<400> SEQUENCE: 1580
tcgtagtact actggaacag gtaatc                                          26

<210> SEQ ID NO 1581
<211> LENGTH: 26
<212> TYPE: DNA
<213> ORGANISM: Artificial
<220> FEATURE:
<223> OTHER INFORMATION: synthetic DNA

<400> SEQUENCE: 1581
atgtcaacat tctaatcatc tctcgg	26

<210> SEQ ID NO 1582
<211> LENGTH: 26
<212> TYPE: DNA
<213> ORGANISM: Artificial
<220> FEATURE:
<223> OTHER INFORMATION: synthetic DNA

<400> SEQUENCE: 1582
agcgcgcaac tgttacggtg atccga	26

<210> SEQ ID NO 1583
<211> LENGTH: 26
<212> TYPE: DNA
<213> ORGANISM: Artificial
<220> FEATURE:
<223> OTHER INFORMATION: synthetic DNA

<400> SEQUENCE: 1583
gcgatagaat aatggtgtca cacacg	26

<210> SEQ ID NO 1584
<211> LENGTH: 26
<212> TYPE: DNA
<213> ORGANISM: Artificial
<220> FEATURE:
<223> OTHER INFORMATION: synthetic DNA

<400> SEQUENCE: 1584
aaggctgcga tgagaggcgt acatcg	26

<210> SEQ ID NO 1585
<211> LENGTH: 26
<212> TYPE: DNA
<213> ORGANISM: Artificial
<220> FEATURE:
<223> OTHER INFORMATION: synthetic DNA

<400> SEQUENCE: 1585
ggttcatggt ctcagtcgtg atcgcg	26

<210> SEQ ID NO 1586
<211> LENGTH: 26
<212> TYPE: DNA
<213> ORGANISM: Artificial
<220> FEATURE:
<223> OTHER INFORMATION: synthetic DNA

<400> SEQUENCE: 1586
tagtgactct atgtcacctc ggagcc	26

<210> SEQ ID NO 1587
<211> LENGTH: 26
<212> TYPE: DNA
<213> ORGANISM: Artificial
<220> FEATURE:
<223> OTHER INFORMATION: synthetic DNA

<400> SEQUENCE: 1587
atgtgatagc aatggcacct ctagtc	26

<210> SEQ ID NO 1588

```
<211> LENGTH: 26
<212> TYPE: DNA
<213> ORGANISM: Artificial
<220> FEATURE:
<223> OTHER INFORMATION: synthetic DNA

<400> SEQUENCE: 1588
tcgcgaagtg taatgcatca tccgct                                          26

<210> SEQ ID NO 1589
<211> LENGTH: 26
<212> TYPE: DNA
<213> ORGANISM: Artificial
<220> FEATURE:
<223> OTHER INFORMATION: synthetic DNA

<400> SEQUENCE: 1589
atgtggcgac gatccaagtt caacgc                                          26

<210> SEQ ID NO 1590
<211> LENGTH: 26
<212> TYPE: DNA
<213> ORGANISM: Artificial
<220> FEATURE:
<223> OTHER INFORMATION: synthetic DNA

<400> SEQUENCE: 1590
accttgtatg agtcggagtg tccggc                                          26

<210> SEQ ID NO 1591
<211> LENGTH: 26
<212> TYPE: DNA
<213> ORGANISM: Artificial
<220> FEATURE:
<223> OTHER INFORMATION: synthetic DNA

<400> SEQUENCE: 1591
acctcaagag agtagacagt tgagtt                                          26

<210> SEQ ID NO 1592
<211> LENGTH: 26
<212> TYPE: DNA
<213> ORGANISM: Artificial
<220> FEATURE:
<223> OTHER INFORMATION: synthetic DNA

<400> SEQUENCE: 1592
ggtgtaatcc tgtgtgcgaa gctggt                                          26

<210> SEQ ID NO 1593
<211> LENGTH: 26
<212> TYPE: DNA
<213> ORGANISM: Artificial
<220> FEATURE:
<223> OTHER INFORMATION: synthetic DNA

<400> SEQUENCE: 1593
atagcggaac tgtacgacgc tccagt                                          26

<210> SEQ ID NO 1594
<211> LENGTH: 26
<212> TYPE: DNA
<213> ORGANISM: Artificial
<220> FEATURE:
<223> OTHER INFORMATION: synthetic DNA

<400> SEQUENCE: 1594
```
aagcacgagt cgaccattag cctgga                                              26

<210> SEQ ID NO 1595
<211> LENGTH: 26
<212> TYPE: DNA
<213> ORGANISM: Artificial
<220> FEATURE:
<223> OTHER INFORMATION: synthetic DNA

<400> SEQUENCE: 1595
attccggtaa catcagaagg tacaat                                              26

<210> SEQ ID NO 1596
<211> LENGTH: 26
<212> TYPE: DNA
<213> ORGANISM: Artificial
<220> FEATURE:
<223> OTHER INFORMATION: synthetic DNA

<400> SEQUENCE: 1596
gtgcaacggc agtccagtat cctggt                                              26

<210> SEQ ID NO 1597
<211> LENGTH: 26
<212> TYPE: DNA
<213> ORGANISM: Artificial
<220> FEATURE:
<223> OTHER INFORMATION: synthetic DNA

<400> SEQUENCE: 1597
ccatcttata cacggtgacc gaagat                                              26

<210> SEQ ID NO 1598
<211> LENGTH: 26
<212> TYPE: DNA
<213> ORGANISM: Artificial
<220> FEATURE:
<223> OTHER INFORMATION: synthetic DNA

<400> SEQUENCE: 1598
gcacttaatc aagcttgagt gatgct                                              26

<210> SEQ ID NO 1599
<211> LENGTH: 26
<212> TYPE: DNA
<213> ORGANISM: Artificial
<220> FEATURE:
<223> OTHER INFORMATION: synthetic DNA

<400> SEQUENCE: 1599
agtattacgt gagtacgaag atagca                                              26

<210> SEQ ID NO 1600
<211> LENGTH: 26
<212> TYPE: DNA
<213> ORGANISM: Artificial
<220> FEATURE:
<223> OTHER INFORMATION: synthetic DNA

<400> SEQUENCE: 1600
ttcttaggtt aagttccttc tggacc                                              26

<210> SEQ ID NO 1601
<211> LENGTH: 26
<212> TYPE: DNA

```
<213> ORGANISM: Artificial
<220> FEATURE:
<223> OTHER INFORMATION: synthetic DNA

<400> SEQUENCE: 1601
gtccttgcta gacactgacc gttgct                                              26

<210> SEQ ID NO 1602
<211> LENGTH: 26
<212> TYPE: DNA
<213> ORGANISM: Artificial
<220> FEATURE:
<223> OTHER INFORMATION: synthetic DNA

<400> SEQUENCE: 1602
gccgctatgt gtgctgcatc ctaagc                                              26

<210> SEQ ID NO 1603
<211> LENGTH: 26
<212> TYPE: DNA
<213> ORGANISM: Artificial
<220> FEATURE:
<223> OTHER INFORMATION: synthetic DNA

<400> SEQUENCE: 1603
ccatcaataa cagacttatg ttgtga                                              26

<210> SEQ ID NO 1604
<211> LENGTH: 26
<212> TYPE: DNA
<213> ORGANISM: Artificial
<220> FEATURE:
<223> OTHER INFORMATION: synthetic DNA

<400> SEQUENCE: 1604
cgcgtgtgct tacaagtgct aacaag                                              26

<210> SEQ ID NO 1605
<211> LENGTH: 26
<212> TYPE: DNA
<213> ORGANISM: Artificial
<220> FEATURE:
<223> OTHER INFORMATION: synthetic DNA

<400> SEQUENCE: 1605
cgatatgtgt tcgcaataag agagcc                                              26

<210> SEQ ID NO 1606
<211> LENGTH: 26
<212> TYPE: DNA
<213> ORGANISM: Artificial
<220> FEATURE:
<223> OTHER INFORMATION: synthetic DNA

<400> SEQUENCE: 1606
cgcggatgtg agcggctcaa ttagca                                              26

<210> SEQ ID NO 1607
<211> LENGTH: 26
<212> TYPE: DNA
<213> ORGANISM: Artificial
<220> FEATURE:
<223> OTHER INFORMATION: synthetic DNA

<400> SEQUENCE: 1607
gctgcatgac tatcggatgg aggcat                                              26
```

```
<210> SEQ ID NO 1608
<211> LENGTH: 26
<212> TYPE: DNA
<213> ORGANISM: Artificial
<220> FEATURE:
<223> OTHER INFORMATION: synthetic DNA

<400> SEQUENCE: 1608
ctatgccgtg tatggtacga gtggcg                                              26

<210> SEQ ID NO 1609
<211> LENGTH: 26
<212> TYPE: DNA
<213> ORGANISM: Artificial
<220> FEATURE:
<223> OTHER INFORMATION: synthetic DNA

<400> SEQUENCE: 1609
ccggctggag ttcattacgt aggctg                                              26

<210> SEQ ID NO 1610
<211> LENGTH: 26
<212> TYPE: DNA
<213> ORGANISM: Artificial
<220> FEATURE:
<223> OTHER INFORMATION: synthetic DNA

<400> SEQUENCE: 1610
tgtaggccta ctgagctagt attaga                                              26

<210> SEQ ID NO 1611
<211> LENGTH: 26
<212> TYPE: DNA
<213> ORGANISM: Artificial
<220> FEATURE:
<223> OTHER INFORMATION: synthetic DNA

<400> SEQUENCE: 1611
ccgtcaagtg actattcttc taatct                                              26

<210> SEQ ID NO 1612
<211> LENGTH: 26
<212> TYPE: DNA
<213> ORGANISM: Artificial
<220> FEATURE:
<223> OTHER INFORMATION: synthetic DNA

<400> SEQUENCE: 1612
ggtcttacgc cagagactgc gcttct                                              26

<210> SEQ ID NO 1613
<211> LENGTH: 26
<212> TYPE: DNA
<213> ORGANISM: Artificial
<220> FEATURE:
<223> OTHER INFORMATION: synthetic DNA

<400> SEQUENCE: 1613
cgaagtgtga ttattaactg taatct                                              26

<210> SEQ ID NO 1614
<211> LENGTH: 26
<212> TYPE: DNA
<213> ORGANISM: Artificial
<220> FEATURE:
```

<223> OTHER INFORMATION: synthetic DNA

<400> SEQUENCE: 1614
gcacgcgtgg ccgtaagcat cgatta                                      26

<210> SEQ ID NO 1615
<211> LENGTH: 26
<212> TYPE: DNA
<213> ORGANISM: Artificial
<220> FEATURE:
<223> OTHER INFORMATION: synthetic DNA

<400> SEQUENCE: 1615
atcctgcgtc ggaacgtact atagct                                      26

<210> SEQ ID NO 1616
<211> LENGTH: 26
<212> TYPE: DNA
<213> ORGANISM: Artificial
<220> FEATURE:
<223> OTHER INFORMATION: synthetic DNA

<400> SEQUENCE: 1616
agtatcatca tatccattcg cagtac                                      26

<210> SEQ ID NO 1617
<211> LENGTH: 26
<212> TYPE: DNA
<213> ORGANISM: Artificial
<220> FEATURE:
<223> OTHER INFORMATION: synthetic DNA

<400> SEQUENCE: 1617
agtcctgacg ttcatatata gactcc                                      26

<210> SEQ ID NO 1618
<211> LENGTH: 26
<212> TYPE: DNA
<213> ORGANISM: Artificial
<220> FEATURE:
<223> OTHER INFORMATION: synthetic DNA

<400> SEQUENCE: 1618
cttgcagtaa tctgaatctg aaggtt                                      26

<210> SEQ ID NO 1619
<211> LENGTH: 26
<212> TYPE: DNA
<213> ORGANISM: Artificial
<220> FEATURE:
<223> OTHER INFORMATION: synthetic DNA

<400> SEQUENCE: 1619
ataacttggt tccagtaacg catagt                                      26

<210> SEQ ID NO 1620
<211> LENGTH: 26
<212> TYPE: DNA
<213> ORGANISM: Artificial
<220> FEATURE:
<223> OTHER INFORMATION: synthetic DNA

<400> SEQUENCE: 1620
gataaggata tggctgtagc gaagtg                                      26

```
<210> SEQ ID NO 1621
<211> LENGTH: 26
<212> TYPE: DNA
<213> ORGANISM: Artificial
<220> FEATURE:
<223> OTHER INFORMATION: synthetic DNA

<400> SEQUENCE: 1621
gtggagcgtt acagacatgc tgaaca                                              26

<210> SEQ ID NO 1622
<211> LENGTH: 26
<212> TYPE: DNA
<213> ORGANISM: Artificial
<220> FEATURE:
<223> OTHER INFORMATION: synthetic DNA

<400> SEQUENCE: 1622
cgcttccggc aggcgtcata taagtc                                              26

<210> SEQ ID NO 1623
<211> LENGTH: 26
<212> TYPE: DNA
<213> ORGANISM: Artificial
<220> FEATURE:
<223> OTHER INFORMATION: synthetic DNA

<400> SEQUENCE: 1623
ataacattct aacctctata agccga                                              26

<210> SEQ ID NO 1624
<211> LENGTH: 26
<212> TYPE: DNA
<213> ORGANISM: Artificial
<220> FEATURE:
<223> OTHER INFORMATION: synthetic DNA

<400> SEQUENCE: 1624
acgatctatg atccatatgg acttcc                                              26

<210> SEQ ID NO 1625
<211> LENGTH: 26
<212> TYPE: DNA
<213> ORGANISM: Artificial
<220> FEATURE:
<223> OTHER INFORMATION: synthetic DNA

<400> SEQUENCE: 1625
tgaagctcag atatcatgcc tcgagc                                              26

<210> SEQ ID NO 1626
<211> LENGTH: 26
<212> TYPE: DNA
<213> ORGANISM: Artificial
<220> FEATURE:
<223> OTHER INFORMATION: synthetic DNA

<400> SEQUENCE: 1626
agacttcacc gcaataactc gtagat                                              26

<210> SEQ ID NO 1627
<211> LENGTH: 26
<212> TYPE: DNA
<213> ORGANISM: Artificial
<220> FEATURE:
<223> OTHER INFORMATION: synthetic DNA
```

<400> SEQUENCE: 1627
agactaagac atacgccatc accgct        26

<210> SEQ ID NO 1628
<211> LENGTH: 26
<212> TYPE: DNA
<213> ORGANISM: Artificial
<220> FEATURE:
<223> OTHER INFORMATION: synthetic DNA

<400> SEQUENCE: 1628
tgtagcgtga tgtatcgtaa ttctgt        26

<210> SEQ ID NO 1629
<211> LENGTH: 26
<212> TYPE: DNA
<213> ORGANISM: Artificial
<220> FEATURE:
<223> OTHER INFORMATION: synthetic DNA

<400> SEQUENCE: 1629
tgtgctattg gcacctcacg ctgacc        26

<210> SEQ ID NO 1630
<211> LENGTH: 26
<212> TYPE: DNA
<213> ORGANISM: Artificial
<220> FEATURE:
<223> OTHER INFORMATION: synthetic DNA

<400> SEQUENCE: 1630
tgtagataag tatccagcga ctctct        26

<210> SEQ ID NO 1631
<211> LENGTH: 26
<212> TYPE: DNA
<213> ORGANISM: Artificial
<220> FEATURE:
<223> OTHER INFORMATION: synthetic DNA

<400> SEQUENCE: 1631
aattcgccaa ttgtgtgtag gcgcaa        26

<210> SEQ ID NO 1632
<211> LENGTH: 26
<212> TYPE: DNA
<213> ORGANISM: Artificial
<220> FEATURE:
<223> OTHER INFORMATION: synthetic DNA

<400> SEQUENCE: 1632
cgattatgag tacttgtaga ccagct        26

<210> SEQ ID NO 1633
<211> LENGTH: 28
<212> TYPE: DNA
<213> ORGANISM: Artificial
<220> FEATURE:
<223> OTHER INFORMATION: synthetic DNA

<400> SEQUENCE: 1633
ttgcaagaac aacgtatctc atatgaac        28

<210> SEQ ID NO 1634
<211> LENGTH: 28

```
<212> TYPE: DNA
<213> ORGANISM: Artificial
<220> FEATURE:
<223> OTHER INFORMATION: synthetic DNA

<400> SEQUENCE: 1634
caccgtgctg ttattacttg gtattcgg                                          28

<210> SEQ ID NO 1635
<211> LENGTH: 28
<212> TYPE: DNA
<213> ORGANISM: Artificial
<220> FEATURE:
<223> OTHER INFORMATION: synthetic DNA

<400> SEQUENCE: 1635
cacgtgtatt gttgcaccag aacgacaa                                          28

<210> SEQ ID NO 1636
<211> LENGTH: 28
<212> TYPE: DNA
<213> ORGANISM: Artificial
<220> FEATURE:
<223> OTHER INFORMATION: synthetic DNA

<400> SEQUENCE: 1636
atgcacgtaa ttacttccgg agaagacg                                          28

<210> SEQ ID NO 1637
<211> LENGTH: 28
<212> TYPE: DNA
<213> ORGANISM: Artificial
<220> FEATURE:
<223> OTHER INFORMATION: synthetic DNA

<400> SEQUENCE: 1637
tatgttgtct gatatggttc atgtggca                                          28

<210> SEQ ID NO 1638
<211> LENGTH: 28
<212> TYPE: DNA
<213> ORGANISM: Artificial
<220> FEATURE:
<223> OTHER INFORMATION: synthetic DNA

<400> SEQUENCE: 1638
agcgcgacta gttgatgcca acattgta                                          28

<210> SEQ ID NO 1639
<211> LENGTH: 28
<212> TYPE: DNA
<213> ORGANISM: Artificial
<220> FEATURE:
<223> OTHER INFORMATION: synthetic DNA

<400> SEQUENCE: 1639
ataggcaggt ccaggctcgg aacaagtc                                          28

<210> SEQ ID NO 1640
<211> LENGTH: 28
<212> TYPE: DNA
<213> ORGANISM: Artificial
<220> FEATURE:
<223> OTHER INFORMATION: synthetic DNA

<400> SEQUENCE: 1640
```
gcggtagtcg gtcaagaact agaaccgt                                28

<210> SEQ ID NO 1641
<211> LENGTH: 28
<212> TYPE: DNA
<213> ORGANISM: Artificial
<220> FEATURE:
<223> OTHER INFORMATION: synthetic DNA

<400> SEQUENCE: 1641
actatacact ctagctatta ggaagcat                                28

<210> SEQ ID NO 1642
<211> LENGTH: 28
<212> TYPE: DNA
<213> ORGANISM: Artificial
<220> FEATURE:
<223> OTHER INFORMATION: synthetic DNA

<400> SEQUENCE: 1642
gatcatcttg cttctcctgt ggagataa                                28

<210> SEQ ID NO 1643
<211> LENGTH: 28
<212> TYPE: DNA
<213> ORGANISM: Artificial
<220> FEATURE:
<223> OTHER INFORMATION: synthetic DNA

<400> SEQUENCE: 1643
ctactacgag tccataactg atagcctc                                28

<210> SEQ ID NO 1644
<211> LENGTH: 28
<212> TYPE: DNA
<213> ORGANISM: Artificial
<220> FEATURE:
<223> OTHER INFORMATION: synthetic DNA

<400> SEQUENCE: 1644
gcacagacac ctgtcctatc tagcagga                                28

<210> SEQ ID NO 1645
<211> LENGTH: 28
<212> TYPE: DNA
<213> ORGANISM: Artificial
<220> FEATURE:
<223> OTHER INFORMATION: synthetic DNA

<400> SEQUENCE: 1645
aagcgaggcg cgaaggagat ggaaggat                                28

<210> SEQ ID NO 1646
<211> LENGTH: 28
<212> TYPE: DNA
<213> ORGANISM: Artificial
<220> FEATURE:
<223> OTHER INFORMATION: synthetic DNA

<400> SEQUENCE: 1646
ctgaagacgc cagtctggat aggtgcct                                28

<210> SEQ ID NO 1647
<211> LENGTH: 28
<212> TYPE: DNA
<213> ORGANISM: Artificial

```
<220> FEATURE:
<223> OTHER INFORMATION: synthetic DNA

<400> SEQUENCE: 1647
gtaagctctg tccttcgaga ttgataag                                    28

<210> SEQ ID NO 1648
<211> LENGTH: 28
<212> TYPE: DNA
<213> ORGANISM: Artificial
<220> FEATURE:
<223> OTHER INFORMATION: synthetic DNA

<400> SEQUENCE: 1648
ggttagagag attattgtgc gcatccat                                    28

<210> SEQ ID NO 1649
<211> LENGTH: 28
<212> TYPE: DNA
<213> ORGANISM: Artificial
<220> FEATURE:
<223> OTHER INFORMATION: synthetic DNA

<400> SEQUENCE: 1649
ccaggaggac ctatgatctt gccgccat                                    28

<210> SEQ ID NO 1650
<211> LENGTH: 28
<212> TYPE: DNA
<213> ORGANISM: Artificial
<220> FEATURE:
<223> OTHER INFORMATION: synthetic DNA

<400> SEQUENCE: 1650
actattcgag ctactgtatg tgtatccg                                    28

<210> SEQ ID NO 1651
<211> LENGTH: 28
<212> TYPE: DNA
<213> ORGANISM: Artificial
<220> FEATURE:
<223> OTHER INFORMATION: synthetic DNA

<400> SEQUENCE: 1651
gacatcgcga tacgtaactc cggagtgt                                    28

<210> SEQ ID NO 1652
<211> LENGTH: 28
<212> TYPE: DNA
<213> ORGANISM: Artificial
<220> FEATURE:
<223> OTHER INFORMATION: synthetic DNA

<400> SEQUENCE: 1652
ccgcaattcg tctatatatt ctagcata                                    28

<210> SEQ ID NO 1653
<211> LENGTH: 28
<212> TYPE: DNA
<213> ORGANISM: Artificial
<220> FEATURE:
<223> OTHER INFORMATION: synthetic DNA

<400> SEQUENCE: 1653
ctacacttga ggttgatgct caagatca                                    28
```

<210> SEQ ID NO 1654
<211> LENGTH: 28
<212> TYPE: DNA
<213> ORGANISM: Artificial
<220> FEATURE:
<223> OTHER INFORMATION: synthetic DNA

<400> SEQUENCE: 1654
cgatcagttc tagttcaccg cggacaat                                28

<210> SEQ ID NO 1655
<211> LENGTH: 28
<212> TYPE: DNA
<213> ORGANISM: Artificial
<220> FEATURE:
<223> OTHER INFORMATION: synthetic DNA

<400> SEQUENCE: 1655
aagaatgatg attggccgcg aaccaagc                                28

<210> SEQ ID NO 1656
<211> LENGTH: 28
<212> TYPE: DNA
<213> ORGANISM: Artificial
<220> FEATURE:
<223> OTHER INFORMATION: synthetic DNA

<400> SEQUENCE: 1656
cacgaccgga actagactcc taccaatt                                28

<210> SEQ ID NO 1657
<211> LENGTH: 28
<212> TYPE: DNA
<213> ORGANISM: Artificial
<220> FEATURE:
<223> OTHER INFORMATION: synthetic DNA

<400> SEQUENCE: 1657
agttgcctgt gagtgaggct actatctc                                28

<210> SEQ ID NO 1658
<211> LENGTH: 28
<212> TYPE: DNA
<213> ORGANISM: Artificial
<220> FEATURE:
<223> OTHER INFORMATION: synthetic DNA

<400> SEQUENCE: 1658
gattcttccg atgatcatgc cactacaa                                28

<210> SEQ ID NO 1659
<211> LENGTH: 28
<212> TYPE: DNA
<213> ORGANISM: Artificial
<220> FEATURE:
<223> OTHER INFORMATION: synthetic DNA

<400> SEQUENCE: 1659
cgctgaagtg aactatgcaa gcaccgca                                28

<210> SEQ ID NO 1660
<211> LENGTH: 28
<212> TYPE: DNA
<213> ORGANISM: Artificial
<220> FEATURE:
<223> OTHER INFORMATION: synthetic DNA

<400> SEQUENCE: 1660
attatcgtga tggtgagact gagctcgt                                          28

<210> SEQ ID NO 1661
<211> LENGTH: 28
<212> TYPE: DNA
<213> ORGANISM: Artificial
<220> FEATURE:
<223> OTHER INFORMATION: synthetic DNA

<400> SEQUENCE: 1661
cgaggccact ctgagccagg taagtatc                                          28

<210> SEQ ID NO 1662
<211> LENGTH: 28
<212> TYPE: DNA
<213> ORGANISM: Artificial
<220> FEATURE:
<223> OTHER INFORMATION: synthetic DNA

<400> SEQUENCE: 1662
tgccgaggac agccgatcac atcttcgt                                          28

<210> SEQ ID NO 1663
<211> LENGTH: 28
<212> TYPE: DNA
<213> ORGANISM: Artificial
<220> FEATURE:
<223> OTHER INFORMATION: synthetic DNA

<400> SEQUENCE: 1663
gttgacatga aggttatcgt cgatattc                                          28

<210> SEQ ID NO 1664
<211> LENGTH: 28
<212> TYPE: DNA
<213> ORGANISM: Artificial
<220> FEATURE:
<223> OTHER INFORMATION: synthetic DNA

<400> SEQUENCE: 1664
gtggtccagg tcaagctctg atcgaatg                                          28

<210> SEQ ID NO 1665
<211> LENGTH: 28
<212> TYPE: DNA
<213> ORGANISM: Artificial
<220> FEATURE:
<223> OTHER INFORMATION: synthetic DNA

<400> SEQUENCE: 1665
ccagtccggt gtactcagac ctaataac                                          28

<210> SEQ ID NO 1666
<211> LENGTH: 28
<212> TYPE: DNA
<213> ORGANISM: Artificial
<220> FEATURE:
<223> OTHER INFORMATION: synthetic DNA

<400> SEQUENCE: 1666
cgagacactg catgagcgta gtcttatt                                          28

<210> SEQ ID NO 1667

```
<211> LENGTH: 28
<212> TYPE: DNA
<213> ORGANISM: Artificial
<220> FEATURE:
<223> OTHER INFORMATION: synthetic DNA

<400> SEQUENCE: 1667
gacggcttgt atacttctct acggtctg                                          28

<210> SEQ ID NO 1668
<211> LENGTH: 28
<212> TYPE: DNA
<213> ORGANISM: Artificial
<220> FEATURE:
<223> OTHER INFORMATION: synthetic DNA

<400> SEQUENCE: 1668
ttagctggat ggaagccata ttccgtag                                          28

<210> SEQ ID NO 1669
<211> LENGTH: 28
<212> TYPE: DNA
<213> ORGANISM: Artificial
<220> FEATURE:
<223> OTHER INFORMATION: synthetic DNA

<400> SEQUENCE: 1669
cagcctacac ttgattactc aacaactc                                          28

<210> SEQ ID NO 1670
<211> LENGTH: 28
<212> TYPE: DNA
<213> ORGANISM: Artificial
<220> FEATURE:
<223> OTHER INFORMATION: synthetic DNA

<400> SEQUENCE: 1670
gtacgtagtg tcacgcgcct acgttcgt                                          28

<210> SEQ ID NO 1671
<211> LENGTH: 28
<212> TYPE: DNA
<213> ORGANISM: Artificial
<220> FEATURE:
<223> OTHER INFORMATION: synthetic DNA

<400> SEQUENCE: 1671
ctacaacttc tcaatcatgc ctctgttg                                          28

<210> SEQ ID NO 1672
<211> LENGTH: 28
<212> TYPE: DNA
<213> ORGANISM: Artificial
<220> FEATURE:
<223> OTHER INFORMATION: synthetic DNA

<400> SEQUENCE: 1672
cgaggacaga attcgacata aggagaga                                          28

<210> SEQ ID NO 1673
<211> LENGTH: 28
<212> TYPE: DNA
<213> ORGANISM: Artificial
<220> FEATURE:
<223> OTHER INFORMATION: synthetic DNA

<400> SEQUENCE: 1673
```
gccgaacgac acagtgagtt gataggta                                           28

<210> SEQ ID NO 1674
<211> LENGTH: 28
<212> TYPE: DNA
<213> ORGANISM: Artificial
<220> FEATURE:
<223> OTHER INFORMATION: synthetic DNA

<400> SEQUENCE: 1674
gaacactata tgctgtcgct gtctgagg                                           28

<210> SEQ ID NO 1675
<211> LENGTH: 28
<212> TYPE: DNA
<213> ORGANISM: Artificial
<220> FEATURE:
<223> OTHER INFORMATION: synthetic DNA

<400> SEQUENCE: 1675
gttaagttct tcggcggtca tgctcatt                                           28

<210> SEQ ID NO 1676
<211> LENGTH: 28
<212> TYPE: DNA
<213> ORGANISM: Artificial
<220> FEATURE:
<223> OTHER INFORMATION: synthetic DNA

<400> SEQUENCE: 1676
ttgcttacag atcgcgtatc catagtat                                           28

<210> SEQ ID NO 1677
<211> LENGTH: 28
<212> TYPE: DNA
<213> ORGANISM: Artificial
<220> FEATURE:
<223> OTHER INFORMATION: synthetic DNA

<400> SEQUENCE: 1677
gaggaccacc tctgcgaagt tcactgtg                                           28

<210> SEQ ID NO 1678
<211> LENGTH: 28
<212> TYPE: DNA
<213> ORGANISM: Artificial
<220> FEATURE:
<223> OTHER INFORMATION: synthetic DNA

<400> SEQUENCE: 1678
aatcctagca tatcgagaac gacactga                                           28

<210> SEQ ID NO 1679
<211> LENGTH: 28
<212> TYPE: DNA
<213> ORGANISM: Artificial
<220> FEATURE:
<223> OTHER INFORMATION: synthetic DNA

<400> SEQUENCE: 1679
tgaatactat agccatagtc gacttccg                                           28

<210> SEQ ID NO 1680
<211> LENGTH: 28
<212> TYPE: DNA

```
<213> ORGANISM: Artificial
<220> FEATURE:
<223> OTHER INFORMATION: synthetic DNA

<400> SEQUENCE: 1680
gacatccacg aagctggtaa tcggaacc                                        28

<210> SEQ ID NO 1681
<211> LENGTH: 28
<212> TYPE: DNA
<213> ORGANISM: Artificial
<220> FEATURE:
<223> OTHER INFORMATION: synthetic DNA

<400> SEQUENCE: 1681
ttagccgtct tagaagtgtc tgaccggc                                        28

<210> SEQ ID NO 1682
<211> LENGTH: 28
<212> TYPE: DNA
<213> ORGANISM: Artificial
<220> FEATURE:
<223> OTHER INFORMATION: synthetic DNA

<400> SEQUENCE: 1682
ctattctgcc gtaattgatt ccttcgtt                                        28

<210> SEQ ID NO 1683
<211> LENGTH: 28
<212> TYPE: DNA
<213> ORGANISM: Artificial
<220> FEATURE:
<223> OTHER INFORMATION: synthetic DNA

<400> SEQUENCE: 1683
acgcctctgg tcgaaggtag attagctc                                        28

<210> SEQ ID NO 1684
<211> LENGTH: 28
<212> TYPE: DNA
<213> ORGANISM: Artificial
<220> FEATURE:
<223> OTHER INFORMATION: synthetic DNA

<400> SEQUENCE: 1684
cagcctattg atcgtaagta gatggtcc                                        28

<210> SEQ ID NO 1685
<211> LENGTH: 28
<212> TYPE: DNA
<213> ORGANISM: Artificial
<220> FEATURE:
<223> OTHER INFORMATION: synthetic DNA

<400> SEQUENCE: 1685
ttaagtgagg tggacaacca tcaacttc                                        28

<210> SEQ ID NO 1686
<211> LENGTH: 28
<212> TYPE: DNA
<213> ORGANISM: Artificial
<220> FEATURE:
<223> OTHER INFORMATION: synthetic DNA

<400> SEQUENCE: 1686
aaggccttgc ggctaagtag tattcatc                                        28
```

```
<210> SEQ ID NO 1687
<211> LENGTH: 28
<212> TYPE: DNA
<213> ORGANISM: Artificial
<220> FEATURE:
<223> OTHER INFORMATION: synthetic DNA

<400> SEQUENCE: 1687
ttgtgatact aattcttctc aagagtca                                    28

<210> SEQ ID NO 1688
<211> LENGTH: 28
<212> TYPE: DNA
<213> ORGANISM: Artificial
<220> FEATURE:
<223> OTHER INFORMATION: synthetic DNA

<400> SEQUENCE: 1688
gcattaggtg acgaccttag tccatcac                                    28

<210> SEQ ID NO 1689
<211> LENGTH: 28
<212> TYPE: DNA
<213> ORGANISM: Artificial
<220> FEATURE:
<223> OTHER INFORMATION: synthetic DNA

<400> SEQUENCE: 1689
gcggatggac gtatacagtg agtcgtgc                                    28

<210> SEQ ID NO 1690
<211> LENGTH: 28
<212> TYPE: DNA
<213> ORGANISM: Artificial
<220> FEATURE:
<223> OTHER INFORMATION: synthetic DNA

<400> SEQUENCE: 1690
gaacatgcca gcctcaacta ggctaaga                                    28

<210> SEQ ID NO 1691
<211> LENGTH: 28
<212> TYPE: DNA
<213> ORGANISM: Artificial
<220> FEATURE:
<223> OTHER INFORMATION: synthetic DNA

<400> SEQUENCE: 1691
tccgtcatta gagtatgagt gactacta                                    28

<210> SEQ ID NO 1692
<211> LENGTH: 28
<212> TYPE: DNA
<213> ORGANISM: Artificial
<220> FEATURE:
<223> OTHER INFORMATION: synthetic DNA

<400> SEQUENCE: 1692
aacacttagt aaccagttcg gactggac                                    28

<210> SEQ ID NO 1693
<211> LENGTH: 28
<212> TYPE: DNA
<213> ORGANISM: Artificial
<220> FEATURE:
```

<223> OTHER INFORMATION: synthetic DNA

<400> SEQUENCE: 1693
cgctaactat tgcgtatatt cgcggctt                                           28

<210> SEQ ID NO 1694
<211> LENGTH: 28
<212> TYPE: DNA
<213> ORGANISM: Artificial
<220> FEATURE:
<223> OTHER INFORMATION: synthetic DNA

<400> SEQUENCE: 1694
gccatctacg atcttcggct tatcctag                                           28

<210> SEQ ID NO 1695
<211> LENGTH: 28
<212> TYPE: DNA
<213> ORGANISM: Artificial
<220> FEATURE:
<223> OTHER INFORMATION: synthetic DNA

<400> SEQUENCE: 1695
cctgagaatg ttgactaaga tcttgtga                                           28

<210> SEQ ID NO 1696
<211> LENGTH: 28
<212> TYPE: DNA
<213> ORGANISM: Artificial
<220> FEATURE:
<223> OTHER INFORMATION: synthetic DNA

<400> SEQUENCE: 1696
tcggttagtc taatcatcac gcaacgga                                           28

<210> SEQ ID NO 1697
<211> LENGTH: 28
<212> TYPE: DNA
<213> ORGANISM: Artificial
<220> FEATURE:
<223> OTHER INFORMATION: synthetic DNA

<400> SEQUENCE: 1697
attatctatt gaagcagtga cagcgatc                                           28

<210> SEQ ID NO 1698
<211> LENGTH: 28
<212> TYPE: DNA
<213> ORGANISM: Artificial
<220> FEATURE:
<223> OTHER INFORMATION: synthetic DNA

<400> SEQUENCE: 1698
gaggagaatc acggaacacg gtcacatg                                           28

<210> SEQ ID NO 1699
<211> LENGTH: 28
<212> TYPE: DNA
<213> ORGANISM: Artificial
<220> FEATURE:
<223> OTHER INFORMATION: synthetic DNA

<400> SEQUENCE: 1699
gctgcaagca ttatgaccat ggcatctg                                           28

```
<210> SEQ ID NO 1700
<211> LENGTH: 28
<212> TYPE: DNA
<213> ORGANISM: Artificial
<220> FEATURE:
<223> OTHER INFORMATION: synthetic DNA

<400> SEQUENCE: 1700
gaacaaccta taacgacgtt gtggacaa                                        28

<210> SEQ ID NO 1701
<211> LENGTH: 28
<212> TYPE: DNA
<213> ORGANISM: Artificial
<220> FEATURE:
<223> OTHER INFORMATION: synthetic DNA

<400> SEQUENCE: 1701
ttaatcatcg atagacgaca tggaatca                                        28

<210> SEQ ID NO 1702
<211> LENGTH: 28
<212> TYPE: DNA
<213> ORGANISM: Artificial
<220> FEATURE:
<223> OTHER INFORMATION: synthetic DNA

<400> SEQUENCE: 1702
tcgagtgtaa gcacactacg atctggaa                                        28

<210> SEQ ID NO 1703
<211> LENGTH: 28
<212> TYPE: DNA
<213> ORGANISM: Artificial
<220> FEATURE:
<223> OTHER INFORMATION: synthetic DNA

<400> SEQUENCE: 1703
gctacgcaca gtctctgcac agctacac                                        28

<210> SEQ ID NO 1704
<211> LENGTH: 28
<212> TYPE: DNA
<213> ORGANISM: Artificial
<220> FEATURE:
<223> OTHER INFORMATION: synthetic DNA

<400> SEQUENCE: 1704
cctgtatgta cgttctggct aatacctt                                        28

<210> SEQ ID NO 1705
<211> LENGTH: 28
<212> TYPE: DNA
<213> ORGANISM: Artificial
<220> FEATURE:
<223> OTHER INFORMATION: synthetic DNA

<400> SEQUENCE: 1705
tgaagcaccg gtacatggtg tatccgga                                        28

<210> SEQ ID NO 1706
<211> LENGTH: 28
<212> TYPE: DNA
<213> ORGANISM: Artificial
<220> FEATURE:
<223> OTHER INFORMATION: synthetic DNA
```

```
<400> SEQUENCE: 1706
tgctggaacc taactcggtg atgacgat                                      28

<210> SEQ ID NO 1707
<211> LENGTH: 28
<212> TYPE: DNA
<213> ORGANISM: Artificial
<220> FEATURE:
<223> OTHER INFORMATION: synthetic DNA

<400> SEQUENCE: 1707
cgctatctta ctgccaagtt ctcatata                                      28

<210> SEQ ID NO 1708
<211> LENGTH: 28
<212> TYPE: DNA
<213> ORGANISM: Artificial
<220> FEATURE:
<223> OTHER INFORMATION: synthetic DNA

<400> SEQUENCE: 1708
aacgcgcgcg tatcggcaat aatctcaa                                      28

<210> SEQ ID NO 1709
<211> LENGTH: 28
<212> TYPE: DNA
<213> ORGANISM: Artificial
<220> FEATURE:
<223> OTHER INFORMATION: synthetic DNA

<400> SEQUENCE: 1709
ccattaggat gaccatcgac tattagag                                      28

<210> SEQ ID NO 1710
<211> LENGTH: 28
<212> TYPE: DNA
<213> ORGANISM: Artificial
<220> FEATURE:
<223> OTHER INFORMATION: synthetic DNA

<400> SEQUENCE: 1710
tactgctaga ctgcgtgcat tcatggcg                                      28

<210> SEQ ID NO 1711
<211> LENGTH: 28
<212> TYPE: DNA
<213> ORGANISM: Artificial
<220> FEATURE:
<223> OTHER INFORMATION: synthetic DNA

<400> SEQUENCE: 1711
cattgcgcgc tccacgaact ctattgtc                                      28

<210> SEQ ID NO 1712
<211> LENGTH: 28
<212> TYPE: DNA
<213> ORGANISM: Artificial
<220> FEATURE:
<223> OTHER INFORMATION: synthetic DNA

<400> SEQUENCE: 1712
gacgcgccta gaactgtata gctctacg                                      28

<210> SEQ ID NO 1713
<211> LENGTH: 28
```

```
<212> TYPE: DNA
<213> ORGANISM: Artificial
<220> FEATURE:
<223> OTHER INFORMATION: synthetic DNA

<400> SEQUENCE: 1713
cattgcaact tgtcggtgat ggcaatcc                                           28

<210> SEQ ID NO 1714
<211> LENGTH: 28
<212> TYPE: DNA
<213> ORGANISM: Artificial
<220> FEATURE:
<223> OTHER INFORMATION: synthetic DNA

<400> SEQUENCE: 1714
ttaatgcaca tgcagtacgg caccacag                                           28

<210> SEQ ID NO 1715
<211> LENGTH: 28
<212> TYPE: DNA
<213> ORGANISM: Artificial
<220> FEATURE:
<223> OTHER INFORMATION: synthetic DNA

<400> SEQUENCE: 1715
agcggtacgt ggacgagtgg taattaat                                           28

<210> SEQ ID NO 1716
<211> LENGTH: 28
<212> TYPE: DNA
<213> ORGANISM: Artificial
<220> FEATURE:
<223> OTHER INFORMATION: synthetic DNA

<400> SEQUENCE: 1716
gacgtattgc tatgcattgg aagatgct                                           28

<210> SEQ ID NO 1717
<211> LENGTH: 28
<212> TYPE: DNA
<213> ORGANISM: Artificial
<220> FEATURE:
<223> OTHER INFORMATION: synthetic DNA

<400> SEQUENCE: 1717
aacacttcga ccattgcgcc tcaatggt                                           28

<210> SEQ ID NO 1718
<211> LENGTH: 28
<212> TYPE: DNA
<213> ORGANISM: Artificial
<220> FEATURE:
<223> OTHER INFORMATION: synthetic DNA

<400> SEQUENCE: 1718
cggtacgctc tagcggtcat aagatgca                                           28

<210> SEQ ID NO 1719
<211> LENGTH: 28
<212> TYPE: DNA
<213> ORGANISM: Artificial
<220> FEATURE:
<223> OTHER INFORMATION: synthetic DNA

<400> SEQUENCE: 1719
```
cctgaataac agccgcgcct aattagat            28

<210> SEQ ID NO 1720
<211> LENGTH: 28
<212> TYPE: DNA
<213> ORGANISM: Artificial
<220> FEATURE:
<223> OTHER INFORMATION: synthetic DNA

<400> SEQUENCE: 1720
aagcgtctaa tgtgccttaa gtcacatg            28

<210> SEQ ID NO 1721
<211> LENGTH: 28
<212> TYPE: DNA
<213> ORGANISM: Artificial
<220> FEATURE:
<223> OTHER INFORMATION: synthetic DNA

<400> SEQUENCE: 1721
gctctccaag aaccagaagt aagcatcg            28

<210> SEQ ID NO 1722
<211> LENGTH: 28
<212> TYPE: DNA
<213> ORGANISM: Artificial
<220> FEATURE:
<223> OTHER INFORMATION: synthetic DNA

<400> SEQUENCE: 1722
gaggagagtt gtccgagtgg tgtgatgt            28

<210> SEQ ID NO 1723
<211> LENGTH: 28
<212> TYPE: DNA
<213> ORGANISM: Artificial
<220> FEATURE:
<223> OTHER INFORMATION: synthetic DNA

<400> SEQUENCE: 1723
taacgagtgg tgcgtctaag caattgag            28

<210> SEQ ID NO 1724
<211> LENGTH: 28
<212> TYPE: DNA
<213> ORGANISM: Artificial
<220> FEATURE:
<223> OTHER INFORMATION: synthetic DNA

<400> SEQUENCE: 1724
ccaacagtat gctgacataa ctatgata            28

<210> SEQ ID NO 1725
<211> LENGTH: 28
<212> TYPE: DNA
<213> ORGANISM: Artificial
<220> FEATURE:
<223> OTHER INFORMATION: synthetic DNA

<400> SEQUENCE: 1725
gatccttgcc acgcctatga gatatcgc            28

<210> SEQ ID NO 1726
<211> LENGTH: 28
<212> TYPE: DNA
<213> ORGANISM: Artificial

```
<220> FEATURE:
<223> OTHER INFORMATION: synthetic DNA

<400> SEQUENCE: 1726
aacgcgctac cgtccttgtg catagagg                                              28

<210> SEQ ID NO 1727
<211> LENGTH: 28
<212> TYPE: DNA
<213> ORGANISM: Artificial
<220> FEATURE:
<223> OTHER INFORMATION: synthetic DNA

<400> SEQUENCE: 1727
ctacatgtgc cttatagtac agaggaac                                              28

<210> SEQ ID NO 1728
<211> LENGTH: 28
<212> TYPE: DNA
<213> ORGANISM: Artificial
<220> FEATURE:
<223> OTHER INFORMATION: synthetic DNA

<400> SEQUENCE: 1728
cagcctcgta gttagcgtga ttcatgcg                                              28

<210> SEQ ID NO 1729
<211> LENGTH: 29
<212> TYPE: DNA
<213> ORGANISM: Artificial
<220> FEATURE:
<223> OTHER INFORMATION: synthetic DNA

<400> SEQUENCE: 1729
ctcctcgccg attgaagtgc gtagaacta                                             29

<210> SEQ ID NO 1730
<211> LENGTH: 29
<212> TYPE: DNA
<213> ORGANISM: Artificial
<220> FEATURE:
<223> OTHER INFORMATION: synthetic DNA

<400> SEQUENCE: 1730
cagcaggcct caataggata agccaacta                                             29

<210> SEQ ID NO 1731
<211> LENGTH: 29
<212> TYPE: DNA
<213> ORGANISM: Artificial
<220> FEATURE:
<223> OTHER INFORMATION: synthetic DNA

<400> SEQUENCE: 1731
gaccatcaat ctcgaagact acgctctgt                                             29

<210> SEQ ID NO 1732
<211> LENGTH: 29
<212> TYPE: DNA
<213> ORGANISM: Artificial
<220> FEATURE:
<223> OTHER INFORMATION: synthetic DNA

<400> SEQUENCE: 1732
ggttgctccg tctgttcagc acactgtta                                             29
```

<210> SEQ ID NO 1733
<211> LENGTH: 29
<212> TYPE: DNA
<213> ORGANISM: Artificial
<220> FEATURE:
<223> OTHER INFORMATION: synthetic DNA

<400> SEQUENCE: 1733
aatgtcgact ggccattatc gccaagtgt                                      29

<210> SEQ ID NO 1734
<211> LENGTH: 29
<212> TYPE: DNA
<213> ORGANISM: Artificial
<220> FEATURE:
<223> OTHER INFORMATION: synthetic DNA

<400> SEQUENCE: 1734
gatagcttgc catgcgaatg gatctccag                                      29

<210> SEQ ID NO 1735
<211> LENGTH: 29
<212> TYPE: DNA
<213> ORGANISM: Artificial
<220> FEATURE:
<223> OTHER INFORMATION: synthetic DNA

<400> SEQUENCE: 1735
ccagaccgga gccaattggc tgccaatat                                      29

<210> SEQ ID NO 1736
<211> LENGTH: 29
<212> TYPE: DNA
<213> ORGANISM: Artificial
<220> FEATURE:
<223> OTHER INFORMATION: synthetic DNA

<400> SEQUENCE: 1736
aacgtcgctc catacgttac ctaatgcag                                      29

<210> SEQ ID NO 1737
<211> LENGTH: 29
<212> TYPE: DNA
<213> ORGANISM: Artificial
<220> FEATURE:
<223> OTHER INFORMATION: synthetic DNA

<400> SEQUENCE: 1737
gaatatgacg cgaacagtct attcggatc                                      29

<210> SEQ ID NO 1738
<211> LENGTH: 29
<212> TYPE: DNA
<213> ORGANISM: Artificial
<220> FEATURE:
<223> OTHER INFORMATION: synthetic DNA

<400> SEQUENCE: 1738
gacgagaatg tattaaggat aagcaaggt                                      29

<210> SEQ ID NO 1739
<211> LENGTH: 29
<212> TYPE: DNA
<213> ORGANISM: Artificial
<220> FEATURE:
<223> OTHER INFORMATION: synthetic DNA

```
<400> SEQUENCE: 1739
aagtcgtatg aatcgctatc acatgagtc                                              29

<210> SEQ ID NO 1740
<211> LENGTH: 29
<212> TYPE: DNA
<213> ORGANISM: Artificial
<220> FEATURE:
<223> OTHER INFORMATION: synthetic DNA

<400> SEQUENCE: 1740
gtcgtggaga ctacaattct cctcacgtt                                              29

<210> SEQ ID NO 1741
<211> LENGTH: 29
<212> TYPE: DNA
<213> ORGANISM: Artificial
<220> FEATURE:
<223> OTHER INFORMATION: synthetic DNA

<400> SEQUENCE: 1741
gttgccaccg ttacacgact atcgacagt                                              29

<210> SEQ ID NO 1742
<211> LENGTH: 29
<212> TYPE: DNA
<213> ORGANISM: Artificial
<220> FEATURE:
<223> OTHER INFORMATION: synthetic DNA

<400> SEQUENCE: 1742
aggataggct acgccttact ctcctaagc                                              29

<210> SEQ ID NO 1743
<211> LENGTH: 29
<212> TYPE: DNA
<213> ORGANISM: Artificial
<220> FEATURE:
<223> OTHER INFORMATION: synthetic DNA

<400> SEQUENCE: 1743
taatcatcct gttcgcctcg aggttgtta                                              29

<210> SEQ ID NO 1744
<211> LENGTH: 29
<212> TYPE: DNA
<213> ORGANISM: Artificial
<220> FEATURE:
<223> OTHER INFORMATION: synthetic DNA

<400> SEQUENCE: 1744
gacaagcagt aataattact gagtggacg                                              29

<210> SEQ ID NO 1745
<211> LENGTH: 29
<212> TYPE: DNA
<213> ORGANISM: Artificial
<220> FEATURE:
<223> OTHER INFORMATION: synthetic DNA

<400> SEQUENCE: 1745
tacagcgtta cgcaggtata tcaaggtag                                              29

<210> SEQ ID NO 1746
```

```
<211> LENGTH: 29
<212> TYPE: DNA
<213> ORGANISM: Artificial
<220> FEATURE:
<223> OTHER INFORMATION: synthetic DNA

<400> SEQUENCE: 1746
ctaacatcac ttactattag cggtctcgt                                       29

<210> SEQ ID NO 1747
<211> LENGTH: 29
<212> TYPE: DNA
<213> ORGANISM: Artificial
<220> FEATURE:
<223> OTHER INFORMATION: synthetic DNA

<400> SEQUENCE: 1747
ccgcgcttct tgacacgttc tccactagg                                       29

<210> SEQ ID NO 1748
<211> LENGTH: 29
<212> TYPE: DNA
<213> ORGANISM: Artificial
<220> FEATURE:
<223> OTHER INFORMATION: synthetic DNA

<400> SEQUENCE: 1748
caagtaacat gagatgctat cggtacatt                                       29

<210> SEQ ID NO 1749
<211> LENGTH: 29
<212> TYPE: DNA
<213> ORGANISM: Artificial
<220> FEATURE:
<223> OTHER INFORMATION: synthetic DNA

<400> SEQUENCE: 1749
cgaccactag gctgtgacca cgatacgct                                       29

<210> SEQ ID NO 1750
<211> LENGTH: 29
<212> TYPE: DNA
<213> ORGANISM: Artificial
<220> FEATURE:
<223> OTHER INFORMATION: synthetic DNA

<400> SEQUENCE: 1750
caggtcatgt gacgcagtcg gcagtcaac                                       29

<210> SEQ ID NO 1751
<211> LENGTH: 29
<212> TYPE: DNA
<213> ORGANISM: Artificial
<220> FEATURE:
<223> OTHER INFORMATION: synthetic DNA

<400> SEQUENCE: 1751
actccatcgt tagttcttcc gccgtgctg                                       29

<210> SEQ ID NO 1752
<211> LENGTH: 29
<212> TYPE: DNA
<213> ORGANISM: Artificial
<220> FEATURE:
<223> OTHER INFORMATION: synthetic DNA

<400> SEQUENCE: 1752
```
ctcaccacgt atgcgtcact cggttacgt                                          29

<210> SEQ ID NO 1753
<211> LENGTH: 29
<212> TYPE: DNA
<213> ORGANISM: Artificial
<220> FEATURE:
<223> OTHER INFORMATION: synthetic DNA

<400> SEQUENCE: 1753
tgcctatgct atggaccttg cgcgactct                                          29

<210> SEQ ID NO 1754
<211> LENGTH: 29
<212> TYPE: DNA
<213> ORGANISM: Artificial
<220> FEATURE:
<223> OTHER INFORMATION: synthetic DNA

<400> SEQUENCE: 1754
aatgaaggtc aacgctctgt agttacgcg                                          29

<210> SEQ ID NO 1755
<211> LENGTH: 29
<212> TYPE: DNA
<213> ORGANISM: Artificial
<220> FEATURE:
<223> OTHER INFORMATION: synthetic DNA

<400> SEQUENCE: 1755
caccattgat tcatggcttc catcactgc                                          29

<210> SEQ ID NO 1756
<211> LENGTH: 29
<212> TYPE: DNA
<213> ORGANISM: Artificial
<220> FEATURE:
<223> OTHER INFORMATION: synthetic DNA

<400> SEQUENCE: 1756
gacacgcaag gtaattcgag attgcagca                                          29

<210> SEQ ID NO 1757
<211> LENGTH: 29
<212> TYPE: DNA
<213> ORGANISM: Artificial
<220> FEATURE:
<223> OTHER INFORMATION: synthetic DNA

<400> SEQUENCE: 1757
caccgagagg aaggttcgat cgcttctcg                                          29

<210> SEQ ID NO 1758
<211> LENGTH: 29
<212> TYPE: DNA
<213> ORGANISM: Artificial
<220> FEATURE:
<223> OTHER INFORMATION: synthetic DNA

<400> SEQUENCE: 1758
cagttatcgg attgtgatat tcactcctg                                          29

<210> SEQ ID NO 1759
<211> LENGTH: 29
<212> TYPE: DNA

```
<213> ORGANISM: Artificial
<220> FEATURE:
<223> OTHER INFORMATION: synthetic DNA

<400> SEQUENCE: 1759
atactgtaac gcctcaacct atgctgact                                29

<210> SEQ ID NO 1760
<211> LENGTH: 29
<212> TYPE: DNA
<213> ORGANISM: Artificial
<220> FEATURE:
<223> OTHER INFORMATION: synthetic DNA

<400> SEQUENCE: 1760
atctgtctta ttctggcaca ctcagactt                                29

<210> SEQ ID NO 1761
<211> LENGTH: 29
<212> TYPE: DNA
<213> ORGANISM: Artificial
<220> FEATURE:
<223> OTHER INFORMATION: synthetic DNA

<400> SEQUENCE: 1761
tccaaccggt gacgtgctct tgatccaac                                29

<210> SEQ ID NO 1762
<211> LENGTH: 29
<212> TYPE: DNA
<213> ORGANISM: Artificial
<220> FEATURE:
<223> OTHER INFORMATION: synthetic DNA

<400> SEQUENCE: 1762
cacactcagt tcggctatct ctgcgatag                                29

<210> SEQ ID NO 1763
<211> LENGTH: 29
<212> TYPE: DNA
<213> ORGANISM: Artificial
<220> FEATURE:
<223> OTHER INFORMATION: synthetic DNA

<400> SEQUENCE: 1763
agctgtaagt caggtctacg actcgtact                                29

<210> SEQ ID NO 1764
<211> LENGTH: 29
<212> TYPE: DNA
<213> ORGANISM: Artificial
<220> FEATURE:
<223> OTHER INFORMATION: synthetic DNA

<400> SEQUENCE: 1764
gtcggcggca cgcacagcta acattcgta                                29

<210> SEQ ID NO 1765
<211> LENGTH: 29
<212> TYPE: DNA
<213> ORGANISM: Artificial
<220> FEATURE:
<223> OTHER INFORMATION: synthetic DNA

<400> SEQUENCE: 1765
atatggtagc cagccacgta tactgaaca                                29
```

<210> SEQ ID NO 1766
<211> LENGTH: 29
<212> TYPE: DNA
<213> ORGANISM: Artificial
<220> FEATURE:
<223> OTHER INFORMATION: synthetic DNA

<400> SEQUENCE: 1766
tggacaatcc gactctaaca cagaggtag                              29

<210> SEQ ID NO 1767
<211> LENGTH: 29
<212> TYPE: DNA
<213> ORGANISM: Artificial
<220> FEATURE:
<223> OTHER INFORMATION: synthetic DNA

<400> SEQUENCE: 1767
tccgccgctg acagttcaat ctatcaatt                              29

<210> SEQ ID NO 1768
<211> LENGTH: 29
<212> TYPE: DNA
<213> ORGANISM: Artificial
<220> FEATURE:
<223> OTHER INFORMATION: synthetic DNA

<400> SEQUENCE: 1768
ggttccttag aatatgcacc tatcagcga                              29

<210> SEQ ID NO 1769
<211> LENGTH: 29
<212> TYPE: DNA
<213> ORGANISM: Artificial
<220> FEATURE:
<223> OTHER INFORMATION: synthetic DNA

<400> SEQUENCE: 1769
cggctgtacg acatggatca taagagtgt                              29

<210> SEQ ID NO 1770
<211> LENGTH: 29
<212> TYPE: DNA
<213> ORGANISM: Artificial
<220> FEATURE:
<223> OTHER INFORMATION: synthetic DNA

<400> SEQUENCE: 1770
tgcagatgta cgctgtggcc agtggagag                              29

<210> SEQ ID NO 1771
<211> LENGTH: 29
<212> TYPE: DNA
<213> ORGANISM: Artificial
<220> FEATURE:
<223> OTHER INFORMATION: synthetic DNA

<400> SEQUENCE: 1771
cctactcact taacaataat cggttcggt                              29

<210> SEQ ID NO 1772
<211> LENGTH: 29
<212> TYPE: DNA
<213> ORGANISM: Artificial
<220> FEATURE:

<223> OTHER INFORMATION: synthetic DNA

<400> SEQUENCE: 1772
cgcttcctac tgcctgtgcc gcgacataa                                29

<210> SEQ ID NO 1773
<211> LENGTH: 29
<212> TYPE: DNA
<213> ORGANISM: Artificial
<220> FEATURE:
<223> OTHER INFORMATION: synthetic DNA

<400> SEQUENCE: 1773
ctagaccgac cggttatgcg ctattgttc                                29

<210> SEQ ID NO 1774
<211> LENGTH: 29
<212> TYPE: DNA
<213> ORGANISM: Artificial
<220> FEATURE:
<223> OTHER INFORMATION: synthetic DNA

<400> SEQUENCE: 1774
ttgtgagcac gtctgcggca agcctatgg                                29

<210> SEQ ID NO 1775
<211> LENGTH: 29
<212> TYPE: DNA
<213> ORGANISM: Artificial
<220> FEATURE:
<223> OTHER INFORMATION: synthetic DNA

<400> SEQUENCE: 1775
tcatcggccg gcgctgttgt tgttaccat                                29

<210> SEQ ID NO 1776
<211> LENGTH: 29
<212> TYPE: DNA
<213> ORGANISM: Artificial
<220> FEATURE:
<223> OTHER INFORMATION: synthetic DNA

<400> SEQUENCE: 1776
gcggttaggt gcagttagga agactatca                                29

<210> SEQ ID NO 1777
<211> LENGTH: 29
<212> TYPE: DNA
<213> ORGANISM: Artificial
<220> FEATURE:
<223> OTHER INFORMATION: synthetic DNA

<400> SEQUENCE: 1777
tatgcggtcg tgaggcgtag cattctaga                                29

<210> SEQ ID NO 1778
<211> LENGTH: 29
<212> TYPE: DNA
<213> ORGANISM: Artificial
<220> FEATURE:
<223> OTHER INFORMATION: synthetic DNA

<400> SEQUENCE: 1778
ccatctattc gtcgaactct cagctcgta                                29

<210> SEQ ID NO 1779
<211> LENGTH: 29
<212> TYPE: DNA
<213> ORGANISM: Artificial
<220> FEATURE:
<223> OTHER INFORMATION: synthetic DNA

<400> SEQUENCE: 1779
atcagatcta ctgatcgcgg tagagtatc                                      29

<210> SEQ ID NO 1780
<211> LENGTH: 29
<212> TYPE: DNA
<213> ORGANISM: Artificial
<220> FEATURE:
<223> OTHER INFORMATION: synthetic DNA

<400> SEQUENCE: 1780
tacacatagg cggcgcagcc ttctaatta                                      29

<210> SEQ ID NO 1781
<211> LENGTH: 29
<212> TYPE: DNA
<213> ORGANISM: Artificial
<220> FEATURE:
<223> OTHER INFORMATION: synthetic DNA

<400> SEQUENCE: 1781
ttaaccgtag ttcttagctt acgccgctc                                      29

<210> SEQ ID NO 1782
<211> LENGTH: 29
<212> TYPE: DNA
<213> ORGANISM: Artificial
<220> FEATURE:
<223> OTHER INFORMATION: synthetic DNA

<400> SEQUENCE: 1782
actatagagg acatggcact cctcttcta                                      29

<210> SEQ ID NO 1783
<211> LENGTH: 29
<212> TYPE: DNA
<213> ORGANISM: Artificial
<220> FEATURE:
<223> OTHER INFORMATION: synthetic DNA

<400> SEQUENCE: 1783
cagttcgtat taagattgaa tgtagcggt                                      29

<210> SEQ ID NO 1784
<211> LENGTH: 29
<212> TYPE: DNA
<213> ORGANISM: Artificial
<220> FEATURE:
<223> OTHER INFORMATION: synthetic DNA

<400> SEQUENCE: 1784
agttatcggt atccgcttat ccgtacgta                                      29

<210> SEQ ID NO 1785
<211> LENGTH: 29
<212> TYPE: DNA
<213> ORGANISM: Artificial
<220> FEATURE:
<223> OTHER INFORMATION: synthetic DNA

```
<400> SEQUENCE: 1785
agcttattca tacactgcac cacagcaag                                29

<210> SEQ ID NO 1786
<211> LENGTH: 29
<212> TYPE: DNA
<213> ORGANISM: Artificial
<220> FEATURE:
<223> OTHER INFORMATION: synthetic DNA

<400> SEQUENCE: 1786
ccgtcggcta gtctatcctc taattagaa                                29

<210> SEQ ID NO 1787
<211> LENGTH: 29
<212> TYPE: DNA
<213> ORGANISM: Artificial
<220> FEATURE:
<223> OTHER INFORMATION: synthetic DNA

<400> SEQUENCE: 1787
gtccgcttcc atgcctgctg tacgaacac                                29

<210> SEQ ID NO 1788
<211> LENGTH: 29
<212> TYPE: DNA
<213> ORGANISM: Artificial
<220> FEATURE:
<223> OTHER INFORMATION: synthetic DNA

<400> SEQUENCE: 1788
tctcttcctc cttcattgtt cgctagctc                                29

<210> SEQ ID NO 1789
<211> LENGTH: 29
<212> TYPE: DNA
<213> ORGANISM: Artificial
<220> FEATURE:
<223> OTHER INFORMATION: synthetic DNA

<400> SEQUENCE: 1789
tctcttgagc ggtcctcata caggtctgc                                29

<210> SEQ ID NO 1790
<211> LENGTH: 29
<212> TYPE: DNA
<213> ORGANISM: Artificial
<220> FEATURE:
<223> OTHER INFORMATION: synthetic DNA

<400> SEQUENCE: 1790
gaccaagtgt aggtgatatc accggtact                                29

<210> SEQ ID NO 1791
<211> LENGTH: 29
<212> TYPE: DNA
<213> ORGANISM: Artificial
<220> FEATURE:
<223> OTHER INFORMATION: synthetic DNA

<400> SEQUENCE: 1791
aagattgtga taggttggta gttaccaca                                29

<210> SEQ ID NO 1792
<211> LENGTH: 29
```

```
<212> TYPE: DNA
<213> ORGANISM: Artificial
<220> FEATURE:
<223> OTHER INFORMATION: synthetic DNA

<400> SEQUENCE: 1792
tcgcctccga agagtatagc atcggcaga                                29

<210> SEQ ID NO 1793
<211> LENGTH: 29
<212> TYPE: DNA
<213> ORGANISM: Artificial
<220> FEATURE:
<223> OTHER INFORMATION: synthetic DNA

<400> SEQUENCE: 1793
gaggtagtta tgagcatcga ggtcctgtt                                29

<210> SEQ ID NO 1794
<211> LENGTH: 29
<212> TYPE: DNA
<213> ORGANISM: Artificial
<220> FEATURE:
<223> OTHER INFORMATION: synthetic DNA

<400> SEQUENCE: 1794
ggacgcaaga tcgcaggtac ttgtaagct                                29

<210> SEQ ID NO 1795
<211> LENGTH: 29
<212> TYPE: DNA
<213> ORGANISM: Artificial
<220> FEATURE:
<223> OTHER INFORMATION: synthetic DNA

<400> SEQUENCE: 1795
actcgtacac gtcatcgtgc aggtctcag                                29

<210> SEQ ID NO 1796
<211> LENGTH: 29
<212> TYPE: DNA
<213> ORGANISM: Artificial
<220> FEATURE:
<223> OTHER INFORMATION: synthetic DNA

<400> SEQUENCE: 1796
taatccgtca ggagtgagat ggctcgaca                                29

<210> SEQ ID NO 1797
<211> LENGTH: 29
<212> TYPE: DNA
<213> ORGANISM: Artificial
<220> FEATURE:
<223> OTHER INFORMATION: synthetic DNA

<400> SEQUENCE: 1797
aagatggttc cgcgcattga ctagcaagt                                29

<210> SEQ ID NO 1798
<211> LENGTH: 29
<212> TYPE: DNA
<213> ORGANISM: Artificial
<220> FEATURE:
<223> OTHER INFORMATION: synthetic DNA

<400> SEQUENCE: 1798
```
tccgcgatct gcggatcttg aatgctcac                                              29

<210> SEQ ID NO 1799
<211> LENGTH: 29
<212> TYPE: DNA
<213> ORGANISM: Artificial
<220> FEATURE:
<223> OTHER INFORMATION: synthetic DNA

<400> SEQUENCE: 1799
ttcacgagag tcaactgcta gtatcctag                                              29

<210> SEQ ID NO 1800
<211> LENGTH: 29
<212> TYPE: DNA
<213> ORGANISM: Artificial
<220> FEATURE:
<223> OTHER INFORMATION: synthetic DNA

<400> SEQUENCE: 1800
ttccaactgg attcttccaa ctcctcgaa                                              29

<210> SEQ ID NO 1801
<211> LENGTH: 29
<212> TYPE: DNA
<213> ORGANISM: Artificial
<220> FEATURE:
<223> OTHER INFORMATION: synthetic DNA

<400> SEQUENCE: 1801
cactactact caagttatac ggtgttgac                                              29

<210> SEQ ID NO 1802
<211> LENGTH: 29
<212> TYPE: DNA
<213> ORGANISM: Artificial
<220> FEATURE:
<223> OTHER INFORMATION: synthetic DNA

<400> SEQUENCE: 1802
caactggatt ctcaggatgc gtctctagc                                              29

<210> SEQ ID NO 1803
<211> LENGTH: 29
<212> TYPE: DNA
<213> ORGANISM: Artificial
<220> FEATURE:
<223> OTHER INFORMATION: synthetic DNA

<400> SEQUENCE: 1803
tggactagag tggagcgatt acgtaatat                                              29

<210> SEQ ID NO 1804
<211> LENGTH: 29
<212> TYPE: DNA
<213> ORGANISM: Artificial
<220> FEATURE:
<223> OTHER INFORMATION: synthetic DNA

<400> SEQUENCE: 1804
gaggtcattc aactggactc gccacggac                                              29

<210> SEQ ID NO 1805
<211> LENGTH: 29
<212> TYPE: DNA
<213> ORGANISM: Artificial

```
<220> FEATURE:
<223> OTHER INFORMATION: synthetic DNA

<400> SEQUENCE: 1805
caggtgtgta acgctgcaat cacatgaat                                29

<210> SEQ ID NO 1806
<211> LENGTH: 29
<212> TYPE: DNA
<213> ORGANISM: Artificial
<220> FEATURE:
<223> OTHER INFORMATION: synthetic DNA

<400> SEQUENCE: 1806
tatgctgagg tattagttct aactatgcg                                29

<210> SEQ ID NO 1807
<211> LENGTH: 29
<212> TYPE: DNA
<213> ORGANISM: Artificial
<220> FEATURE:
<223> OTHER INFORMATION: synthetic DNA

<400> SEQUENCE: 1807
cgtctgagtc ggataaggaa ggttaccgc                                29

<210> SEQ ID NO 1808
<211> LENGTH: 29
<212> TYPE: DNA
<213> ORGANISM: Artificial
<220> FEATURE:
<223> OTHER INFORMATION: synthetic DNA

<400> SEQUENCE: 1808
gtactatcgt cgcaggcact atctctgcc                                29

<210> SEQ ID NO 1809
<211> LENGTH: 29
<212> TYPE: DNA
<213> ORGANISM: Artificial
<220> FEATURE:
<223> OTHER INFORMATION: synthetic DNA

<400> SEQUENCE: 1809
gcttcctcct tgcaacttca ttgcttcga                                29

<210> SEQ ID NO 1810
<211> LENGTH: 29
<212> TYPE: DNA
<213> ORGANISM: Artificial
<220> FEATURE:
<223> OTHER INFORMATION: synthetic DNA

<400> SEQUENCE: 1810
tgtctacgaa gtagaagaca cgaataatg                                29

<210> SEQ ID NO 1811
<211> LENGTH: 29
<212> TYPE: DNA
<213> ORGANISM: Artificial
<220> FEATURE:
<223> OTHER INFORMATION: synthetic DNA

<400> SEQUENCE: 1811
ccgtcatcta aggcagagta catccgcga                                29
```

<210> SEQ ID NO 1812
<211> LENGTH: 29
<212> TYPE: DNA
<213> ORGANISM: Artificial
<220> FEATURE:
<223> OTHER INFORMATION: synthetic DNA

<400> SEQUENCE: 1812
ccggaggcgt actaactgac cacaacacc                                     29

<210> SEQ ID NO 1813
<211> LENGTH: 29
<212> TYPE: DNA
<213> ORGANISM: Artificial
<220> FEATURE:
<223> OTHER INFORMATION: synthetic DNA

<400> SEQUENCE: 1813
aactcgtcgc tgcctgaata ggtcagagt                                     29

<210> SEQ ID NO 1814
<211> LENGTH: 29
<212> TYPE: DNA
<213> ORGANISM: Artificial
<220> FEATURE:
<223> OTHER INFORMATION: synthetic DNA

<400> SEQUENCE: 1814
ttataagatt aatgtcggtc agtgtcgga                                     29

<210> SEQ ID NO 1815
<211> LENGTH: 29
<212> TYPE: DNA
<213> ORGANISM: Artificial
<220> FEATURE:
<223> OTHER INFORMATION: synthetic DNA

<400> SEQUENCE: 1815
cgtctcgatg gatccacacg aacctgttg                                     29

<210> SEQ ID NO 1816
<211> LENGTH: 29
<212> TYPE: DNA
<213> ORGANISM: Artificial
<220> FEATURE:
<223> OTHER INFORMATION: synthetic DNA

<400> SEQUENCE: 1816
atgccatcat ggtcgtccta tcttaaggc                                     29

<210> SEQ ID NO 1817
<211> LENGTH: 29
<212> TYPE: DNA
<213> ORGANISM: Artificial
<220> FEATURE:
<223> OTHER INFORMATION: synthetic DNA

<400> SEQUENCE: 1817
gcgcttcagc gattcgtcat gcaaggcac                                     29

<210> SEQ ID NO 1818
<211> LENGTH: 29
<212> TYPE: DNA
<213> ORGANISM: Artificial
<220> FEATURE:
<223> OTHER INFORMATION: synthetic DNA

```
<400> SEQUENCE: 1818
ccaagcgata ccgaggtacg gttaacgag                                29

<210> SEQ ID NO 1819
<211> LENGTH: 29
<212> TYPE: DNA
<213> ORGANISM: Artificial
<220> FEATURE:
<223> OTHER INFORMATION: synthetic DNA

<400> SEQUENCE: 1819
atatgacaga caggtggacc taagcaagc                                29

<210> SEQ ID NO 1820
<211> LENGTH: 29
<212> TYPE: DNA
<213> ORGANISM: Artificial
<220> FEATURE:
<223> OTHER INFORMATION: synthetic DNA

<400> SEQUENCE: 1820
cactacatcg tcaggcctgg aagcctcag                                29

<210> SEQ ID NO 1821
<211> LENGTH: 29
<212> TYPE: DNA
<213> ORGANISM: Artificial
<220> FEATURE:
<223> OTHER INFORMATION: synthetic DNA

<400> SEQUENCE: 1821
gccgtgtaga cgaggacatt atgtcgtat                                29

<210> SEQ ID NO 1822
<211> LENGTH: 29
<212> TYPE: DNA
<213> ORGANISM: Artificial
<220> FEATURE:
<223> OTHER INFORMATION: synthetic DNA

<400> SEQUENCE: 1822
caacgtatat acacaccttg tgaagagaa                                29

<210> SEQ ID NO 1823
<211> LENGTH: 29
<212> TYPE: DNA
<213> ORGANISM: Artificial
<220> FEATURE:
<223> OTHER INFORMATION: synthetic DNA

<400> SEQUENCE: 1823
tccaacgtaa ttccgccgtc tgtcgagac                                29

<210> SEQ ID NO 1824
<211> LENGTH: 29
<212> TYPE: DNA
<213> ORGANISM: Artificial
<220> FEATURE:
<223> OTHER INFORMATION: synthetic DNA

<400> SEQUENCE: 1824
aattcgtgct tcgatcaccg tagactcag                                29

<210> SEQ ID NO 1825
```

```
<211> LENGTH: 30
<212> TYPE: DNA
<213> ORGANISM: Artificial
<220> FEATURE:
<223> OTHER INFORMATION: synthetic DNA

<400> SEQUENCE: 1825
actatattgt attcacgtcc gacgactcgc                                          30

<210> SEQ ID NO 1826
<211> LENGTH: 30
<212> TYPE: DNA
<213> ORGANISM: Artificial
<220> FEATURE:
<223> OTHER INFORMATION: synthetic DNA

<400> SEQUENCE: 1826
gacgagcttg tggtacacta tacctatgag                                          30

<210> SEQ ID NO 1827
<211> LENGTH: 30
<212> TYPE: DNA
<213> ORGANISM: Artificial
<220> FEATURE:
<223> OTHER INFORMATION: synthetic DNA

<400> SEQUENCE: 1827
tgattcaagc accaggcatg cttaagctag                                          30

<210> SEQ ID NO 1828
<211> LENGTH: 30
<212> TYPE: DNA
<213> ORGANISM: Artificial
<220> FEATURE:
<223> OTHER INFORMATION: synthetic DNA

<400> SEQUENCE: 1828
cggtctccta taggaaggct cattctgacg                                          30

<210> SEQ ID NO 1829
<211> LENGTH: 30
<212> TYPE: DNA
<213> ORGANISM: Artificial
<220> FEATURE:
<223> OTHER INFORMATION: synthetic DNA

<400> SEQUENCE: 1829
agtcagtgtc gaatcaatca aggcgtcctt                                          30

<210> SEQ ID NO 1830
<211> LENGTH: 30
<212> TYPE: DNA
<213> ORGANISM: Artificial
<220> FEATURE:
<223> OTHER INFORMATION: synthetic DNA

<400> SEQUENCE: 1830
cgaacgtaat ggccatcacg cgctggccta                                          30

<210> SEQ ID NO 1831
<211> LENGTH: 30
<212> TYPE: DNA
<213> ORGANISM: Artificial
<220> FEATURE:
<223> OTHER INFORMATION: synthetic DNA

<400> SEQUENCE: 1831
```
cgaacctgga ccacctggca ttaccattac                                     30

<210> SEQ ID NO 1832
<211> LENGTH: 30
<212> TYPE: DNA
<213> ORGANISM: Artificial
<220> FEATURE:
<223> OTHER INFORMATION: synthetic DNA

<400> SEQUENCE: 1832
acattaggtt cctgtaatgt cttatcaacg                                     30

<210> SEQ ID NO 1833
<211> LENGTH: 30
<212> TYPE: DNA
<213> ORGANISM: Artificial
<220> FEATURE:
<223> OTHER INFORMATION: synthetic DNA

<400> SEQUENCE: 1833
cgtctaatgc accgtatcgt cttcgcgcat                                     30

<210> SEQ ID NO 1834
<211> LENGTH: 30
<212> TYPE: DNA
<213> ORGANISM: Artificial
<220> FEATURE:
<223> OTHER INFORMATION: synthetic DNA

<400> SEQUENCE: 1834
tctatgactt acaacggaat cttacttcgt                                     30

<210> SEQ ID NO 1835
<211> LENGTH: 30
<212> TYPE: DNA
<213> ORGANISM: Artificial
<220> FEATURE:
<223> OTHER INFORMATION: synthetic DNA

<400> SEQUENCE: 1835
gtaaccgatc ggtaccgtct gctattgttc                                     30

<210> SEQ ID NO 1836
<211> LENGTH: 30
<212> TYPE: DNA
<213> ORGANISM: Artificial
<220> FEATURE:
<223> OTHER INFORMATION: synthetic DNA

<400> SEQUENCE: 1836
ggtgattgat aagcaacaca tattaggagg                                     30

<210> SEQ ID NO 1837
<211> LENGTH: 30
<212> TYPE: DNA
<213> ORGANISM: Artificial
<220> FEATURE:
<223> OTHER INFORMATION: synthetic DNA

<400> SEQUENCE: 1837
aattatcgac gctaataggc gagctgttca                                     30

<210> SEQ ID NO 1838
<211> LENGTH: 30
<212> TYPE: DNA

```
<213> ORGANISM: Artificial
<220> FEATURE:
<223> OTHER INFORMATION: synthetic DNA

<400> SEQUENCE: 1838
ggaggtacat gacgagtgga cagacagacc                              30

<210> SEQ ID NO 1839
<211> LENGTH: 30
<212> TYPE: DNA
<213> ORGANISM: Artificial
<220> FEATURE:
<223> OTHER INFORMATION: synthetic DNA

<400> SEQUENCE: 1839
ctctaatccg ttatgcggtg atgtaatccg                              30

<210> SEQ ID NO 1840
<211> LENGTH: 30
<212> TYPE: DNA
<213> ORGANISM: Artificial
<220> FEATURE:
<223> OTHER INFORMATION: synthetic DNA

<400> SEQUENCE: 1840
gcaagcacgc ggcttggcga acttctatgc                              30

<210> SEQ ID NO 1841
<211> LENGTH: 30
<212> TYPE: DNA
<213> ORGANISM: Artificial
<220> FEATURE:
<223> OTHER INFORMATION: synthetic DNA

<400> SEQUENCE: 1841
tagatgtagg cctggtaggc agaggagtaa                              30

<210> SEQ ID NO 1842
<211> LENGTH: 30
<212> TYPE: DNA
<213> ORGANISM: Artificial
<220> FEATURE:
<223> OTHER INFORMATION: synthetic DNA

<400> SEQUENCE: 1842
ccgagtggcg accacacagg tacgcattaa                              30

<210> SEQ ID NO 1843
<211> LENGTH: 30
<212> TYPE: DNA
<213> ORGANISM: Artificial
<220> FEATURE:
<223> OTHER INFORMATION: synthetic DNA

<400> SEQUENCE: 1843
gtcctggctc agattagtgc acttagttat                              30

<210> SEQ ID NO 1844
<211> LENGTH: 30
<212> TYPE: DNA
<213> ORGANISM: Artificial
<220> FEATURE:
<223> OTHER INFORMATION: synthetic DNA

<400> SEQUENCE: 1844
gcggtaccta catgttatga ctcagacgac                              30
```

<210> SEQ ID NO 1845
<211> LENGTH: 30
<212> TYPE: DNA
<213> ORGANISM: Artificial
<220> FEATURE:
<223> OTHER INFORMATION: synthetic DNA

<400> SEQUENCE: 1845
tctctgccaa tgctggtctc atcgaatcca                              30

<210> SEQ ID NO 1846
<211> LENGTH: 30
<212> TYPE: DNA
<213> ORGANISM: Artificial
<220> FEATURE:
<223> OTHER INFORMATION: synthetic DNA

<400> SEQUENCE: 1846
tctctacaca gctacatact atactgtaac                              30

<210> SEQ ID NO 1847
<211> LENGTH: 30
<212> TYPE: DNA
<213> ORGANISM: Artificial
<220> FEATURE:
<223> OTHER INFORMATION: synthetic DNA

<400> SEQUENCE: 1847
tacgacggac gctggtggtg taagagaagg                              30

<210> SEQ ID NO 1848
<211> LENGTH: 30
<212> TYPE: DNA
<213> ORGANISM: Artificial
<220> FEATURE:
<223> OTHER INFORMATION: synthetic DNA

<400> SEQUENCE: 1848
gcctcgatat atctacgtat agttcaagtt                              30

<210> SEQ ID NO 1849
<211> LENGTH: 30
<212> TYPE: DNA
<213> ORGANISM: Artificial
<220> FEATURE:
<223> OTHER INFORMATION: synthetic DNA

<400> SEQUENCE: 1849
ggctcctgca ttcattgaag gtcggccttg                              30

<210> SEQ ID NO 1850
<211> LENGTH: 30
<212> TYPE: DNA
<213> ORGANISM: Artificial
<220> FEATURE:
<223> OTHER INFORMATION: synthetic DNA

<400> SEQUENCE: 1850
cagttcggtg attcaagaga acaatggtgg                              30

<210> SEQ ID NO 1851
<211> LENGTH: 30
<212> TYPE: DNA
<213> ORGANISM: Artificial
<220> FEATURE:

<223> OTHER INFORMATION: synthetic DNA

<400> SEQUENCE: 1851
tataacgaag ccggctggaa cggtaactca       30

<210> SEQ ID NO 1852
<211> LENGTH: 30
<212> TYPE: DNA
<213> ORGANISM: Artificial
<220> FEATURE:
<223> OTHER INFORMATION: synthetic DNA

<400> SEQUENCE: 1852
ctgtatcaat tcaagtgaca gtggcacgtc       30

<210> SEQ ID NO 1853
<211> LENGTH: 30
<212> TYPE: DNA
<213> ORGANISM: Artificial
<220> FEATURE:
<223> OTHER INFORMATION: synthetic DNA

<400> SEQUENCE: 1853
agcaattgcg gttcataggc gtaattatat       30

<210> SEQ ID NO 1854
<211> LENGTH: 30
<212> TYPE: DNA
<213> ORGANISM: Artificial
<220> FEATURE:
<223> OTHER INFORMATION: synthetic DNA

<400> SEQUENCE: 1854
catatggacc tggagatcac cgttcagtcc       30

<210> SEQ ID NO 1855
<211> LENGTH: 30
<212> TYPE: DNA
<213> ORGANISM: Artificial
<220> FEATURE:
<223> OTHER INFORMATION: synthetic DNA

<400> SEQUENCE: 1855
gaaggccgtt ggtctatctc ttactggagc       30

<210> SEQ ID NO 1856
<211> LENGTH: 30
<212> TYPE: DNA
<213> ORGANISM: Artificial
<220> FEATURE:
<223> OTHER INFORMATION: synthetic DNA

<400> SEQUENCE: 1856
gtgcgttcat ctagcctaag acgctgacct       30

<210> SEQ ID NO 1857
<211> LENGTH: 30
<212> TYPE: DNA
<213> ORGANISM: Artificial
<220> FEATURE:
<223> OTHER INFORMATION: synthetic DNA

<400> SEQUENCE: 1857
gagtaactta tatcctctct acgacatcga       30

```
<210> SEQ ID NO 1858
<211> LENGTH: 30
<212> TYPE: DNA
<213> ORGANISM: Artificial
<220> FEATURE:
<223> OTHER INFORMATION: synthetic DNA

<400> SEQUENCE: 1858
attctacgct gatgtctccg ctgaacagga                              30

<210> SEQ ID NO 1859
<211> LENGTH: 30
<212> TYPE: DNA
<213> ORGANISM: Artificial
<220> FEATURE:
<223> OTHER INFORMATION: synthetic DNA

<400> SEQUENCE: 1859
tcatcaacgt tactcactag taccacggct                              30

<210> SEQ ID NO 1860
<211> LENGTH: 30
<212> TYPE: DNA
<213> ORGANISM: Artificial
<220> FEATURE:
<223> OTHER INFORMATION: synthetic DNA

<400> SEQUENCE: 1860
aaccattctt gaacgttgag aacctggtgg                              30

<210> SEQ ID NO 1861
<211> LENGTH: 30
<212> TYPE: DNA
<213> ORGANISM: Artificial
<220> FEATURE:
<223> OTHER INFORMATION: synthetic DNA

<400> SEQUENCE: 1861
acgacacctc cgcggaacat acctgattag                              30

<210> SEQ ID NO 1862
<211> LENGTH: 30
<212> TYPE: DNA
<213> ORGANISM: Artificial
<220> FEATURE:
<223> OTHER INFORMATION: synthetic DNA

<400> SEQUENCE: 1862
gcgcacttat tgaagtaatc tcatggccaa                              30

<210> SEQ ID NO 1863
<211> LENGTH: 30
<212> TYPE: DNA
<213> ORGANISM: Artificial
<220> FEATURE:
<223> OTHER INFORMATION: synthetic DNA

<400> SEQUENCE: 1863
gcgccaattc agccagttag cgtctccgtg                              30

<210> SEQ ID NO 1864
<211> LENGTH: 30
<212> TYPE: DNA
<213> ORGANISM: Artificial
<220> FEATURE:
<223> OTHER INFORMATION: synthetic DNA
```

```
<400> SEQUENCE: 1864
agcaacaagt cgctgtatat cgactggccg                                          30

<210> SEQ ID NO 1865
<211> LENGTH: 30
<212> TYPE: DNA
<213> ORGANISM: Artificial
<220> FEATURE:
<223> OTHER INFORMATION: synthetic DNA

<400> SEQUENCE: 1865
ccttacaata gacctcgcgg cgttcatgcc                                          30

<210> SEQ ID NO 1866
<211> LENGTH: 30
<212> TYPE: DNA
<213> ORGANISM: Artificial
<220> FEATURE:
<223> OTHER INFORMATION: synthetic DNA

<400> SEQUENCE: 1866
ggatccaact tcagcgaagc accaacgtcg                                          30

<210> SEQ ID NO 1867
<211> LENGTH: 30
<212> TYPE: DNA
<213> ORGANISM: Artificial
<220> FEATURE:
<223> OTHER INFORMATION: synthetic DNA

<400> SEQUENCE: 1867
gcgccagttc tcgtactctc gagaagcgac                                          30

<210> SEQ ID NO 1868
<211> LENGTH: 30
<212> TYPE: DNA
<213> ORGANISM: Artificial
<220> FEATURE:
<223> OTHER INFORMATION: synthetic DNA

<400> SEQUENCE: 1868
gagtgcggcc aatctggaac tcatgacgtt                                          30

<210> SEQ ID NO 1869
<211> LENGTH: 30
<212> TYPE: DNA
<213> ORGANISM: Artificial
<220> FEATURE:
<223> OTHER INFORMATION: synthetic DNA

<400> SEQUENCE: 1869
cctgagagtg attcgtgtct gcgaagatgc                                          30

<210> SEQ ID NO 1870
<211> LENGTH: 30
<212> TYPE: DNA
<213> ORGANISM: Artificial
<220> FEATURE:
<223> OTHER INFORMATION: synthetic DNA

<400> SEQUENCE: 1870
gtgactggtt aaggcaatat tggtcgaccg                                          30

<210> SEQ ID NO 1871
<211> LENGTH: 30
```

```
<212> TYPE: DNA
<213> ORGANISM: Artificial
<220> FEATURE:
<223> OTHER INFORMATION: synthetic DNA

<400> SEQUENCE: 1871
ctatcaagcc ttacaaggtc acgtccacta                                30

<210> SEQ ID NO 1872
<211> LENGTH: 30
<212> TYPE: DNA
<213> ORGANISM: Artificial
<220> FEATURE:
<223> OTHER INFORMATION: synthetic DNA

<400> SEQUENCE: 1872
actgcgtcct tgcgtcggaa ctccttgtgt                                30

<210> SEQ ID NO 1873
<211> LENGTH: 30
<212> TYPE: DNA
<213> ORGANISM: Artificial
<220> FEATURE:
<223> OTHER INFORMATION: synthetic DNA

<400> SEQUENCE: 1873
tgcaactcag tggcggcgac accaagagct                                30

<210> SEQ ID NO 1874
<211> LENGTH: 30
<212> TYPE: DNA
<213> ORGANISM: Artificial
<220> FEATURE:
<223> OTHER INFORMATION: synthetic DNA

<400> SEQUENCE: 1874
ttcggttcta ctaggatctc tatctgagct                                30

<210> SEQ ID NO 1875
<211> LENGTH: 30
<212> TYPE: DNA
<213> ORGANISM: Artificial
<220> FEATURE:
<223> OTHER INFORMATION: synthetic DNA

<400> SEQUENCE: 1875
agctaatcta ttaagacaga ttagacagga                                30

<210> SEQ ID NO 1876
<211> LENGTH: 30
<212> TYPE: DNA
<213> ORGANISM: Artificial
<220> FEATURE:
<223> OTHER INFORMATION: synthetic DNA

<400> SEQUENCE: 1876
ggaccgctct taggttatgc acctgcgtat                                30

<210> SEQ ID NO 1877
<211> LENGTH: 30
<212> TYPE: DNA
<213> ORGANISM: Artificial
<220> FEATURE:
<223> OTHER INFORMATION: synthetic DNA

<400> SEQUENCE: 1877
```
ctctaatact agtccacagg ttagtacgaa 30

<210> SEQ ID NO 1878
<211> LENGTH: 30
<212> TYPE: DNA
<213> ORGANISM: Artificial
<220> FEATURE:
<223> OTHER INFORMATION: synthetic DNA

<400> SEQUENCE: 1878
atccatatat gctcgtcgtc agccagtgtt 30

<210> SEQ ID NO 1879
<211> LENGTH: 30
<212> TYPE: DNA
<213> ORGANISM: Artificial
<220> FEATURE:
<223> OTHER INFORMATION: synthetic DNA

<400> SEQUENCE: 1879
gctattactg tgttgatgtc cacaggagaa 30

<210> SEQ ID NO 1880
<211> LENGTH: 30
<212> TYPE: DNA
<213> ORGANISM: Artificial
<220> FEATURE:
<223> OTHER INFORMATION: synthetic DNA

<400> SEQUENCE: 1880
gctacggcgc agatctagac aactggaagt 30

<210> SEQ ID NO 1881
<211> LENGTH: 30
<212> TYPE: DNA
<213> ORGANISM: Artificial
<220> FEATURE:
<223> OTHER INFORMATION: synthetic DNA

<400> SEQUENCE: 1881
gcctcttgtg ttagccgaat accaatgacc 30

<210> SEQ ID NO 1882
<211> LENGTH: 30
<212> TYPE: DNA
<213> ORGANISM: Artificial
<220> FEATURE:
<223> OTHER INFORMATION: synthetic DNA

<400> SEQUENCE: 1882
tgaggacgat aacattacct ctcgagtcgc 30

<210> SEQ ID NO 1883
<211> LENGTH: 30
<212> TYPE: DNA
<213> ORGANISM: Artificial
<220> FEATURE:
<223> OTHER INFORMATION: synthetic DNA

<400> SEQUENCE: 1883
cgattaccaa tccgacgact tcgcagcagc 30

<210> SEQ ID NO 1884
<211> LENGTH: 30
<212> TYPE: DNA
<213> ORGANISM: Artificial

```
<220> FEATURE:
<223> OTHER INFORMATION: synthetic DNA

<400> SEQUENCE: 1884
atgacacgag tccagtacat atgcgaagac                                    30

<210> SEQ ID NO 1885
<211> LENGTH: 30
<212> TYPE: DNA
<213> ORGANISM: Artificial
<220> FEATURE:
<223> OTHER INFORMATION: synthetic DNA

<400> SEQUENCE: 1885
gcgctcgcat gcactagtgt agactgacga                                    30

<210> SEQ ID NO 1886
<211> LENGTH: 30
<212> TYPE: DNA
<213> ORGANISM: Artificial
<220> FEATURE:
<223> OTHER INFORMATION: synthetic DNA

<400> SEQUENCE: 1886
gcacatctca gaattgatgg tctatgtcgc                                    30

<210> SEQ ID NO 1887
<211> LENGTH: 30
<212> TYPE: DNA
<213> ORGANISM: Artificial
<220> FEATURE:
<223> OTHER INFORMATION: synthetic DNA

<400> SEQUENCE: 1887
ttcttcgacg ccgcgtacta ataggtcaat                                    30

<210> SEQ ID NO 1888
<211> LENGTH: 30
<212> TYPE: DNA
<213> ORGANISM: Artificial
<220> FEATURE:
<223> OTHER INFORMATION: synthetic DNA

<400> SEQUENCE: 1888
ggaagcgcct ctaacaaccg atgcttgtgg                                    30

<210> SEQ ID NO 1889
<211> LENGTH: 30
<212> TYPE: DNA
<213> ORGANISM: Artificial
<220> FEATURE:
<223> OTHER INFORMATION: synthetic DNA

<400> SEQUENCE: 1889
ctctagacgc gtcgtgactc caatctgttg                                    30

<210> SEQ ID NO 1890
<211> LENGTH: 30
<212> TYPE: DNA
<213> ORGANISM: Artificial
<220> FEATURE:
<223> OTHER INFORMATION: synthetic DNA

<400> SEQUENCE: 1890
gtagttcgtc ggagtgacct cgtactcact                                    30
```

<210> SEQ ID NO 1891
<211> LENGTH: 30
<212> TYPE: DNA
<213> ORGANISM: Artificial
<220> FEATURE:
<223> OTHER INFORMATION: synthetic DNA

<400> SEQUENCE: 1891
atgctgtcga gtgtccggca tagagcacac                                    30

<210> SEQ ID NO 1892
<211> LENGTH: 30
<212> TYPE: DNA
<213> ORGANISM: Artificial
<220> FEATURE:
<223> OTHER INFORMATION: synthetic DNA

<400> SEQUENCE: 1892
gcgcatcttg cagcgtcctg tagttctgaa                                    30

<210> SEQ ID NO 1893
<211> LENGTH: 30
<212> TYPE: DNA
<213> ORGANISM: Artificial
<220> FEATURE:
<223> OTHER INFORMATION: synthetic DNA

<400> SEQUENCE: 1893
gcgattgttg aggaaccaca gcggcaccta                                    30

<210> SEQ ID NO 1894
<211> LENGTH: 30
<212> TYPE: DNA
<213> ORGANISM: Artificial
<220> FEATURE:
<223> OTHER INFORMATION: synthetic DNA

<400> SEQUENCE: 1894
cacgcgtact ctgcttgctg tgtggtcggt                                    30

<210> SEQ ID NO 1895
<211> LENGTH: 30
<212> TYPE: DNA
<213> ORGANISM: Artificial
<220> FEATURE:
<223> OTHER INFORMATION: synthetic DNA

<400> SEQUENCE: 1895
catccaacgc aggacctagt agtcatgctt                                    30

<210> SEQ ID NO 1896
<211> LENGTH: 30
<212> TYPE: DNA
<213> ORGANISM: Artificial
<220> FEATURE:
<223> OTHER INFORMATION: synthetic DNA

<400> SEQUENCE: 1896
ttctagttgt gatgagaatc gctagcgtgc                                    30

<210> SEQ ID NO 1897
<211> LENGTH: 30
<212> TYPE: DNA
<213> ORGANISM: Artificial
<220> FEATURE:
<223> OTHER INFORMATION: synthetic DNA

```
<400> SEQUENCE: 1897
cattctgaat ctggtctctc tcgatcatcc                                30

<210> SEQ ID NO 1898
<211> LENGTH: 30
<212> TYPE: DNA
<213> ORGANISM: Artificial
<220> FEATURE:
<223> OTHER INFORMATION: synthetic DNA

<400> SEQUENCE: 1898
attaatgtag aggatagttc cgttctctcc                                30

<210> SEQ ID NO 1899
<211> LENGTH: 30
<212> TYPE: DNA
<213> ORGANISM: Artificial
<220> FEATURE:
<223> OTHER INFORMATION: synthetic DNA

<400> SEQUENCE: 1899
gtatcgcgct tacgaatgag gtgtggcttc                                30

<210> SEQ ID NO 1900
<211> LENGTH: 30
<212> TYPE: DNA
<213> ORGANISM: Artificial
<220> FEATURE:
<223> OTHER INFORMATION: synthetic DNA

<400> SEQUENCE: 1900
gctggtgaga gagccagatt atcggtggag                                30

<210> SEQ ID NO 1901
<211> LENGTH: 30
<212> TYPE: DNA
<213> ORGANISM: Artificial
<220> FEATURE:
<223> OTHER INFORMATION: synthetic DNA

<400> SEQUENCE: 1901
ggcacgagca ggtagaacta gaacctagat                                30

<210> SEQ ID NO 1902
<211> LENGTH: 30
<212> TYPE: DNA
<213> ORGANISM: Artificial
<220> FEATURE:
<223> OTHER INFORMATION: synthetic DNA

<400> SEQUENCE: 1902
tgtattatct cgaagcggtg cgttagagtc                                30

<210> SEQ ID NO 1903
<211> LENGTH: 30
<212> TYPE: DNA
<213> ORGANISM: Artificial
<220> FEATURE:
<223> OTHER INFORMATION: synthetic DNA

<400> SEQUENCE: 1903
cacgtgttct agctactaat ggcgtcaatt                                30

<210> SEQ ID NO 1904
```

```
<211> LENGTH: 30
<212> TYPE: DNA
<213> ORGANISM: Artificial
<220> FEATURE:
<223> OTHER INFORMATION: synthetic DNA

<400> SEQUENCE: 1904
cgcgctacat tacttcctac accatgcgta                                30

<210> SEQ ID NO 1905
<211> LENGTH: 30
<212> TYPE: DNA
<213> ORGANISM: Artificial
<220> FEATURE:
<223> OTHER INFORMATION: synthetic DNA

<400> SEQUENCE: 1905
tgaggcaact agtgttcgca agatgacgga                                30

<210> SEQ ID NO 1906
<211> LENGTH: 30
<212> TYPE: DNA
<213> ORGANISM: Artificial
<220> FEATURE:
<223> OTHER INFORMATION: synthetic DNA

<400> SEQUENCE: 1906
ttattattgt ctgtggaacg cacgccagtc                                30

<210> SEQ ID NO 1907
<211> LENGTH: 30
<212> TYPE: DNA
<213> ORGANISM: Artificial
<220> FEATURE:
<223> OTHER INFORMATION: synthetic DNA

<400> SEQUENCE: 1907
gctatagtat tatccatgaa ttccgtcggc                                30

<210> SEQ ID NO 1908
<211> LENGTH: 30
<212> TYPE: DNA
<213> ORGANISM: Artificial
<220> FEATURE:
<223> OTHER INFORMATION: synthetic DNA

<400> SEQUENCE: 1908
gtatcaatag ctcaattcgt cagagttgtg                                30

<210> SEQ ID NO 1909
<211> LENGTH: 30
<212> TYPE: DNA
<213> ORGANISM: Artificial
<220> FEATURE:
<223> OTHER INFORMATION: synthetic DNA

<400> SEQUENCE: 1909
tagtccatgc gtggatatat tgagagctga                                30

<210> SEQ ID NO 1910
<211> LENGTH: 30
<212> TYPE: DNA
<213> ORGANISM: Artificial
<220> FEATURE:
<223> OTHER INFORMATION: synthetic DNA

<400> SEQUENCE: 1910
```

```
gcacagtacg acttataaca ggtctagatc                                              30

<210> SEQ ID NO 1911
<211> LENGTH: 30
<212> TYPE: DNA
<213> ORGANISM: Artificial
<220> FEATURE:
<223> OTHER INFORMATION: synthetic DNA

<400> SEQUENCE: 1911
actcaatggt ggcacgctcg gcgcagcata                                              30

<210> SEQ ID NO 1912
<211> LENGTH: 30
<212> TYPE: DNA
<213> ORGANISM: Artificial
<220> FEATURE:
<223> OTHER INFORMATION: synthetic DNA

<400> SEQUENCE: 1912
gtagtaccac tccgccttag gcagcttaag                                              30

<210> SEQ ID NO 1913
<211> LENGTH: 30
<212> TYPE: DNA
<213> ORGANISM: Artificial
<220> FEATURE:
<223> OTHER INFORMATION: synthetic DNA

<400> SEQUENCE: 1913
cgctcaactg atgcgtgcaa ccaatgttat                                              30

<210> SEQ ID NO 1914
<211> LENGTH: 30
<212> TYPE: DNA
<213> ORGANISM: Artificial
<220> FEATURE:
<223> OTHER INFORMATION: synthetic DNA

<400> SEQUENCE: 1914
gcagcttgac tgcctagaca gcagttacag                                              30

<210> SEQ ID NO 1915
<211> LENGTH: 30
<212> TYPE: DNA
<213> ORGANISM: Artificial
<220> FEATURE:
<223> OTHER INFORMATION: synthetic DNA

<400> SEQUENCE: 1915
gcaacttctt agtacgaatt catcgtccaa                                              30

<210> SEQ ID NO 1916
<211> LENGTH: 30
<212> TYPE: DNA
<213> ORGANISM: Artificial
<220> FEATURE:
<223> OTHER INFORMATION: synthetic DNA

<400> SEQUENCE: 1916
atccgtatgc tgcggcagtg gaggtggctt                                              30

<210> SEQ ID NO 1917
<211> LENGTH: 30
<212> TYPE: DNA
```

```
<213> ORGANISM: Artificial
<220> FEATURE:
<223> OTHER INFORMATION: synthetic DNA

<400> SEQUENCE: 1917
tgcggatcaa tccagttctg tgtactgtga                                    30

<210> SEQ ID NO 1918
<211> LENGTH: 30
<212> TYPE: DNA
<213> ORGANISM: Artificial
<220> FEATURE:
<223> OTHER INFORMATION: synthetic DNA

<400> SEQUENCE: 1918
ttatgattat caccggcgta acattccgaa                                    30

<210> SEQ ID NO 1919
<211> LENGTH: 30
<212> TYPE: DNA
<213> ORGANISM: Artificial
<220> FEATURE:
<223> OTHER INFORMATION: synthetic DNA

<400> SEQUENCE: 1919
gctacctaga ttcttcaact catcgctacc                                    30

<210> SEQ ID NO 1920
<211> LENGTH: 30
<212> TYPE: DNA
<213> ORGANISM: Artificial
<220> FEATURE:
<223> OTHER INFORMATION: synthetic DNA

<400> SEQUENCE: 1920
cagtgttaga atggcggtgt gtagccgcta                                    30

<210> SEQ ID NO 1921
<211> LENGTH: 35
<212> TYPE: DNA
<213> ORGANISM: Artificial
<220> FEATURE:
<223> OTHER INFORMATION: synthetic DNA

<400> SEQUENCE: 1921
gcttatagac tacagctgcg aggtataagg tcact                              35

<210> SEQ ID NO 1922
<211> LENGTH: 35
<212> TYPE: DNA
<213> ORGANISM: Artificial
<220> FEATURE:
<223> OTHER INFORMATION: synthetic DNA

<400> SEQUENCE: 1922
cgctcagcag gatgctatcc taagttaatg tggtg                              35

<210> SEQ ID NO 1923
<211> LENGTH: 35
<212> TYPE: DNA
<213> ORGANISM: Artificial
<220> FEATURE:
<223> OTHER INFORMATION: synthetic DNA

<400> SEQUENCE: 1923
gaactgagcg gacatcagct aggcctacaa tacat                              35
```

<210> SEQ ID NO 1924
<211> LENGTH: 35
<212> TYPE: DNA
<213> ORGANISM: Artificial
<220> FEATURE:
<223> OTHER INFORMATION: synthetic DNA

<400> SEQUENCE: 1924
tcgtgaactt ctgcgttggt ctctaccaag gcggt                              35

<210> SEQ ID NO 1925
<211> LENGTH: 35
<212> TYPE: DNA
<213> ORGANISM: Artificial
<220> FEATURE:
<223> OTHER INFORMATION: synthetic DNA

<400> SEQUENCE: 1925
taagtcaggt atcttatcag tggtacacgg tacga                              35

<210> SEQ ID NO 1926
<211> LENGTH: 35
<212> TYPE: DNA
<213> ORGANISM: Artificial
<220> FEATURE:
<223> OTHER INFORMATION: synthetic DNA

<400> SEQUENCE: 1926
taataatgtt gcgcgtgacc gaggaggaat ccact                              35

<210> SEQ ID NO 1927
<211> LENGTH: 35
<212> TYPE: DNA
<213> ORGANISM: Artificial
<220> FEATURE:
<223> OTHER INFORMATION: synthetic DNA

<400> SEQUENCE: 1927
ctaggagttc tcgtaagctg gagtaccgta acgtg                              35

<210> SEQ ID NO 1928
<211> LENGTH: 35
<212> TYPE: DNA
<213> ORGANISM: Artificial
<220> FEATURE:
<223> OTHER INFORMATION: synthetic DNA

<400> SEQUENCE: 1928
ggactctcct cagaggatcc ttcttgcgca ggcat                              35

<210> SEQ ID NO 1929
<211> LENGTH: 35
<212> TYPE: DNA
<213> ORGANISM: Artificial
<220> FEATURE:
<223> OTHER INFORMATION: synthetic DNA

<400> SEQUENCE: 1929
gctagaggcc tgagtacacc ttctcgcatc aggat                              35

<210> SEQ ID NO 1930
<211> LENGTH: 35
<212> TYPE: DNA
<213> ORGANISM: Artificial
<220> FEATURE:

<223> OTHER INFORMATION: synthetic DNA

<400> SEQUENCE: 1930
atatcgcgag cactaacgtc gttgtcgttc tagga    35

<210> SEQ ID NO 1931
<211> LENGTH: 35
<212> TYPE: DNA
<213> ORGANISM: Artificial
<220> FEATURE:
<223> OTHER INFORMATION: synthetic DNA

<400> SEQUENCE: 1931
agcggttact atacctggcg gctgacgttg ttagt    35

<210> SEQ ID NO 1932
<211> LENGTH: 35
<212> TYPE: DNA
<213> ORGANISM: Artificial
<220> FEATURE:
<223> OTHER INFORMATION: synthetic DNA

<400> SEQUENCE: 1932
gagctaggta gatctccaag tgtagctaag aagag    35

<210> SEQ ID NO 1933
<211> LENGTH: 35
<212> TYPE: DNA
<213> ORGANISM: Artificial
<220> FEATURE:
<223> OTHER INFORMATION: synthetic DNA

<400> SEQUENCE: 1933
ggagtcgctg gtgacgtatg ccgaggatga gcttc    35

<210> SEQ ID NO 1934
<211> LENGTH: 35
<212> TYPE: DNA
<213> ORGANISM: Artificial
<220> FEATURE:
<223> OTHER INFORMATION: synthetic DNA

<400> SEQUENCE: 1934
cgccgacctc ctgttcacga agccgcctga tgtaa    35

<210> SEQ ID NO 1935
<211> LENGTH: 35
<212> TYPE: DNA
<213> ORGANISM: Artificial
<220> FEATURE:
<223> OTHER INFORMATION: synthetic DNA

<400> SEQUENCE: 1935
agtaggcact tagttatcga ttacgttagt tagtc    35

<210> SEQ ID NO 1936
<211> LENGTH: 35
<212> TYPE: DNA
<213> ORGANISM: Artificial
<220> FEATURE:
<223> OTHER INFORMATION: synthetic DNA

<400> SEQUENCE: 1936
ggatgacgtc tcagtctacc tcgcagtgtc gtcta    35

<210> SEQ ID NO 1937
<211> LENGTH: 35
<212> TYPE: DNA
<213> ORGANISM: Artificial
<220> FEATURE:
<223> OTHER INFORMATION: synthetic DNA

<400> SEQUENCE: 1937
ctggttcgcg ttagcaatac taaggcagtc aggag        35

<210> SEQ ID NO 1938
<211> LENGTH: 35
<212> TYPE: DNA
<213> ORGANISM: Artificial
<220> FEATURE:
<223> OTHER INFORMATION: synthetic DNA

<400> SEQUENCE: 1938
atatggtcat attggcctct tcgaacacag actgt        35

<210> SEQ ID NO 1939
<211> LENGTH: 35
<212> TYPE: DNA
<213> ORGANISM: Artificial
<220> FEATURE:
<223> OTHER INFORMATION: synthetic DNA

<400> SEQUENCE: 1939
tatcagagga tagcaggtct gagttgcaag gctaa        35

<210> SEQ ID NO 1940
<211> LENGTH: 35
<212> TYPE: DNA
<213> ORGANISM: Artificial
<220> FEATURE:
<223> OTHER INFORMATION: synthetic DNA

<400> SEQUENCE: 1940
ggtggtctga ccatagctgt tcttctcaca gagac        35

<210> SEQ ID NO 1941
<211> LENGTH: 35
<212> TYPE: DNA
<213> ORGANISM: Artificial
<220> FEATURE:
<223> OTHER INFORMATION: synthetic DNA

<400> SEQUENCE: 1941
gcaataccaa cgagatgagt attcgttgaa gctct        35

<210> SEQ ID NO 1942
<211> LENGTH: 35
<212> TYPE: DNA
<213> ORGANISM: Artificial
<220> FEATURE:
<223> OTHER INFORMATION: synthetic DNA

<400> SEQUENCE: 1942
ccaagtcgac gctgcatgaa tgagcgctat tcact        35

<210> SEQ ID NO 1943
<211> LENGTH: 35
<212> TYPE: DNA
<213> ORGANISM: Artificial
<220> FEATURE:
<223> OTHER INFORMATION: synthetic DNA

<400> SEQUENCE: 1943
ccattagatc gcttcgagac aattaggaga catga                           35

<210> SEQ ID NO 1944
<211> LENGTH: 35
<212> TYPE: DNA
<213> ORGANISM: Artificial
<220> FEATURE:
<223> OTHER INFORMATION: synthetic DNA

<400> SEQUENCE: 1944
gatgactgta cctcctatca ttgagtgtgg accaa                           35

<210> SEQ ID NO 1945
<211> LENGTH: 35
<212> TYPE: DNA
<213> ORGANISM: Artificial
<220> FEATURE:
<223> OTHER INFORMATION: synthetic DNA

<400> SEQUENCE: 1945
atatctggat gaatagtggt taggtaagca agtaa                           35

<210> SEQ ID NO 1946
<211> LENGTH: 35
<212> TYPE: DNA
<213> ORGANISM: Artificial
<220> FEATURE:
<223> OTHER INFORMATION: synthetic DNA

<400> SEQUENCE: 1946
accgactatg ttaattcgtg tctggatggc agaat                           35

<210> SEQ ID NO 1947
<211> LENGTH: 35
<212> TYPE: DNA
<213> ORGANISM: Artificial
<220> FEATURE:
<223> OTHER INFORMATION: synthetic DNA

<400> SEQUENCE: 1947
gtggcagtct tgctagtatc ttagaccatc accaa                           35

<210> SEQ ID NO 1948
<211> LENGTH: 35
<212> TYPE: DNA
<213> ORGANISM: Artificial
<220> FEATURE:
<223> OTHER INFORMATION: synthetic DNA

<400> SEQUENCE: 1948
cgctatctta gtcgagcaca atgtcttcgt atagg                           35

<210> SEQ ID NO 1949
<211> LENGTH: 35
<212> TYPE: DNA
<213> ORGANISM: Artificial
<220> FEATURE:
<223> OTHER INFORMATION: synthetic DNA

<400> SEQUENCE: 1949
attagtacgg cacgaaccgg ccattcatgg cagct                           35

<210> SEQ ID NO 1950
<211> LENGTH: 35

```
<212> TYPE: DNA
<213> ORGANISM: Artificial
<220> FEATURE:
<223> OTHER INFORMATION: synthetic DNA

<400> SEQUENCE: 1950
agtacgacta tcaagactcc agcgctctcc ttgga                                 35

<210> SEQ ID NO 1951
<211> LENGTH: 35
<212> TYPE: DNA
<213> ORGANISM: Artificial
<220> FEATURE:
<223> OTHER INFORMATION: synthetic DNA

<400> SEQUENCE: 1951
atgagcctcg gagcgaacgt tatcgatcag gctgt                                 35

<210> SEQ ID NO 1952
<211> LENGTH: 35
<212> TYPE: DNA
<213> ORGANISM: Artificial
<220> FEATURE:
<223> OTHER INFORMATION: synthetic DNA

<400> SEQUENCE: 1952
ttgcgtgcag tagcaccgat acacagcgct tgtat                                 35

<210> SEQ ID NO 1953
<211> LENGTH: 35
<212> TYPE: DNA
<213> ORGANISM: Artificial
<220> FEATURE:
<223> OTHER INFORMATION: synthetic DNA

<400> SEQUENCE: 1953
aacggctgca tcacctacac tatactcaac atcta                                 35

<210> SEQ ID NO 1954
<211> LENGTH: 35
<212> TYPE: DNA
<213> ORGANISM: Artificial
<220> FEATURE:
<223> OTHER INFORMATION: synthetic DNA

<400> SEQUENCE: 1954
gtcgctatgc gagaagtggc gtggaatgct atggt                                 35

<210> SEQ ID NO 1955
<211> LENGTH: 35
<212> TYPE: DNA
<213> ORGANISM: Artificial
<220> FEATURE:
<223> OTHER INFORMATION: synthetic DNA

<400> SEQUENCE: 1955
catggatacc tactgacttg acttctagag gaccg                                 35

<210> SEQ ID NO 1956
<211> LENGTH: 35
<212> TYPE: DNA
<213> ORGANISM: Artificial
<220> FEATURE:
<223> OTHER INFORMATION: synthetic DNA

<400> SEQUENCE: 1956
```
gagtgacgca gacaccgtaa cgtcgaatct tctag                                35

<210> SEQ ID NO 1957
<211> LENGTH: 35
<212> TYPE: DNA
<213> ORGANISM: Artificial
<220> FEATURE:
<223> OTHER INFORMATION: synthetic DNA

<400> SEQUENCE: 1957
agtaccgtct gtgtgaatat tgttcctacg ttaca                                35

<210> SEQ ID NO 1958
<211> LENGTH: 35
<212> TYPE: DNA
<213> ORGANISM: Artificial
<220> FEATURE:
<223> OTHER INFORMATION: synthetic DNA

<400> SEQUENCE: 1958
ggctaatcga tagtgacgag ttctgcacgc ctgaa                                35

<210> SEQ ID NO 1959
<211> LENGTH: 35
<212> TYPE: DNA
<213> ORGANISM: Artificial
<220> FEATURE:
<223> OTHER INFORMATION: synthetic DNA

<400> SEQUENCE: 1959
ggcgagcgct cgtggttctg agtcgctgtt agatg                                35

<210> SEQ ID NO 1960
<211> LENGTH: 35
<212> TYPE: DNA
<213> ORGANISM: Artificial
<220> FEATURE:
<223> OTHER INFORMATION: synthetic DNA

<400> SEQUENCE: 1960
tatctccagc gttataagct actggagccg ctcgg                                35

<210> SEQ ID NO 1961
<211> LENGTH: 35
<212> TYPE: DNA
<213> ORGANISM: Artificial
<220> FEATURE:
<223> OTHER INFORMATION: synthetic DNA

<400> SEQUENCE: 1961
ccttctgcgc aagtcaagga ttcgcttaga tggac                                35

<210> SEQ ID NO 1962
<211> LENGTH: 35
<212> TYPE: DNA
<213> ORGANISM: Artificial
<220> FEATURE:
<223> OTHER INFORMATION: synthetic DNA

<400> SEQUENCE: 1962
gttgctgaca gccgttgcgt acttgcctta agaac                                35

<210> SEQ ID NO 1963
<211> LENGTH: 35
<212> TYPE: DNA
<213> ORGANISM: Artificial
<220> FEATURE:
<223> OTHER INFORMATION: synthetic DNA

<400> SEQUENCE: 1963
gtggcctaat cactcgcgct tcataggccg atagg    35

<210> SEQ ID NO 1964
<211> LENGTH: 35
<212> TYPE: DNA
<213> ORGANISM: Artificial
<220> FEATURE:
<223> OTHER INFORMATION: synthetic DNA

<400> SEQUENCE: 1964
tgcatctagc ctacatcgga ccttgttatg gtaat    35

<210> SEQ ID NO 1965
<211> LENGTH: 35
<212> TYPE: DNA
<213> ORGANISM: Artificial
<220> FEATURE:
<223> OTHER INFORMATION: synthetic DNA

<400> SEQUENCE: 1965
ggacagctac tggacaccac cgaactggta gtgtc    35

<210> SEQ ID NO 1966
<211> LENGTH: 35
<212> TYPE: DNA
<213> ORGANISM: Artificial
<220> FEATURE:
<223> OTHER INFORMATION: synthetic DNA

<400> SEQUENCE: 1966
aactggcgat ggacggccgc tcttccgcta catag    35

<210> SEQ ID NO 1967
<211> LENGTH: 35
<212> TYPE: DNA
<213> ORGANISM: Artificial
<220> FEATURE:
<223> OTHER INFORMATION: synthetic DNA

<400> SEQUENCE: 1967
ggagcagtta gctatggagc aggccgataa cctga    35

<210> SEQ ID NO 1968
<211> LENGTH: 35
<212> TYPE: DNA
<213> ORGANISM: Artificial
<220> FEATURE:
<223> OTHER INFORMATION: synthetic DNA

<400> SEQUENCE: 1968
actctacggt gcacctcagc cttcatgcaa taggc    35

<210> SEQ ID NO 1969
<211> LENGTH: 35
<212> TYPE: DNA
<213> ORGANISM: Artificial
<220> FEATURE:
<223> OTHER INFORMATION: synthetic DNA

<400> SEQUENCE: 1969
cttgtagcac aatacattac tctccacgtg atagc    35

<210> SEQ ID NO 1970
<211> LENGTH: 35
<212> TYPE: DNA
<213> ORGANISM: Artificial
<220> FEATURE:
<223> OTHER INFORMATION: synthetic DNA

<400> SEQUENCE: 1970
ggacgctatc gataccgtta ttcctactct gtcgg         35

<210> SEQ ID NO 1971
<211> LENGTH: 35
<212> TYPE: DNA
<213> ORGANISM: Artificial
<220> FEATURE:
<223> OTHER INFORMATION: synthetic DNA

<400> SEQUENCE: 1971
ggatgatcgt caacgatcaa ctgacagtta gtcga         35

<210> SEQ ID NO 1972
<211> LENGTH: 35
<212> TYPE: DNA
<213> ORGANISM: Artificial
<220> FEATURE:
<223> OTHER INFORMATION: synthetic DNA

<400> SEQUENCE: 1972
tgacagtagc aatgtctcac gtctgcacaa cggaa         35

<210> SEQ ID NO 1973
<211> LENGTH: 35
<212> TYPE: DNA
<213> ORGANISM: Artificial
<220> FEATURE:
<223> OTHER INFORMATION: synthetic DNA

<400> SEQUENCE: 1973
gtcgcaggac ctcacggata gtagtgcgag gtcta         35

<210> SEQ ID NO 1974
<211> LENGTH: 35
<212> TYPE: DNA
<213> ORGANISM: Artificial
<220> FEATURE:
<223> OTHER INFORMATION: synthetic DNA

<400> SEQUENCE: 1974
atatcggcgg acgcaatgac agttgttggc tgatg         35

<210> SEQ ID NO 1975
<211> LENGTH: 35
<212> TYPE: DNA
<213> ORGANISM: Artificial
<220> FEATURE:
<223> OTHER INFORMATION: synthetic DNA

<400> SEQUENCE: 1975
aagcaccaag gaggtatgtt ccatcgaggc gctcg         35

<210> SEQ ID NO 1976
<211> LENGTH: 35
<212> TYPE: DNA
<213> ORGANISM: Artificial
<220> FEATURE:
<223> OTHER INFORMATION: synthetic DNA

```
<400> SEQUENCE: 1976
gaccgcacct tatagctata tcctggtcta gtact                                35

<210> SEQ ID NO 1977
<211> LENGTH: 35
<212> TYPE: DNA
<213> ORGANISM: Artificial
<220> FEATURE:
<223> OTHER INFORMATION: synthetic DNA

<400> SEQUENCE: 1977
tctcagagga aggttgagcg tctgaccagg ttggc                                35

<210> SEQ ID NO 1978
<211> LENGTH: 35
<212> TYPE: DNA
<213> ORGANISM: Artificial
<220> FEATURE:
<223> OTHER INFORMATION: synthetic DNA

<400> SEQUENCE: 1978
tggacctaga gacctagctc gtctcttcgc gatcg                                35

<210> SEQ ID NO 1979
<211> LENGTH: 35
<212> TYPE: DNA
<213> ORGANISM: Artificial
<220> FEATURE:
<223> OTHER INFORMATION: synthetic DNA

<400> SEQUENCE: 1979
cggagtggtt ccacgcgacc tcgcaactaa tcctt                                35

<210> SEQ ID NO 1980
<211> LENGTH: 35
<212> TYPE: DNA
<213> ORGANISM: Artificial
<220> FEATURE:
<223> OTHER INFORMATION: synthetic DNA

<400> SEQUENCE: 1980
ggagccgcgc gcagactgac cttgcttgat ctact                                35

<210> SEQ ID NO 1981
<211> LENGTH: 35
<212> TYPE: DNA
<213> ORGANISM: Artificial
<220> FEATURE:
<223> OTHER INFORMATION: synthetic DNA

<400> SEQUENCE: 1981
actctaagta tatgcgcagt tagtatactg aacca                                35

<210> SEQ ID NO 1982
<211> LENGTH: 35
<212> TYPE: DNA
<213> ORGANISM: Artificial
<220> FEATURE:
<223> OTHER INFORMATION: synthetic DNA

<400> SEQUENCE: 1982
gagcattgct tcgcttcgat gtctattctg atcag                                35

<210> SEQ ID NO 1983
```

<211> LENGTH: 35
<212> TYPE: DNA
<213> ORGANISM: Artificial
<220> FEATURE:
<223> OTHER INFORMATION: synthetic DNA

<400> SEQUENCE: 1983
gcttgtattg ccactcgagt aggtcgtggc agtag    35

<210> SEQ ID NO 1984
<211> LENGTH: 35
<212> TYPE: DNA
<213> ORGANISM: Artificial
<220> FEATURE:
<223> OTHER INFORMATION: synthetic DNA

<400> SEQUENCE: 1984
atctggacat tgcattcggt gtgtatacag aaggc    35

<210> SEQ ID NO 1985
<211> LENGTH: 35
<212> TYPE: DNA
<213> ORGANISM: Artificial
<220> FEATURE:
<223> OTHER INFORMATION: synthetic DNA

<400> SEQUENCE: 1985
ggttgcgatc agcttgatag caggtcatat cctca    35

<210> SEQ ID NO 1986
<211> LENGTH: 35
<212> TYPE: DNA
<213> ORGANISM: Artificial
<220> FEATURE:
<223> OTHER INFORMATION: synthetic DNA

<400> SEQUENCE: 1986
gcaggtacta acctgagatg cgtagctaac acagg    35

<210> SEQ ID NO 1987
<211> LENGTH: 35
<212> TYPE: DNA
<213> ORGANISM: Artificial
<220> FEATURE:
<223> OTHER INFORMATION: synthetic DNA

<400> SEQUENCE: 1987
atctgcaagg acgtaacgtc ctcggaaggt gaggt    35

<210> SEQ ID NO 1988
<211> LENGTH: 35
<212> TYPE: DNA
<213> ORGANISM: Artificial
<220> FEATURE:
<223> OTHER INFORMATION: synthetic DNA

<400> SEQUENCE: 1988
ataatcttac gagcctccag tgaataatgc aagca    35

<210> SEQ ID NO 1989
<211> LENGTH: 35
<212> TYPE: DNA
<213> ORGANISM: Artificial
<220> FEATURE:
<223> OTHER INFORMATION: synthetic DNA

<400> SEQUENCE: 1989
caatctccgc acagtcttgt tcaggtacag actta                35

<210> SEQ ID NO 1990
<211> LENGTH: 35
<212> TYPE: DNA
<213> ORGANISM: Artificial
<220> FEATURE:
<223> OTHER INFORMATION: synthetic DNA

<400> SEQUENCE: 1990
atgtgcgcaa ttcagcgtaa gtgcctattc ataat                35

<210> SEQ ID NO 1991
<211> LENGTH: 35
<212> TYPE: DNA
<213> ORGANISM: Artificial
<220> FEATURE:
<223> OTHER INFORMATION: synthetic DNA

<400> SEQUENCE: 1991
tcggacgcac acatcctgtt gtcgagaaga ggaag                35

<210> SEQ ID NO 1992
<211> LENGTH: 35
<212> TYPE: DNA
<213> ORGANISM: Artificial
<220> FEATURE:
<223> OTHER INFORMATION: synthetic DNA

<400> SEQUENCE: 1992
tcggaagcat cacatgagca tcaggagttc attgc                35

<210> SEQ ID NO 1993
<211> LENGTH: 35
<212> TYPE: DNA
<213> ORGANISM: Artificial
<220> FEATURE:
<223> OTHER INFORMATION: synthetic DNA

<400> SEQUENCE: 1993
atctggttgt ggacttctat acagtaccag agtgg                35

<210> SEQ ID NO 1994
<211> LENGTH: 35
<212> TYPE: DNA
<213> ORGANISM: Artificial
<220> FEATURE:
<223> OTHER INFORMATION: synthetic DNA

<400> SEQUENCE: 1994
cgtctgaata tagttagcta gtagtgtaat ccagg                35

<210> SEQ ID NO 1995
<211> LENGTH: 35
<212> TYPE: DNA
<213> ORGANISM: Artificial
<220> FEATURE:
<223> OTHER INFORMATION: synthetic DNA

<400> SEQUENCE: 1995
taatatctga tccgacctat tatctaggac tactc                35

<210> SEQ ID NO 1996
<211> LENGTH: 35
<212> TYPE: DNA

```
<213> ORGANISM: Artificial
<220> FEATURE:
<223> OTHER INFORMATION: synthetic DNA

<400> SEQUENCE: 1996
tatgcggccg tccgtacctc gtctgcttca gttgg                      35

<210> SEQ ID NO 1997
<211> LENGTH: 35
<212> TYPE: DNA
<213> ORGANISM: Artificial
<220> FEATURE:
<223> OTHER INFORMATION: synthetic DNA

<400> SEQUENCE: 1997
tggctcaagt tccatattgc caagacgacc tggag                      35

<210> SEQ ID NO 1998
<211> LENGTH: 35
<212> TYPE: DNA
<213> ORGANISM: Artificial
<220> FEATURE:
<223> OTHER INFORMATION: synthetic DNA

<400> SEQUENCE: 1998
gcagttctgc taggcggtcc gaggcaattg aagag                      35

<210> SEQ ID NO 1999
<211> LENGTH: 35
<212> TYPE: DNA
<213> ORGANISM: Artificial
<220> FEATURE:
<223> OTHER INFORMATION: synthetic DNA

<400> SEQUENCE: 1999
catggcacag acgaagtatg caccacgctc attaa                      35

<210> SEQ ID NO 2000
<211> LENGTH: 35
<212> TYPE: DNA
<213> ORGANISM: Artificial
<220> FEATURE:
<223> OTHER INFORMATION: synthetic DNA

<400> SEQUENCE: 2000
ggagcgtact acgaccattc aaccgaatat gttac                      35

<210> SEQ ID NO 2001
<211> LENGTH: 35
<212> TYPE: DNA
<213> ORGANISM: Artificial
<220> FEATURE:
<223> OTHER INFORMATION: synthetic DNA

<400> SEQUENCE: 2001
gcgtagatct cgcgacagag acaaggtgcg aatgg                      35

<210> SEQ ID NO 2002
<211> LENGTH: 35
<212> TYPE: DNA
<213> ORGANISM: Artificial
<220> FEATURE:
<223> OTHER INFORMATION: synthetic DNA

<400> SEQUENCE: 2002
tggactgagg ttctccggtc tatactcctg tagga                      35
```

<210> SEQ ID NO 2003
<211> LENGTH: 35
<212> TYPE: DNA
<213> ORGANISM: Artificial
<220> FEATURE:
<223> OTHER INFORMATION: synthetic DNA

<400> SEQUENCE: 2003
tggctatagc aacggcttct tgtgatcgca ttgca                          35

<210> SEQ ID NO 2004
<211> LENGTH: 35
<212> TYPE: DNA
<213> ORGANISM: Artificial
<220> FEATURE:
<223> OTHER INFORMATION: synthetic DNA

<400> SEQUENCE: 2004
ggcgaagaat catgcgagac ggagtagacg gacgt                          35

<210> SEQ ID NO 2005
<211> LENGTH: 35
<212> TYPE: DNA
<213> ORGANISM: Artificial
<220> FEATURE:
<223> OTHER INFORMATION: synthetic DNA

<400> SEQUENCE: 2005
gagcattgcg agttgcacac gtgatatcag actgt                          35

<210> SEQ ID NO 2006
<211> LENGTH: 35
<212> TYPE: DNA
<213> ORGANISM: Artificial
<220> FEATURE:
<223> OTHER INFORMATION: synthetic DNA

<400> SEQUENCE: 2006
ctgttgacct atgccagaat caatacctca gatta                          35

<210> SEQ ID NO 2007
<211> LENGTH: 35
<212> TYPE: DNA
<213> ORGANISM: Artificial
<220> FEATURE:
<223> OTHER INFORMATION: synthetic DNA

<400> SEQUENCE: 2007
gttaacaagt agatgccaag atacaacgag agacc                          35

<210> SEQ ID NO 2008
<211> LENGTH: 35
<212> TYPE: DNA
<213> ORGANISM: Artificial
<220> FEATURE:
<223> OTHER INFORMATION: synthetic DNA

<400> SEQUENCE: 2008
gagcaagatt atagttagga agatagttaa ctcgc                          35

<210> SEQ ID NO 2009
<211> LENGTH: 35
<212> TYPE: DNA
<213> ORGANISM: Artificial
<220> FEATURE:

<223> OTHER INFORMATION: synthetic DNA

<400> SEQUENCE: 2009
tccggagtcg agcatatgtg accaactctc aacgc                                    35

<210> SEQ ID NO 2010
<211> LENGTH: 35
<212> TYPE: DNA
<213> ORGANISM: Artificial
<220> FEATURE:
<223> OTHER INFORMATION: synthetic DNA

<400> SEQUENCE: 2010
ggagctgcga tgccgttacc gacgtcatct tcaag                                    35

<210> SEQ ID NO 2011
<211> LENGTH: 35
<212> TYPE: DNA
<213> ORGANISM: Artificial
<220> FEATURE:
<223> OTHER INFORMATION: synthetic DNA

<400> SEQUENCE: 2011
gctctatctt acacattggc gtactggact cgcga                                    35

<210> SEQ ID NO 2012
<211> LENGTH: 35
<212> TYPE: DNA
<213> ORGANISM: Artificial
<220> FEATURE:
<223> OTHER INFORMATION: synthetic DNA

<400> SEQUENCE: 2012
ttctacatat tcatcgccta ccgagttgcg cgaag                                    35

<210> SEQ ID NO 2013
<211> LENGTH: 35
<212> TYPE: DNA
<213> ORGANISM: Artificial
<220> FEATURE:
<223> OTHER INFORMATION: synthetic DNA

<400> SEQUENCE: 2013
tggacgtctg acctgtgtct acatcggtgg tgcta                                    35

<210> SEQ ID NO 2014
<211> LENGTH: 35
<212> TYPE: DNA
<213> ORGANISM: Artificial
<220> FEATURE:
<223> OTHER INFORMATION: synthetic DNA

<400> SEQUENCE: 2014
ggcaggacag ctccgtgttc tactcgaacc gcact                                    35

<210> SEQ ID NO 2015
<211> LENGTH: 35
<212> TYPE: DNA
<213> ORGANISM: Artificial
<220> FEATURE:
<223> OTHER INFORMATION: synthetic DNA

<400> SEQUENCE: 2015
tgacaacctc atgtctccga ccgcaggcat acaat                                    35

```
<210> SEQ ID NO 2016
<211> LENGTH: 35
<212> TYPE: DNA
<213> ORGANISM: Artificial
<220> FEATURE:
<223> OTHER INFORMATION: synthetic DNA

<400> SEQUENCE: 2016
gcaggcctaa caagtggtca cgaggagtcc ttatt                          35

<210> SEQ ID NO 2017
<211> LENGTH: 90
<212> TYPE: DNA
<213> ORGANISM: Artificial
<220> FEATURE:
<223> OTHER INFORMATION: synthetic DNA

<400> SEQUENCE: 2017
cccatacaca caccatgaag cttgaactaa ttaacattct caaactaatt aacaagcatg  60
caagcatgtt tttacacaat gacaatatat                                  90

<210> SEQ ID NO 2018
<211> LENGTH: 90
<212> TYPE: DNA
<213> ORGANISM: Artificial
<220> FEATURE:
<223> OTHER INFORMATION: synthetic DNA

<400> SEQUENCE: 2018
atgggtgagg gcgcagaggc aaagacatgg aggtccggaa gggtagaagc tcacatcaag  60
tcgagtatgt tgaatgcaat cccatatata                                  90

<210> SEQ ID NO 2019
<211> LENGTH: 24
<212> TYPE: DNA
<213> ORGANISM: Artificial
<220> FEATURE:
<223> OTHER INFORMATION: synthetic DNA

<400> SEQUENCE: 2019
cccatacaca caccatgaag cttg                                        24

<210> SEQ ID NO 2020
<211> LENGTH: 24
<212> TYPE: DNA
<213> ORGANISM: Artificial
<220> FEATURE:
<223> OTHER INFORMATION: synthetic DNA

<400> SEQUENCE: 2020
ggtagaagct cacatcaagt cgag                                        24

<210> SEQ ID NO 2021
<211> LENGTH: 90
<212> TYPE: DNA
<213> ORGANISM: Artificial
<220> FEATURE:
<223> OTHER INFORMATION: synthetic DNA

<400> SEQUENCE: 2021
aatcacagaa cgaggtctgg acgagaacag agctggacat ctacacgcac cgcatggtag  60
tagagcatgt actgcaaaag cttgaagcgc                                  90

<210> SEQ ID NO 2022
```

```
<211> LENGTH: 90
<212> TYPE: DNA
<213> ORGANISM: Artificial
<220> FEATURE:
<223> OTHER INFORMATION: synthetic DNA

<400> SEQUENCE: 2022
gatgctgagg gcgaagttgt cagccaagtc ctcaatgtca taggcgagat cgcagtagtt    60
ctgtaaccat tccctgctaa actggtccat                                     90

<210> SEQ ID NO 2023
<211> LENGTH: 24
<212> TYPE: DNA
<213> ORGANISM: Artificial
<220> FEATURE:
<223> OTHER INFORMATION: synthetic DNA

<400> SEQUENCE: 2023
acgagaacag agctggacat ctac                                           24

<210> SEQ ID NO 2024
<211> LENGTH: 24
<212> TYPE: DNA
<213> ORGANISM: Artificial
<220> FEATURE:
<223> OTHER INFORMATION: synthetic DNA

<400> SEQUENCE: 2024
tcaatgtcat aggcgagatc gcag                                           24

<210> SEQ ID NO 2025
<211> LENGTH: 90
<212> TYPE: DNA
<213> ORGANISM: Artificial
<220> FEATURE:
<223> OTHER INFORMATION: synthetic DNA

<400> SEQUENCE: 2025
agaccaacaa gcagcaagta gtcagagaag tacaagagaa ggagagcaag aaggatagta    60
agttgcaagc ttaccgttac aaagatgata                                     90

<210> SEQ ID NO 2026
<211> LENGTH: 90
<212> TYPE: DNA
<213> ORGANISM: Artificial
<220> FEATURE:
<223> OTHER INFORMATION: synthetic DNA

<400> SEQUENCE: 2026
ggaggagcac aactaggcgt ttatcaagat gggtcatcga gctcttggtg tcttcaacct    60
tcttgacatc aacttctcca atcttcgtct                                     90

<210> SEQ ID NO 2027
<211> LENGTH: 26
<212> TYPE: DNA
<213> ORGANISM: Artificial
<220> FEATURE:
<223> OTHER INFORMATION: synthetic DNA

<400> SEQUENCE: 2027
ggagagcaag aaggatagta agttgc                                         26

<210> SEQ ID NO 2028
<211> LENGTH: 25
```

```
<212> TYPE: DNA
<213> ORGANISM: Artificial
<220> FEATURE:
<223> OTHER INFORMATION: synthetic DNA

<400> SEQUENCE: 2028
cgagctcttg gtgtcttcaa ccttc                                           25

<210> SEQ ID NO 2029
<211> LENGTH: 90
<212> TYPE: DNA
<213> ORGANISM: Artificial
<220> FEATURE:
<223> OTHER INFORMATION: synthetic DNA

<400> SEQUENCE: 2029
tggggtagtc ctgaagctct aggtatgcct cttcatctcc ctgcacctct ggtgctagca     60
cctcctgctc ttcgggcacc tctaccgggg                                      90

<210> SEQ ID NO 2030
<211> LENGTH: 90
<212> TYPE: DNA
<213> ORGANISM: Artificial
<220> FEATURE:
<223> OTHER INFORMATION: synthetic DNA

<400> SEQUENCE: 2030
ggatactgat gtagctttca cccgggagta ttccaaggta tcgattttcc acggggaacg     60
cgaagtgcac tagttgaggt ttagattgcc                                      90

<210> SEQ ID NO 2031
<211> LENGTH: 25
<212> TYPE: DNA
<213> ORGANISM: Artificial
<220> FEATURE:
<223> OTHER INFORMATION: synthetic DNA

<400> SEQUENCE: 2031
gaagctctag gtatgcctct tcatc                                           25

<210> SEQ ID NO 2032
<211> LENGTH: 25
<212> TYPE: DNA
<213> ORGANISM: Artificial
<220> FEATURE:
<223> OTHER INFORMATION: synthetic DNA

<400> SEQUENCE: 2032
gtgcactagt tgaggtttag attgc                                           25

<210> SEQ ID NO 2033
<211> LENGTH: 90
<212> TYPE: DNA
<213> ORGANISM: Artificial
<220> FEATURE:
<223> OTHER INFORMATION: synthetic DNA

<400> SEQUENCE: 2033
tcgggaaaac gaacgggcga actacagatg tcagtacgaa gtagtctatg gcaggaaata     60
cgtagtccat acgtggtgcc agcccaagcc                                      90

<210> SEQ ID NO 2034
<211> LENGTH: 90
<212> TYPE: DNA
```

```
<213> ORGANISM: Artificial
<220> FEATURE:
<223> OTHER INFORMATION: synthetic DNA

<400> SEQUENCE: 2034
agcaggaggg agaaaggaaa cgtggcattc atcggctgtc tgccattgcc atgtgagaca      60
aggaaatcta cttcaccccc atctatcgag                                      90

<210> SEQ ID NO 2035
<211> LENGTH: 24
<212> TYPE: DNA
<213> ORGANISM: Artificial
<220> FEATURE:
<223> OTHER INFORMATION: synthetic DNA

<400> SEQUENCE: 2035
gggcgaacta cagatgtcag tacg                                            24

<210> SEQ ID NO 2036
<211> LENGTH: 24
<212> TYPE: DNA
<213> ORGANISM: Artificial
<220> FEATURE:
<223> OTHER INFORMATION: synthetic DNA

<400> SEQUENCE: 2036
ctgtctgcca ttgccatgtg agac                                            24

<210> SEQ ID NO 2037
<211> LENGTH: 90
<212> TYPE: DNA
<213> ORGANISM: Artificial
<220> FEATURE:
<223> OTHER INFORMATION: synthetic DNA

<400> SEQUENCE: 2037
agacataaga ttaactatga acaaattcac gggtccgatt cctttgggat ttgcagcttg      60
caagaacctt caaatactca ttatatcttc                                      90

<210> SEQ ID NO 2038
<211> LENGTH: 90
<212> TYPE: DNA
<213> ORGANISM: Artificial
<220> FEATURE:
<223> OTHER INFORMATION: synthetic DNA

<400> SEQUENCE: 2038
ttaagttgca gaatttgata cgaagaactt gaagcatggt gaggttgccg agctcattgg      60
ggatggttcc agaaaggcta ttgtagctta                                      90

<210> SEQ ID NO 2039
<211> LENGTH: 24
<212> TYPE: DNA
<213> ORGANISM: Artificial
<220> FEATURE:
<223> OTHER INFORMATION: synthetic DNA

<400> SEQUENCE: 2039
gaacaaattc acgggtccga ttcc                                            24

<210> SEQ ID NO 2040
<211> LENGTH: 24
<212> TYPE: DNA
<213> ORGANISM: Artificial
```

```
<220> FEATURE:
<223> OTHER INFORMATION: synthetic DNA

<400> SEQUENCE: 2040
cgaagaactt gaagcatggt gagg                                            24

<210> SEQ ID NO 2041
<211> LENGTH: 10
<212> TYPE: DNA
<213> ORGANISM: Artificial
<220> FEATURE:
<223> OTHER INFORMATION: synthetic DNA

<400> SEQUENCE: 2041
gttacacacg                                                            10

<210> SEQ ID NO 2042
<211> LENGTH: 70
<212> TYPE: DNA
<213> ORGANISM: Artificial
<220> FEATURE:
<223> OTHER INFORMATION: synthetic DNA

<400> SEQUENCE: 2042
aatgatacgg cgaccaccga gatctacacc tctctattcg tcggcagcgt cagatgtgta     60
taagagacag                                                            70

<210> SEQ ID NO 2043
<211> LENGTH: 66
<212> TYPE: DNA
<213> ORGANISM: Artificial
<220> FEATURE:
<223> OTHER INFORMATION: synthetic DNA

<400> SEQUENCE: 2043
caagcagaag acggcatacg agattaaggc gagtctcgtg ggctcggaga tgtgtataag     60
agacag                                                                66

<210> SEQ ID NO 2044
<211> LENGTH: 12
<212> TYPE: DNA
<213> ORGANISM: Artificial
<220> FEATURE:
<223> OTHER INFORMATION: synthetic DNA

<400> SEQUENCE: 2044
taagagacag aa                                                         12

<210> SEQ ID NO 2045
<211> LENGTH: 12
<212> TYPE: DNA
<213> ORGANISM: Artificial
<220> FEATURE:
<223> OTHER INFORMATION: synthetic DNA

<400> SEQUENCE: 2045
taagagacag at                                                         12

<210> SEQ ID NO 2046
<211> LENGTH: 12
<212> TYPE: DNA
<213> ORGANISM: Artificial
<220> FEATURE:
<223> OTHER INFORMATION: synthetic DNA
```

```
<400> SEQUENCE: 2046
taagagacag ac                                                    12

<210> SEQ ID NO 2047
<211> LENGTH: 12
<212> TYPE: DNA
<213> ORGANISM: Artificial
<220> FEATURE:
<223> OTHER INFORMATION: synthetic DNA

<400> SEQUENCE: 2047
taagagacag ag                                                    12

<210> SEQ ID NO 2048
<211> LENGTH: 12
<212> TYPE: DNA
<213> ORGANISM: Artificial
<220> FEATURE:
<223> OTHER INFORMATION: synthetic DNA

<400> SEQUENCE: 2048
taagagacag ta                                                    12

<210> SEQ ID NO 2049
<211> LENGTH: 12
<212> TYPE: DNA
<213> ORGANISM: Artificial
<220> FEATURE:
<223> OTHER INFORMATION: synthetic DNA

<400> SEQUENCE: 2049
taagagacag tt                                                    12

<210> SEQ ID NO 2050
<211> LENGTH: 12
<212> TYPE: DNA
<213> ORGANISM: Artificial
<220> FEATURE:
<223> OTHER INFORMATION: synthetic DNA

<400> SEQUENCE: 2050
taagagacag tc                                                    12

<210> SEQ ID NO 2051
<211> LENGTH: 12
<212> TYPE: DNA
<213> ORGANISM: Artificial
<220> FEATURE:
<223> OTHER INFORMATION: synthetic DNA

<400> SEQUENCE: 2051
taagagacag tg                                                    12

<210> SEQ ID NO 2052
<211> LENGTH: 12
<212> TYPE: DNA
<213> ORGANISM: Artificial
<220> FEATURE:
<223> OTHER INFORMATION: synthetic DNA

<400> SEQUENCE: 2052
taagagacag ca                                                    12

<210> SEQ ID NO 2053
<211> LENGTH: 12
```

```
<212> TYPE: DNA
<213> ORGANISM: Artificial
<220> FEATURE:
<223> OTHER INFORMATION: synthetic DNA

<400> SEQUENCE: 2053
taagagacag ct                                                              12

<210> SEQ ID NO 2054
<211> LENGTH: 12
<212> TYPE: DNA
<213> ORGANISM: Artificial
<220> FEATURE:
<223> OTHER INFORMATION: synthetic DNA

<400> SEQUENCE: 2054
taagagacag cc                                                              12

<210> SEQ ID NO 2055
<211> LENGTH: 12
<212> TYPE: DNA
<213> ORGANISM: Artificial
<220> FEATURE:
<223> OTHER INFORMATION: synthetic DNA

<400> SEQUENCE: 2055
taagagacag cg                                                              12

<210> SEQ ID NO 2056
<211> LENGTH: 12
<212> TYPE: DNA
<213> ORGANISM: Artificial
<220> FEATURE:
<223> OTHER INFORMATION: synthetic DNA

<400> SEQUENCE: 2056
taagagacag ga                                                              12

<210> SEQ ID NO 2057
<211> LENGTH: 12
<212> TYPE: DNA
<213> ORGANISM: Artificial
<220> FEATURE:
<223> OTHER INFORMATION: synthetic DNA

<400> SEQUENCE: 2057
taagagacag gt                                                              12

<210> SEQ ID NO 2058
<211> LENGTH: 12
<212> TYPE: DNA
<213> ORGANISM: Artificial
<220> FEATURE:
<223> OTHER INFORMATION: synthetic DNA

<400> SEQUENCE: 2058
taagagacag gc                                                              12

<210> SEQ ID NO 2059
<211> LENGTH: 12
<212> TYPE: DNA
<213> ORGANISM: Artificial
<220> FEATURE:
<223> OTHER INFORMATION: synthetic DNA

<400> SEQUENCE: 2059
```

| | |
|---|---|
| taagagacag gg | 12 |

```
<210> SEQ ID NO 2060
<211> LENGTH: 12
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (11)..(12)
<223> OTHER INFORMATION: n is a, c, g, or t

<400> SEQUENCE: 2060
```

| | |
|---|---|
| taagagacag nn | 12 |

```
<210> SEQ ID NO 2061
<211> LENGTH: 13
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (11)..(13)
<223> OTHER INFORMATION: n is a, c, g, or t

<400> SEQUENCE: 2061
```

| | |
|---|---|
| taagagacag nnn | 13 |

```
<210> SEQ ID NO 2062
<211> LENGTH: 10
<212> TYPE: DNA
<213> ORGANISM: Artificial
<220> FEATURE:
<223> OTHER INFORMATION: synthetic DNA

<400> SEQUENCE: 2062
```

| | |
|---|---|
| taagagacag | 10 |

```
<210> SEQ ID NO 2063
<211> LENGTH: 12
<212> TYPE: DNA
<213> ORGANISM: Artificial
<220> FEATURE:
<223> OTHER INFORMATION: synthetic DNA

<400> SEQUENCE: 2063
```

| | |
|---|---|
| taagagacag tg | 12 |

```
<210> SEQ ID NO 2064
<211> LENGTH: 13
<212> TYPE: DNA
<213> ORGANISM: Artificial
<220> FEATURE:
<223> OTHER INFORMATION: synthetic DNA

<400> SEQUENCE: 2064
```

| | |
|---|---|
| taagagacag tgc | 13 |

```
<210> SEQ ID NO 2065
<211> LENGTH: 12
<212> TYPE: DNA
<213> ORGANISM: Artificial
<220> FEATURE:
<223> OTHER INFORMATION: synthetic DNA

<400> SEQUENCE: 2065
```
taagagacag aa                                                    12

<210> SEQ ID NO 2066
<211> LENGTH: 12
<212> TYPE: DNA
<213> ORGANISM: Artificial
<220> FEATURE:
<223> OTHER INFORMATION: synthetic DNA

<400> SEQUENCE: 2066
taagagacag at                                                    12

<210> SEQ ID NO 2067
<211> LENGTH: 12
<212> TYPE: DNA
<213> ORGANISM: Artificial
<220> FEATURE:
<223> OTHER INFORMATION: synthetic DNA

<400> SEQUENCE: 2067
taagagacag ac                                                    12

<210> SEQ ID NO 2068
<211> LENGTH: 12
<212> TYPE: DNA
<213> ORGANISM: Artificial
<220> FEATURE:
<223> OTHER INFORMATION: synthetic DNA

<400> SEQUENCE: 2068
taagagacag ag                                                    12

<210> SEQ ID NO 2069
<211> LENGTH: 12
<212> TYPE: DNA
<213> ORGANISM: Artificial
<220> FEATURE:
<223> OTHER INFORMATION: synthetic DNA

<400> SEQUENCE: 2069
taagagacag ta                                                    12

<210> SEQ ID NO 2070
<211> LENGTH: 12
<212> TYPE: DNA
<213> ORGANISM: Artificial
<220> FEATURE:
<223> OTHER INFORMATION: synthetic DNA

<400> SEQUENCE: 2070
taagagacag tt                                                    12

<210> SEQ ID NO 2071
<211> LENGTH: 12
<212> TYPE: DNA
<213> ORGANISM: Artificial
<220> FEATURE:
<223> OTHER INFORMATION: synthetic DNA

<400> SEQUENCE: 2071
taagagacag tc                                                    12

<210> SEQ ID NO 2072
<211> LENGTH: 12
<212> TYPE: DNA

```
<213> ORGANISM: Artificial
<220> FEATURE:
<223> OTHER INFORMATION: synthetic DNA

<400> SEQUENCE: 2072
taagagacag ca                                                          12

<210> SEQ ID NO 2073
<211> LENGTH: 12
<212> TYPE: DNA
<213> ORGANISM: Artificial
<220> FEATURE:
<223> OTHER INFORMATION: synthetic DNA

<400> SEQUENCE: 2073
taagagacag ct                                                          12

<210> SEQ ID NO 2074
<211> LENGTH: 12
<212> TYPE: DNA
<213> ORGANISM: Artificial
<220> FEATURE:
<223> OTHER INFORMATION: synthetic DNA

<400> SEQUENCE: 2074
taagagacag cc                                                          12

<210> SEQ ID NO 2075
<211> LENGTH: 12
<212> TYPE: DNA
<213> ORGANISM: Artificial
<220> FEATURE:
<223> OTHER INFORMATION: synthetic DNA

<400> SEQUENCE: 2075
taagagacag cg                                                          12

<210> SEQ ID NO 2076
<211> LENGTH: 12
<212> TYPE: DNA
<213> ORGANISM: Artificial
<220> FEATURE:
<223> OTHER INFORMATION: synthetic DNA

<400> SEQUENCE: 2076
taagagacag ga                                                          12

<210> SEQ ID NO 2077
<211> LENGTH: 12
<212> TYPE: DNA
<213> ORGANISM: Artificial
<220> FEATURE:
<223> OTHER INFORMATION: synthetic DNA

<400> SEQUENCE: 2077
taagagacag gt                                                          12

<210> SEQ ID NO 2078
<211> LENGTH: 12
<212> TYPE: DNA
<213> ORGANISM: Artificial
<220> FEATURE:
<223> OTHER INFORMATION: synthetic DNA

<400> SEQUENCE: 2078
taagagacag gc                                                          12
```

```
<210> SEQ ID NO 2079
<211> LENGTH: 12
<212> TYPE: DNA
<213> ORGANISM: Artificial
<220> FEATURE:
<223> OTHER INFORMATION: synthetic DNA

<400> SEQUENCE: 2079
taagagacag gg                                                        12

<210> SEQ ID NO 2080
<211> LENGTH: 13
<212> TYPE: DNA
<213> ORGANISM: Artificial
<220> FEATURE:
<223> OTHER INFORMATION: synthetic DNA

<400> SEQUENCE: 2080
taagagacag aaa                                                       13

<210> SEQ ID NO 2081
<211> LENGTH: 13
<212> TYPE: DNA
<213> ORGANISM: Artificial
<220> FEATURE:
<223> OTHER INFORMATION: synthetic DNA

<400> SEQUENCE: 2081
taagagacag aac                                                       13

<210> SEQ ID NO 2082
<211> LENGTH: 13
<212> TYPE: DNA
<213> ORGANISM: Artificial
<220> FEATURE:
<223> OTHER INFORMATION: synthetic DNA

<400> SEQUENCE: 2082
taagagacag aag                                                       13

<210> SEQ ID NO 2083
<211> LENGTH: 13
<212> TYPE: DNA
<213> ORGANISM: Artificial
<220> FEATURE:
<223> OTHER INFORMATION: synthetic DNA

<400> SEQUENCE: 2083
taagagacag aat                                                       13

<210> SEQ ID NO 2084
<211> LENGTH: 13
<212> TYPE: DNA
<213> ORGANISM: Artificial
<220> FEATURE:
<223> OTHER INFORMATION: synthetic DNA

<400> SEQUENCE: 2084
taagagacag aca                                                       13

<210> SEQ ID NO 2085
<211> LENGTH: 13
<212> TYPE: DNA
<213> ORGANISM: Artificial
<220> FEATURE:
```

<223> OTHER INFORMATION: synthetic DNA

<400> SEQUENCE: 2085
taagagacag acc                                                          13

<210> SEQ ID NO 2086
<211> LENGTH: 13
<212> TYPE: DNA
<213> ORGANISM: Artificial
<220> FEATURE:
<223> OTHER INFORMATION: synthetic DNA

<400> SEQUENCE: 2086
taagagacag acg                                                          13

<210> SEQ ID NO 2087
<211> LENGTH: 13
<212> TYPE: DNA
<213> ORGANISM: Artificial
<220> FEATURE:
<223> OTHER INFORMATION: synthetic DNA

<400> SEQUENCE: 2087
taagagacag act                                                          13

<210> SEQ ID NO 2088
<211> LENGTH: 13
<212> TYPE: DNA
<213> ORGANISM: Artificial
<220> FEATURE:
<223> OTHER INFORMATION: synthetic DNA

<400> SEQUENCE: 2088
taagagacag aga                                                          13

<210> SEQ ID NO 2089
<211> LENGTH: 13
<212> TYPE: DNA
<213> ORGANISM: Artificial
<220> FEATURE:
<223> OTHER INFORMATION: synthetic DNA

<400> SEQUENCE: 2089
taagagacag agc                                                          13

<210> SEQ ID NO 2090
<211> LENGTH: 13
<212> TYPE: DNA
<213> ORGANISM: Artificial
<220> FEATURE:
<223> OTHER INFORMATION: synthetic DNA

<400> SEQUENCE: 2090
taagagacag agg                                                          13

<210> SEQ ID NO 2091
<211> LENGTH: 13
<212> TYPE: DNA
<213> ORGANISM: Artificial
<220> FEATURE:
<223> OTHER INFORMATION: synthetic DNA

<400> SEQUENCE: 2091
taagagacag agt                                                          13

```
<210> SEQ ID NO 2092
<211> LENGTH: 13
<212> TYPE: DNA
<213> ORGANISM: Artificial
<220> FEATURE:
<223> OTHER INFORMATION: synthetic DNA

<400> SEQUENCE: 2092
taagagacag ata                                                        13

<210> SEQ ID NO 2093
<211> LENGTH: 13
<212> TYPE: DNA
<213> ORGANISM: Artificial
<220> FEATURE:
<223> OTHER INFORMATION: synthetic DNA

<400> SEQUENCE: 2093
taagagacag atc                                                        13

<210> SEQ ID NO 2094
<211> LENGTH: 13
<212> TYPE: DNA
<213> ORGANISM: Artificial
<220> FEATURE:
<223> OTHER INFORMATION: synthetic DNA

<400> SEQUENCE: 2094
taagagacag atg                                                        13

<210> SEQ ID NO 2095
<211> LENGTH: 13
<212> TYPE: DNA
<213> ORGANISM: Artificial
<220> FEATURE:
<223> OTHER INFORMATION: synthetic DNA

<400> SEQUENCE: 2095
taagagacag att                                                        13

<210> SEQ ID NO 2096
<211> LENGTH: 13
<212> TYPE: DNA
<213> ORGANISM: Artificial
<220> FEATURE:
<223> OTHER INFORMATION: synthetic DNA

<400> SEQUENCE: 2096
taagagacag caa                                                        13

<210> SEQ ID NO 2097
<211> LENGTH: 13
<212> TYPE: DNA
<213> ORGANISM: Artificial
<220> FEATURE:
<223> OTHER INFORMATION: synthetic DNA

<400> SEQUENCE: 2097
taagagacag cac                                                        13

<210> SEQ ID NO 2098
<211> LENGTH: 13
<212> TYPE: DNA
<213> ORGANISM: Artificial
<220> FEATURE:
<223> OTHER INFORMATION: synthetic DNA
```

```
<400> SEQUENCE: 2098
taagagacag cag                                                        13

<210> SEQ ID NO 2099
<211> LENGTH: 13
<212> TYPE: DNA
<213> ORGANISM: Artificial
<220> FEATURE:
<223> OTHER INFORMATION: synthetic DNA

<400> SEQUENCE: 2099
taagagacag cat                                                        13

<210> SEQ ID NO 2100
<211> LENGTH: 13
<212> TYPE: DNA
<213> ORGANISM: Artificial
<220> FEATURE:
<223> OTHER INFORMATION: synthetic DNA

<400> SEQUENCE: 2100
taagagacag cca                                                        13

<210> SEQ ID NO 2101
<211> LENGTH: 13
<212> TYPE: DNA
<213> ORGANISM: Artificial
<220> FEATURE:
<223> OTHER INFORMATION: synthetic DNA

<400> SEQUENCE: 2101
taagagacag ccc                                                        13

<210> SEQ ID NO 2102
<211> LENGTH: 13
<212> TYPE: DNA
<213> ORGANISM: Artificial
<220> FEATURE:
<223> OTHER INFORMATION: synthetic DNA

<400> SEQUENCE: 2102
taagagacag ccg                                                        13

<210> SEQ ID NO 2103
<211> LENGTH: 13
<212> TYPE: DNA
<213> ORGANISM: Artificial
<220> FEATURE:
<223> OTHER INFORMATION: synthetic DNA

<400> SEQUENCE: 2103
taagagacag cct                                                        13

<210> SEQ ID NO 2104
<211> LENGTH: 13
<212> TYPE: DNA
<213> ORGANISM: Artificial
<220> FEATURE:
<223> OTHER INFORMATION: synthetic DNA

<400> SEQUENCE: 2104
taagagacag cga                                                        13

<210> SEQ ID NO 2105
<211> LENGTH: 13
```

```
<212> TYPE: DNA
<213> ORGANISM: Artificial
<220> FEATURE:
<223> OTHER INFORMATION: synthetic DNA

<400> SEQUENCE: 2105
taagagacag cgc                                                        13

<210> SEQ ID NO 2106
<211> LENGTH: 13
<212> TYPE: DNA
<213> ORGANISM: Artificial
<220> FEATURE:
<223> OTHER INFORMATION: synthetic DNA

<400> SEQUENCE: 2106
taagagacag cgg                                                        13

<210> SEQ ID NO 2107
<211> LENGTH: 13
<212> TYPE: DNA
<213> ORGANISM: Artificial
<220> FEATURE:
<223> OTHER INFORMATION: synthetic DNA

<400> SEQUENCE: 2107
taagagacag cgt                                                        13

<210> SEQ ID NO 2108
<211> LENGTH: 13
<212> TYPE: DNA
<213> ORGANISM: Artificial
<220> FEATURE:
<223> OTHER INFORMATION: synthetic DNA

<400> SEQUENCE: 2108
taagagacag cta                                                        13

<210> SEQ ID NO 2109
<211> LENGTH: 13
<212> TYPE: DNA
<213> ORGANISM: Artificial
<220> FEATURE:
<223> OTHER INFORMATION: synthetic DNA

<400> SEQUENCE: 2109
taagagacag ctc                                                        13

<210> SEQ ID NO 2110
<211> LENGTH: 13
<212> TYPE: DNA
<213> ORGANISM: Artificial
<220> FEATURE:
<223> OTHER INFORMATION: synthetic DNA

<400> SEQUENCE: 2110
taagagacag ctg                                                        13

<210> SEQ ID NO 2111
<211> LENGTH: 13
<212> TYPE: DNA
<213> ORGANISM: Artificial
<220> FEATURE:
<223> OTHER INFORMATION: synthetic DNA

<400> SEQUENCE: 2111
```

```
taagagacag ctt                                                         13

<210> SEQ ID NO 2112
<211> LENGTH: 13
<212> TYPE: DNA
<213> ORGANISM: Artificial
<220> FEATURE:
<223> OTHER INFORMATION: synthetic DNA

<400> SEQUENCE: 2112
taagagacag gaa                                                         13

<210> SEQ ID NO 2113
<211> LENGTH: 13
<212> TYPE: DNA
<213> ORGANISM: Artificial
<220> FEATURE:
<223> OTHER INFORMATION: synthetic DNA

<400> SEQUENCE: 2113
taagagacag gac                                                         13

<210> SEQ ID NO 2114
<211> LENGTH: 13
<212> TYPE: DNA
<213> ORGANISM: Artificial
<220> FEATURE:
<223> OTHER INFORMATION: synthetic DNA

<400> SEQUENCE: 2114
taagagacag gag                                                         13

<210> SEQ ID NO 2115
<211> LENGTH: 13
<212> TYPE: DNA
<213> ORGANISM: Artificial
<220> FEATURE:
<223> OTHER INFORMATION: synthetic DNA

<400> SEQUENCE: 2115
taagagacag gat                                                         13

<210> SEQ ID NO 2116
<211> LENGTH: 13
<212> TYPE: DNA
<213> ORGANISM: Artificial
<220> FEATURE:
<223> OTHER INFORMATION: synthetic DNA

<400> SEQUENCE: 2116
taagagacag gca                                                         13

<210> SEQ ID NO 2117
<211> LENGTH: 13
<212> TYPE: DNA
<213> ORGANISM: Artificial
<220> FEATURE:
<223> OTHER INFORMATION: synthetic DNA

<400> SEQUENCE: 2117
taagagacag gcc                                                         13

<210> SEQ ID NO 2118
<211> LENGTH: 13
<212> TYPE: DNA
<213> ORGANISM: Artificial
```

```
<220> FEATURE:
<223> OTHER INFORMATION: synthetic DNA

<400> SEQUENCE: 2118
taagagacag gcg                                                         13

<210> SEQ ID NO 2119
<211> LENGTH: 13
<212> TYPE: DNA
<213> ORGANISM: Artificial
<220> FEATURE:
<223> OTHER INFORMATION: synthetic DNA

<400> SEQUENCE: 2119
taagagacag gct                                                         13

<210> SEQ ID NO 2120
<211> LENGTH: 13
<212> TYPE: DNA
<213> ORGANISM: Artificial
<220> FEATURE:
<223> OTHER INFORMATION: synthetic DNA

<400> SEQUENCE: 2120
taagagacag gga                                                         13

<210> SEQ ID NO 2121
<211> LENGTH: 13
<212> TYPE: DNA
<213> ORGANISM: Artificial
<220> FEATURE:
<223> OTHER INFORMATION: synthetic DNA

<400> SEQUENCE: 2121
taagagacag ggc                                                         13

<210> SEQ ID NO 2122
<211> LENGTH: 13
<212> TYPE: DNA
<213> ORGANISM: Artificial
<220> FEATURE:
<223> OTHER INFORMATION: synthetic DNA

<400> SEQUENCE: 2122
taagagacag ggg                                                         13

<210> SEQ ID NO 2123
<211> LENGTH: 13
<212> TYPE: DNA
<213> ORGANISM: Artificial
<220> FEATURE:
<223> OTHER INFORMATION: synthetic DNA

<400> SEQUENCE: 2123
taagagacag ggt                                                         13

<210> SEQ ID NO 2124
<211> LENGTH: 13
<212> TYPE: DNA
<213> ORGANISM: Artificial
<220> FEATURE:
<223> OTHER INFORMATION: synthetic DNA

<400> SEQUENCE: 2124
taagagacag gta                                                         13
```

<210> SEQ ID NO 2125
<211> LENGTH: 13
<212> TYPE: DNA
<213> ORGANISM: Artificial
<220> FEATURE:
<223> OTHER INFORMATION: synthetic DNA

<400> SEQUENCE: 2125
taagagacag gtc                                                          13

<210> SEQ ID NO 2126
<211> LENGTH: 13
<212> TYPE: DNA
<213> ORGANISM: Artificial
<220> FEATURE:
<223> OTHER INFORMATION: synthetic DNA

<400> SEQUENCE: 2126
taagagacag gtg                                                          13

<210> SEQ ID NO 2127
<211> LENGTH: 13
<212> TYPE: DNA
<213> ORGANISM: Artificial
<220> FEATURE:
<223> OTHER INFORMATION: synthetic DNA

<400> SEQUENCE: 2127
taagagacag gtt                                                          13

<210> SEQ ID NO 2128
<211> LENGTH: 13
<212> TYPE: DNA
<213> ORGANISM: Artificial
<220> FEATURE:
<223> OTHER INFORMATION: synthetic DNA

<400> SEQUENCE: 2128
taagagacag taa                                                          13

<210> SEQ ID NO 2129
<211> LENGTH: 13
<212> TYPE: DNA
<213> ORGANISM: Artificial
<220> FEATURE:
<223> OTHER INFORMATION: synthetic DNA

<400> SEQUENCE: 2129
taagagacag tac                                                          13

<210> SEQ ID NO 2130
<211> LENGTH: 13
<212> TYPE: DNA
<213> ORGANISM: Artificial
<220> FEATURE:
<223> OTHER INFORMATION: synthetic DNA

<400> SEQUENCE: 2130
taagagacag tag                                                          13

<210> SEQ ID NO 2131
<211> LENGTH: 13
<212> TYPE: DNA
<213> ORGANISM: Artificial
<220> FEATURE:
<223> OTHER INFORMATION: synthetic DNA

<400> SEQUENCE: 2131
taagagacag tat                                                           13

<210> SEQ ID NO 2132
<211> LENGTH: 13
<212> TYPE: DNA
<213> ORGANISM: Artificial
<220> FEATURE:
<223> OTHER INFORMATION: synthetic DNA

<400> SEQUENCE: 2132
taagagacag tca                                                           13

<210> SEQ ID NO 2133
<211> LENGTH: 13
<212> TYPE: DNA
<213> ORGANISM: Artificial
<220> FEATURE:
<223> OTHER INFORMATION: synthetic DNA

<400> SEQUENCE: 2133
taagagacag tcc                                                           13

<210> SEQ ID NO 2134
<211> LENGTH: 13
<212> TYPE: DNA
<213> ORGANISM: Artificial
<220> FEATURE:
<223> OTHER INFORMATION: synthetic DNA

<400> SEQUENCE: 2134
taagagacag tcg                                                           13

<210> SEQ ID NO 2135
<211> LENGTH: 13
<212> TYPE: DNA
<213> ORGANISM: Artificial
<220> FEATURE:
<223> OTHER INFORMATION: synthetic DNA

<400> SEQUENCE: 2135
taagagacag tct                                                           13

<210> SEQ ID NO 2136
<211> LENGTH: 13
<212> TYPE: DNA
<213> ORGANISM: Artificial
<220> FEATURE:
<223> OTHER INFORMATION: synthetic DNA

<400> SEQUENCE: 2136
taagagacag tga                                                           13

<210> SEQ ID NO 2137
<211> LENGTH: 13
<212> TYPE: DNA
<213> ORGANISM: Artificial
<220> FEATURE:
<223> OTHER INFORMATION: synthetic DNA

<400> SEQUENCE: 2137
taagagacag tgg                                                           13

<210> SEQ ID NO 2138

```
<211> LENGTH: 13
<212> TYPE: DNA
<213> ORGANISM: Artificial
<220> FEATURE:
<223> OTHER INFORMATION: synthetic DNA

<400> SEQUENCE: 2138
taagagacag tgt                                                        13

<210> SEQ ID NO 2139
<211> LENGTH: 13
<212> TYPE: DNA
<213> ORGANISM: Artificial
<220> FEATURE:
<223> OTHER INFORMATION: synthetic DNA

<400> SEQUENCE: 2139
taagagacag tta                                                        13

<210> SEQ ID NO 2140
<211> LENGTH: 13
<212> TYPE: DNA
<213> ORGANISM: Artificial
<220> FEATURE:
<223> OTHER INFORMATION: synthetic DNA

<400> SEQUENCE: 2140
taagagacag ttc                                                        13

<210> SEQ ID NO 2141
<211> LENGTH: 13
<212> TYPE: DNA
<213> ORGANISM: Artificial
<220> FEATURE:
<223> OTHER INFORMATION: synthetic DNA

<400> SEQUENCE: 2141
taagagacag ttg                                                        13

<210> SEQ ID NO 2142
<211> LENGTH: 13
<212> TYPE: DNA
<213> ORGANISM: Artificial
<220> FEATURE:
<223> OTHER INFORMATION: synthetic DNA

<400> SEQUENCE: 2142
taagagacag ttt                                                        13

<210> SEQ ID NO 2143
<211> LENGTH: 70
<212> TYPE: DNA
<213> ORGANISM: Artificial
<220> FEATURE:
<223> OTHER INFORMATION: synthetic DNA

<400> SEQUENCE: 2143
aatgatacgg cgaccaccga gatctacacg tcgtgcatcg tcggcagcgt cagatgtgta    60
taagagacag                                                            70

<210> SEQ ID NO 2144
<211> LENGTH: 70
<212> TYPE: DNA
<213> ORGANISM: Artificial
<220> FEATURE:
<223> OTHER INFORMATION: synthetic DNA
```

<400> SEQUENCE: 2144
aatgatacgg cgaccaccga gatctacact cgctgcatcg tcggcagcgt cagatgtgta    60
taagagacag                                                            70

<210> SEQ ID NO 2145
<211> LENGTH: 70
<212> TYPE: DNA
<213> ORGANISM: Artificial
<220> FEATURE:
<223> OTHER INFORMATION: synthetic DNA

<400> SEQUENCE: 2145
aatgatacgg cgaccaccga gatctacacc acagtagtcg tcggcagcgt cagatgtgta    60
taagagacag                                                            70

<210> SEQ ID NO 2146
<211> LENGTH: 70
<212> TYPE: DNA
<213> ORGANISM: Artificial
<220> FEATURE:
<223> OTHER INFORMATION: synthetic DNA

<400> SEQUENCE: 2146
aatgatacgg cgaccaccga gatctacact gctcgattcg tcggcagcgt cagatgtgta    60
taagagacag                                                            70

<210> SEQ ID NO 2147
<211> LENGTH: 70
<212> TYPE: DNA
<213> ORGANISM: Artificial
<220> FEATURE:
<223> OTHER INFORMATION: synthetic DNA

<400> SEQUENCE: 2147
aatgatacgg cgaccaccga gatctacact gacgagttcg tcggcagcgt cagatgtgta    60
taagagacag                                                            70

<210> SEQ ID NO 2148
<211> LENGTH: 70
<212> TYPE: DNA
<213> ORGANISM: Artificial
<220> FEATURE:
<223> OTHER INFORMATION: synthetic DNA

<400> SEQUENCE: 2148
aatgatacgg cgaccaccga gatctacacg catatgttcg tcggcagcgt cagatgtgta    60
taagagacag                                                            70

<210> SEQ ID NO 2149
<211> LENGTH: 66
<212> TYPE: DNA
<213> ORGANISM: Artificial
<220> FEATURE:
<223> OTHER INFORMATION: synthetic DNA

<400> SEQUENCE: 2149
caagcagaag acggcatacg agataagagg cagtctcgtg ggctcggaga tgtgtataag    60
agacag                                                                66

<210> SEQ ID NO 2150

```
<211> LENGTH: 66
<212> TYPE: DNA
<213> ORGANISM: Artificial
<220> FEATURE:
<223> OTHER INFORMATION: synthetic DNA

<400> SEQUENCE: 2150
caagcagaag acggcatacg ataggagt ccgtctcgtg ggctcggaga tgtgtataag    60
agacag                                                             66

<210> SEQ ID NO 2151
<211> LENGTH: 66
<212> TYPE: DNA
<213> ORGANISM: Artificial
<220> FEATURE:
<223> OTHER INFORMATION: synthetic DNA

<400> SEQUENCE: 2151
caagcagaag acggcatacg atagtgagag aggtctcgtg ggctcggaga tgtgtataag   60
agacag                                                             66

<210> SEQ ID NO 2152
<211> LENGTH: 66
<212> TYPE: DNA
<213> ORGANISM: Artificial
<220> FEATURE:
<223> OTHER INFORMATION: synthetic DNA

<400> SEQUENCE: 2152
caagcagaag acggcatacg atcctctc tggtctcgtg ggctcggaga tgtgtataag     60
agacag                                                             66

<210> SEQ ID NO 2153
<211> LENGTH: 349
<212> TYPE: DNA
<213> ORGANISM: Zea mays

<400> SEQUENCE: 2153
gtgggtaggt agagaatacc taggggcgcg agacaactct ctctaaggaa ctcggcaaaa   60
tagccccgta acttcgggag aagggggtgcc ccctcgcaaa aggggggtcgc agtgaccagg  120 cccgggcgac tgtataccaa aaacacaggt ctccgcaaag tcgtaagacc atgtatgggg   180
gctgacgcct gcccagtgcc ggaaggtcaa ggaagttggt gaactgatga cagggaagcc   240
ggcgaccgaa gccccggtga acggcggccg taactataac ggtcctaagg tagcgaaatt   300
ccttgtcggg taagttccga cccgcacgaa aggcgtaacg atctgggca                349

<210> SEQ ID NO 2154
<211> LENGTH: 348
<212> TYPE: DNA
<213> ORGANISM: Oryza sativa

<400> SEQUENCE: 2154
gtgggtaggt agagaatacc taggggcgcg agacaactct ctctaaggaa ctcggcaaaa   60
tagccccgta acttcgggag aagggggtgcc ccctcgcaaa aggggggtcgc agtgaccagg  120 cccgggcgac tgtttaccaa aaacacaggt ctccgcaaag tcgtaagacc atgtatgggg   180
gctgacgcct gcccagtgcc ggaagtcaag gaagttggtg aactgatgac agggaagccg   240
gcgaccgaag ccccggtgaa cggcggccgt aactataacg gtcctaaggt agcgaaattc   300
cttgtcgggt aagttccgac ccgcacgaaa ggcgtaacga tctgggca                348
```

<210> SEQ ID NO 2155
<211> LENGTH: 348
<212> TYPE: DNA
<213> ORGANISM: Solanum tuberosum

<400> SEQUENCE: 2155

```
gtgggtaggt agagaatacc tagggggcgcg agacaactct ctctaaggaa ctcggcaaaa      60
tagcccccgta acttcgggag aaggggtgcc tcctcacaaa gggggtcgca gtgaccaggc     120
ccgggcgact gtttaccaaa aacacaggtc tccgcaaagt cgtaagacca tgtatggggg     180
ctgacgcctg cccagtgccg gaaggtcaag gaagttggtg acctgatgac aggggagccg     240
gcgaccgaag ccccggtgaa cggcggccgt aactataacg gtcctaaggt agcgaaattc     300
cttgtcgggt aagttccgac ccgcacgaaa ggcgtaacga tctgggca                  348
```

<210> SEQ ID NO 2156
<211> LENGTH: 348
<212> TYPE: DNA
<213> ORGANISM: Glycine max

<400> SEQUENCE: 2156

```
gtgggtaggt agagaatacc tagaggcgcg agacaactct ctctaaggaa ctcggcaaaa      60
tagcccccgta acttcgggag aaggggtgcc tcctcacaaa gggggtcgca gtgaccaggc     120
ccgggcgact gtttaccaaa aacacaggtc tccgcaaagt cgtaagacca tgtatggggg     180
ctgacgcctg cccagtgccg gaaggtcaag gaagttggtg acctgatgac aggggagccg     240
acgaccgaag ccccggtgaa cggcggccgt aactataacg gtcctaaggt agcgaaattc     300
cttgtcgggt aagttccgac ccgcacgaaa ggcgtaacga tctgggca                  348
```

<210> SEQ ID NO 2157
<211> LENGTH: 349
<212> TYPE: DNA
<213> ORGANISM: Zea mays

<400> SEQUENCE: 2157

```
gtgggtaggt agagaatacc tagggggcgcg agacaactct ctctaaggaa ctcggcaaaa      60
tagcccccgta acttcgggag aaggggtgcc ccctcgcaaa aggggggtcgc agtgaccagg     120
cccgggcgac tgtataccaa aaacacaggt ctccgcaaag tcgtaagacc atgtatgggg     180
gctgacgcct gcccagtgcc ggaaggtcaa ggaagttggt gaactgatga cagggaagcc     240
ggcgaccgaa gccccggtga acggcggccg taactataac ggtcctaagg tagcgaaatt     300
ccttgtcggg taagttccga cccgcacgaa aggcgtaacg atctgggca                 349
```

<210> SEQ ID NO 2158
<211> LENGTH: 348
<212> TYPE: DNA
<213> ORGANISM: Oryza sativa

<400> SEQUENCE: 2158

```
gtgggtaggt agagaatacc tagggggcgcg agacaactct ctctaaggaa ctcggcaaaa      60
tagcccccgta acttcgggag aaggggtgcc ccctcgcaaa aggggggtcgc agtgaccagg     120
cccgggcgac tgtttaccaa aaacacaggt ctccgcaaag tcgtaagacc atgtatgggg     180
gctgacgcct gcccagtgcc ggaagtcaag gaagttggtg aactgatgac agggaagccg     240
gcgaccgaag ccccggtgaa cggcggccgt aactataacg gtcctaaggt agcgaaattc     300
```

```
cttgtcgggt aagttccgac ccgcacgaaa ggcgtaacga tctgggca            348

<210> SEQ ID NO 2159
<211> LENGTH: 348
<212> TYPE: DNA
<213> ORGANISM: Solanum tuberosum

<400> SEQUENCE: 2159
gtgggtaggt agagaatacc tagggcgcg  agacaactct ctctaaggaa ctcggcaaaa    60
tagccccgta acttcgggag aagggtgcc  tcctcacaaa ggggtcgca  gtgaccaggc   120 ccgggcgact gtttaccaaa aacacaggtc tccgcaaagt cgtaagacca tgtatggggg   180
ctgacgcctg cccagtgccg gaaggtcaag gaagttggtg acctgatgac aggggagccg   240
gcgaccgaag ccccggtgaa cggcggccgt aactataacg gtcctaaggt agcgaaattc   300
cttgtcgggt aagttccgac ccgcacgaaa ggcgtaacga tctgggca               348

<210> SEQ ID NO 2160
<211> LENGTH: 348
<212> TYPE: DNA
<213> ORGANISM: Glycine max

<400> SEQUENCE: 2160
gtgggtaggt agagaatacc tagaggcgcg agacaactct ctctaaggaa ctcggcaaaa    60
tagccccgta acttcgggag aagggtgcc  tcctcacaaa ggggtcgca  gtgaccaggc   120 ccgggcgact gtttaccaaa aacacaggtc tccgcaaagt cgtaagacca tgtatggggg   180
ctgacgcctg cccagtgccg gaaggtcaag gaagttggtg acctgatgac aggggagccg   240
acgaccgaag ccccggtgaa cggcggccgt aactataacg gtcctaaggt agcgaaattc   300
cttgtcgggt aagttccgac ccgcacgaaa ggcgtaacga tctgggca               348

<210> SEQ ID NO 2161
<211> LENGTH: 114
<212> TYPE: DNA
<213> ORGANISM: Oryza sativa

<400> SEQUENCE: 2161
gtattgcgag acagccagaa gcagaaggta aaatacgcgg tactttattg cttagtctag    60
cttttatgga agctttaaca atttatggac tagttgtggc actggcgctt ttat         114

<210> SEQ ID NO 2162
<211> LENGTH: 87
<212> TYPE: DNA
<213> ORGANISM: Oryza sativa

<400> SEQUENCE: 2162
ccagaagcag aaggtaaaat acgcggtact ttattgctta gtctagcttt tatggaagct    60
ttaacaattt atggactagt tgtggca                                       87
```